US008620589B2

(12) United States Patent
Morgan

(10) Patent No.: US 8,620,589 B2

(45) Date of Patent: Dec. 31, 2013

(54) SYNTHETIC BINDING PROTEINS

(75) Inventor: Richard D. Morgan, Middleton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 47 days.

(21) Appl. No.: 12/849,673

(22) Filed: Aug. 3, 2010

(65) Prior Publication Data

US 2010/0304462 A1 Dec. 2, 2010

Related U.S. Application Data

(63) Continuation-in-part of application No. 12/143,498, filed on Jun. 20, 2008, now abandoned.

(60) Provisional application No. 60/936,504, filed on Jun. 20, 2007.

(51) Int. Cl.

*G01N 33/48* (2006.01)
*G01N 31/00* (2006.01)
*G06G 7/48* (2006.01)
*G06G 7/58* (2006.01)

(52) U.S. Cl.

USPC .................... 702/19; 702/22; 703/11; 703/12

(58) Field of Classification Search

None

See application file for complete search history.

(56) References Cited

U.S. PATENT DOCUMENTS

| | | | |
|---|---|---|---|
| 7,115,407 | B2 | 10/2006 | Morgan et al. |
| 7,186,538 | B2 | 3/2007 | Morgan et al. |

OTHER PUBLICATIONS

Pearson (www.bigre.ulb.ac.be/Users/jvanheld/bioinformatics_introductory_course/web_course/articles/; 1998, pp. 1-32).*

* cited by examiner

*Primary Examiner* — Larry D Riggs, II

(74) *Attorney, Agent, or Firm* — New England Biolabs, Inc.; Harriet M. Strimpel

(57) ABSTRACT

Methods and compositions are provided for creating a binding protein that recognizes a rationally chosen recognition sequence in which a first amino acid has been substituted for a second amino acid using site-directed mutagenesis of a member protein of a set of proteins at an identified position or positions correlated with recognition of a chosen specified target module in the recognition sequence. A system is provided for automating the storage and manipulation of the correlations between positions and types of amino acid residues in the binding protein with specific modules at specified positions in the target recognition sequence and for designing and creating proteins with novel specificities.

3 Claims, 120 Drawing Sheets

ALIGNED DNA RECOGNITION SEQUENCES:

| POSITION | 0123456 |
|---|---|
| MmeI | TCCRAC |
| EsaSSI | GACCAC |
| ApyPI | ATCGAC |
| BsbI | CAACAC |
| NlaCI | CATCAC |
| DrdIV | TACGAC |
| RpaB5I | CGRGGAC |
| DraRI | CAAGNAC |
| MaqI | CRTTGAC |
| NhaXI | CAAGRAG |
| NmeAIII | GCCGAG |
| CdpI | GCGGAG |
| AquIII | GAGGAG |
| CstMI | AAGGAG |
| SdeAI | CAGRAG |
| PspPRI | CCYCAG |
| PlaDI | CATCAG |
| SpoDI | GCGGAAG |
| AquIV | GRGGAAG |
| PspOMII | CGCCCAR |

DIVERSITY OF DNA BASES OBSERVED: (5 = A)

| 0 | 1 | 2 | 3 | 4 | 6 | TOTAL |
|---|---|---|---|---|---|---|
| A= 0 | A= 4 | A= 10 | A= 1 | A= 2 | A= 0 | 17 |
| C= 5 | C= 6 | C= 5 | C= 6 | C= 6 | C= 9 | 37 |
| G= 2 | G= 6 | G= 2 | G= 9 | G= 8 | G= 10 | 37 |
| T= 0 | T= 2 | T= 2 | T= 3 | T= 0 | T= 0 | 7 |
| R= 0 | R= 2 | R= 1 | R= 0 | R= 3 | R= 1 | 7 |
| Y= 0 | Y= 0 | Y= 0 | Y= 1 | Y= 0 | Y= 0 | 1 |
| N= 13 | N= 0 | N= 0 | N= 0 | N= 1 | N= 0 | (14) |

NOT OBSERVED TO DATE: B,D,H,K,M,S,V,W

FIG. 10B

ALIGNED DNA RECOGNITION SEQUENCES:

| POSITION | 0123456 |
|---|---|
| MmeI | TCCRAC |
| EsaSSI | GACCAC |
| ApyPI | ATCGAC |
| BsbI | CAACAC |
| NlaCI | CATCAC |
| DrdIV | TACGAC |
| RpaB5I | CGRGGAC |
| DraRI | CAAGNAC |
| MaqI | CRTTGAC |
| NhaXI | CAAGRAG |
| NmeAIII | GCCGAG |
| CdpI | GCGGAG |
| AquIII | GAGGAG |
| CstMI | AAGGAG |
| SdeAI | CAGRAG |
| PspPRI | CCYCAG |
| PlaDI | CATCAG |
| SpoDI | GCGGAAG |
| AquIV | GRGGAAG |
| PspOMII | CGCCCAR |

POSITION 3

A= 1
C= 6
G= 9
T= 3
R= 0
Y= 1
N= 0

POSITION 4

A= 2
C= 6
G= 8
T= 0
R= 3
Y= 0
N= 1

POSITION 6

POSITION 3 RECOGNITION:
(CORRESPONDING TO MmeI
POSITIONS 751(E) AND 773(N)).

| DNA BASE RECOGNIZED | AMINO ACID PAIR DETERMINING RECOGNITION (POSITION 751 + POSITION 773) |
|---|---|
| C | E + N, S + N, S + S, E + S |
| G | K + D, R + D, R + S |
| T | K + G, K + Q |
| Y | V + N, L + S |

POSITION 4 RECOGNITION:
(CORRESPONDING TO MmeI
POSITIONS 774(A) AND 810(R)).

| DNA BASE RECOGNIZED | AMINO ACID PAIR DETERMINING RECOGNITION (POSITION 774 + POSITION 810 (+POSITION 809)) |
|---|---|
| A | A + R (+ 809=P), S + R (+ 809=T) |
| C | K + Q, K + S, K + M, K + V, S + Q |
| G | L + R, M + R, E + R, T + R (+ 809=P) |
| R | A + R (+ 809=Y OR F, NOT P), T + R (+ 809=Y OR F, NOT P) |
| N | G + M |

POSITION 6 RECOGNITION:
(CORRESPONDING TO MmeI
POSITIONS 806(E) AND 808(R)).

| DNA BASE RECOGNIZED | AMINO ACID PAIR DETERMINING RECOGNITION (POSITION 806 + POSITION 808) |
|---|---|
| C | E + R, T + R |
| G | K + D, R + D, G + D |
| R | D + D |
| N | W + A, M + E, G + E, F + E, S + E, T + G |
| B | G + T |

POSITION 0 RECOGNITION:
(CORRESPONDING TO Gaut27I
POSITIONS 790(R) AND 802(E)).

| DNA BASE RECOGNIZED | AMINO ACID PAIR DETERMINING RECOGNITION (POSITION 790 + POSITION 802) |
|---|---|
| C | R + E, R + W |
| G | D + R, R + R, H + R |

FIG. 11B

```
                                3                                  34                                                   6 64
AquIII___GAGGAG 740 EYLLIPKVSSERRNYIPIGFLNQSTLSSDLVFIVGNATLFHFGIFTSVMHMAWVKYVCGRL---KSDYRYSKDIVYNNFPFP 818 SEQ ID NO: 64
SdeAI____CAGRAG 730 DYIFIPRVSSENRDYIPMEFFTKDFICGDTGLAVPNATLFHFGILTSKMHMDWVRYVAGRL---KSDYRYSNEIVYNNFPFP 808 SEQ ID NO: 65
PspPRI___CCYCAG 761 PYVAIPWVSSENRRFIPIGFIDGNTVAGNKLFVIVDGNTYQFGTLSSSMHNAFMRLTAGRM---KSDYSYSSTIVYNNFPYP 839 SEQ ID NO: 66
EsaSSI___GACCAC 755 PFMVIPEVSSERREFIPLGYLQPPTLASNKLRLMPDATLYHFAVLNSTMHMAWTRAVCGRL---ESRYQYSVTIVYNNFPWP 833 SEQ ID NO: 67
MmeI_____TCCRAC_745 DYLLIPETSSENRQFIPIGFVDRNVISSNATYHIPSAEPLIFGLLSSTMHNCWMRNVGGRL---ESRYRYSASLVYNTFPWI 823 SEQ ID NO: 68
PlaDI____CATCAG 753 PYLVIPNTSSERRDYVPIGWLTPEVVANQKLRILPDADPWIFGLLTSGMHMAWMRAITGRM---KSDYMYSVGVVYNTFPWP 831 SEQ ID NO: 69
NlaCI____CATCAC 781 RYLLLPKVSSENRRFLPIGYIEPETIANGSALIIPNATLCHFGILSSTMHNAFMRTVAGRL---ESRYQYSASIVYNNFPFP 859 SEQ ID NO: 70
NmeAIII__GCCGAG 755 NYLIIPSVSSESRRFIPIGYLSFETVVSNLAFILPNATLYHFGILSSTMHNAFMRTVAGRL---KSDYRYSNTVVYNNFPFP 833 SEQ ID NO: 71
ApyPI____ATCGAC 787 DFLCVPSVVSENRPYFTAADIEEGTVVSSLAFAVEDSDRSQFALISSSMFITWQKMIGGRL---ESRLRFANTLTWNTFPVP 865 SEQ ID NO: 72
CstMI____AAGGAG 789 DYLCLPKVVSERRSYFTVQRYPSNVIASDLVFHAQDPDGLMFALASSSMFITWQKSIGGRL---KSDLRFANTLTWNTFPVP 867 SEQ ID NO: 73
CdpI_____GCGGAG 764 TYIGIPKVSSERRKYVPFAFVTDGMIPGDMLYFVPTDSLFVFGVLVSQFQNAWMRVVAGRL---KSDYRYGNTTVYNNFVFP 842 SEQ ID NO: 74
RpaB5I___CGRGGAC 839 RYIGTARTA----KHRIFSMLAGHSLPESEVIAVGSDDAFILGVLSSRLHVRWSLSKGGTL---EDRRRYNNSMCFDPFPFP 913 SEQ ID NO: 75
PspOMII_CGCCCAR 873 RYIATVETA----KHRIFSLLDATILPDNKLIIIALADTWHFSIVSSRIHWVWAIANAAKIGMYDGDAVYPKGQCFDPFPFP 950 SEQ ID NO: 76
MaqI_____CRTTGAC 843 TAIATSLTA----KHRVFVHLDSNSICDSTTVMFALPGAQYLGVLSSRVHVLWSLFAGGTL---ENRPRYNKTLCFETFPFP 917 SEQ ID NO: 77
DrdIV____TACGAC 859 RYVVTLETA----KHQVFQFLDSSIVPDSTIVTFGTEDAFHLGVLSSRVHVTWALAQGGTL---EDRPRYNKTRCFETFPFP 933 SEQ ID NO: 78
SpoDI___GCGGAAG 758 RFIVTPRVG----KHRIFVWLDSNALADSATFIVARDDETTFGILHSSFHELWSLRMGTFLG-VGNDRRYTPSTTFETFPFP 834 SEQ ID NO: 79
AquIV___GRGGAAG 737 LYFAVPRHS----KWFIFIPCKLDWLPADSTTVVASDDFYVLGILTSDVHRQWVKAQSSTL---KGDTRYTHNTCFETFPFP 811 SEQ ID NO: 80
NhaXI___CAAGRAG 776 RYIVCARVT----HRPIFEFVSTAIHPNDALSVFALEDDYSFGILQSGIHWEWFINRCSTL---KADFRYTSDTVFDSFPWP 850 SEQ ID NO: 81
DraRI___CAAGNAC_766 RYIVCSRVT----KRQVFEFLDNGIRPSDGLQIFAFEDDYSFGVIQSSVHWQWLIARGGTL---TARLMYTSDTVFDTFPWP 840 SEQ ID NO: 82
```

FIG. 13

| | | |
|---|---|---|
| MmeI___TCCRAC/1-919 | FGLLSSTMHNCWMRN---VGGRLESRYRYSASLVYNTFPWI | SEQ ID NO: 132 |
| EsaSSI___GACCAC/1-933 | FAVLNSTMHHAWTRA---VCGRLESRYQYSVTIVYNNFPWP | SEQ ID NO: 133 |
| ApyPI___ATCGAC/1-948 | FALISSSMFITWQKM---IGGRLESRLRFANTLTWNTFPVP | SEQ ID NO: 134 |
| NlaCI___CATCAC/1-954 | FGILSSTMHNAFMRT---VAGRLESRYQYSASIVYNNFPFP | SEQ ID NO: 135 |
| DrdIV___TACGAC/1-1144 | LGVLSSRVHVTWALA---QGGTLEDRPRYNKTRCFETFPFP | SEQ ID NO: 136 |
| RpaB5I__CGRGGAC/1-1184 | LGVLSSRLHVRWSLS---KGGTLEDRPRYNNSMCFDPFPFP | SEQ ID NO: 137 |
| DraRI__CAAGNAC/1-956 | FGVIQSSVHWQWLIA---RGGTLTARLMYTSDTVFDTFPWP | SEQ ID NO: 138 |
| MaqI___CRTTGAC/1-1151 | LGVLSSRVHVLWSLF---AGGTLENRPRYNKTLCFETFPFP | SEQ ID NO: 139 |
| NhaXI__CAAGRAG/1-978 | FGILQSGIHWEWFIN---RCSTLKADFRYTSDTVFDSFPWP | SEQ ID NO: 140 |
| NmeAIII__GCCGAG/1-937 | FGILSSTMHNAFMRT---VAGRLKSDYRYSNTVVYNNFPFP | SEQ ID NO: 141 |
| CdpI___GCGGAG/1-926 | FGVLVSQFQNAWMRV---VAGRLKSDYRYGNTTVYNNFVFP | SEQ ID NO: 142 |
| AquIII___GAGGAG/1-917 | FGIFTSVMHHAWVKY---VCGRLKSDYRYSKDIVYNNFPFP | SEQ ID NO: 143 |
| CstMI___AAGGAG/1-952 | FALASSSMFITWQKS---IGGRLKSDLRFANTLTWNTFPVP | SEQ ID NO: 144 |
| SdeAI___CAGRAG/1-908 | FGILTSKMHMDWVRY---VAGRLKSDYRYSNEIVYNNFPFP | SEQ ID NO: 145 |
| PspPRI___CCYCAG/1-934 | FGTLSSSMHNAFMRL---TAGRMKSDYSYSSTIVYNNFPYP | SEQ ID NO: 146 |
| PlaDI___CATCAG/1-928 | FGLLTSGMHMAWMRA---ITGRMKSDYMYSVGVVYNTFPWP | SEQ ID NO: 147 |
| SpoDI___GCGGAAG/1-965 | FGILHSSFHELWSLRMG-TFLGVGNDPRYTPSTTFETFPFP | SEQ ID NO: 148 |
| AquIV___GRGGAAG/1-914 | LGILTSDVHRQWVKA---QSSTLKGDTRYTHNTCFETFPFP | SEQ ID NO: 149 |
| PspOMII_CGCCCAR/1-1160 | FSIVSSRIHWVWAIANAAKIGMYDGDAVYPKGQCFDPFPFP | SEQ ID NO: 150 |

| | | |
|---|---|---|
| MmeI___TCCRAC/1-919 | FGLLSSTMHNCWMRN---VGGRLESRYRYSASLVYNTFPWI | SEQ ID NO: 132 |
| EsaSSI___GACCAC/1-933 | FAVLNSTMHHAWTRA---VCGRLESRYQYSVTIVYNNFPWP | SEQ ID NO: 133 |
| ApyPI___ATCGAC/1-948 | FALISSSMFITWQKM---IGGRLESRLRFANTLTWNTFPVP | SEQ ID NO: 134 |
| NlaCI___CATCAC/1-954 | FGILSSTMHNAFMRT---VAGRLESRYQYSASIVYNNFPFP | SEQ ID NO: 135 |
| DrdIV___TACGAC/1-1144 | LGVLSSRVHVTWALA---QGGTLEDRPRYNKTRCFETFPFP | SEQ ID NO: 136 |
| RpaB5I__CGRGGAC/1-1184 | LGVLSSRLHVRWSLS---KGGTLEDRPRYNNSMCFDPFPFP | SEQ ID NO: 137 |
| DraRI__CAAGNAC/1-956 | FGVIQSSVHWQWLIA---RGGTLTARLMYTSDTVFDTFPWP | SEQ ID NO: 138 |
| MaqI___CRTTGAC/1-1151 | LGVLSSRVHVLWSLF---AGGTLENRPRYNKTLCFETFPFP | SEQ ID NO: 139 |
| NhaXI__CAAGRAG/1-978 | FGILQSGIHWEWFIN---RCSTLKADFRYTSDTVFDSFPWP | SEQ ID NO: 140 |
| NmeAIII__GCCGAG/1-937 | FGILSSTMHNAFMRT---VAGRLKSDYRYSNTVVYNNFPFP | SEQ ID NO: 141 |
| CdpI___GCGGAG/1-926 | FGVLVSQFQNAWMRV---VAGRLKSDYRYGNTTVYNNFVFP | SEQ ID NO: 142 |
| AquIII___GAGGAG/1-917 | FGIFTSVMHHAWVKY---VCGRLKSDYRYSKDIVYNNFPFP | SEQ ID NO: 143 |
| CstMI___AAGGAG/1-952 | FALASSSMFITWQKS---IGGRLKSDLRFANTLTWNTFPVP | SEQ ID NO: 144 |
| SdeAI___CAGRAG/1-908 | FGILTSKMHMDWVRY---VAGRLKSDYRYSNEIVYNNFPFP | SEQ ID NO: 145 |
| PspPRI___CCYCAG/1-934 | FGTLSSSMHNAFMRL---TAGRMKSDYSYSSTIVYNNFPYP | SEQ ID NO: 146 |
| PlaDI___CATCAG/1-928 | FGLLTSGMHMAWMRA---ITGRMKSDYMYSVGVVYNTFPWP | SEQ ID NO: 147 |
| SpoDI___GCGGAAG/1-965 | FGILHSSFHELWSLRMG-TFLGVGNDPRYTPSTTFETFPFP | SEQ ID NO: 148 |
| AquIV___GRGGAAG/1-914 | LGILTSDVHRQWVKA---QSSTLKGDTRYTHNTCFETFPFP | SEQ ID NO: 149 |
| PspOMII_CGCCCAR/1-1160 | FSIVSSRIHWVWAIANAAKIGMYDGDAVYPKGQCFDPFPFP | SEQ ID NO: 150 |

FIG. 14

| BASE / AMINO ACID | E | T | K | G | D |
|---|---|---|---|---|---|
| C | 7 | 1 | 0 | 0 | 0 |
| G | 0 | 0 | 9 | 1 | 0 |
| R | 0 | 0 | 0 | 0 | 1 |

CHI SQUARE VALUE = 38
DEGREES OF FREEDOM = 8
Pvalue = 0.0001

FIG. 15

ALIGNED DNA RECOGNITION SEQUENCES:

| | |
|---|---|
| POSITION | 0123456 |
| MmeI | TCCRAC |
| EsaSSI | GACCAC |
| ApyPI | ATCGAC |
| BsbI | CAACAC |
| NlaCI | CATCAC |
| DrdIV | TACGAC |
| RpaB5I | CGRGGAC |
| DraRI | CAAGNAC |
| MaqI | CRTTGAC |
| NhaXI | CAAGRAG |
| NmeAIII | GCCGAG |
| CdpI | GCGGAG |
| AquIII | GAGGAG |
| CstMI | AAGGAG |
| SdeAI | CAGRAG |
| PspPRI | CCYCAG |
| PlaDI | CATCAG |
| SpoDI | GCGGAAG |
| AquIV | GRGGAAG |
| PspOMII | CGCCCAR |

| | | | | |
|---|---|---|---|---|
| MmeI_____TCCRAC | 788 | LLSSTMHNCWMRNVGGRL---ESRYRYSASLVYNTFPWI | 823 | SEQ ID NO: 45 |
| EsaSSI___GACCAC | 798 | VLNSTMHMAWTRAVCGRL---ESRYQYSVTIVYNNFPWP | 833 | SEQ ID NO: 46 |
| ApyPI____ATCGAC | 830 | LISSSMFITWQKMIGGRL---ESRLRFANTLTWNTFPVP | 865 | SEQ ID NO: 47 |
| NlaCI____CATCAC | 824 | ILSSTMHNAFMRTVAGRL---ESRYQYSASIVYNNFPFP | 859 | SEQ ID NO: 48 |
| DrdIV____TACGAC | 898 | VLSSRVHVTWALAQGGTL---EDRPRYNKTRCFETFPFP | 933 | SEQ ID NO: 49 |
| RpaB5I__CGRGGAC | 878 | VLSSRLHVRWSLSKGGTL---EDRPRYNNSMCFDPFPFP | 913 | SEQ ID NO: 50 |
| DraRI___CAAGNAC | 805 | VIQSSVHWQWLIARGGTL---TARLMYTSDTVFDTFPWP | 840 | SEQ ID NO: 51 |
| MaqI____CRTTGAC | 882 | VLSSRVHVLWSLFAGGTL---ENRPRYNKTLCFETFPFP | 917 | SEQ ID NO: 52 |
| NhaXI___CAAGRAG | 815 | ILQSGIHWEWFINRCSTL---KADFRYTSDTVFDSFPWP | 850 | SEQ ID NO: 53 |
| NmeAIII__GCCGAG | 798 | ILSSTMHNAFMRTVAGRL---KSDYRYSNTVVYNNFPFP | 833 | SEQ ID NO: 54 |
| CdpI_____GCGGAG | 807 | VLVSQFQNAWMRVVAGRL---KSDYRYGNTTVYNNFVFP | 842 | SEQ ID NO: 55 |
| AquIII___GAGGAG | 783 | IFTSVMHMAWVKYVCGRL---KSDYRYSKDIVYNNFPFP | 818 | SEQ ID NO: 56 |
| CstMI____AAGGAG | 832 | LASSSMFITWQKSIGGRL---KSDLRFANTLTWNTFPVP | 867 | SEQ ID NO: 57 |
| SdeAI____CAGRAG | 773 | ILTSKMHMDWVRYVAGRL---KSDYRYSNEIVYNNFPFP | 808 | SEQ ID NO: 58 |
| PspPRI___CCYCAG | 804 | TLSSSMHNAFMRLTAGRM---KSDYSYSSTIVYNNFPYP | 839 | SEQ ID NO: 59 |
| PlaDI____CATCAG | 786 | LLTSGMHMAWMRAITGRM---KSDYMYSVGVVYNTFPWP | 831 | SEQ ID NO: 60 |
| SpoDI___GCGGAAG | 797 | ILHSSFHELWSLRMGTFLG-VGNDPRYTPSTTFETFPFP | 835 | SEQ ID NO: 61 |
| AquIV___GRGGAAG | 776 | ILTSDVHRQWVKAQSSTL---KGDTRYTHNTCFETFPFP | 811 | SEQ ID NO: 62 |
| PspOMII_CGCCCAR | 912 | IVSSRIHWVWAIANAAKIGMYDGDAVYPKGQCFDPFPFP | 950 | SEQ ID NO: 63 |

*FIG. 16-1*

| | SCORE (BITS) | E VALUE |
|---|---|---|
| ref\|YP_167160.1\| hypothetical protein SPO1926 [Silicibacter p... | 1974 | 0.0 |
| ref\|YP_001953905.1\| conserved hypothetical protein [Geobacter... | 974 | 0.0 |
| ref\|NP_419643.1\| hypothetical protein CC_0826 [Caulobacter cr... | 924 | 0.0 |
| ref\|ZP_02300517.1\| conserved hypothetical protein [Rhodopseud... | 910 | 0.0 |
| ref\|YP_195496.1\| N6 adenine-specific DNA methyltransferase pr... | 906 | 0.0 |
| emb\|CAD31540.1\| PUTATIVE DNA METHYLASE PROTEIN [Mesorhizobium... | 863 | 0.0 |
| ref\|YP_001544138.1\| hypothetical protein Haur_1365 [Herpetosi... | 845 | 0.0 |
| ref\|YP_760309.1\| hypothetical protein HNE_1600 [Hyphomonas ne... | 708 | 0.0 |
| ref\|YP_983122.1\| N6 adenine-specific DNA methyltransferase pr... | 528 | 1e-147 |
| ref\|NP_285443.1\| hypothetical protein DR_A0119.1 [Deinococcus... | 472 | 5e-131 |
| ref\|YP_973977.1\| hypothetical protein Pnap_4987 [Polaromonas ... | 455 | 8e-126 |
| ref\|YP_956924.1\| hypothetical protein Maqu_4156 [Marinobacter... | 424 | 2e-116 |
| ref\|YP_001733624.1\| Type II restriction enzyme, methylase sub... | 421 | 2e-115 |
| ref\|ZP_02843625.1\| conserved hypothetical protein [Thauera sp... | 410 | 3e-112 |
| ref\|YP_516011.1\| hypothetical protein Rfer_4327 [Rhodoferax f... | 397 | 2e-108 |
| ref\|ZP_01002825.1\| RNA-binding region [Loktanella vestfoldens... | 394 | 1e-107 |
| ref\|YP_594849.1\| putative DNA methylase protein [Lawsonia int... | 391 | 2e-106 |
| ref\|YP_570364.1\| hypothetical protein RPD_3238 [Rhodopseudomo... | 389 | 5e-106 |
| ref\|YP_531341.1\| Type II restriction enzyme methylase subunit... | 385 | 1e-104 |
| ref\|ZP_01748422.1\| hypothetical protein SSE37_25258 [Sagittul... | 379 | 5e-103 |
| ref\|YP_001691301.1\| hypothetical protein M446_7058 [Methyloba... | 374 | 2e-101 |
| ref\|ZP_01624419.1\| DNA modification methyltransferase-related... | 317 | 3e-84 |
| ref\|YP_001660135.1\| DNA modification methyltransferase relate... | 303 | 5e-80 |
| ref\|YP_001735547.1\| DNA modification methyltransferase [Synec... | 302 | 1e-79 |
| ref\|NP_295988.1\| DNA modification methyltransferase-related p... | 272 | 9e-71 |
| **ref\|YP_511167.1\| hypothetical protein Jann_3225 [Jannaschia s...** | **254** | **3e-65** |
| ref\|ZP_01438131.1\| hypothetical protein FP2506_09801 [Fulvima... | 250 | 5e-64 |
| ref\|YP_579008.1\| DNA modification methyltransferase-related p... | 245 | 1e-62 |
| ref\|ZP_00515525.1\| similar to Type II restriction enzyme meth... | 244 | 2e-62 |
| ref\|ZP_01736371.1\| hypothetical protein MELB17_22390 [Marinob... | 232 | 1e-58 |
| emb\|CAO90051.1\| unnamed protein product [Microcystis aerugino... | 210 | 4e-52 |
| ref\|ZP_02154167.1\| hypothetical protein OIHEL45_15444 [Oceani... | 208 | 2e-51 |
| ref\|YP_983119.1\| N6 adenine-specific DNA methyltransferase pr... | 206 | 9e-51 |
| gb\|ACC85607.1\| MmeI [Methylophilus methylotrophus] | 192 | 1e-46 |
| ref\|YP_860317.1\| conserved hypothetical protein-most likely a... | 189 | 1e-45 |
| ref\|NP_940094.1\| Putative DNA methyltransferase [Corynebacter... | 185 | 1e-44 |
| ref\|YP_001735369.1\| DNA methyltransferase [Synechococcus sp. ... | 183 | 6e-44 |
| ref\|YP_001274371.1\| Type II restriction enzyme methylase subu... | 182 | 1e-43 |
| emb\|CAO90010.1\| unnamed protein product [Microcystis aerugino... | 181 | 3e-43 |
| emb\|CAO90962.1\| unnamed protein product [Microcystis aerugino... | 180 | 5e-43 |
| ref\|YP_001658275.1\| DNA methylase [Microcystis aeruginosa NIE... | 177 | 3e-42 |
| ref\|NP_284504.1\| hypothetical protein NMA1791 [Neisseria meni... | 169 | 1e-39 |
| ref\|YP_001144220.1\| hypothetical protein ASA_P4G174 [Aeromona... | 162 | 1e-37 |
| ref\|YP_001928074.1\| hypothetical protein [Klebsiella pneumoni... | 162 | 2e-37 |
| ref\|YP_001678552.1\| conserved hypothetical protein [Francisel... | 161 | 3e-37 |

*FIG. 16-2*

| | | | |
|---|---|---|---|
| ref\|YP_392994.1\| | hypothetical protein Suden_0478 [Sulfurimona... | 159 | 1e-36 |
| ref\|YP_379070.1\| | hypothetical protein Cag_0759 [Chlorobium ch... | 156 | 7e-36 |
| ref\|NP_783835.1\| | putative YeeA protein [Lactobacillus ferment... | 156 | 7e-36 |
| ref\|YP_379612.1\| | methylase [Chlorobium chlorochromatii CaD3] ... | 156 | 9e-36 |
| ref\|ZP_00991173.1\| | hypothetical protein V12B01_09796 [Vibrio ... | 155 | 2e-35 |
| ref\|YP_343482.1\| | hypothetical protein Noc_1465 [Nitrosococcus... | 155 | 2e-35 |
| ref\|YP_001413872.1\| | methylase [Parvibaculum lavamentivorans D... | 155 | 2e-35 |
| ref\|ZP_02001775.1\| | conserved hypothetical protein [Beggiatoa ... | 150 | 4e-34 |
| ref\|YP_193255.1\| | methylase [Lactobacillus acidophilus NCFM] >... | 150 | 4e-34 |
| ref\|YP_351470.1\| | RNA-binding region RNP-1 [Rhodobacter sphaer... | 145 | 2e-32 |
| ref\|YP_001599624.1\| | hypothetical protein NMCC_1507 [Neisseria... | 144 | 3e-32 |
| ref\|ZP_02059607.1\| | Type II restriction enzyme methylase subun... | 142 | 9e-32 |
| ref\|YP_321845.1\| | hypothetical protein Ava_1326 [Anabaena vari... | 140 | 5e-31 |
| ref\|ZP_01927653.1\| | hypothetical protein LMHG_01083 [Listeria ... | 139 | 1e-30 |
| ref\|YP_001136762.1\| | hypothetical protein Mflv_5513 [Mycobacte... | 137 | 5e-30 |
| emb\|CAE14722.1\| | unnamed protein product [Leptospira biflexa t... | 132 | 9e-29 |
| gb\|ABX75590.1\| | putative DNA methylase [Lactococcus lactis sub... | 132 | 1e-28 |
| ref\|YP_001070527.1\| | hypothetical protein Mjls_2250 [Mycobacte... | 130 | 7e-28 |
| ref\|ZP_02921208.1\| | hypothetical protein STRINF_02092 [Strepto... | 129 | 1e-27 |
| ref\|YP_996520.1\| | putative DNA methylase [Verminephrobacter ei... | 128 | 3e-27 |
| ref\|ZP_01386477.1\| | hypothetical protein CferDRAFT_0756 [Chlor... | 127 | 4e-27 |
| ref\|YP_001903805.1\| | Site-specific DNA-methyltransferase (aden... | 126 | 1e-26 |
| ref\|ZP_01772253.1\| | Hypothetical protein COLAER_01256 [Collins... | 125 | 1e-26 |
| ref\|ZP_01943585.1\| | hypothetical protein LMSG_01238 [Listeria ... | 124 | 4e-26 |
| ref\|YP_320497.1\| | hypothetical protein Ava_C0223 [Anabaena var... | 123 | 7e-26 |
| ref\|YP_001612833.1\| | hypothetical protein sce2194 [Sorangium c... | 122 | 1e-25 |
| ref\|YP_911756.1\| | hypothetical protein Cpha266_1300 [Chlorobiu... | 120 | 8e-25 |
| ref\|YP_637987.1\| | hypothetical protein Mmcs_0812 [Mycobacteriu... | 117 | 4e-24 |
| ref\|YP_342071.1\| | hypothetical protein Noc_A0028 [Nitrosococcu... | 117 | 4e-24 |
| ref\|YP_789386.1\| | possible Type II restriction enzyme, methyla... | 117 | 6e-24 |
| ref\|NP_285442.1\| | hypothetical protein DR_A0119 [Deinococcus r... | 117 | 6e-24 |
| ref\|ZP_01039292.1\| | putative DNA methylase [Erythrobacter sp. ... | 116 | 1e-23 |
| ref\|ZP_01037573.1\| | putative DNA methylase [Roseovarius sp. 21... | 115 | 1e-23 |
| ref\|ZP_02170275.1\| | NUDIX hydrolase [Bacillus selenitireducens... | 114 | 3e-23 |
| ref\|YP_001501134.1\| | hypothetical protein Spea_1272 [Shewanell... | 113 | 7e-23 |
| ref\|NP_875022.1\| | Type II restriction enzyme, methylase subuni... | 111 | 2e-22 |
| ref\|NP_767505.1\| | hypothetical protein blr0865 [Bradyrhizobium... | 111 | 3e-22 |
| ref\|NP_388558.1\| | hypothetical protein BSU06760 [Bacillus subt... | 111 | 3e-22 |
| gb\|AAB66474.1\| | YeeA [Bacillus subtilis] | 111 | 3e-22 |
| ref\|YP_363896.1\| | putative DNA methylase [Xanthomonas campestr... | 111 | 4e-22 |
| ref\|YP_495543.1\| | type II restriction enzyme, methylase subuni... | 110 | 6e-22 |
| ref\|YP_986766.1\| | putative DNA methylase [Acidovorax sp. JS42]... | 109 | 1e-21 |
| ref\|YP_745336.1\| | DNA modification methyltransferase-related p... | 108 | 2e-21 |
| ref\|ZP_00874695.1\| | similar to hypothetical proteins [Streptoc... | 108 | 3e-21 |
| ref\|YP_571912.1\| | putative DNA methylase [Nitrobacter hamburge... | 107 | 3e-21 |

*FIG. 16-3*

| | | | |
|---|---|---|---|
| ref\|ZP_02055504.1\| | Type II restriction enzyme methylase subun... | 107 | 4e-21 |
| ref\|YP_001359531.1\| | hypothetical protein SUN_2234 [Sulfurovum... | 107 | 6e-21 |
| ref\|YP_001350665.1\| | type II restriction enzyme, methylase sub... | 107 | 6e-21 |
| ref\|ZP_01101074.1\| | N6 adenine-specific DNA methyltransferase,... | 105 | 1e-20 |
| ref\|YP_001276864.1\| | hypothetical protein RoseRS_2538 [Roseifl... | 105 | 2e-20 |
| ref\|YP_001799427.1\| | putative methylase [Corynebacterium ureal... | 104 | 4e-20 |
| ref\|ZP_01080509.1\| | hypothetical protein RS9917_00527 [Synecho... | 103 | 7e-20 |
| ref\|YP_001959313.1\| | conserved hypothetical protein [Chlorobiu... | 103 | 9e-20 |
| ref\|YP_001545252.1\| | hypothetical protein Haur_2486 [Herpetosi... | 102 | 1e-19 |
| ref\|YP_001613881.1\| | hypothetical protein sce3242 [Sorangium c... | 100 | 5e-19 |
| ref\|NP_862240.1\| | GcrY [Corynebacterium striatum] >gb\|AAG03371... | 99.8 | 9e-19 |
| ref\|YP_001067909.1\| | hypothetical protein BURPS1106A_3678 [Bur... | 99.4 | 1e-18 |
| ref\|YP_847951.1\| | hypothetical protein Sfum_3847 [Syntrophobac... | 99.4 | 1e-18 |
| ref\|YP_919231.1\| | hypothetical protein Noca_4784 [Nocardioides... | 98.2 | 3e-18 |
| emb\|CAO90050.1\| | unnamed protein product [Microcystis aerugino... | 97.4 | 5e-18 |
| ref\|YP_001338326.1\| | ATP phosphoribosyltransferase [Klebsiella... | 96.3 | 1e-17 |
| ref\|YP_481817.1\| | hypothetical protein Francci3_2728 [Frankia ... | 94.7 | 3e-17 |
| ref\|ZP_02836056.1\| | conserved hypothetical protein [Arthrobact... | 92.4 | 2e-16 |
| ref\|YP_710538.1\| | conserved hypothetical protein; putative N-6... | 92.4 | 2e-16 |
| ref\|NP_940747.1\| | GcrY [Arcanobacterium pyogenes] >gb\|AAR07009... | 88.6 | 3e-15 |
| ref\|YP_995969.1\| | hypothetical protein Veis_1179 [Verminephrob... | 88.2 | 3e-15 |
| ref\|YP_001799410.1\| | putative methylase [Corynebacterium ureal... | 86.3 | 1e-14 |
| ref\|ZP_02730973.1\| | hypothetical protein GobsU_04184 [Gemmata ... | 84.3 | 5e-14 |
| ref\|YP_001323819.1\| | N-6 DNA methylase [Methanococcus vannieli... | 83.2 | 1e-13 |
| ref\|YP_511166.1\| | hypothetical protein Jann_3224 [Jannaschia s... | 81.3 | 3e-13 |
| ref\|ZP_02477028.1\| | hypothetical protein BpseB_40173 [Burkhold... | 79.7 | 1e-12 |
| ref\|ZP_01890275.1\| | type II restriction enzyme, methylase [uni... | 79.3 | 1e-12 |
| ref\|NP_044172.1\| | hypothetical protein MJECS02 [Methanocaldoco... | 75.5 | 2e-11 |
| ref\|ZP_01061350.1\| | type IV site-specific deoxyribonuclease Ec... | 75.5 | 2e-11 |
| ref\|ZP_02836057.1\| | conserved hypothetical protein [Arthrobact... | 74.7 | 3e-11 |
| ref\|NP_111200.1\| | Type II restriction enzyme, methylase subuni... | 73.2 | 1e-10 |

FIG. 17

DNA BASE RECOGNITION TABLE:

| DNA BASE RECOGNITION | DEFINITION |
|---|---|
| 1. A | |
| 2. C | |
| 3. G | |
| 4. T | |
| 5. R | R = A OR G |
| 6. Y | Y = C OR T |
| 7. S | S = C OR G |
| 8. W | W = A OR T |
| 9. M | M = A OR C |
| 10. K | K = G OR T |
| 11. B | B = C OR G OR T |
| 12. D | D = A OR G OR T |
| 13. H | H = A OR C OR T |
| 14. V | V = A OR C OR G |
| 15. N | N = A OR C OR G OR T |

*FIG. 18-1*

| | SCORE (BITS) | E VALUE |
|---|---|---|
| gb\|ACC85607.1\| MmeI [Methylophilus methylotrophus] | 1904 | 0.0 |
| emb\|CAO90962.1\| unnamed protein product [Microcystis aerugino... | 1045 | 0.0 |
| ref\|YP_001735369.1\| DNA methyltransferase [Synechococcus sp. ... | 1033 | 0.0 |
| emb\|CAO90010.1\| unnamed protein product [Microcystis aerugino... | 997 | 0.0 |
| ref\|YP_001658275.1\| DNA methylase [Microcystis aeruginosa NIE... | 968 | 0.0 |
| ref\|YP_860317.1\| conserved hypothetical protein-most likely a... | 957 | 0.0 |
| ref\|YP_379612.1\| methylase [Chlorobium chlorochromatii CaD3] ... | 947 | 0.0 |
| ref\|YP_392994.1\| hypothetical protein Suden_0478 [Sulfurimona... | 889 | 0.0 |
| ref\|YP_001413872.1\| methylase [Parvibaculum lavamentivorans D... | 888 | 0.0 |
| ref\|ZP_02059607.1\| Type II restriction enzyme methylase subun... | 864 | 0.0 |
| emb\|CAE14722.1\| unnamed protein product [Leptospira biflexa t... | 857 | 0.0 |
| ref\|YP_001274371.1\| Type II restriction enzyme methylase subu... | 743 | 0.0 |
| ref\|ZP_02001775.1\| conserved hypothetical protein [Beggiatoa ... | 701 | 0.0 |
| ref\|YP_343482.1\| hypothetical protein Noc_1465 [Nitrosococcus... | 669 | 0.0 |
| ref\|ZP_00991173.1\| hypothetical protein V12B01_09796 [Vibrio ... | 657 | 0.0 |
| ref\|YP_001928074.1\| hypothetical protein [Klebsiella pneumoni... | 655 | 0.0 |
| ref\|NP_284504.1\| hypothetical protein NMA1791 [Neisseria meni... | 653 | 0.0 |
| ref\|YP_001144220.1\| hypothetical protein ASA_P4G174 [Aeromona... | 646 | 0.0 |
| ref\|NP_862240.1\| GcrY [Corynebacterium striatum] >gb\|AAG03371... | 617 | 1e-174 |
| ref\|YP_001678552.1\| conserved hypothetical protein [Francisel... | 613 | 2e-173 |
| ref\|YP_193255.1\| methylase [Lactobacillus acidophilus NCFM] >... | 612 | 6e-173 |
| ref\|YP_342071.1\| hypothetical protein Noc_A0028 [Nitrosococcu... | 603 | 2e-170 |
| ref\|ZP_01772253.1\| Hypothetical protein COLAER_01256 [Collins... | 584 | 9e-165 |
| ref\|YP_379070.1\| hypothetical protein Cag_0759 [Chlorobium ch... | 582 | 4e-164 |
| ref\|NP_388558.1\| hypothetical protein BSU06760 [Bacillus subt... | 579 | 4e-163 |
| gb\|AAB66474.1\| YeeA [Bacillus subtilis] | 578 | 5e-163 |
| ref\|NP_940747.1\| GcrY [Arcanobacterium pyogenes] >gb\|AAR07009... | 558 | 5e-157 |
| ref\|YP_001070527.1\| hypothetical protein Mjls_2250 [Mycobacte... | 553 | 2e-155 |
| ref\|YP_001599624.1\| hypothetical protein NMCC_1507 [Neisseria... | 551 | 8e-155 |
| ref\|NP_940094.1\| Putative DNA methyltransferase [Corynebacter... | 551 | 1e-154 |
| ref\|NP_783835.1\| putative YeeA protein [Lactobacillus ferment... | 546 | 2e-153 |
| gb\|ABX75590.1\| putative DNA methylase [Lactococcus lactis sub... | 528 | 7e-148 |
| ref\|YP_001136762.1\| hypothetical protein Mflv_5513 [Mycobacte... | 528 | 9e-148 |
| emb\|CAO87897.1\| unnamed protein product [Microcystis aerugino... | 528 | 9e-148 |
| ref\|ZP_02921208.1\| hypothetical protein STRINF_02092 [Strepto... | 519 | 5e-145 |
| ref\|ZP_01927653.1\| hypothetical protein LMHG_01083 [Listeria ... | 507 | 2e-141 |
| ref\|YP_986766.1\| putative DNA methylase [Acidovorax sp. JS42]... | 496 | 4e-138 |
| ref\|ZP_01943585.1\| hypothetical protein LMSG_01238 [Listeria ... | 495 | 8e-138 |
| ref\|YP_996520.1\| putative DNA methylase [Verminephrobacter ei... | 465 | 6e-129 |
| ref\|YP_363896.1\| putative DNA methylase [Xanthomonas campestr... | 456 | 4e-126 |
| ref\|YP_789386.1\| possible Type II restriction enzyme, methyla... | 454 | 1e-125 |
| ref\|YP_571912.1\| putative DNA methylase [Nitrobacter hamburge... | 446 | 5e-123 |
| ref\|YP_001350665.1\| type II restriction enzyme, methylase sub... | 443 | 3e-122 |
| ref\|ZP_01101074.1\| N6 adenine-specific DNA methyltransferase,... | 441 | 1e-121 |
| ref\|YP_495543.1\| type II restriction enzyme, methylase subuni... | 436 | 6e-120 |

FIG. 18-2

| | | | |
|---|---|---|---|
| ref\|ZP_01037573.1\| | putative DNA methylase [Roseovarius sp. 21... | 435 | 8e-120 |
| ref\|ZP_02170275.1\| | NUDIX hydrolase [Bacillus selenitireducens... | 434 | 2e-119 |
| ref\|NP_875022.1\| | Type II restriction enzyme, methylase subuni... | 433 | 4e-119 |
| ref\|YP_001903805.1\| | Site-specific DNA-methyltransferase (aden... | 430 | 2e-118 |
| ref\|YP_001799427.1\| | putative methylase [Corynebacterium ureal... | 429 | 6e-118 |
| ref\|ZP_02055504.1\| | Type II restriction enzyme methylase subun... | 422 | 5e-116 |
| ref\|YP_745336.1\| | DNA modification methyltransferase-related p... | 421 | 2e-115 |
| ref\|YP_001799410.1\| | putative methylase [Corynebacterium ureal... | 412 | 9e-113 |
| ref\|ZP_01039292.1\| | putative DNA methylase [Erythrobacter sp. ... | 401 | 1e-109 |
| ref\|ZP_00943963.1\| | DNA modification methyltransferase-related... | 391 | 1e-106 |
| ref\|YP_001096236.1\| | hypothetical protein pLEW279a_p37 [Coryne... | 386 | 5e-105 |
| ref\|ZP_02836057.1\| | conserved hypothetical protein [Arthrobact... | 334 | 2e-89 |
| ref\|ZP_00874696.1\| | similar to hypothetical proteins [Streptoc... | 268 | 2e-69 |
| ref\|YP_001660135.1\| | DNA modification methyltransferase relate... | 268 | 2e-69 |
| ref\|ZP_00874695.1\| | similar to hypothetical proteins [Streptoc... | 247 | 3e-63 |
| ref\|YP_001735547.1\| | DNA modification methyltransferase [Synec... | 246 | 5e-63 |
| ref\|YP_001243439.1\| | Putative type II restriction enzyme, meth... | 243 | 6e-62 |
| ref\|ZP_01624419.1\| | DNA modification methyltransferase-related... | 237 | 4e-60 |
| ref\|YP_001544138.1\| | hypothetical protein Haur_1365 [Herpetosi... | 234 | 3e-59 |
| ref\|YP_001844595.1\| | hypothetical protein LAF_1779 [Lactobacil... | 227 | 3e-57 |
| emb\|CAO90051.1\| | unnamed protein product [Microcystis aerugino... | 227 | 3e-57 |
| ref\|NP_295988.1\| | DNA modification methyltransferase-related p... | 224 | 3e-56 |
| ref\|ZP_02836056.1\| | conserved hypothetical protein [Arthrobact... | 221 | 3e-55 |
| gb\|AAO14619.1\|AF465251_2 | unknown [Lactobacillus reuteri] | 219 | 9e-55 |
| ref\|ZP_01161197.1\| | hypothetical protein SKA34_17533 [Photobac... | 211 | 3e-52 |
| ref\|YP_579008.1\| | DNA modification methyltransferase-related p... | 200 | 4e-49 |
| ref\|YP_195496.1\| | N6 adenine-specific DNA methyltransferase pr... | 196 | 7e-48 |
| ref\|ZP_00515525.1\| | similar to Type II restriction enzyme meth... | 195 | 1e-47 |
| ref\|YP_167160.1\| | hypothetical protein SPO1926 [Silicibacter p... | 193 | 6e-47 |
| ref\|ZP_02843625.1\| | conserved hypothetical protein [Thauera sp... | 190 | 4e-46 |
| ref\|YP_956924.1\| | hypothetical protein Maqu_4156 [Marinobacter... | 189 | 6e-46 |
| ref\|YP_570364.1\| | hypothetical protein RPD_3238 [Rhodopseudomo... | 187 | 4e-45 |
| ref\|ZP_01748422.1\| | hypothetical protein SSE37_25258 [Sagittul... | 185 | 2e-44 |
| ref\|YP_001953905.1\| | conserved hypothetical protein [Geobacter... | 176 | 1e-41 |
| ref\|NP_285443.1\| | hypothetical protein DR_A0119.1 [Deinococcus... | 173 | 5e-41 |
| ref\|NP_938118.1\| | Sea13 [Serratia entomophila] >gb\|AAR13140.1\|... | 168 | 2e-39 |
| ref\|YP_531341.1\| | Type II restriction enzyme methylase subunit... | 168 | 2e-39 |
| ref\|YP_516011.1\| | hypothetical protein Rfer_4327 [Rhodoferax f... | 165 | 1e-38 |
| ref\|ZP_02300517.1\| | conserved hypothetical protein [Rhodopseud... | 159 | 1e-36 |
| ref\|YP_001733624.1\| | Type II restriction enzyme, methylase sub... | 156 | 8e-36 |
| ref\|YP_983122.1\| | N6 adenine-specific DNA methyltransferase pr... | 153 | 6e-35 |
| ref\|YP_594849.1\| | putative DNA methylase protein [Lawsonia int... | 152 | 2e-34 |
| emb\|CAD31540.1\| | PUTATIVE DNA METHYLASE PROTEIN [Mesorhizobium... | 150 | 7e-34 |
| ref\|YP_973977.1\| | hypothetical protein Pnap_4987 [Polaromonas ... | 144 | 3e-32 |
| ref\|NP_637468.1\| | hypothetical protein XCC2104 [Xanthomonas ca... | 144 | 4e-32 |

*FIG. 18-3*

| | | |
|---|---|---|
| ref\|ZP_01002825.1\| RNA-binding region [Loktanella vestfoldens... | 139 | 8e-31 |
| ref\|YP_001691301.1\| hypothetical protein M446_7058 [Methyloba... | 126 | 1e-26 |
| ref\|YP_760309.1\| hypothetical protein HNE_1600 [Hyphomonas ne... | 115 | 2e-23 |
| ref\|ZP_01736371.1\| hypothetical protein MELB17_22390 [Marinob... | 110 | 4e-22 |
| ref\|ZP_02170276.1\| chemotaxis sensory transducer [Bacillus se... | 108 | 2e-21 |
| ref\|NP_419643.1\| hypothetical protein CC_0826 [Caulobacter cr... | 107 | 4e-21 |
| ref\|ZP_01438131.1\| hypothetical protein FP2506_09801 [Fulvima... | 105 | 2e-20 |
| gb\|AAN32874.1\|AF461726_1 unknown [Pseudomonas fluorescens] | 100 | 4e-19 |
| **ref\|YP_511167.1\| hypothetical protein Jann_3225 [Jannaschia s...** | **94.0** | **5e-17** |
| ref\|YP_001799409.1\| hypothetical protein cu0015 [Corynebacter... | 87.0 | 6e-15 |
| ref\|YP_001799411.1\| putative methylase [Corynebacterium ureal... | 86.3 | 1e-14 |
| ref\|YP_001799429.1\| putative methylase [Corynebacterium ureal... | 83.6 | 7e-14 |
| ref\|ZP_02004474.1\| methylase [Beggiatoa sp. PS] >gb\|EDN65526.... | 83.2 | 9e-14 |
| ref\|YP_001272192.1\| hypothetical protein Lreu_1615 [Lactobaci... | 81.6 | 3e-13 |
| ref\|NP_044172.1\| hypothetical protein MJECS02 [Methanocaldoco... | 79.0 | 2e-12 |
| ref\|YP_001612833.1\| hypothetical protein sce2194 [Sorangium c... | 75.5 | 2e-11 |
| ref\|YP_001501134.1\| hypothetical protein Spea_1272 [Shewanell... | 69.7 | 1e-09 |

FIG. 19

ALIGNED DNA RECOGNITION SEQUENCES:

| POSITION | 0123456 |
|---|---|
| MmeI | TCCRAC |
| EsaSSI | GACCAC |
| ApyPI | ATCGAC |
| BsbI | CAACAC |
| NlaCI | CATCAC |
| DrdIV | TACGAC |
| RpaB5I | CGRGGAC |
| DraRI | CAAGNAC |
| MaqI | CRTTGAC |
| NhaXI | CAAGRAG |
| NmeAIII | GCCGAG |
| CdpI | GCGGAG |
| AquIII | GAGGAG |
| CstMI | AAGGAG |
| SdeAI | CAGRAG |
| PspPRI | CCYCAG |
| PlaDI | CATCAG |
| SpoDI | GCGGAAG |
| AquIV | GRGGAAG |
| PspOMII | CGCCCAR |

1. ALIGN BASED ON COMMON FUNCTION:

DNA CUTTING DIRECTIONALITY:

5'-(N)NNNNAN(N20)/-3'

2. ANCHOR ON COMMON FEATURE:

ADENINE BASE THAT IS METHYLATED: (POSITION 5)

5'-(N)NNNNAN-3'

*FIG. 20-1*

```
AquIII__GAGGAG    1  M------------------PLSWNEIKSRAIAFSKEWEFE---ESEKSEAQSFWNDFFQVF-GISRK---   45
SdeAI___CAGRAG    1  M-------------------ISLREIRERSIKFAKEWEGA---SHEKQEAQSFWIDFFKIF-DVSP----   43
PspPRI__CCYCAG    1  M------------------SIDYKHVRQQLQQIVHDYKDS--EGYERGQSQNFWTQVFNAY-GVSGQ---   46
EsaSSI__GACCAC    1  M-----------------AALSFPEIRTRLQAFAKQWKQA---ERENADAKLFWARFYECF-GIRPE---   46
MmeI____TCCRAC_   1  M------------------ALSWNEIRRKAIEFSKRWEDA---SDENSQAKPFLIDFFEVF-GITNK---   45
PlaDI___CATCAG    1  M------------------RLSWNEIRARAARFSEEWKGV---TRERAETQTFYNEFFQIF-DIPRR---   45
NlaCI___CATCAC    1  MPSESTLQTAFSQQARIMT-PDLQTLQHNAEQFIRDCEPL---HYEMGHAQKFIAALCKVY-GLDAH---   62
NmeAIII_GCCGAG    1  M-------------------KTLLQLQTAAQNFAAYYKDQ---TDERREKDTFWNEFFAIF-GIDRK---   44
ApyPI___ATCGAC    1  MLSDPV-------FDRATIRHKLIEFKIRWRGHIDQWKAENRPATESSHDQQFWGDLLACF-GVNAR---   59
CstMI___AAGGAG    1  MVMAPTT-----VFDRATIRHNLTEFKLRWLDRIKQWEAENRPATESSHDQQFWGDLLDCF-GVNAR---   61
CdpI____GCGGAG    1  M-----------------SSSSPSEKKLAAKLFANKWADR---GNEKSDTHSFWLELLRDVVGMQDV---   47
RpaB5I__CGRGGAC   1  M--------------------GDSISVPAVEQFIARWQGRE-GGQERANYVSFLTELIALL-GLDKPDPA   48
PspOMII_CGCCCAR   1  MEI-------------GLSVPKQAGPILSVDDFIARWTTS--GGSERANFQQFAIELTQLL-DVPAPKPA   54
MaqI____CRTTGAC   1  M-------------------EAFIAASAAVDEFLKRWKGN--TGSERANFQSFMRDLCTLL-DLPHPDPG   48
DrdIV___TACGAC    1  M---------------------------TPEEFITRWSPS--GGAERANYVLFLSELCDLL-GVPKPDPT   40
SpoDI___GCGGAAG   1  M---------------------------TPQDFITKWRNT--ELKERSASQSHFIDLCRLL-DIEDPTTA   40
AquIV___GRGGAAG   1  M----------------------AVTRDSLQAFVDYCNAYI-QGDEKSEAQTFLTRFFQAF-GHAGIK--   44
NhaXI___CAAGRAG   1  M----------------------SERVEQIEAFVAYAKTL--KGDEKGEAQVFCDRLFQAF-GHEGYK--   43
DraRI___CAAGNAC_  1  M--------------------PQTETAQRMEDFVAYWRTL--KGDEKGESQVFLDRLFQAF-GHAGYK--   45
Consensus_ss:                               hhhhhhhhhhhhhh        hhhhhhhhhhhh

AquIII__GAGGAG   46  ------RIATFEKSVNKLG-----NKKGSIDLLWKG-----NILVEHKSRGK------------------   81
SdeAI___CAGRAG   44  ------RSMQFEYPIKKID-----GSYGYIDVFWRG-----QLLIEQKSRGK------------------   79
PspPRI__CCYCAG   47  -----TQTKAFEHRLKDK------SNQKYVDAFIPK-----LVIIEQKSRGV------------------   82
EsaSSI__GACCAC   47  ------SATIYEKAVDKLD-----GSRGFIDSFIPG-----LLIVEHKSKGK------------------   82
MmeI____TCCRAC_  46  ------RVATFEHAVKKFAKAHKEQSRGFVDLFWPG-----ILLIEMKSRGK------------------   86
PlaDI___CATCAG   46  ------RVASYEEPVKGLG-----DKRGYIDLFWKG-----TLLVEHKTTGR------------------   81
NlaCI___CATCAC   63  ------FAVQYEHRVRKAD----LKGINRIDGFFPG-----LLMIEMKSAGE------------------   99
NmeAIII_GCCGAG   45  ------NVAHFEYPVKDPA-----DNTQFVDIFWEG-----IFLAEHKSANK------------------   80
ApyPI___ATCGAC   60  ------DLYLYQRSAKRAS----TGHTGKIDMFIPG-----KVIGEAKSLGI------------------   96
CstMI___AAGGAG   62  ------DLYLYQRSAKRAS----TGRTGKIDMFMPG-----KVIGEAKSLGV------------------   98
CdpI____GCGGAG   48  -----TTNVRFESRTSQ---------RGYIDVVIQD----AKTFIEQKSIDV------------------   81
RpaB5I__CGRGGAC  49  DATHEHNDYVFERAVKKTAE--DSASYGRIDLYKRN-----SFVLEAKQSRIKGGKKEVRGQYDLLKTEA  111
PspOMII_CGCCCAR  55  TADAQNDDYRFERPVTFIHT--GTQSRGFIDLYRRG-----CFVMEAKQGTGAAPEEGQLDLLAA--APP  115
MaqI____CRTTGAC  49  EGDTTQNAYVFERFIASAR-VDGNTDNRYIDLYRRD-----CFVLEGKQTGKELA---------------   97
DrdIV___TACGAC   41  QADEAKNAYVFEKDVPDLH-DDGGLSQRRIDLYRRG-----AFILEAKQGVEKEATAEEALLST----KG  100
SpoDI___GCGGAAG  41  --DPKGEWFTFEKGASKTS-----GGEGWADVWRKD-----CFAWEYKGKRA------------------   80
AquIV___GRGGAAG  45  -----EVGAEFEERVKKAS---KKDKTGFADLVWSPAPGVKGVVVEMKKRGT------------------   88
NhaXI___CAAGRAG  44  -----EAGAELESRVKKAS----GKGVNFADLIWKP-----RVLIEMKKSSE------------------   81
DraRI___CAAGNAC_ 46  -----EAGAELEYRVAKQG-----GGKKFADLLWRP-----RVLIEMKKRGE------------------   82
Consensus_ss:                eeeee                 eeee     eeeeee
```

FIG. 20-2

```
AquIII___GAGGAG    82  ----------------SLDKAFEQAKDYFPGLK----EHELPRYILVSDFAQ-FRLYDLETD--------  122
SdeAI____CAGRAG    80  ----------------DLVKAKEQALEYLPNLK----QRDLPKFILVCDFVS-FYLYDLDTN--------  120
PspPRI___CCYCAG    83  ----------------DLNKAYTQVSEYYDRIN----AKDKPRYIILCNFDE-IWLYDINNPL-------  124
EsaSSI___GACCAC    83  ----------------DLNSAFTQASDYFTALA----EGERPRYIIVSDFAR-FRLYDLKTD--------  123
MmeI_____TCCRAC_   87  ----------------DLDKAYDQALDYFSGIA----ERDLPRYVLVCDFQR-FRLTDLITK--------  127
PlaDI____CATCAG    82  ----------------DLKKAKIQALDYFPGLK----DKELPRYLLLCDFQS-FELYDLDED--------  122
NlaCI____CATCAC   100  ----------------DLEAAFIQALEYVQLIE---RIEDKPRHILVSDFKN-LHLYELNQGF----TGI  145
NmeAIII__GCCGAG    81  ----------------NLTKAKEQAERYLQEIGR-TKPSALPEYYAVSDFAH-FHLYRRVPEE-------  125
ApyPI____ATCGAC    97  ----------------DLDKAHEQALDYLLGGTI--PNSQMPAYVLCSNFET-LRITRLNRDY----VGD  143
CstMI____AAGGAG    99  ----------------PLDDAYAQALDYLLGGTI--ANSHMPAYVVCSNFET-LRVTRLNRTY----VGD  145
CdpI_____GCGGAG    82  ------SLDKADIRQGRVVTAFRQALNYANTMP----NKLRPDYIITCNFAE-FRIHDLNKVN-------  133
RpaB5I__CGRGGAC   112  TAATLGRRGADRAWDVLMLNAKRQAEEYARALP---ASHGWPPFILVCDVGHCIEVYADFSGQGKNYTQF  178
PspOMII_CGCCCAR   116  VQRQGHGVRGSKRWDDTMLRARNQADGYARAVA---REDGWPPFLLIVDVGHVIEVYADFSGQGQGYTQF  182
MaqI____CRTTGAC    98  ----------SRSQQNAVNAAVAQAERYIRGLPQEEVEHGRPPFIVIVDVGNAIYTYSEFSRTGGNYVPF  157
DrdIV____TACGAC   101  KKKKGHGTRGTKGWDTFMRRAREQAERYAHLLP---ASEGRPPFLLVVDVGHVIEVYAEFTRTGGAYLPF  167
SpoDI___GCGGAAG    81  ----------------NLDKAFDQLLQYAIAL-------ENPPLLIVSDMDV-IRIHTNWTN--------  118
AquIV___GRGGAAG    89  ----------------DLALHYSQLEKYWLRLT------PKPRYSILCNFDE-FWVYDFNNQ--------  127
NhaXI___CAAGRAG    82  ----------------KLHLHYQQAFDYWLNAV-----PNRPRYVVLCNFKE-FWIYDFDKQ--------  121
DraRI___CAAGNAC_   83  ----------------KLANHYQQAFDYWLKLV-----PDRPRYAVLCNFDE-LWVYDFNQQ--------  122
Consensus_ss:                             hhhhhhhhhhhhh      h       eeeee   e eeeee

AquIII___GAGGAG   123  ---QTHEFLLKDFVNYVHLFDFIAG----YEQRTYKDEDPVNIHAAELMGKLHDRLREI----GY-----  176
SdeAI____CAGRAG   121  ---QDYKFLLHELPKNIELFSFIAG----YTKKTYKEEEPTNRKAAELMGKLHDKLLEN----GY-----  174
PspPRI___CCYCAG   125  -DIKKHQCPLSDLPNNAEWFEFLSPE--SQQSNEIIEENPINRQATEKLAKLHQAFIED----GV-----  182
EsaSSI___GACCAC   124  ---TQVECKLADISKHAGWFRFLVE---GEATPEIVEESPINRQAAYAVSKLHEALLQA----NF-----  178
MmeI_____TCCRAC_  128  ---ESVEFLLKDLYQNVRSFGFIAG----YQTQVIKPQDPINIKAAERMGKLHDTLKLV----GY-----  181
PlaDI____CATCAG   123  ---TEVRFRLADLKDHVEAFGFMIG----VQKRTFKDQDPVNIEASELMGKLHDALKES----GY-----  176
NlaCI____CATCAC   146  VLDKTLKIKLTGFRAHVQDFAFIAG----YEAAIAERNEALTIAAAAKLAALHQEFHKQ----GY-----  202
NmeAIII__GCCGAG   126  GAENQWQFPLEELPEYITRGVFDFMFG--IEAKVRQIQEEANIQAAATIGRLHDALKEE----GIYE---  186
ApyPI____ATCGAC   144  SAEWDVTFDLDEIDEHLEQLAFLAD----YETSAYHEEEQASLEASRLMVELFRAMNGDEADEAVGDEAP  209
CstMI____AAGGAG   146  SADWDITFPLAEIDEHIEQLAFLAD----YETSAYREEEKASLEASRLMVELFRAMNGDDVDEAVGDDAP  211
CdpI_____GCGGAG   134  AETDYISFTLAELPDQIHLLDFLID----PQKSRAVREEKVSMDAGTLVGKLYDALRDQ----YL-DPNS  194
RpaB5I__CGRGGAC   179  PDRQNFRIYLEDLRDHDVRERLRKIWSEPTALDPSQQSAKVTRDIAKRLAQVSLALEKQ----NY-----  239
PspOMII_CGCCCAR   183  PDGNRYRITLDDLRDAATLDRLQAIWTDPHSLDPTRVSAQVTRQVAEHLAELGRSFEAQ----GH-----  243
MaqI____CRTTGAC   158  PDPRHYEIRLEDLHKPDVQHRLRQLWLEPDQLDPSKHAARVTREVSTKLAELAKSLEHN----GY-----  218
DrdIV____TACGAC   168  PSARAHQIQLADLARPEVRELLRTIWLDPLSLDPSIHAAEVTKDVARKLAEISRSMEGQ----PDAQ-GQ  232
SpoDI___GCGGAAG   119  TVQQVHTLTLDDLKDAANRDKLRNAFLNPDVFKPSKTRQLVTEQAAQNFANLAQRLRER----GH-----  179
AquIV___GRGGAAG   128  VDEPVDRVKLEDLPNRVGTFSFMEIG--GREPIFRNNQVEVTERTAKRMGEFYRLVRSR----GEREKFV  191
NhaXI___CAAGRAG   122  LNEPVDVVRLQDLPARYTALNFLFPD--NPDPLFGNDREEVSRVAASKVAQLFRSMVAR----GI-----  180
DraRI___CAAGNAC_  123  LDEPMDRLRIEELPERYTVLNFMFEQ--ERAPLFGNNRVDVTREAADSVAKVLNSVIAR----GE-----  181
Consensus_ss:                        hhhhhhhhhhhhhhhh    hhhhhhhhhhhhhhhhhhhhhhhhhhhhhh
```

FIG. 20-3

```
AquIII__GAGGAG    177  --------TGHDLEVYLVRLLFCLFADDTGIFEK-GIFEEYLDIHTK-EDGSDLAMHLGHIFHVLNTPPE  236
SdeAI___CAGRAG    175  --------SGHQLELFLTRLLFCMFAEDTGIFAK-NSFREFIENQTD-ESGRDLGSQISYLFELFDTPNE  234
PspPRI__CCYCAG    183  --------DPDELALFLTRLIFCFFADDTAIFGK-KHVLHNLLKNHAATDGSNLQQILTTLFDTLNTEHR  243
EsaSSI__GACCAC    179  --------RGRDLEVFLTRLLFCFFADDTGIFGQ-DGVFRRYVEATR-DNGRDTGQSLAILFDVLDTPDN  238
MmeI_____TCCRAC_  182  --------EGHALELYLVRLLFCLFAEDTTIFEK-SLFQEYIETKTL-EDGSDLAHHINTLFYVLNTPEQ  241
PlaDI____CATCAG   177  --------DGHDLEQYLVRLLFCLFADDTGIFEPKDILLDFIQNRTS-ADGSDLGSRLNELFEVLNTPED  237
NlaCI____CATCAC   203  --------QGAELQTMLVRILFCLFADDTGLFAQ-NKAFEQLVEESL-ADGADLGSRLNALYKWLDTPED  262
NmeAIII__GCCGAG   187  ---------EHELRLFITRLLFLFFADDSAVFRR-NYLFQDFLENC--KEADTLGDKLNQLFEFLNTPDQ  244
ApyPI____ATCGAC   210  TTPEEEDERVMRTSVYLTRILFLLFGDDAGLWDT-PHLFTTFVRNE--TTPESLGPQLNELFRVLNTPED  276
CstMI____AAGGAG   212  TTPEEEDERVMRTSIYLTRILFLLFGDDAGLWDT-PHLFADFVRNE--TTPESLGPQLNELFSVLNTAPE  278
CdpI_____GCGGAG   195  DA------SQHSLNVLCVRLVFCLFAEDAGLFEK-DAFYRYLDGLR----ADQVRVALRDLFEVLNTPVD  253
RpaB5I__CGRGGAC   240  --------PADDVAMFLMRCLFTMFAEDVELLPE-KSFKLLLEDCE--KNPEAFVHDVGQLWEAMDTGQ-  297
PspOMII_CGCCCAR   244  --------APEAVARFLMRALFTMFAEDVQLIPE-GAFSKLLQDRR--GHPEHAAPMLESLWQTMNTGG-  301
MaqI____CRTTGAC   219  --------DVERVASFLKRCLFTMFAEDVELLPK-ASFQNLLIDIKD-RNPEAFPHAVKALWETMNAGG-  277
DrdIV____TACGAC   233  AM------TPERVSQFLMRMIFTMFAEDVGLLPN-TKFRDKLKSLL--GRPQAFIPTITDLWQAMAKGG-  292
SpoDI___GCGGAAG   180  --------DAQQVAHFVNRLVFCMFAEDVELLPN-KMFERMIKAAR--PDPASFAIHAKALFAAMKDGG-  237
AquIV___GRGGAAG   192  YF------TEAQLQRFTLQCVLAMFAEDRNLLPR-DLFVGLVQDCL--AGRDNAYDAFSGLFRAMNLPG-  251
NhaXI___CAAGRAG   181  --------PREQAQRFVLQAVVAMFAEDIDMMPA-GTTLRLVQDCL--EHGQNSYDVFGGLFLQMNNKA-  238
DraRI___CAAGNAC_  182  --------DRARAQRFLLQCVMAMFAEDFELIPR-GFFTELADDAR--AGRGSSFDLFGGLFRQMNTSE-  239
Consensus_ss:                  hhhhhhhhhhhhhhhhhhh     h hhhhhhhhhh  h hhhhhhhhhhhhhhh

AquIII__GAGGAG    237  KRL-------KNLDESLGQFPYVNGKLFEEQLAPAAFDRKM---REMLLEA--CGFNWGKISPAIFGSMF  294
SdeAI___CAGRAG    235  ERQ-------KNLDESFTQFPYINGSIFTEQLKTAHFDRSM---REMLLDA--CAFDWSLISPSIFGSMF  292
PspPRI__CCYCAG    244  S---------SRLPEHYAQFAYINGGLFEETINIPYFDEKL---YNLVMEC--DALDWTEISPAIFGSMF  299
EsaSSI__GACCAC    239  QRS-------SNLDEHLTAFAYINGSLFSERTRIPSFDADM---RTLLVKC--AELDWSGISPAIFGAMF  296
MmeI_____TCCRAC_  242  KRL-------KNLDEHLAAFPYINGKLFEEPLPPAQFDKAM---REALLDL--CSLDWSRISPAIFGSLF  299
PlaDI____CATCAG   238  KRQ-------KTLDEDLGNFPYVNGALFAERLRTPAFNAAM---RLILIEA--CEFKWEAISPAIFGALF  295
NlaCI____CATCAC   263  KRRTTPRALLDQYSGFRLKFPYINGKLFSDGIDEFVFNASM---RRTLLEC--CEIDWSLISPDIFGTLF  327
NmeAIII__GCCGAG   245  KRS-------KTQSEKFKGFEYVNGGLFKERLRTFDFTAKQ---HRALIDC--GNFDWRNISPEIFGTLF  302
ApyPI____ATCGAC   277  KRP-------KRLPGTLAKFPYVNGAIFAEQLDPEYFDYAM---REALLNA--CDFDWSKIDVSVFGSLF  334
CstMI____AAGGAG   279  KRP-------KRLPSTLAKFPYVNGALFAEPLASEYFDYQM---REALLAA--CDFDWSTIDVSVFGSLF  336
CdpI_____GCGGAG   254  SRD-------PYLSEQLKNFPYVNGGLFAKVEQIPNFTDEI---LDLLVHEVSEKTNWAEISPTIFGGVF  313
RpaB5I__CGRGGAC   298  -----------WAHALKTKVKKFNGEFFKSRAALP-LGREE---IGELRRA--AEYDWNEVDPSIFGTLL  350
PspOMII_CGCCCAR   302  -----------FSPALSCDLKRFNGGLFREATALP-LSAMQ---LGLLIQA--ASHDWREVEPAIFGTLL  354
MaqI____CRTTGAC   278  -----------YSERLMQTIKRFNGGLFKGIDPIP-LNVQQ---IQLLIDA--AKADWRFVEPAIFGTLL  330
DrdIV____TACGAC   293  -----------YSVALDAQIKHFNGGLFEGVEVLP-VTDGQ---LKLFIEA--AESDWSRVEPSIFGTLV  345
SpoDI___GCGGAAG   238  -------------LVGFEKVDWFNGGLFDNDDVLP-LEWED---LDDLIRA--AHLDWSDIDPSILGTLF  288
AquIV___GRGGAAG   252  ----------IVPQGRYKGVDYFNGGLFGEIQPIP-LEKNE---LEILDVC--ARDNWANIRPSIFGNIF  305
NhaXI___CAAGRAG   239  ----------AAQGGRYKGVPYFNGGLFATVQPIELTTDELELLGKKDEGA--AWQNWAKINPAIFGTIF  296
DraRI___CAAGNAC_  240  ----------RARGGRFAPIPYFNGGLFRAVDPIELNRDEL---YLLHKAA--LENNWARIQPQIFGVLF  294
Consensus_ss:                    hhhhhhhhhhhhhhhhh  hhh    hhhh   hhhhhhh h   hh    hhhhhhhh
```

*FIG. 20-4*

```
AquIII___GAGGAG   295  QAAMD----------QQTRRNLGAHYTSEKNIQKVIKPLFLDELHEKFKKAKG-----------------  337
SdeAI____CAGRAG   293  QASMD----------VSKRGELGAHFTSETNILKAIKPLFLDELSEEFAKIKN-----------------  335
PspPRI___CCYCAG   300  QSVLDASG---GDSTEDKRREFGAHYTSEKNILKVINSLFLQELRDEFSKCTN-----------------  349
EsaSSI___GACCAC   297  QGVLEAHTP--DEKRQASRRELGAHYTSERNILRVINPLFMDDLRVEFERARR-----------------  347
MmeI_____TCCRAC_  300  QSIMD----------AKKRRNLGAHYTSEANILKLIKPLFLDELWVEFEKVKN-----------------  342
PlaDI____CATCAG   296  QSVMN----------KTERRALGAHYTTEKNILKLIQPLFLDGLHEEFARAKALK---------------  340
NlaCI____CATCAC   328  QNIMENADALGGGKKSAHRRELGAHYTSEKNIKRAIAPLFLDRLKAELEQAAG-----------------  380
NmeAIII__GCCGAG   303  QSVMD----------AQERREAGAHYTEAANIDKVINGLFLENLRAEFEAVKALK---------------  347
ApyPI____ATCGAC   335  QLVKS----------KEARRGDGEHYTSKTNILKTIGPLFLDELRAQADKLVSNP---------------  379
CstMI____AAGGAG   337  QLVKS----------KEARRSDGEHYTSKANIMKTIGPLFLDELRAEADKLVSSP---------------  381
CdpI_____GCGGAG   314  ESTLN----------PETRARGGMHYTSPENIHKVIDPLFLDSLKAELDSILNASGIT------------  361
RpaB5I__CGRGGAC   351  EQALD----------PTDRKKLGAHYTPRAYVERLVIATIIEPLREDWRNVQATAETLRGAGD-------  403
PspOMII_CGCCCAR   355  ERALD----------TRQRHKLGAHYTPRAYVERLVNPTVIEPLRAEWRDIQAAAVTLAGQDK-------  407
MaqI____CRTTGAC   331  ERALD----------PRERHKLGAHYTPRAYVERLVMPTLIEPLREQWGDIRGAAETLLRQGK-------  383
DrdIV____TACGAC   346  ERALN----------PRERHRLGAHYTPRAYVERLVHQVVMEPLREDWRTVQVQVQDTLDRGNGD-----  400
SpoDI___GCGGAAG   289  ERGLD----------PAKRSQLGAHYTDRDKIMQIVNPVIVEPLLAEWAEVKAQIEDLIDKAPKATKDKL  348
AquIV___GRGGAAG   306  ESAID----------ADERHARGIHYTSEKDIRQIVRPTIADYWEGKIDEATT-----------------  348
NhaXI___CAAGRAG   297  QQSMD----------KGERHAFGAHFTHEADIQRIVGPTIVRPWRERIDAAKT-----------------  339
DraRI___CAAGNAC_  295  QSSMD----------KKEQHAKGAHYTSEADIMRVVLPTIVTPFQRQIEAATT-----------------  337
Consensus_ss:          hhhh           hhh            hhhhhhhhhhhhhhhhhhhhhh

AquIII___GAGGAG   338  ---------------SPTALKRLHDELGELHFLDPACGCGNFLIISYRELRDLELLILKELYKKEG---  389
SdeAI____CAGRAG   336  ---------------NPKQLQIFHAKISNLKFLDPACGSGNFLVIAYRELKLVEFEVLKSL---------  381
PspPRI___CCYCAG   350  ---------------NTPRAVQLYEKLPTLKFFDPACGCGNFLIIAYRELRLLENQLIAKIFGDQKG---  401
EsaSSI___GACCAC   348  ---------------NKPRLQALYEKLPTLTFFDPACGCGNFLVIAYRELRRLENDVIAALFADFQHG-K  401
MmeI_____TCCRAC_  343  ---------------NKNKLLAFHKKLRGLTFFDPACGCGNFLVITYRELRLLEIEVLRGLHRGGQQ---  394
PlaDI____CATCAG   341  -------------RGRQQALEALHEKLGQLTFFDPACGCGNFLVIAYRELRALEQEILRVLHDGKDQ---  394
NlaCI____CATCAC   381  ---------------DPKKLARYITRLQTLQILDPACGCGNFLIVAYREIRLLEMQAIRQLARIP-----  430
NmeAIII__GCCGAG   348  -------------RDKAKKLAAFYQKIQNLQFLDPACGCGNFLIVAYDRIRALEDDIIAEALKDKAD---  401
ApyPI____ATCGAC   380  -------------ATPVRKLEEFRDSLAAHIFCDPACGAGNFLLTAYKELRRIETDLIVAIRQRRGET-G  435
CstMI____AAGGAG   382  -------------STSVAALERFRDSLSELVFADMACGSGNFLLLAYRELRRIETDIIVAIRQRRGET-G  437
CdpI_____GCGGAG   362  ------------ANKRKKQLEAFHTKISELKFFDPACGSGNFLTETYIHLRKIENKILSELAGDQTQ---  416
RpaB5I__CGRGGAC   404  ------------LAAAAAAVQAYHDRLCETRVLDPACGTGNFLYVSLELMKRLEGEVLEALLDLGGQ---  458
PspOMII_CGCCCAR   408  ------------LDEARATVRDFHRRLCEVRVVDPACGSGNFLYVALELMKRLEGEVIALLRELGED---  462
MaqI____CRTTGAC   384  ------------TDKALQEVQAFHYQLCQTRVLDPACGSANFLYVALEHMKRLEGEVLGFISELTQG---  438
DrdIV____TACGAC   401  ---------DKARARAQQLVAQFHAQLRQTQVLDPACGTGNFIYVSMELIKRLEAEVIETLVALG-----  456
SpoDI___GCGGAAG   349  LSTSQKAARTRALDKAEALHQAFLDRLKAFRVLDPACGSGNFLYIALLELKNIEHRVNLEAEALG-----  413
AquIV___GRGGAAG   349  ----------------YEDLEKLKQELREYRVLDPACGSGNFLYVAYQELKRLERVLLNKIYERRKRFQG  402
NhaXI___CAAGRAG   340  ----------------MAELLEIRKALLNFRVLDPACGSGNFLYVAYREMVRLEIKLMARLDKEFSWK-T  392
DraRI___CAAGNAC_  338  ----------------QKELRAILDELASFQVLDPACGSGNFLYVAYRELRRLEARALLRLRDLSA----  387
Consensus_ss:                          hhhhhhhh      eee       hhhhhhhhhhhhhhhhhhhhhhh
```

FIG. 20-5

```
AquIII___GAGGAG   390  -FIDIRLFLKVDVDQFGGIEYDEFPARVAEVAMWLIDHQMNIKVSNEFGQYFVR-----LPLKKAARIV-  452
SdeAI____CAGRAG   382  ----KILTQLVHIDQFYGFEIEELPSRITQTAMLLIDHQMNLLFAQMFGEPHFN-----IPIKDSANIF-  441
PspPRI___CCYCAG   402  -LLDISSMCNVTVDQFYGIEIEPHAVHIARVAMWITDHQLNMTTAERFGTTRPT-----TPIVYSPHII-  464
EsaSSI___GACCAC   402  GLLDVSTLCRVRVNQFYGLEIDDAAAHIARVAMWITDHQMNLESADRFGNTRPT-----VPLVDTPHIH-  465
MmeI_____TCCRAC_  395  -VLDIEHLIQINVDQFFGIEIEEFPAQIAQVALWLTDHQMNMKISDEFGNYFAR-----IPLKSTPHIL-  457
PlaDI____CATCAG   395  RIFDVAQLSKVNVDQFYGIEIGEFPARIAEVAMWMMDHIMNNRLGLSFGSNYAR-----IPLRTSPHIL-  458
NlaCI____CATCAC   431  --GAQQMQSQCDVHQFHGIEIDPAAVEIATVAMWLTDHQMNRLYQDGYKR---------IPLAHKADIR-  488
NmeAIII__GCCGAG   402  -GLFDSPSVQCRLKQFHGIEIDEFAVLIARTAMWLKNHQCNIRTQIRFDGEVACH---TLPLEDAAEII-  466
ApyPI____ATCGAC   436  MSLNIEWEQKLSIGQFYGFELNWWPAKIAETAMFLVDHQANKELANAVGRPPQR-----LPITITAHIV-  499
CstMI____AAGGAG   438  MSLNIEWEQKLSIGQFYGIELNWWPAKIAETAMFLVDHQANKELANAVGRPPER-----LPIKITAHIV-  501
CdpI_____GCGGAG   417  -LGFSNVTLKVSLDQFYGIEINDFAVSVASTALWIAQLQANIEAESIVTANIES-----LPLRDAAHIH-  479
RpaB5I__CGRGGAC   459  EALRGLGSHSVDPHQFLGLEINPRAAAIAELVLWIGYLQWHFRTKGAPPDE--------PILRAFKNIK-  519
PspOMII_CGCCCAR   463  QGALALAGHTVDPHQFLGIEVNPWAAAVAELVLWIGYLQWHFRTHGTASPAE-------PVLRDFRNIE-  524
MaqI____CRTTGAC   439  QGVLESEGLTVDPHQFLGLEINPRAAQIAELVLWIGYLQWHYRLNDRLDLPE-------PILRDFKNIE-  500
DrdIV____TACGAC   457  ---GLPPLIEVNPEQFHGIEVNPRAASVAELVLWIGYLQLYAREHGNAAPPE-------PILRAFHNIE-  515
SpoDI___GCGGAAG   414  ---LPRGFPQIGPEVVLGIELSAYAAELARVSVWIGEIQWMRRNGFEAAKN--------PILRSLKTIE-  471
AquIV___GRGGAAG   403  EVLQQEEIGIVTPLQFFGMDTNPFAVQLARVTMMIARKIAIDKFGLTEPALP--------LDSLDQNIV-  463
NhaXI___CAAGRAG   393  VQKQAQATSLISPRQFFGVERDSFGVELTKVTLMLAKKLALDEAADVLERDQIE-----LPLAEDEALPL  457
DraRI___CAAGNAC_  388  -PGTALPPARVSIRQMHGLEYDPFGVELAKVTLTLAKELAIREMHDLLGNTGLDFDQPLPLDNLDDRIV-  455
Consensus_ss:             hhhhhhhhhh eeeee  hhhhhhhhhhhhhhhhhhhhhh

AquIII___GAGGAG   453  --------NGNALRID---------------------------------------------WEEVI-PKE  468
SdeAI____CAGRAG   442  --------NVNALRVD---------------------------------------------WEKIL-DGV  457
PspPRI___CCYCAG   465  --------EGNALQID---------------------------------------------WETVL-PAN  480
EsaSSI___GACCAC   466  --------KENALRAD---------------------------------------------WTSVL-APA  481
MmeI_____TCCRAC_  458  --------NANALQID---------------------------------------------WNDVL-EAK  473
PlaDI____CATCAG   459  --------HADALEAD---------------------------------------------WAALL-PPE  474
NlaCI____CATCAC   489  --------CANALQTD---------------------------------------------WADTI-SPQ  504
NmeAIII__GCCGAG   467  --------HANSLRT----------------------------------------------------PWQ  476
ApyPI____ATCGAC   500  --------HGNALALD---------------------------------------------WTEALPKAV  516
CstMI____AAGGAG   502  --------HGNALQLD---------------------------------------------WADILSASA  518
CdpI_____GCGGAG   480  --------LGNALRTD---------------------------------------------WASVL-APE  495
RpaB5I__CGRGGAC   520  --------VKNAVLDWDGAPLPK-----------------------------IVEGKETYPNPRRP-EWP  551
PspOMII_CGCCCAR   525  --------NRDAVLAWDGTRPRLDDAGQPVTRWDGVSTIRHPVTGEQVPDPAARVQVLDYLKPRPA-RWP  585
MaqI____CRTTGAC   501  --------CRDALIEYDSREPELNKNGEPVTIWDGISMKVSPTTGELIPDETGRAKVYRYHNPRRA-EWP  561
DrdIV____TACGAC   516  --------NRDAVLSYSHTTPKVDRDGQPVTRWDGVTFRRHPVTGDPVPDERAQIPEEVYHNPMTT-EWP  576
SpoDI___GCGGAAG   472  --------NRDAVLNP---------------------------------------------DGTRA-DWP  487
AquIV___GRGGAAG   464  --------CQDALFN----------------------------------------------------DWP  473
NhaXI___CAAGRAG   458  DNLDGNILCRDALLS----------------------------------------------------DWP  475
DraRI___CAAGNAC_  456  --------QGDALFT----------------------------------------------------PWP  465
Consensus_ss:                                                                        hhh
```

FIG. 20-6

```
AquIII___GAGGAG   469  KLNYILGNPPFVGSKMMTKDQRADLLSVFES--AKGAGVMDYVSAWYVKAADFIQEK-----KIKTAFVS  531
SdeAI____CAGRAG   458  KIDFIIGNPPFLGSKMQSKEQKEDMAEVFSG--VKNGKELDFVTAWYIKSAKYLQGK-----NTKVALVS  520
PspPRI___CCYCAG   481  DCSYVMGNPPFIGKSNQSSEQKSDIKLVASH--IKNHKSLDYVAGWYIKSMHYMQSVNNANHYIDTAFVS  548
EsaSSI___GACCAC   482  QCSYVMGNPPFVGAKWLNEEQRADARAVFAN--VKNGGLLDYVAAWYVKALAYIQANP----AIDVAFVS  545
MmeI_____TCCRAC_  474  KCCFILGNPPFVGKSKQTPGQKADLLSVFGN--LKSASDLDLVAAWYPKAAHYIQTNA----NIRCAFVS  537
PlaDI____CATCAG   475  KCSYVFGNPPFIGSKFQTAEQRRQVRDIAKL--GGSGGTLDFVTAWFLKAGEYVQHG-----KADIAFVA  537
NlaCI____CATCAC   505  NLDYIVGNPPFLGKKEQNAEQKKDMEKVVGH--LKGSGILDYVTAWYFKANELMKHNP----KIRTAFVS  568
NmeAIII__GCCGAG   477  AADYIFGNPPFIGSTYQTKEQKNDLESICGH--IKGYGLLDYVCNWYVKAAGIMAQHP----QVQTAFVS  540
ApyPI____ATCGAC   517  GETFIFGNPPFIGQDTRTKQQLEEMKAVWRR---KNISRLDYVTCWHIKSLDLFSTR-----NGRFAFVT  578
CstMI____AAGGAG   519  AKTYIFGNPPFLGHATRTAEQAQELRDLWGT---KDISRLDYVTGWHAKCLDFFKSR-----EGRFAFVT  580
CdpI_____GCGGAG   496  QCNYIIGNPPFLGYSRLDDAQKEDRKAIFG----KNGGVLDYVACWHRKAAEYMHGT-----DAEAALVS  556
RpaB5I__CGRGGAC   552  AAEFIVGNPPFIGASFLRARLGDTHAEALWSAHPQMNESADFVMYWWDRAAELLTRKGT--VLRRFGFVT  619
PspOMII_CGCCCAR   586  EAEFIVGNPPFIGASRMREALGDGYAEALRAAYPRMPESADFVMFWWDKAALATRAGK----TRRFGFIT  651
MaqI____CRTTGAC   562  AAEYIIGNPPYIGARRIRSALGDGYLQALRGVYTDIPEHVDFVMYWWAKASENMASGK----TKAFGLIT  627
DrdIV____TACGAC   577  KADFIVGNPPFIGSKRMRELLGNGYVDALQRVFADVPQATDFVLRWWYKAALLTRQEE----VRRFGFIT  642
SpoDI___GCGGAAG   488  KADVVVGNPPFLGVYKMGEELGEDYTIALRDAWPEMPGAADLVTYWFAKAWSQMQCGD----LSRAGLVA  553
AquIV___GRGGAAG   474  KADAIIGNPPFLGGSRVRLELGDKYVERIFEKFSDVKDKVDFCVYWFRLAHENLNKT------GRAGLVG  537
NhaXI___CAAGRAG   476  EVDTIIGNPPYQSKNKAQQEFGRAYLNKIRSVFPEIDGRADYCVYWFRKAHDQLKQG------QRAGLVG  539
DraRI___CAAGNAC_  466  RVDAIVGNPPFQSKNKLQREMGAAYVKKLRAHYPDVPGRADYCVYWIRKAHDQLGSG------QRAGLVG  529
Consensus_ss:             eeeee           hhhhhhhhhh          hhhhhhhhhhhhhh          eeeee

AquIII___GAGGAG   532  TNSISQGEQVGILWGLLFEKY-QIKIHFAHRTFKWSNEAKGKAAVYCVIIGFATFNIKGK--RLFEYEDI  598
SdeAI____CAGRAG   521  TNSITQGEQVGILWQEMFNKY-KIKIHFAHKTFKWNNDAKGVAQVYCVIIGFAGFDIKEK--RLFEYESV  587
PspPRI___CCYCAG   549  TNSIVQGEQVDILWRYLIDDC-KGHINFAHHTFKWSNEGKGIAAVHCIIVGFSLVEKKEK--TIFEYSDI  615
EsaSSI___GACCAC   546  TNSITQGEQVSALWPTLLQG--GVKIRFAHRTFQWSNEGKGNAAVHCVIIGFGLRVPDRC--TIFDYSHD  611
MmeI_____TCCRAC_  538  TNSITQGEQVSLLWPLLLSL--GIKINFAHRTFSWTNEASGVAAVHCVIIGFGLKDSDEK--IIYEYESI  603
PlaDI____CATCAG   538  TNSITQGEQVAQLWPLLFQRC-KLEIAFAHRTFAWGSDARGVAHVHVVIIGLTRRDREWPEKRLFSYADI  606
NlaCI____CATCAC   569  TNSITQGEQVPALWKPLLSD--GIRIRFAHRTFKWNNEGKGTAAVHCVIIGFDRDEIQKG--ERLSLWDY  634
NmeAIII__GCCGAG   541  TNSICQGQQVEILWGSLLNQ--GIEIHFAHRTFQWTSQAAGKAAVHCIIVGFRQKPPMPSEKTLYDYPDI  608
ApyPI____ATCGAC   579  TNSITQGEQVPLLFGPIFAA--GWRIRFAHRTFSWDSDAPGKASVHCVIVGFDRAHEPRP--QLWDYPNV  644
CstMI____AAGGAG   581  TNSITQGDQVPRLFGPIFKA--GWRIRFAHRTFAWDSEAPGKAAVHCVIVGFDKESQPRP--RLWDYPDV  646
CdpI_____GCGGAG   557  TNSICQGQQVTPLWKPLFDA--GIHINFAHRTFVWSNEAADQAHVLCIIVGFSYIDRPVK--QAWTYRKN  622
RpaB5I__CGRGGAC   620  TNSITQVFQRRVIERHFKAKR-PISLAMAIPDHPWTKATTDAAAVRIAMSVGETGRGDGL--LQIVVNEA  686
PspOMII_CGCCCAR   652  TNSLRQTFNRQVLEPHLADPKKPLSLAFAIPDHPWVDAG-DGAAVRIAMTVAAAGSAPGR--LFTVTDER  718
MaqI____CRTTGAC   628  TNSLRQSFSRKVVEKTLDINS-DCSIKFVIPDHPWVDSA-DGAAVRVTLISVDSNKAPGI--VALIRNEE  693
DrdIV____TACGAC   643  TNSISQAFNRRAIEPHLNADVRPLSLVYVTPDHPWVDESDGAAVRIASTVGELGQRPGLL--ARVVKEYD  710
SpoDI___GCGGAAG   554  TNSIRGGANRTVLKPIAEHG----GIFDAWSDEAWTVE---GAAVRVSMICFGSKLPSHP--KLN-----  609
AquIV___GRGGAAG   538  TNSISQGFSRRASLEYIVNN--GGIIHDAISTQVWSG----QANVHVSLVNWQYLKPPEY--VLD-----  594
NhaXI___CAAGRAG   540  TNTIRQNYSRISGLDYIAKH--NGTITEAVSTMPWSG----DAVVHVSIVNWVKGEDDGK--KRLYIQSG  601
DraRI___CAAGNAC_  530  TNTIRQNDSRVGGLDYVVQH--GGTITDAVGTQVWSG----DAAVHVSIVNWVKGPAEGP--KHLAWQVG  591
Consensus_ss:             hh   hhhhhhhhhh     eeeeee               eeeeeeeee         eeeee
```

FIG. 20-7

```
AquIII___GAGGAG   599 KG--------EALEIKVSNINPYLVNGDDLIIL-----RRRQPLCNVP--NIGIGNKPIDGGHYLFTTEE 653
SdeAI____CAGRAG   588 KS--------EPHEIKVANINPYLVNGDDFFIS-----SRRKHIQSFIP-QIVFGSMPNDGGNLLFDDKE 643
PspPRI___CCYCAG   616 SS--------EPSPKKARTINAYLTDAPIVFFS-----RRSKQVSNES--SMVSGNKATDGGNLILSDSE 670
EsaSSI___GACCAC   612 IKAD------LGSVLHASRINPYLVDAPDVVLT-----NRRAPICQVP--EIGIGNKPIDGGHYLFTDEG 668
MmeI_____TCCRAC_  604 NG--------EPLAIKAKNINPYLRDGVDVIAC-----KRQQPISKLP--SMRYGNKPTDDGNFLFTDEE 658
PlaDI____CATCAG   607 KG--------DPVETRHKALTAYLFDAVNVADRHLVVEERNTPLCEAP--KLKTGVQMIDNGILTFTTME 666
NlaCI____CATCAC   635 SQGI----GGDGKEHQVRKINPYLLEADNILPA-----KRSRPVSADVP-AMNYGSMPIDNGLLILSQEA 694
NmeAIII__GCCGAG   609 KG--------EPEKHAVANINPYLIDAPDLIIA-----KRSRPIHCEP--DMVNGSKPTEGGNLILSTAE 663
ApyPI____ATCGAC   645 SS-------APVAVPVERVINAYLVDGPNVLVQ-----KMTSPISCEIK-PAVLGAMAKDGGGLIVEAQD 701
CstMI____AAGGAG   647 KG-------EPVSVEVGQSINAYLVDGPNVLVD-----KSRHPISSEIS-PATFGNMARDGGNLLVEVDE 703
CdpI_____GCGGAG   623 ----------EVEYSEPVHLNGYLADAPDAFLT-----RRSKPISDVL--EMAQGFKPADGGHLLLTQEE 675
RpaB5I__CGRGGAC   687 HLDSD--TPIVELQGRVGPINSDLTIGTDLTT--------TVPLRASE--GLASRGVTLAGSGFLITSEE 744
PspOMII_CGCCCAR   719 RGEREAEGRPVTLSGQIGKIHANLRIGADVAG--------AKPLRANA--GISSPGVKLHGAGFIVTPAE 778
MaqI____CRTTGAC   694 AEGSG--AYKITLDNKSGHITPNLTIGADPGE--------ATCLSSNS--SVSCVGYQLTGKGFVLTQSQ 751
DrdIV____TACGAC   711 EAAEG--DLVAEFAFETGVIHADLSIGADLTE--------TQPLMANL--GLCAVGMKTIGAGFLVERTK 768
SpoDI___GCGGAAG   610 -------------GKVVDKILSDLTANAAGFDL-----TKSSRISENK--GVCIRGI-ETGGPFEFSQAD 658
AquIV___GRGGAAG   595 -------------HEIVKNINSSLKSETDVSN--------AVKLKVNL--NQSFKGVQPTGKDFLISEKK 641
NhaXI___CAAGRAG   602 NDPA-----GGWDYKDLDEINTSLSFSTDVSQ--------AQRINANAEKGGCYQGQTHGHKGFLPEPAE 658
DraRI___CAAGNAC_  592 DHRT-----SPWQSTELPVINSALSAGTDVTQ--------AQKLRVNMNSGACYQGQTHGHKGFLLDGLE 648
Consensus_ss:                                      hh                         ee     ee  hhh

AquIII___GAGGAG   654 KEDFLK-----LEPKAEKWFRKWLGSREFINK----EERWCLWLGDCPPNELK----KMPHALERV-KAV 709
SdeAI____CAGRAG   644 KEEFLA-----LEPKAELYMKPLISAKEYLNG----KTRWCLWLKDCPPNELK----SMPKVIERV-ENI 699
PspPRI___CCYCAG   671 YIDLIN-----SEPLAKKYIKRFMMGYEFLNN----IKRWCLWFDNVDPIQLSKDLEKMPLIKKRI-HNV 730
EsaSSI___GACCAC   669 KAAFLA-----VEPKAAPFFHRWVGAEEFINN----TSRWCLWLGNAKPHELR----ALPECMKRV-EAV 724
MmeI_____TCCRAC_  659 KNQFIT-----NEPSSEKYFRRFVGGDEFINN----TSRWCLWLDGADISEIR----AMPLVLARI-KKV 714
PlaDI____CATCAG   667 KEEFLR-----QEPEAEPLFRKYIGGDEYING----FFRWILYLADAEPSFLR----QLPLVQERI-RQV 722
NlaCI____CATCAC   695 FQTALN-----EDPENSELIRPYMGGSEFLNN----EKRYCLWLENVDQERLS----QSKFASERV-GQV 750
NmeAIII__GCCGAG   664 KDALIA-----AEPLAEQYIRPFIGADEFLNG----KTRWCLWFHGVSDVKRNHDLKQMPQVQARI-QAV 723
ApyPI____ATCGAC   702 VQEAL------DDPIAAKYLRPYVGSRELVRG----LSRWCLWMVDLDPADVQ----ASTFLRSRI-EQV 756
CstMI____AAGGAG   704 YDEVM------SDPVAAKYVRPFRGSRELMNG----LDRWCLWLVDVAPSDIA----QSPVLKKRL-EAV 758
CdpI_____GCGGAG   676 RDELLA-----KEPLAAPWIRKFSMGAEFING----KDRYCLWLPEITGVELK----RLPLVRARI-DAC 731
RpaB5I__CGRGGAC   745 AEHFGL----GTHEKLKQHIRGLHNGRDLNQTS---RRILVLDFLGLSEEEVRR---HFPEAYQHLLRTV 804
PspOMII_CGCCCAR   779 AQALGL----GTVPGLEAHIRSYRNGRDLTATP---RGVMVIDLFGLSEAEVRT---RFPAVYQHVLDKV 838
MaqI____CRTTGAC   752 KEEHE-------NEWPESVIKPLWSGRDITQSP---RKNWAIDVCDWGIDALKV---SSPSLYQWLLTRV 808
DrdIV____TACGAC   769 AEALG--------LGQDNRIRPYINGRDLMGRT---RGVYVIDLFGVSEEDVRD---QYPKLYQHLRNAV 824
SpoDI___GCGGAAG   659 FEALATKPLNPNGLPNTRVIRRILNGNNILKRQ---PERYAIDFSDFRTKEEAA---LFEAVYSWLEQAY 722
AquIV___GRGGAAG   642 VENWIQ-----KNTKNNQVLKLFVSASDLASNKNGEPSRWIIDFNDFSLEDAS----TYKEPFDHVNFFV 702
NhaXI___CAAGRAG   659 AKAMIK-----ASKANAKVLFPFLIADDFLGAVDKLECRYVIDFQTRDLLQAK----AFKRPFEHLEKTV 719
DraRI___CAAGNAC_  649 AGQMLS-----AERKNAEVIFPYLTGDELLRTSPPHPTRYVIDFQPRDVFGAR----AYKLPFARIEREV 709
Consensus_ss:         hhhhhh           hhhhhhh  hhhh          eeeee     hhhhh      hhhhhhh hhh
```

FIG. 20-8

```
AquIII___GAGGAG   710  KETRLNSNSK-------------------PTQK----------------------LAQT----PTRFHVE   734
SdeAI____CAGRAG   700  RKLRNESSRE-------------------ATQK----------------------LAKF----PALFGED   724
PspPRI___CCYCAG   731  KELRLNSTKK-------------------STVK----------------------KAET----PHLFDER   755
EsaSSI___GACCAC   725  RQYRLASPSA-------------------PTQK----------------------LAET----PTRFHVE   749
MmeI_____TCCRAC_  715  QEFRLKSSAK-------------------PTRQ----------------------SAST----PMKFFYI   739
PlaDI____CATCAG   723  RQYRLSSSRP-------------------STVR----------------------MADY----PTQVGVD   747
NlaCI____CATCAC   751  RAYRLSSSRA-------------------ATVK----------------------LAGT----PHLFGEI   775
NmeAIII__GCCGAG   724  KTMREASSDK-------------------QTQK----------------------DAAT----PWLFQKI   748
ApyPI____ATCGAC   757  RAYRTTSSAP-------------------TTRS----------------------MAKI----PHLFAQR   781
CstMI____AAGGAG   759  KSFRADSKAA-------------------STRK----------------------MAET----PHLFGQR   783
CdpI_____GCGGAG   732  REWRLEQIKT------------------GDAYK----------------------LSDR----PHLLRPT   757
RpaB5I__CGRGGAC   805  KPERETNKRA-------------------SYRQ----------------------NWWVFAEPRKEMRPA   833
PspOMII_CGCCCAR   839  KPERDQNNRD-------------------SYKR----------------------NWWIHGEPRRDLRPA   867
MaqI____CRTTGAC   809  KPEREQNNRA-------------------SLKE----------------------RWWIYGEARNTFRPA   837
DrdIV____TACGAC   825  YDIRRQNNNR-------------------VFRD----------------------LWWVIGHPRPIFREF   853
SpoDI___GCGGAAG   723  ESYERKSKRR-------------------IVRRQ---------------------DWWLHRRSGAALKNA   752
AquIV___GRGGAAG   703  KPQRENNRDQ-------------------KTRE----------------------YWWLFPRARPAMRQA   731
NhaXI___CAAGRAG   720  LPTRKEAAKKEKDRNKEALDADPEAKVNKHHENFL-------------------KRWWLMSYAREDLMQT   770
DraRI___CAAGNAC_  710  LPTRQAAAAE-------------------EEARNAEVLAANPKAKTNKHHRNFLNQWWALSYGRSEMIEK   760
Consensus_ss:          hhhhhh                       hhh                         hhh     hhhhhhh

AquIII___GAGGAG   735  NMP-ESEYLLIPKVSSERRNYIPIGFLNQSTLSSDLVFIVGNATLFHFGIFTSVMHMAWVKYVCGRL---   800
SdeAI____CAGRAG   725  RQP-ESDYIFIPRVSSENRDYIPMEFFTKDFICGDTGLAVPNATLFHFGILTSKMHMDWVRYVAGRL---   790
PspPRI___CCYCAG   756  RHT-NKPYVAIPVVSSENRRFIPIGFIDGNTVAGNKLFVIVDGNTYQFGTLSSSMHNAFMRLTAGRM---   821
EsaSSI___GACCAC   750  FMP-DAPFMVIPEVSSERREFIPLGYLQPPTLASNKLRLMPDATLYHFAVLNSTMHMAWTRAVCGRL---   815
MmeI_____TCCRAC_  740  SQP-DTDYLLIPETSSENRQFIPIGFVDRNVISSNATYHIPSAEPLIFGLLSSTMHNCWMRNVGGRL---   805
PlaDI____CATCAG   748  ERL-SGPYLVIPNTSSERRDYVPIGWLTPEVVANQKLRILPDADPWIFGLLTSGMHMAWMRAITGRM---   813
NlaCI____CATCAC   776  RQP-DSRYLLLPKVSSENRRFLPIGYIEPETIANGSALIIPNATLCHFGILSSTMHNAFMRTVAGRL---   841
NmeAIII__GCCGAG   749  RQPSDGNYLIIPSVSSESRRFIPIGYLSFETVVSNLAFILPNATLYHFGILSSTMHNAFMRTVAGRL---   815
ApyPI____ATCGAC   782  YRP-QTDFLCVPSVVSENRPYFTAADIEEGTVVSSLAFAVEDSDRSQFALISSSMFITWQKMIGGRL---   847
CstMI____AAGGAG   784  SQP-DTDYLCLPKVVSERRSYFTVQRYPSNVIASDLVFHAQDPDGLMFALASSSMFITWQKSIGGRL---   849
CdpI_____GCGGAG   758  SRFKDGTYIGIPKVSSERRKYVPFAFVTDGMIPGDMLYFVPTDSLFVFGVLVSQFQNAWMRVVAGRL---   824
RpaB5I__CGRGGAC   834  LKD-LGRYIGTARTA----KHRIFSMLAGHSLPESEVIAVGSDDAFILGVLSSRLHVRWSLSKGGTL---   895
PspOMII_CGCCCAR   868  LEG-LPRYIATVETA----KHRIFSLLDATILPDNKLIIIALADTWHFSIVSSRIHWVWAIANAAKIGMY   932
MaqI____CRTTGAC   838  LIG-IETAIATSLTA----KHRVFVHLDSNSICDSTTVMFALPGAQYLGVLSSRVHVLWSLFAGGTL---   899
DrdIV____TACGAC   854  TRG-LKRYVVTLETA----KHQVFQFLDSSIVPDSTIVTFGTEDAFHLGVLSSRVHVTWALAQGGTL---   915
SpoDI___GCGGAAG   753  VSR-LSRFIVTPRVG----KHRIFVWLDSNALADSATFIVARDDETTFGILHSSFHELWSLRMGTFLG-V   816
AquIV___GRGGAAG   732  IEL-LALYFAVPRHS----KWFIFIPCKLDWLPADSTTVVASDDFYVLGILTSDVHRQWVKAQSSTL---   793
NhaXI___CAAGRAG   771  LAP-LSRYIVCARVT----HRPIFEFVSTAIHPNDALSVFALEDDYSFGILQSGIHWEWFINRCSTL---   832
DraRI___CAAGNAC_  761  ISS-LSRYIVCSRVT----KRQVFEFLDNGIRPSDGLQIFAFEDDYSFGVIQSSVHWQWLIARGGTL---   822
Consensus_ss:          h      eeeeee        eeeeeee   eee    eeeee   hhhhhhhhhhhhhhhhhhh
```

FIG. 20-9

AquIII___GAGGAG 801 KSDYRYSKDIVYNNFPFPQNV----------TDKQKQTVEKAAQLVLDTRDKYP--------------- 844
SdeAI___CAGRAG 791 KSDYRYSNEIVYNNFPFPLEI----------NDKQKDQIEQLAQNILDIRAEFV--------------- 834
PspPRI___CCYCAG 822 KSDYSYSSTIVYNNFPYPFMADDH----SDKAQKARESIAKASQQVLDARKHYQDGS------------ 874
EsaSSI___GACCAC 816 ESRYQYSVTIVYNNFPWPSP-----------SDAQLEALEAAGQAILDAQAMYL--------------- 858
MmeI____TCCRAC_ 806 ESRYRYSASLVYNTFPWIQP-----------NEKQSKAIEEAAFAILKARSNYP--------------- 848
PlaDI___CATCAG 814 KSDYMYSVGVVYNTFPWPDI-----------TEAQKQKIRALAQAVLDARALYP--------------- 856
NlaCI___CATCAC 842 ESRYQYSASIVYNNFPFPE-------------NPCRTAIETAAQAVLDARAAETERIRRLNRI------- 891
NmeAIII__GCCGAG 816 KSDYRYSNTVVYNNFPFPESCRLPS--ENDRPDPLRAAVEAAAQTVLDARGQYRREAQE----------- 872
ApyPI___ATCGAC 848 ESRLRFANTLTWNTFPVPEL-----------DEKTRKRIIKAGQKVLAARALHP--------------- 890
CstMI___AAGGAG 850 KSDLRFANTLTWNTFPVPEL-----------DEKTRQRIIKAGKKVLDARALHP--------------- 892
CdpI____GCGGAG 825 KSDYRYGNTTVYNNFVFPEV-----------DDSVRVDVEKRAQAVIDARSLYP--------------- 867
RpaB5I__CGRGGAC 896 EDRPRYNNSMCFDPFPFPDA-----------NPIQKQTIRVIAEELDAHRKRVLAE------------- 940
PspOMII_CGCCCAR 933 DGDAVYPKGQCFDPFPFPDA-----------TEAQKARLRALGEELDAHRKAQQAA------------- 977
MaqI____CRTTGAC 900 ENRPRYNKTLCFETFPFPKM-----------SSDQSEKISDLAEKIDQVRKGQQAK------------- 944
DrdIV___TACGAC 916 EDRPRYNKTRCFETFPFPAA-----------TPEQQQRIRDLAERLDAHRKAFLAE------------- 960
SpoDI___GCGGAAG 817 GNDPRYTPSTTFETFPFPEGLTPNIPADEYADAPRAIKIAAAAKRLNEFRENWLNPADLVDRVPEVVSGY 886
AquIV___GRGGAAG 794 KGDTRYTHNTCFETFPFPQTA----------IAKLTQQIRQGMIDLHEYRTAQME-------------- 838
NhaXI___CAAGRAG 833 KADFRYTSDTVFDSFPWPQEP----------SADAVRLVAKRAVEVRQLRSKLKV-------------- 877
DraRI___CAAGNAC_ 823 TARLMYTSDTVFDTFPWPEDP----------TLAQVRAVAAAAVKLRELRNKVMR-------------- 867
Consensus_ss: ee eeee hhhhhhhhhhhhhhhhhhhhhh AquIII___GAGGAG 845 ----------------DSSLADLYDPLT------------------------------------------ 856
SdeAI___CAGRAG 835 ----------------GSSLADLYNPLT------------------------------------------ 846
PspPRI___CCYCAG 875 --------------ENAPTLAQLYNTYL------------------------------------------ 888
EsaSSI___GACCAC 859 --------------DQGSSLADLYDPRT------------------------------------------ 872
MmeI____TCCRAC_ 849 ----------------NESLAGLYDPKT------------------------------------------ 860
PlaDI___CATCAG 857 ----------------GATLADLYDPDL------------------------------------------ 868
NlaCI___CATCAC 892 --------LPEKEHRPNPTPATLYNPDT------------------------------------------ 911
NmeAIII__GCCGAG 873 ------------AGLPEPTLAELYAPDA------------------------------------------ 888
ApyPI___ATCGAC 891 ----------------ERSLAEHYNPLA------------------------------------------ 902
CstMI___AAGGAG 893 ----------------ERSLAEHYNPLA------------------------------------------ 904
CdpI____GCGGAG 868 ----------------EATLADMYDPDNDF---------------------------------------- 881
RpaB5I__CGRGGAC 941 --------------HPHLTLTGLYNVLERLRAGAVPQAQPSPAGLTRGSTSSRGAAKKDLDGRGTGRQDG 996
PspOMII_CGCCCAR 978 --------------HPRLTLTALYNVLEKLRAGERIEGRDRETYD------------------------- 1008
MaqI____CRTTGAC 945 --------------HPDLTLTGMYNVLEKLRSGEELTNKEKTIHE------------------------- 975
DrdIV___TACGAC 961 --------------HPKLTMTDMYNALAALRAGQPLEGKLKTAHD------------------------- 991
SpoDI___GCGGAAG 887 PDRILPKNDAAAKELKKRTLTNLYNA-------------------------------------------- 912
AquIV___GRGGAAG 839 ----------------AKQWGITKLYNAFFDE-------------------------------------- 854
NhaXI___CAAGRAG 878 --------------KHHLSLRELYRAIEGP---------------------------------------- 893
DraRI___CAAGNAC_ 868 --------------EQGWSLRDLYRTLDMP---------------------------------------- 883
Consensus_ss: hhhh

FIG. 20-10

```
AquIII__GAGGAG    857  --------------------------MPPDLMKAHQKLDKAVDLCYRPQAF-------------------  881
SdeAI___CAGRAG    847  --------------------------MPPKLLKAHETLDRAVDKLYSKTLF-------------------  871
PspPRI__CCYCAG    889  ------------------------IDPYPLLTKAHKALDKAVDSAYGYRGK-------------------  915
EsaSSI__GACCAC    873  --------------------------MPSELRKAHAANDRAVDAAYKFKGD-------------------  897
MmeI____TCCRAC_   861  --------------------------MPSELLKAHQKLDKAVDSVYGFKGP-------------------  885
PlaDI___CATCAG    869  --------------------------MKRELRQAHRALDAAVDKLYRGQAF-------------------  893
NlaCI___CATCAC    912  --------------------------MPPALAAAHNALDDAVDEAYGYTGG-------------------  936
NmeAIII_GCCGAG    889  --------------------------GYTALDKAHATLDKAVDKAYGYKTGKN-----------------  915
ApyPI___ATCGAC    903  --------------------------MTPELVKAHDALDREVDKAMGAARKL------------------  928
CstMI___AAGGAG    905  --------------------------MAPELIKAHDALDREVDKAFGAPRKL------------------  930
CdpI____GCGGAG    882  --------------------------LYPELMKAHRELDRAVEMAYGVDFG-------------------  906
RpaB5I__CGRGGAC   997  ASRLSPGHDDAEMVLTPDEQCIFDDGLVLILKELHDRLDVAVAEAYGWPAN------------------- 1047
PspOMII_CGCCCAR  1009  ------------------------AGLVGILRDIHDRIDAAVAEAYGWPAD------------------- 1035
MaqI____CRTTGAC   976  ------------------------QGLVSVLRELHDDLDRAVFQAYGWSDLADKLVGRPGATTPLPDKPA 1021
DrdIV___TACGAC    992  ------------------------QGLVTTLRQLHDDLDVAVLAAYGWPTG------------------- 1018
SpoDI___GCGGAAG   913  --------------------------RPAWLDHAHKALDEAVAEAYGWGDDWRA----------------  940
AquIV___GRGGAAG   855  --------------------------PASQLHKLHKKLDALVLKAYGFK---------------------  877
NhaXI___CAAGRAG   894  --------------------------GEHALKKAHKLLDEAVRGAYGMS---------------------  916
DraRI___CAAGNAC_  884  --------------------------GKNPLRDAQERLDAAVSAAYGLP---------------------  906
Consensus_ss:                                      hhhhhhhhhhhhhhhhh

AquIII__GAGGAG    882  ---TSELNRIEFLFNEYEKLITPLLQSTKQKKA-------------------------------------  911
SdeAI___CAGRAG    872  ---KTDTERVAHLFELNKQLTSLIVENEKKAKK-------------------------------------  901
PspPRI__CCYCAG    916  ---GDDASRVEFLIKKIAELKN------------------------------------------------  934
EsaSSI__GACCAC    898  ---KSDAVRVAFLFSLYGRLTSLLPSEKPKRAR-------------------------------------  927
MmeI____TCCRAC_   886  ---NTEIARIAFLFETYQKMTSLLPPEKEIKKS-------------------------------------  915
PlaDI___CATCAG    894  ---ANDRERVEHLFGLYEKLSSPLTAAPKPIKR-------------------------------------  923
NlaCI___CATCAC    937  ---NSDSERTAFLFRLYKNAV-------------------------------------------------  954
NmeAIII_GCCGAG    916  --TDDEAERVAFLFELYRKAAAIA----------------------------------------------  937
ApyPI___ATCGAC    929  ---TSERQRQELLFANYAKLTNN-----------------------------------------------  948
CstMI___AAGGAG    931  ---TTVRQRQELLFANYEKLISHQP---------------------------------------------  952
CdpI____GCGGAG    907  ---GDEQQIVAHLFKLYNEKVEK-----------------------------------------------  926
RpaB5I__CGRGGAC  1048  ---LSDDEILARLVALNKQRADEEKRGLVR--WLRPDYQIPRFAKGVDKQAAKEEGAQIAASLDLGE-TR 1111
PspOMII_CGCCCAR  1036  ---LDDEAILTRLVDLNRARAAEEAAGLVR--WLRPDYQNPAGRIAAAK------GQQVELDVGAAAEAA 1094
MaqI____CRTTGAC  1022  EQAEAEDELLMRLLELNKQRAEEESRGIVR--WLRPDYQARDAVQTEVDI----APKAAATKTEAST-SK 1084
DrdIV___TACGAC   1019  ---LDEQGLLERLAALNAERVQEEKAGRIR--YLRPAYQDPHGTAQEN--------LGMAVASRPAK-AA 1074
SpoDI___GCGGAAG   941  -GVLTEDEILARLFKLNQERAAKEKA--------------------------------------------  965
AquIV___GRGGAAG   878  ----KDDDILEKLLDLNLALAEKEKNGENIVG--------------------------------------  905
NhaXI___CAAGRAG   917  ----KKADVLETLLELNETVVAAEADGKQVVGPGIPPSASKLKN----------------LVTTDKL-TI  965
DraRI___CAAGNAC_  907  ----AGADMLDFLLALNAEVAAAEARGAAVTGPGLP-AGLNTAD----------------FVTADAV-RP  954
Consensus_ss:              hhhhhhhhhhhhhhhhh
```

FIG. 20-11

```
AquIII___GAGGAG   912  -----------------------------------RKNKTS-------------------------- 917
SdeAI____CAGRAG   902  -----------------------------------VKKI---------------------------I 906
PspPRI___CCYCAG        -------------------------------------------------------------------
EsaSSI___GACCAC   928  -----------------------------------KEKAVA-------------------------- 933
MmeI_____TCCRAC_  916  -----------------------------------KGKN---------------------------- 919
PlaDI____CATCAG   924  -----------------------------------KRKKE--------------------------- 928
NlaCI____CATCAC        -------------------------------------------------------------------
NmeAIII__GCCGAG        -------------------------------------------------------------------
ApyPI____ATCGAC        -------------------------------------------------------------------
CstMI____AAGGAG        -------------------------------------------------------------------
CdpI_____GCGGAG        -------------------------------------------------------------------
RpaB5I__CGRGGAC  1112  QKPSFPTGAVEQTAAVFAALAAASGPLDAKSLAAQFRRTKTTEKKLAEVLASLARLGYVATTD---GVSF 1178
PspOMII_CGCCCAR  1095  DKALWPKALPEQIAAVRAVLSDMG-EATPEQVARQFKRARA--ASVKPLLESLSALGQARLIE---GGRF 1158
MaqI____CRTTGAC  1085  GKASFPKAIPDQLRVLREALAERS--HTTESLAEMFKRKPM--KSVEEGLQSLVAVGVAEYDP--ETQTW 1148
DrdIV____TACGAC  1075  QVMPFPTALPLQVQAVRSALMQAGQALSPQEVAQAFQGAKE--KQVEDIMQTLVLLGQAHLREHNGEVRY 1142
SpoDI___GCGGAAG        -------------------------------------------------------------------
AquIV___GRGGAAG   906  ---PWAIDNPPK------------------------------------------------------- 914
NhaXI___CAAGRAG   966  SPTSWANNAPVKT------------------------------------------------------ 978
DraRI___CAAGNAC_  955  LG----------------------------------------------------------------- 956
Consensus_ss:

AquIII___GAGGAG        ------        SEQ ID NO: 42
SdeAI____CAGRAG   907  TK----  908   SEQ ID NO:  6
PspPRI___CCYCAG        ------        SEQ ID NO: 10
EsaSSI___GACCAC        ------        SEQ ID NO:  4
MmeI_____TCCRAC_       ------        SEQ ID NO:  2
PlaDI____CATCAG        ------        SEQ ID NO: 40
NlaCI____CATCAC        ------        SEQ ID NO:  8
NmeAIII__GCCGAG        ------        SEQ ID NO: 14
ApyPI____ATCGAC        ------        SEQ ID NO: 18
CstMI____AAGGAG        ------        SEQ ID NO: 12
CdpI_____GCGGAG        ------        SEQ ID NO: 16
RpaB5I__CGRGGAC  1179  ALRRVA 1184   SEQ ID NO: 26
PspOMII_CGCCCAR  1159  AA---- 1160   SEQ ID NO: 34
MaqI____CRTTGAC  1149  HTV--- 1151   SEQ ID NO: 38
DrdIV____TACGAC  1143  AA---- 1144   SEQ ID NO: 36
SpoDI___GCGGAAG        ------        SEQ ID NO: 20
AquIV___GRGGAAG        ------        SEQ ID NO: 44
NhaXI___CAAGRAG        ------        SEQ ID NO: 24
DraRI___CAAGNAC_       ------        SEQ ID NO: 22
Consensus_ss:
```

FIG. 21

| AMINO ACID: | AAobs1 | AAobs2 | ... | Aaobsx | ROW SUM |
|---|---|---|---|---|---|
| BASE: | | | | | |
| BASEobs1 | AA1-B1 | AA2-B1 | ... | AAx-B1 | (AA1-B1+...+Aax-B1) |
| BASEobs2 | AA1-B2 | AA2-B2 | ... | Aax-B2 | (AA1-B2+...+Aax-B2) |
| ... | ... | ... | ... | ... | ... |
| BASEobsy | AA1-By | AA2-By | ... | Aax-By | (AA1-By+...+Aax-By) |
| COLUMN SUM: | AA1 SUM | AA2 SUM | ... | Aax SUM | N = TOTAL COUNTS |

CHI SQUARE VALUE = CALCULATE:
GENERAL FORMULA: CHI SQUARE VALUE IS THE SUM FOR ALL OBSERVATIONS (POSITIONS IN THE TABLE) OF THE: ((OBSERVED FREQUENCY MINUS THE EXPECTED FREQUENCY) SQUARED) DIVIDED BY THE EXPECTED FREQUENCY:

$$\chi^2 = \sum_{i=1}^{n} \frac{(O_i - E_i)^2}{E_i}$$

THE OBSERVED FREQUENCY IS THE COUNT OF AMINO ACID RESIDUES AT THE ALIGNED POSITION FOR THE DNA BASE RECOGNIZED.
THE EXPECTED FREQUENCY IS THE SUM OF THE COLUMN IN WHICH THE OBSERVATION OCCURS TIMES THE SUM OF THE ROW IN WHICH THE OBSERVATION OCCURS, DIVIDED BY THE TOTAL COUNT OF ALL OBSERVATIONS

DEGREES OF FREEDOM = (# ROWS - 1) (# COLUMNS - 1)

Pvalue IS READ FROM CHI SQUARE CONTINGENCY TABLE FOR THE CHI SQUARE VALUE DETERMINED AND THE DEGREES OF FREEDOM OF THE TABLE

FIG. 22

```
Recognition sequence position:         3
M.BstLVI_ATCGAT  434  YEIWVPHDPSLW--DKPKIIFPDISPEP------KFFY------EDKGSVVDGN--CYWIIPKK  481  SEQ ID NO: 83
M.BanIII_ATCGAT  437  YQIWLPQNPDHW--ALPKILFPDISPEP------KFFY------EDEGCCIDGN--CYWIIPKE  484  SEQ ID NO: 84
M.BstVI__CTCGAG  422  FRTIDRIYPEIV--HQPKLLIPDMKNTN------HIVK------DDGAFYPHHN--LYYILPGN  469  SEQ ID NO: 85
M.XhoI___CTCGAG  434  FRTIDRIYPALA--KTPKLLVPDIKGDA------HIVY------EEGKLYPHHN--LYFITANE  481  SEQ ID NO: 86
M.PaeR7I_CTCGAG  392  YRTIDRITPALA--ARPKLLIPDIKGES------HIVF------EGGELYPSHN--LYYVTSDD  439  SEQ ID NO: 87
M.XamI___GTCGAC  434  WSVGLK--------APAPILCTYMARRP-----PQFTL------NACDARHINI--AHGLYPRE  476  SEQ ID NO: 88
M.AcuI___CTGAAG  384  FVI-----PSIK--LSDALFIRRNNLFP------RLIL------NEAQAYTTDT--MHRVFIKQ  426  SEQ ID NO: 89
M.XveI___CTGCAG  476  ---------------KPCVLLQRTTAKEQARRLIAAEMPASFIKRHAGVTIENH--LNMMIPTV  522  SEQ ID NO: 90
M.BsuBI__CTGCAG  371  --------P-----NGHYVVVKRFSSKEE-KRRIVAGVLTPESVNDPVVGFENG--LNVLHYNK  418  SEQ ID NO: 91
M.PstI___CTGCAG  383  --------P-----NGIYVLTRRLTAKEE-KRRIVASIYYPDIANVDTVGFDNK--INYFHANG  430  SEQ ID NO: 92
M.Rle39B_CTGCAG  478  ---------------VPCVLLQRTTSKEQARRLIAAELPEAFIKAHGRVIVENH--LNMVKPTA  524  SEQ ID NO: 93
M.XphI___CTGCAG  475  ---------------KPCVLLQRTTAKEQARRLIAAEMPASFIKRHAGVTIENH--LNMMIPTV  521  SEQ ID NO: 94
M.BpmI___CTGGAG  398  YIT-----PSRW--VPDAFALRQVDGYP------KLIL------NETDASSTDT--IHRVRFKE  440  SEQ ID NO: 95
M.BseRI__GAGGAG  533  YML-----PRLTGRHKSELFIPRINNLHP-----KTLL------NSNNTVIDANFSTLWVNKET  580  SEQ ID NO: 96
M.VspI___ATTAAT  434  --------------AEEKLIYKFISSEL------VFFH------DTKKRFILNS--ANMLVLQD  469  SEQ ID NO: 97
M.SfeI___CTRYAG  505  YEYGRSQALNS---HVPKIIFPTNSLNP------NFVY------FTDYALFNNG--YAIYGVNN  551  SEQ ID NO: 98
M.AccI___GTMKAC  397  YSLENRK--------PAPIWVSVFNRSG-----LRFIR------NEANISNLTS--YHCIIQNK  439  SEQ ID NO: 99
Consensus_ss:                        eeeeee         eeeeee     e   e      ee     eeeee
```

FIG. 23A-1

MmeI

| RECOGNITION SEQUENCE | POSITION 3 DETERMINANTS | POSITION 4 DETERMINANTS | POSITION 6 DETERMINANTS |
|---|---|---|---|
| TCCAAC | 751E + 773N | 774A + 810R +809P | 806E + 808R |
| TCCAAG | 751E + 773N | 774A + 810R +809P | 806K + 808D |
| TCCAAR | 751E + 773N | 774A + 810R +809P | 806D + 808D |
| TCCAAN | 751E + 773N | 774A + 810R +809P | 806W + 808A |
| TCCCAC | 751E + 773N | 774K + 810S | 806E + 808R |
| TCCCAG | 751E + 773N | 774K + 810S | 806K + 808D |
| TCCCAR | 751E + 773N | 774K + 810S | 806D + 808D |
| TCCCAN | 751E + 773N | 774K + 810S | 806W + 808A |
| TCCGAC | 751E + 773N | 774L + 810R | 806E + 808R |
| TCCGAG | 751E + 773N | 774L + 810R | 806K + 808D |
| TCCGAR | 751E + 773N | 774L + 810R | 806D + 808D |
| TCCGAN | 751E + 773N | 774L + 810R | 806W + 808A |
| TCCRAC | 751E + 773N | 774A + 810R +809F | 806E + 808R |
| TCCRAG | 751E + 773N | 774A + 810R +809F | 806K + 808D |
| TCCRAR | 751E + 773N | 774A + 810R +809F | 806D + 808D |
| TCCRAN | 751E + 773N | 774A + 810R +809F | 806W + 808A |
| TCCNAC | 751E + 773N | 774G + 810M | 806E + 808R |
| TCCNAG | 751E + 773N | 774G + 810M | 806K + 808D |
| TCCNAR | 751E + 773N | 774G + 810M | 806D + 808D |
| TCCNAN | 751E + 773N | 774G + 810M | 806W + 808A |
| TCGAAC | 751R + 773D | 774A + 810R +809P | 806E + 808R |
| TCGAAG | 751R + 773D | 774A + 810R +809P | 806K + 808D |
| TCGAAR | 751R + 773D | 774A + 810R +809P | 806D + 808D |
| TCGAAN | 751R + 773D | 774A + 810R +809P | 806W + 808A |
| TCGCAC | 751R + 773D | 774K + 810S | 806E + 808R |
| TCGCAG | 751R + 773D | 774K + 810S | 806K + 808D |
| TCGCAR | 751R + 773D | 774K + 810S | 806D + 808D |
| TCGCAN | 751R + 773D | 774K + 810S | 806W + 808A |
| TCGGAC | 751R + 773D | 774L + 810R | 806E + 808R |
| TCGGAG | 751R + 773D | 774L + 810R | 806K + 808D |
| TCGGAR | 751R + 773D | 774L + 810R | 806D + 808D |
| TCGGAN | 751R + 773D | 774L + 810R | 806W + 808A |
| TCGRAC | 751R + 773D | 774A + 810R +809F | 806E + 808R |
| TCGRAG | 751R + 773D | 774A + 810R +809F | 806K + 808D |
| TCGRAR | 751R + 773D | 774A + 810R +809F | 806D + 808D |
| TCGRAN | 751R + 773D | 774A + 810R +809F | 806W + 808A |
| TCGNAC | 751R + 773D | 774G + 810M | 806E + 808R |
| TCGNAG | 751R + 773D | 774G + 810M | 806K + 808D |
| TCGNAR | 751R + 773D | 774G + 810M | 806D + 808D |
| TCGNAN | 751R + 773D | 774G + 810M | 806W + 808A |

FIG. 23A-2

MmeI

| RECOGNITION SEQUENCE | POSITION 3 DETERMINANTS | POSITION 4 DETERMINANTS | POSITION 6 DETERMINANTS |
|---|---|---|---|
| TCTAAC | 751K + 773Q | 774A + 810R +809P | 806E + 808R |
| TCTAAG | 751K + 773Q | 774A + 810R +809P | 806K + 808D |
| TCTAAR | 751K + 773Q | 774A + 810R +809P | 806D + 808D |
| TCTAAN | 751K + 773Q | 774A + 810R +809P | 806W + 808A |
| TCTCAC | 751K + 773Q | 774K + 810S | 806E + 808R |
| TCTCAG | 751K + 773Q | 774K + 810S | 806K + 808D |
| TCTCAR | 751K + 773Q | 774K + 810S | 806D + 808D |
| TCTCAN | 751K + 773Q | 774K + 810S | 806W + 808A |
| TCTGAC | 751K + 773Q | 774L + 810R | 806E + 808R |
| TCTGAG | 751K + 773Q | 774L + 810R | 806K + 808D |
| TCTGAR | 751K + 773Q | 774L + 810R | 806D + 808D |
| TCTGAN | 751K + 773Q | 774L + 810R | 806W + 808A |
| TCTRAC | 751K + 773Q | 774A + 810R +809F | 806E + 808R |
| TCTRAG | 751K + 773Q | 774A + 810R +809F | 806K + 808D |
| TCTRAR | 751K + 773Q | 774A + 810R +809F | 806D + 808D |
| TCTRAN | 751K + 773Q | 774A + 810R +809F | 806W + 808A |
| TCTNAC | 751K + 773Q | 774G + 810M | 806E + 808R |
| TCTNAG | 751K + 773Q | 774G + 810M | 806K + 808D |
| TCTNAR | 751K + 773Q | 774G + 810M | 806D + 808D |
| TCTNAN | 751K + 773Q | 774G + 810M | 806W + 808A |
| TCYAAC | 751V + 773N | 774A + 810R +809P | 806E + 808R |
| TCYAAG | 751V + 773N | 774A + 810R +809P | 806K + 808D |
| TCYAAR | 751V + 773N | 774A + 810R +809P | 806D + 808D |
| TCYAAN | 751V + 773N | 774A + 810R +809P | 806W + 808A |
| TCYCAC | 751V + 773N | 774K + 810S | 806E + 808R |
| TCYCAG | 751V + 773N | 774K + 810S | 806K + 808D |
| TCYCAR | 751V + 773N | 774K + 810S | 806D + 808D |
| TCYCAN | 751V + 773N | 774K + 810S | 806W + 808A |
| TCYGAC | 751V + 773N | 774L + 810R | 806E + 808R |
| TCYGAG | 751V + 773N | 774L + 810R | 806K + 808D |
| TCYGAR | 751V + 773N | 774L + 810R | 806D + 808D |
| TCYGAN | 751V + 773N | 774L + 810R | 806W + 808A |
| TCYRAC | 751V + 773N | 774A + 810R +809F | 806E + 808R |
| TCYRAG | 751V + 773N | 774A + 810R +809F | 806K + 808D |
| TCYRAR | 751V + 773N | 774A + 810R +809F | 806D + 808D |
| TCYRAN | 751V + 773N | 774A + 810R +809F | 806W + 808A |
| TCYNAC | 751V + 773N | 774G + 810M | 806E + 808R |
| TCYNAG | 751V + 773N | 774G + 810M | 806K + 808D |
| TCYNAR | 751V + 773N | 774G + 810M | 806D + 808D |
| TCYNAN | 751V + 773N | 774G + 810M | 806W + 808A |

FIG. 23B-1

NmeAIII

| RECOGNITION SEQUENCE | Position 3 DETERMINANTS | Position 4 DETERMINATES | Position 6 DETERMINANTS |
|---|---|---|---|
| GCCAAC | 761E + 783N | 784A + 820R +819P | 816E + 818R |
| GCCAAG | 761E + 783N | 784A + 820R +819P | 816K + 818D |
| GCCAAR | 761E + 783N | 784A + 820R +819P | 816D + 818D |
| GCCAAN | 761E + 783N | 784A + 820R +819P | 816W + 818A |
| GCCCAC | 761E + 783N | 784K + 820S | 816E + 818R |
| GCCCAG | 761E + 783N | 784K + 820S | 816K + 818D |
| GCCCAR | 761E + 783N | 784K + 820S | 816D + 818D |
| GCCCAN | 761E + 783N | 784K + 820S | 816W + 818A |
| GCCGAC | 761E + 783N | 784L + 820R | 816E + 818R |
| GCCGAG | 761E + 783N | 784L + 820R | 816K + 818D |
| GCCGAR | 761E + 783N | 784L + 820R | 816D + 818D |
| GCCGAN | 761E + 783N | 784L + 820R | 816W + 818A |
| GCCRAC | 761E + 783N | 784A + 820R +819F | 816E + 818R |
| GCCRAG | 761E + 783N | 784A + 820R +819F | 816K + 818D |
| GCCRAR | 761E + 783N | 784A + 820R +819F | 816D + 818D |
| GCCRAN | 761E + 783N | 784A + 820R +819F | 816W + 818A |
| GCCNAC | 761E + 783N | 784G + 820M | 816E + 818R |
| GCCNAG | 761E + 783N | 784G + 820M | 816K + 818D |
| GCCNAR | 761E + 783N | 784G + 820M | 816D + 818D |
| GCCNAN | 761E + 783N | 784G + 820M | 816W + 818A |
| GCGAAC | 761R + 783D | 784A + 820R +819P | 816E + 818R |
| GCGAAG | 761R + 783D | 784A + 820R +819P | 816K + 818D |
| GCGAAR | 761R + 783D | 784A + 820R +819P | 816D + 818D |
| GCGAAN | 761R + 783D | 784A + 820R +819P | 816W + 818A |
| GCGCAC | 761R + 783D | 784K + 820S | 816E + 818R |
| GCGCAG | 761R + 783D | 784K + 820S | 816K + 818D |
| GCGCAR | 761R + 783D | 784K + 820S | 816D + 818D |
| GCGCAN | 761R + 783D | 784K + 820S | 816W + 818A |
| GCGGAC | 761R + 783D | 784L + 820R | 816E + 818R |
| GCGGAG | 761R + 783D | 784L + 820R | 816K + 818D |
| GCGGAR | 761R + 783D | 784L + 820R | 816D + 818D |
| GCGGAN | 761R + 783D | 784L + 820R | 816W + 818A |
| GCGRAC | 761R + 783D | 784A + 820R +819F | 816E + 818R |
| GCGRAG | 761R + 783D | 784A + 820R +819F | 816K + 818D |
| GCGRAR | 761R + 783D | 784A + 820R +819F | 816D + 818D |
| GCGRAN | 761R + 783D | 784A + 820R +819F | 816W + 818A |
| GCGNAC | 761R + 783D | 784G + 820M | 816E + 818R |
| GCGNAG | 761R + 783D | 784G + 820M | 816K + 818D |
| GCGNAR | 761R + 783D | 784G + 820M | 816D + 818D |
| GCGNAN | 761R + 783D | 784G + 820M | 816W + 818A |

FIG. 23B-2

NmeAIII

| RECOGNITION SEQUENCE | POSITION 3 DETERMINANTS | POSITION 4 DETERMINANTS | POSITION 6 DETERMINANTS |
|---|---|---|---|
| GCTAAC | 761K + 783Q | 784A + 820R +819P | 816E + 818R |
| GCTAAG | 761K + 783Q | 784A + 820R +819P | 816K + 818D |
| GCTAAR | 761K + 783Q | 784A + 820R +819P | 816D + 818D |
| GCTAAN | 761K + 783Q | 784A + 820R +819P | 816W + 818A |
| GCTCAC | 761K + 783Q | 784K + 820S | 816E + 818R |
| GCTCAG | 761K + 783Q | 784K + 820S | 816K + 818D |
| GCTCAR | 761K + 783Q | 784K + 820S | 816D + 818D |
| GCTCAN | 761K + 783Q | 784K + 820S | 816W + 818A |
| GCTGAC | 761K + 783Q | 784L + 820R | 816E + 818R |
| GCTGAG | 761K + 783Q | 784L + 820R | 816K + 818D |
| GCTGAR | 761K + 783Q | 784L + 820R | 816D + 818D |
| GCTGAN | 761K + 783Q | 784L + 820R | 816W + 818A |
| GCTRAC | 761K + 783Q | 784A + 820R +819F | 816E + 818R |
| GCTRAG | 761K + 783Q | 784A + 820R +819F | 816K + 818D |
| GCTRAR | 761K + 783Q | 784A + 820R +819F | 816D + 818D |
| GCTRAN | 761K + 783Q | 784A + 820R +819F | 816W + 818A |
| GCTNAC | 761K + 783Q | 784G + 820M | 816E + 818R |
| GCTNAG | 761K + 783Q | 784G + 820M | 816K + 818D |
| GCTNAR | 761K + 783Q | 784G + 820M | 816D + 818D |
| GCTNAN | 761K + 783Q | 784G + 820M | 816W + 818A |
| GCYAAC | 761V + 783N | 784A + 820R +819P | 816E + 818R |
| GCYAAG | 761V + 783N | 784A + 820R +819P | 816K + 818D |
| GCYAAR | 761V + 783N | 784A + 820R +819P | 816D + 818D |
| GCYAAN | 761V + 783N | 784A + 820R +819P | 816W + 818A |
| GCYCAC | 761V + 783N | 784K + 820S | 816E + 818R |
| GCYCAG | 761V + 783N | 784K + 820S | 816K + 818D |
| GCYCAR | 761V + 783N | 784K + 820S | 816D + 818D |
| GCYCAN | 761V + 783N | 784K + 820S | 816W + 818A |
| GCYGAC | 761V + 783N | 784L + 820R | 816E + 818R |
| GCYGAG | 761V + 783N | 784L + 820R | 816K + 818D |
| GCYGAR | 761V + 783N | 784L + 820R | 816D + 818D |
| GCYGAN | 761V + 783N | 784L + 820R | 816W + 818A |
| GCYRAC | 761V + 783N | 784A + 820R +819F | 816E + 818R |
| GCYRAG | 761V + 783N | 784A + 820R +819F | 816K + 818D |
| GCYRAR | 761V + 783N | 784A + 820R +819F | 816D + 818D |
| GCYRAN | 761V + 783N | 784A + 820R +819F | 816W + 818A |
| GCYNAC | 761V + 783N | 784G + 820M | 816E + 818R |
| GCYNAG | 761V + 783N | 784G + 820M | 816K + 818D |
| GCYNAR | 761V + 783N | 784G + 820M | 816D + 818D |
| GCYNAN | 761V + 783N | 784G + 820M | 816W + 818A |

FIG. 23C-1

SdeAI

| RECOGNITION SEQUENCE | POSITION 3 DETERMINANT | POSITION 4 DETERMINANT | POSITION 6 DETERMINANT |
|---|---|---|---|
| CACAAC | 736E + 758N | 759A + 795R +794P | 791E + 793R |
| CACAAG | 736E + 758N | 759A + 795R +794P | 791K + 793D |
| CACAAR | 736E + 758N | 759A + 795R +794P | 791D + 793D |
| CACAAN | 736E + 758N | 759A + 795R +794P | 791W + 793A |
| CACCAC | 736E + 758N | 759K + 795S | 791E + 793R |
| CACCAG | 736E + 758N | 759K + 795S | 791K + 793D |
| CACCAR | 736E + 758N | 759K + 795S | 791D + 793D |
| CACCAN | 736E + 758N | 759K + 795S | 791W + 793A |
| CACGAC | 736E + 758N | 759L + 795R | 791E + 793R |
| CACGAG | 736E + 758N | 759L + 795R | 791K + 793D |
| CACGAR | 736E + 758N | 759L + 795R | 791D + 793D |
| CACGAN | 736E + 758N | 759L + 795R | 791W + 793A |
| CACRAC | 736E + 758N | 759A + 795R +794F | 791E + 793R |
| CACRAG | 736E + 758N | 759A + 795R +794F | 791K + 793D |
| CACRAR | 736E + 758N | 759A + 795R +794F | 791D + 793D |
| CACRAN | 736E + 758N | 759A + 795R +794F | 791W + 793A |
| CACNAC | 736E + 758N | 759G + 795M | 791E + 793R |
| CACNAG | 736E + 758N | 759G + 795M | 791K + 793D |
| CACNAR | 736E + 758N | 759G + 795M | 791D + 793D |
| CACNAN | 736E + 758N | 759G + 795M | 791W + 793A |
| CAGAAC | 736R + 758D | 759A + 795R +794P | 791E + 793R |
| CAGAAG | 736R + 758D | 759A + 795R +794P | 791K + 793D |
| CAGAAR | 736R + 758D | 759A + 795R +794P | 791D + 793D |
| CAGAAN | 736R + 758D | 759A + 795R +794P | 791W + 793A |
| CAGCAC | 736R + 758D | 759K + 795S | 791E + 793R |
| CAGCAG | 736R + 758D | 759K + 795S | 791K + 793D |
| CAGCAR | 736R + 758D | 759K + 795S | 791D + 793D |
| CAGCAN | 736R + 758D | 759K + 795S | 791W + 793A |
| CAGGAC | 736R + 758D | 759L + 795R | 791E + 793R |
| CAGGAG | 736R + 758D | 759L + 795R | 791K + 793D |
| CAGGAR | 736R + 758D | 759L + 795R | 791D + 793D |
| CAGGAN | 736R + 758D | 759L + 795R | 791W + 793A |
| CAGRAC | 736R + 758D | 759A + 795R +794F | 791E + 793R |
| CAGRAG | 736R + 758D | 759A + 795R +794F | 791K + 793D |
| CAGRAR | 736R + 758D | 759A + 795R +794F | 791D + 793D |
| CAGRAN | 736R + 758D | 759A + 795R +794F | 791W + 793A |
| CAGNAC | 736R + 758D | 759G + 795M | 791E + 793R |
| CAGNAG | 736R + 758D | 759G + 795M | 791K + 793D |
| CAGNAR | 736R + 758D | 759G + 795M | 791D + 793D |
| CAGNAN | 736R + 758D | 759G + 795M | 791W + 793A |

FIG. 23C-2

SdeAI

| RECOGNITION SEQUENCE | POSITION 3 DETERMINANT | POSITION 4 DETERMINANT | POSITION 6 DETERMINANT |
|---|---|---|---|
| CATAAC | 736K + 758Q | 759A + 795R +794P | 791E + 793R |
| CATAAG | 736K + 758Q | 759A + 795R +794P | 791K + 793D |
| CATAAR | 736K + 758Q | 759A + 795R +794P | 791D + 793D |
| CATAAN | 736K + 758Q | 759A + 795R +794P | 791W + 793A |
| CATCAC | 736K + 758Q | 759K + 795S | 791E + 793R |
| CATCAG | 736K + 758Q | 759K + 795S | 791K + 793D |
| CATCAR | 736K + 758Q | 759K + 795S | 791D + 793D |
| CATCAN | 736K + 758Q | 759K + 795S | 791W + 793A |
| CATGAC | 736K + 758Q | 759L + 795R | 791E + 793R |
| CATGAG | 736K + 758Q | 759L + 795R | 791K + 793D |
| CATGAR | 736K + 758Q | 759L + 795R | 791D + 793D |
| CATGAN | 736K + 758Q | 759L + 795R | 791W + 793A |
| CATRAC | 736K + 758Q | 759A + 795R +794F | 791E + 793R |
| CATRAG | 736K + 758Q | 759A + 795R +794F | 791K + 793D |
| CATRAR | 736K + 758Q | 759A + 795R +794F | 791D + 793D |
| CATRAN | 736K + 758Q | 759A + 795R +794F | 791W + 793A |
| CATNAC | 736K + 758Q | 759G + 795M | 791E + 793R |
| CATNAG | 736K + 758Q | 759G + 795M | 791K + 793D |
| CATNAR | 736K + 758Q | 759G + 795M | 791D + 793D |
| CATNAN | 736K + 758Q | 759G + 795M | 791W + 793A |
| CAYAAC | 736V + 758N | 759A + 795R +794P | 791E + 793R |
| CAYAAG | 736V + 758N | 759A + 795R +794P | 791K + 793D |
| CAYAAR | 736V + 758N | 759A + 795R +794P | 791D + 793D |
| CAYAAN | 736V + 758N | 759A + 795R +794P | 791W + 793A |
| CAYCAC | 736V + 758N | 759K + 795S | 791E + 793R |
| CAYCAG | 736V + 758N | 759K + 795S | 791K + 793D |
| CAYCAR | 736V + 758N | 759K + 795S | 791D + 793D |
| CAYCAN | 736V + 758N | 759K + 795S | 791W + 793A |
| CAYGAC | 736V + 758N | 759L + 795R | 791E + 793R |
| CAYGAG | 736V + 758N | 759L + 795R | 791K + 793D |
| CAYGAR | 736V + 758N | 759L + 795R | 791D + 793D |
| CAYGAN | 736V + 758N | 759L + 795R | 791W + 793A |
| CAYRAC | 736V + 758N | 759A + 795R +794F | 791E + 793R |
| CAYRAG | 736V + 758N | 759A + 795R +794F | 791K + 793D |
| CAYRAR | 736V + 758N | 759A + 795R +794F | 791D + 793D |
| CAYRAN | 736V + 758N | 759A + 795R +794F | 791W + 793A |
| CAYNAC | 736V + 758N | 759G + 795M | 791E + 793R |
| CAYNAG | 736V + 758N | 759G + 795M | 791K + 793D |
| CAYNAR | 736V + 758N | 759G + 795M | 791D + 793D |
| CAYNAN | 736V + 758N | 759G + 795M | 791W + 793A |

FIG. 23D-1

CstMI

| RECOGNITION SEQUENCE | POSITION 3 DETERMINANTS | POSITION 4 DETERMINANTS | POSITION 6 DETERMINANTS |
|---|---|---|---|
| AACAAC | 795E + 817N | 818A + 854R +853P | 850E + 852R |
| AACAAG | 795E + 817N | 818A + 854R +853P | 850K + 852D |
| AACAAR | 795E + 817N | 818A + 854R +853P | 850D + 852D |
| AACAAN | 795E + 817N | 818A + 854R +853P | 850W + 852A |
| AACCAC | 795E + 817N | 818K + 854S | 850E + 852R |
| AACCAG | 795E + 817N | 818K + 854S | 850K + 852D |
| AACCAR | 795E + 817N | 818K + 854S | 850D + 852D |
| AACCAN | 795E + 817N | 818K + 854S | 850W + 852A |
| AACGAC | 795E + 817N | 818L + 854R | 850E + 852R |
| AACGAG | 795E + 817N | 818L + 854R | 850K + 852D |
| AACGAR | 795E + 817N | 818L + 854R | 850D + 852D |
| AACGAN | 795E + 817N | 818L + 854R | 850W + 852A |
| AACRAC | 795E + 817N | 818A + 854R +853F | 850E + 852R |
| AACRAG | 795E + 817N | 818A + 854R +853F | 850K + 852D |
| AACRAR | 795E + 817N | 818A + 854R +853F | 850D + 852D |
| AACRAN | 795E + 817N | 818A + 854R +853F | 850W + 852A |
| AACNAC | 795E + 817N | 818G + 854M | 850E + 852R |
| AACNAG | 795E + 817N | 818G + 854M | 850K + 852D |
| AACNAR | 795E + 817N | 818G + 854M | 850D + 852D |
| AACNAN | 795E + 817N | 818G + 854M | 850W + 852A |
| AAGAAC | 795R + 817D | 818A + 854R +853P | 850E + 852R |
| AAGAAG | 795R + 817D | 818A + 854R +853P | 850K + 852D |
| AAGAAR | 795R + 817D | 818A + 854R +853P | 850D + 852D |
| AAGAAN | 795R + 817D | 818A + 854R +853P | 850W + 852A |
| AAGCAC | 795R + 817D | 818K + 854S | 850E + 852R |
| AAGCAG | 795R + 817D | 818K + 854S | 850K + 852D |
| AAGCAR | 795R + 817D | 818K + 854S | 850D + 852D |
| AAGCAN | 795R + 817D | 818K + 854S | 850W + 852A |
| AAGGAC | 795R + 817D | 818L + 854R | 850E + 852R |
| AAGGAG | 795R + 817D | 818L + 854R | 850K + 852D |
| AAGGAR | 795R + 817D | 818L + 854R | 850D + 852D |
| AAGGAN | 795R + 817D | 818L + 854R | 850W + 852A |
| AAGRAC | 795R + 817D | 818A + 854R +853F | 850E + 852R |
| AAGRAG | 795R + 817D | 818A + 854R +853F | 850K + 852D |
| AAGRAR | 795R + 817D | 818A + 854R +853F | 850D + 852D |
| AAGRAN | 795R + 817D | 818A + 854R +853F | 850W + 852A |
| AAGNAC | 795R + 817D | 818G + 854M | 850E + 852R |
| AAGNAG | 795R + 817D | 818G + 854M | 850K + 852D |
| AAGNAR | 795R + 817D | 818G + 854M | 850D + 852D |
| AAGNAN | 795R + 817D | 818G + 854M | 850W + 852A |

FIG. 23D-2

CstMI

| RECOGNITION SEQUENCE | POSITION 3 DETERMINANTS | POSITION 4 DETERMINANTS | POSITION 6 DETERMINANTS |
|---|---|---|---|
| AATAAC | 795K + 817Q | 818A + 854R +853P | 850E + 852R |
| AATAAG | 795K + 817Q | 818A + 854R +853P | 850K + 852D |
| AATAAR | 795K + 817Q | 818A + 854R +853P | 850D + 852D |
| AATAAN | 795K + 817Q | 818A + 854R +853P | 850W + 852A |
| AATCAC | 795K + 817Q | 818K + 854S | 850E + 852R |
| AATCAG | 795K + 817Q | 818K + 854S | 850K + 852D |
| AATCAR | 795K + 817Q | 818K + 854S | 850D + 852D |
| AATCAN | 795K + 817Q | 818K + 854S | 850W + 852A |
| AATGAC | 795K + 817Q | 818L + 854R | 850E + 852R |
| AATGAG | 795K + 817Q | 818L + 854R | 850K + 852D |
| AATGAR | 795K + 817Q | 818L + 854R | 850D + 852D |
| AATGAN | 795K + 817Q | 818L + 854R | 850W + 852A |
| AATRAC | 795K + 817Q | 818A + 854R +853F | 850E + 852R |
| AATRAG | 795K + 817Q | 818A + 854R +853F | 850K + 852D |
| AATRAR | 795K + 817Q | 818A + 854R +853F | 850D + 852D |
| AATRAN | 795K + 817Q | 818A + 854R +853F | 850W + 852A |
| AATNAC | 795K + 817Q | 818G + 854M | 850E + 852R |
| AATNAG | 795K + 817Q | 818G + 854M | 850K + 852D |
| AATNAR | 795K + 817Q | 818G + 854M | 850D + 852D |
| AATNAN | 795K + 817Q | 818G + 854M | 850W + 852A |
| AAYAAC | 795V + 817N | 818A + 854R +853P | 850E + 852R |
| AAYAAG | 795V + 817N | 818A + 854R +853P | 850K + 852D |
| AAYAAR | 795V + 817N | 818A + 854R +853P | 850D + 852D |
| AAYAAN | 795V + 817N | 818A + 854R +853P | 850W + 852A |
| AAYCAC | 795V + 817N | 818K + 854S | 850E + 852R |
| AAYCAG | 795V + 817N | 818K + 854S | 850K + 852D |
| AAYCAR | 795V + 817N | 818K + 854S | 850D + 852D |
| AAYCAN | 795V + 817N | 818K + 854S | 850W + 852A |
| AAYGAC | 795V + 817N | 818L + 854R | 850E + 852R |
| AAYGAG | 795V + 817N | 818L + 854R | 850K + 852D |
| AAYGAR | 795V + 817N | 818L + 854R | 850D + 852D |
| AAYGAN | 795V + 817N | 818L + 854R | 850W + 852A |
| AAYRAC | 795V + 817N | 818A + 854R +853F | 850E + 852R |
| AAYRAG | 795V + 817N | 818A + 854R +853F | 850K + 852D |
| AAYRAR | 795V + 817N | 818A + 854R +853F | 850D + 852D |
| AAYRAN | 795V + 817N | 818A + 854R +853F | 850W + 852A |
| AAYNAC | 795V + 817N | 818G + 854M | 850E + 852R |
| AAYNAG | 795V + 817N | 818G + 854M | 850K + 852D |
| AAYNAR | 795V + 817N | 818G + 854M | 850D + 852D |
| AAYNAN | 795V + 817N | 818G + 854M | 850W + 852A |

FIG. 23E-1

ApyPI

| RECOGNITION SEQUENCE | POSITION 3 DETERMINANTS | POSITION 4 DETERMINANTS | POSITION 6 DETERMINANTS |
|---|---|---|---|
| ATCAAC | 793E + 815N | 816A + 852R +851P | 848E + 850R |
| ATCAAG | 793E + 815N | 816A + 852R +851P | 848K + 850D |
| ATCAAR | 793E + 815N | 816A + 852R +851P | 848D + 850D |
| ATCAAN | 793E + 815N | 816A + 852R +851P | 848W + 850A |
| ATCCAC | 793E + 815N | 816K + 852S | 848E + 850R |
| ATCCAG | 793E + 815N | 816K + 852S | 848K + 850D |
| ATCCAR | 793E + 815N | 816K + 852S | 848D + 850D |
| ATCCAN | 793E + 815N | 816K + 852S | 848W + 850A |
| ATCGAC | 793E + 815N | 816L + 852R | 848E + 850R |
| ATCGAG | 793E + 815N | 816L + 852R | 848K + 850D |
| ATCGAR | 793E + 815N | 816L + 852R | 848D + 850D |
| ATCGAN | 793E + 815N | 816L + 852R | 848W + 850A |
| ATCRAC | 793E + 815N | 816A + 852R +851F | 848E + 850R |
| ATCRAG | 793E + 815N | 816A + 852R +851F | 848K + 850D |
| ATCRAR | 793E + 815N | 816A + 852R +851F | 848D + 850D |
| ATCRAN | 793E + 815N | 816A + 852R +851F | 848W + 850A |
| ATCNAC | 793E + 815N | 816G + 852M | 848E + 850R |
| ATCNAG | 793E + 815N | 816G + 852M | 848K + 850D |
| ATCNAR | 793E + 815N | 816G + 852M | 848D + 850D |
| ATCNAN | 793E + 815N | 816G + 852M | 848W + 850A |
| ATGAAC | 793R + 815D | 816A + 852R +851P | 848E + 850R |
| ATGAAG | 793R + 815D | 816A + 852R +851P | 848K + 850D |
| ATGAAR | 793R + 815D | 816A + 852R +851P | 848D + 850D |
| ATGAAN | 793R + 815D | 816A + 852R +851P | 848W + 850A |
| ATGCAC | 793R + 815D | 816K + 852S | 848E + 850R |
| ATGCAG | 793R + 815D | 816K + 852S | 848K + 850D |
| ATGCAR | 793R + 815D | 816K + 852S | 848D + 850D |
| ATGCAN | 793R + 815D | 816K + 852S | 848W + 850A |
| ATGGAC | 793R + 815D | 816L + 852R | 848E + 850R |
| ATGGAG | 793R + 815D | 816L + 852R | 848K + 850D |
| ATGGAR | 793R + 815D | 816L + 852R | 848D + 850D |
| ATGGAN | 793R + 815D | 816L + 852R | 848W + 850A |
| ATGRAC | 793R + 815D | 816A + 852R +851F | 848E + 850R |
| ATGRAG | 793R + 815D | 816A + 852R +851F | 848K + 850D |
| ATGRAR | 793R + 815D | 816A + 852R +851F | 848D + 850D |
| ATGRAN | 793R + 815D | 816A + 852R +851F | 848W + 850A |
| ATGNAC | 793R + 815D | 816G + 852M | 848E + 850R |
| ATGNAG | 793R + 815D | 816G + 852M | 848K + 850D |
| ATGNAR | 793R + 815D | 816G + 852M | 848D + 850D |
| ATGNAN | 793R + 815D | 816G + 852M | 848W + 850A |

FIG. 23E-2

ApyPI

| RECOGNITION SEQUENCE | POSITION 3 DETERMINANTS | POSITION 4 DETERMINANTS | POSITION 6 DETERMINANTS |
|---|---|---|---|
| ATTAAC | 793K + 815Q | 816A + 852R +851P | 848E + 850R |
| ATTAAG | 793K + 815Q | 816A + 852R +851P | 848K + 850D |
| ATTAAR | 793K + 815Q | 816A + 852R +851P | 848D + 850D |
| ATTAAN | 793K + 815Q | 816A + 852R +851P | 848W + 850A |
| ATTCAC | 793K + 815Q | 816K + 852S | 848E + 850R |
| ATTCAG | 793K + 815Q | 816K + 852S | 848K + 850D |
| ATTCAR | 793K + 815Q | 816K + 852S | 848D + 850D |
| ATTCAN | 793K + 815Q | 816K + 852S | 848W + 850A |
| ATTGAC | 793K + 815Q | 816L + 852R | 848E + 850R |
| ATTGAG | 793K + 815Q | 816L + 852R | 848K + 850D |
| ATTGAR | 793K + 815Q | 816L + 852R | 848D + 850D |
| ATTGAN | 793K + 815Q | 816L + 852R | 848W + 850A |
| ATTRAC | 793K + 815Q | 816A + 852R +851F | 848E + 850R |
| ATTRAG | 793K + 815Q | 816A + 852R +851F | 848K + 850D |
| ATTRAR | 793K + 815Q | 816A + 852R +851F | 848D + 850D |
| ATTRAN | 793K + 815Q | 816A + 852R +851F | 848W + 850A |
| ATTNAC | 793K + 815Q | 816G + 852M | 848E + 850R |
| ATTNAG | 793K + 815Q | 816G + 852M | 848K + 850D |
| ATTNAR | 793K + 815Q | 816G + 852M | 848D + 850D |
| ATTNAN | 793K + 815Q | 816G + 852M | 848W + 850A |
| ATYAAC | 793V + 815N | 816A + 852R +851P | 848E + 850R |
| ATYAAG | 793V + 815N | 816A + 852R +851P | 848K + 850D |
| ATYAAR | 793V + 815N | 816A + 852R +851P | 848D + 850D |
| ATYAAN | 793V + 815N | 816A + 852R +851P | 848W + 850A |
| ATYCAC | 793V + 815N | 816K + 852S | 848E + 850R |
| ATYCAG | 793V + 815N | 816K + 852S | 848K + 850D |
| ATYCAR | 793V + 815N | 816K + 852S | 848D + 850D |
| ATYCAN | 793V + 815N | 816K + 852S | 848W + 850A |
| ATYGAC | 793V + 815N | 816L + 852R | 848E + 850R |
| ATYGAG | 793V + 815N | 816L + 852R | 848K + 850D |
| ATYGAR | 793V + 815N | 816L + 852R | 848D + 850D |
| ATYGAN | 793V + 815N | 816L + 852R | 848W + 850A |
| ATYRAC | 793V + 815N | 816A + 852R +851F | 848E + 850R |
| ATYRAG | 793V + 815N | 816A + 852R +851F | 848K + 850D |
| ATYRAR | 793V + 815N | 816A + 852R +851F | 848D + 850D |
| ATYRAN | 793V + 815N | 816A + 852R +851F | 848W + 850A |
| ATYNAC | 793V + 815N | 816G + 852M | 848E + 850R |
| ATYNAG | 793V + 815N | 816G + 852M | 848K + 850D |
| ATYNAR | 793V + 815N | 816G + 852M | 848D + 850D |
| ATYNAN | 793V + 815N | 816G + 852M | 848W + 850A |

FIG. 23F-1

PspRI

| RECOGNITION SEQUENCE | POSITION 3 DETERMINANTS | POSITION 4 DETERMINANTS | POSITION 6 DETERMINANTS |
|---|---|---|---|
| CCCAAC | 767E + 789N | 790A + 826R +825P | 822E + 824R |
| CCCAAG | 767E + 789N | 790A + 826R +825P | 822K + 824D |
| CCCAAR | 767E + 789N | 790A + 826R +825P | 822D + 824D |
| CCCAAN | 767E + 789N | 790A + 826R +825P | 822W + 824A |
| CCCCAC | 767E + 789N | 790K + 826S | 822E + 824R |
| CCCCAG | 767E + 789N | 790K + 826S | 822K + 824D |
| CCCCAR | 767E + 789N | 790K + 826S | 822D + 824D |
| CCCCAN | 767E + 789N | 790K + 826S | 822W + 824A |
| CCCGAC | 767E + 789N | 790L + 826R | 822E + 824R |
| CCCGAG | 767E + 789N | 790L + 826R | 822K + 824D |
| CCCGAR | 767E + 789N | 790L + 826R | 822D + 824D |
| CCCGAN | 767E + 789N | 790L + 826R | 822W + 824A |
| CCCRAC | 767E + 789N | 790A + 826R +825F | 822E + 824R |
| CCCRAG | 767E + 789N | 790A + 826R +825F | 822K + 824D |
| CCCRAR | 767E + 789N | 790A + 826R +825F | 822D + 824D |
| CCCRAN | 767E + 789N | 790A + 826R +825F | 822W + 824A |
| CCCNAC | 767E + 789N | 790G + 826M | 822E + 824R |
| CCCNAG | 767E + 789N | 790G + 826M | 822K + 824D |
| CCCNAR | 767E + 789N | 790G + 826M | 822D + 824D |
| CCCNAN | 767E + 789N | 790G + 826M | 822W + 824A |
| CCGAAC | 767R + 789D | 790A + 826R +825P | 822E + 824R |
| CCGAAG | 767R + 789D | 790A + 826R +825P | 822K + 824D |
| CCGAAR | 767R + 789D | 790A + 826R +825P | 822D + 824D |
| CCGAAN | 767R + 789D | 790A + 826R +825P | 822W + 824A |
| CCGCAC | 767R + 789D | 790K + 826S | 822E + 824R |
| CCGCAG | 767R + 789D | 790K + 826S | 822K + 824D |
| CCGCAR | 767R + 789D | 790K + 826S | 822D + 824D |
| CCGCAN | 767R + 789D | 790K + 826S | 822W + 824A |
| CCGGAC | 767R + 789D | 790L + 826R | 822E + 824R |
| CCGGAG | 767R + 789D | 790L + 826R | 822K + 824D |
| CCGGAR | 767R + 789D | 790L + 826R | 822D + 824D |
| CCGGAN | 767R + 789D | 790L + 826R | 822W + 824A |
| CCGRAC | 767R + 789D | 790A + 826R +825F | 822E + 824R |
| CCGRAG | 767R + 789D | 790A + 826R +825F | 822K + 824D |
| CCGRAR | 767R + 789D | 790A + 826R +825F | 822D + 824D |
| CCGRAN | 767R + 789D | 790A + 826R +825F | 822W + 824A |
| CCGNAC | 767R + 789D | 790G + 826M | 822E + 824R |
| CCGNAG | 767R + 789D | 790G + 826M | 822K + 824D |
| CCGNAR | 767R + 789D | 790G + 826M | 822D + 824D |
| CCGNAN | 767R + 789D | 790G + 826M | 822W + 824A |

FIG. 23F-2

PspRI

| RECOGNITION SEQUENCE | POSITION 3 DETERMINANTS | POSITION 4 DETERMINANTS | POSITION 6 DETERMINANTS |
|---|---|---|---|
| CCTAAC | 767K + 789Q | 790A + 826R +825P | 822E + 824R |
| CCTAAG | 767K + 789Q | 790A + 826R +825P | 822K + 824D |
| CCTAAR | 767K + 789Q | 790A + 826R +825P | 822D + 824D |
| CCTAAN | 767K + 789Q | 790A + 826R +825P | 822W + 824A |
| CCTCAC | 767K + 789Q | 790K + 826S | 822E + 824R |
| CCTCAG | 767K + 789Q | 790K + 826S | 822K + 824D |
| CCTCAR | 767K + 789Q | 790K + 826S | 822D + 824D |
| CCTCAN | 767K + 789Q | 790K + 826S | 822W + 824A |
| CCTGAC | 767K + 789Q | 790L + 826R | 822E + 824R |
| CCTGAG | 767K + 789Q | 790L + 826R | 822K + 824D |
| CCTGAR | 767K + 789Q | 790L + 826R | 822D + 824D |
| CCTGAN | 767K + 789Q | 790L + 826R | 822W + 824A |
| CCTRAC | 767K + 789Q | 790A + 826R +825F | 822E + 824R |
| CCTRAG | 767K + 789Q | 790A + 826R +825F | 822K + 824D |
| CCTRAR | 767K + 789Q | 790A + 826R +825F | 822D + 824D |
| CCTRAN | 767K + 789Q | 790A + 826R +825F | 822W + 824A |
| CCTNAC | 767K + 789Q | 790G + 826M | 822E + 824R |
| CCTNAG | 767K + 789Q | 790G + 826M | 822K + 824D |
| CCTNAR | 767K + 789Q | 790G + 826M | 822D + 824D |
| CCTNAN | 767K + 789Q | 790G + 826M | 822W + 824A |
| CCYAAC | 767V + 789N | 790A + 826R +825P | 822E + 824R |
| CCYAAG | 767V + 789N | 790A + 826R +825P | 822K + 824D |
| CCYAAR | 767V + 789N | 790A + 826R +825P | 822D + 824D |
| CCYAAN | 767V + 789N | 790A + 826R +825P | 822W + 824A |
| CCYCAC | 767V + 789N | 790K + 826S | 822E + 824R |
| CCYCAG | 767V + 789N | 790K + 826S | 822K + 824D |
| CCYCAR | 767V + 789N | 790K + 826S | 822D + 824D |
| CCYCAN | 767V + 789N | 790K + 826S | 822W + 824A |
| CCYGAC | 767V + 789N | 790L + 826R | 822E + 824R |
| CCYGAG | 767V + 789N | 790L + 826R | 822K + 824D |
| CCYGAR | 767V + 789N | 790L + 826R | 822D + 824D |
| CCYGAN | 767V + 789N | 790L + 826R | 822W + 824A |
| CCYRAC | 767V + 789N | 790A + 826R +825F | 822E + 824R |
| CCYRAG | 767V + 789N | 790A + 826R +825F | 822K + 824D |
| CCYRAR | 767V + 789N | 790A + 826R +825F | 822D + 824D |
| CCYRAN | 767V + 789N | 790A + 826R +825F | 822W + 824A |
| CCYNAC | 767V + 789N | 790G + 826M | 822E + 824R |
| CCYNAG | 767V + 789N | 790G + 826M | 822K + 824D |
| CCYNAR | 767V + 789N | 790G + 826M | 822D + 824D |
| CCYNAN | 767V + 789N | 790G + 826M | 822W + 824A |

FIG. 23G-1

AquIII

| RECOGNITION SEQUENCE | POSITION 3 DETERMINANTS | POSITION 4 DETERMINANTS | POSITION 6 DETERMINANTS |
|---|---|---|---|
| GACAAC | 746E + 768N | 769A + 805R +804P | 801E + 803R |
| GACAAG | 746E + 768N | 769A + 805R +804P | 801K + 803D |
| GACAAR | 746E + 768N | 769A + 805R +804P | 801D + 803D |
| GACAAN | 746E + 768N | 769A + 805R +804P | 801W + 803A |
| GACCAC | 746E + 768N | 769K + 805S | 801E + 803R |
| GACCAG | 746E + 768N | 769K + 805S | 801K + 803D |
| GACCAR | 746E + 768N | 769K + 805S | 801D + 803D |
| GACCAN | 746E + 768N | 769K + 805S | 801W + 803A |
| GACGAC | 746E + 768N | 769L + 805R | 801E + 803R |
| GACGAG | 746E + 768N | 769L + 805R | 801K + 803D |
| GACGAR | 746E + 768N | 769L + 805R | 801D + 803D |
| GACGAN | 746E + 768N | 769L + 805R | 801W + 803A |
| GACRAC | 746E + 768N | 769A + 805R +804F | 801E + 803R |
| GACRAG | 746E + 768N | 769A + 805R +804F | 801K + 803D |
| GACRAR | 746E + 768N | 769A + 805R +804F | 801D + 803D |
| GACRAN | 746E + 768N | 769A + 805R +804F | 801W + 803A |
| GACNAC | 746E + 768N | 769G + 805M | 801E + 803R |
| GACNAG | 746E + 768N | 769G + 805M | 801K + 803D |
| GACNAR | 746E + 768N | 769G + 805M | 801D + 803D |
| GACNAN | 746E + 768N | 769G + 805M | 801W + 803A |
| GAGAAC | 746R + 768D | 769A + 805R +804P | 801E + 803R |
| GAGAAG | 746R + 768D | 769A + 805R +804P | 801K + 803D |
| GAGAAR | 746R + 768D | 769A + 805R +804P | 801D + 803D |
| GAGAAN | 746R + 768D | 769A + 805R +804P | 801W + 803A |
| GAGCAC | 746R + 768D | 769K + 805S | 801E + 803R |
| GAGCAG | 746R + 768D | 769K + 805S | 801K + 803D |
| GAGCAR | 746R + 768D | 769K + 805S | 801D + 803D |
| GAGCAN | 746R + 768D | 769K + 805S | 801W + 803A |
| GAGGAC | 746R + 768D | 769L + 805R | 801E + 803R |
| GAGGAG | 746R + 768D | 769L + 805R | 801K + 803D |
| GAGGAR | 746R + 768D | 769L + 805R | 801D + 803D |
| GAGGAN | 746R + 768D | 769L + 805R | 801W + 803A |
| GAGRAC | 746R + 768D | 769A + 805R +804F | 801E + 803R |
| GAGRAG | 746R + 768D | 769A + 805R +804F | 801K + 803D |
| GAGRAR | 746R + 768D | 769A + 805R +804F | 801D + 803D |
| GAGRAN | 746R + 768D | 769A + 805R +804F | 801W + 803A |
| GAGNAC | 746R + 768D | 769G + 805M | 801E + 803R |
| GAGNAG | 746R + 768D | 769G + 805M | 801K + 803D |
| GAGNAR | 746R + 768D | 769G + 805M | 801D + 803D |
| GAGNAN | 746R + 768D | 769G + 805M | 801W + 803A |

FIG. 23G-2

AquIII

| RECOGNITION SEQUENCE | POSITION 3 DETERMINANTS | POSITION 4 DETERMINANTS | POSITION 6 DETERMINANTS |
|---|---|---|---|
| GATAAC | 746K + 768Q | 769A + 805R +804P | 801E + 803R |
| GATAAG | 746K + 768Q | 769A + 805R +804P | 801K + 803D |
| GATAAR | 746K + 768Q | 769A + 805R +804P | 801D + 803D |
| GATAAN | 746K + 768Q | 769A + 805R +804P | 801W + 803A |
| GATCAC | 746K + 768Q | 769K + 805S | 801E + 803R |
| GATCAG | 746K + 768Q | 769K + 805S | 801K + 803D |
| GATCAR | 746K + 768Q | 769K + 805S | 801D + 803D |
| GATCAN | 746K + 768Q | 769K + 805S | 801W + 803A |
| GATGAC | 746K + 768Q | 769L + 805R | 801E + 803R |
| GATGAG | 746K + 768Q | 769L + 805R | 801K + 803D |
| GATGAR | 746K + 768Q | 769L + 805R | 801D + 803D |
| GATGAN | 746K + 768Q | 769L + 805R | 801W + 803A |
| GATRAC | 746K + 768Q | 769A + 805R +804F | 801E + 803R |
| GATRAG | 746K + 768Q | 769A + 805R +804F | 801K + 803D |
| GATRAR | 746K + 768Q | 769A + 805R +804F | 801D + 803D |
| GATRAN | 746K + 768Q | 769A + 805R +804F | 801W + 803A |
| GATNAC | 746K + 768Q | 769G + 805M | 801E + 803R |
| GATNAG | 746K + 768Q | 769G + 805M | 801K + 803D |
| GATNAR | 746K + 768Q | 769G + 805M | 801D + 803D |
| GATNAN | 746K + 768Q | 769G + 805M | 801W + 803A |
| GAYAAC | 746V + 768N | 769A + 805R +804P | 801E + 803R |
| GAYAAG | 746V + 768N | 769A + 805R +804P | 801K + 803D |
| GAYAAR | 746V + 768N | 769A + 805R +804P | 801D + 803D |
| GAYAAN | 746V + 768N | 769A + 805R +804P | 801W + 803A |
| GAYCAC | 746V + 768N | 769K + 805S | 801E + 803R |
| GAYCAG | 746V + 768N | 769K + 805S | 801K + 803D |
| GAYCAR | 746V + 768N | 769K + 805S | 801D + 803D |
| GAYCAN | 746V + 768N | 769K + 805S | 801W + 803A |
| GAYGAC | 746V + 768N | 769L + 805R | 801E + 803R |
| GAYGAG | 746V + 768N | 769L + 805R | 801K + 803D |
| GAYGAR | 746V + 768N | 769L + 805R | 801D + 803D |
| GAYGAN | 746V + 768N | 769L + 805R | 801W + 803A |
| GAYRAC | 746V + 768N | 769A + 805R +804F | 801E + 803R |
| GAYRAG | 746V + 768N | 769A + 805R +804F | 801K + 803D |
| GAYRAR | 746V + 768N | 769A + 805R +804F | 801D + 803D |
| GAYRAN | 746V + 768N | 769A + 805R +804F | 801W + 803A |
| GAYNAC | 746V + 768N | 769G + 805M | 801E + 803R |
| GAYNAG | 746V + 768N | 769G + 805M | 801K + 803D |
| GAYNAR | 746V + 768N | 769G + 805M | 801D + 803D |
| GAYNAN | 746V + 768N | 769G + 805M | 801W + 803A |

FIG. 23H-1

DrdIV

| RECOGNITION SEQUENCE | POSITION 3 DETERMINANTS | POSITION 4 DETERMINANTS | POSITION 6 DETERMINANTS |
|---|---|---|---|
| TACAAC | 865E + 883N | 884A + 920R +919P | 916E + 918R |
| TACAAG | 865E + 883N | 884A + 920R +919P | 916K + 918D |
| TACAAR | 865E + 883N | 884A + 920R +919P | 916D + 918D |
| TACAAN | 865E + 883N | 884A + 920R +919P | 916W + 918A |
| TACCAC | 865E + 883N | 884K + 920S | 916E + 918R |
| TACCAG | 865E + 883N | 884K + 920S | 916K + 918D |
| TACCAR | 865E + 883N | 884K + 920S | 916D + 918D |
| TACCAN | 865E + 883N | 884K + 920S | 916W + 918A |
| TACGAC | 865E + 883N | 884L + 920R | 916E + 918R |
| TACGAG | 865E + 883N | 884L + 920R | 916K + 918D |
| TACGAR | 865E + 883N | 884L + 920R | 916D + 918D |
| TACGAN | 865E + 883N | 884L + 920R | 916W + 918A |
| TACRAC | 865E + 883N | 884A + 920R +919F | 916E + 918R |
| TACRAG | 865E + 883N | 884A + 920R +919F | 916K + 918D |
| TACRAR | 865E + 883N | 884A + 920R +919F | 916D + 918D |
| TACRAN | 865E + 883N | 884A + 920R +919F | 916W + 918A |
| TACNAC | 865E + 883N | 884G + 920M | 916E + 918R |
| TACNAG | 865E + 883N | 884G + 920M | 916K + 918D |
| TACNAR | 865E + 883N | 884G + 920M | 916D + 918D |
| TACNAN | 865E + 883N | 884G + 920M | 916W + 918A |
| TAGAAC | 865R + 883D | 884A + 920R +919P | 916E + 918R |
| TAGAAG | 865R + 883D | 884A + 920R +919P | 916K + 918D |
| TAGAAR | 865R + 883D | 884A + 920R +919P | 916D + 918D |
| TAGAAN | 865R + 883D | 884A + 920R +919P | 916W + 918A |
| TAGCAC | 865R + 883D | 884K + 920S | 916E + 918R |
| TAGCAG | 865R + 883D | 884K + 920S | 916K + 918D |
| TAGCAR | 865R + 883D | 884K + 920S | 916D + 918D |
| TAGCAN | 865R + 883D | 884K + 920S | 916W + 918A |
| TAGGAC | 865R + 883D | 884L + 920R | 916E + 918R |
| TAGGAG | 865R + 883D | 884L + 920R | 916K + 918D |
| TAGGAR | 865R + 883D | 884L + 920R | 916D + 918D |
| TAGGAN | 865R + 883D | 884L + 920R | 916W + 918A |
| TAGRAC | 865R + 883D | 884A + 920R +919F | 916E + 918R |
| TAGRAG | 865R + 883D | 884A + 920R +919F | 916K + 918D |
| TAGRAR | 865R + 883D | 884A + 920R +919F | 916D + 918D |
| TAGRAN | 865R + 883D | 884A + 920R +919F | 916W + 918A |
| TAGNAC | 865R + 883D | 884G + 920M | 916E + 918R |
| TAGNAG | 865R + 883D | 884G + 920M | 916K + 918D |
| TAGNAR | 865R + 883D | 884G + 920M | 916D + 918D |
| TAGNAN | 865R + 883D | 884G + 920M | 916W + 918A |

FIG. 23H-2

DrdIV

| RECOGNITION SEQUENCE | POSITION 3 DETERMINANTS | POSITION 4 DETERMINANTS | POSITION 6 DETERMINANTS |
|---|---|---|---|
| TATAAC | 865K + 883Q | 884A + 920R +919P | 916E + 918R |
| TATAAG | 865K + 883Q | 884A + 920R +919P | 916K + 918D |
| TATAAR | 865K + 883Q | 884A + 920R +919P | 916D + 918D |
| TATAAN | 865K + 883Q | 884A + 920R +919P | 916W + 918A |
| TATCAC | 865K + 883Q | 884K + 920S | 916E + 918R |
| TATCAG | 865K + 883Q | 884K + 920S | 916K + 918D |
| TATCAR | 865K + 883Q | 884K + 920S | 916D + 918D |
| TATCAN | 865K + 883Q | 884K + 920S | 916W + 918A |
| TATGAC | 865K + 883Q | 884L + 920R | 916E + 918R |
| TATGAG | 865K + 883Q | 884L + 920R | 916K + 918D |
| TATGAR | 865K + 883Q | 884L + 920R | 916D + 918D |
| TATGAN | 865K + 883Q | 884L + 920R | 916W + 918A |
| TATRAC | 865K + 883Q | 884A + 920R +919F | 916E + 918R |
| TATRAG | 865K + 883Q | 884A + 920R +919F | 916K + 918D |
| TATRAR | 865K + 883Q | 884A + 920R +919F | 916D + 918D |
| TATRAN | 865K + 883Q | 884A + 920R +919F | 916W + 918A |
| TATNAC | 865K + 883Q | 884G + 920M | 916E + 918R |
| TATNAG | 865K + 883Q | 884G + 920M | 916K + 918D |
| TATNAR | 865K + 883Q | 884G + 920M | 916D + 918D |
| TATNAN | 865K + 883Q | 884G + 920M | 916W + 918A |
| TAYAAC | 865V + 883N | 884A + 920R +919P | 916E + 918R |
| TAYAAG | 865V + 883N | 884A + 920R +919P | 916K + 918D |
| TAYAAR | 865V + 883N | 884A + 920R +919P | 916D + 918D |
| TAYAAN | 865V + 883N | 884A + 920R +919P | 916W + 918A |
| TAYCAC | 865V + 883N | 884K + 920S | 916E + 918R |
| TAYCAG | 865V + 883N | 884K + 920S | 916K + 918D |
| TAYCAR | 865V + 883N | 884K + 920S | 916D + 918D |
| TAYCAN | 865V + 883N | 884K + 920S | 916W + 918A |
| TAYGAC | 865V + 883N | 884L + 920R | 916E + 918R |
| TAYGAG | 865V + 883N | 884L + 920R | 916K + 918D |
| TAYGAR | 865V + 883N | 884L + 920R | 916D + 918D |
| TAYGAN | 865V + 883N | 884L + 920R | 916W + 918A |
| TAYRAC | 865V + 883N | 884A + 920R +919F | 916E + 918R |
| TAYRAG | 865V + 883N | 884A + 920R +919F | 916K + 918D |
| TAYRAR | 865V + 883N | 884A + 920R +919F | 916D + 918D |
| TAYRAN | 865V + 883N | 884A + 920R +919F | 916W + 918A |
| TAYNAC | 865V + 883N | 884G + 920M | 916E + 918R |
| TAYNAG | 865V + 883N | 884G + 920M | 916K + 918D |
| TAYNAR | 865V + 883N | 884G + 920M | 916D + 918D |
| TAYNAN | 865V + 883N | 884G + 920M | 916W + 918A |

FIG. 23I-1

PspOMII

| RECOGNITION SEQUENCE | POSITION 3 DETERMINANTS | POSITION 4 DETERMINANTS | POSITION 6 DETERMINANTS |
|---|---|---|---|
| CGCCAAC | 879E + 897N | 898A + 937R +936P | 933E + 935R |
| CGCCAAG | 879E + 897N | 898A + 937R +936P | 933K + 935D |
| CGCCAAR | 879E + 897N | 898A + 937R +936P | 933D + 935D |
| CGCCAAN | 879E + 897N | 898A + 937R +936P | 933W + 935A |
| CGCCCAC | 879E + 897N | 898K + 937S | 933E + 935R |
| CGCCCAG | 879E + 897N | 898K + 937S | 933K + 935D |
| CGCCCAR | 879E + 897N | 898K + 937S | 933D + 935D |
| CGCCCAN | 879E + 897N | 898K + 937S | 933W + 935A |
| CGCCGAC | 879E + 897N | 898L + 937R | 933E + 935R |
| CGCCGAG | 879E + 897N | 898L + 937R | 933K + 935D |
| CGCCGAR | 879E + 897N | 898L + 937R | 933D + 935D |
| CGCCGAN | 879E + 897N | 898L + 937R | 933W + 935A |
| CGCCRAC | 879E + 897N | 898A + 937R +936F | 933E + 935R |
| CGCCRAG | 879E + 897N | 898A + 937R +936F | 933K + 935D |
| CGCCRAR | 879E + 897N | 898A + 937R +936F | 933D + 935D |
| CGCCRAN | 879E + 897N | 898A + 937R +936F | 933W + 935A |
| CGCCNAC | 879E + 897N | 898G + 937M | 933E + 935R |
| CGCCNAG | 879E + 897N | 898G + 937M | 933K + 935D |
| CGCCNAR | 879E + 897N | 898G + 937M | 933D + 935D |
| CGCCNAN | 879E + 897N | 898G + 937M | 933W + 935A |
| CGCGAAC | 879R + 897D | 898A + 937R +936P | 933E + 935R |
| CGCGAAG | 879R + 897D | 898A + 937R +936P | 933K + 935D |
| CGCGAAR | 879R + 897D | 898A + 937R +936P | 933D + 935D |
| CGCGAAN | 879R + 897D | 898A + 937R +936P | 933W + 935A |
| CGCGCAC | 879R + 897D | 898K + 937S | 933E + 935R |
| CGCGCAG | 879R + 897D | 898K + 937S | 933K + 935D |
| CGCGCAR | 879R + 897D | 898K + 937S | 933D + 935D |
| CGCGCAN | 879R + 897D | 898K + 937S | 933W + 935A |
| CGCGGAC | 879R + 897D | 898L + 937R | 933E + 935R |
| CGCGGAG | 879R + 897D | 898L + 937R | 933K + 935D |
| CGCGGAR | 879R + 897D | 898L + 937R | 933D + 935D |
| CGCGGAN | 879R + 897D | 898L + 937R | 933W + 935A |
| CGCGRAC | 879R + 897D | 898A + 937R +936F | 933E + 935R |
| CGCGRAG | 879R + 897D | 898A + 937R +936F | 933K + 935D |
| CGCGRAR | 879R + 897D | 898A + 937R +936F | 933D + 935D |
| CGCGRAN | 879R + 897D | 898A + 937R +936F | 933W + 935A |
| CGCGNAC | 879R + 897D | 898G + 937M | 933E + 935R |
| CGCGNAG | 879R + 897D | 898G + 937M | 933K + 935D |
| CGCGNAR | 879R + 897D | 898G + 937M | 933D + 935D |
| CGCGNAN | 879R + 897D | 898G + 937M | 933W + 935A |

FIG. 23I-2

PspOMII

| RECOGNITION SEQUENCE | POSITION 3 DETERMINANTS | POSITION 4 DETERMINANTS | POSITION 6 DETERMINANTS |
|---|---|---|---|
| CGCTAAC | 879K + 897Q | 898A + 937R +936P | 933E + 935R |
| CGCTAAG | 879K + 897Q | 898A + 937R +936P | 933K + 935D |
| CGCTAAR | 879K + 897Q | 898A + 937R +936P | 933D + 935D |
| CGCTAAN | 879K + 897Q | 898A + 937R +936P | 933W + 935A |
| CGCTCAC | 879K + 897Q | 898K + 937S | 933E + 935R |
| CGCTCAG | 879K + 897Q | 898K + 937S | 933K + 935D |
| CGCTCAR | 879K + 897Q | 898K + 937S | 933D + 935D |
| CGCTCAN | 879K + 897Q | 898K + 937S | 933W + 935A |
| CGCTGAC | 879K + 897Q | 898L + 937R | 933E + 935R |
| CGCTGAG | 879K + 897Q | 898L + 937R | 933K + 935D |
| CGCTGAR | 879K + 897Q | 898L + 937R | 933D + 935D |
| CGCTGAN | 879K + 897Q | 898L + 937R | 933W + 935A |
| CGCTRAC | 879K + 897Q | 898A + 937R +936F | 933E + 935R |
| CGCTRAG | 879K + 897Q | 898A + 937R +936F | 933K + 935D |
| CGCTRAR | 879K + 897Q | 898A + 937R +936F | 933D + 935D |
| CGCTRAN | 879K + 897Q | 898A + 937R +936F | 933W + 935A |
| CGCTNAC | 879K + 897Q | 898G + 937M | 933E + 935R |
| CGCTNAG | 879K + 897Q | 898G + 937M | 933K + 935D |
| CGCTNAR | 879K + 897Q | 898G + 937M | 933D + 935D |
| CGCTNAN | 879K + 897Q | 898G + 937M | 933W + 935A |
| CGCYAAC | 879V + 897N | 898A + 937R +936P | 933E + 935R |
| CGCYAAG | 879V + 897N | 898A + 937R +936P | 933K + 935D |
| CGCYAAR | 879V + 897N | 898A + 937R +936P | 933D + 935D |
| CGCYAAN | 879V + 897N | 898A + 937R +936P | 933W + 935A |
| CGCYCAC | 879V + 897N | 898K + 937S | 933E + 935R |
| CGCYCAG | 879V + 897N | 898K + 937S | 933K + 935D |
| CGCYCAR | 879V + 897N | 898K + 937S | 933D + 935D |
| CGCYCAN | 879V + 897N | 898K + 937S | 933W + 935A |
| CGCYGAC | 879V + 897N | 898L + 937R | 933E + 935R |
| CGCYGAG | 879V + 897N | 898L + 937R | 933K + 935D |
| CGCYGAR | 879V + 897N | 898L + 937R | 933D + 935D |
| CGCYGAN | 879V + 897N | 898L + 937R | 933W + 935A |
| CGCYRAC | 879V + 897N | 898A + 937R +936F | 933E + 935R |
| CGCYRAG | 879V + 897N | 898A + 937R +936F | 933K + 935D |
| CGCYRAR | 879V + 897N | 898A + 937R +936F | 933D + 935D |
| CGCYRAN | 879V + 897N | 898A + 937R +936F | 933W + 935A |
| CGCYNAC | 879V + 897N | 898G + 937M | 933E + 935R |
| CGCYNAG | 879V + 897N | 898G + 937M | 933K + 935D |
| CGCYNAR | 879V + 897N | 898G + 937M | 933D + 935D |
| CGCYNAN | 879V + 897N | 898G + 937M | 933W + 935A |

FIG. 23J-1

RpaB5I

| RECOGNITION SEQUENCE | POSITION 3 DETERMINANTS | POSITION 4 DETERMINANTS | POSITION 6 DETERMINANTS |
|---|---|---|---|
| CGRCAAC | 845E + 863N | 864A + 900R +899P | 896E + 898R |
| CGRCAAG | 845E + 863N | 864A + 900R +899P | 896K + 898D |
| CGRCAAR | 845E + 863N | 864A + 900R +899P | 896D + 898D |
| CGRCAAN | 845E + 863N | 864A + 900R +899P | 896W + 898A |
| CGRCCAC | 845E + 863N | 864K + 900S | 896E + 898R |
| CGRCCAG | 845E + 863N | 864K + 900S | 896K + 898D |
| CGRCCAR | 845E + 863N | 864K + 900S | 896D + 898D |
| CGRCCAN | 845E + 863N | 864K + 900S | 896W + 898A |
| CGRCGAC | 845E + 863N | 864L + 900R | 896E + 898R |
| CGRCGAG | 845E + 863N | 864L + 900R | 896K + 898D |
| CGRCGAR | 845E + 863N | 864L + 900R | 896D + 898D |
| CGRCGAN | 845E + 863N | 864L + 900R | 896W + 898A |
| CGRCRAC | 845E + 863N | 864A + 900R +899F | 896E + 898R |
| CGRCRAG | 845E + 863N | 864A + 900R +899F | 896K + 898D |
| CGRCRAR | 845E + 863N | 864A + 900R +899F | 896D + 898D |
| CGRCRAN | 845E + 863N | 864A + 900R +899F | 896W + 898A |
| CGRCNAC | 845E + 863N | 864G + 900M | 896E + 898R |
| CGRCNAG | 845E + 863N | 864G + 900M | 896K + 898D |
| CGRCNAR | 845E + 863N | 864G + 900M | 896D + 898D |
| CGRCNAN | 845E + 863N | 864G + 900M | 896W + 898A |
| CGRGAAC | 845R + 863D | 864A + 900R +899P | 896E + 898R |
| CGRGAAG | 845R + 863D | 864A + 900R +899P | 896K + 898D |
| CGRGAAR | 845R + 863D | 864A + 900R +899P | 896D + 898D |
| CGRGAAN | 845R + 863D | 864A + 900R +899P | 896W + 898A |
| CGRGCAC | 845R + 863D | 864K + 900S | 896E + 898R |
| CGRGCAG | 845R + 863D | 864K + 900S | 896K + 898D |
| CGRGCAR | 845R + 863D | 864K + 900S | 896D + 898D |
| CGRGCAN | 845R + 863D | 864K + 900S | 896W + 898A |
| CGRGGAC | 845R + 863D | 864L + 900R | 896E + 898R |
| CGRGGAG | 845R + 863D | 864L + 900R | 896K + 898D |
| CGRGGAR | 845R + 863D | 864L + 900R | 896D + 898D |
| CGRGGAN | 845R + 863D | 864L + 900R | 896W + 898A |
| CGRGRAC | 845R + 863D | 864A + 900R +899F | 896E + 898R |
| CGRGRAG | 845R + 863D | 864A + 900R +899F | 896K + 898D |
| CGRGRAR | 845R + 863D | 864A + 900R +899F | 896D + 898D |
| CGRGRAN | 845R + 863D | 864A + 900R +899F | 896W + 898A |
| CGRGNAC | 845R + 863D | 864G + 900M | 896E + 898R |
| CGRGNAG | 845R + 863D | 864G + 900M | 896K + 898D |
| CGRGNAR | 845R + 863D | 864G + 900M | 896D + 898D |
| CGRGNAN | 845R + 863D | 864G + 900M | 896W + 898A |

FIG. 23J-2

RpaB5I

| RECOGNITION SEQUENCE | POSITION 3 DETERMINANTS | POSITION 4 DETERMINANTS | POSITION 6 DETERMINANTS |
|---|---|---|---|
| CGRTAAC | 845K + 863Q | 864A + 900R +899P | 896E + 898R |
| CGRTAAG | 845K + 863Q | 864A + 900R +899P | 896K + 898D |
| CGRTAAR | 845K + 863Q | 864A + 900R +899P | 896D + 898D |
| CGRTAAN | 845K + 863Q | 864A + 900R +899P | 896W + 898A |
| CGRTCAC | 845K + 863Q | 864K + 900S | 896E + 898R |
| CGRTCAG | 845K + 863Q | 864K + 900S | 896K + 898D |
| CGRTCAR | 845K + 863Q | 864K + 900S | 896D + 898D |
| CGRTCAN | 845K + 863Q | 864K + 900S | 896W + 898A |
| CGRTGAC | 845K + 863Q | 864L + 900R | 896E + 898R |
| CGRTGAG | 845K + 863Q | 864L + 900R | 896K + 898D |
| CGRTGAR | 845K + 863Q | 864L + 900R | 896D + 898D |
| CGRTGAN | 845K + 863Q | 864L + 900R | 896W + 898A |
| CGRTRAC | 845K + 863Q | 864A + 900R +899F | 896E + 898R |
| CGRTRAG | 845K + 863Q | 864A + 900R +899F | 896K + 898D |
| CGRTRAR | 845K + 863Q | 864A + 900R +899F | 896D + 898D |
| CGRTRAN | 845K + 863Q | 864A + 900R +899F | 896W + 898A |
| CGRTNAC | 845K + 863Q | 864G + 900M | 896E + 898R |
| CGRTNAG | 845K + 863Q | 864G + 900M | 896K + 898D |
| CGRTNAR | 845K + 863Q | 864G + 900M | 896D + 898D |
| CGRTNAN | 845K + 863Q | 864G + 900M | 896W + 898A |
| CGRYAAC | 845V + 863N | 864A + 900R +899P | 896E + 898R |
| CGRYAAG | 845V + 863N | 864A + 900R +899P | 896K + 898D |
| CGRYAAR | 845V + 863N | 864A + 900R +899P | 896D + 898D |
| CGRYAAN | 845V + 863N | 864A + 900R +899P | 896W + 898A |
| CGRYCAC | 845V + 863N | 864K + 900S | 896E + 898R |
| CGRYCAG | 845V + 863N | 864K + 900S | 896K + 898D |
| CGRYCAR | 845V + 863N | 864K + 900S | 896D + 898D |
| CGRYCAN | 845V + 863N | 864K + 900S | 896W + 898A |
| CGRYGAC | 845V + 863N | 864L + 900R | 896E + 898R |
| CGRYGAG | 845V + 863N | 864L + 900R | 896K + 898D |
| CGRYGAR | 845V + 863N | 864L + 900R | 896D + 898D |
| CGRYGAN | 845V + 863N | 864L + 900R | 896W + 898A |
| CGRYRAC | 845V + 863N | 864A + 900R +899F | 896E + 898R |
| CGRYRAG | 845V + 863N | 864A + 900R +899F | 896K + 898D |
| CGRYRAR | 845V + 863N | 864A + 900R +899F | 896D + 898D |
| CGRYRAN | 845V + 863N | 864A + 900R +899F | 896W + 898A |
| CGRYNAC | 845V + 863N | 864G + 900M | 896E + 898R |
| CGRYNAG | 845V + 863N | 864G + 900M | 896K + 898D |
| CGRYNAR | 845V + 863N | 864G + 900M | 896D + 898D |
| CGRYNAN | 845V + 863N | 864G + 900M | 896W + 898A |

FIG. 23K-1

MaqI

| RECOGNITION SEQUENCE | POSITION 3 DETERMINANTS | POSITION 4 DETERMINANTS | POSITION 6 DETERMINANTS |
|---|---|---|---|
| CRTCAAC | 849E + 867N | 868A + 904R +903P | 900E + 902R |
| CRTCAAG | 849E + 867N | 868A + 904R +903P | 900K + 902D |
| CRTCAAR | 849E + 867N | 868A + 904R +903P | 900D + 902D |
| CRTCAAN | 849E + 867N | 868A + 904R +903P | 900W + 902A |
| CRTCCAC | 849E + 867N | 868K + 904S | 900E + 902R |
| CRTCCAG | 849E + 867N | 868K + 904S | 900K + 902D |
| CRTCCAR | 849E + 867N | 868K + 904S | 900D + 902D |
| CRTCCAN | 849E + 867N | 868K + 904S | 900W + 902A |
| CRTCGAC | 849E + 867N | 868L + 904R | 900E + 902R |
| CRTCGAG | 849E + 867N | 868L + 904R | 900K + 902D |
| CRTCGAR | 849E + 867N | 868L + 904R | 900D + 902D |
| CRTCGAN | 849E + 867N | 868L + 904R | 900W + 902A |
| CRTCRAC | 849E + 867N | 868A + 904R +903F | 900E + 902R |
| CRTCRAG | 849E + 867N | 868A + 904R +903F | 900K + 902D |
| CRTCRAR | 849E + 867N | 868A + 904R +903F | 900D + 902D |
| CRTCRAN | 849E + 867N | 868A + 904R +903F | 900W + 902A |
| CRTCNAC | 849E + 867N | 868G + 904M | 900E + 902R |
| CRTCNAG | 849E + 867N | 868G + 904M | 900K + 902D |
| CRTCNAR | 849E + 867N | 868G + 904M | 900D + 902D |
| CRTCNAN | 849E + 867N | 868G + 904M | 900W + 902A |
| CRTGAAC | 849R + 867D | 868A + 904R +903P | 900E + 902R |
| CRTGAAG | 849R + 867D | 868A + 904R +903P | 900K + 902D |
| CRTGAAR | 849R + 867D | 868A + 904R +903P | 900D + 902D |
| CRTGAAN | 849R + 867D | 868A + 904R +903P | 900W + 902A |
| CRTGCAC | 849R + 867D | 868K + 904S | 900E + 902R |
| CRTGCAG | 849R + 867D | 868K + 904S | 900K + 902D |
| CRTGCAR | 849R + 867D | 868K + 904S | 900D + 902D |
| CRTGCAN | 849R + 867D | 868K + 904S | 900W + 902A |
| CRTGGAC | 849R + 867D | 868L + 904R | 900E + 902R |
| CRTGGAG | 849R + 867D | 868L + 904R | 900K + 902D |
| CRTGGAR | 849R + 867D | 868L + 904R | 900D + 902D |
| CRTGGAN | 849R + 867D | 868L + 904R | 900W + 902A |
| CRTGRAC | 849R + 867D | 868A + 904R +903F | 900E + 902R |
| CRTGRAG | 849R + 867D | 868A + 904R +903F | 900K + 902D |
| CRTGRAR | 849R + 867D | 868A + 904R +903F | 900D + 902D |
| CRTGRAN | 849R + 867D | 868A + 904R +903F | 900W + 902A |
| CRTGNAC | 849R + 867D | 868G + 904M | 900E + 902R |
| CRTGNAG | 849R + 867D | 868G + 904M | 900K + 902D |
| CRTGNAR | 849R + 867D | 868G + 904M | 900D + 902D |
| CRTGNAN | 849R + 867D | 868G + 904M | 900W + 902A |

FIG. 23K-2

MaqI

| RECOGNITION SEQUENCE | POSITION 3 DETERMINANTS | POSITION 4 DETERMINANTS | POSITION 6 DETERMINANTS |
|---|---|---|---|
| CRTTAAC | 849K + 867Q | 868A + 904R +903P | 900E + 902R |
| CRTTAAG | 849K + 867Q | 868A + 904R +903P | 900K + 902D |
| CRTTAAR | 849K + 867Q | 868A + 904R +903P | 900D + 902D |
| CRTTAAN | 849K + 867Q | 868A + 904R +903P | 900W + 902A |
| CRTTCAC | 849K + 867Q | 868K + 904S | 900E + 902R |
| CRTTCAG | 849K + 867Q | 868K + 904S | 900K + 902D |
| CRTTCAR | 849K + 867Q | 868K + 904S | 900D + 902D |
| CRTTCAN | 849K + 867Q | 868K + 904S | 900W + 902A |
| CRTTGAC | 849K + 867Q | 868L + 904R | 900E + 902R |
| CRTTGAG | 849K + 867Q | 868L + 904R | 900K + 902D |
| CRTTGAR | 849K + 867Q | 868L + 904R | 900D + 902D |
| CRTTGAN | 849K + 867Q | 868L + 904R | 900W + 902A |
| CRTTRAC | 849K + 867Q | 868A + 904R +903F | 900E + 902R |
| CRTTRAG | 849K + 867Q | 868A + 904R +903F | 900K + 902D |
| CRTTRAR | 849K + 867Q | 868A + 904R +903F | 900D + 902D |
| CRTTRAN | 849K + 867Q | 868A + 904R +903F | 900W + 902A |
| CRTTNAC | 849K + 867Q | 868G + 904M | 900E + 902R |
| CRTTNAG | 849K + 867Q | 868G + 904M | 900K + 902D |
| CRTTNAR | 849K + 867Q | 868G + 904M | 900D + 902D |
| CRTTNAN | 849K + 867Q | 868G + 904M | 900W + 902A |
| CRTYAAC | 849V + 867N | 868A + 904R +903P | 900E + 902R |
| CRTYAAG | 849V + 867N | 868A + 904R +903P | 900K + 902D |
| CRTYAAR | 849V + 867N | 868A + 904R +903P | 900D + 902D |
| CRTYAAN | 849V + 867N | 868A + 904R +903P | 900W + 902A |
| CRTYCAC | 849V + 867N | 868K + 904S | 900E + 902R |
| CRTYCAG | 849V + 867N | 868K + 904S | 900K + 902D |
| CRTYCAR | 849V + 867N | 868K + 904S | 900D + 902D |
| CRTYCAN | 849V + 867N | 868K + 904S | 900W + 902A |
| CRTYGAC | 849V + 867N | 868L + 904R | 900E + 902R |
| CRTYGAG | 849V + 867N | 868L + 904R | 900K + 902D |
| CRTYGAR | 849V + 867N | 868L + 904R | 900D + 902D |
| CRTYGAN | 849V + 867N | 868L + 904R | 900W + 902A |
| CRTYRAC | 849V + 867N | 868A + 904R +903F | 900E + 902R |
| CRTYRAG | 849V + 867N | 868A + 904R +903F | 900K + 902D |
| CRTYRAR | 849V + 867N | 868A + 904R +903F | 900D + 902D |
| CRTYRAN | 849V + 867N | 868A + 904R +903F | 900W + 902A |
| CRTYNAC | 849V + 867N | 868G + 904M | 900E + 902R |
| CRTYNAG | 849V + 867N | 868G + 904M | 900K + 902D |
| CRTYNAR | 849V + 867N | 868G + 904M | 900D + 902D |
| CRTYNAN | 849V + 867N | 868G + 904M | 900W + 902A |

FIG. 23L-1

NhaXI

| RECOGNITION SEQUENCE | POSITION 3 DETERMINANTS | POSITION 4 DETERMINANTS | POSITION 6 DETERMINANTS |
|---|---|---|---|
| CAACAAC | 782E + 800N | 801A + 837R +836P | 833E + 835R |
| CAACAAG | 782E + 800N | 801A + 837R +836P | 833K + 835D |
| CAACAAR | 782E + 800N | 801A + 837R +836P | 833D + 835D |
| CAACAAN | 782E + 800N | 801A + 837R +836P | 833W + 835A |
| CAACCAC | 782E + 800N | 801K + 837S | 833E + 835R |
| CAACCAG | 782E + 800N | 801K + 837S | 833K + 835D |
| CAACCAR | 782E + 800N | 801K + 837S | 833D + 835D |
| CAACCAN | 782E + 800N | 801K + 837S | 833W + 835A |
| CAACGAC | 782E + 800N | 801L + 837R | 833E + 835R |
| CAACGAG | 782E + 800N | 801L + 837R | 833K + 835D |
| CAACGAR | 782E + 800N | 801L + 837R | 833D + 835D |
| CAACGAN | 782E + 800N | 801L + 837R | 833W + 835A |
| CAACRAC | 782E + 800N | 801A + 837R +836F | 833E + 835R |
| CAACRAG | 782E + 800N | 801A + 837R +836F | 833K + 835D |
| CAACRAR | 782E + 800N | 801A + 837R +836F | 833D + 835D |
| CAACRAN | 782E + 800N | 801A + 837R +836F | 833W + 835A |
| CAACNAC | 782E + 800N | 801G + 837M | 833E + 835R |
| CAACNAG | 782E + 800N | 801G + 837M | 833K + 835D |
| CAACNAR | 782E + 800N | 801G + 837M | 833D + 835D |
| CAACNAN | 782E + 800N | 801G + 837M | 833W + 835A |
| CAAGAAC | 782R + 800D | 801A + 837R +836P | 833E + 835R |
| CAAGAAG | 782R + 800D | 801A + 837R +836P | 833K + 835D |
| CAAGAAR | 782R + 800D | 801A + 837R +836P | 833D + 835D |
| CAAGAAN | 782R + 800D | 801A + 837R +836P | 833W + 835A |
| CAAGCAC | 782R + 800D | 801K + 837S | 833E + 835R |
| CAAGCAG | 782R + 800D | 801K + 837S | 833K + 835D |
| CAAGCAR | 782R + 800D | 801K + 837S | 833D + 835D |
| CAAGCAN | 782R + 800D | 801K + 837S | 833W + 835A |
| CAAGGAC | 782R + 800D | 801L + 837R | 833E + 835R |
| CAAGGAG | 782R + 800D | 801L + 837R | 833K + 835D |
| CAAGGAR | 782R + 800D | 801L + 837R | 833D + 835D |
| CAAGGAN | 782R + 800D | 801L + 837R | 833W + 835A |
| CAAGRAC | 782R + 800D | 801A + 837R +836F | 833E + 835R |
| CAAGRAG | 782R + 800D | 801A + 837R +836F | 833K + 835D |
| CAAGRAR | 782R + 800D | 801A + 837R +836F | 833D + 835D |
| CAAGRAN | 782R + 800D | 801A + 837R +836F | 833W + 835A |
| CAAGNAC | 782R + 800D | 801G + 837M | 833E + 835R |
| CAAGNAG | 782R + 800D | 801G + 837M | 833K + 835D |
| CAAGNAR | 782R + 800D | 801G + 837M | 833D + 835D |
| CAAGNAN | 782R + 800D | 801G + 837M | 833W + 835A |

FIG. 23L-2

NhaXI

| RECOGNITION SEQUENCE | POSITION 3 DETERMINANTS | POSITION 4 DETERMINANTS | POSITION 6 DETERMINANTS |
|---|---|---|---|
| CAATAAC | 782K + 800Q | 801A + 837R +836P | 833E + 835R |
| CAATAAG | 782K + 800Q | 801A + 837R +836P | 833K + 835D |
| CAATAAR | 782K + 800Q | 801A + 837R +836P | 833D + 835D |
| CAATAAN | 782K + 800Q | 801A + 837R +836P | 833W + 835A |
| CAATCAC | 782K + 800Q | 801K + 837S | 833E + 835R |
| CAATCAG | 782K + 800Q | 801K + 837S | 833K + 835D |
| CAATCAR | 782K + 800Q | 801K + 837S | 833D + 835D |
| CAATCAN | 782K + 800Q | 801K + 837S | 833W + 835A |
| CAATGAC | 782K + 800Q | 801L + 837R | 833E + 835R |
| CAATGAG | 782K + 800Q | 801L + 837R | 833K + 835D |
| CAATGAR | 782K + 800Q | 801L + 837R | 833D + 835D |
| CAATGAN | 782K + 800Q | 801L + 837R | 833W + 835A |
| CAATRAC | 782K + 800Q | 801A + 837R +836F | 833E + 835R |
| CAATRAG | 782K + 800Q | 801A + 837R +836F | 833K + 835D |
| CAATRAR | 782K + 800Q | 801A + 837R +836F | 833D + 835D |
| CAATRAN | 782K + 800Q | 801A + 837R +836F | 833W + 835A |
| CAATNAC | 782K + 800Q | 801G + 837M | 833E + 835R |
| CAATNAG | 782K + 800Q | 801G + 837M | 833K + 835D |
| CAATNAR | 782K + 800Q | 801G + 837M | 833D + 835D |
| CAATNAN | 782K + 800Q | 801G + 837M | 833W + 835A |
| CAAYAAC | 782V + 800N | 801A + 837R +836P | 833E + 835R |
| CAAYAAG | 782V + 800N | 801A + 837R +836P | 833K + 835D |
| CAAYAAR | 782V + 800N | 801A + 837R +836P | 833D + 835D |
| CAAYAAN | 782V + 800N | 801A + 837R +836P | 833W + 835A |
| CAAYCAC | 782V + 800N | 801K + 837S | 833E + 835R |
| CAAYCAG | 782V + 800N | 801K + 837S | 833K + 835D |
| CAAYCAR | 782V + 800N | 801K + 837S | 833D + 835D |
| CAAYCAN | 782V + 800N | 801K + 837S | 833W + 835A |
| CAAYGAC | 782V + 800N | 801L + 837R | 833E + 835R |
| CAAYGAG | 782V + 800N | 801L + 837R | 833K + 835D |
| CAAYGAR | 782V + 800N | 801L + 837R | 833D + 835D |
| CAAYGAN | 782V + 800N | 801L + 837R | 833W + 835A |
| CAAYRAC | 782V + 800N | 801A + 837R +836F | 833E + 835R |
| CAAYRAG | 782V + 800N | 801A + 837R +836F | 833K + 835D |
| CAAYRAR | 782V + 800N | 801A + 837R +836F | 833D + 835D |
| CAAYRAN | 782V + 800N | 801A + 837R +836F | 833W + 835A |
| CAAYNAC | 782V + 800N | 801G + 837M | 833E + 835R |
| CAAYNAG | 782V + 800N | 801G + 837M | 833K + 835D |
| CAAYNAR | 782V + 800N | 801G + 837M | 833D + 835D |
| CAAYNAN | 782V + 800N | 801G + 837M | 833W + 835A |

FIG. 23M-1

SpoDI

| RECOGNITION SEQUENCE | POSITION 3 DETERMINANTS | POSITION 4 DETERMINANTS | POSITION 6 DETERMINANTS |
|---|---|---|---|
| GCGCAAC | 764E + 782N | 783A + 821R +820P | 817E + 819R |
| GCGCAAG | 764E + 782N | 783A + 821R +820P | 817K + 819D |
| GCGCAAR | 764E + 782N | 783A + 821R +820P | 817D + 819D |
| GCGCAAN | 764E + 782N | 783A + 821R +820P | 817W + 819A |
| GCGCCAC | 764E + 782N | 783K + 821S | 817E + 819R |
| GCGCCAG | 764E + 782N | 783K + 821S | 817K + 819D |
| GCGCCAR | 764E + 782N | 783K + 821S | 817D + 819D |
| GCGCCAN | 764E + 782N | 783K + 821S | 817W + 819A |
| GCGCGAC | 764E + 782N | 783L + 821R | 817E + 819R |
| GCGCGAG | 764E + 782N | 783L + 821R | 817K + 819D |
| GCGCGAR | 764E + 782N | 783L + 821R | 817D + 819D |
| GCGCGAN | 764E + 782N | 783L + 821R | 817W + 819A |
| GCGCRAC | 764E + 782N | 783A + 821R +820F | 817E + 819R |
| GCGCRAG | 764E + 782N | 783A + 821R +820F | 817K + 819D |
| GCGCRAR | 764E + 782N | 783A + 821R +820F | 817D + 819D |
| GCGCRAN | 764E + 782N | 783A + 821R +820F | 817W + 819A |
| GCGCNAC | 764E + 782N | 783G + 821M | 817E + 819R |
| GCGCNAG | 764E + 782N | 783G + 821M | 817K + 819D |
| GCGCNAR | 764E + 782N | 783G + 821M | 817D + 819D |
| GCGCNAN | 764E + 782N | 783G + 821M | 817W + 819A |
| GCGGAAC | 764R + 782D | 783A + 821R +820P | 817E + 819R |
| GCGGAAG | 764R + 782D | 783A + 821R +820P | 817K + 819D |
| GCGGAAR | 764R + 782D | 783A + 821R +820P | 817D + 819D |
| GCGGAAN | 764R + 782D | 783A + 821R +820P | 817W + 819A |
| GCGGCAC | 764R + 782D | 783K + 821S | 817E + 819R |
| GCGGCAG | 764R + 782D | 783K + 821S | 817K + 819D |
| GCGGCAR | 764R + 782D | 783K + 821S | 817D + 819D |
| GCGGCAN | 764R + 782D | 783K + 821S | 817W + 819A |
| GCGGGAC | 764R + 782D | 783L + 821R | 817E + 819R |
| GCGGGAG | 764R + 782D | 783L + 821R | 817K + 819D |
| GCGGGAR | 764R + 782D | 783L + 821R | 817D + 819D |
| GCGGGAN | 764R + 782D | 783L + 821R | 817W + 819A |
| GCGGRAC | 764R + 782D | 783A + 821R +820F | 817E + 819R |
| GCGGRAG | 764R + 782D | 783A + 821R +820F | 817K + 819D |
| GCGGRAR | 764R + 782D | 783A + 821R +820F | 817D + 819D |
| GCGGRAN | 764R + 782D | 783A + 821R +820F | 817W + 819A |
| GCGGNAC | 764R + 782D | 783G + 821M | 817E + 819R |
| GCGGNAG | 764R + 782D | 783G + 821M | 817K + 819D |
| GCGGNAR | 764R + 782D | 783G + 821M | 817D + 819D |
| GCGGNAN | 764R + 782D | 783G + 821M | 817W + 819A |

FIG. 23M-2

SpoDI

| RECOGNITION SEQUENCE | POSITION 3 DETERMINANTS | POSITION 4 DETERMINANTS | POSITION 6 DETERMINANTS |
|---|---|---|---|
| GCGTAAC | 764K + 782Q | 783A + 821R +820P | 817E + 819R |
| GCGTAAG | 764K + 782Q | 783A + 821R +820P | 817K + 819D |
| GCGTAAR | 764K + 782Q | 783A + 821R +820P | 817D + 819D |
| GCGTAAN | 764K + 782Q | 783A + 821R +820P | 817W + 819A |
| GCGTCAC | 764K + 782Q | 783K + 821S | 817E + 819R |
| GCGTCAG | 764K + 782Q | 783K + 821S | 817K + 819D |
| GCGTCAR | 764K + 782Q | 783K + 821S | 817D + 819D |
| GCGTCAN | 764K + 782Q | 783K + 821S | 817W + 819A |
| GCGTGAC | 764K + 782Q | 783L + 821R | 817E + 819R |
| GCGTGAG | 764K + 782Q | 783L + 821R | 817K + 819D |
| GCGTGAR | 764K + 782Q | 783L + 821R | 817D + 819D |
| GCGTGAN | 764K + 782Q | 783L + 821R | 817W + 819A |
| GCGTRAC | 764K + 782Q | 783A + 821R +820F | 817E + 819R |
| GCGTRAG | 764K + 782Q | 783A + 821R +820F | 817K + 819D |
| GCGTRAR | 764K + 782Q | 783A + 821R +820F | 817D + 819D |
| GCGTRAN | 764K + 782Q | 783A + 821R +820F | 817W + 819A |
| GCGTNAC | 764K + 782Q | 783G + 821M | 817E + 819R |
| GCGTNAG | 764K + 782Q | 783G + 821M | 817K + 819D |
| GCGTNAR | 764K + 782Q | 783G + 821M | 817D + 819D |
| GCGTNAN | 764K + 782Q | 783G + 821M | 817W + 819A |
| GCGYAAC | 764V + 782N | 783A + 821R +820P | 817E + 819R |
| GCGYAAG | 764V + 782N | 783A + 821R +820P | 817K + 819D |
| GCGYAAR | 764V + 782N | 783A + 821R +820P | 817D + 819D |
| GCGYAAN | 764V + 782N | 783A + 821R +820P | 817W + 819A |
| GCGYCAC | 764V + 782N | 783K + 821S | 817E + 819R |
| GCGYCAG | 764V + 782N | 783K + 821S | 817K + 819D |
| GCGYCAR | 764V + 782N | 783K + 821S | 817D + 819D |
| GCGYCAN | 764V + 782N | 783K + 821S | 817W + 819A |
| GCGYGAC | 764V + 782N | 783L + 821R | 817E + 819R |
| GCGYGAG | 764V + 782N | 783L + 821R | 817K + 819D |
| GCGYGAR | 764V + 782N | 783L + 821R | 817D + 819D |
| GCGYGAN | 764V + 782N | 783L + 821R | 817W + 819A |
| GCGYRAC | 764V + 782N | 783A + 821R +820F | 817E + 819R |
| GCGYRAG | 764V + 782N | 783A + 821R +820F | 817K + 819D |
| GCGYRAR | 764V + 782N | 783A + 821R +820F | 817D + 819D |
| GCGYRAN | 764V + 782N | 783A + 821R +820F | 817W + 819A |
| GCGYNAC | 764V + 782N | 783G + 821M | 817E + 819R |
| GCGYNAG | 764V + 782N | 783G + 821M | 817K + 819D |
| GCGYNAR | 764V + 782N | 783G + 821M | 817D + 819D |
| GCGYNAN | 764V + 782N | 783G + 821M | 817W + 819A |

FIG. 23N-1

AquIV

| RECOGNITION SEQUENCE | POSITION 3 DETERMINANTS | POSITION 4 DETERMINANTS | POSITION 6 DETERMINANTS |
|---|---|---|---|
| GRGCAAC | 743E + 761N | 762A + 798R +797P | 794E + 796R |
| GRGCAAG | 743E + 761N | 762A + 798R +797P | 794K + 796D |
| GRGCAAR | 743E + 761N | 762A + 798R +797P | 794D + 796D |
| GRGCAAN | 743E + 761N | 762A + 798R +797P | 794W + 796A |
| GRGCCAC | 743E + 761N | 762K + 798S | 794E + 796R |
| GRGCCAG | 743E + 761N | 762K + 798S | 794K + 796D |
| GRGCCAR | 743E + 761N | 762K + 798S | 794D + 796D |
| GRGCCAN | 743E + 761N | 762K + 798S | 794W + 796A |
| GRGCGAC | 743E + 761N | 762L + 798R | 794E + 796R |
| GRGCGAG | 743E + 761N | 762L + 798R | 794K + 796D |
| GRGCGAR | 743E + 761N | 762L + 798R | 794D + 796D |
| GRGCGAN | 743E + 761N | 762L + 798R | 794W + 796A |
| GRGCRAC | 743E + 761N | 762A + 798R +797F | 794E + 796R |
| GRGCRAG | 743E + 761N | 762A + 798R +797F | 794K + 796D |
| GRGCRAR | 743E + 761N | 762A + 798R +797F | 794D + 796D |
| GRGCRAN | 743E + 761N | 762A + 798R +797F | 794W + 796A |
| GRGCNAC | 743E + 761N | 762G + 798M | 794E + 796R |
| GRGCNAG | 743E + 761N | 762G + 798M | 794K + 796D |
| GRGCNAR | 743E + 761N | 762G + 798M | 794D + 796D |
| GRGCNAN | 743E + 761N | 762G + 798M | 794W + 796A |
| GRGGAAC | 743R + 761D | 762A + 798R +797P | 794E + 796R |
| GRGGAAG | 743R + 761D | 762A + 798R +797P | 794K + 796D |
| GRGGAAR | 743R + 761D | 762A + 798R +797P | 794D + 796D |
| GRGGAAN | 743R + 761D | 762A + 798R +797P | 794W + 796A |
| GRGGCAC | 743R + 761D | 762K + 798S | 794E + 796R |
| GRGGCAG | 743R + 761D | 762K + 798S | 794K + 796D |
| GRGGCAR | 743R + 761D | 762K + 798S | 794D + 796D |
| GRGGCAN | 743R + 761D | 762K + 798S | 794W + 796A |
| GRGGGAC | 743R + 761D | 762L + 798R | 794E + 796R |
| GRGGGAG | 743R + 761D | 762L + 798R | 794K + 796D |
| GRGGGAR | 743R + 761D | 762L + 798R | 794D + 796D |
| GRGGGAN | 743R + 761D | 762L + 798R | 794W + 796A |
| GRGGRAC | 743R + 761D | 762A + 798R +797F | 794E + 796R |
| GRGGRAG | 743R + 761D | 762A + 798R +797F | 794K + 796D |
| GRGGRAR | 743R + 761D | 762A + 798R +797F | 794D + 796D |
| GRGGRAN | 743R + 761D | 762A + 798R +797F | 794W + 796A |
| GRGGNAC | 743R + 761D | 762G + 798M | 794E + 796R |
| GRGGNAG | 743R + 761D | 762G + 798M | 794K + 796D |
| GRGGNAR | 743R + 761D | 762G + 798M | 794D + 796D |
| GRGGNAN | 743R + 761D | 762G + 798M | 794W + 796A |

FIG. 23N-2

AquIV

| RECOGNITION SEQUENCE | POSITION 3 DETERMINANTS | POSITION 4 DETERMINANTS | POSITION 6 DETERMINANTS |
|---|---|---|---|
| GRGTAAC | 743K + 761Q | 762A + 798R +797P | 794E + 796R |
| GRGTAAG | 743K + 761Q | 762A + 798R +797P | 794K + 796D |
| GRGTAAR | 743K + 761Q | 762A + 798R +797P | 794D + 796D |
| GRGTAAN | 743K + 761Q | 762A + 798R +797P | 794W + 796A |
| GRGTCAC | 743K + 761Q | 762K + 798S | 794E + 796R |
| GRGTCAG | 743K + 761Q | 762K + 798S | 794K + 796D |
| GRGTCAR | 743K + 761Q | 762K + 798S | 794D + 796D |
| GRGTCAN | 743K + 761Q | 762K + 798S | 794W + 796A |
| GRGTGAC | 743K + 761Q | 762L + 798R | 794E + 796R |
| GRGTGAG | 743K + 761Q | 762L + 798R | 794K + 796D |
| GRGTGAR | 743K + 761Q | 762L + 798R | 794D + 796D |
| GRGTGAN | 743K + 761Q | 762L + 798R | 794W + 796A |
| GRGTRAC | 743K + 761Q | 762A + 798R +797F | 794E + 796R |
| GRGTRAG | 743K + 761Q | 762A + 798R +797F | 794K + 796D |
| GRGTRAR | 743K + 761Q | 762A + 798R +797F | 794D + 796D |
| GRGTRAN | 743K + 761Q | 762A + 798R +797F | 794W + 796A |
| GRGTNAC | 743K + 761Q | 762G + 798M | 794E + 796R |
| GRGTNAG | 743K + 761Q | 762G + 798M | 794K + 796D |
| GRGTNAR | 743K + 761Q | 762G + 798M | 794D + 796D |
| GRGTNAN | 743K + 761Q | 762G + 798M | 794W + 796A |
| GRGYAAC | 743V + 761N | 762A + 798R +797P | 794E + 796R |
| GRGYAAG | 743V + 761N | 762A + 798R +797P | 794K + 796D |
| GRGYAAR | 743V + 761N | 762A + 798R +797P | 794D + 796D |
| GRGYAAN | 743V + 761N | 762A + 798R +797P | 794W + 796A |
| GRGYCAC | 743V + 761N | 762K + 798S | 794E + 796R |
| GRGYCAG | 743V + 761N | 762K + 798S | 794K + 796D |
| GRGYCAR | 743V + 761N | 762K + 798S | 794D + 796D |
| GRGYCAN | 743V + 761N | 762K + 798S | 794W + 796A |
| GRGYGAC | 743V + 761N | 762L + 798R | 794E + 796R |
| GRGYGAG | 743V + 761N | 762L + 798R | 794K + 796D |
| GRGYGAR | 743V + 761N | 762L + 798R | 794D + 796D |
| GRGYGAN | 743V + 761N | 762L + 798R | 794W + 796A |
| GRGYRAC | 743V + 761N | 762A + 798R +797F | 794E + 796R |
| GRGYRAG | 743V + 761N | 762A + 798R +797F | 794K + 796D |
| GRGYRAR | 743V + 761N | 762A + 798R +797F | 794D + 796D |
| GRGYRAN | 743V + 761N | 762A + 798R +797F | 794W + 796A |
| GRGYNAC | 743V + 761N | 762G + 798M | 794E + 796R |
| GRGYNAG | 743V + 761N | 762G + 798M | 794K + 796D |
| GRGYNAR | 743V + 761N | 762G + 798M | 794D + 796D |
| GRGYNAN | 743V + 761N | 762G + 798M | 794W + 796A |

>MmeI TCCRAC 2760 nt (SEQ ID NO:1) FIG. 24A-1

GTGGCTTTAA GCTGGAACGA GATAAGAAGA AAAGCTATTG AGTTTTCTAA AAGATGGGAA
GACGCCTCAG ATGAAAACAG TCAAGCCAAA CCCTTTTTAA TAGATTTTTT CGAAGTTTTT
GGAATAACTA ATAAGAGAGT TGCAACATTT GAGCATGCTG TGAAAAAGTT CGCCAAGGCC
CATAAGGAAC AATCTCGAGG ATTCGTAGAT TTGTTTTGGC CTGGCATTCT TCTTATTGAA
ATGAAAAGCA GAGGTAAAGA CCTCGACAAA GCGTATGACC AGGCACTTGA TTACTTTTCT
GGCATTGCAG AAAGAGACTT ACCCAGATAC GTTTTAGTTT GCGACTTCCA GCGTTTCAGA
TTAACAGACC TAATAACAAA AGAGTCAGTT GAATTTCTTT TAAAGGACTT ATACCAAAAT
GTGAGGTCTT TTGGTTTTAT AGCTGGTTAT CAAACTCAAG TAATCAAGCC ACAAGACCCT
ATTAATATTA AGGCGGCTGA ACGGATGGGT AAGCTTCATG ACACCCTGAA GTTGGTTGGA
TATGAGGGAC ACGCTTTAGA ACTTTATCTA GTGCGTTTAC TTTTTTGCTT ATTCGCAGAA
GACACAACTA TTTTTGAGAA AAGTTTATTC CAAGAATATA TCGAGACAAA GACGCTAGAG
GACGGCAGTG ACCTTGCACA TCATATCAAT ACACTTTTTT ATGTTCTCAA TACCCCAGAA
CAAAAAAGAT TAAAGAATCT AGACGAACAC CTTGCTGCAT TTCCATATAT CAATGGAAAA
CTTTTCGAGG AGCCACTTCC GCCAGCTCAG TTTGATAAAG CAATGAGAGA GGCATTGCTT
GACTTGTGCT CATTAGATTG GAGCAGGATT TCACCAGCAA TATTTGGAAG TTTATTCCAA
AGCATTATGG ATGCTAAAAA GAGAAGAAAT CTTGGGGCAC ACTACACCAG CGAAGCAAAT
ATTCTCAAGT TAATCAAGCC ATTGTTTCTT GACGAGCTCT GGGTAGAGTT CGAGAAAGTT
AAAAATAATA AAAATAAATT ACTAGCGTTC CACAAAAAAC TAAGAGGACT TACATTTTTC
GACCCTGCAT GCGGTTGCGG AAATTTTCTT GTAATCACAT ACCGAGAACT AAGACTTTTA
GAAATTGAAG TGTTAAGAGG ATTGCATAGA GGTGGTCAAC AAGTTTTGGA TATTGAGCAT
CTTATTCAGA TTAACGTAGA CCAGTTTTTT GGTATCGAAA TAGAGGAGTT TCCCGCACAG
ATTGCTCAGG TTGCTCTCTG GCTTACAGAC CACCAAATGA ATATGAAAAT TTCAGATGAG
TTTGGAAACT ACTTTGCCCG TATCCCACTA AAATCTACTC CTCACATTTT GAATGCTAAT
GCTTTACAGA TTGATTGGAA CGATGTTTTA GAGGCTAAAA AATGTTGCTT CATATTAGGA
AATCCTCCAT TTGTTGGTAA AAGTAAACAA ACACCGGGAC AAAAAGCGGA TTTACTATCT
GTTTTTGGAA ATCTTAAATC CGCTTCAGAC TTAGACCTAG TTGCTGCTTG GTATCCCAAA
GCAGCACATT ACATTCAAAC AAATGCAAAC ATACGCTGTG CATTTGTCTC AACGAATAGT
ATTACTCAAG GTGAGCAAGT ATCGTTGCTT TGGCCGCTTC TGCTCTCATT AGGCATAAAA
ATAAACTTTG CTCACAGAAC TTTCAGCTGG ACAAATGAGG CGTCAGGAGT AGCGGCGGTT
CACTGCGTAA TTATCGGATT TGGGTTGAAG GATTCAGATG AAAAAATAAT CTATGAGTAT
GAAAGTATTA ATGGAGAACC ATTAGCTATT AAGGCAAAAA ATATTAATCC ATATTTGAGA
GACGGGGTGG ATGTGATTGC CTGCAAGCGT CAGCAGCCAA TCTCAAAATT ACCAAGCATG
CGTTATGGCA ACAAACCAAC AGATGATGGA AATTTCCTAT TTACTGACGA AGAAAAAAAC
CAATTTATTA CAAATGAGCC ATCTTCCGAA AAATACTTCA GACGGTTTGT GGGCGGGGAT
GAGTTCATAA ACAATACAAG TCGATGGTGT TTATGGCTTG ACGGTGCTGA CATTTCAGAA
ATACGAGCGA TGCCTTTGGT CTTGGCTAGG ATAAAAAAAG TCCAAGAATT CAGATTAAAA
AGCTCGGCCA AACCAACTCG ACAAAGTGCT TCGACACCAA TGAAGTTCTT TTATATATCT
CAGCCGGATA CGGACTATCT GTTGATACCT GAAACATCAT CTGAAAACAG ACAATTTATT
CCAATTGGTT TTGTTGATAG AAATGTCATT TCAAGTAACG CAACGTATCA TATTCCTAGT
GCTGAACCTT TGATATTTGG CCTGCTTTCA TCGACCATGC ACAACTGCTG GATGAGAAAT
GTAGGAGGAA GGTTAGAAAG TCGTTATAGA TATTCTGCCA GCCTGGTTTA CAACACGTTT
CCATGGATTC AACCCAACGA AAAACAATCG AAAGCGATAG AAGAAGCTGC ATTTGCGATT
TTAAAAGCTA GAAGCAATTA TCCAAACGAA AGTTTAGCTG GTTTATACGA CCCAAAAACA
ATGCCTAGTG AGCTTCTTAA AGCACATCAA AAACTTGATA AGGCTGTGGA TTCTGTCTAT
GGATTTAAAG GACCAAACAC AGAAATTGCT CGAATAGCTT TTTTGTTTGA AACATACCAA
AAGATGACTT CACTCTTACC ACCAGAAAAA GAAATTAAGA AATCTAAGGG CAAAAATTAA

FIG. 24A-2

>EsaSSI GACCAC 2802 nt (SEQ ID NO:3)

ATGGCTGCCC TCTCGTTCCC GGAAATCCGC ACCCGCTTGC AAGCGTTCGC CAAACAATGG
AAGCAAGCGG AGCGCGAAAA CGCCGACGCA AAGTTGTTTT GGGCACGGTT TTACGAGTGC
TTCGGCATCC GCCCGGAGTC CGCGACCATC TACGAGAAGG CGGTGGACAA ACTTGATGGC
TCGCGGGGCT TCATCGACTC GTTTATTCCG GGGCTGTTGA TCGTCGAGCA CAAGAGTAAG
GGCAAGGACC TGAACTCGGC CTTCACCCAA GCCTCCGACT ACTTCACGGC GCTGGCTGAA
GGTGAGCGTC CGCGGTACAT CATCGTGTCG GATTTCGCCC GTTTTAGGCT GTACGACCTG
AAAACCGACA CCCAGGTGGA GTGCAAACTC GCGGACATCT CCAAGCACGC CGGCTGGTTC
CGGTTCCTAG TCGAGGGTGA GGCTACGCCA GAAATCGTCG AGGAGTCACC GATCAACCGG
CAGGCTGCGT ACGCCGTCTC GAAGTTGCAC GAGGCGCTGT TGCAGGCAAA CTTCCGAGGC
CGTGACTTGG AGGTGTTCCT GACGCGGCTG CTGTTCTGCT TCTTCGCCGA TGATACTGGC
ATCTTTGGCC AAGACGGTGT CTTCCGTCGG TACGTCGAAG CCACGCGCGA CAATGGCCGG
GACACCGGGC AAAGCCTCGC GATCCTGTTT GACGTGCTGG ACACGCCGGA TAACCAGCGT
TCGTCCAACC TGGACGAGCA CCTGACCGCG TTCGCCTACA TCAACGGGTC GCTGTTTTCT
GAGCGTACGC GTATCCCGTC ATTCGACGCG GACATGCGAA CCTTGTTGGT GAAGTGCGCA
GAACTGGACT GGAGCGGGAT CAGCCCCGCG ATCTTCGGGG CGATGTTTCA AGGCGTGCTG
GAAGCCCACA CGCCAGACGA AAAGCGCCAG GCCAGTCGTC GGGAACTGGG TGCTCACTAC
ACCTCGGAAC GTAACATCTT GCGGGTGATC AATCCGCTGT TCATGGACGA CTTGCGCGTA
GAGTTCGAGA GGGCGCGCAG GAACAAGCCC CGATTGCAGG CGCTGTACGA GAAGTTGCCA
ACGCTCACAT TCTTCGATCC CGCGTGCGGC TGCGGGAACT TCTTGGTGAT CGCGTACCGG
GAACTGCGCC GTCTGGAAAA CGATGTCATC GCCGCACTGT TCGCGGACTT CCAGCACGGC
AAGGGTTTGC TAGACGTGTC GACGCTCTGC AGGGTTCGGG TCAATCAGTT TTACGGCCTG
GAGATCGACG ACGCGGCGGC GCACATCGCG CGCGTGGCCA TGTGGATCAC GGACCATCAG
ATGAACCTGG AGTCGGCAGA CCGCTTCGGC AATACTCGCC CGACAGTTCC GCTGGTCGAC
ACTCCCCACA TTCACAAAGA GAACGCGCTA CGCGCCGATT GGACATCGGT TCTCGCGCCC
GCGCAGTGTT CGTACGTGAT GGGCAATCCT CCGTTCGTAG GTGCGAAGTG GCTGAACGAG
GAACAGCGTG CCGACGCCCG GGCGGTGTTC GCTAACGTTA AGAACGGCGG ACTGTTGGAC
TACGTGGCCG CTTGGTATGT TAAGGCGCTG GCTTACATCC AAGCTAACCC GGCCATCGAC
GTGGCGTTTG TTTCAACCAA CTCGATCACG CAAGGTGAGC AAGTGTCAGC CCTCTGGCCG
ACGCTGCTGC AAGGTGGGGT AAAAATCCGC TTTGCCCACC GGACGTTTCA GTGGAGCAAC
GAAGGGAAAG GCAATGCTGC CGTCCATTGC GTCATCATCG GCTTCGGCCT GCGTGTCCCG
GATCGCTGCA CGATCTTCGA TTACAGCCAC GACATCAAGG CCGACCTGGG TTCGGTTCTT
CACGCGTCTC GCATCAATCC GTACTTGGTG GACGCCCCGG ACGTCGTGCT GACAAATCGG
CGTGCGCCGA TTTGTCAGGT GCCGGAAATC GGCATAGGGA ACAAACCCAT CGACGGCGGG
CATTACCTGT TTACTGACGA AGGAAAGGCC GCGTTCCTGG CCGTCGAGCC GAAAGCCGCC
CCGTTTTTCC ATCGCTGGGT CGGCGCGGAA GAGTTCATCA ACAACACAAG CCGTTGGTGT
CTATGGTTGG GTAACGCGAA GCCGCATGAA CTCCGCGCGC TCCCCGAATG TATGAAGCGC
GTTGAGGCAG TGCGTCAATA TCGCCTCGCC AGCCCCAGCG CTCCGACGCA GAAACTGGCC
GAGACCCCGA CCCGGTTTCA CGTCGAGTTC ATGCCAGACG CCCCGTTCAT GGTGATCCCT
GAAGTATCGT CCGAACGTCG CGAGTTCATC CCACTGGGGT ACCTGCAACC GCCAACGCTG
GCGAGCAACA AACTGCGCTT GATGCCAGAT GCGACGCTGT ATCACTTCGC GGTGTTGAAC
TCCACCATGC ATATGGCTTG GACACGGGCG GTATGCGGCC GGCTGGAAAG CCGATATCAG
TACTCGGTCA CCATCGTGTA CAACAACTTT CCATGGCCCA GTCCATCCGA CGCCCAACTT
GAAGCGCTGG AAGCGGCAGG ACAGGCAATC CTCGATGCCC AGGCTATGTA TTTGGACCAG
GGTTCATCGC TAGCCGATCT GTACGATCCG CGCACGATGC CGTCAGAACT TCGCAAGGCC
CATGCTGCGA ACGATCGCGC CGTTGATGCG GCGTACAAGT TCAAGGGCGA CAAGTCCGAC
GCCGTGCGGG TCGCTTTCTT GTTTAGCCTG TACGGAAGGT TGACGAGCCT TCTTCCGTCC
GAGAAGCCGA AGCGTGCTCG GAAAGAGAAA GCAGTCGCGT AA

>SdeAI CAGRAG 2727 nt (SEQ ID NO:5)

FIG. 24A-3

ATGATAAGCT TAAGAGAGAT ACGAGAACGA AGCATAAAGT TTGCCAAAGA GTGGGAGGGT
GCTTCTCATG AAAAACAAGA AGCGCAGAGT TTTTGGATAG ATTTTTTTAA AATATTTGAT
GTAAGTCCAC GAAGTATGCA GTTTGAGTAT CCCATCAAAA AAATAGACGG CTCTTATGGT
TACATAGATG TTTTTTGGAG AGGGCAGCTT CTTATAGAGC AAAAAAGCAG AGGCAAGGAT
TTAGTAAAGG CAAAAGAACA AGCGTTAGAG TACCTTCCAA ATCTAAAACA GAGAGATTTA
CCGAAGTTTA TTTTGGTTTG TGATTTTGTA AGCTTCTATC TTTACGATTT GGACACAAAT
CAAGATTATA AATTTCTACT CCATGAGTTA CCAAAAAATA TAGAGCTGTT TTCATTTATA
GCAGGATACA CAAAAAAAAC CTACAAAGAA GAGGAACCGA CCAACCGCAA AGCCGCCGAA
CTTATGGGTA AACTTCATGA CAAGCTACTT GAAAACGGTT ACAGCGGACA TCAACTCGAA
CTCTTTTTAA CAAGGCTTCT TTTTTGTATG TTTGCAGAAG ATACGGGCAT ATTTGCTAAA
AACTCTTTTC GTGAATTTAT AGAAAATCAA ACAGATGAGA GCGGCAGAGA TTTAGGCTCG
CAGATAAGCT ACCTCTTTGA GCTTTTTGAC ACTCCAAATG AGGAGCGACA AAAAAATCTT
GATGAGAGTT TTACTCAGTT TCCTTACATC AACGGCTCAA TTTTTACAGA ACAGCTCAAA
ACAGCCCACT TTGACCGCTC CATGCGTGAA ATGCTTTTGG ATGCGTGTGC CTTTGACTGG
AGTTTGATAA GTCCTTCCAT TTTCGGTTCA ATGTTTCAAG CTTCTATGGA CGTTAGTAAA
AGAGGCGAAC TCGGTGCGCA CTTTACAAGT GAGACAAATA TATTAAAAGC CATCAAACCG
CTATTTTTGG ATGAACTTAG CGAAGAGTTT GCAAAAATAA AAAACAACCC AAAACAGCTT
CAAATTTTTC ATGCAAAAAT CTCAAATCTC AAATTTTTAG ACCCAGCATG TGGAAGTGGG
AACTTTTTGG TAATCGCTTA CAGAGAGTTG AAGCTTGTAG AGTTTGAAGT GCTGAAATCT
CTTAAAATAC TCACACAACT CGTCCATATA GACCAATTTT ATGGTTTCGA GATAGAAGAG
TTGCCAAGTC GAATAACTCA AACTGCGATG CTTCTCATCG ACCATCAAAT GAACCTGCTT
TTTGCTCAAA TGTTTGGAGA GCCACATTTT AATATCCCCA TAAAAGATAG TGCAAATATT
TTTAATGTCA ATGCTTTGAG GGTGGATTGG GAAAAGATTT TGGATGGTGT GAAAATTGAT
TTTATTATTG GAAATCCGCC GTTTTTAGGT TCAAAAATGC AATCTAAAGA GCAAAAAGAG
GATATGGCAG AGGTTTTTAG CGGTGTTAAA AATGGAAAAG AACTTGATTT TGTAACGGCT
TGGTATATAA AATCTGCAAA ATATTTACAA GGTAAAAACA CAAAAGTAGC CTTAGTTTCA
ACGAACTCCA TTACGCAAGG CGAACAAGTA GGGATTTTGT GGCAAGAGAT GTTTAACAAA
TATAAAATCA AAATCCACTT TGCACACAAA ACTTTTAAAT GGAATAATGA TGCAAAAGGC
GTTGCACAAG TTTATTGTGT AATTATCGGT TTTGCGGGGT TTGACATCAA AGAAAAAAGA
CTTTTTGAGT ATGAGAGCGT AAAATCTGAA CCGCATGAGA TAAAAGTTGC AAATATAAAT
CCCTATCTTG TAAACGGAGA TGATTTTTTT ATCAGCTCAA GAAGAAAGCA TATACAGAGC
TTTATACCTC AAATAGTTTT TGGAAGTATG CCAAATGACG GTGGTAACCT GCTTTTTGAC
GATAAAGAAA AAGAGGAGTT TTTAGCCCTT GAACCAAAAG CAGAGCTGTA CATGAAGCCT
CTTATCTCTG CAAAAGAGTA TCTTAACGGC AAAACAAGAT GGTGTTTATG GCTAAAAGAT
TGTCCGCCAA ATGAACTAAA ATCTATGCCC AAAGTGATTG AGAGAGTTGA AAATATCAGA
AAACTTAGGA ACGAAAGCTC AAGAGAAGCA ACTCAAAAAT TAGCAAAGTT CCCAGCACTT
TTTGGAGAAG ATAGACAGCC TGAGAGTGAT TATATTTTTA TTCCTCGTGT ATCGTCAGAA
AACAGAGATT ATATTCCAAT GGAATTTTTT ACAAAAGATT TTATTTGTGG AGATACTGGA
CTTGCCGTTC CAAATGCCAC ACTTTTTCAT TTCGGAATTT TGACTTCAAA AATGCACATG
GACTGGGTGC GGTATGTTGC TGGAAGATTA AAAAGTGATT ATAGATATTC AAATGAAATT
GTTTATAACA ACTTCCCTTT TCCTTTAGAA ATAAACGACA AACAAAAAGA TCAAATCGAA
CAATTAGCAC AAAATATTCT AGACATAAGA GCCGAATTTG TAGGAAGCTC TTTAGCCGAT
TTGTACAATC CTCTAACTAT GCCACCAAAA CTCCTAAAAG CTCACGAAAC GCTAGACAGA
GCAGTAGATA AACTCTACTC AAAAACACTC TTCAAAACAG ATACAGAAAG AGTCGCCCAT
TTGTTTGAAT TAAATAAACA ACTTACTAGC TTGATTGTGG AAAATGAGAA AAAAGCTAAA
AAAGTTAAAA AAATAATAAC AAAATGA

FIG. 24A-4

>NlaCI CATCAC 2865 nt (SEQ ID NO:7)

ATGCCGTCTG AAAGCACACT TCAGACGGCA TTTTCCCAAC AGGCACGCAT CATGACCCCA
GACCTCCAAA CCCTCCAACA CAACGCCGAA CAATTCATCC GCGACTGCGA ACCCCTGCAT
TACGAAATGG GTCATGCCCA AAAATTCATC GCCGCCCTAT GCAAAGTGTA CGGCCTCGAT
GCCCACTTCG CCGTCCAATA CGAACACCGC GTCCGCAAAG CTGACCTCAA AGGCATCAAC
CGCATCGACG GCTTCTTCCC CGGCCTGCTG ATGATAGAAA TGAAATCCGC CGGCGAAGAC
CTCGAAGCCG CCTTCATCCA AGCCCTGGAA TACGTCCAAC TCATAGAGCG CATCGAAGAC
AAGCCCCGCC ACATCCTCGT CTCCGACTTC AAAAACCTCC ACCTTTACGA GCTGAATCAA
GGATTTACCG GCATCGTCCT CGACAAAACC CTCAAAATCA AACTCACCGG CTTCCGCGCC
CACGTCCAAG ACTTCGCCTT CATCGCAGGC TACGAAGCCG CCATTGCCGA GCGCAACGAA
GCCCTGACCA TAGCCGCCGC CGCCAAACTC GCCGCCCTGC ACCAAGAATT CCACAAACAA
GGCTACCAAG GCGCAGAACT CCAAACCATG CTCGTCCGCA TCCTCTTCTG CCTCTTTGCC
GACGACACCG GACTCTTCGC CCAAAAACAA GCCTTCGAGC AGCTTGTCGA AGAAAGCCTC
GCCGACGGCG CAGACCTCGG CAGCCGCCTC AACGCCCTCT ACAAATGGCT TGACACCCCC
GAAGACAAAC GCCGCACCAC CCCGCGGGCC CTGCTTGACC AATACAGCGG CTTCCGCCTC
AAATTCCCCT ACATCAACGG CAAACTCTTT TCAGACGGCA TAGACGAATT CGTCTTCAAC
GCCTCCATGC GCCGCACCCT CCTCGAATGC TGCGAAATCG ACTGGAGCCT CATCTCCCCC
GACATCTTCG GCACACTCTT CCAAAACATC ATGGAAAACG CCGACGCACT CGGCGGCGGC
AAAAAATCTG CCCACCGCCG CGAACTCGGC GCACACTACA CCAGCGAAAA AAACATCAAA
CGCGCCATCG CCCCCCTCTT TCTCGACCGC CTCAAAGCCG AGCTTGAGCA GGCTGCCGGC
GACCCCAAAA AACTCGCCCG CTACATTACC CGCCTGCAAA CCCTCCAAAT CCTCGATCCC
GCCTGTGGCT GCGGCAACTT CCTCATCGTC GCCTACCGCG AAATCCGCCT GCTCGAAATG
CAGGCAATCC GCCAACTCGC CCGCATCCCC GGCGCGCAGC AAATGCAGTC CCAATGCGAC
GTCCACCAAT TCCACGGCAT CGAAATCGAC CCCGCCGCCG TCGAAATCGC CACCGTTGCC
ATGTGGCTCA CCGACCACCA GATGAACCGC CTCTACCAAG ACGGCTACAA ACGCATCCCC
CTCGCCCACA AAGCCGACAT CCGCTGCGCC AACGCCCTCC AAACCGACTG GGCAGACACC
ATATCCCCCC AAAACCTCGA CTATATCGTC GGCAACCCCC CGTTTTTAGG CAAAAAAGAA
CAAAATGCCG AACAGAAAAA AGATATGGAA AAAGTGGTAG GACATCTCAA AGGTTCGGGG
ATTCTCGATT ACGTTACGGC TTGGTATTTC AAAGCAAACG AATTGATGAA ACACAACCCC
AAAATCCGCA CCGCCTTCGT TTCCACCAAC TCCATCACCC AAGGCGAACA AGTCCCCGCC
CTCTGGAAGC CCCTGCTTTC AGACGGCATC CGCATCCGCT TCGCCCACCG CACCTTCAAA
TGGAACAACG AAGGCAAAGG CACCGCCGCC GTCCACTGCG TCATCATCGG CTTCGACCGC
GACGAAATCC AAAAAGGCGA ACGCCTCAGC CTTTGGGATT ACAGCCAAGG CATCGGCGGC
GACGGCAAAG AACACCAAGT CCGCAAAATC AATCCTTATC TGCTTGAAGC AGACAATATC
CTGCCCGCCA AAAGAAGCCG CCCCGTATCA GCAGATGTTC CGGCAATGAA TTACGGAAGT
ATGCCGATTG ACAACGGCTT GCTGATTCTG TCCCAAGAAG CGTTTCAGAC GGCATTAAAC
GAAGACCCCG AAAATAGCGA ACTGATCCGC CCCTATATGG GCGGCAGCGA ATTCCTGAAC
AATGAAAAAC GTTATTGCCT GTGGTTGGAA AACGTCGATC AAGAACGCCT GTCCCAAAGC
AAATTTGCTT CGGAACGGGT AGGGCAAGTC AGAGCCTACC GCCTGTCCAG TTCGCGCGCA
GCCACTGTAA AACTGGCTGG AACACCGCAC TTGTTCGGCG AAATCCGCCA ACCTGACAGC
CGTTATCTGC TGTTGCCCAA AGTGTCGTCT GAAAACCGCC GTTTTCTTCC CATCGGTTAC
ATCGAACCTG AAACCATTGC CAACGGAAGC GCATTGATTA TCCCCAACGC CACCCTCTGC
CACTTCGGCA TCCTAAGCTC CACCATGCAC AACGCCTTCA TGCGCACCGT CGCAGGCAGA
TTGGAAAGCC GTTACCAATA CTCGGCAAGT ATCGTGTACA ACAATTTCCC CTTCCCCGAA
AACCCCTGCC GCACCGCCAT CGAAACCGCA GCCCAAGCCG TCCTCGACGC ACGCGCCGCC
GAAACCGAAC GCATCCGCCG CCTCAACCGG ATCCTGCCCG AAAAAGAACA CCGCCCCATG
CCCACACCCG CCACCCTCTA CAACCCCGAC ACCATGCCCC CCGCCCTCGC CGCCGCCCAC
AACGCCCTCG ACGATGCCGT GGACGAAGCC TACGGCTACA CGGGCGGCAA CAGCGACAGC
GAACGCACCG CCTTCCTCTT CCGCCTCTAC AAAAATGCCG TCTGA

FIG. 24A-5

>PspPRI CCYCAG 2805 nt (SEQ ID NO:9)

ATGAGTATAG ATTACAAGCA CGTCAGACAA CAATTACAAC AAATCGTTCA CGACTATAAA
GACTCTGAGG GCTATGAGCG TGGCCAAAGC CAAAACTTTT GGACTCAAGT GTTTAATGCT
TATGGCGTGT CTGGCCAAAC TCAAACTAAA GCATTTGAAC ATCGTCTTAA AGACAAATCT
AATCAAAAAT ACGTTGATGC TTTCATCCCC AAATTGGTCA TAATTGAGCA AAAAAGTCGT
GGTGTAGATT TAAATAAAGC CTATACACAG GTGTCTGAGT ATTACGATCG TATTAACGCT
AAAGACAAGC CTAGATACAT CATCTTATGC AACTTCGATG AAATTTGGCT GTATGACATC
AACAACCCAT TAGATATTAA AAAGCATCAA TGTCCACTCT CTGATCTGCC AAACAACGCT
GAATGGTTCG AGTTCTTATC GCCTGAAAGC CAACAATCTA ATGAGATTAT CGAAGAAAAC
CCCATCAACC GACAAGCTAC TGAAAAGCTA GCTAAACTGC ACCAGGCTTT CATTGAGGAT
GGTGTAGATC CTGATGAATT AGCCTTATTT TTAACACGCC TAATCTTCTG TTTCTTTGCT
GACGACACCG CTATTTTTGG TAAAAAACAC GTACTGCACA ATTTGTTAAA AAACCATGCA
GCCACCGATG GTAGTAACTT ACAGCAGATA CTAACCACTT TATTTGACAC ATTAAACACT
GAGCATCGTT CAAGCAGATT GCCTGAGCAT TATGCTCAAT TCGCCTATAT CAATGGCGGT
CTTTTTGAAG AAACTATCAA CATCCCTTAT TTCGATGAAA AGCTATATAA CCTAGTTATG
GAGTGTGATG CACTCGATTG GACTGAGATT AGCCCTGCAA TCTTCGGTTC GATGTTCCAG
AGTGTATTGG ATGCTAGTGG GGGAGATAGC ACTGAGGATA AACGGCGTGA GTTTGGTGCT
CACTACACCA GTGAGAAGAA TATTCTAAAA GTCATCAACT CATTGTTTTT ACAAGAGTTA
CGTGATGAGT TTTCTAAGTG TACTAACAAC ACACCAAGAG CCGTACAGCT ATATGAAAAA
CTGCCTACAC TAAAGTTCTT TGACCCTGCT TGTGGTTGCG GTAACTTTTT AATCATTGCC
TATCGTGAAT TACGTCTATT AGAAAACCAG TTGATTGCCA AGATATTTGG TGATCAAAAG
GGATTACTTG ATATTAGCAG TATGTGTAAT GTGACCGTAG ATCAGTTTTA CGGCATTGAG
ATTGAACCTC ATGCCGTTCA TATCGCTCGT GTTGCTATGT GGATCACTGA CCACCAGTTA
AACATGACCA CTGCGGAGCG TTTTGGCACA ACCAGACCGA CCACACCGAT TGTTTATAGC
CCTCATATTA TTGAAGGTAA TGCCTTACAA ATAGATTGGG AAACAGTCTT ACCTGCCAAT
GATTGTAGCT ATGTAATGGG AAATCCTCCA TTTATCGGGA AATCCAATCA AAGTTCTGAA
CAAAAGTCAG ATATAAAATT AGTAGCTAGC CATATTAAAA ATCACAAGTC TTTAGACTAT
GTAGCAGGTT GGTATATAAA ATCCATGCAT TATATGCAAT CAGTTAATAA TGCAAATCAT
TATATAGATA CAGCTTTTGT ATCAACAAAC TCGATAGTTC AAGGTGAGCA AGTTGACATC
CTATGGAGAT ATCTAATTGA TGATTGCAAA GGCCATATAA ACTTCGCACA TCATACCTTT
AAATGGAGCA ATGAGGGCAA AGGGATAGCT GCGGTTCATT GCATTATTGT TGGCTTTTCT
TTAGTAGAAA AGAAAGAGAA AACCATCTTC GAATACTCTG ACATTTCGTC AGAACCAAGC
CCCAAAAAAG CTAGAACCAT CAATGCATAT TTAACTGACG CTCCAATAGT TTTCTTTAGT
AGAAGAAGTA AACAAGTTTC CAACGAAAGT AGTATGGTTA GTGGCAACAA GGCAACAGAT
GGAGGTAACT TAATTCTGTC AGACTCAGAG TATATAGATT TAATTAATTC AGAGCCATTA
GCTAAGAAAT ACATTAAACG TTTTATGATG GGCTATGAAT TTCTTAACAA TATTAAGCGA
TGGTGTCTGT GGTTTGATAA TGTTGACCCA ATACAATTAA GTAAAGATCT TGAAAAAATG
CCTCTTATTA AAAAGCGCAT TCATAATGTC AAAGAACTGC GTTTGAACAG CACTAAAAAG
TCTACTGTCA AAAAGGCAGA AACACCTCAT TTGTTCGATG AAAGACGGCA TACTAATAAA
CCTTACGTTG CAATACCCGT CGTATCATCA GAGAACAGAA GATTTATACC GATTGGCTTT
ATTGATGGTA ACACCGTAGC AGGTAACAAG TTATTTGTAA TTGTAGATGG TAATACCTAT
CAGTTCGGTA CTCTGTCTAG CAGTATGCAT AACGCATTTA TGAGACTAAC AGCGGGTAGA
ATGAAAAGTG ACTATAGCTA TTCAAGCACC ATTGTTTATA ACAACTTTCC TTACCCATTT
ATGGCTGATG ATCATAGTGA TAAAGCACAA AAAGCGAGAG AAAGCATAGC TAAGGCTTCA
CAACAGGTTT TAGATGCTCG TAAACACTAT CAAGACGGTA GTGAGAACGC ACCAACCCTG
GCTCAGTTAT ACAATACCTA TCTAATTGAT CCATATCCAC TACTAACCAA GGCTCATAAA
GCGTTAGATA AGGCCGTTGA TAGTGCTTAT GGTTATCGTG GCAAAGGTGA TGATGCGAGT
CGAGTCGAGT TTTTGATTAA GAAGATTGCT GAGTTAAAAA ATTAA

FIG. 24A-6

>CstMI AAGGAG 2859 nt (SEQ ID NO:11)

ATGGTTATGG CCCCTACGAC TGTTTTTGAC CGCGCTACCA TTCGCCACAA TCTCACCGAA
TTCAAACTCC GGTGGCTTGA CCGCATTAAG CAATGGGAGG CGGAAAACCG ACCCGCAACC
GAGTCGAGTC ACGACCAACA GTTCTGGGGT GACCTGCTCG ACTGCTTCGG TGTCAACGCC
CGCGACCTGT ACTTGTACCA ACGCAGCGCT AAACGCGCTT CGACGGGGCG CACCGGCAAG
ATCGACATGT TTATGCCGGG CAAAGTCATA GGCGAGGCTA AGTCCCTCGG CGTCCCGCTC
GATGATGCTT ATGCCCAAGC TTTGGATTAT TTGCTGGGCG GTACTATCGC GAACTCGCAC
ATGCCGGCCT ATGTTGTCTG CTCCAACTTC GAGACCCTGC GGGTTACCCG TCTTAACCGC
ACCTATGTCG GCGATAGCGC CGACTGGGAC ATTACATTCC CTTTAGCTGA GATTGACGAG
CACATCGAAC AACTCGCTTT TCTCGCCGAC TATGAAACCT CCGCCTACCG GGAGGAAGAA
AAGGCTTCCC TGGAAGCCTC TCGGTTAATG GTGGAGCTCT TCCGCGCCAT GAACGGCGAC
GACGTGGACG AGGCAGTAGG CGATGACGCT CCCACCACGC CGGAGGAAGA AGACGAGCGC
GTCATGCGCA CCTCTATCTA CCTCACCCGA ATCCTCTTCC TTCTCTTCGG CGACGACGCA
GGACTCTGGG ATACCCCGCA TTTGTTTGCG GACTTTGTGC GCAATGAAAC CACCCCAGAA
TCGCTCGGCC CGCAGCTCAA TGAGCTATTT AGCGTGCTTA ATACCGCCCC GGAAAAGCGG
CCTAAGCGTT TGCCATCAAC GTTGGCGAAG TTTCCTTATG TCAATGGTGC CCTATTTGCT
GAACCGTTGG CCTCGGAGTA CTTCGACTAC CAGATGCGCG AAGCATTGCT TGCTGCCTGC
GACTTCGACT GGTCGACCAT TGACGTCTCC GTCTTTGGTT CGTTGTTCCA ATTGGTGAAA
TCGAAGGAAG CGCGCCGCAG CGACGGCGAA CACTACACGT CTAAGGCCAA CATCATGAAG
ACCATCGGCC CGCTGTTTTT GGACGAGCTG AGGGCTGAGG CCGATAAGTT GGTGTCTTCT
CCGTCGACGT CGGTGGCCGC ATTAGAGCGC TTCCGCGACT CCCTGTCTGA GCTGGTATTC
GCTGATATGG CTTGTGGTTC TGGAAACTTC CTGCTTCTGG CGTATCGGGA GTTGCGCCGG
ATTGAAACCG ACATCATTGT CGCTATACGC CAGCGCCGCG GTGAAACGGG CATGTCGTTG
AATATTGAGT GGGAGCAGAA ACTGTCCATT GGGCAGTTCT ACGGCATTGA GCTGAATTGG
TGGCCTGCCA AGATTGCTGA GACTGCCATG TTCCTAGTTG ACCATCAGGC CAACAAGGAG
CTTGCCAACG CTGTGGGTAG GCCTCCGGAG CGGTTGCCGA TTAAGATTAC CGCGCACATT
GTGCACGGCA ATGCCCTGCA GCTTGATTGG GCAGACATAC TCTCGGCTTC TGCCGCCAAG
ACGTATATCT TCGGTAACCC GCCGTTTTTG GGGCATGCGA CGAGAACTGC TGAACAAGCT
CAAGAACTCC GAGACTTGTG GGGCACTAAG GACATTTCAC GCTTGGACTA CGTCACCGGC
TGGCATGCAA AGTGCTTGGA TTTCTTTAAG TCCCGAGAGG GTCGTTTTGC GTTTGTCACC
ACCAATTCAA TTACTCAAGG TGATCAAGTT CCACGGCTAT TTGGGCCTAT CTTCAAAGCA
GGGTGGCGTA TTCGTTTCGC TCACCGCACG TTTGCGTGGG ACTCTGAAGC ACCCGGTAAA
GCTGCTGTTC ACTGCGTCAT TGTTGGCTTC GATAAGGAGA GTCAACCACG TCCACGTCTG
TGGGATTATC CCGATGTAAA GGGCGAGCCA GTCTCAGTGG AAGTAGGCCA GTCCATTAAT
GCCTATTTAG TAGACGGCCC TAATGTTCTT GTCGATAAAT CCCGGCATCC TATTTCGTCG
GAAATATCGC CCGCAACTTT TGGAAATATG GCGCGAGATG GCGGCAACCT TCTAGTTGAG
GTCGACGAAT ACGACGAGGT TATGAGTGAC CCCGTAGCGG CAAAGTATGT TCGCCCTTTC
CGGGGTAGTC GAGAGCTAAT GAACGGCTTA GATCGGTGGT GTCTATGGCT TGTAGATGTA
GCACCGTCAG ACATTGCCCA GAGTCCGGTT CTGAAAAAGC GTCTAGAAGC GGTTAAGTCT
TTTCGAGCCG ACAGTAAAGC GGCAAGTACA CGGAAAAATGG CTGAAACTCC GCACTTATTC
GGCCAGCGGT CGCAACCGGA TACTGATTAC CTTTGCCTGC CGAAGGTAGT AAGCGAACGC
CGCTCGTATT TCACCGTACA AAGGTATCCA TCAAACGTAA TCGCTTCTGA CCTAGTATTC
CATGCTCAAG ATCCAGACGG CCTGATGTTT GCGCTAGCGT CGTCGTCGAT GTTCATTACG
TGGCAGAAAA GCATCGGAGG ACGACTCAAG TCTGATCTCC GTTTTGCTAA CACTTTGACG
TGGAATACTT TCCCAGTGCC AGAACTCGAC GAGAAGACGC GGCAGCGAAT TATTAAAGCG
GGCAAGAAGG TGCTCGACGC CCGCGCGCTG CACCCAGAAC GCTCGCTGGC CGAGCACTAC
AACCCACTCG CGATGGCACC GGAACTCATC AAAGCGCATG ATGCGCTCGA CCGCGAGGTG
GATAAAGCGT TTGGCGCGCC ACGAAAGCTG ACAACTGTTC GGCAGCGCCA GGAGCTATTG
TTTGCCAATT ACGAAAAACT CATCTCACAC CAGCCCTAG

FIG. 24A-7

>NmeAIII GCCGAG 2814 nt (SEQ ID NO:13)

ATGAAAACCC TGCTCCAACT CCAAACCGCC GCACAAAACT TCGCCGCCTA CTACAAAGAC
CAAACCGACG AACGCCGCGA GAAAGACACC TTCTGGAACG AATTTTTCGC CATTTTCGGC
ATCGACCGCA AAAACGTCGC CCACTTCGAA TACCCCGTCA AAGACCCTGC CGACAACACC
CAATTCGTCG ATATATTTTG GGAAGGCATC TTCCTTGCCG AACACAAATC CGCCAACAAA
AACCTGACCA AGGCCAAAGA GCAGGCGGAA CGTTATTTAC AGGAAATCGG GCGCACCAAG
CCCTCCGCGC TGCCCGAATA TTACGCCGTC AGCGATTTTG CCCATTTCCA CCTTTACCGC
CGCGTACCTG AAGAAGGCGC AGAAAACCAA TGGCAGTTCC CTTTGGAAGA ATTGCCTGAA
TACATCACGC GCGGCGTTTT CGACTTCATG TTCGGCATCG AAGCCAAAGT CCGCCAAATT
CAAGAAGAAG CCAACATTCA AGCGGCGGCG ACCATCGGCA GGCTGCACGA CGCGCTCAAA
GAAGAAGGCA TTTACGAAGA ACACGAGCTG CGCCTCTTCA TCACGCGCCT GCTTTTCCTC
TTTTTTGCCG ACGACAGCGC CGTTTTCCGG CGCAACTACC TTTTCCAAGA CTTTTTAGAA
AACTGCAAAG AAGCCGACAC GCTCGGCGAC AAGCTCAATC AACTCTTTGA ATTTCTCAAC
ACACCCGACC AAAAGCGCAG CAAGACCCAA AGCGAAAAAT TTAAAGGTTT CGAATACGTC
AACGGCGGTC TTTTCAAAGA ACGCCTGCGC ACTTTCGACT TCACTGCCAA GCAGCACCGC
GCCTTAATCG ACTGCGGCAA TTTCGACTGG CGCAACATCA GTCCAGAAAT CTTCGGCACG
CTCTTCCAAT CCGTCATGGA CGCGCAAGAG CGGCGCGAAG CGGGCGCGCA CTACACCGAA
GCCGCCAATA TCGACAAAGT CATCAACGGC CTTTTTTTAG AAAACCTGCG TGCCGAATTT
GAAGCCGTCA AAGCCCTCAA ACGCGACAAA GCCAAAAAAC TCGCCGCCTT CTACCAAAAA
ATCCAAAACC TGCAATTCCT CGACCCTGCC TGCGGCTGCG GCAACTTCCT TATCGTCGCC
TACGACCGCA TCCGCGCCCT TGAAGACGAC ATCATCGCCG AAGCCCTCAA AGACAAAGCA
GACGGCCTGT TCGACAGCCC GTCCGTCCAA TGCCGTCTGA AACAGTTTCA CGGCATCGAA
ATAGACGAAT TTGCCGTCCT CATCGCCCGC ACCGCCATGT GGCTCAAAAA CCACCAATGC
AACATCCGCA CACAAATCCG CTTCGACGGC GAAGTCGCCT GCCATACGCT GCCGCTCGAA
GACGCCGCCG AAATCATCCA CGCCAACAGC CTCCGCACAC CTTGGCAGGC GGCGGACTAC
ATCTTCGGCA ATCCCCCCTT TATCGGCTCG ACCTACCAAA CCAAAGAGCA GAAAAACGAC
CTCGAAAGCA TCTGCGGCCA TATCAAAGGC TACGGCCTGT TGGATTACGT CTGCAACTGG
TACGTCAAAG CCGCAGGCAT CATGGCGCAG CATCCCCAAG TTCAGACGGC ATTTGTTTCC
ACCAATTCCA TCTGCCAAGG CCAGCAGGTC GAAATCCTCT GGGGCAGCCT TTTAAACCAA
GGCATCGAAA TCCACTTTGC CCACCGCACC TTCCAATGGA CGAGCCAAGC CGCAGGCAAA
GCCGCCGTCC ACTGCATCAT CGTCGGCTTC CGCCAAAAGC CGCCAATGCC GTCTGAAAAA
ACCCTCTACG ACTATCCCGA CATCAAAGGC GAACCCGAAA AACACGCCGT AGCCAACATC
AATCCTTATC TGATCGATGC GCCCGATTTG ATTATCGCCA AGCGCAGCCG TCCCATACAT
TGCGAACCTG ATATGGTCAA CGGAAGCAAA CCGACCGAAG GCGGCAACCT TATCCTTTCA
ACCGCCGAAA AAGATGCCCT GATTGCCGCC GAACCCTTGG CGGAGCAATA CATCCGCCCC
TTTATCGGCG CGGATGAGTT TCTCAACGGC AAAACCCGTT GGTGCCTGTG GTTTCACGGC
GTATCCGATG TCAAACGCAA CCACGACCTG AAACAAATGC CCCAAGTTCA AGCCCGTATT
CAGGCGGTCA AAACCATGCG CGAAGCCAGC AGCGACAAAC AAACTCAAAA AGATGCAGCA
ACCCCGTGGC TTTTTCAAAA AATCCGCCAG CCTTCAGACG GCAATTATCT GATTATTCCG
AGCGTGTCGT CTGAAAGCCG CCGTTTCATC CCCATCGGTT ATCTGTCGTT TGAAACAGTT
GTCAGCAATC TGGCATTTAT CCTTCCAAAC GCCACCCTCT ACCACTTCGG CATCCTCAGC
TCCACCATGC ACAACGCCTT TATGCGTACC GTTGCAGGTC GTCTGAAAAG CGATTATCGC
TACTCTAATA CCGTCGTGTA CAACAACTTC CCCTTCCCCG AAAGCTGCCG GTTGCCGTCT
GAAAACGACC GCCCCGACCC GCTCCGCGCC GCCGTCGAAG CCGCCGCCCA AACCGTCCTC
GACGCGCGCG GACAATACCG CCGAGAAGCG CAGGAAGCCG GTTTGCCCGA GCCGACCCTC
GCCGAACTCT ATGCGCCCGA CGCAGGCTAT ACCGCCCTCG ACAAAGCCCA CGCCACCCTC
GACAAGGCAG TCGATAAAGC CTACGGCTAC AAAACAGGCA AAAATACCGA CGACGAGGCA
GAACGCGTCG CCTTCCTGTT CGAGCTGTAC CGCAAGGCGG CGGCAATTGC GTAG

FIG. 24A-8

>CdpI GCGGAG 2781 nt (SEQ ID NO:15)

ATGTCATCGA GTTCTCCAAG TGAAAAGAAA CTAGCCGCCA AGCTATTTGC TAATAAGTGG
GCAGACCGTG GCAATGAGAA AAGCGACACT CACAGTTTCT GGTTGGAGCT TCTTCGTGAT
GTTGTAGGTA TGCAAGATGT GACTACCAAC GTGCGATTCG AATCGCGCAC GAGTCAACGC
GGCTACATCG ATGTGGTGAT CCAAGACGCC AAAACTTTCA TTGAACAAAA ATCCATCGAT
GTTAGTTTGG ACAAAGCTGA TATCCGTCAG GGGCGAGTTG TCACTGCTTT TAGACAAGCA
CTGAATTACG CCAACACTAT GCCGAACAAA CTGCGACCTG ACTACATTAT TACGTGTAAT
TTCGCAGAGT TTCGTATTCA TGACTTAAAT AAGGTGAATG CGGAAACTGA CTATATTTCC
TTTACCTTGG CAGAATTGCC TGACCAAATC CATCTTCTAG ATTTTCTCAT CGACCCACAA
AAATCTCGTG CTGTTCGTGA AGAAAAAGTG TCGATGGATG CTGGCACACT CGTCGGCAAG
CTTTACGACG CCCTGCGTGA TCAGTATTTA GACCCCAACA GTGATGCGAG CCAGCACTCC
CTCAACGTTT TGTGCGTGCG CCTTGTATTT TGTTTGTTTG CTGAAGACGC CGGCCTCTTT
GAAAAGGATG CGTTTTATCG TTATCTTGAC GGATTACGCG CCGATCAAGT TCGCGTCGCG
CTGAGAGATT TGTTCGAAGT ACTCAATACA CCAGTTGATT CACGTGACCC TTATCTTTCT
GAACAGCTTA AAAACTTCCC TTATGTCAAC GGTGGTTTAT TCGCCAAAGT CGAGCAGATC
CCTAATTTCA CTGATGAAAT TCTTGACCTA TTAGTTCATG AGGTATCGGA GAAAACTAAC
TGGGCCGAAA TCTCGCCTAC AATCTTTGGC GGTGTTTTTG AATCCACCCT CAACCCAGAA
ACTCGCGCCC GTGGAGGCAT GCATTACACG AGTCCCGAAA ACATCCATAA GGTGATTGAC
CCGCTGTTTC TTGACTCTCT CAAGGCAGAG CTAGATTCCA TCCTTAACGC ATCAGGGATA
ACTGCAAACA AGCGCAAGAA ACAACTCGAG GCATTCCACA CCAAGATCTC AGAGCTAAAA
TTTTTCGACC CTGCCTGCGG TTCGGGAAAC TTCCTCACAG AAACCTATAT CCACCTGCGC
AAGATCGAAA ACAAGATCCT TTCAGAGCTT GCCGGCGACC AAACCCAGCT CGGCTTTAGC
AACGTCACTC TCAAGGTCAG CTTGGACCAG TTCTACGGCA TCGAGATCAA TGATTTCGCC
GTCTCCGTCG CCTCCACCGC CCTATGGATT GCGCAGCTCC AGGCCAACAT CGAGGCCGAA
TCGATCGTCA CCGCAAACAT CGAAAGTCTT CCGCTTCGCG ACGCCGCCCA CATCCACCTC
GGTAATGCGC TGCGCACCGA CTGGGCTTCG GTACTCGCGC CTGAACAGTG CAATTACATT
ATTGGAAATC CGCCGTTTTT AGGCTACTCG CGGCTTGACG ACGCTCAAAA GGAAGACCGC
AAGGCCATCT TCGGCAAGAA TGGCGGTGTG CTCGATTACG TAGCGTGCTG GCACCGCAAA
GCCGCCGAAT ATATGCACGG AACGGATGCT GAAGCCGCGC TCGTTTCCAC CAATTCGATC
TGCCAAGGCC AGCAAGTCAC TCCGCTGTGG AAGCCGCTTT TCGACGCCGG GATCCACATC
AACTTCGCCC ACCGCACTTT CGTGTGGAGC AACGAGGCAG CAGATCAGGC GCATGTCTTA
TGTATCATCG TCGGGTTTTC CTACATCGAT CGACCAGTCA AGCAGGCGTG GACCTACCGG
AAGAACGAGG TGGAATACTC GGAGCCTGTA CATTTGAACG GTTACTTGGC AGATGCCCCG
GATGCGTTCC TGACACGCAG GTCAAAGCCG ATTTCGGATG TGCTGGAAAT GGCTCAGGGA
TTCAAGCCCG CCGATGGTGG ACATCTCTTG CTCACTCAAG AAGAACGAGA CGAACTCCTT
GCAAAAGAAC CACTAGCTGC GCCGTGGATT CGAAAGTTCT CCATGGGCGC CGAATTCATC
AACGGCAAGG ACCGCTATTG CCTATGGTTG CCGGAAATTA CAGGCGTTGA GCTAAAGAGA
TTGCCTCTCG TTCGCGCGCG AATTGACGCA TGCCGTGAGT GGAGGCTTGA ACAAATCAAA
ACTGGAGATG CATACAAATT GTCAGACCGG CCACACCTAC TGCGGCCAAC CAGCAGGTTT
AAGGACGGAA CCTACATCGG CATCCCAAAG GTTTCTTCAG AGCGACGGAA GTATGTACCG
TTTGCTTTTG TGACAGATGG AATGATTCCT GGCGACATGC TCTACTTCGT CCCTACGGAT
TCTCTATTTG TGTTTGGGGT TCTCGTTTCA CAATTCCAAA ACGCCTGGAT GCGTGTAGTG
GCAGGCCGTC TCAAGAGCGA CTACCGCTAT GGCAACACCA CTGTCTACAA CAACTTCGTT
TTCCCCGAGG TAGATGATTC AGTGCGAGTG GACGTCGAAA AGCGTGCTCA GGCGGTGATC
GACGCACGCT CTCTTTACCC CGAAGCGACG CTTGCTGACA TGTATGATCC CGACAATGAC
TTCCTCTACC CCGAGCTCAT GAAGGCCCAC CGCGAGCTAG ACCGCGCTGT CGAGATGGCT
TATGGCGTGG ACTTCGGTGG CGACGAGCAG CAGATAGTGG CTCACCTCTT CAAGCTGTAC
AACGAGAAAG TAGAGAAATG A

FIG. 24A-9

>ApyPI 2847 nt (SEQ ID NO:17)

ATGCTCTCTG ATCCTGTCTT TGACCGTGCC ACCATCCGCC ATAAACTCAT
TGAGTTCAAA ATCCGCTGGC GCGGCCATAT CGACCAGTGG AAAGCAGAAA
ACCGCCCCGC CACCGAGTCC AGCCACGATC AACAGTTCTG GGGTGACCTC
CTAGCCTGCT TCGGCGTCAA CGCCCGCGAC CTTTACCTGT ATCAGCGCAG
CGCGAAACGA GCCTCCACCG GCCACACCGG CAAGATTGAC ATGTTCATCC
CCGGCAAAGT CATCGGCGAG GCCAAGTCCC TCGGTATCGA CCTGGACAAG
GCTCACGAGC AAGCACTCGA CTACCTGCTC GGCGGCACCA TTCCGAACTC
ACAAATGCCG GCCTATGTCC TCTGCTCCAA CTTCGAGACC CTGCGCATCA
CCCGCCTTAA CCGCGACTAC GTCGGCGACT CTGCAGAATG GGACGTTACC
TTCGACCTGG ACGAAATCGA CGAGCATCTG GAACAGCTCG CGTTCCTGGC
GGACTATGAG ACCTCGGCCT ATCACGAGGA AGAACAAGCC TCCCTTGAGG
CCTCACGCCT GATGGTCGAG CTGTTCCGCG CCATGAACGG CGACGAGGCA
GACGAAGCCG TGGGCGATGA AGCCCCAACC ACCCCGGAGG AAGAAGACGA
AAGGGTCATG CGCACCTCGG TCTACCTAAC GCGCATCCTC TTCCTCCTTT
TCGGCGACGA TGCAGGCCTG TGGGACACCC CGCACCTGTT TACGACGTTC
GTGCGCAACG AAACCACCCC GGAATCTCTC GGACCTCAGC TCAACGAACT
TTTCCGAGTC CTCAACACCC CGGAGGACAA GCGGCCTAAG CGCTTGCCCG
GCACCTTGGC GAAATTCCCC TACGTCAACG GCGCAATCTT CGCCGAACAG
CTCGACCCTG AATACTTCGA CTACGCCATG CGCGAAGCCC TGCTCAACGC
CTGCGACTTC GACTGGTCAA AAATCGACGT GTCCGTCTTC GGCTCACTGT
TCCAGCTGGT TAAGTCGAAA GAAGCCCGCC GTGGCGATGG TGAGCACTAC
ACCTCGAAGA CCAACATCCT CAAGACCATC GGACCGCTCT TCCTCGACGA
GTTGCGTGCC CAGGCTGACA AGCTGGTCTC CAACCCCGCC ACCCCGGTGC
GCAAGTTAGA AGAATTCCGC GACTCACTGG CTGCCCATAT TTTCTGCGAC
CCGGCCTGTG GTGCGGGAAA CTTCCTGCTC ACCGCCTATA AAGAACTGCG
CCGTATTGAA ACGGACCTTA TCGTGGCTAT CCGTCAGCGC CGTGGCGAGA
CGGGTATGTC GCTAAATATT GAGTGGGAGC AGAAACTGTC GATTGGGCAG
TTCTACGGAT TTGAGCTGAA CTGGTGGCCG GCAAAGATTG CAGAGACGGC
GATGTTCCTG GTGGATCATC AGGCGAATAA GGAGTTGGCG AATGCGGTGG
GGCGTCCGCC GCAGCGTTTG CCTATTACGA TTACCGCCCA CATCGTCCAC
GGAAACGCTC TCGCCCTGGA CTGGACGGAA GCGCTGCCCA AAGCAGTGGG
GGAGACGTTT ATCTTTGGCA ACCCACCATT TATCGGTCAA GATACGCGCA
CAAAACAGCA GCTCGAGGAA ATGAAAGCTG TATGGAGACG TAAAAACATC
TCGAGATTGG ACTACGTCAC GTGTTGGCAC ATAAAAAGCC TTGACCTTTT
CAGTACCCGT AACGGACGGT TCGCTTTCGT AACAACTAAC TCGATTACCC
AAGGCGAACA AGTGCCGCTT TTATTCGGCC CCATCTTCGC AGCAGGTTGG
CGTATCCGCT TCGCCCATCG CACATTCTCA TGGGATTCCG ATGCTCCCGG
TAAAGCCTCA GTCCACTGCG TCATCGTCGG TTTCGACCGT GCACACGAAC
CTCGCCCCCA GCTCTGGGAT TACCCGAATG TCAGCAGTGC CCCCGTGGCT
GTGCCTGTGG AGCGCGTGAT TAATGCTTAC CTCGTCGACG GCCCTAATGT
CCTTGTCCAA AAGATGACTT CGCCCATCTC CTGCGAGATT AAACCCGCAG
TTCTAGGCGC AATGGCAAAA GACGGAGGTG GCTTGATAGT TGAAGCCCAG
GACGTGCAAG AAGCTTTGGA CGATCCGATA GCGGCAAAGT ACCTACGTCC
GTACGTTGGC TCGCGAGAAC TTGTTCGCGG CCTTAGTCGG TGGTGTCTCT
GGATGGTCGA TCTCGACCCC GCCGACGTTC AGGCAAGTAC TTTTCTGCGT
TCACGAATTG AACAAGTACG CGCCTACAGA ACAACGTCCT CGGCTCCTAC
TACACGGAGC ATGGCAAAGA TTCCTCATCT TTTCGCACAA CGTTATCGGC

FIG. 24A-10

CACAAACAGA TTTCCTTTGC GTTCCATCCG TTGTTAGCGA GAACCGGCCA
TACTTCACAG CTGCGGATAT TGAGGAAGGA ACAGTTGTCT CCAGCCTTGC
GTTTGCGGTT GAAGATTCTG ATAGGTCACA GTTCGCGTTG ATTTCTTCGT
CAATGTTCAT TACTTGGCAA AAGATGATTG GAGGAAGGCT AGAATCTCGC
CTGCGTTTTG CGAACACACT GACGTGGAAC ACGTTCCCCG TACCAGAACT
CGATGAGAAG ACGCGCAAGC GGATTATTAA GGCTGGGCAG AAAGTACTCG
CCGCGCGCAC TGCACCCGGA GCGTTCCCTC GCGGAGCACT ACAACCCGCT
GGCTATGACA CCAGAACTGG TGAAGGCGCA TGA

>SpoDI GCGGAAG 2898 nt (SEQ ID NO:19)

ATGACGCCCC AAGATTTCAT CACCAAATGG CGCAACACCG AACTCAAGGA ACGGTCCGCA
TCCCAGTCGC ATTTCATTGA CCTGTGCCGC CTTCTGGACA TCGAAGACCC GACAACCGCA
GACCCCAAGG GCGAGTGGTT CACCTTCGAA AAAGGAGCGT CCAAGACAAG TGGCGGCGAA
GGCTGGGCGG ACGTCTGGCG CAAGGATTGC TTTGCGTGGG AATACAAGGG CAAGCGCGCC
AATCTGGACA AGGCGTTTGA CCAGCTCTTG CAATACGCCA TCGCGCTGGA GAACCCGCCG
CTTCTGATCG TGTCGGACAT GGATGTGATA CGCATCCACA CCAACTGGAC CAACACGGTG
CAGCAGGTGC ACACCCTTAC ACTGGACGAC CTCAAGGACG CCGCCAACCG TGACAAGCTA
CGCAACGCTT TTCTCAACCC CGACGTCTTC AAGCCCTCCA AGACCCGGCA ACTTGTTACC
GAACAGGCGG CACAGAACTT TGCCAACCTT GCCCAGCGTC TCCGGGAACG TGGCCACGAC
GCGCAACAGG TGGCGCATTT CGTCAACCGT CTGGTGTTCT GCATGTTTGC CGAGGATGTG
GAGCTTTTGC CGAACAAGAT GTTCGAGCGG ATGATCAAGG CCGCGCGCCC TGACCCCGCC
AGCTTTGCCA TCCACGCCAA GGCGCTCTTT GCAGCTATGA AAGACGGCGG GCTTGTGGGC
TTCGAAAAGG TGGACTGGTT CAACGGCGGC CTGTTCGACA ATGACGACGT GCTGCCGCTG
GAATGGGAAG ACTTAGACGA CCTCATTCGC GCGGCACATC TGGACTGGTC CGACATTGAC
CCGTCCATCC TTGGCACCTT GTTCGAACGC GGGTTGGACC CGGCCAAGCG CAGCCAGTTG
GGCGCGCATT ACACCGACCG CGACAAGATC ATGCAGATCG TGAACCCGGT CATTGTCGAA
CCGCTCTTGG CCGAATGGGC CGAGGTGAAA GCCCAGATCG AAGACCTGAT CGACAAAGCC
CCCAAGGCGA CGAAGGACAA GCTTCTCAGC ACGTCGCAGA AGGCCGCCCG CACCCGCGCG
CTGGACAAGG CCGAGGCGCT GCACCAAGCG TTTCTGGACC GGCTCAAGGC GTTCCGTGTG
CTGGACCCGG CCTGTGGGTC TGGCAACTTC CTCTACATCG CGCTTCTGGA ACTCAAGAAC
ATCGAACATC GGGTGAACCT AGAGGCCGAG GCGCTGGGCC TGCCCCGAGG GTTCCCGCAA
ATCGGCCCCG AGGTTGTGCT GGGCATCGAA CTCAGCGCCT ATGCGGCGGA ACTGGCCCGC
GTGTCAGTCT GGATTGGCGA AATCCAATGG ATGCGCCGCA ACGGATTCGA GGCGGCGAAG
AACCCGATCT TGCGGTCCCT TAAGACGATT GAGAACCGGG ACGCGGTGTT GAACCCGGAC
GGGACGCGGG CGGACTGGCC GAAGGCGGAT GTGGTTGTCG GGAACCCCCC GTTTTTGGGC
GTCTACAAAA TGGGAGAAGA ACTAGGGGAA GATTACACAA TTGCATTGCG CGATGCTTGG
CCGGAAATGC CGGGAGCCGC AGACCTTGTT ACCTATTGGT TCGCCAAAGC TTGGTCACAG
ATGCAATGCG GAGACCTAAG TCGTGCTGGA CTTGTGGCAA CGAACTCTAT TCGCGGTGGT
GCAAATAGGA CTGTCCTAAA ACCGATTGCC GAACATGGCG GAATTTTTGA TGCATGGTCG
GACGAAGCAT GGACAGTAGA GGGCGCAGCA GTGCGTGTAT CTATGATTTG CTTTGGAAGC
AAACTGCCGT CTCACCCCAA GTTAAATGGC AAAGTTGTGG ATAAAATTCT TTCTGATTTA
ACTGCAAACG CTGCCGGGTT TGATCTTACA AAATCATCTC GAATTTCAGA AAATAAAGGT
GTTTGCATCC GGGGCATTGA AACCGGCGGT CCATTTGAAT TTTCGCAGGC GGATTTCGAA
GCACTTGCTA CAAAGCCTCT GAATCCCAAC GGGCTACCCA ACACACGAGT TATCCGGAGA
ATTCTAAATG GGAACAATAT TCTGAAGCGG CAACCAGAAC GTTATGCGAT AGACTTCTCT
GACTTCCGCA CGAAGGAAGA GGCCGCATTG TTCGAAGCGG TCTATTCATG GCTTGAACAA
GCCTACGAAA GCTATGAGCG GAAATCGAAG CGCCGGATTG TAAGACGTCA GGACTGGTGG
CTGCATCGAA GATCAGGAGC AGCGCTCAAA AATGCGGTAA GTAGACTTTC CCGATTTATT
GTTACACCGC GTGTTGGAAA ACACAGAATA TTCGTATGGC TTGACTCAAA TGCACTTGCA

FIG. 24A-11

GATAGCGCCA CGTTCATAGT GGCCCGCGAC GATGAAACCA CCTTCGGCAT TCTGCATTCC
AGTTTTCATG AACTCTGGTC ACTGCGTATG GGCACTTTCC TTGGGGTGGG TAACGACCCC
CGCTACACCC CCTCTACCAC CTTCGAAACC TTTCCCTTCC CCGAAGGCCT CACCCCCAAC
ATCCCCGCCG ACGAGTATGC CGATGCCCCC CGCGCCATCA AAATCGCCGC CGCCGCCAAG
CGCCTAAACG AGTTTCGGGA AAACTGGCTC AACCCCGCCG ATCTGGTGGA CCGCGTGCCA
GAGGTCGTTT CCGGCTACCC CGACCGCATC CTTCCCAAGA ACGACGCCGC CGCCAAGGAA
CTCAAGAAAC GCACCCTGAC GAACCTCTAC AACGCCCGCC CCGCATGGCT CGACCACGCC
CACAAGGCGT TAGACGAAGC GGTGGCCGAA GCCTACGGCT GGGGCGACGA CTGGCGCGCG
GGCGTGCTGA CCGAAGACGA AATCCTGGCC CGCCTGTTCA AGCTCAACCA AGAGCGCGCA
GCGAAGGAGA AAGCATGA

>DraRI 2871 nt (SEQ ID NO:21)

ATGCCTCAGACCGAGACCGCGCAGCGTATGGAAGACTTCGTTGCCTACTG
GCGCACCCTGAAAGGGGACGAGAAGGGCGAAAGTCAGGTATTTCTGGACC
GGCTCTTTCAGGCCTTTGGGCACGCCGGATACAAGGAAGCGGGCGCGGAA
CTGGAGTACCGGGTCGCCAAGCAGGGCGGCGGCAAAAAATTCGCTGACCT
GCTGTGGCGGCCCCGCGTGCTGATAGAGATGAAAAAGCGCGGCGAGAAAC
TGGCGAACCACTACCAGCAGGCCTTCGACTACTGGCTCAAGCTGGTGCCG
GACCGCCCACGTTACGCCGTGCTGTGCAATTTCGACGAGCTGTGGGTCTA
CGACTTCAATCAGCAGCTCGACGAGCCGATGGACCGGCTGCGGATAGAAG
AACTGCCTGAGCGGTACACGGTGCTGAACTTCATGTTTGAGCAGGAAAGG
GCGCCGCTGTTCGGCAACAACCGGGTGGACGTAACCCGCGAGGCCGCCGA
CAGCGTAGCGAAGGTGCTCAACAGTGTGATTGCCCGTGGTGAAGACCGCG
CCCGCGCTCAGCGTTTCCTCTTGCAGTGCGTCATGGCGATGTTCGCCGAG
GACTTCGAGTTGATTCCGCGTGGCTTTTTTACCGAATTGGCCGACGACGC
CAGGGCAGGCCGGGGAAGCAGCTTCGACCTCTTCGGCGGGCTGTTCCGGC
AGATGAATACCTCCGAACGGGCACGGGGCGGGCGTTTTGCGCCCATTCCG
TATTTCAACGGCGGGCTGTTCCGCGCCGTGGACCCCATTGAACTTAACCG
CGATGAGCTTTACCTGCTGCACAAAGCCGCGCTGGAAAACAACTGGGCCA
GGATTCAGCCGCAGATTTTCGGGGTGCTGTTTCAGAGCAGCATGGACAAG
AAAGAGCAGCACGCCAAGGGGGCGCACTACACCAGCGAGGCCGACATCAT
GCGGGTGGTGTTGCCCACCATCGTCACCCCGTTTCAGCGGCAAATCGAGG
CGGCGACCACGCAAAAGGAACTGCGGGCCATTCTGGACGAACTCGCCAGC
TTTCAGGTGCTCGACCCCGCGTGTGGCAGCGGCAACTTCCTGTATGTCGC
CTACCGCGAACTGCGCCGCCTGGAAGCCCGCGCCCTGCTGCGGCTGCGTG
ACCTCTCCGCACCGGGGACCGCCCTGCCGCCTGCCCGCGTGAGCATCCGG
CAGATGCACGGGCTGGAATACGACCCCTTCGGCGTGGAACTCGCCAAAGT
GACCCTCACGCTCGCCAAAGAACTCGCCATCCGTGAGATGCACGACCTGC
TGGGCAACACCGGCCTGGACTTCGACCAGCCGCTGCCGCTGGACAACCTC
GACGACCGTATCGTGCAGGGCGACGCCCTCTTTACCCCGTGGCCCCGTGT
GGACGCCATCGTCGGCAACCCCCCGTTTCAGAGCAAAAACAAGTTGCAGC
GCGAGATGGGCGCGGCCTATGTCAAAAAGCTCCGTGCCCACTACCCCGAC
GTGCCGGGCCGCGCCGACTACTGCGTCTACTGGATTCGCAAGGCGCATGA
CCAACTGGGCAGCGGCCAGCGGGCGGGTCTGGTGGGCACCAACACCATTC
GTCAGAACGACAGCCGTGTCGGGGGGCTGGATTATGTCGTGCAGCACGGC
GGCACCATCACCGACGCCGTGGGCACGCAAGTCTGGTCCGGCGACGCCGC
TGTGCATGTCAGCATCGTCAACTGGGTCAAGGGGCCAGCCGAAGGCCCCA
AGCATCTGGCGTGGCAGGTGGGCGACCACCGCACCAGCCCCTGGCAAAGC
ACCGAGTTGCCCGTCATCAACTCTGCCCTGTCTGCCGGAACCGATGTCAC

FIG. 24A-12

GCAGGCGCAAAAGCTGCGCGTCAACATGAACAGCGGCGCGTGCTACCAGG
GCCAGACCCACGGCCACAAAGGCTTTTTGCTGGACGGTCTGGAAGCCGGG
CAGATGCTCAGCGCCGAGCGCAAAAACGCCGAGGTTATTTTTCCGTACCT
CACGGGTGATGAACTGCTCCGCACCAGCCCGCCGCACCCGACCCGTTATG
TCATTGATTTTCAGCCGCGTGACGTGTTCGGCGCGAGGGCCTACAAATTG
CCCTTTGCCCGCATAGAACGCGAAGTGCTGCCTACGCGCCAGGCCGCCGC
CGCCGAGGAAGAAGCCCGCAACGCCGAAGTGCTGGCCGCCAACCCAAAGG
CCAAGACCAACAAACACCACCGCAATTTCCTGAATCAGTGGTGGGCACTG
TCGTATGGGCGCAGTGAAATGATTGAGAAAATTTCATCACTGAGCCGTTA
TATTGTCTGCTCGCGCGTTACCAAAAGGCAAGTATTTGAGTTTCTAGATA
ATGGTATCCGTCCTAGTGACGGTCTTCAAATTTTCGCCTTTGAAGATGAT
TATTCATTTGGAGTCATCCAAAGTTCTGTCCATTGGCAGTGGTTAATTGC
ACGTGGGGGAACATTAACGGCCCGTCTTATGTACACCTCCGATACCGTTT
TCGACACCTTCCCCTGGCCTCAAGACCCGACACTGGCGCAGGTGCGGGCG
GTGGCGGCGGCAGCGGTGAAGCTGCGGGAACTGCGGAACAAGGTGATGCG
CGAGCAGGGCTGGAGCCTGCGCGACCTGTACCGGACGCTGGACATGCCGG
GCAAAAACCCGCTGCGTGACGCTCAGGAACGGCTGGACGCGGCGGTGAGT
GCGGCTTATGGCCTGCCAGCGGGGGCGGACATGTTGGACTTTTTGCTGGC
CCTGAACGCARAAGTGGCGGCGGCGGAAGCGCGGGGCGCGGCGGTGACGG
GGCCGGGCCTGCCTGCGGGCCTGAACACGGCGGACTTCGTGACGGCAGAT
GCGGTGCGGCCTCTGGGCTGA

>NhaXI 2937 nt (SEQ ID NO:23)

GTGAGCGAAC GGGTCGAGCA GATCGAGGCA TTTGTTGCCT ATGCGAAAAC GTTAAAGGGT
GACGAGAAGG GCGAAGCACA GGTGTTCTGT GATCGCCTTT TCCAAGCTTT TGGCCACGAA
GGTTATAAGG AAGCCGGCGC GGAACTGGAG AGTCGGGTGA AGAAGGCGTC CGGAAAGGGC
GTCAACTTCG CAGACTTGAT CTGGAAACCC CGGGTTCTGA TCGAAATGAA GAAAAGCAGC
GAAAAGCTGC ATCTTCATTA CCAGCAAGCC TTCGATTACT GGCTGAACGC GGTCCCTAAC
CGCCCGCGAT ATGTGGTGCT CTGCAATTTC AAAGAGTTCT GGATTTACGA CTTTGATAAG
CAATTAAACG AGCCAGTAGA CGTCGTCCGG CTTCAAGACC TGCCCGCCCG GTACACGGCG
CTAAACTTTC TTTTTCCAGA CAATCCAGAC CCGCTGTTTG GCAACGATCG CGAAGAGGTC
TCGCGTGTAG CGGCCTCAAA GGTCGCGCAG TTATTTCGGT CGATGGTCGC TCGCGGCATT
CCGCGAGAGC AGGCACAACG ATTTGTACTG CAGGCCGTGG TGGCGATGTT TGCTGAAGAT
ATCGACATGA TGCCGGCCGG GACGACCCTG CGGCTAGTGC AGGACTGCCT GGAGCACGGC
CAAAATTCGT ACGACGTGTT CGGTGGCCTG TTTCTCCAAA TGAACAATAA GGCGGCGGCG
CAGGGCGGCC GCTACAAGGG AGTTCCTTAT TTTAACGGCG GGCTATTTGC GACGGTCCAG
CCGATCGAAT TGACTACGGA CGAGCTAGAG TTGCTCGGCA AGAAGGATGA AGGTGCTGCT
TGGCAAAACT GGGCCAAGAT CAACCCTGCC ATCTTCGGCA CCATTTTCCA ACAGAGCATG
GACAAGGGGG AGCGGCATGC GTTCGGCGCG CACTTCACCC ATGAGGCCGA CATTCAGCGG
ATTGTCGGGC CCACGATTGT GCGTCCCTGG CGCGAACGCA TCGATGCAGC GAAGACCATG
GCGGAGCTGC TGGAGATTCG CAAAGCGCTT CTCAATTTCC GCGTCCTCGA TCCCGCCTGC
GGAAGCGGCA ATTTTCTGTA CGTGGCCTAC AGAGAGATGG TGCGTCTCGA AATCAAGCTC
ATGGCCAGAC TGGACAAGGA GTTTAGCTGG AAGACCGTAC AAAAGCAGGC TCAGGCCACA
TCGCTCATCA GCCCTCGCCA GTTTTTTGGT GTCGAGCGGG ATTCGTTCGG CGTCGAGTTG
ACCAAGGTCA CCCTAATGCT GGCAAAAAAG CTGGCCCTAG ACGAGGCCGC CGATGTTTTG
GAGCGCGACC AGATTGAGTT GCCATTGGCG GAGGATGAGG CGCTCCCACT GGACAACCTC

FIG. 24A-13

GATGGCAACA TTCTTTGCCG CGATGCGCTC CTATCGGACT GGCCCGAAGT AGACACCATT
ATCGGAAATC CCCCGTACCA AAGCAAAAAC AAGGCACAGC AAGAGTTCGG GCGTGCCTAT
CTGAACAAGA TTCGATCGGT TTTCCCGGAG ATTGACGGAA GGGCCGATTA TTGCGTCTAC
TGGTTTAGAA AAGCGCACGA CCAGCTGAAG CAAGGCCAAA GAGCTGGTCT CGTCGGCACC
AATACGATCC GGCAAAACTA TTCCCGAATC AGCGGGCTGG ATTACATAGC CAAGCACAAC
GGTACGATTA CGGAAGCGGT CTCTACCATG CCGTGGTCGG GCGACGCGGT CGTGCACGTT
TCCATCGTCA ACTGGGTGAA AGGCGAGGAT GACGGCAAGA AACGCCTGTA CATTCAGTCA
GGCAATGATC CGGCCGGCGG CTGGGATTAC AAGGACCTCG ACGAAATCAA CACCTCGCTT
TCGTTTTCAA CGGATGTGAG CCAGGCGCAA CGCATCAATG CGAACGCTGA AAAGGGCGGT
TGCTATCAGG GCCAGACACA CGGGCATAAG GGTTTTCTCC CGGAACCGGC CGAAGCGAAG
GCGATGATCA AGGCCAGCAA GGCAAACGCT AAGGTCCTCT TCCCATTTTT GATCGCCGAC
GATTTCTTGG GTGCGGTAGA CAAACTCGAA TGCAGATACG TCATCGATTT CCAAACCCGC
GACCTCCTCC AGGCCAAGGC GTTCAAAAGA CCGTTTGAGC ATCTTGAAAA GACGGTCCTT
CCTACCCGAA AGGAAGCTGC AAAGAAGGAA AAGGATCGAA ACAAGGAAGC TTTGGACGCC
GACCCGGAAG CCAAGGTCAA CAAGCACCAC GAAAACTTTC TAAAGCGCTG GTGGCTGATG
TCTTACGCGC GCGAGGACCT GATGCAGACG TTGGCTCCTT TGAGCCGCTA CATCGTTTGC
GCACGCGTTA CGCACAGGCC AATCTTTGAA TTCGTCTCGA CAGCCATTCA TCCGAATGAC
GCACTGAGCG TTTTCGCCTT GGAGGATGAT TACTCCTTTG GAATCCTTCA ATCGGGCATC
CATTGGGAGT GGTTTATCAA TCGATGCTCG ACCCTCAAGG CTGACTTTCG CTACACTTCG
GATACTGTCT TTGATAGTTT TCCGTGGCCC CAGGAACCCA GTGCCGATGC GGTGCGCCTG
GTCGCGAAGC GAGCTGTCGA GGTTAGGCAA CTTCGGTCTA AGCTGAAGGT CAAACATCAC
CTGTCGCTAA GGGAGTTGTA TCGAGCAATC GAAGGTCCTG GAGAACACGC TCTCAAGAAA
GCCCACAAGC TTCTGGACGA GGCCGTGCGC GGAGCTTACG GCATGTCTAA GAAGGCGGAT
GTATTAGAAA CATTACTGGA ACTGAACGAG ACCGTAGTAG CTGCGGAGGC CGACGGAAAA
CAAGTCGTCG GCCCTGGAAT CCCGCCTTCG GCCTCGAAGC TAAAGAACCT CGTCACTACT
GATAAGCTGA CGATCTCGCC GACGAGTTGG GCCAATAATG CTCCTGTAAA AACGTGA

>RpaB5I 3555 nt (SEQ ID NO:25)

ATGGGGGACT CAATAAGCGT ACCGGCAGTC GAGCAGTTCA TCGCGCGTTG GCAAGGCCGT
GAAGGCGGAC AGGAACGCGC GAACTACGTC TCGTTTCTCA CCGAGTTGAT CGCGCTGCTC
GGGCTGGACA AGCCCGACCC GGCCGACGCG ACGCATGAGC ACAACGACTA CGTGTTCGAA
CGCGCGGTGA AGAAGACCGC CGAAGACAGC GCTTCCTATG GCCGCATCGA TCTCTACAAG
CGCAACAGCT TCGTCCTCGA AGCCAAGCAG AGCCGGATCA AGGGCGGCAA GAAGGAAGTC
AGGGGACAGT ACGATCTGTT GAAGACCGAG GCCACCGCAG CAACGCTCGG CCGCCGCGGC
GCCGATCGCG CCTGGGACGT GCTGATGCTG AACGCCAAGC GGCAGGCCGA GGAATATGCC
CGCGCCCTGC CCGCCTCGCA CGGCTGGCCG CCCTTCATTC TGGTCTGCGA CGTCGGCCAT
TGTATCGAGG TCTATGCCGA CTTCTCCGGC CAGGGAAAGA ACTACACGCA GTTTCCCGAT
CGCCAGAACT TCCGCATCTA TCTCGAGGAT CTGCGCGACC ACGACGTCCG CGAGCGGCTG
CGCAAGATCT GGAGCGAGCC GACCGCGCTC GACCCGTCGC AGCAATCGGC GAAAGTCACG
CGCGACATCG CCAAGCGGCT CGCGCAAGTG TCGCTGGCGC TGGAGAAACA GAACTATCCG
GCCGACGACG TCGCGATGTT CCTGATGCGC TGCCTGTTCA CGATGTTCGC CGAGGACGTC
GAACTGTTGC CGGAAAAAATC CTTCAAGCTG CTGCTCGAAG ACTGCGAGAA AAACCCCGAG
GCCTTCGTCC ACGACGTCGG TCAGCTCTGG GAGGCGATGG ACACCGGGCA ATGGGCGCAC
GCGCTCAAGA CCAAGGTCAA GAAATTCAAC GGCGAGTTCT TCAAGAGCCG CGCCCGCGCTG
CCGCTCGGCC GCGAGGAGAT CGGCGAGCTG CGGCGGGCCG CCGAGTATGA CTGGAACGAG
GTCGATCCCT CGATCTTCGG CACGCTGCTG GAACAGGCGC TCGATCCGAC CGACCGCAAG
AAGCTCGGCG CGCACTACAC GCCGCGCGCT TATGTCGAAC GGCTGGTGAT CGCCACCATC
ATCGAGCCGC TGCGCGAGGA CTGGCGCAAC GTCCAGGCCA CCGCCGAAAC GCTGCGCGGC
GCAGGCGATC TCGCTGCCGC CGCCGCCGCG GTGCAGGCGT ATCACGACCG GCTGTGCGAG

FIG. 24A-14

ACGCGGGTGC TCGACCCGGC CTGCGGCACC GGCAACTTCC TTTACGTCTC GCTCGAACTG
ATGAAGCGGC TGGAAGGCGA AGTGCTGGAA GCTTTGCTCG ACCTCGGCGG CCAGGAAGCG
CTGCGCGGCC TCGGCTCGCA CTCGGTCGAT CCGCATCAGT TCCTCGGCCT CGAAATCAAT
CCGCGCGCCG CGGCGATCGC CGAGCTGGTG CTGTGGATCG GCTATCTGCA ATGGCACTTC
CGCACCAAGG GCGCCCCGCC CGACGAGCCG ATCCTGCGCG CCTTCAAGAA CATCAAGGTC
AAGAACGCGG TGCTCGACTG GGACGGCGCG CCGCTGCCGA AGATCGTCGA GGGCAAAGAG
ACCTATCCGA ACCCGCGCCG GCCGGAATGG CCGGCGGCGG AATTCATCGT GGGGAATCCG
CCGTTCATTG GGGCGAGCTT TTTGCGAGCG CGGCTTGGTG ACACCCACGC TGAAGCGCTT
TGGAGTGCCC ATCCTCAAAT GAATGAGTCG GCCGACTTCG TGATGTACTG GTGGGACCGC
GCGGCCGAAT TGCTGACCCG CAAAGGAACG GTGCTGCGGC GGTTCGGTTT TGTCACGACA
AACTCGATAA CCCAAGTATT TCAGCGTCGA GTGATCGAAA GGCACTTCAA GGCAAAGAGG
CCGATTTCGC TTGCTATGGC AATTCCAGAT CATCCCTGGA CCAAAGCTAC AACGGATGCC
GCAGCGGTAC GGATCGCAAT GAGCGTTGGA GAGACTGGCC GAGGCGATGG ACTGCTCCAG
ATCGTCGTCA ACGAGGCTCA CTTGGATTCA GATACTCCAA TCGTTGAGCT TCAGGGCCGC
GTAGGACCGA TAAACTCAGA CCTCACAATT GGCACAGACC TGACCACCAC CGTGCCTCTA
CGTGCATCTG AAGGCTTGGC ATCTCGTGGA GTTACGCTTG CAGGCTCTGG ATTCTTGATA
ACTTCAGAAG AAGCCGAACA TTTTGGTCTC GGTACGCACG AGAAGCTAAA GCAACATATT
CGAGGACTCC ATAATGGACG CGACCTGAAT CAGACATCAC GTCGAATTCT TGTGCTCGAC
TTCTTAGGGC TGAGCGAAGA GGAAGTCCGA AGGCATTTTC CAGAAGCATA TCAGCATCTA
CTCCGGACAG TGAAACCCGA ACGGGAAACG AACAAGAGAG CATCCTATAG GCAGAATTGG
TGGGTGTTTG CTGAGCCGCG GAAGGAGATG CGTCCCGCGC TGAAGGACTT GGGGCGCTAT
ATCGGTACGG CACGCACCGC TAAGCATAGG ATTTTCTCCA TGTTGGCGGG CCACTCCTTA
CCAGAGAGTG AGGTTATTGC GGTGGGGTCA GACGACGCGT TTATATTGGG AGTACTTTCG
TCACGACTTC ATGTTCGCTG GAGTCTGTCC AAAGGTGGCA CGCTGGAAGA CAGGCCTCGG
TACAATAACA GCATGTGCTT CGATCCCTTC CCCTTCCCCG ACGCCAATCC GATTCAGAAG
CAGACCATTC GGGTCATCGC CGAGGAGCTC GACGCGCATC GCAAGCGGGT GCTGGCGGAG
CATCCGCATC TGACGCTGAC CGGGCTGTAT AATGTGCTGG AGCGGTTGCG GGCGGGGGCT
GTGCCGCAGG CACAGCCGTC ACCCGCGGGC TTGACCCGCG GGTCCACGTC GTCACGCGGT
GCGGCGAAGA AAGACCTGGA TGGCCGGGGC ACTGGACGGC AAGACGGCGC TTCGCGCCTT
TCGCCCGGCC ATGACGATGC AGAGATGGTG CTCACACCCG ACGAGCAGTG CATCTTCGAC
GATGGCCTGG TGCTGATCCT GAAAGAACTG CACGACAGGC TCGATGTCGC GGTGGCCGAG
GCCTATGGCT GGCCGGCGAA CCTGTCCGAC GACGAGATTT TGGCGCGGCT CGTCGCTTTG
AACAAGCAGC GCGCCGACGA GGAAAAGCGC GGGCTGGTGC GCTGGCTGCG GCCCGACTAC
CAGATTCCGC GATTCGCCAA GGGCGTCGAC AAGCAGGCGG CGAAGGAAGA AGGCGCGCAG
ATCGCAGCGT CGCTCGATCT CGGCGAGACC CGGCAGAAGC CGTCGTTCCC GACCGGTGCG
GTGGAGCAGA CCGCCGCGGT GTTCGCAGCG CTGGCCGCAG CCTCCGGCCC GCTCGACGCC
AAATCGCTCG CCGCGCAGTT CAGGCGCACG AAGACGACCG AGAAGAAACT CGCCGAGGTG
CTCGCCTCAC TGGCGCGGCT CGGCTACGTG GCGACCACCG ACGGCGTCAG CTTCGCGCTG
CGCCGGGTCG CGTAG

FIG. 24A-15

>PspOMII CGCCCAR 3483 nt (SEQ ID NO:33)

CTGGAAATCG GCTTGAGTGT CCCGAAACAG GCAGGACCGA TCTTGAGCGT
CGATGATTTC ATCGCCCGCT GGACGACCTC GGGTGGCAGC GAGCGGGCCA
ATTTCCAGCA GTTCGCCATC GAGCTGACGC AGCTCTTGGA CGTTCCGGCC
CCCAAGCCCG CGACGGCGGA TGCGCAGAAC GACGACTACC GCTTCGAGCG
GCCCGTGACC TTCATTCATA CCGGCACGCA GTCGCGCGGC TTCATCGACC
TCTACCGGCG CGGCTGCTTC GTCATGGAAG CCAAGCAGGG CACAGGCGCC
GCGCCCGAGG AAGGCCAGCT TGATCTTCTA GCCGCGGCCC CGCCCGTGCA
GCGGCAAGGG CATGGCGTTC GCGGCTCGAA GCGATGGGAC GACACCATGC
TGCGCGCCCG CAACCAGGCC GACGGCTATG CCCGCGCCGT GGCGCGCGAG
GACGGCTGGC CCCCGTTCCT GCTGATCGTG GACGTGGGCC ATGTGATCGA
GGTCTATGCC GACTTCTCGG GCCAGGGGCA GGGCTACACG CAGTTCCCGG
ACGGCAACCG CTACCGGATC ACGCTGGACG ACCTGCGCGA CGCGGCGACC
CTTGACCGCC TGCAAGCCAT CTGGACCGAT CCGCACAGCC TCGACCCGAC
CCGCGTCAGC GCCCAGGTCA CGCGGCAGGT GGCCGAGCAT CTGGCCGAAC
TGGGTCGGTC CTTCGAGGCG CAGGGCCATG CCCCCGAGGC GGTGGCGCGC
TTCCTGATGC GCGCCCTGTT CACCATGTTC GCCGAGGACG TGCAACTGAT
CCCCGAGGGG GCCTTTTCGA AGCTGCTGCA GGACAGGCGC GGCCACCCCG
AACACGCCGC CCCGATGCTG GAAAGCCTGT GGCAGACGAT GAACACCGGC
GGCTTTTCCC CGGCGCTGTC CTGCGACCTC AAACGGTTCA ACGGCGGCCT
GTTTCGGGAG GCAACCGCCC TGCCGCTGTC CGCCATGCAG CTTGGCCTGC
TGATCCAGGC CGCGTCCCAC GACTGGCGCG AGGTCGAGCC GGCGATCTTC
GGCACCCTGC TGGAACGCGC GCTCGACACG CGGCAGCGCC ACAAGCTGGG
CGCGCACTAC ACCCCCCGCG CCTATGTCGA ACGGCTGGTG AACCCCACGG
TGATCGAGCC GCTGCGGGCC GAATGGCGCG ACATCCAGGC CGCGGCCGTC
ACGCTGGCAG GCCAGGACAA GCTGGACGAG GCGCGCGCGA CCGTGCGCGA
CTTCCACCGG CGCCTGTGCG AGGTGCGGGT GGTGGACCCG GCCTGCGGGT
CGGGAAACTT CCTGTATGTC GCGCTGGAGC TGATGAAGCG CCTGGAAGGC
GAGGTGATCG CGCTGCTGCG CGAGTTGGGC GAGGACCAGG GCGCCCTTGC
CCTGGCAGGC CACACCGTTG ACCCGCACCA GTTCCTGGGC ATCGAGGTGA
ACCCCTGGGC CGCCGCCGTG GCCGAGCTGG TGCTGTGGAT CGGCTATCTG
CAATGGCATT TCCGCACCCA TGGCACCGCC AGCCCGGCCG AGCCGGTCCT
GCGCGACTTC CGCAACATCG AGAACCGCGA CGCCGTGCTG GCCTGGGACG
GCACCCGGCC GAGGCTGGAC GATGCCGGGC AGCCCGTGAC CCGCTGGGAC
GGGGTGTCCA CCATCCGCCA CCCGGTCACG GGCGAACAGG TGCCCGATCC
GGCCGCGCGG GTGCAGGTTC TGGATTACCT CAAGCCGCGC CCGGCCAGAT
GGCCCGAGGC CGAGTTCATC GTCGGCAACC CGCCCTTCAT CGGCGCGTCG
CGGATGCGCG AGGCCCTGGG CGACGGCTAT GCCGAGGCCT TGCGCGCGGC
CTATCCCAGG ATGCCCGAAA GCGCCGATTT CGTGATGTTC TGGTGGGATA
AGGCGGCGCT GGCGACCCGC GCGGGCAAGA CCCGGCGCTT TGGCTTCATC
ACCACCAATT CGCTGCGCCA GACCTTCAAC CGGCAGGTGC TGGAACCGCA
TCTGGCCGAC CCGAAGAAGC CCTTGTCGCT GGCCTTCGCC ATCCCCGATC
ACCCCTGGGT CGATGCGGGG GACGGCGCGG CGGTGCGGAT CGCCATGACC
GTGGCAGCGG CCGGATCGGC GCCGGGGCGG CTGTTTACCG TCACGGACGA
ACGCCGGGGC GAGCGCGAGG CCGAGGGGCG CCCCGTCACC CTGTCCGGGC
AGATCGGCAA GATCCACGCC AACCTGCGGA TTGGCGCGGA TGTGGCGGGA
GCGAAACCGC TGCGGGCGAA CGCAGGCATC TCATCGCCGG GGGTGAAGCT
GCACGGCGCA GGCTTCATCG TCACCCCGGC CGAGGCACAG GCGCTTGGCT
TGGGCACCGT GCCGGGTCTT GAGGCGCATA TCCGCAGCTA TCGCAACGGC

FIG. 24A-16

CGCGACCTGA CCGCCACCCC GCGTGGCGTC ATGGTGATCG ACCTGTTCGG
CCTGTCCGAG GCCGAGGTGC GGACCCGGTT TCCCGCCGTT TATCAGCACG
TCCTGGACAA GGTGAAACCC GAGCGCGACC AGAACAACCG CGACAGCTAC
AAGCGCAACT GGTGGATTCA CGGCGAGCCG CGCCGCGACC TGCGCCCGGC
CTTGGAAGGC TTGCCCCGCT ACATCGCCAC GGTGGAAACG GCCAAACATA
GAATATTCAG CTTACTCGAC GCGACGATTT TACCCGACAA CAAGTTGATC
ATCATCGCTC TGGCAGACAC ATGGCATTTT TCGATTGTGT CATCGCGTAT
CCACTGGGTC TGGGCGATAG CAAATGCTGC GAAAATCGGC ATGTATGATG
GCGATGCCGT TTACCCCAAG GGTCAATGCT TCGACCCCTT CCCTTTCCCA
GATGCCACCG AGGCACAGAA AGCCCGCCTG CGCGCCTTGG GCGAGGAACT
GGACGCGCAT CGCAAGGCGC AGCAGGCCGC GCATCCCCGG CTGACCCTGA
CGGCCCTCTA CAACGTGCTG GAAAAGCTGC GCGCCGGCGA GCGGATCGAG
GGGCGCGACC GGGAAACCTA TGACGCGGGC CTCGTCGGCA TCCTGCGGGA
CATCCACGAC CGCATCGACG CCGCCGTGGC CGAGGCCTAT GGCTGGCCTG
CCGACCTGGA CGACGAGGCC ATCCTGACCC GCCTGGTCGA TCTGAACCGC
GCCCGCGCCG CCGAGGAAGC GGCGGGCCTG GTCCGCTGGC TGCGCCCCGA
CTATCAGAAC CCCGCAGGCC GCATTGCCGC CGCCAAGGGC CAGCAGGTCG
AACTGGACGT GGGCGCGGCG GCCGAGGCCG CCGACAAGGC GCTGTGGCCC
AAGGCCCTGC CCGAACAGAT CGCCGCCGTC CGCGCCGTCC TGTCGGACAT
GGGCGAGGCC ACGCCCGAAC AGGTCGCGCG CCAGTTCAAA CGCGCCCGCG
CGGCGTCGGT GAAGCCCCTG CTGGAAAGCC TCAGCGCCTT GGGTCAAGCC
CGCCTCATCG AAGGCGGGCG GTTCGCGGCC TGA

>DrdIV TACGAC 3435 nt (SEQ ID NO:35)

ATGACGCCTG AGGAATTTAT AACCCGCTGG TCGCCCTCCG GAGGCGCGGA
ACGCGCCAAT TACGTCCTCT TTCTCAGTGA GCTGTGCGAT CTGCTCGGCG
TGCCCAAGCC CGACCCCACC CAGGCCGATG AAGCTAAGAA CGCTTACGTC
TTCGAGAAGG ACGTTCCCGA CCTGCACGAT GACGGCGGCC TCAGCCAGCG
CCGCATCGAC CTCTACCGGC GGGGCGCGTT CATCTTGGAG GCCAAGCAGG
GGGTCGAGAA GGAAGCTACC GCTGAAGAAG CTCTCCTCAG CACCAAGGGC
AAGAAGAAAA AGGGACATGG CACGCGGGGC ACCAAAGGCT GGGACACCTT
CATGCGCCGC GCCAGGGAGC AAGCGGAGCG CTACGCGCAC CTGCTGCCCG
CATCCGAGGG CCGGCCCCCC TTCCTGCTCG TGGTGGATGT CGGGCATGTC
ATCGAGGTCT ACGCTGAGTT CACGCGTACC GGTGGGGCGT ATCTCCCCTT
CCCCAGTGCC AGAGCGCACC AGATCCAATT GGCTGACCTG GCCCGACCTG
AAGTCCGTGA GCTGCTGCGC ACCATCTGGC TCGATCCCCT GAGTCTCGAC
CCCAGCATCC ACGCGGCTGA GGTCACCAAG GACGTGGCCC GCAAGCTCGC
GGAGATCAGC CGCAGCATGG AAGGGCAGCC CGATGCCCAG GGACAGGCGA
TGACGCCAGA GCGCGTTTCG CAGTTCCTGA TGCGCATGAT CTTCACCATG
TTCGCCGAGG ACGTCGGCCT GCTGCCCAAC ACCAAGTTCC GCGACAAGCT
CAAGTCCTTG CTCGGACGGC CCCAGGCCTT CATTCCCACC ATCACCGATC
TGTGGCAGGC AATGGCGAAG GGCGGATACA GCGTGGCCCT CGATGCACAG
ATCAAGCATT TCAACGGCGG TCTGTTCGAG GGCGTGGAAG TCCTGCCTGT
GACCGATGGG CAGCTCAAGC TCTTTATCGA AGCTGCCGAG TCCGACTGGA
GCCGCGTCGA ACCCAGCATC TTCGGCACGC TCGTCGAGCG TGCCCTGAAC
CCCCGCGAGC GCCACCGCCT GGGAGCCCAC TACACCCCCC GTGCCTATGT
CGAGCGCCTG GTGCATCAGG TGGTGATGGA GCCTCTGCGC GAGGACTGGC

FIG. 24A-17

GCACCGTGCA GGTTCAGGTG CAGGACACCC TCGACCGGGG CAACGGGGAC
GACAAGGCCC GGGCCAGGGC ACAGCAACTC GTCGCGCAGT TCCATGCCCA
GCTGCGGCAG ACCCAGGTGC TCGATCCTGC CTGTGGGACG GGGAACTTCA
TCTACGTCAG CATGGAACTG ATCAAGCGGC TGGAGGCGGA GGTCATTGAA
ACGCTGGTGG CCCTGGGCGG CCTGCCGCCC CTGATCGAGG TGAACCCCGA
GCAGTTTCAC GGCATCGAGG TCAACCCACG TGCCGCGAGC GTGGCCGAGC
TGGTGCTGTG GATCGGCTAC CTGCAGCTCT ACGCCCGTGA GCACGGCAAC
GCCGCGCCGC CCGAGCCGAT CCTGCGGGCC TTCCACAACA TCGAGAACCG
CGACGCCGTG CTGAGTTACA GCCATACGAC GCCGAAAGTA GATAGGGACG
GCCAGCCCGT GACCCGCTGG GACGGGGTGA CATTCAGGCG TCACCCAGTG
ACCGGAGATC CTGTGCCCGA CGAAAGGGCA CAGATACCGG AAGAGGTCTA
CCACAATCCA ATGACTACCG AGTGGCCCAA GGCGGACTTT ATTGTCGGCA
ATCCTCCGTT CATTGGTAGT AAACGCATGC GGGAACTGCT GGGCAATGGT
TATGTGGACG CTTTACAAAG GGTATTTGCT GACGTGCCAC AGGCCACCGA
TTTTGTTCTT CGTTGGTGGT ATAAAGCTGC GTTACTGACC AGGCAGGAGG
AAGTTAGGCG ATTCGGTTTC ATCACGACTA ACAGCATTAG CCAAGCGTTT
AATCGCCGTG CTATCGAACC TCACTTAAAC GCTGACGTTA GACCTCTTTC
ACTCGTGTAC GTCACACCAG ACCATCCGTG GGTAGATGAA TCCGACGGTG
CAGCCGTACG TATTGCGAGT ACGGTTGGGG AGCTCGGACA ACGCCCTGGC
TTACTTGCGC GTGTGGTCAA AGAATATGAT GAAGCTGCAG AGGGCGATCT
GGTAGCTGAA TTTGCCTTTG AAACAGGTGT AATTCATGCT GACTTGAGCA
TAGGGGCGGA CTTAACGGAG ACTCAGCCAC TCATGGCAAA TCTCGGTCTT
TGTGCCGTAG GCATGAAGAC TATAGGGGCC GGTTTTCTCG TGGAGCGTAC
GAAAGCCGAG GCTCTGGGCC TTGGTCAGGA TAATCGGATT CGTCCCTATA
TCAACGGGCG CGATCTAATG GGTCGTACTC GCGGTGTGTA TGTAATCGAT
CTCTTCGGTG TCTCGGAAGA AGATGTGCGC GATCAATATC CAAAACTCTA
TCAACATTTG AGAAATGCTG TGTACGACAT ACGTCGCCAG AACAACAATA
GGGTTTTTCG TGATTTATGG TGGGTTATTG GCCATCCACG TCCAATCTTC
CGTGAATTTA CGCGGGGCTT GAAAAGATAT GTGGTTACTT TAGAAACTGC
CAAGCACCAA GTATTCCAAT TCCTTGACAG CTCTATCGTT CCAGACAGTA
CCATCGTCAC CTTTGGAACT GAGGATGCAT TTCACCTTGG CGTCCTGAGC
AGCCGTGTCC ATGTCACCTG GGCGCTCGCG CAAGGGGGCA CCCTGGAGGA
CAGGCCCCGC TACAACAAGA CCCGGTGCTT CGAAACCTTC CCCTTCCCGG
CGGCCACGCC TGAGCAGCAG CAACGCATCC GTGACCTCGC CGAGCGCCTG
GACGCCCACC GCAAGGCGAG ACTGGCCGAG CATCCCAAGC TGACCATGAC
GGATATGTAC AACGCCCTGG CCGCCCTTCG TGCCGGGCAA CCCCTGGAGG
GCAAGCTCAA GACGGCCCAC GACCAGGGCC TGGTGACCAC CCTCAGGCAG
CTGCATGACG ACCTCGACGT GGCAGTCCTG GCTGCCTACG GCTGGCCTAC
AGGACTCGAT GAGCAAGGCC TGCTGGAAAG GCTCGCTGCC CTGAACGCCG
AGCGGGTACA GGAGGAAAAG GCAGGCCGCA TTCGCTATCT CCGGCCGGCC
TACCAGGATC CGCACGGCAC CGCGCAGGAG AACCTAGGGA TGGCCGTGGC
CAGCCGCCCG GCGAAGGCTG CTCAGGTCAT GCCCTTTCCC ACGGCCCTGC
CCCTTCAGGT GCAGGCCGTC AGAAGTGCCC TTATGCAGGC GGGGCAGGCC
CTCAGCCCCC AGGAGGTCGC CCAGGCCTTC CAAGGGGCCA AAGAAAAGCA
GGTCGAGGAC ATCATGCAGA CCCTGGTGCT GCTGGGGCAG GCCCACCTCC
GCGAGCACAA TGGGGAGGTG AGGTATGCCG CCTGA

FIG. 24A-18

>MaqI CRTTGAC 3456 nt (SEQ ID NO:37)

TTGGAAGCCT TCATTGCAGC CTCCGCTGCT GTCGACGAAT TCCTCAAACG
CTGGAAAGGC AACACAGGTA GTGAACGCGC AAACTTTCAA TCGTTCATGC
GAGACCTGTG TACGCTGCTG GACCTTCCTC ATCCAGACCC AGGTGAAGGT
GACACCACTC AGAACGCCTA TGTATTTGAG CGGTTTATCG CGTCGGCTCG
AGTCGATGGC AATACCGACA ACCGGTACAT CGACCTGTAT CGTCGGGACT
GCTTCGTACT GGAAGGGAAG CAGACTGGCA AGGAGCTGGC ATCCCGAAGC
CAACAGAACG CTGTTAATGC AGCTGTAGCA CAGGCTGAGC GATACATTCG
AGGACTGCCC CAGGAAGAAG TAGAGCATGG CCGCCCGCCA TTCATCGTGA
TCGTCGATGT GGGCAACGCC ATCTACACGT ACTCCGAGTT CTCGCGAACT
GGCGGTAACT ATGTTCCATT CCCTGATCCC AGACACTATG AGATCCGACT
GGAAGACCTG CACAAACCAG ATGTTCAGCA CCGTCTTCGT CAGTTATGGC
TAGAACCGGA TCAGCTCGAT CCGAGTAAGC ATGCTGCCAG GGTGACCCGA
GAGGTCAGCA CCAAGCTGGC TGAATTGGCA AAGTCCCTGG AGCATAATGG
ATACGATGTC GAGCGAGTAG CCAGCTTTCT CAAGCGCTGC CTGTTCACGA
TGTTTGCCGA AGACGTAGAG TTGCTGCCCA AGGCATCCTT CCAGAACCTT
TTGATCGACA TTAAGGACCG GAACCCTGAA GCCTTCCCCC ACGCCGTGAA
GGCGCTTTGG GAAACCATGA ATGCTGGTGG CTACAGTGAG CGTCTGATGC
AGACCATCAA GCGATTTAAC GGTGGGTTGT TCAAAGGCAT CGATCCAATC
CCGCTGAATG TTCAGCAGAT CCAACTTCTC ATAGATGCGG CCAAAGCCGA
CTGGCGTTTC GTTGAACCTG CCATCTTCGG GACGCTGCTA GAGCGTGCCC
TTGATCCTCG GGAGCGCCAC AAGCTGGGCG CCCATTACAC TCCCAGGGCC
TACGTTGAAC GCTTGGTCAT GCCGACCCTG ATTGAACCGC TTCGTGAGCA
ATGGGGCGAC ATCCGAGGTG CGGCGGAAAC CCTGCTGCGG CAAGGCAAAA
CAGACAAAGC TCTTCAGGAA GTCCAAGCCT TCCATTATCA GCTTTGCCAG
ACCCGAGTAC TTGATCCCGC TTGTGGTAGC GCTAACTTCC TTTACGTGGC
CCTTGAACAC ATGAAGCGCC TGGAGGGGGA GGTCCTGGGT TTTATCTCCG
AGCTGACCCA GGGGCAAGGC GTGCTGGAAA GTGAAGGCCT GACCGTCGAT
CCGCACCAGT TCCTGGGCTT GGAGATAAAC CCACGAGCAG CCCAGATTGC
CGAACTCGTT TTGTGGATTG GCTACCTTCA GTGGCACTAC CGGCTGAACG
ACCGGCTGGA CCTCCCCGAG CCCATCTTGC GGGACTTCAA AAACATTGAG
TGCAGGGATG CTCTGATCGA GTATGACAGT CGAGAACCGG AGCTAAATAA
AAATGGGGAA CCGGTGACCA TCTGGGATGG CATCAGCATG AAGGTGAGCC
CGACAACGGG TGAATTAATC CCCGATGAAA CAGGGCGAGC TAAGGTCTAC
CGTTACCACA ATCCACGCAG GGCTGAGTGG CCAGCAGCAG AGTACATAAT
AGGAAATCCT CCTTATATTG GCGCTCGCCG AATTAGATCC GCCTTGGGTG
ACGGTTATTT ACAAGCGTTG CGAGGCGTAT ACACCGATAT TCCAGAACAC
GTCGATTTCG TCATGTATTG GTGGGCAAAG GCTTCAGAGA ACATGGCAAG
TGGTAAAACA AAAGCGTTTG GATTAATTAC CACGAATAGT CTTCGGCAAA
GCTTTTCTCG AAAGGTTGTA GAAAAAACCT TAGATATCAA TTCGGACTGT
TCCATAAAAT TCGTGATTCC TGATCATCCG TGGGTTGATA GCGCCGACGG
TGCGGCGGTT CGGGTCACAT TGATTTCTGT TGACAGCAAT AAAGCGCCCG
GAATAGTTGC TCTCATCAGA AACGAGGAAG CAGAAGGTAG TGGAGCCTAC
AAGATTACCT TGGATAACAA GTCGGGGCAT ATAACGCCGA ACCTCACGAT
AGGGGCGGAC CCCGGAGAAG CTACGTGCTT ATCATCAAAT TCCTCAGTGT
CATGCGTAGG TTATCAACTA ACCGGCAAAG GGTTTGTTCT TACTCAAAGC
CAAAAAGAAG AGCACGAAAA TGAATGGCCC GAAAGTGTCA TTAAACCTTT
GTGGAGCGGG CGTGACATCA CGCAGTCACC CAGAAAAAAC TGGGCAATTG
ATGTTTGTGA TTGGGGAATT GACGCTTTAA AAGTTTCATC ACCAAGTCTC

FIG. 24A-19

TATCAATGGC TTCTCACTCG GGTAAAGCCG GAGCGCGAAC AGAACAATAG
AGCCAGTCTA AAGGAGCGTT GGTGGATTTA CGGCGAAGCC AGAAACACTT
TCCGGCCCGC TCTTATTGGC ATAGAAACAG CTATCGCAAC TTCTTTAACT
GCGAAACATC GGGTGTTTGT GCACCTAGAT TCAAACAGCA TTTGCGATAG
CACCACTGTC ATGTTCGCAC TACCAGGAGC CCAGTACCTT GGTGTTTTAA
GTTCCAGGGT GCATGTACTT TGGTCACTTT TTGCTGGGGG GACACTCGAG
AATCGTCCGA GGTATAACAA GACACTGTGC TTTGAAACAT TTCCTTTTCC
AAAAATGAGT TCTGATCAGT CTGAAAAAAT AAGTGACCTC GCAGAAAAAA
TAGATCAAGT ACGCAAAGGC CAACAGGCAA AACACCCCGA TCTAACACTA
ACGGGGATGT ACAACGTGCT CGAAAAACTA CGTTCCGGTG AAGAGCTAAC
CAACAAAGAA AAGACCATCC ACGAACAAGG CTTGGTGTCC GTACTCCGTG
AGCTCCACGA CGACCTCGAT CGTGCCGTTT TCCAGGCCTA TGGTTGGTCA
GACTTGGCAG ATAAGCTTGT AGGTCGCCCA GGCGCCACAA CCCCACTTCC
AGACAAACCG GCTGAACAAG CGGAGGCTGA GGACGAGCTG TTGATGCGAT
TGCTCGAACT CAACAAGCAG CGTGCAGAGG AAGAATCACG GGGCATAGTT
CGCTGGTTAC GTCCGGATTA CCAGGCGCGC GATGCTGTAC AGACAGAAGT
GGATATCGCG CCGAAGGCCG CCGCCACAAA AACGGAAGCC TCTACCAGCA
AAGGAAAAGC CTCATTCCCG AAAGCGATTC CCGATCAGCT TCGAGTGCTC
CGAGAGGCAC TCGCAGAGCG ATCTCACACG ACGGAAAGTT TGGCTGAGAT
GTTCAAGCGG AAACCTATGA AATCGGTCGA GGAGGGTTTG CAGTCACTTG
TAGCTGTGGG TGTTGCCGAA TACGACCCGG AAACTCAAAC ATGGCATACG
GTATGA

>PlaDI CATCAG 2787 nt (SEQ ID NO:39)

ATGCGGCTGA GCTGGAACGA GATTCGCGCC CGCGCAGCGC GTTTTTCCGA
GGAATGGAAA GGTGTCACGC GCGAACGCGC CGAGACGCAG ACCTTCTATA
ATGAGTTCTT CCAGATTTTC GACATCCCGC GCCGTCGCGT CGCCTCTTAC
GAAGAGCCGG TAAAGGGCCT TGGCGACAAG CGCGGCTATA TCGACCTTTT
CTGGAAAGGC ACGCTTCTTG TCGAGCACAA GACCACGGGC CGCGACCTCA
AAAAGGCAAA GATTCAGGCG CTCGATTATT TCCCGGGCCT GAAGGACAAG
GAACTCCCAC GCTACCTCCT CCTCTGCGAT TTCCAGAGCT TCGAGCTTTA
CGATCTGGAC GAAGACACCG AGGTCCGTTT CCGCCTCGCC GATCTGAAAG
ATCATGTGGA AGCCTTCGGC TTCATGATCG GCGTCCAGAA GCGCACCTTC
AAGGATCAGG ACCCCGTCAA CATCGAAGCC TCGGAGCTGA TGGGCAAGCT
CCACGATGCA CTGAAGGAAT CGGGTTACGA CGGCCACGAC CTTGAGCAAT
ATCTGGTCCG GCTTCTCTTC TGCCTCTTTG CCGACGACAC CGGCATTTTC
GAGCCCAAGG ACATCCTTCT CGATTTCATC CAGAACCGCA CAAGCGCGGA
TGGCAGCGAT CTCGGCTCCC GCCTCAATGA ATTGTTCGAG GTGTTGAACA
CGCCGGAAGA CAAGCGCCAG AAAACCCTTG ATGAAGACCT CGGAAATTTC
CCTTATGTGA ATGGCGCGCT TTTCGCCGAG CGTCTGCGCA CGCCTGCCTT
CAACGCCGCC ATGCGGCTGA TCCTTATCGA AGCCTGCGAG TTCAAATGGG
AGGCAATCTC GCCTGCCATT TTCGGTGCTC TGTTCCAGTC CGTCATGAAC
AAGACAGAGC GCCGCGCCCT CGGCGCGCAT TACACGACCG AGAAAAACAT
CCTGAAACTC ATTCAGCCGC TTTTCCTCGA CGGCCTGCAT GAAGAGTTCG
CGCGCGCAAA GGCGCTGAAG CGCGGCCGCC AGCAGGCGCT GGAAGCCTTG
CACGAGAAAC TCGGCCAGCT CACCTTCTTC GATCCCGCCT GCGGCTGCGG
TAACTTCCTC GTCATCGCCT ATCGCGAGCT ACGCGCGCTG GAACAGGAAA
TTCTGCGCGT CCTGCACGAC GGCAAAGACC AGCGCATTTT CGACGTGGCG

FIG. 24A-20

CAATTGTCGA AAGTCAATGT CGATCAGTTT TACGGCATCG AAATAGGCGA
GTTTCCCGCC CGCATAGCCG AAGTCGCGAT GTGGATGATG GACCACATCA
TGAATAACAG GCTCGGCCTC TCCTTCGGCT CCAACTATGC GCGCATCCCC
CTTCGGACCT CACCGCACAT CCTCCATGCC GACGCGCTGG AAGCCGATTG
GGCCGCTCTC CTCCCGCCGG AAAAATGCTC CTATGTCTTC GGCAATCCGC
CTTTCATCGG CTCAAAATTC CAGACGGCGG AACAGCGTCG GCAAGTGCGT
GACATCGCAA AGCTCGGCGG CTCCGGCGGC ACGCTTGATT TCGTCACCGC
ATGGTTCCTG AAGGCCGGCG AATATGTGCA GCATGGAAAA GCGGACATCG
CCTTCGTCGC CACCAACTCA ATCACGCAGG GCGAACAGGT CGCCCAGCTC
TGGCCGCTCC TCTTTCAGCG CTGCAAGCTC GAAATCGCCT TCGCCCACCG
TACCTTCGCC TGGGGCTCGG ACGCGCGCGG CGTCGCCCAT GTTCATGTCG
TCATCATCGG CCTCACAAGG CGCGACCGCG AATGGCCCGA GAAGCGCCTC
TTCTCTTACG CCGACATCAA GGGCGATCCG GTCGAGACAC GCCACAAGGC
TCTGACGGCT TATCTTTTTG ATGCCGTCAA TGTAGCTGAC AGACATCTAG
TAGTCGAAGA ACGAAACACT CCTTTGTGCG AAGCGCCGAA ACTCAAAACT
GGCGTTCAGA TGATCGACAA CGGCATCCTC ACTTTCACGA CAATGGAAAA
GGAGGAATTT CTTCGTCAGG AGCCGGAAGC GGAACCGCTG TTCCGCAAAT
ACATCGGTGG CGATGAGTAT ATAAATGGAT TTTTCCGATG GATACTCTAT
CTCGCAGATG CCGAGCCGAG TTTTCTTCGA CAGCTTCCGC TTGTTCAAGA
AAGAATACGG CAGGTACGTC AATACCGGTT ATCGAGTTCT CGGCCCAGCA
CGGTGAGAAT GGCGGACTAT CCAACGCAGG TTGGTGTGGA CGAGCGATTG
AGCGGACCCT ATTTGGTGAT ACCCAATACA AGCTCGGAGC GACGCGACTA
CGTACCGATC GGCTGGCTGA CTCCCGAGGT AGTAGCCAAT CAGAAATTGC
GCATTCTTCC TGACGCAGAT CCGTGGATAT TCGGTTTGCT GACAAGCGGC
ATGCACATGG CTTGGATGCG CGCAATCACC GGTCGCATGA AAAGCGACTA
CATGTATTCT GTCGGCGTCG TCTACAACAC TTTCCCTTGG CCGGATATTA
CCGAAGCTCA GAAACAGAAA ATCCGTGCGC TAGCGCAAGC TGTGCTCGAC
GCCCGCGCGC TTTATCCCGG TGCAACGCTG GCCGATCTCT ACGATCCCGA
CCTGATGAAA CGCGAACTCC GTCAGGCTCA CCGAGCCCTC GATGCCGCCG
TCGACAAACT CTATCGCGGC CAAGCCTTCG CAAATGACCG CGAGCGTGTC
GAACACCTCT TCGGCCTATA CGAAAAACTC TCCTCCCCGC TGACAGCAGC
ACCGAAGCCC ATTAAGCGGA AACGAAAGAA AGAGTAG

>AquIII GAGGAG 2754 nt (SEQ ID NO:41)

ATGCCTTTAA GTTGGAATGA AATCAAAAGT CGGGCGATCG CCTTCTCGAA
GGAGTGGGAA TTTGAGGAGT CAGAAAAATC AGAAGCACAA TCGTTTTGGA
ATGATTTTTT TCAGGTATTT GGCATTTCTC GTAAGCGAAT CGCAACATTT
GAGAAGTCAG TTAACAAATT AGGGAATAAG AAAGGTTCTA TTGACCTGTT
ATGGAAGGGA AATATCCTTG TTGAGCATAA ATCACGAGGC AAAAGTTTAG
ATAAGGCGTT TGAACAGGCA AAAGATTATT TTCCGGGGTT AAAGGAGCAT
GAGCTACCTC GATATATTTT GGTGTCGGAT TTCGCTCAAT TCCGGCTTTA
TGACCTCGAA ACGGATCAGA CCCATGAATT TCTACTAAAA GATTTCGTCA
ATTATGTTCA TCTGTTTGAT TTTATTGCGG GATATGAGCA GCGAACCTAT
AAGGATGAAG ATCCGGTTAA TATTCACGCG GCGGAGTTGA TGGGTAAGCT
GCATGACCGT CTCAGGGAGA TTGGTTATAC GGGTCATGAT CTAGAAGTTT
ACTTAGTGAG GTTGTTATTT TGCTTATTTG CAGATGACAC AGGCATTTTT
GAAAAGGGAA TTTTTGAGGA ATATCTCGAT ATTCATACCA AAGAAGATGG
TAGTGATTTG GCGATGCACT TGGGGCATAT TTTCCATGTG TTGAATACGC
CACCGGAGAA GCGGTTAAAA AATCTGGATG AGAGTTTAGG ACAGTTTCCC

FIG. 24A-21

TATGTGAATG GCAAGTTATT TGAAGAGCAG TTAGCGCCTG CGGCTTTTGA
TCGCAAAATG CGAGAAATGT TATTAGAAGC TTGTGGATTT AATTGGGGGA
AAATTTCTCC GGCCATTTTT GGGTCAATGT TCCAAGCGGC GATGGATCAA
CAGACTCGAC GAAATTTGGG GGCGCATTAT ACGTCTGAGA AAAATATTCA
GAAGGTGATT AAGCCTTTGT TTTTGGATGA GTTGCACGAG AAATTTAAGA
AGGCAAAAGG CAGTCCAACG GCGTTAAAGC GGCTCCATGA TGAGCTTGGG
GAATTACATT TTCTTGATCC GGCTTGTGGC TGTGGAAATT TTTTGATTAT
TTCTTATCGG GAATTGCGAG ATCTAGAGTT ATTGATTCTC AAAGAGCTTT
ACAAGAAGAA GGAGGGGTTT ATTGATATTC GTTTGTTCCT AAAGGTGGAT
GTGGATCAGT TTGGGGGCAT TGAATATGAT GAGTTTCCGG CACGGGTGGC
AGAGGTGGCG ATGTGGCTCA TCGATCATCA GATGAATATC AAGGTGAGTA
ATGAGTTTGG GCAGTATTTT GTCCGGTTGC CGCTAAAGAA GGCTGCCAGA
ATTGTGAATG GGAATGCGTT ACGGATTGAT TGGGAAGAAG TGATTCCAAA
GGAAAAGTTA AATTACATTC TCGGTAATCC ACCTTTTGTG GGTTCAAAGA
TGATGACGAA AGATCAGCGA GCAGATCTTT TATCTGTTTT TGAAAGTGCC
AAGGGTGCAG GGGTAATGGA TTATGTTTCT GCTTGGTATG TTAAAGCGGC
AGATTTTATT CAAGAGAAAA AGATAAAAAC AGCTTTTGTA AGTACAAATT
CTATCTCTCA AGGTGAGCAA GTTGGAATTT TATGGGGACT ACTTTTTGAA
AAATATCAAA TTAAGATTCA TTTTGCACAC CGTACTTTTA AATGGTCAAA
TGAGGCAAAA GGGAAAGCGG CTGTTTATTG TGTGATTATT GGATTTGCAA
CTTTTAACAT TAAAGGAAAG CGTTTATTCG AGTATGAAGA TATCAAGGGA
GAAGCGTTAG AAATCAAAGT AAGTAACATC AATCCATATT TGGTAAATGG
TGATGATTTA ATTATTCTAA GACGGCGGCA ACCTTTATGT AATGTCCCTA
ATATTGGCAT TGGCAATAAG CCCATTGATG GCGGCCATTA CTTGTTCACC
ACAGAAGAAA AGGAGGATTT TTTAAAACTA GAGCCAAAAG CAGAAAAATG
GTTTAGGAAA TGGTTGGGTT CTAGGGAGTT TATCAATAAA GAAGAAAGAT
GGTGTTTGTG GTTGGGAGAC TGTCCACCTA ACGAACTCAA AAAAATGCCC
CATGCTTTAG AGCGAGTCAA GGCAGTTAAA GAAACTCGAT TAAATAGCAA
CAGTAAACCG ACCCAAAAGC TAGCGCAAAC ACCGACAAGA TTTCATGTTG
AAAATATGCC AGAATCAGAA TATTTACTTA TTCCAAAAGT TTCTAGTGAA
AGGCGCAACT ATATTCCTAT TGGGTTTTTA AATCAAAGTA CGTTATCTAG
TGACTTGGTG TTTATTGTTG GTAATGCCAC CTTGTTTCAT TTTGGTATCT
TTACTTCAGT AATGCACATG GCATGGGTTA AATATGTTTG TGGAAGATTA
AAAAGTGATT ATCGTTATTC AAAAGATATT GTCTATAATA ATTTTCCTTT
TCCGCAGAAC GTAACTGACA AACAAAAACA AACAGTTGAA AAAGCAGCGC
AGTTAGTTTT AGACACTAGA GACAAATATC CCGATAGTAG CCTTGCCGAT
CTTTACGATC CCCTCACCAT GCCCCCCGAC TTAATGAAAG CCCACCAAAA
ACTCGATAAA GCAGTGGATC TCTGTTACCG TCCTCAAGCT TTTACCAGCG
AACTCAACCG CATCGAATTT TTATTTAACG AATATGAGAA ACTGATAACA
CCACTCCTAC AAAGTACAAA ACAGAAAAAA GCCCGCAAAA ACAAAACATC
TTAA

>AquIV GRGGAAG 2745 nt (SEQ ID NO:43)

ATGGCAGTAA CCCGTGATTC TCTCCAGGCG TTTGTGGATT ACTGTAATGC
CTACATCCAA GGGGATGAGA AGTCAGAGGC ACAGACATTT TTAACGCGAT
TTTTCCAAGC CTTTGGCCAT GCTGGGATCA AGGAAGTTGG GGCCGAGTTT
GAGGAGCGGG TCAAAAAAGC GAGCAAGAAA GATAAAACAG GTTTTGCGGA
TTTGGTCTGG TCGCCCGCCC CTGGGGTAAA GGGGGTCGTG GTGGAGATGA
AAAAGCGCGG GACAGATCTG GCGCTGCATT ATTCTCAGCT CGAAAAATAT

FIG. 24A-22

TGGCTGCGGC TCACCCCGAA ACCACGCTAT TCGATTCTCT GTAATTTTGA
TGAGTTTTGG GTCTATGACT TTAACAACCA GGTCGATGAG CCTGTAGACC
GGGTCAAGCT AGAAGATCTC CCGAACCGGG TAGGGACATT TTCGTTTATG
GAGATCGGTG GTCGGGAGCC GATCTTTCGG AACAATCAGG TCGAGGTGAC
GGAACGCACG GCCAAGCGCA TGGGGGAATT TTATCGGCTG GTGCGATCGC
GGGGCGAAAG GGAAAAGTTT GTTTATTTCA CAGAAGCGCA ACTGCAACGG
TTTACCCTGC AATGTGTGCT AGCGATGTTT GCCGAAGACC GGAATCTCCT
GCCACGGGAT CTGTTTGTGG GGTTGGTGCA GGACTGTTTA GCGGGGCGGG
ATAATGCCTA TGATGCCTTT AGTGGTTTGT TTCGGGCGAT GAACTTGCCG
GGGATCGTGC CCCAGGGTCG TTACAAGGGG GTGGATTATT TTAATGGGGG
TTTGTTTGGG GAAATTCAGC CGATTCCCTT AGAAAAGAAC GAGCTAGAAA
TTCTCGATGT GTGTGCGCGG GATAATTGGG CGAATATCCG ACCGTCGATT
TTTGGAAATA TTTTTGAGAG TGCCATTGAT GCGGATGAGC GCCATGCCAG
GGGAATTCAT TACACTTCTG AGAAGGATAT CCGGCAGATT GTGCGCCCGA
CGATCGCCGA CTATTGGGAA GGGAAAATCG ACGAGGCGAC GACCTACGAA
GATCTCGAAA AGCTGAAGCA GGAATTACGG GAATATCGGG TATTGGATCC
GGCGTGCGGT TCGGGAAATT TCCTTTATGT GGCTTATCAG GAGTTGAAGC
GGCTGGAACG GGTTTTGCTC AACAAAATCT ATGAGCGGCG CAAACGGTTC
CAGGGGGAAG TTTTACAGCA GGAAGAAATC GGGATTGTGA CGCCGTTGCA
GTTTTTTGGG ATGGATACGA ATCCGTTTGC GGTGCAGTTG GCGCGGGTGA
CGATGATGAT CGCCCGGAAG ATTGCGATTG ATAAGTTTGG GTTAACTGAG
CCTGCTTTGC CGTTGGATTC TTTGGATCAA AATATTGTCT GCCAAGATGC
GCTATTTAAT GACTGGCCAA AGGCTGACGC GATTATCGGC AATCCGCCTT
TTCTTGGTGG CTCAAGAGTA CGTTTAGAGC TTGGGGATAA ATATGTTGAA
CGAATTTTTG AAAAGTTTTC TGATGTTAAG GACAAAGTAG ACTTTTGCGT
TTATTGGTTT CGTCTAGCAC ACGAAAATCT TAATAAAACT GGTCGAGCTG
GTTTAGTTGG GACAAATTCA ATTAGTCAAG GCTTTAGCAG AAGGGCAAGC
TTAGAATATA TTGTCAATAA CGGCGGAATT ATTCACGATG CAATCTCTAC
ACAGGTTTGG TCTGGACAAG CGAATGTCCA CGTTAGCTTG GTTAATTGGC
AATATTTAAA GCCTCCAGAA TATGTCTTAG ATCATGAAAT TGTCAAAAAT
ATAAATTCAT CTTTAAAGTC TGAAACGGAT GTTTCCAATG CCGTTAAGCT
AAAAGTTAAT CTGAATCAAT CTTTCAAAGG TGTGCAACCC ACGGGAAAAG
ACTTTCTGAT TTCTGAGAAA AAAGTAGAAA ATTGGATCCA GAAAAATACA
AAAAACAATC AAGTCTTGAA ACTATTTGTA TCAGCTTCAG ATTTAGCCAG
CAATAAAAAT GGTGAACCCA GTCGATGGAT TATTGATTTT AATGATTTTT
CTTTAGAAGA CGCATCTACA TACAAAGAGC CTTTTGATCA TGTTAATTTT
TTTGTTAAGC CTCAGCGTGA AAATAACAGA GATCAAAAAA CTAGGGAATA
CTGGTGGTTA TTTCCAAGAG CTAGGCCTGC AATGCGTCAA GCAATCGAGT
TACTAGCTCT TTACTTTGCA GTTCCTAGAC ATTCTAAATG GTTTATTTTT
ATTCCTTGTA AATTAGATTG GCTTCCTGCT GACTCAACAA CTGTTGTGGC
TTCGGATGAT TTTTATGTGT TGGGAATTTT GACATCAGAT GTTCATCGCC
AATGGGTCAA AGCCCAAAGC TCAACCCTAA AAGGTGATAC CCGCTACACC
CACAATACCT GTTTTGAAAC TTTTCCCTTT CCCCAGACGG CGATCGCAAA
ACTCACCCAA CAGATCCGCC AAGGGATGAT CGACCTCCAC GAATATCGCA
CCGCCCAAAT GGAAGCCAAA CAATGGGGGA TCACCAAACT TTACAACGCC
TTTTTCGACG AACCCGCCAG CCAACTCCAT AAACTCCACA AAAAGCTCGA
TGCCCTTGTG CTCAAAGCCT ACGGCTTCAA AAAAGACGAC GACATTCTCG
AAAAACTTTT AGACTTGAAC CTTGCCCTGG CCGAAAAAGA AAAAAATGGC
GAAAATATAG TTGGCCCCTG GGCGATCGAT AACCCACCAA AATAA

FIG. 24B-1

Amino Acid Sequences for Enzymes of the Application:

>MmeI_TCCRAC (SEQ ID NO:2)

MALSWNEIRR KAIEFSKRWE DASDENSQAK PFLIDFFEVF GITNKRVATF EHAVKKFAKA
HKEQSRGFVD LFWPGILLIE MKSRGKDLDK AYDQALDYFS GIAERDLPRY VLVCDFQRFR
LTDLITKESV EFLLKDLYQN VRSFGFIAGY QTQVIKPQDP INIKAAERMG KLHDTLKLVG
YEGHALELYL VRLLFCLFAE DTTIFEKSLF QEYIETKTLE DGSDLAHHIN TLFYVLNTPE
QKRLKNLDEH LAAFPYINGK LFEEPLPPAQ FDKAMREALL DLCSLDWSRI SPAIFGSLFQ
SIMDAKKRRN LGAHYTSEAN ILKLIKPLFL DELWVEFEKV KNNKNKLLAF HKKLRGLTFF
DPACGCGNFL VITYRELRLL EIEVLRGLHR GGQQVLDIEH LIQINVDQFF GIEIEEFPAQ
IAQVALWLTD HQMNMKISDE FGNYFARIPL KSTPHILNAN ALQIDWNDVL EAKKCCFILG
NPPFVGKSKQ TPGQKADLLS VFGNLKSASD LDLVAAWYPK AAHYIQTNAN IRCAFVSTNS
ITQGEQVSLL WPLLLSLGIK INFAHRTFSW TNEASGVAAV HCVIIGFGLK DSDEKIIYEY
ESINGEPLAI KAKNINPYLR DGVDVIACKR QQPISKLPSM RYGNKPTDDG NFLFTDEEKN
QFITNEPSSE KYFRRFVGGD EFINNTSRWC LWLDGADISE IRAMPLVLAR IKKVQEFRLK
SSAKPTRQSA STPMKFFYIS QPDTDYLLIP ETSSENRQFI PIGFVDRNVI SSNATYHIPS
AEPLIFGLLS STMHNCWMRN VGGRLESRYR YSASLVYNTF PWIQPNEKQS KAIEEAAFAI
LKARSNYPNE SLAGLYDPKT MPSELLKAHQ KLDKAVDSVY GFKGPNTEIA RIAFLFETYQ
KMTSLLPPEK EIKKSKGKN

>EsaSSI_GACCAC (SEQ ID NO:4)

MAALSFPEIR TRLQAFAKQW KQAERENADA KLFWARFYEC FGIRPESATI YEKAVDKLDG
SRGFIDSFIP GLLIVEHKSK GKDLNSAFTQ ASDYFTALAE GERPRYIIVS DFARFRLYDL
KTDTQVECKL ADISKHAGWF RFLVEGEATP EIVEESPINR QAAYAVSKLH EALLQANFRG
RDLEVFLTRL LFCFFADDTG IFGQDGVFRR YVEATRDNGR DTGQSLAILF DVLDTPDNQR
SSNLDEHLTA FAYINGSLFS ERTRIPSFDA DMRTLLVKCA ELDWSGISPA IFGAMFQGVL
EAHTPDEKRQ ASRRELGAHY TSERNILRVI NPLFMDDLRV EFERARRNKP RLQALYEKLP
TLTFFDPACG CGNFLVIAYR ELRRLENDVI AALFADFQHG KGLLDVSTLC RVRVNQFYGL
EIDDAAAHIA RVAMWITDHQ MNLESADRFG NTRPTVPLVD TPHIHKENAL RADWTSVLAP
AQCSYVMGNP PFVGAKWLNE EQRADARAVF ANVKNGGLLD YVAAWYVKAL AYIQANPAID
VAFVSTNSIT QGEQVSALWP TLLQGGVKIR FAHRTFQWSN EGKGNAAVHC VIIGFGLRVP
DRCTIFDYSH DIKADLGSVL HASRINPYLV DAPDVVLTNR RAPICQVPEI GIGNKPIDGG
HYLFTDEGKA AFLAVEPKAA PFFHRWVGAE EFINNTSRWC LWLGNAKPHE LRALPECMKR
VEAVRQYRLA SPSAPTQKLA ETPTRFHVEF MPDAPFMVIP EVSSERREFI PLGYLQPPTL
ASNKLRLMPD ATLYHFAVLN STMHMAWTRA VCGRLESRYQ YSVTIVYNNF PWPSPSDAQL
EALEAAGQAI LDAQAMYLDQ GSSLADLYDP RTMPSELRKA HAANDRAVDA AYKFKGDKSD
AVRVAFLFSL YGRLTSLLPS EKPKRARKEK AVA

FIG. 24B-2

>SdeAI_CAGRAG (SEQ ID NO:6)

MISLREIRER SIKFAKEWEG ASHEKQEAQS FWIDFFKIFD VSPRSMQFEY PIKKIDGSYG
YIDVFWRGQL LIEQKSRGKD LVKAKEQALE YLPNLKQRDL PKFILVCDFV SFYLYDLDTN
QDYKFLLHEL PKNIELFSFI AGYTKKTYKE EEPTNRKAAE LMGKLHDKLL ENGYSGHQLE
LFLTRLLFCM FAEDTGIFAK NSFREFIENQ TDESGRDLGS QISYLFELFD TPNEERQKNL
DESFTQFPYI NGSIFTEQLK TAHFDRSMRE MLLDACAFDW SLISPSIFGS MFQASMDVSK
RGELGAHFTS ETNILKAIKP LFLDELSEEF AKIKNNPKQL QIFHAKISNL KFLDPACGSG
NFLVIAYREL KLVEFEVLKS LKILTQLVHI DQFYGFEIEE LPSRITQTAM LLIDHQMNLL
FAQMFGEPHF NIPIKDSANI FNVNALRVDW EKILDGVKID FIIGNPPFLG SKMQSKEQKE
DMAEVFSGVK NGKELDFVTA WYIKSAKYLQ GKNTKVALVS TNSITQGEQV GILWQEMFNK
YKIKIHFAHK TFKWNNDAKG VAQVYCVIIG FAGFDIKEKR LFEYESVKSE PHEIKVANIN
PYLVNGDDFF ISSRRKHIQS FIPQIVFGSM PNDGGNLLFD DKEKEEFLAL EPKAELYMKP
LISAKEYLNG KTRWCLWLKD CPPNELKSMP KVIERVENIR KLRNESSREA TQKLAKFPAL
FGEDRQPESD YIFIPRVSSE NRDYIPMEFF TKDFICGDTG LAVPNATLFH FGILTSKMHM
DWVRYVAGRL KSDYRYSNEI VYNNFPFPLE INDKQKDQIE QLAQNILDIR AEFVGSSLAD
LYNPLTMPPK LLKAHETLDR AVDKLYSKTL FKTDTERVAH LFELNKQLTS LIVENEKKAK
KVKKIITK

>NlaCI_CATCAC (SEQ ID NO:8)

MPSESTLQTA FSQQARIMTP DLQTLQHNAE QFIRDCEPLH YEMGHAQKFI AALCKVYGLD
AHFAVQYEHR VRKADLKGIN RIDGFFPGLL MIEMKSAGED LEAAFIQALE YVQLIERIED
KPRHILVSDF KNLHLYELNQ GFTGIVLDKT LKIKLTGFRA HVQDFAFIAG YEAAIAERNE
ALTIAAAAKL AALHQEFHKQ GYQGAELQTM LVRILFCLFA DDTGLFAQNK AFEQLVEESL
ADGADLGSRL NALYKWLDTP EDKRRTTPRA LLDQYSGFRL KFPYINGKLF SDGIDEFVFN
ASMRRTLLEC CEIDWSLISP DIFGTLFQNI MENADALGGG KKSAHRRELG AHYTSEKNIK
RAIAPLFLDR LKAELEQAAG DPKKLARYIT RLQTLQILDP ACGCGNFLIV AYREIRLLEM
QAIRQLARIP GAQQMQSQCD VHQFHGIEID PAAVEIATVA MWLTDHQMNR LYQDGYKRIP
LAHKADIRCA NALQTDWADT ISPQNLDYIV GNPPFLGKKE QNAEQKKDME KVVGHLKGSG
ILDYVTAWYF KANELMKHNP KIRTAFVSTN SITQGEQVPA LWKPLLSDGI RIRFAHRTFK
WNNEGKGTAA VHCVIIGFDR DEIQKGERLS LWDYSQGIGG DGKEHQVRKI NPYLLEADNI
LPAKRSRPVS ADVPAMNYGS MPIDNGLLIL SQEAFQTALN EDPENSELIR PYMGGSEFLN
NEKRYCLWLE NVDQERLSQS KFASERVGQV RAYRLSSSRA ATVKLAGTPH LFGEIRQPDS
RYLLLPKVSS ENRRFLPIGY IEPETIANGS ALIIPNATLC HFGILSSTMH NAFMRTVAGR
LESRYQYSAS IVYNNFPFPE NPCRTAIETA AQAVLDARAA ETERIRRLNR ILPEKEHRPM
PTPATLYNPD TMPPALAAAH NALDDAVDEA YGYTGGNSDS ERTAFLFRLY KNAV

FIG. 24B-3

>PspPRI_CCYCAG (SEQ ID NO:10)

MSIDYKHVRQ QLQQIVHDYK DSEGYERGQS QNFWTQVFNA YGVSGQTQTK
AFEHRLKDKS NQKYVDAFIP KLVIIEQKSR GVDLNKAYTQ VSEYYDRINA
KDKPRYIILC NFDEIWLYDI NNPLDIKKHQ CPLSDLPNNA EWFEFLSPES
QQSNEIIEEN PINRQATEKL AKLHQAFIED GVDPDELALF LTRLIFCFFA
DDTAIFGKKH VLHNLLKNHA ATDGSNLQQI LTTLFDTLNT EHRSSRLPEH
YAQFAYINGG LFEETINIPY FDEKLYNLVM ECDALDWTEI SPAIFGSMFQ
SVLDASGGDS TEDKRREFGA HYTSEKNILK VINSLFLQEL RDEFSKCTNN
TPRAVQLYEK LPTLKFFDPA CGCGNFLIIA YRELRLLENQ LIAKIFGDQK
GLLDISSMCN VTVDQFYGIE IEPHAVHIAR VAMWITDHQL NMTTAERFGT
TRPTTPIVYS PHIIEGNALQ IDWETVLPAN DCSYVMGNPP FIGKSNQSSE
QKSDIKLVAS HIKNHKSLDY VAGWYIKSMH YMQSVNNANH YIDTAFVSTN
SIVQGEQVDI LWRYLIDDCK GHINFAHHTF KWSNEGKGIA AVHCIIVGFS
LVEKKEKTIF EYSDISSEPS PKKARTINAY LTDAPIVFFS RRSKQVSNES
SMVSGNKATD GGNLILSDSE YIDLINSEPL AKKYIKRFMM GYEFLNNIKR
WCLWFDNVDP IQLSKDLEKM PLIKKRIHNV KELRLNSTKK STVKKAETPH
LFDERRHTNK PYVAIPVVSS ENRRFIPIGF IDGNTVAGNK LFVIVDGNTY
QFGTLSSSMH NAFMRLTAGR MKSDYSYSST IVYNNFPYPF MADDHSDKAQ
KARESIAKAS QQVLDARKHY QDGSENAPTL AQLYNTYLID PYPLLTKAHK
ALDKAVDSAY GYRGKGDDAS RVEFLIKKIA ELKN

>CstMI_AAGGAG (SEQ ID NO:12)

MVMAPTTVFD RATIRHNLTE FKLRWLDRIK QWEAENRPAT ESSHDQQFWG DLLDCFGVNA
RDLYLYQRSA KRASTGRTGK IDMFMPGKVI GEAKSLGVPL DDAYAQALDY LLGGTIANSH
MPAYVVCSNF ETLRVTRLNR TYVGDSADWD ITFPLAEIDE HIEQLAFLAD YETSAYREEE
KASLEASRLM VELFRAMNGD DVDEAVGDDA PTTPEEEDER VMRTSIYLTR ILFLLFGDDA
GLWDTPHLFA DFVRNETTPE SLGPQLNELF SVLNTAPEKR PKRLPSTLAK FPYVNGALFA
EPLASEYFDY QMREALLAAC DFDWSTIDVS VFGSLFQLVK SKEARRSDGE HYTSKANIMK
TIGPLFLDEL RAEADKLVSS PSTSVAALER FRDSLSELVF ADMACGSGNF LLLAYRELRR
IETDIIVAIR QRRGETGMSL NIEWEQKLSI GQFYGIELNW WPAKIAETAM FLVDHQANKE
LANAVGRPPE RLPIKITAHI VHGNALQLDW ADILSASAAK TYIFGNPPFL GHATRTAEQA
QELRDLWGTK DISRLDYVTG WHAKCLDFFK SREGRFAFVT TNSITQGDQV PRLFGPIFKA
GWRIRFAHRT FAWDSEAPGK AAVHCVIVGF DKESQPRPRL WDYPDVKGEP VSVEVGQSIN
AYLVDGPNVL VDKSRHPISS EISPATFGNM ARDGGNLLVE VDEYDEVMSD PVAAKYVRPF
RGSRELMNGL DRWCLWLVDV APSDIAQSPV LKKRLEAVKS FRADSKAAST RKMAETPHLF
GQRSQPDTDY LCLPKVVSER RSYFTVQRYP SNVIASDLVF HAQDPDGLMF ALASSSMFIT
WQKSIGGRLK SDLRFANTLT WNTFPVPELD EKTRQRIIKA GKKVLDARAL HPERSLAEHY
NPLAMAPELI KAHDALDREV DKAFGAPRKL TTVRQRQELL FANYEKLISH QP

FIG. 24B-4

>NmeAIII_GCCGAG (SEQ ID NO:14)

MKTLLQLQTA AQNFAAYYKD QTDERREKDT FWNEFFAIFG IDRKNVAHFE
YPVKDPADNT QFVDIFWEGI FLAEHKSANK NLTKAKEQAE RYLQEIGRTK
PSALPEYYAV SDFAHFHLYR RVPEEGAENQ WQFPLEELPE YITRGVFDFM
FGIEAKVRQI QEEANIQAAA TIGRLHDALK EEGIYEEHEL RLFITRLLFL
FFADDSAVFR RNYLFQDFLE NCKEADTLGD KLNQLFEFLN TPDQKRSKTQ
SEKFKGFEYV NGGLFKERLR TFDFTAKQHR ALIDCGNFDW RNISPEIFGT
LFQSVMDAQE RREAGAHYTE AANIDKVING LFLENLRAEF EAVKALKRDK
AKKLAAFYQK IQNLQFLDPA CGCGNFLIVA YDRIRALEDD IIAEALKDKA
DGLFDSPSVQ CRLKQFHGIE IDEFAVLIAR TAMWLKNHQC NIRTQIRFDG
EVACHTLPLE DAAEIIHANS LRTPWQAADY IFGNPPFIGS TYQTKEQKND
LESICGHIKG YGLLDYVCNW YVKAAGIMAQ HPQVQTAFVS TNSICQGQQV
EILWGSLLNQ GIEIHFAHRT FQWTSQAAGK AAVHCIIVGF RQKPPMPSEK
TLYDYPDIKG EPEKHAVANI NPYLIDAPDL IIAKRSRPIH CEPDMVNGSK
PTEGGNLILS TAEKDALIAA EPLAEQYIRP FIGADEFLNG KTRWCLWFHG
VSDVKRNHDL KQMPQVQARI QAVKTMREAS SDKQTQKDAA TPWLFQKIRQ
PSDGNYLIIP SVSSESRRFI PIGYLSFETV VSNLAFILPN ATLYHFGILS
STMHNAFMRT VAGRLKSDYR YSNTVVYNNF PFPESCRLPS ENDRPDPLRA
AVEAAAQTVL DARGQYRREA QEAGLPEPTL AELYAPDAGY TALDKAHATL
DKAVDKAYGY KTGKNTDDEA ERVAFLFELY RKAAAIA

>CdpI_GCGGAG (SEQ ID NO:16)

MSSSSPSEKK LAAKLFANKW ADRGNEKSDT HSFWLELLRD VVGMQDVTTN
VRFESRTSQR GYIDVVIQDA KTFIEQKSID VSLDKADIRQ GRVVTAFRQA
LNYANTMPNK LRPDYIITCN FAEFRIHDLN KVNAETDYIS FTLAELPDQI
HLLDFLIDPQ KSRAVREEKV SMDAGTLVGK LYDALRDQYL DPNSDASQHS
LNVLCVRLVF CLFAEDAGLF EKDAFYRYLD GLRADQVRVA LRDLFEVLNT
PVDSRDPYLS EQLKNFPYVN GGLFAKVEQI PNFTDEILDL LVHEVSEKTN
WAEISPTIFG GVFESTLNPE TRARGGMHYT SPENIHKVID PLFLDSLKAE
LDSILNASGI TANKRKKQLE AFHTKISELK FFDPACGSGN FLTETYIHLR
KIENKILSEL AGDQTQLGFS NVTLKVSLDQ FYGIEINDFA VSVASTALWI
AQLQANIEAE SIVTANIESL PLRDAAHIHL GNALRTDWAS VLAPEQCNYI
IGNPPFLGYS RLDDAQKEDR KAIFGKNGGV LDYVACWHRK AAEYMHGTDA
EAALVSTNSI CQGQQVTPLW KPLFDAGIHI NFAHRTFVWS NEAADQAHVL
CIIVGFSYID RPVKQAWTYR KNEVEYSEPV HLNGYLADAP DAFLTRRSKP
ISDVLEMAQG FKPADGGHLL LTQEERDELL AKEPLAAPWI RKFSMGAEFI
NGKDRYCLWL PEITGVELKR LPLVRARIDA CREWRLEQIK TGDAYKLSDR
PHLLRPTSRF KDGTYIGIPK VSSERRKYVP FAFVTDGMIP GDMLYFVPTD
SLFVFGVLVS QFQNAWMRVV AGRLKSDYRY GNTTVYNNFV FPEVDDSVRV
DVEKRAQAVI DARSLYPEAT LADMYDPDND FLYPELMKAH RELDRAVEMA
YGVDFGGDEQ QIVAHLFKLY NEKVEK

FIG. 24B-5

>ApyPI_ATCGAC (SEQ ID NO:18)

MLSDPVFDRA TIRHKLIEFK IRWRGHIDQW KAENRPATES SHDQQFWGDL LACFGVNARD
LYLYQRSAKR ASTGHTGKID MFIPGKVIGE AKSLGIDLDK AHEQALDYLL GGTIPNSQMP
AYVLCSNFET LRITRLNRDY VGDSAEWDVT FDLDEIDEHL EQLAFLADYE TSAYHEEEQA
SLEASRLMVE LFRAMNGDEA DEAVGDEAPT TPEEEDERVM RTSVYLTRIL FLLFGDDAGL
WDTPHLFTTF VRNETTPESL GPQLNELFRV LNTPEDKRPK RLPGTLAKFP YVNGAIFAEQ
LDPEYFDYAM REALLNACDF DWSKIDVSVF GSLFQLVKSK EARRGDGEHY TSKTNILKTI
GPLFLDELRA QADKLVSNPA TPVRKLEEFR DSLAAHIFCD PACGAGNFLL TAYKELRRIE
TDLIVAIRQR RGETGMSLNI EWEQKLSIGQ FYGFELNWWP AKIAETAMFL VDHQANKELA
NAVGRPPQRL PITITAHIVH GNALALDWTE ALPKAVGETF IFGNPPFIGQ DTRTKQQLEE
MKAVWRRKNI SRLDYVTCWH IKSLDLFSTR NGRFAFVTTN SITQGEQVPL LFGPIFAAGW
RIRFAHRTFS WDSDAPGKAS VHCVIVGFDR AHEPRPQLWD YPNVSSAPVA VPVERVINAY
LVDGPNVLVQ KMTSPISCEI KPAVLGAMAK DGGGLIVEAQ DVQEALDDPI AAKYLRPYVG
SRELVRGLSR WCLWMVDLDP ADVQASTFLR SRIEQVRAYR TTSSAPTTRS MAKIPHLFAQ
RYRPQTDFLC VPSVVSENRP YFTAADIEEG TVVSSLAFAV EDSDRSQFAL ISSSMFITWQ
KMIGGRLESR LRFANTLTWN TFPVPELDEK TRKRIIKAGQ KVLAAR ALHPERSLAEHY
NPLAMTPELVKAHDALDREVDKAM GAARKLTSERQRQELLFANYAKLTNN

>SpoDI_GCGGAAG (SEQ ID NO:20)

MTPQDFITKW RNTELKERSA SQSHFIDLCR LLDIEDPTTA DPKGEWFTFE KGASKTSGGE
GWADVWRKDC FAWEYKGKRA NLDKAFDQLL QYAIALENPP LLIVSDMDVI RIHTNWTNTV
QQVHTLTLDD LKDAANRDKL RNAFLNPDVF KPSKTRQLVT EQAAQNFANL AQRLRERGHD
AQQVAHFVNR LVFCMFAEDV ELLPNKMFER MIKAARPDPA SFAIHAKALF AAMKDGGLVG
FEKVDWFNGG LFDNDDVLPL EWEDLDDLIR AAHLDWSDID PSILGTLFER GLDPAKRSQL
GAHYTDRDKI MQIVNPVIVE PLLAEWAEVK AQIEDLIDKA PKATKDKLLS TSQKAARTRA
LDKAEALHQA FLDRLKAFRV LDPACGSGNF LYIALLELKN IEHRVNLEAE ALGLPRGFPQ
IGPEVVLGIE LSAYAAELAR VSVWIGEIQW MRRNGFEAAK NPILRSLKTI ENRDAVLNPD
GTRADWPKAD VVVGNPPFLG VYKMGEELGE DYTIALRDAW PEMPGAADLV TYWFAKAWSQ
MQCGDLSRAG LVATNSIRGG ANRTVLKPIA EHGGIFDAWS DEAWTVEGAA VRVSMICFGS
KLPSHPKLNG KVVDKILSDL TANAAGFDLT KSSRISENKG VCIRGIETGG PFEFSQADFE
ALATKPLNPN GLPNTRVIRR ILNGNNILKR QPERYAIDFS DFRTKEEAAL FEAVYSWLEQ
AYESYERKSK RRIVRRQDWW LHRRSGAALK NAVSRLSRFI VTPRVGKHRI FVWLDSNALA
DSATFIVARD DETTFGILHS SFHELWSLRM GTFLGVGNDP RYTPSTTFET FPFPEGLTPN
IPADEYADAP RAIKIAAAAK RLNEFRENWL NPADLVDRVP EVVSGYPDRI LPKNDAAAKE
LKKRTLTNLY NARPAWLDHA HKALDEAVAE AYGWGDDWRA GVLTEDEILA RLFKLNQERA AKEKA

FIG. 24B-6

>DraRI_CAAGMAC (SEQ ID NO:22)

MPQTETAQRMEDFVAYWRTLKGDEKGESQVFLDRLFQAFGHAGYKEAGAE
LEYRVAKQGGGKKFADLLWRPRVLIEMKKRGEKLANHYQQAFDYWLKLVP
DRPRYAVLCNFDELWVYDFNQQLDEPMDRLRIEELPERYTVLNFMFEQER
APLFGNNRVDVTREAADSVAKVLNSVIARGEDRARAQRFLLQCVMAMFAE
DFELIPRGFFTELADDARAGRGSSFDLFGGLFRQMNTSERARGGRFAPIP
YFNGGLFRAVDPIELNRDELYLLHKAALENNWARIQPQIFGVLFQSSMDK
KEQHAKGAHYTSEADIMRVVLPTIVTPFQRQIEAATTQKELRAILDELAS
FQVLDPACGSGNFLYVAYRELRRLEARALLRLRDLSAPGTALPPARVSIR
QMHGLEYDPFGVELAKVTLTLAKELAIREMHDLLGNTGLDFDQPLPLDNL
DDRIVQGDALFTPWPRVDAIVGNPPFQSKNKLQREMGAAYVKKLRAHYPD
VPGRADYCVYWIRKAHDQLGSGQRAGLVGTNTIRQNDSRVGGLDYVVQHG
GTITDAVGTQVWSGDAAVHVSIVNWVKGPAEGPKHLAWQVGDHRTSPWQS
TELPVINSALSAGTDVTQAQKLRVNMNSGACYQGQTHGHKGFLLDGLEAG
QMLSAERKNAEVIFPYLTGDELLRTSPPHPTRYVIDFQPRDVFGARAYKL
PFARIEREVLPTRQAAAAEEEARNAEVLAANPKAKTNKHHRNFLNQWWAL
SYGRSEMIEKISSLSRYIVCSRVTKRQVFEFLDNGIRPSDGLQIFAFEDD
YSFGVIQSSVHWQWLIARGGTLTARLMYTSDTVFDTFPWPEDPTLAQVRA
VAAAAVKLRELRNKVMREQGWSLRDLYRTLDMPGKNPLRDAQERLDAAVS
AAYGLPAGADMLDFLLALNAEVAAAEARGAAVTGPGLPAGLNTADFVTAD
AVRPLG

>NhaXI_CAAGRAG (SEQ ID NO:24)

MSERVEQIEA FVAYAKTLKG DEKGEAQVFC DRLFQAFGHE GYKEAGAELE
SRVKKASGKG VNFADLIWKP RVLIEMKKSS EKLHLHYQQA FDYWLNAVPN
RPRYVVLCNF KEFWIYDFDK QLNEPVDVVR LQDLPARYTA LNFLFPDNPD
PLFGNDREEV SRVAASKVAQ LFRSMVARGI PREQAQRFVL QAVVAMFAED
IDMMPAGTTL RLVQDCLEHG QNSYDVFGGL FLQMNNKAAA QGGRYKGVPY
FNGGLFATVQ PIELTTDELE LLGKKDEGAA WQNWAKINPA IFGTIFQQSM
DKGERHAFGA HFTHEADIQR IVGPTIVRPW RERIDAAKTM AELLEIRKAL
LNFRVLDPAC GSGNFLYVAY REMVRLEIKL MARLDKEFSW KTVQKQAQAT
SLISPRQFFG VERDSFGVEL TKVTLMLAKK LALDEAADVL ERDQIELPLA
EDEALPLDNL DGNILCRDAL LSDWPEVDTI IGNPPYQSKN KAQQEFGRAY
LNKIRSVFPE IDGRADYCVY WFRKAHDQLK QGQRAGLVGT NTIRQNYSRI
SGLDYIAKHN GTITEAVSTM PWSGDAVVHV SIVNWVKGED DGKKRLYIQS
GNDPAGGWDY KDLDEINTSL SFSTDVSQAQ RINANAEKGG CYQGQTHGHK
GFLPEPAEAK AMIKASKANA KVLFPFLIAD DFLGAVDKLE CRYVIDFQTR
DLLQAKAFKR PFEHLEKTVL PTRKEAAKKE KDRNKEALDA DPEAKVNKHH
ENFLKRWWLM SYAREDLMQT LAPLSRYIVC ARVTHRPIFE FVSTAIHPND
ALSVFALEDD YSFGILQSGI HWEWFINRCS TLKADFRYTS DTVFDSFPWP
QEPSADAVRL VAKRAVEVRQ LRSKLKVKHH LSLRELYRAI EGPGEHALKK
AHKLLDEAVR GAYGMSKKAD VLETLLELNE TVVAAEADGK QVVGPGIPPS
ASKLKNLVTT DKLTISPTSW ANNAPVKT

FIG. 24B-7

>RpaB5I_CGRGGAC (SEQ ID NO:26)

MGDSISVPAV EQFIARWQGR EGGQERANYV SFLTELIALL GLDKPDPADA
THEHNDYVFE RAVKKTAEDS ASYGRIDLYK RNSFVLEAKQ SRIKGGKKEV
RGQYDLLKTE ATAATLGRRG ADRAWDVLML NAKRQAEEYA RALPASHGWP
PFILVCDVGH CIEVYADFSG QGKNYTQFPD RQNFRIYLED LRDHDVRERL
RKIWSEPTAL DPSQQSAKVT RDIAKRLAQV SLALEKQNYP ADDVAMFLMR
CLFTMFAEDV ELLPEKSFKL LLEDCEKNPE AFVHDVGQLW EAMDTGQWAH
ALKTKVKKFN GEFFKSRAAL PLGREEIGEL RRAAEYDWNE VDPSIFGTLL
EQALDPTDRK KLGAHYTPRA YVERLVIATI IEPLREDWRN VQATAETLRG
AGDLAAAAAA VQAYHDRLCE TRVLDPACGT GNFLYVSLEL MKRLEGEVLE
ALLDLGGQEA LRGLGSHSVD PHQFLGLEIN PRAAAIAELV LWIGYLQWHF
RTKGAPPDEP ILRAFKNIKV KNAVLDWDGA PLPKIVEGKE TYPNPRRPEW
PAAEFIVGNP PFIGASFLRA RLGDTHAEAL WSAHPQMNES ADFVMYWWDR
AAELLTRKGT VLRRFGFVTT NSITQVFQRR VIERHFKAKR PISLAMAIPD
HPWTKATTDA AAVRIAMSVG ETGRGDGLLQ IVVNEAHLDS DTPIVELQGR
VGPINSDLTI GTDLTTTVPL RASEGLASRG VTLAGSGFLI TSEEAEHFGL
GTHEKLKQHI RGLHNGRDLN QTSRRILVLD FLGLSEEEVR RHFPEAYQHL
LRTVKPERET NKRASYRQNW WVFAEPRKEM RPALKDLGRY IGTARTAKHR
IFSMLAGHSL PESEVIAVGS DDAFILGVLS SRLHVRWSLS KGGTLEDRPR
YNNSMCFDPF PFPDANPIQK QTIRVIAEEL DAHRKRVLAE HPHLTLTGLY
NVLERLRAGA VPQAQPSPAG LTRGSTSSRG AAKKDLDGRG TGRQDGASRL
SPGHDDAEMV LTPDEQCIFD DGLVLILKEL HDRLDVAVAE AYGWPANLSD
DEILARLVAL NKQRADEEKR GLVRWLRPDY QIPRFAKGVD KQAAKEEGAQ
IAASLDLGET RQKPSFPTGA VEQTAAVFAA LAAASGPLDA KSLAAQFRRT
KTTEKKLAEV LASLARLGYV ATTDGVSFAL RRVA

>PspOMII CGCCCAR 1160 aa (SEQ ID NO:34)

MEIGLSVPKQ AGPILSVDDF IARWTTSGGS ERANFQQFAI ELTQLLDVPA
PKPATADAQN DDYRFERPVT FIHTGTQSRG FIDLYRRGCF VMEAKQGTGA
APEEGQLDLL AAAPPVQRQG HGVRGSKRWD DTMLRARNQA DGYARAVARE
DGWPPFLLIV DVGHVIEVYA DFSGQGQGYT QFPDGNRYRI TLDDLRDAAT
LDRLQAIWTD PHSLDPTRVS AQVTRQVAEH LAELGRSFEA QGHAPEAVAR
FLMRALFTMF AEDVQLIPEG AFSKLLQDRR GHPEHAAPML ESLWQTMNTG
GFSPALSCDL KRFNGGLFRE ATALPLSAMQ LGLLIQAASH DWREVEPAIF
GTLLERALDT RQRHKLGAHY TPRAYVERLV NPTVIEPLRA EWRDIQAAAV
TLAGQDKLDE ARATVRDFHR RLCEVRVVDP ACGSGNFLYV ALELMKRLEG
EVIALLRELG EDQGALALAG HTVDPHQFLG IEVNPWAAAV AELVLWIGYL
QWHFRTHGTA SPAEPVLRDF RNIENRDAVL AWDGTRPRLD DAGQPVTRWD
GVSTIRHPVT GEQVPDPAAR VQVLDYLKPR PARWPEAEFI VGNPPFIGAS
RMREALGDGY AEALRAAYPR MPESADFVMF WWDKAALATR AGKTRRFGFI
TTNSLRQTFN RQVLEPHLAD PKKPLSLAFA IPDHPWVDAG DGAAVRIAMT
VAAAGSAPGR LFTVTDERRG EREAEGRPVT LSGQIGKIHA NLRIGADVAG
AKPLRANAGI SSPGVKLHGA GFIVTPAEAQ ALGLGTVPGL EAHIRSYRNG
RDLTATPRGV MVIDLFGLSE AEVRTRFPAV YQHVLDKVKP ERDQNNRDSY
KRNWWIHGEP RRDLRPALEG LPRYIATVET AKHRIFSLLD ATILPDNKLI
IIALADTWHF SIVSSRIHWV WAIANAAKIG MYDGDAVYPK GQCFDPFPFP
DATEAQKARL RALGEELDAH RKAQQAAHPR LTLTALYNVL EKLRAGERIE
GRDRETYDAG LVGILRDIHD RIDAAVAEAY GWPADLDDEA ILTRLVDLNR
ARAAEEAAGL VRWLRPDYQN PAGRIAAAKG QQVELDVGAA AEAADKALWP
KALPEQIAAV RAVLSDMGEA TPEQVARQFK RARAASVKPL LESLSALGQA
RLIEGGRFAA

FIG. 24B-8

>DrdIV TACGAC 1144 aa (SEQ ID NO:36)

MTPEEFITRW SPSGGAERAN YVLFLSELCD LLGVPKPDPT QADEAKNAYV
FEKDVPDLHD DGGLSQRRID LYRRGAFILE AKQGVEKEAT AEEALLSTKG
KKKKGHGTRG TKGWDTFMRR AREQAERYAH LLPASEGRPP FLLVVDVGHV
IEVYAEFTRT GGAYLPFPSA RAHQIQLADL ARPEVRELLR TIWLDPLSLD
PSIHAAEVTK DVARKLAEIS RSMEGQPDAQ GQAMTPERVS QFLMRMIFTM
FAEDVGLLPN TKFRDKLKSL LGRPQAFIPT ITDLWQAMAK GGYSVALDAQ
IKHFNGGLFE GVEVLPVTDG QLKLFIEAAE SDWSRVEPSI FGTLVERALN
PRERHRLGAH YTPRAYVERL VHQVVMEPLR EDWRTVQVQV QDTLDRGNGD
DKARARAQQL VAQFHAQLRQ TQVLDPACGT GNFIYVSMEL IKRLEAEVIE
TLVALGGLPP LIEVNPEQFH GIEVNPRAAS VAELVLWIGY LQLYAREHGN
AAPPEPILRA FHNIENRDAV LSYSHTTPKV DRDGQPVTRW DGVTFRRHPV
TGDPVPDERA QIPEEVYHNP MTTEWPKADF IVGNPPFIGS KRMRELLGNG
YVDALQRVFA DVPQATDFVL RWWYKAALLT RQEEVRRFGF ITTNSISQAF
NRRAIEPHLN ADVRPLSLVY VTPDHPWVDE SDGAAVRIAS TVGELGQRPG
LLARVVKEYD EAAEGDLVAE FAFETGVIHA DLSIGADLTE TQPLMANLGL
CAVGMKTIGA GFLVERTKAE ALGLGQDNRI RPYINGRDLM GRTRGVYVID
LFGVSEEDVR DQYPKLYQHL RNAVYDIRRQ NNNRVFRDLW WVIGHPRPIF
REFTRGLKRY VVTLETAKHQ VFQFLDSSIV PDSTIVTFGT EDAFHLGVLS
SRVHVTWALA QGGTLEDRPR YNKTRCFETF PFPAATPEQQ QRIRDLAERL
DAHRKARLAE HPKLTMTDMY NALAALRAGQ PLEGKLKTAH DQGLVTTLRQ
LHDDLDVAVL AAYGWPTGLD EQGLLERLAA LNAERVQEEK AGRIRYLRPA
YQDPHGTAQE NLGMAVASRP AKAAQVMPFP TALPLQVQAV RSALMQAGQA
LSPQEVAQAF QGAKEKQVED IMQTLVLLGQ AHLREHNGEV RYAA

MaqI CRTTGAC 1151 aa (SEQ ID NO:38)

MEAFIAASAA VDEFLKRWKG NTGSERANFQ SFMRDLCTLL DLPHPDPGEG
DTTQNAYVFE RFIASARVDG NTDNRYIDLY RRDCFVLEGK QTGKELASRS
QQNAVNAAVA QAERYIRGLP QEEVEHGRPP FIVIVDVGNA IYTYSEFSRT
GGNYVPFPDP RHYEIRLEDL HKPDVQHRLR QLWLEPDQLD PSKHAARVTR
EVSTKLAELA KSLEHNGYDV ERVASFLKRC LFTMFAEDVE LLPKASFQNL
LIDIKDRNPE AFPHAVKALW ETMNAGGYSE RLMQTIKRFN GGLFKGIDPI
PLNVQQIQLL IDAAKADWRF VEPAIFGTLL ERALDPRERH KLGAHYTPRA
YVERLVMPTL IEPLREQWGD IRGAAETLLR QGKTDKALQE VQAFHYQLCQ
TRVLDPACGS ANFLYVALEH MKRLEGEVLG FISELTQGQG VLESEGLTVD
PHQFLGLEIN PRAAQIAELV LWIGYLQWHY RLNDRLDLPE PILRDFKNIE
CRDALIEYDS REPELNKNGE PVTIWDGISM KVSPTTGELI PDETGRAKVY
RYHNPRRAEW PAAEYIIGNP PYIGARRIRS ALGDGYLQAL RGVYTDIPEH
VDFVMYWWAK ASENMASGKT KAFGLITTNS LRQSFSRKVV EKTLDINSDC
SIKFVIPDHP WVDSADGAAV RVTLISVDSN KAPGIVALIR NEEAEGSGAY
KITLDNKSGH ITPNLTIGAD PGEATCLSSN SSVSCVGYQL TGKGFVLTQS
QKEEHENEWP ESVIKPLWSG RDITQSPRKN WAIDVCDWGI DALKVSSPSL
YQWLLTRVKP EREQNNRASL KERWWIYGEA RNTFRPALIG IETAIATSLT
AKHRVFVHLD SNSICDSTTV MFALPGAQYL GVLSSRVHVL WSLFAGGTLE
NRPRYNKTLC FETFPFPKMS SDQSEKISDL AEKIDQVRKG QQAKHPDLTL
TGMYNVLEKL RSGEELTNKE KTIHEQGLVS VLRELHDDLD RAVFQAYGWS
DLADKLVGRP GATTPLPDKP AEQAEAEDEL LMRLLELNKQ RAEEESRGIV
RWLRPDYQAR DAVQTEVDIA PKAAATKTEA STSKGKASFP KAIPDQLRVL
REALAERSHT TESLAEMFKR KPMKSVEEGL QSLVAVGVAE YDPETQTWHT
V

*FIG. 24B-9*

>PlaDI CATCAG 928 aa (SEQ ID NO:40)

MRLSWNEIRA RAARFSEEWK GVTRERAETQ TFYNEFFQIF DIPRRRVASY
EEPVKGLGDK RGYIDLFWKG TLLVEHKTTG RDLKKAKIQA LDYFPGLKDK
ELPRYLLLCD FQSFELYDLD EDTEVRFRLA DLKDHVEAFG FMIGVQKRTF
KDQDPVNIEA SELMGKLHDA LKESGYDGHD LEQYLVRLLF CLFADDTGIF
EPKDILLDFI QNRTSADGSD LGSRLNELFE VLNTPEDKRQ KTLDEDLGNF
PYVNGALFAE RLRTPAFNAA MRLILIEACE FKWEAISPAI FGALFQSVMN
KTERRALGAH YTTEKNILKL IQPLFLDGLH EEFARAKALK RGRQQALEAL
HEKLGQLTFF DPACGCGNFL VIAYRELRAL EQEILRVLHD GKDQRIFDVA
QLSKVNVDQF YGIEIGEFPA RIAEVAMWMM DHIMNNRLGL SFGSNYARIP
LRTSPHILHA DALEADWAAL LPPEKCSYVF GNPPFIGSKF QTAEQRRQVR
DIAKLGGSGG TLDFVTAWFL KAGEYVQHGK ADIAFVATNS ITQGEQVAQL
WPLLFQRCKL EIAFAHRTFA WGSDARGVAH VHVVIIGLTR RDREWPEKRL
FSYADIKGDP VETRHKALTA YLFDAVNVAD RHLVVEERNT PLCEAPKLKT
GVQMIDNGIL TFTTMEKEEF LRQEPEAEPL FRKYIGGDEY INGFFRWILY
LADAEPSFLR QLPLVQERIR QVRQYRLSSS RPSTVRMADY PTQVGVDERL
SGPYLVIPNT SSERRDYVPI GWLTPEVVAN QKLRILPDAD PWIFGLLTSG
MHMAWMRAIT GRMKSDYMYS VGVVYNTFPW PDITEAQKQK IRALAQAVLD
ARALYPGATL ADLYDPDLMK RELRQAHRAL DAAVDKLYRG QAFANDRERV
EHLFGLYEKL SSPLTAAPKP IKRKRKKE

>AquIII GAGGAG 917 aa (SEQ ID NO:42)

MPLSWNEIKS RAIAFSKEWE FEESEKSEAQ SFWNDFFQVF GISRKRIATF
EKSVNKLGNK KGSIDLLWKG NILVEHKSRG KSLDKAFEQA KDYFPGLKEH
ELPRYILVSD FAQFRLYDLE TDQTHEFLLK DFVNYVHLFD FIAGYEQRTY
KDEDPVNIHA AELMGKLHDR LREIGYTGHD LEVYLVRLLF CLFADDTGIF
EKGIFEEYLD IHTKEDGSDL AMHLGHIFHV LNTPPEKRLK NLDESLGQFP
YVNGKLFEEQ LAPAAFDRKM REMLLEACGF NWGKISPAIF GSMFQAAMDQ
QTRRNLGAHY TSEKNIQKVI KPLFLDELHE KFKKAKGSPT ALKRLHDELG
ELHFLDPACG CGNFLIISYR ELRDLELLIL KELYKKKEGF IDIRLFLKVD
VDQFGGIEYD EFPARVAEVA MWLIDHQMNI KVSNEFGQYF VRLPLKKAAR
IVNGNALRID WEEVIPKEKL NYILGNPPFV GSKMMTKDQR ADLLSVFESA
KGAGVMDYVS AWYVKAADFI QEKKIKTAFV STNSISQGEQ VGILWGLLFE
KYQIKIHFAH RTFKWSNEAK GKAAVYCVII GFATFNIKGK RLFEYEDIKG
EALEIKVSNI NPYLVNGDDL IILRRRQPLC NVPNIGIGNK PIDGGHYLFT
TEEKEDFLKL EPKAEKWFRK WLGSREFINK EERWCLWLGD CPPNELKKMP
HALERVKAVK ETRLNSNSKP TQKLAQTPTR FHVENMPESE YLLIPKVSSE
RRNYIPIGFL NQSTLSSDLV FIVGNATLFH FGIFTSVMHM AWVKYVCGRL
KSDYRYSKDI VYNNFPFPQN VTDKQKQTVE KAAQLVLDTR DKYPDSSLAD
LYDPLTMPPD LMKAHQKLDK AVDLCYRPQA FTSELNRIEF LFNEYEKLIT
PLLQSTKQKK ARKNKTS

*FIG. 24B-10*

>AquIV GRGGAAG 914 aa (SEQ ID NO:44)

MAVTRDSLQA FVDYCNAYIQ GDEKSEAQTF LTRFFQAFGH AGIKEVGAEF
EERVKKASKK DKTGFADLVW SPAPGVKGVV VEMKKRGTDL ALHYSQLEKY
WLRLTPKPRY SILCNFDEFW VYDFNNQVDE PVDRVKLEDL PNRVGTFSFM
EIGGREPIFR NNQVEVTERT AKRMGEFYRL VRSRGEREKF VYFTEAQLQR
FTLQCVLAMF AEDRNLLPRD LFVGLVQDCL AGRDNAYDAF SGLFRAMNLP
GIVPQGRYKG VDYFNGGLFG EIQPIPLEKN ELEILDVCAR DNWANIRPSI
FGNIFESAID ADERHARGIH YTSEKDIRQI VRPTIADYWE GKIDEATTYE
DLEKLKQELR EYRVLDPACG SGNFLYVAYQ ELKRLERVLL NKIYERRKRF
QGEVLQQEEI GIVTPLQFFG MDTNPFAVQL ARVTMMIARK IAIDKFGLTE
PALPLDSLDQ NIVCQDALFN DWPKADAIIG NPPFLGGSRV RLELGDKYVE
RIFEKFSDVK DKVDFCVYWF RLAHENLNKT GRAGLVGTNS ISQGFSRRAS
LEYIVNNGGI IHDAISTQVW SGQANVHVSL VNWQYLKPPE YVLDHEIVKN
INSSLKSETD VSNAVKLKVN LNQSFKGVQP TGKDFLISEK KVENWIQKNT
KNNQVLKLFV SASDLASNKN GEPSRWIIDF NDFSLEDAST YKEPFDHVNF
FVKPQRENNR DQKTREYWWL FPRARPAMRQ AIELLALYFA VPRHSKWFIF
IPCKLDWLPA DSTTVVASDD FYVLGILTSD VHRQWVKAQS STLKGDTRYT
HNTCFETFPF PQTAIAKLTQ QIRQGMIDLH EYRTAQMEAK QWGITKLYNA
FFDEPASQLH KLHKKLDALV LKAYGFKKDD DILEKLLDLN LALAEKEKNG
ENIVGPWAID NPPK

*FIG. 25B-5*

*TABLE 2*

(i) ALTER AMINO ACID AT THE SINGLE HIGHEST SCORING POSITION
(ii) ALTER AMINO ACID AT THE SECOND HIGHEST SCORING POSITION
(iii) ALTER AMINO ACID AT THE THIRD HIGHEST SCORING POSITION
(iv) ALTER AMINO ACID AT THE FOURTH HIGHEST SCORING POSITION
(v) ALTER AMINO ACID AT THE FIRST AND SECOND HIGHEST SCORING POSITIONS
(vi) ALTER AMINO ACID AT THE FIRST AND THIRD HIGHEST SCORING POSITIONS
(vii) ALTER AMINO ACID AT THE FIRST AND FOURTH HIGHEST SCORING POSITIONS
(viii) ALTER AMINO ACID AT THE SECOND AND THIRD HIGHEST SCORING POSITIONS
(ix) ALTER AMINO ACID AT THE SECOND AND FOURTH HIGHEST SCORING POSITIONS
(x) ALTER AMINO ACID AT THE THIRD AND FOURTH HIGHEST SCORING POSITIONS
(xi) ALTER AMINO ACID AT THE FIRST, SECOND AND FOURTH HIGHEST SCORING POSITIONS
(xii) ALTER AMINO ACID AT THE FIRST, THIRD AND FOURTH HIGHEST SCORING POSITIONS
(xiii) ALTER AMINO ACID AT THE SECOND, THIRD AND FOURTH HIGHEST SCORING POSITIONS

Figure 26

| | | | | | |
|---|---|---|---|---|---|
| Position | 0123456 | | | | |
| RceI | CATCGAC | 827 | PAAFQHVMLYVKPERDHN-RRDSIKKLWWRFAWERPTLREALKGLDRYIATTE-TS | 880 | (SEQ ID NO:173) |
| RpaBI | CCCGCAG | 791 | PEIYQKLLLKVKPDRDAN-PRPSRRDNWWLFGENQPKMRNAIASLGRYIGTVD-TS | 844 | (SEQ ID NO:174) |
| SstE37I | CGAAGAC | 804 | PTLFAYLLDRVKPVREEN-SRPQYKKLWWIFAEPRPALRSAIGGIRQFIGTTY-TA | 857 | (SEQ ID NO:175) |
| GauT27I | CGCGCAGG | 771 | PLLFDIVRDRVKPERDAN-ARAVYRTYWWRFGEARRDWRSFVAGLPRYIATVK-TA | 824 | (SEQ ID NO:176) |
| PspOMII | CGCCCAR | 828 | PAVYQHVLDKVKPERDQN-NRDSYKRNWWIHGEPRRDLRPALEGLPRYIATVE-TA | 881 | (SEQ ID NO:177) |
| RpaB5I | CGRGGAC | 794 | PEAYQHLLRTVKPERETN-KRASYRQNWWVFAEPRKEMRPALKDLGRYIGTAR-TA | 847 | (SEQ ID NO:178) |
| PliMI | CGCCGAC | 814 | PAVYQHVHDHVKPERDQN-NRAVYRDSWWMFGEPRAAFRPSLKGLARYIATVE-TA | 867 | (SEQ ID NO:179) |
| MaqI | CRTTGAC | 798 | PSLYQWLLTRVKPEREQN-NRASLKERWWIYGEARNTFRPALIGIETAIATSL-TA | 851 | (SEQ ID NO:180) |
| AquII | GCCGNAC | 799 | PKTYQWLSETVKLERSTN-NDPKLKREWWRYRRANTSIRDGIKDLNRYIATVR-TA | 852 | (SEQ ID NO:181) |
| AquIV | GRGGAAG | 692 | KEPFDHVNFFVKPQRENN-RDQKTREYWWLFPRARPAMRQAIELLALYFAVPR-HS | 745 | (SEQ ID NO:182) |
| SpoDI | GCGGRAG | 712 | EAVYSWLEQAYESYERKSKRRIVRRQDWWLHRRSGAALKNAVSRLSRFIVTPR-VG | 766 | (SEQ ID NO:183) |
| RpaTI | GRTGGAG | 718 | EGPFQYILEHVKEYRNEE-AHESSKMNWWIHQRPRHALRLAIDGQSRYLATAR-VA | 771 | (SEQ ID NO:184) |

Figure 31 (SEQ ID NO:193)

>RceI CATCGAC 1165 aa (YP_002299341)

MPQTMSMPPV LTAVTDPVER FPVERFIERW SPSGGAELAN YGLFISELCD
LIGVPRPDPR TGDDARDSYV LEKPVTIRHT DDSTSSGRID CYRKDCFVLE
AKQGVDAESQ TALPLLGVAG APAAPSGTRR RGHGVRGSKG WDDAMIRARG
QAEKYAKALP EWPPFLIVLD VGHEIQLFAG FSRTGKDYTH FPDASSFRIR
MTDLRRQETR DLLKAVWLDP LSLDPSKRTA KVTREIAERL AVLAKSLEQA
GHSAANVATF LMRCLFTMFA EDVELLPKDS FRDLLRNLRG HPQDFVPTMR
VLWKSMNDGD FCGVLTQKVL RFNGGLFKHA DALPLTPEQL ELLIQAAEAN
WRDVEPAIFG TLLERALDKT ERHKLGAHYT PRAYVERLVL PTVIEPLREE
WEAVKVAAAE QERDAAVALV MEFHRKLCDT RVLDPACGTG NFLYVTMELM
KKLEGEVLDF LSITLDVRQD ALDLAGHTVD PHQFLGIEVN PRAAAIAELV
LWIGYLQWHF KTRGKVMPAE PVLKDFKNIE NRDAILAWDR TEIVRDESGR
PVTRWDGVTM KKHPVTGEDV PDETARVELV RYVKPRPAKW PKADYIVGNP
PFIGTKLMRA ALGDGYVNQL RETIDHIPDS ADYVMYWWDH AAKLLWNGKI
FRFGFVTTNS ITQTFNRRVL TNRLKTGAQI YIIFAIPDHP WSDADGSAAV
RISMTVVAKG NSAGRLLLPI REEHLGSETP NIEFNEKHGA ISADLRIGAN
IGNATELISN ERICGFGMAL HGQGFLLSRA KSDELKKFGS QVIRPFLGGK
DLLSAARERY VIDFSGLTEE EAQIANPAAF QHVMLYVKPE RDHNRRDSIK
KLWWRFAWER PTLREALKGL DRYIATTETS KHRVFQFIEA IYLTDHMGIV
ISSQDALILG ALSSWPHRLW AIKAGGTLED RPRYNKTRCF DPFPFPDPAE
ELKARIRVLG ERLDSFRKER QAAHPDLTLT QMYNVLERLR ELDRDPAAKP
LDAKEKAIHE KGLISVLRQI HDDLDRAVFD AYGWPHDLTD EQILERLVAL
NKERAAEEKR GIIRWLRPEF QAPKTARPVQ TAMEVGPEET SAPAAPAAKA
PWPKSLPEQA QQVLAALTAL GRPATPTEVA RTFRSAPAPR VAEVMATLET
MGRAWKVENT DRYAA

Figure 32 (SEQ ID NO:194)

>RpaBI CCCGCAG 1186 aa (YP_531341)

MGTASIPDVE QFISRWQGRE GGQERANYVS FLNELIALLG LPKPDPADAT
HEHNDYVFER AVKKHKDDGA SHGRIDLYKK NSFVLEAKQS RLKGVKKVAG
QNDLFNADVP EASRGRRGAD RAWDVLMLNA KRQAEEYARA LPASHGWPPF
ILVCDVGHCI EVYADFSGQG KNYTQFPDRQ SFRIYLEDLR DETVRERLQK
IWTEPQALDP AQASAKVTRD IAKRLAQVSL ALEKKGFVAD DVAMFLMRCL
FTMFAEDVGL LPDKSFKTVL EECEKNPEAF VHDVGQLWEA MDLGAWAHAL
KTKVKKFNGE FFKNRAALPL GREEIGELRQ AASYDWNEVD PSIFGTLLEQ
ALDPQDRKKL GAHYTPRAYV ERLVVATIIE PLREDWRNVQ ATAETRRGAG
DLKGAAAAVQ AFHDKLCATR VLDPACGTGN FLYVSLELMK RLEGEVLEAL
LDLGGQEALR GLGSHSVDPR QFLGLEINPR AAAIAELVLW IGYLQWHFRT
KGGPPDEPIL KAFKNIQVKN AVLTWDGAPL PKIVDGKETY PNAKRPEWPA
AEFIVGNPPF TAGQDFRREF GESYAQALWL NYKHISGAAD LVMYWWDRAA
ELLNRKGTAL RRFGFVTTRT ITHEFSGRVV ARHLNANDPI SIVLAVPNHP
WTRGRDAAAV RIAMTVVEAG HRNGLLQNVI SESDLDADEP TILLEDRCGK
INPNLTIGID LASAGRLRAT DGICHDGVKL HGKGFIVQSA ELEHLGLDRR
KGIEKVIRPY LNGRDINQRT RGLFVIDLFG LAEDEVRLNF PEIYQKLLLK
VKPDRDANPR PSRRDNWWLF GENQPKMRNA IASLGRYIGT VDTSRHRIFS
FLDEKMLCDD KVVIVASTDA FDLGVLSSRI HCTWSNKSGV RLGVGNDPVY
ASNRCFDPFP FPAANNIQKQ TIRVIAEELD AHRKRVLKEH PHLTLTGLYN
VLERLRAGAA IAPSSASAAR GAGGAGGDAG AVARGKTPHP NPPHRSAGGG
DQAAAAASAV PALTPDEQRI FDDGLVLILK ELHDKLDVAV AEAYGWPADL
SDDEILAKLV ALNKERAEEE KRGLVRWLRP DYQIPRFGKG LDKQAAREEG
AQVTADLIGV ETVQKRAFPT VAVEQTAAVF AALAAASAPL DAKTLAAQFK
RTKTTEKKVG EVLASLARLG YVTSDDGMTF ALRRVA

Figure 33 (SEQ ID NO:195)

>SstE37I CGAAGAC 1131 aa (ZP_-1748422)

MQDQEVEEFI DRWKNTGGSE HANYQLFVIE LTGLLGLDRP NPATDDDSND
HYRFERPVIF AHTQKRSTGF IDVYRAGHFV LETKQGVNQK KSRAADLTTG
TAARTQKRTG HGVRGTAAWD DTMLKARNQA DNYARAVARD DGWPPFLMIV
DVGHVIELYA DFSKQGQGYN QYPDGNRYRI FLDDLRKDET RDLLRTIWTE
PFTLDPSLKA AEVTRDIAAH LAELGKSFEG QGHSSETVAR FLMRCLFSMF
AEDVDLIPRG SFTELLRKLR GHPEHAEPAL KGLWETMNTG GFSQVLMQDL
KRFNGGLFRD ADALPLNNLQ LGLLIEAAEA DWKQVEPAIF GTLLERALDK
RQRHKLGAHY TPRAYVQRLV TPTIIEPLRD DWRDVQTAVQ RLTEDGKKDE
ARKLVADFHA QLCETTVLDP ACGSGNFLYV ALEMMKRLEG EVTSLMVDLG
DTKPLITVDP HQFLGIELNP WAANVAELVL WIGYLQWHYR THGQAAPSEP
VLRDFRNIAN ADAVLKWDDR TPRMDAEGNP VTRWDGVTTM RHPVTGEEVP
DPAARVQVYD YAKPRATVWP RANFIVGNPP FIGARKIKSA LSEEYVETLR
AVYQNVPNTV DFVMYWWAKA AEAVKHKSAR RFGLITTNSI TQDYSRKLVD
KNISGGKPKL NLVFATTNHP WVDSSDGASV RIAMTVASGR KIKKPRILEN
AGTEDQKEKS VDRINSRLAD VPDFSELQPL RSNYRMCFQG VVPAGDGFKL
GSSEKDALEM RLSEKEKAKI KRYYIGKDII DRPRHQSIID LFGVDLEELK
RDYPTLFAYL LDRVKPVREE NSRPQYKKLW WIFAEPRPAL RSAIGGIRQF
IGTTYTAKHR VFQFCGSEIV PDAMVYAIAT DQPELLACLS SRVHLVWCKG
STGTLEDRPR YNSANTFSPF PFPDLGNNER ESLRTLGEHL DAHRKRQQAA
HPKLTLTQMY NVLEKLRAGE PIEGKDREIY DQGLIGILRD LHDQIDAEVA
RAYGWPADLS DEDILFRLVA LNKERAEEEA QGHIRWLRPD YQNPTGQQAT
KGKQAELDVG MAAKIEKAPW PKTLPDQIAA VREALAEMGE ATPEQIARRF
MRARTTSVAP LLDSLAALGQ AEKGGDGRYA A

Figure 34 (SEQ ID NO:196)

>GauT27I CGCGCAGG 1112 aa (YP_002760842)

MSSSNAAVTP AVALRALRER WAGVPAAERA NAQSYLRDLC EALGVPAPLP
AGSGYEFELP VKLITRDGTE TTGFVDCYKV GHFILEAKDV QGGASDVALR
RAYGQARQYA AHDPSGTAPP YLLVLDVAKT LLVYHRWGGV YQGFAAGHRI
DLPTLDQRPS DIELLRDIWT QPTKRDPRQH AQAVTQEIAA KLATLAATLE
DRGFGPERVA RFLMRVVFSC FAEDVDLLPR EAFRQTVQNA GVQGDAALFQ
RALGSLWQTM DSGGLFGFEN ILQFNGHFFK DAEVLPLERE EIALVLEAAR
ADWRDVEPTI FGTLLTRALD PVERHRLGAE YTPRAFIERL VRPTVEEPVR
ERWTAVQAEV LQLRESGKAK DRAAAEQRLR EFLGWLQGLR VLDPACGSGN
FLYVTMHVLK DLEYEVVREL EALTGHAELR MQEIGPKNFL GIEVKPWARE
IAELTLWIGF HQYWKRHHHV QPPEPVLMDT GTLELRDAVL AWDAVRHVPE
KDRFDPTPRI THTVTGELVP DPAATLPYME HVGARQAPWP EADFIVGNPP
FLGQFRQRES LGDGYVEALR SAYPGVPDAA DLVMYWISKA TRAVESGRTL
RAGLITTQSI TQKQNRKVLE DAAVRGLRPV WAIADHYWND GSDDARVRVA
MTVFAREPAA ATLVTVDGEA KVVNTVRVPR LNTDLTVHAD VPSAAAVALQ
ANAWLCSNGY KPHGTGFLLS DEEARRLLSL DPRNAEVLRP YRNGMDLATQ
PRRVWIIDFG FADESEARTY PLLFDIVRDR VKPERDANAR AVYRTYWWRF
GEARRDWRSF VAGLPRYIAT VKTAKHRFFT FLESTVAPDD KLTCIASSEG
FVLGVLSSLI HSTWALAAGS RLGIDGTPSY DKGTCFDAFP FPDCSADVRN
RIATIAERID AHRKSAIERS AKVGMTVMYN VIDKLRVGAT LTSKEREVHE
VAACGVLRDL HDELDATVAE AYGWSWPEPP ALILERLVAL HDRRVEEEAG
GTIRWLRPEY QRPRFGGATD GANVAPTLDL PATPTTLTGA GTVIASAPWP
SDAIGQITVL RSMAAMTPVS IEEAVQRLVG AKRDIVHRHL ETLAMLGEVR
DVGDGRYAVT GS

Figure 35 (SEQ ID NO:197)

>PliMI CGCCGAC 1173 aa (YP_003631006)

MTAASVASID PAAFIARWAP SGGSERSNYT LFLSELCDLL GVPRPEPAQA
DTSRSFYVFE RDVTFHNSDG TTSTGRIDLY KRGCFILEAK QGVEQADAVE
ILSSTPAKRR KGHGTRGTKA YDDTMLRARS QAEQYAKALP ADEGWPPFLI
VVDVGHSIEL FADFTRSGKT YLPFPDPKSY RILLNQLAHD DIRHTLKTVW
TDPVSLDPSR RAAKVTRELA DRLARLAKSL EASKFDPGRV AQFLMRCLFT
MFAEDVDLIP RESFTNLLKS LRDDVANFPE MIRSLWVSMD KGQFDPVLRK
KLRRFNGGLF EDCEALPLTR DQLELLIEAS QAQWRDVEPA IFGTLLERAL
DPRERHKLGA HYTPRAYVER LVMPTIMEPL REEWDTVRAA AFTEAGRGHR
EAAIQILRDF HRQLCETRVL DPACGSGNFL YVALEHMKRL EGEVLNTLHD
LGYKQREIIT VDPHQFKGIE VNPRAAAIAD LVLWIGYLQW HTRTRNLDDI
SEPIIQNFHN IECRDAVLAW DAIEEVRDEH GQPVTRWDGR TMKKHPVTGE
DVPDDTARVP VVKYINPRKA EWPKAEYIVG NPPFIGNSRM RHALGDGYAE
CIRQTYNRLP ETCDFVMYWW DRAAEFTSDN QVNRFGFITT NSIRQKFSRR
ILEQYINGPV AALSLIFAIP DHPWVDSSDG AAVRIAMTVA APGTKVGRLN
NVASESIGVD DVAEVNLRER IGRIQTDLTI GANVAGTLTL KATQGLSCPG
VKLHGAGFIV SPEEARHLGL GSVPGLELHI RQYRNGRDLT ASPREVMVID
LFGLGVDELR QRFPAVYQHV HDHVKPERDQ NNRAVYRDSW WMFGEPRAAF
RPSLKGLARY IATVETAKHR VFQFLDASIL PDNMLVVIAL NESLHLGVLS
SRIHIVWSLA AGGTLEDRPR YNKSRCFEPF PFPEMPNPRT PRIRELGEQL
DAHRKRQQAA HPDLTLTGMY NVLEKLRSGE LLTAKEKVIH EQGLVSVLKQ
IHDDLDAAVF EAYGWPVTLT DEEILERLVA LNAERAEEEK RGLIRWLRPE
FQNPSGGQAI QPELELELET EAEDEEETAA ATTKKGGKAK KGAGKTAPGG
KTKAPAKQPW PTKLSEQVQA LIQKLQTADS PLTAQELAKA FTRANADTID
ELLETLVAIG KARQVGDDKF TAV

Figure 36 (SEQ ID NO:198)

>AquII GCCGNAC 1168 aa (YP_001733624)

MTDFIQKWQN SEGNERANYQ SFLNDFCEFL GVEKSPPKGS GNNSYCFDRD
VKIIAPSGAE TTNFIDFYKE DCFVLETKQG SNTSNKGHGK RGTAAYRKEM
KKAFGQALKY ARFVEPKPPF LITCDIGDHF RVWQDFSESW LSANGNYGTY
DSVPKIPFTD LEKPEIQDFF YKVFTDPQSL NPEKIAAQVT REVAADLAEL
AKTLEQTTKP QEVAQFLMRC IFTMFAEDVG LLKEHLFTEA LKERWIPQPQ
DFKPQVEALW QAMNDGTSFG FHGQLLRFNG GLFAKPQAIA LTADQLKILL
TAAERDWKNV EPAIFGTLLE RALEKKERSK LGAHYTPRAY VERLVRPVII
EPLQEKWQLI QGEVETLLEE EEAAKSASAK TKKRNAAAEK LTEFLGELRK
IRVLDPACGS GNFLYVTMDL MKTLELEVLN RLGTVMGASQ LRLDFDQINP
SQFLGIEINP RAAEIADLVI WIGYLQWHFR LFGSLPPVEP VLREYKNIEN
RDAVLDYDGT KPAIDPKTGK VRTRWGGRTM KHPVTGEDVP DPSDQVEILE
YINPREAQWQ QADYIVSNPP FLGNARMREY LGDGYTETLR KVYKDVPDTV
DFVMYWWHKA AELIRKEKTL RFGFITTNSI RQARLRSVID FHFNQKKRIR
LFFAIPDHPW SDGEVAVRIS MTGVELKKKR RQYSQLTHIL EESKLNTPEE
TAFSLKFSYV KANEIFSNLQ FGYDVNQANS LSSNQNLASQ GFVVGGSGFV
LKNQALVENL EQEIIHPFKT GRDLTQSPEF RQTIDVNHLS KKQLLSSYPK
TYQWLSETVK LERSTNNDPK LKREWWRYRR ANTSIRDGIK DLNRYIATVR
TAKHRVFQFL NSEIMAESGV VMIFLDDSYF LGICSSSLHI IWALAQGGRL
EDRPVYNHDA CFYRFPFPDP SEELKQEIRE LGERLDSHRK QVQAAHPEVT
ITAMYNCLEK MRSGEPFTDG DREFNNKALI TTLKQIHDDL DQAVFCAYGW
EDLIPLWQKV SLPKGDLEGC QTEPNNTETK EQLEQSILQR LVDLNAERAE
EERNGFVRWL RPEYQAPDQV VTQKVIEGIG VEEETKEAVI APPEQQKFPT
KLKGQLAAIR DLLRTQGGEW TITQIAAQFK GTSAKKLETI QNCLEILEDL
GVILSHTETE TKCYYATL

Figure 37 (SEQ ID NO:199)

>RpaTI GRTGGAG 973 aa (YP_001992830)

MTPAEFIKKW KPVALTERAA AQTHFLDLCK LFEHEDPVSA DPTGEWFTFE
KGATKTGGGD GFADVWKKNY FAWEYKKKKR DLGVAMNQLV RYAAALENPP
LQVVCDTDRF VIRTAWTNTV PKEYEIELDD LADPEKRKIL WAVFHDPEQL
RPQQTRTAIT KEAADKFSTI ALRLQGRGTP EEIAHFVNQL VFCFFASSVK
LLPEGFFPKL LKRAAQKPQH AIDYFNKLFE AMENGGEYDL TDIAHFNGGL
FDGRRALKLD EGDIGLLIEA GSLDWGQIDP TIFGTLFERF LDPDKRAQIG
AHYTDPDKIL MIVEPVILRP LRAEWDAARA KIAEIAGEAN ALQQTGFSKQ
GAKSFDKKIT NIRAKAEVIR DQFIERLRGI TILDPACGSG NFLYLALQGV
KDIELRANLE CEALGLSPRL PVIGPEIVHG LEINELAAEL ARTTIWIGDI
QWRIRNGIYS NPRPILRKLD SIECRDALIT KLTDGTYAEA EWPTAEFIVG
NPPFLGDKFM LDRLGVRYTQ ALREAFLGRV PGGSDLVCYW LEKARAQILS
NETFGAGFVA TNSIRGGANR TVVDRVTADL DIFCAWADED WTIEGADVRV
SLICFSSKGR AQLLVELNGQ SVARIFSDLT SSATDFTRAR SLRSCREVAF
IGNQKGGAFD LPGSIARSFL TLPQNPNGNS NADVVKPWIN GLDIVRRPRD
YWIIDFTGLQ ESEAALYEGP FQYILEHVKE YRNEEAHESS KMNWWIHQRP
RHALRLAIDG QSRYLATARV AKHRLFIWVD HQVVPDSQVV AIARSDDATF
GILHSSFHES WTLRLCTWLG VGNDPRYTPT TTFETFPFPE GLTPDIPAGD
YADDPRAQAI AKAAKRLDEL RKAWLNPPDL VRIEPEVVPG YPDRILPKDT
KAASELKKRT LTNLYNARPQ WLADAHRDLD AAVAAAYGWP ADITEDDALA
KLLELNLSRA GASSPPPANK DEG

FIG. 38-1

RpaBSI

| RECOGNITION SEQUENCE | POSITION 3 DETERMINANTS | POSITION 4 DETERMINANTS | POSITION 6 DETERMINANTS | POSITION 0 DETERMINANTS |
|---|---|---|---|---|
| CGRCAAC | 845E + 863N | 864A + 900R +899P | 896E + 898R | |
| CGRCAAG | 845E + 863N | 864A + 900R +899P | 896K + 898D | |
| CGRCAAR | 845E + 863N | 864A + 900R +899P | 896D + 898D | |
| CGRCAAN | 845E + 863N | 864A + 900R +899P | 896W + 898A | |
| CGRCCAC | 845E + 863N | 864K + 900S | 896E + 898R | |
| CGRCCAG | 845E + 863N | 864K + 900S | 896K + 898D | |
| CGRCCAR | 845E + 863N | 864K + 900S | 896D + 898D | |
| CGRCCAN | 845E + 863N | 864K + 900S | 896W + 898A | |
| CGRCGAC | 845E + 863N | 864L + 900R | 896E + 898R | |
| CGRCGAG | 845E + 863N | 864L + 900R | 896K + 898D | |
| CGRCGAR | 845E + 863N | 864L + 900R | 896D + 898D | |
| CGRCGAN | 845E + 863N | 864L + 900R | 896W + 898A | |
| CGRCRAC | 845E + 863N | 864A + 900R +899F | 896E + 898R | |
| CGRCRAG | 845E + 863N | 864A + 900R +899F | 896K + 898D | |
| CGRCRAR | 845E + 863N | 864A + 900R +899F | 896D + 898D | |
| CGRCRAN | 845E + 863N | 864A + 900R +899F | 896W + 898A | |
| CGRCNAC | 845E + 863N | 864G + 900M | 896E + 898R | |
| CGRCNAG | 845E + 863N | 864G + 900M | 896K + 898D | |
| CGRCNAR | 845E + 863N | 864G + 900M | 896D + 898D | |
| CGRCNAN | 845E + 863N | 864G + 900M | 896W + 898A | |
| CGRGAAC | 845R + 863D | 864A + 900R +899P | 896E + 898R | |
| CGRGAAG | 845R + 863D | 864A + 900R +899P | 896K + 898D | |
| CGRGAAR | 845R + 863D | 864A + 900R +899P | 896D + 898D | |
| CGRGAAN | 845R + 863D | 864A + 900R +899P | 896W + 898A | |
| CGRGCAC | 845R + 863D | 864K + 900S | 896E + 898R | |
| CGRGCAG | 845R + 863D | 864K + 900S | 896K + 898D | |
| CGRGCAR | 845R + 863D | 864K + 900S | 896D + 898D | |
| CGRGCAN | 845R + 863D | 864K + 900S | 896W + 898A | |
| CGRGGAC | 845R + 863D | 864L + 900R | 896E + 898R | |
| CGRGGAG | 845R + 863D | 864L + 900R | 896K + 898D | |
| CGRGGAR | 845R + 863D | 864L + 900R | 896D + 898D | |
| CGRGGAN | 845R + 863D | 864L + 900R | 896W + 898A | |
| CGRGRAC | 845R + 863D | 864A + 900R +899F | 896E + 898R | |
| CGRGRAG | 845R + 863D | 864A + 900R +899F | 896K + 898D | |
| CGRGRAR | 845R + 863D | 864A + 900R +899F | 896D + 898D | |
| CGRGRAN | 845R + 863D | 864A + 900R +899F | 896W + 898A | |
| CGRGNAC | 845R + 863D | 864G + 900M | 896E + 898R | |
| CGRGNAG | 845R + 863D | 864G + 900M | 896K + 898D | |
| CGRGNAR | 845R + 863D | 864G + 900M | 896D + 898D | |
| CGRGNAN | 845R + 863D | 864G + 900M | 896W + 898A | |

FIG. 38-2

RpaBSI

| RECOGNITION SEQUENCE | POSITION 3 DETERMINANTS | POSITION 4 DETERMINANTS | POSITION 6 DETERMINANTS | POSITION 0 DETERMINANTS |
|---|---|---|---|---|
| CGRTAAC | 845K + 863Q | 864A + 900R +899P | 896E + 898R | |
| CGRTAAG | 845K + 863Q | 864A + 900R +899P | 896K + 898D | |
| CGRTAAR | 845K + 863Q | 864A + 900R +899P | 896D + 898D | |
| CGRTAAN | 845K + 863Q | 864A + 900R +899P | 896W + 898A | |
| CGRTCAC | 845K + 863Q | 864K + 900S | 896E + 898R | |
| CGRTCAG | 845K + 863Q | 864K + 900S | 896K + 898D | |
| CGRTCAR | 845K + 863Q | 864K + 900S | 896D + 898D | |
| CGRTCAN | 845K + 863Q | 864K + 900S | 896W + 898A | |
| CGRTGAC | 845K + 863Q | 864L + 900R | 896E + 898R | |
| CGRTGAG | 845K + 863Q | 864L + 900R | 896K + 898D | |
| CGRTGAR | 845K + 863Q | 864L + 900R | 896D + 898D | |
| CGRTGAN | 845K + 863Q | 864L + 900R | 896W + 898A | |
| CGRTRAC | 845K + 863Q | 864A + 900R +899F | 896E + 898R | |
| CGRTRAG | 845K + 863Q | 864A + 900R +899F | 896K + 898D | |
| CGRTRAR | 845K + 863Q | 864A + 900R +899F | 896D + 898D | |
| CGRTRAN | 845K + 863Q | 864A + 900R +899F | 896W + 898A | |
| CGRTNAC | 845K + 863Q | 864G + 900M | 896E + 898R | |
| CGRTNAG | 845K + 863Q | 864G + 900M | 896K + 898D | |
| CGRTNAR | 845K + 863Q | 864G + 900M | 896D + 898D | |
| CGRTNAN | 845K + 863Q | 864G + 900M | 896W + 898A | |
| CGRYAAC | 845V + 863N | 864A + 900R +899P | 896E + 898R | |
| CGRYAAG | 845V + 863N | 864A + 900R +899P | 896K + 898D | |
| CGRYAAR | 845V + 863N | 864A + 900R +899P | 896D + 898D | |
| CGRYAAN | 845V + 863N | 864A + 900R +899P | 896W + 898A | |
| CGRYCAC | 845V + 863N | 864K + 900S | 896E + 898R | |
| CGRYCAG | 845V + 863N | 864K + 900S | 896K + 898D | |
| CGRYCAR | 845V + 863N | 864K + 900S | 896D + 898D | |
| CGRYCAN | 845V + 863N | 864K + 900S | 896W + 898A | |
| CGRYGAC | 845V + 863N | 864L + 900R | 896E + 898R | |
| CGRYGAG | 845V + 863N | 864L + 900R | 896K + 898D | |
| CGRYGAR | 845V + 863N | 864L + 900R | 896D + 898D | |
| CGRYGAN | 845V + 863N | 864L + 900R | 896W + 898A | |
| CGRYRAC | 845V + 863N | 864A + 900R +899F | 896E + 898R | |
| CGRYRAG | 845V + 863N | 864A + 900R +899F | 896K + 898D | |
| CGRYRAR | 845V + 863N | 864A + 900R +899F | 896D + 898D | |
| CGRYRAN | 845V + 863N | 864A + 900R +899F | 896W + 898A | |
| CGRYNAC | 845V + 863N | 864G + 900M | 896E + 898R | |
| CGRYNAG | 845V + 863N | 864G + 900M | 896K + 898D | |
| CGRYNAR | 845V + 863N | 864G + 900M | 896D + 898D | |
| CGRYNAN | 845V + 863N | 864G + 900M | 896W + 898A | |

FIG. 38-3

RpaBSI

| RECOGNITION SEQUENCE | POSITION 3 DETERMINANTS | POSITION 4 DETERMINANTS | POSITION 6 DETERMINANTS | POSITION 0 DETERMINANTS |
|---|---|---|---|---|
| GGRCAAC | 845E + 863N | 864A + 900R +899P | 896E + 898R | 813D + 825R |
| GGRCAAG | 845E + 863N | 864A + 900R +899P | 896K + 898D | 813D + 825R |
| GGRCAAR | 845E + 863N | 864A + 900R +899P | 896D + 898D | 813D + 825R |
| GGRCAAN | 845E + 863N | 864A + 900R +899P | 896W + 898A | 813D + 825R |
| GGRCCAC | 845E + 863N | 864K + 900S | 896E + 898R | 813D + 825R |
| GGRCCAG | 845E + 863N | 864K + 900S | 896K + 898D | 813D + 825R |
| GGRCCAR | 845E + 863N | 864K + 900S | 896D + 898D | 813D + 825R |
| GGRCCAN | 845E + 863N | 864K + 900S | 896W + 898A | 813D + 825R |
| GGRCGAC | 845E + 863N | 864L + 900R | 896E + 898R | 813D + 825R |
| GGRCGAG | 845E + 863N | 864L + 900R | 896K + 898D | 813D + 825R |
| GGRCGAR | 845E + 863N | 864L + 900R | 896D + 898D | 813D + 825R |
| GGRCGAN | 845E + 863N | 864L + 900R | 896W + 898A | 813D + 825R |
| GGRCRAC | 845E + 863N | 864A + 900R +899F | 896E + 898R | 813D + 825R |
| GGRCRAG | 845E + 863N | 864A + 900R +899F | 896K + 898D | 813D + 825R |
| GGRCRAR | 845E + 863N | 864A + 900R +899F | 896D + 898D | 813D + 825R |
| GGRCRAN | 845E + 863N | 864A + 900R +899F | 896W + 898A | 813D + 825R |
| GGRCNAC | 845E + 863N | 864G + 900M | 896E + 898R | 813D + 825R |
| GGRCNAG | 845E + 863N | 864G + 900M | 896K + 898D | 813D + 825R |
| GGRCNAR | 845E + 863N | 864G + 900M | 896D + 898D | 813D + 825R |
| GGRCNAN | 845E + 863N | 864G + 900M | 896W + 898A | 813D + 825R |
| GGRGAAC | 845R + 863D | 864A + 900R +899P | 896E + 898R | 813D + 825R |
| GGRGAAG | 845R + 863D | 864A + 900R +899P | 896K + 898D | 813D + 825R |
| GGRGAAR | 845R + 863D | 864A + 900R +899P | 896D + 898D | 813D + 825R |
| GGRGAAN | 845R + 863D | 864A + 900R +899P | 896W + 898A | 813D + 825R |
| GGRGCAC | 845R + 863D | 864K + 900S | 896E + 898R | 813D + 825R |
| GGRGCAG | 845R + 863D | 864K + 900S | 896K + 898D | 813D + 825R |
| GGRGCAR | 845R + 863D | 864K + 900S | 896D + 898D | 813D + 825R |
| GGRGCAN | 845R + 863D | 864K + 900S | 896W + 898A | 813D + 825R |
| GGRGGAC | 845R + 863D | 864L + 900R | 896E + 898R | 813D + 825R |
| GGRGGAG | 845R + 863D | 864L + 900R | 896K + 898D | 813D + 825R |
| GGRGGAR | 845R + 863D | 864L + 900R | 896D + 898D | 813D + 825R |
| GGRGGAN | 845R + 863D | 864L + 900R | 896W + 898A | 813D + 825R |
| GGRGRAC | 845R + 863D | 864A + 900R +899F | 896E + 898R | 813D + 825R |
| GGRGRAG | 845R + 863D | 864A + 900R +899F | 896K + 898D | 813D + 825R |
| GGRGRAR | 845R + 863D | 864A + 900R +899F | 896D + 898D | 813D + 825R |
| GGRGRAN | 845R + 863D | 864A + 900R +899F | 896W + 898A | 813D + 825R |
| GGRGNAC | 845R + 863D | 864G + 900M | 896E + 898R | 813D + 825R |
| GGRGNAG | 845R + 863D | 864G + 900M | 896K + 898D | 813D + 825R |
| GGRGNAR | 845R + 863D | 864G + 900M | 896D + 898D | 813D + 825R |
| GGRGNAN | 845R + 863D | 864G + 900M | 896W + 898A | 813D + 825R |

FIG. 38-4

RpaBSI

| RECOGNITION SEQUENCE | POSITION 3 DETERMINANTS | POSITION 4 DETERMINANTS | POSITION 6 DETERMINANTS | POSITION 0 DETERMINANTS |
|---|---|---|---|---|
| GGRTAAC | 845K + 863Q | 864A + 900R +899P | 896E + 898R | 813D + 825R |
| GGRTAAG | 845K + 863Q | 864A + 900R +899P | 896K + 898D | 813D + 825R |
| GGRTAAR | 845K + 863Q | 864A + 900R +899P | 896D + 898D | 813D + 825R |
| GGRTAAN | 845K + 863Q | 864A + 900R +899P | 896W + 898A | 813D + 825R |
| GGRTCAC | 845K + 863Q | 864K + 900S | 896E + 898R | 813D + 825R |
| GGRTCAG | 845K + 863Q | 864K + 900S | 896K + 898D | 813D + 825R |
| GGRTCAR | 845K + 863Q | 864K + 900S | 896D + 898D | 813D + 825R |
| GGRTCAN | 845K + 863Q | 864K + 900S | 896W + 898A | 813D + 825R |
| GGRTGAC | 845K + 863Q | 864L + 900R | 896E + 898R | 813D + 825R |
| GGRTGAG | 845K + 863Q | 864L + 900R | 896K + 898D | 813D + 825R |
| GGRTGAR | 845K + 863Q | 864L + 900R | 896D + 898D | 813D + 825R |
| GGRTGAN | 845K + 863Q | 864L + 900R | 896W + 898A | 813D + 825R |
| GGRTRAC | 845K + 863Q | 864A + 900R +899F | 896E + 898R | 813D + 825R |
| GGRTRAG | 845K + 863Q | 864A + 900R +899F | 896K + 898D | 813D + 825R |
| GGRTRAR | 845K + 863Q | 864A + 900R +899F | 896D + 898D | 813D + 825R |
| GGRTRAN | 845K + 863Q | 864A + 900R +899F | 896W + 898A | 813D + 825R |
| GGRTNAC | 845K + 863Q | 864G + 900M | 896E + 898R | 813D + 825R |
| GGRTNAG | 845K + 863Q | 864G + 900M | 896K + 898D | 813D + 825R |
| GGRTNAR | 845K + 863Q | 864G + 900M | 896D + 898D | 813D + 825R |
| GGRTNAN | 845K + 863Q | 864G + 900M | 896W + 898A | 813D + 825R |
| GGRYAAC | 845V + 863N | 864A + 900R +899P | 896E + 898R | 813D + 825R |
| GGRYAAG | 845V + 863N | 864A + 900R +899P | 896K + 898D | 813D + 825R |
| GGRYAAR | 845V + 863N | 864A + 900R +899P | 896D + 898D | 813D + 825R |
| GGRYAAN | 845V + 863N | 864A + 900R +899P | 896W + 898A | 813D + 825R |
| GGRYCAC | 845V + 863N | 864K + 900S | 896E + 898R | 813D + 825R |
| GGRYCAG | 845V + 863N | 864K + 900S | 896K + 898D | 813D + 825R |
| GGRYCAR | 845V + 863N | 864K + 900S | 896D + 898D | 813D + 825R |
| GGRYCAN | 845V + 863N | 864K + 900S | 896W + 898A | 813D + 825R |
| GGRYGAC | 845V + 863N | 864L + 900R | 896E + 898R | 813D + 825R |
| GGRYGAG | 845V + 863N | 864L + 900R | 896K + 898D | 813D + 825R |
| GGRYGAR | 845V + 863N | 864L + 900R | 896D + 898D | 813D + 825R |
| GGRYGAN | 845V + 863N | 864L + 900R | 896W + 898A | 813D + 825R |
| GGRYRAC | 845V + 863N | 864A + 900R +899F | 896E + 898R | 813D + 825R |
| GGRYRAG | 845V + 863N | 864A + 900R +899F | 896K + 898D | 813D + 825R |
| GGRYRAR | 845V + 863N | 864A + 900R +899F | 896D + 898D | 813D + 825R |
| GGRYRAN | 845V + 863N | 864A + 900R +899F | 896W + 898A | 813D + 825R |
| GGRYNAC | 845V + 863N | 864G + 900M | 896E + 898R | 813D + 825R |
| GGRYNAG | 845V + 863N | 864G + 900M | 896K + 898D | 813D + 825R |
| GGRYNAR | 845V + 863N | 864G + 900M | 896D + 898D | 813D + 825R |
| GGRYNAN | 845V + 863N | 864G + 900M | 896W + 898A | 813D + 825R |

SYNTHETIC BINDING PROTEINS

CROSS REFERENCE

This is a continuation-in-part application of U.S. patent application Ser. No. 12/143,498 filed Jun. 20, 2008 now abandoned, which claims priority from U.S. provisional application Ser. No. 60/936,504 filed Jun. 20, 2007, herein incorporated by reference.

BACKGROUND

A long standing goal of molecular biotechnology has been the ability to design and generate DNA binding proteins that specifically bind at a DNA sequence of choice, rather than rely on the limited set of DNA sequences bound by those proteins identified from nature. To this end, the structures of a number of DNA binding proteins complexed with their DNA target sequence have been determined by crystallography (Lukacs, et al. *Nat. Struct. Biol.* 7: 134-140 (2000) and the amino acid residues conferring specific DNA base recognition have been determined (Pingoud, et al. *Nucleic Acids Res.* 29:3705-3727 (2001)). However, to date, rational design experiments in which specific amino acid residues are altered to form DNA binding proteins having new, predetermined specificities have been unsuccessful. For example, attempts to generate restriction endonucleases with new DNA recognition specificities have not achieved their desired goals. As a result, methods have been designed that depend on random alteration of a DNA binding protein, followed by a selection from the pool of randomly altered proteins for those proteins that may bind a differing DNA sequence. Often such attempts result in proteins that bind a relaxed specificity relative to the starting protein or have lowered specificity toward their target DNA binding sequence as compared with similar, non-target DNA sequences.

Nonetheless, an effective method of rational design of binding proteins would permit the expansion of the number of unique recognition sequences that could be bound and acted upon to generate a biological event.

SUMMARY

Embodiments of the invention provide a method for identifying relationships between selected amino acid residues at specific positions in a binding protein and a module in a recognition sequence to which the binding protein binds. The method involves creating a set of binding proteins using an initial binding protein to query a database in a BLAST search. The properties of each binding protein includes a defined amino acid sequence, the amino acid sequences in the set sharing an expectation value (E) of less than e-20 for sequences of more than 200 amino acids or less than e-10 for sequences of less than 200 amino acids in the BLAST search results. The binding proteins additionally bind to specific target recognition sequences in a substrate that contain position-specific modules. The method further includes aligning the amino acid sequences in the set of proteins. The target recognition sequences recognized by the binding proteins in the set are also aligned where this may occur by means of a position dependent feature in the specific target recognition sequence. Correlations between the aligned position-specific modules in the recognition sequences and one or more position-specific amino acids in the aligned amino acid sequences of the binding proteins are identified.

In an additional embodiment of the invention, a method is provided for expanding the set of binding proteins by using a member of the set of binding proteins to query a database in an additional BLAST search.

In an additional embodiment of the invention, a method is provided for identifying the type and location of an amino acid residue or amino acid residues in a plurality of the binding proteins in the set that determines recognition of one or more position-specific modules in the recognition sequence. The type and location of amino acid residue may be recorded in a catalog along with the association with one or more position-specific modules in one or more aligned recognition sequences of the set of binding proteins. This catalog may be used to rationally modify the amino acid sequence of the aligned binding proteins to recognize an altered specific target recognition sequence. Rational modification of the amino acid sequences may be achieved by mutating non-randomly one or more amino acids at correlated positions in a single binding protein to cause a predictable change in the specific target recognition sequence of the binding protein.

In an additional embodiment of the invention, a method is provided wherein a binding protein member of the set has a known amino acid sequence but an uncharacterized specific target recognition sequence. The method involves the steps of identifying position-specific modules in the recognition sequence by (i) reviewing the alignment of the amino acid sequence of the binding protein member in the aligned set of binding proteins; (ii) reading out amino acid residues at the positions recorded in the catalog; and (iii) comparing the amino acid residues in the binding protein member to the amino acid residues recorded in the catalog so as to determine the specific target recognition sequence of the binding protein member.

In an additional embodiment, each position-specific module is one or more nucleotides in a DNA substrate. Additionally, the set of binding proteins may be a set of DNA binding proteins such as MmeI-like proteins.

In an additional embodiment of the invention, a method is provided for altering the DNA recognition sequence of an MmeI-like DNA binding protein by changing the amino acid residues at a predetermined position or positions in the amino acid sequence of MmeI or an equivalent aligned position or positions in an MmeI-like DNA binding protein. An example of predetermined positions as targets of amino acid modification in Mme I binding protein are any of positions 751+773, 806+808, 774+810, 774, 774+810+809 and 809. Changes in these predetermined positions may further comprise a change in one or more of the nucleotides recognized at one or more of positions at 3, 4 and 6 of the DNA recognition sequence.

An embodiment of the invention provides a method for generating a binding protein, which recognizes a rationally chosen recognition sequence that includes substituting a first amino acid with a second amino acid using site-directed mutagenesis of a member protein of a set of proteins at an identified position or positions correlated with recognition of a chosen specified target module.

An embodiment of the invention provides a method of automating the above that includes: storing amino acid sequences for the binding proteins in a database in a computer-readable memory and performing one or more of the above steps by executing instructions stored in a computer. More particularly, a method is provided for automating one or more functions described in FIG. 25A in boxes 1, 2, 3, 4, 6, and 7B. An additional method is provided for automating one or more steps in FIG. 25B such that steps requiring wet chemistry are performed by a device capable of performing wet chemistry that is linked to a computer.

An embodiment of the invention provides a composition of an MmeI-like enzyme having a mutation resulting in at least one altered amino acid residue at a predetermined position that has a specificity for a DNA recognition sequence that is different by at least one base compared with the DNA recognition sequence of the unaltered enzyme. The difference in at least one base may be a difference in length of the recognition sequence that corresponds to an addition or deletion of a nucleotide from the recognition sequence or corresponds to an alternative recognized nucleotide at a specific position.

An embodiment of the invention provides a system that includes a memory for storing instructions and a computer for executing the instructions, which when executed create a set of binding proteins using an initial binding protein to query a database in a BLAST search, wherein each binding protein has a defined amino acid sequence, the amino acid sequences sharing an expectation value (E) of less than e-20 for sequences of more than 200 amino acids or less than e-10 for sequences of less than 200 amino acids; the binding proteins binding to specific target recognition sequences in a substrate, the target recognition sequences containing position-specific modules. The system may additionally include instructions, which when executed align the specific target recognition sequences recognized by the binding proteins; and align the amino acid sequences of the binding proteins of the set. The system may additionally include instructions which when executed identify correlations between the aligned position-specific modules in the recognition sequences and one or more position-specific amino acids in the aligned amino acid sequences of the binding proteins. The system may further include a means for receiving data from a device for protein synthesis and protein binding analysis and containing instructions, which when executed use the data to validate the correlations by confirming a prediction of binding to a predetermined recognition sequence by a mutated protein; and organize the data into a catalog of validated amino acid or amino acids at identified positions that determine recognition for a position and type of module in the recognition sequence.

In another embodiment of the invention, a system is provided which has a memory for storing instructions and a computer for executing the instructions, which when executed, (a) collect and align a sorted set of amino acid sequences of binding proteins in a first database, and collect and align a sorted set of recognition sequences for at least a subset of the binding proteins in a second database, wherein the first database is obtained from an automated search of a third database of amino acid or nucleotide sequences; (b) identify correlations between amino acids at selected aligned positions in the set of amino acid sequences and modules at selected aligned positions of modules in the recognition sequences; (c) from an instrument for protein synthesis and protein binding analysis receive data on the correlations for using the data to validate the correlations by confirming a prediction of binding to a predetermined recognition sequence by a mutated protein; and (d) organize the data into a catalog of validated amino acid or amino acids at identified positions that determine recognition for a position and type of module in the recognition sequence.

In an additional embodiment of the invention, a system is provided having a memory for storing instructions and a computer for executing the instructions that stores positional information on one or more amino acid residues in a first binding protein for targeted mutation to create a second binding protein having a predicted alteration of a module in a sequence position within a sequence of modules recognized by the protein. An example of such stored instructions is provided in FIG. 7A.

BRIEF DESCRIPTION OF THE DRAWINGS

FIG. 5 shows the cleavage activity of rationally altered Mme3GI enzyme: MmeI E751R+N773D.

FIG. 6 shows the cleavage activity of rationally altered Mme6RI: MmeI E806G+R808G (+S807N).

FIG. 10 shows DNA bases observed at each position in the recognition sequence alignment for the characterized members of the set.

FIG. 10A shows in the left panel the DNA recognition sequence alignment of the characterized members of the set containing MmeI as a member (the MmeI-like set). These recognition sequences include BsbI enzyme, for which the DNA recognition sequence and cutting positions are known, but for which the amino acid sequence has not yet been determined. The right panel shows the count for the various DNA bases, or combination of bases, recognized at each position in the DNA recognition sequence alignment.

FIG. 10B shows in the left panel the alignment of the recognition sequence of 20 members of the MmeI-like set. The right panel is a position-defined base frequency chart showing the DNA bases observed at position 3, 4 or 6 in the recognition sequence alignment for the characterized members of the set. Nineteen of twenty enzymes recognize G or C at the sixth position.

FIG. 11A shows a partial code for the amino acids correlated with DNA base recognition at position 0, 3, 4 or 6 in the recognition sequence alignment. For example, to alter recognition at position 6 of the aligned recognition sequences in a member of the set, the positions in the amino acid sequence alignment corresponding to MmeI E806 and R808 are the targets for mutating the amino acid to one of the coded alternative amino acid residues to redesign DNA base recognition. For example, inserting the code E+R into a member of the MmeI-like set at these aligned positions would cause the enzyme to recognize a C base at position 6 of that enzyme's recognition sequence. The code can be expanded as the members of the set increase, and their amino acid substitutions are tested for changes in DNA recognition sequence specificities. In another example, in position 0, recognition corresponding to positions 790 (R) and 802(E) in GauT27I determines whether DNA base C or G is recognized FIG. 11B shows the identified positions within the aligned amino acid sequences (SEQ ID NOS:64-82), and the amino acid residues occupying those positions, that determine recognition at position 3, 4 or 6 in the aligned DNA recognition sequences. The number above the alignment indicates the position in the recognition sequence for which that amino acid position determines the DNA base recognized. The enzyme name and the DNA sequence recognized is shown. The number preceding the aligned amino acid sequence indicates the position of the first amino acid residue listed within the amino acid sequence of the enzyme, while the number following the line of amino acid sequence indicates the position of the last amino acid residue listed in the sequence of the enzyme.

FIG. 13 shows the prioritization of correlated positions for alteration. The first priority for alteration to change the specificity of a member of the set are those positions that exhibit a 1:1 correlation between the amino acid residue present at that position in the alignment and the DNA base recognized at the position in the recognition sequence alignment being interrogated.

Figure 1A:
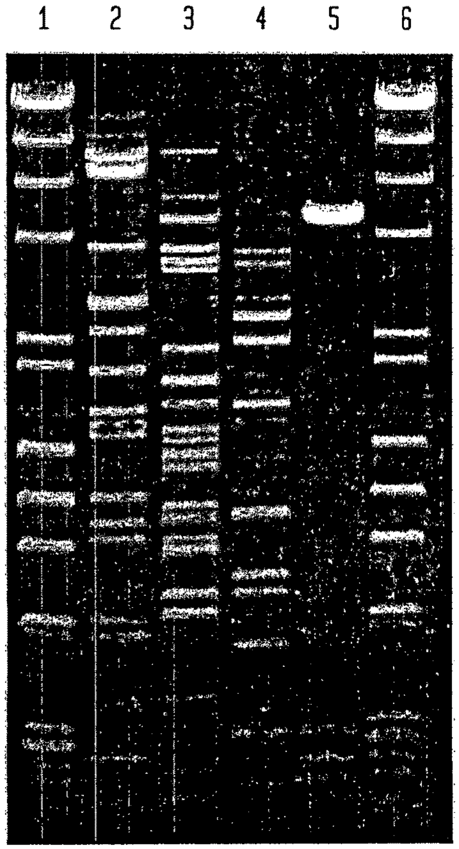
In FIG. 1A, lanes 2-5 show the cleavage pattern produced by the rationally altered MmeI E806K+R808D enzyme on various DNA substrates. The DNA substrate in lane 2 is lambda DNA, in lane 3-T7 DNA, in lane 4-T3 DNA and in lane 5-pBC4 DNA. Lanes 1 and 6 are Lambda-HindIII+PhiX174-HaeIII size standards.
Figure 1B:
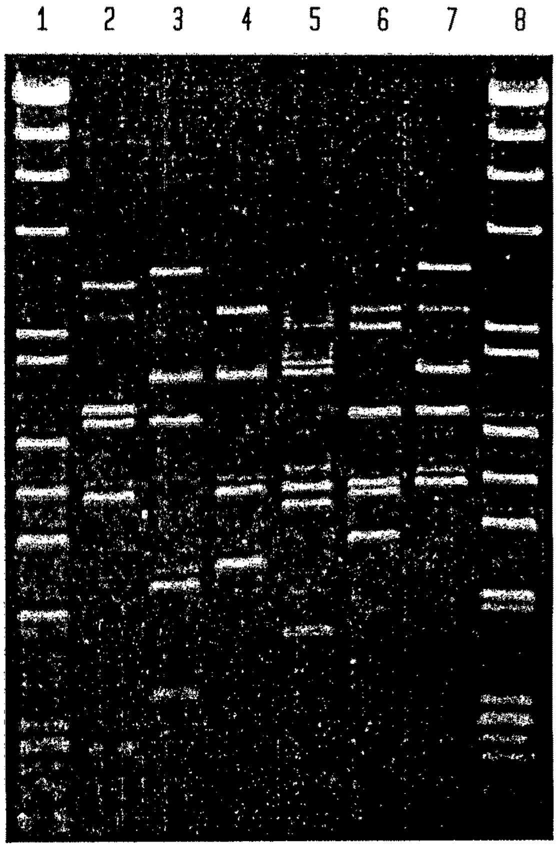
In FIG. 1B, lanes 2-7 show mapping of the cleavage activity of rationally altered MmeI E806K+R808D on pBR322 DNA. Lanes 2-7 are pBR322 DNA cut with the rationally altered MmeI E806K+R808D enzyme plus the following single site enzymes: lane 2-EcoRI, lane 3-NruI, lane 4-PvuII, lane 5-NdeI, lane 6-PstI, and lane 7-rationally altered MmeI only. Lanes 1 and 8 are Lambda-HindIII+PhiX174-HaeIII size standards.
Figure 1C:
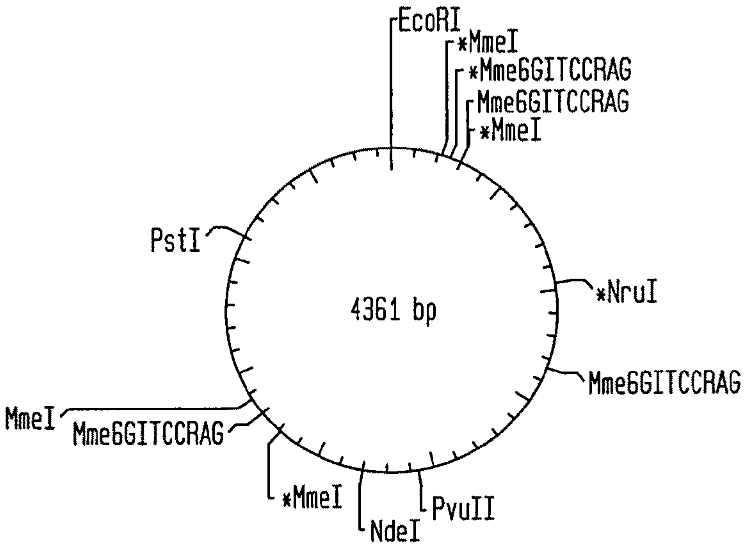
In FIG. 1C, the panel shows the location of the wild type MmeI sites, TCCRAC, and of the rationally altered MmeI E806K+R808D sites, TCCRAG, in pBR322 DNA, along with the locations of the enzymes used for mapping.

The top panel shows the amino acid sequence alignment of SEQ ID NOS:132-150) that is ordered with respect to position 6 of the recognition sequence alignment, in which the residues at the aligned position encompassing MmeI R808 (indicated by the arrow) are correlated one to one with the DNA base recognized at position 6. At this position all enzymes that recognize C, cytosine, have an arginine residue, R, and all enzymes that recognize a G, guanine, have an aspartate residue, D.

The lower panel has two arrows, one to identify the 1:1 correlating position described above, and the second to indicate the second highest scoring position. This second position, while not correlating 1:1, is still statistically significantly correlated with recognition of the DNA base at position 6, as exemplified in FIG. 14. In addition, the amino acid residue at this position co-varies with the residue at the 1:1 correlating position described above in 7 of 8 enzymes that recognize C and 9 of 10 enzymes that recognize G, indicating this position is likely to be partnering with the 1:1 correlating position to recognize the base position in question. This position becomes the second highest priority for change, and may be rationally altered together with the first highest priority position to effect the desired alteration in DNA recognition specificity.

FIG. 14 shows a Chi square calculation for one position in the amino acid alignment that correlates with recognition of the base at position 6 of the aligned recognition sequences. For the Chi square calculation a table is formed consisting of a row for each different DNA base recognized at the position in the recognition sequence alignment under investigation, and a column for each amino acid residue present at the given position in the amino acid sequence alignment. Here such a table consists of three rows, one each for the DNA base patterns, C, G and R, recognized at position 6 of the recognition sequence alignment, and of five columns, one each for the amino acid residues present at the position interrogated in the amino acid sequence alignment. The position interrogated is that which aligns with MmeI position E806. The count of the amino acid residues present at this position is shown. The calculated Chi square value for the table is 38. There are 8 degrees of freedom in the table. The resulting probability value, P, is 0.0001, which is less than the cut off for significance of 0.05. The result indicates this amino acid position is significantly correlated with recognition of the DNA base at position 6 of the DNA recognition sequence alignment.

FIG. 15 shows correlations between aligned DNA recognition sequences at position 6 and two positions in the amino acid sequence alignment.

In the left panel, the aligned DNA recognition sites are grouped into the 9 enzymes, which have a C at position 6, followed by the 10 enzymes, which have a G at this position, followed by the one enzyme that has an R at this position.

In the right panel, a portion of the amino acid sequence for nineteen enzymes from the MmeI-like set is aligned to reveal a region where a correlation is observed between the DNA base recognized at position 6 and the amino acid residue(s) present in the aligned protein sequences. Arrows indicate the two correlating amino acid positions identified. They correspond to E806 and R808 of MmeI. At position R808 of the gapped alignment shown there is a 1:1 correspondence between the amino acid and the DNA base recognized in position 6, such that whenever an enzyme recognizes a C base there is an arginine, R, at this position, while those enzymes recognizing a G base have an aspartic acid residue, D, at this position. The enzyme recognizing R, which is G or A, also has an aspartate, D, at this position. The E806 position does not have complete 1:1 correspondence, due to the biological flexibility allowing more than one amino acid residue to partner with either the arginine of position R808 to recognize a C base, in this case either E, glutamic acid or T, threonine, or with the aspartic acid residue of position R808 to recognize a G base, here either a K, lysine or a G, glycine, or with the arginine of position R808 to recognize R (A or G), which here is a D residue. There is also a three amino acid residue insertion just preceding this aspartic acid residue in the enzyme recognizing R, PspOMII.

FIGS. 16-1, 16-2 and 16-3 show that the set of sequences may be enlarged through a BLAST search initiated from previously identified members of the set. Here, the SpoDI amino acid sequence was used as the query.

The results of a BLAST search demonstrate that a member of the set of related proteins identified through the initial BLAST search can be used as the query sequence for a subsequent BLAST search. In this case a sequence identified in a BLAST search starting with MmeI as the query, ref|YP_167160.1 “hypothetical protein SPO1926,” was used as the query to perform a subsequent BLAST search. The default parameters of the blastp program at the ncbi BLAST server were used: www.ncbi.nlm.nih.gov/BLAST. Use of a different member of the set as the BLAST query resulted in identification of several additional members of the set. For example, the ref|YP_511167.1 "hypothetical protein Jann_3225" sequence was excluded from the set by the stringent threshold of E<e-20 when the search was initiated using the MmeI sequence (E=5e-17, FIGS. 18-1, 18-2 and 18-3), but this Jann_3225 sequence is shown to be a member of the set when the BLAST search is made using as query the "SPO1926" member of the set, for in this case the Expectation value returned is E=3e-65. The set may be enlarged by searches in which the various members of the set serve as the query sequence. Because the Expectation value cut off is stringent, the set will not be enlarged unendingly, but will merely expand to encompass more members of the related set than may be found by searching from a single starting sequence.

FIG. 17 shows a DNA base recognition table listing the 15 different DNA bases or combinations of DNA bases that may be recognized at any given position within a DNA recognition sequence.

FIGS. 18-1, 18-2 and 18-3 show the BLAST search results identifying a set of sequences highly similar to MmeI when the MmeI amino acid sequence was used a the query.

The default parameters of the blastp program at the ncbi BLAST server www.ncbi.nlm.nih.gov/BLAST/. Ninety-seven protein sequences are identified that have Expectation Values, E, of E<e-20. One such sequence, ref|YP_167160.1 "hypothetical protein SPO1926," returns an E value in this search of E=6e-47. As an example, this member of the set may be used in a subsequent BLAST search to enlarge the set of related proteins. Such a search may enlarge the set by identifying proteins that are related to the family as a whole, but which happen to be just distant enough from the sequence used for the first BLAST search that they return Expectation values just outside of the cut off threshold in the initial search. Such a sequence, ref|YP_511167.1 "hypothetical protein Jann_3225," that falls just outside of the cut off threshold in the search using the MmeI amino acid sequence, but that is included in the set (FIGS. 16-1, 16-2 an 16-3) when enlarged by a search using a different member of the set, the "SPO1926" sequence, is underlined.

FIG. 19 shows the alignment of DNA recognition sequences recognized by 20 characterized members of the MmeI-like set of related DNA binding proteins. The alignment was made in relation to a common function. The single strand chosen for alignment from the double stranded DNA that is recognized by the enzyme is the strand that is cut 3' to the recognition sequence. The alignment is then anchored about the common adenine base at position 5 that is functionally conserved, in that it is the base modified by the methyltransferase activity of the enzymes.

Figure 25A:
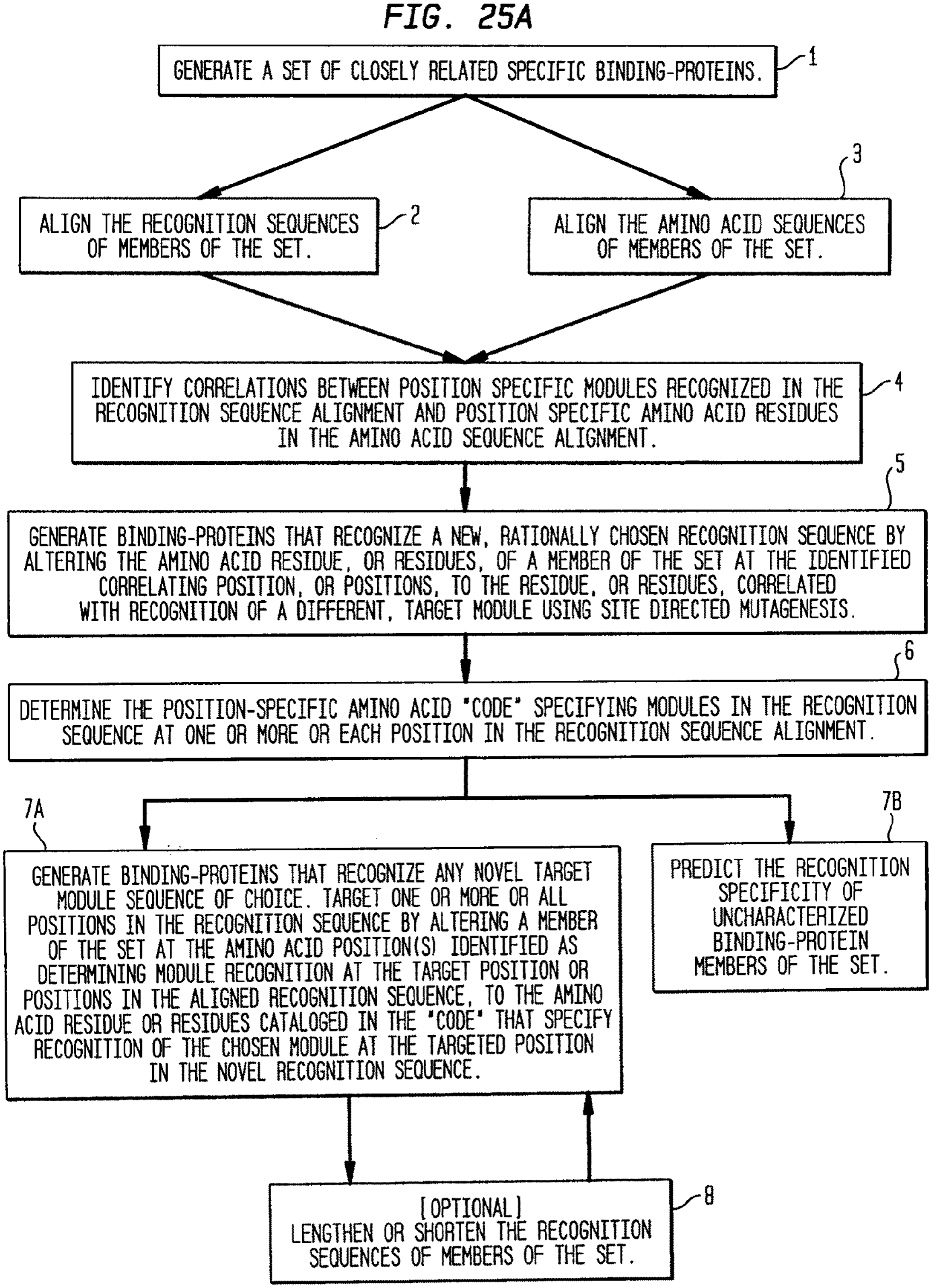
Figures 1, 25B:
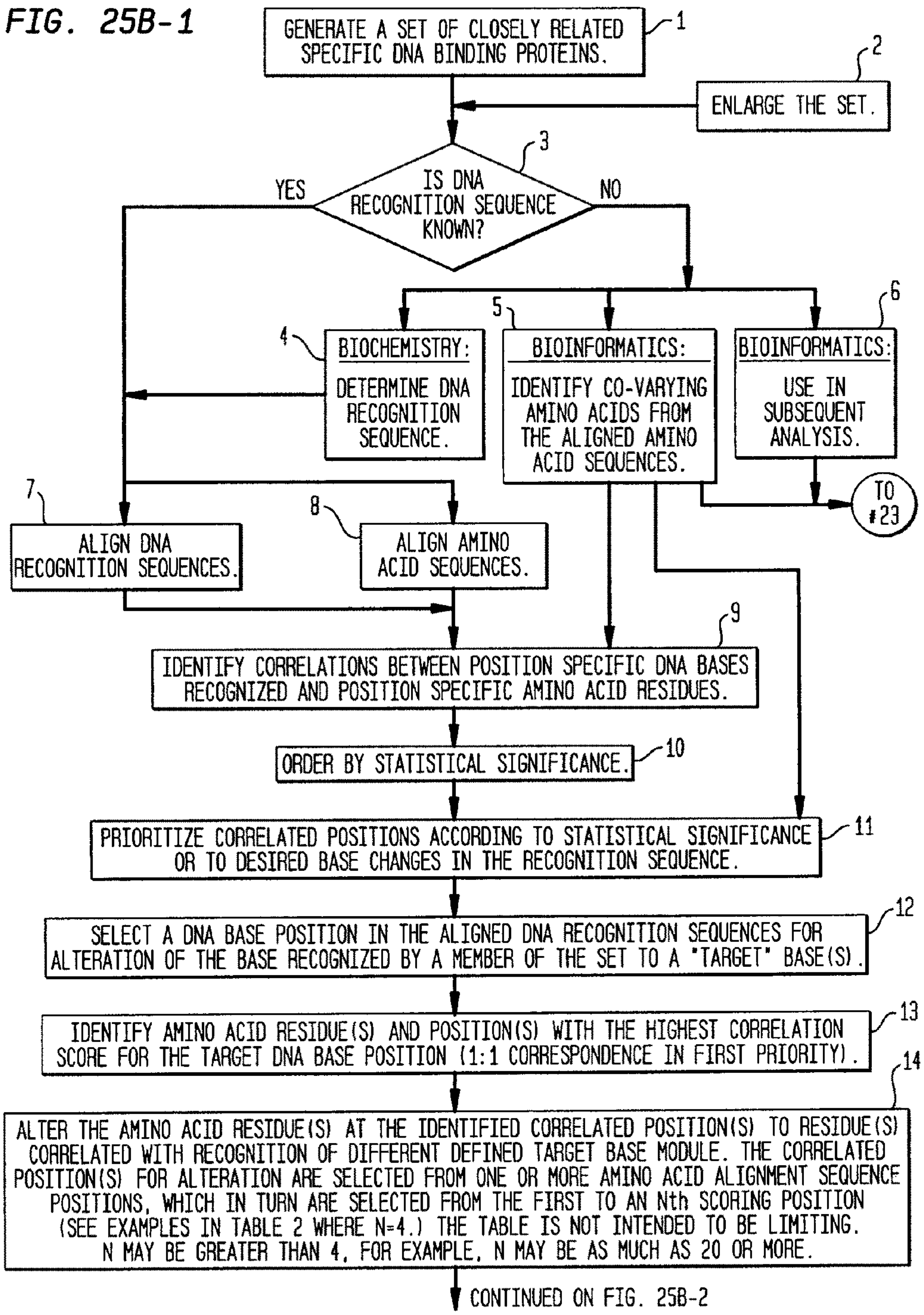
FIG. 1 shows the cleavage activity of rationally altered MmeI E806K+R808D.
Figures 2, 25B:
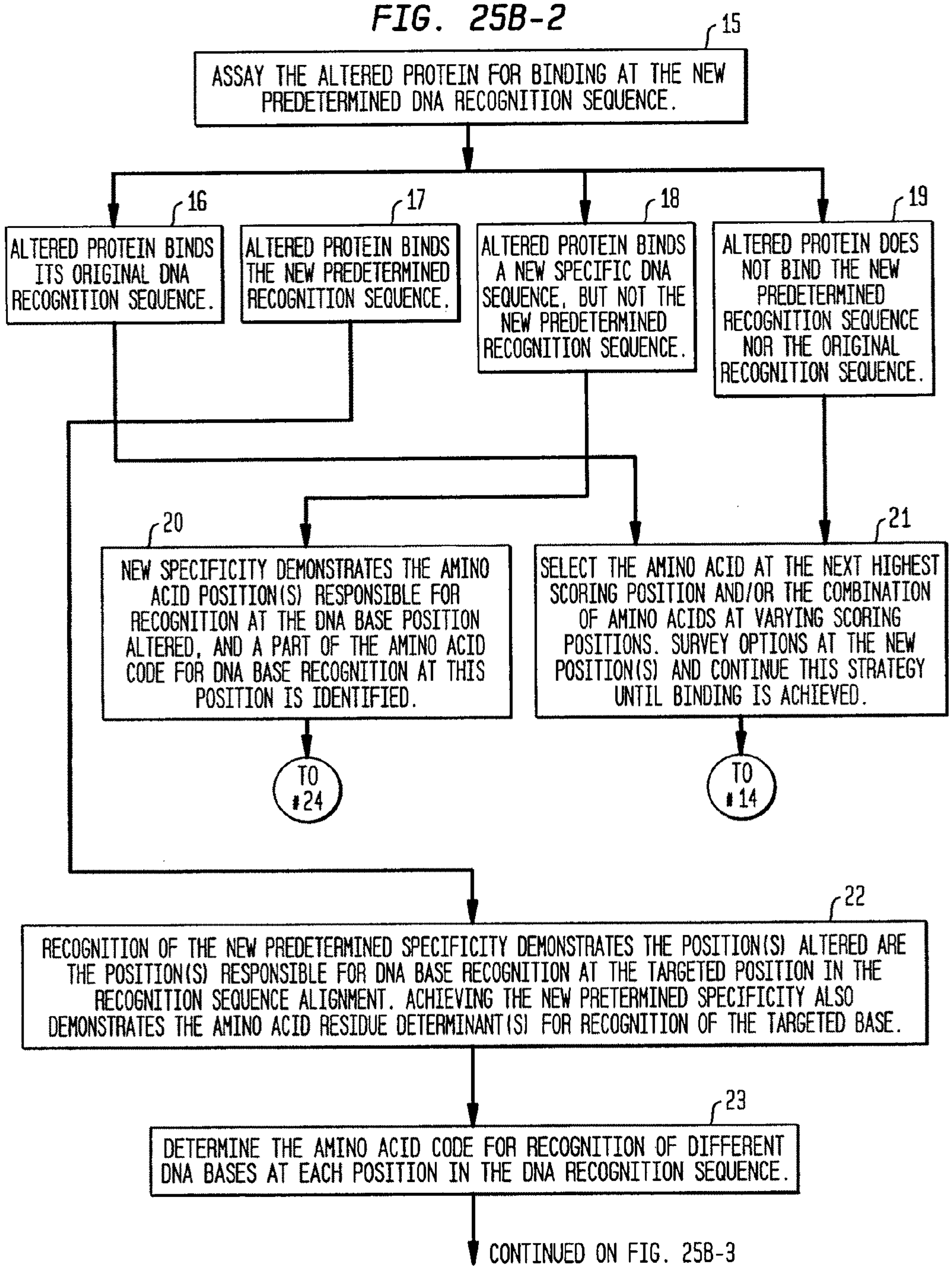

FIGS. 20-1 to 20-11 show an amino acid sequence alignment of SEQ ID NOS:42, 6, 10, 4, 2, 40, 8, 14, 18, 12, 16, 26, 34, 38, 36, 20, 44, 24, and 22, formed using the algorithm PROMALS, for 19 characterized members of the set of related DNA binding proteins whose recognition sequences are shown in FIG. 19.

FIG. 21 shows a Chi square calculation for aligned positions in an amino acid sequence alignment. Chi square value is the sum for all observations (positions in the table) of the: ((observed frequency minus the expected frequency) squared) divided by the expected frequency). A contingency table is constructed where one row is utilized for each DNA base recognized at the position within the DNA recognition sequence alignment being interrogated. The rows are the DNA base observed (Bobs1) through as many different DNA bases as are observed at the position in the recognition sequence alignment being examined. One column is utilized for each amino acid residue observed at the given position in the amino acid sequence alignment being examined. The columns are labeled from the first amino acid residue observed (AA-obs1) through as many different amino acid residues observed at the aligned position.

The observed frequency is the count of amino acid residues at the aligned position for the DNA base recognized. The expected frequency is the sum of the column in which the observation occurs times the sum of the row in which the observation occurs, divided by the total count of all observations.

The table is then populated with the observed counts for the amino acid residues present at the given position in the amino acid sequence alignment, placing the amino acid residue counts within their particular columns in the row corresponding to the DNA base recognized by the binding protein in which that amino acid residue occurs.

The Chi square value for the observed counts is calculated from the table. The statistical significance (P-value) of the Chi square value is obtained by comparing the Chi square value to a Chi square statistics table, where the degrees of freedom equal [(the number of columns minus one) times (the number of rows minus 1)]. If the P-value is less than the preset threshold (0.05 is the default), the algorithm reports this amino acid alignment position as significantly correlated to the interrogated position of the DNA recognition sequence.

The analysis is repeated for each position in the DNA recognition alignment together with each position in the amino acid recognition alignment.

FIG. 22 shows identification of a position in an amino acid sequence alignment, and the specific amino acids at that position, that participates in recognition of the third position in the aligned DNA recognition sequences of a set of gamma-class N6A DNA methyltransferases. The figure shows an alignment of the DNA recognition sequences of the members of the set, anchored about the adenine target of methylation at position 5. A portion of the aligned amino acid sequences of the proteins is shown (SEQ ID NOS:83-99). The particular amino acid coordinates for each protein are indicated before and following the sequence for each enzyme. A position in the alignment that correlates significantly with the DNA base recognized by the enzymes at position 3 is indicated by a box and labeled with a "3" above the alignment.

FIGS. 23A-23N show a partial list of enzymes having differing DNA recognition sequences. The position-specific amino acids required to generate these enzymes within the sequence context of the starting enzyme are listed for each recognition sequence. Specifically, the positions within the amino acid sequence of the starting protein and the amino acids required at those positions for recognition of the listed DNA recognition sequence are described. To create using chemistry any of the specificities provided in the left column, the columns to the right are consulted and, if an alteration in the amino acid at the listed position is required, this is introduced by rationally altering the starting protein listed at the top of the figure at the specified position. FIGS. 23A-23N provide starting enzymes having the listed recognition sequences: MmeI (SEQ ID NO: 2), NmeAIII (SEQ ID NO: 14), SdeAI (SEQ ID NO: 6), CstMI (SEQ ID NO: 12), ApyPI (SEQ ID NO: 18), PspRI (SEQ ID NO: 10), AquIII, (SEQ ID NO: 42), DrdIV (SEQ ID NO: 36), PspOMII (SEQ ID NO: 34) RpaB5I (SEQ ID NO: 26), MaqI (SEQ ID NO: 38), NhaXI (SEQ ID NO: 24), SpoDI (SEQ ID NO: 20) and AquIV (SEQ ID NO: 44). These enzymes may be modified at the specified positions by a targeted mutation to provide the desired amino acid residues at the specified positions to generate an enzyme recognizing the listed DNA sequence.

FIGS. 24A-1 to 24A-22 and 24B-1 to 24B-10 contain the DNA sequences (SEQ ID NOS:1, 3, 5, 7, 9, 11, 13, 15, 17, 19, 21, 23, 25, 33, 35, 37, 39, 41 and 43) and corresponding amino acid sequences (2, 4, 6, 8, 10, 12, 14, 16, 18, 20, 22, 24, 26, 34, 36, 38, 40, 42 and 44) for the 19 characterized proteins in the MmeI-like set in FIGS. 20-1 to 20-11.

FIGS. 25A and 25B-1 to 25B-5 show a summary flow diagram and a detailed example describing the methods.

FIG. 25A describes the generation of a set of closely related specific binding proteins capable of recognizing localized position-specific defined modules in a specific substrate (recognition sequence) (1) where the module recognition sequences of members of the set are aligned (2) and the amino acid sequences of the members of the set are separately aligned (3). Correlations are identified between position-specific modules in the recognition sequence alignment and position-specific amino acid residues in the amino acid sequence alignment (4). Binding proteins are generated that recognize new rationally chosen module sequences by altering amino acid residue(s) of a member of the set at the identified correlating position(s) to the residue(s) correlated with recognition of a different target module using site-directed mutagenesis (5). The ability to create a specific amino acid "code" specifying a particular module recognition at one or more or each position in the recognition alignment is thus improved using the steps of 1-5 (6). Binding proteins are generated with a novel recognition sequence by determining the position of the module in a recognition sequence to be rationally altered. The amino acid(s) in the binding protein correlated with the binding specificity for that position-specific module is rationally altered according to amino acid residue(s) in the cataloged code (7A). Alternatively, the module recognition specificity of uncharacterized or new binding protein members of a set can be predicted using the cataloged code (7B). Optionally, additionally, the recognition sequences can be lengthened or shortened for members of the set of binding proteins (8).

Figures 3, 25B:
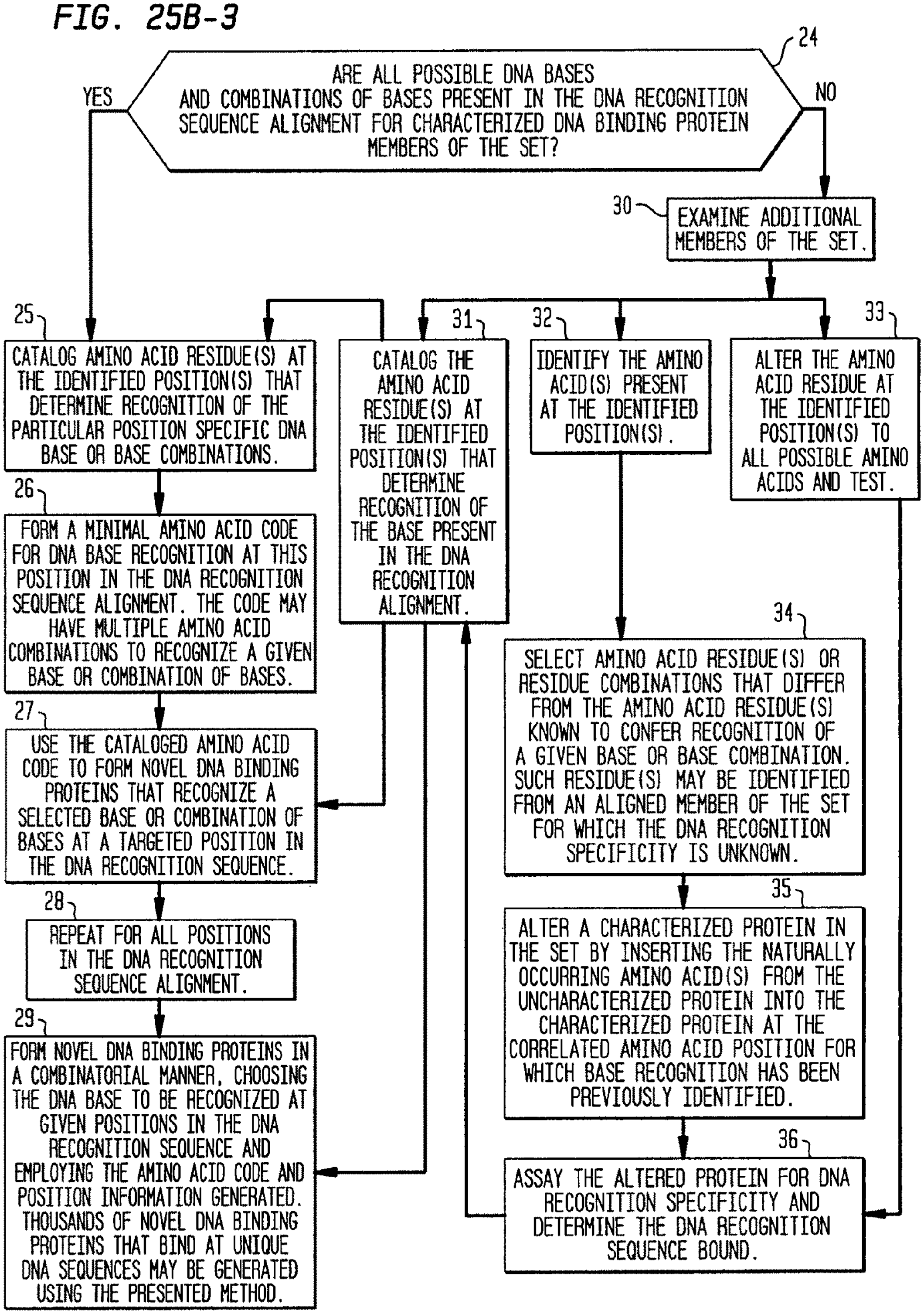
FIG. 3 shows the cleavage activity of rationally altered Mme4GI: MmeI A774L.
Figures 4, 25B:
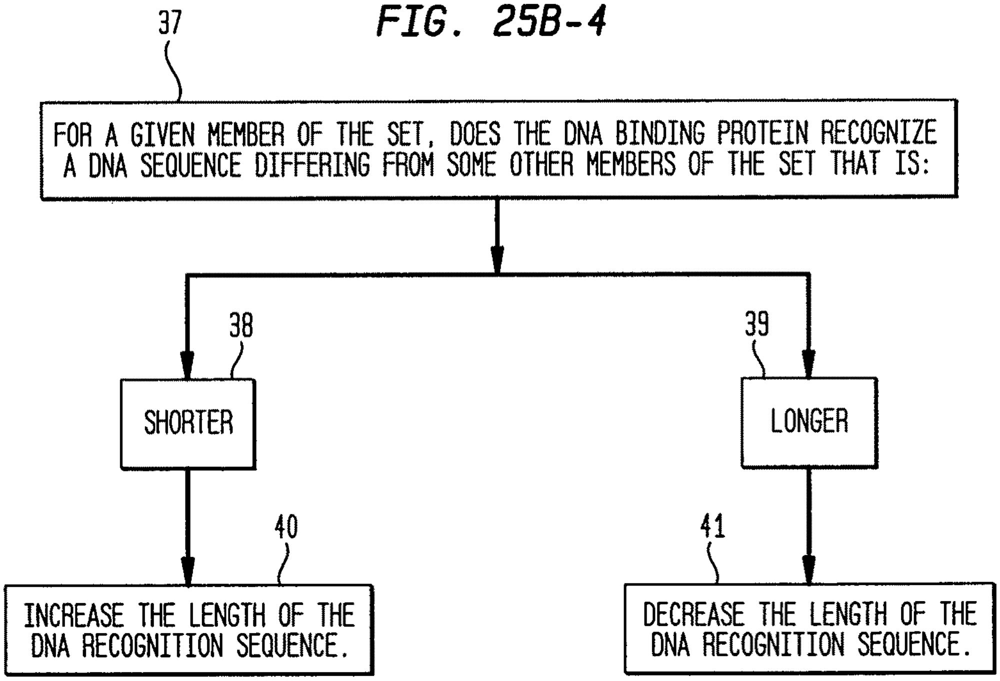
FIG. 4 shows the cleavage activity of rationally altered Mme4CI enzyme: MmeI A774K+R801S.

FIGS. 25B-1 to 25B-4 show a multi-step approach to analyzing correlations between amino acid sequences in binding proteins that bind position-specific modules in specific recognition sequences to which the binding protein binds. In this Figure, the method is illustrated by means of a DNA binding protein but the method can be equally applied to any binding protein that recognizes a substrate defined by position specific modules in a specific recognition sequence. The information obtained in steps 1-23 is stored as a cataloged code and used to rationally design novel binding proteins (steps 24-30) or to characterize specific recognition sequences for binding proteins whose amino acid sequence already exists in sequence databases (steps 24-37). In addition, steps are provided to generate binding proteins with increased or decreased base pairs in the DNA recognition sequence (steps 38-41).

The text in the numbered boxes is as follows:

1. Generate a set of closely related specific DNA binding proteins.
2. Enlarge the set, 3. Is DNA recognition sequence known?
4. Biochemistry: Determine DNA recognition sequence.
5. Bioinformatics: Identify co-varying amino acids from the aligned amino acid sequences. 6. Bioinformatics: Use in subsequent analysis. 7. Align DNA recognition sequences. 8. Align amino acid sequences. 9. Identify correlations between position specific DNA bases recognized and position specific amino acid residues. 10. Order by statistical significance. 11. Prioritize correlated positions according to statistical significance or to desired base changes in the recognition sequence. 12. Select a DNA base position in the aligned DNA recognition sequences for alteration of the base recognized by a member of the set to a "target" base(s).
13. Identify amino acid residue(s) and position(s) with the highest correlation score for the target DNA base position (1:1 correspondence in first priority). 14. Alter the amino acid residue(s) at the identified correlated position(s) to residue(s) correlated with recognition of a different defined target base module. The correlated position(s) for alteration are selected from one or more amino acid alignment sequence positions, which in turn are selected from the first to an Nth scoring position (see examples in Table 1 where N=4.) The Table is not intended to be limiting. N may be greater than 4, for example, N may be as much as 20 or more.).
15. Assay the rationally altered protein for binding at the new predetermined DNA recognition sequence. 16. Rationally altered protein binds its original DNA recognition sequence. 17. Altered protein binds the new predetermined recognition sequence. 18. Altered protein binds a new specific DNA sequence, but not the new predetermined recognition sequence. 19. Altered protein does not bind the new predetermined recognition sequence nor the original recognition sequence. 20. New specificity demonstrates the amino acid position(s) responsible for recognition at the DNA base position altered, and a part of the amino acid code for DNA base recognition at this position is identified. 21. Select the amino acid at the next highest scoring position and/or the combination of amino acids at varying scoring positions. Survey options at the new position(s) and continue this strategy until binding is achieved.
22. Recognition of the new predetermined specificity demonstrates the position(s) altered are the position(s) responsible for DNA base recognition at the targeted position in the recognition sequence alignment. Achieving the new predetermined specificity also demonstrates the amino acid residue determinant(s) for recognition of the targeted base. 23. Determine the amino acid code for recognition of different DNA bases at each position in the DNA recognition sequence. 24. Are all possible DNA bases and combinations of bases present in the DNA recognition sequence alignment for characterized DNA binding protein members of the set? 25. Catalog amino acid residue(s) at the identified position(s) that determine recognition of the particular position specific DNA base or base combinations. 26. Form a minimal amino acid code for DNA base recognition at this position in the DNA recognition sequence alignment. The code may have multiple amino acid combinations to recognize a given base or combination of bases.
27. Use the cataloged amino acid code to form novel DNA binding proteins that recognize a selected base or combination of bases at a targeted position in the DNA recognition sequence. 28. Repeat for all positions in the DNA recognition sequence alignment. 29. Form novel DNA binding proteins in a combinatorial manner, choosing the DNA base to be recognized at given positions in the DNA recognition sequence and employing the amino acid code and position information generated. Thousands of novel DNA binding proteins that bind at unique DNA sequences may be generated using the presented method. 30. Examine additional members of the set.
31. Catalog the amino acid residue(s) at the identified position(s) that determine recognition of the base present in the DNA recognition alignment. 32. Identify the amino acid(s) present at the identified position(s). 33. Alter the amino acid residue at the identified position(s) to all possible amino acids and test. 34. Select amino acid residue(s) or residue combinations that differ from the amino acid residue(s) known to confer recognition of a given base or base combination. Such residue(s) may be identified from an aligned member of the set for which the DNA recognition specificity is unknown. 35. Alter a characterized protein in the set by inserting the naturally occurring amino acid(s) from the uncharacterized protein into the characterized protein at the correlated amino acid position for which base recognition has been previously identified. 36. Assay the altered protein for DNA recognition specificity and determine the DNA recognition sequence bound. 37. For a given member of the set, does the DNA binding protein recognize a DNA sequence differing from some other members of the set that is: 38. Shorter, 39. Longer?

40. Increase the length of the DNA recognition sequence.

41. Decrease the length of the DNA recognition sequence

FIG. 25B-5 shows a scheme for prioritizing the amino acid position or positions at which to alter the amino acid residue or residues to residues correlated with recognition of a differing module in the recognition sequence alignment in order to determine the positions that determine recognition of the module at the position in the recognition sequence being investigated. The position in the amino acid sequence alignment that produces the highest correlation score, i.e., the lowest P value, is the first position to test, followed by the second highest correlation scoring position, etc. Since recognition of a module may require more than one amino acid residue in the protein, the two positions having the highest correlation score are the first priority for alteration of two residues together. If alteration at the first two highest scoring positions fails to produce an alteration in recognition, the first and third highest scoring positions may be altered, and the process repeated if necessary as indicated in Table 2 until the positions specifying recognition of the position-specific module are determined. In some cases it may be necessary to alter three or more positions to achieve alteration of the module recognized.

FIG. 26 shows the alignment of a portion of the amino-acid sequence of characterized 7 or 8-base pair recognizing MmeI family enzymes, grouped according to DNA base recognition at position 0 of the recognition sequence alignment. The two amino acid positions indicated by the arrows in bold, large font correlate with the DNA base recognized at position 0.

FIGS. 27A and 27B show the digestion patterns of GauT27I wild type and GauT27I altered at position 0 to G (GauT27I(0G)). FIG. 27A shows an agarose gel showing the digestion products of pAd$_2$-BsaBI plasmid DNA digested with GauT27I and the altered GauT27I $R_{790}D/E_{802}R$ enzyme GauT27I(0G). Lane M: HindIII-lambda and HaeIII-PhiX174 DNA size standards. FIG. 27B shows computer-generated digestion patterns for cleavage at the predicted wild type and altered recognition sequences. Lane 1: GauT27I wild type (CGCGCAGG19/17), Lane 2: GauT27I(0G) (GGCGCAGG19/17).

FIGS. 28A and 28B show how DNA cleavage positions were determined for GauT27I wild type and GauT27I altered at $R_{790}D/E_{802}R$ (GauT27I(0G)) using pBsaBI plasmid DNA substrate cleaved by the respective enzymes. FIG. 28A shows the run-off dideoxy sequencing through the GauT27I site at 3603, which shows DNA cleavage in the bottom strand 17 bp 3' to the CGCGCAGG GauT27I site. FIG. 28B shows the run-off dideoxy sequencing through the altered GauT27I(0G) (GauT27I $R_{790}D/E_{802}R$) site at 1699, which shows DNA cleavage in the bottom strand 17 bp 3' to the new GGCGCAGG GauT27I(0G) recognition site.

FIGS. 29A and 29B show the digestion patterns of MaqI wild type and MaqI altered at position 0 to G (MaqI(0G)). FIG. 29A is an agarose gel showing the digestion products of pAd$_2$-BsaBI plasmid DNA digested with MaqI and the altered MaqI $R_{817}D/E_{829}R$ enzyme MaqI(0G). Lane M: HindIII-lambda and HaeIII-PhiX174 DNA size standards. FIG. 29B shows the computer-generated digestion patterns for cleavage at the predicted wild type and altered recognition sequences. Lane 1: MaqI wild type (CRTTGAC20/18), Lane 2: GauT27I(0G) (GRTTGAC20/18).

FIGS. 30A and 30B show how the DNA cleavage positions were determined for MaqI wild type and MaqI altered at $R_{817}D/E_{829}R$ (MaqI(0G)) using pBsaBI plasmid DNA substrate cleaved by the respective enzymes. FIG. 30A shows the run-off dideoxy sequencing through the MaqI site at 10,732 showing DNA cleavage in the bottom strand 18 bp 3' to the CGTTGAC MaqI site. FIG. 30B shows the run-off dideoxy sequencing through the altered MaqI(0G) (MaqI $R_{817}D/E_{829}R$) site at 3598 shows DNA cleavage in the bottom strand 18 bp 3' to the new GGTTGAC MaqI(0G) recognition site.

FIGS. 31-37 show the amino acid sequences of restriction endonucleases RceI (SEQ ID NO:193), RpaBI (SEQ ID NO:194), SstE37I (SEQ ID NO:195), GauT27I (SEQ ID NO:196), PliMI (SEQ ID NO:197), AquII (SEQ ID NO:198) and RpaTI (SEQ ID NO:199).

FIGS. 38-1 to 38-4 provides a list of recognition sequences capable of being engineered for RpaB5I based on changes in position 0.

DETAILED DESCRIPTION OF THE EMBODIMENTS

Present embodiments of the invention provide methods for rationally designing and making enzymes with novel recognition specificities, which have been selected or reliably predicted in advance. Catalogs based on correlations between position-specific amino acids in aligned binding proteins and position-specific modules in their recognition sequences in a substrate can be created. The catalog can be expanded by analyzing additional members of the set of binding proteins that recognize new combinations of modules in the recognition sequence or that contain an unexpected amino acid at a correlated position within the amino acid sequence. Using the catalog, large numbers of novel DNA binding proteins may be created based on various combinations of position-specific amino acid mutations.

Although the examples describe DNA binding proteins, the methods and compositions described herein are broadly applicable to any binding protein that recognizes a substrate that contains a characteristic position-specific sequence of modules recognized by the binding protein.

An overview of steps of an embodiment of the method is described in the flow diagram in FIG. 25A. A detailed description of multiple method steps of an analysis as executed for a set of DNA binding proteins is provided in FIG. 25B. Embodiments of the method may utilize one or more of the individual method steps described in each of boxes 1-8 in FIG. 25A and in each of boxes 1-41 in FIG. 25B and are not restricted to execution of the entire described set of method steps in FIG. 25A or 25B.

As described generally in the flow diagram in FIG. 25A and more particularly for a specific DNA binding protein in FIG. 25B, a polynucleotide may be generated that encodes a binding protein having an altered substrate specificity following steps that include: (a) identifying a set of closely related binding proteins having known amino acid sequences and preferably also having known module recognition specificity;

(b) aligning the recognition sequences of the set of closely related binding proteins; (c) aligning the amino acid sequences of the set of closely related binding proteins; (d) identifying the position-specific amino acid residues that correlate with the position-specific module recognized by the members of the set of binding proteins; and (e) forming a novel binding protein that specifically recognizes a new, rationally chosen recognition sequence by changing the amino acid residue(s) of that protein identified by correlation as recognizing the module at a given position in the recognition sequence alignment. The identified amino acids can be changed to those amino acid residue(s) identified by correlation among members of the set that recognize a different module at the given position in the recognition sequence alignment. The exchange of amino acid residues may be accomplished by site-directed mutagenesis. By rationally altering the amino acid residues that confer specificity at the various positions within the recognition sequence, a very large number of proteins having specificity for novel recognition sequences may be created.

Embodiments of the method may be executed by a computer having been programmed to accomplish at least one of the steps outlined in either or both of FIGS. 25A and 25B. The predictions provided by computer analysis may be tested using high-through-put techniques that facilitate examination of large numbers of mutated proteins or by laboratory techniques that examine a small number of rationally designed proteins or examine single proteins.

The systems and methods described herein are amenable to complete automation using established devices for accomplishing the wet chemistry component can communicate with a computer for prior instructions as well as post-chemistry computation.

The computer would calculate steps 1-4, 6 and 7A in FIG. 25A. The device would perform the chemistry necessary for Boxes 5 and 7A in FIG. 25A sending data about binding of a mutated protein to a predetermined recognition sequence back to the computer, which could then process that data to confirm novel specificity, build iteratively the catalog and analyze novel binding proteins for hypothetical recognition sequences.

The instrument or device for conducting the wet chemistry steps might perform DNA synthesis and in vitro transcription and translation steps or alternatively directly synthesize a protein by programmed amino acid synthesis and then provide a high-through-put assay format known within the art (Kawahashi, et al. *J Biochem* 141:19-24 (2007)) for determining binding of multiple mutants to preselected recognition sequences such that the bound molecules emit a signal for detection, digitization and storage in a memory of a computer.

The method described herein is applicable to any protein that is capable of recognizing a specific sequence containing position-specific modules where the sequence or module may be represented for example by a nucleic acid, a monosaccharide, an amino acid or a chemical group. The methods described herein may be most broadly applied to any binding protein of which a DNA binding protein is a subset.

A "binding protein" as used herein may refer to a protein that binds to position-specific modules in a binding protein-specific recognition sequence. "Binding" means having an electrochemical attraction to or forming a covalent bond with the specific substrate sufficient to favor association in a disordered environment. Examples of binding proteins include those that bind biological macromolecules such as nucleic acid binding proteins for example, restriction endonucleases, homing endonucleases, and zinc finger proteins; RNA-binding proteins; carbohydrate-binding proteins; glycoprotein-binding proteins; glycolipid-binding proteins; lipid-binding proteins; and binding proteins that bind small molecules that contain a range of chemical groups or a single chemical group arranged in a specific predetermined order.

The term "module" is used generally to describe individual position-specific components in a specific recognition sequence, which forms a substrate for the binding protein.

A "substrate" as used herein refers to a molecule that has a number of modules having specific positions in a sequence, some or all of which are capable of having an electrochemical attraction to or forming a covalent bond with one or more specific amino acids in the binding protein. The number of different modules in a substrate may vary from 1 to as many as 20 modules or more, while a substrate may be composed of a few to millions or more modules.

"One or more specific amino acids" refers to a target of rational design where one or more optional changes of the target causes a change in the specificity of the protein to at least one module in the substrate. The one or more amino acids are likely to be a subset of the protein sequence required for binding the substrate.

"Prediction" as used herein refers to obtaining an improved approximation of accuracy of reproduction of alignment patterns.

"Correlation" may be used herein to mean an indication of the strength and direction of a linear relationship between two random variables. In general statistical usage, correlation or co-relation refers to the departure of two variables from independence. A statistically significant correlation may be calculated within the context of creating a catalog by using any one of a variety of tests such as a Chi square test, a mutual information analysis that for two random variables provides a quantity that measures the mutual dependence of the two (Gloor, et al. *Biochemistry* 44:7156-7165 (2005)) and a Pearson product-moment correlation coefficient (Spiegel, M. R. "Correlation Theory." Ch. 14 in *Theory and Problems of Probability and Statistics,* 2nd ed. New York: McGraw-Hill, pp. 294-323, 1992).

"Set" is used herein as a related group of molecules of two or more members.

"Catalog" is a list of positionally defined amino acids that determine recognition of specific modules in a recognition sequence in a substrate.

"Recognition sequence" is a sequence of modules in a substrate, which is bound specifically by a binding protein.

"MmeI-like proteins" are proteins that belong to a set of amino acid sequences wherein each amino acid sequence in the set consists of part or all of a binding protein wherein the amino acid sequences (i) share an expectation value (E) of less than e-20 in a BLAST Search using MmeI as a query; and (ii) bind to specific DNA recognition sequences in a substrate, the DNA recognition sequences containing position-specific DNA bases.

Embodiments of the method may include one or more of the following steps:

1) Identify and collect a set or sets of closely related binding proteins for which both the sequence recognized by the protein and the amino acid sequence of the protein are known. Such a set of sequences may be identified in various ways. For example, a BLAST search of all sequences available in a database, such as Genbank, may be performed. Typically the query sequence is the amino acid sequence of a binding protein of interest, for example, in one such embodiment, a DNA binding protein exemplified here by MmeI restriction endonuclease may be used for the query. Alternatively, an amino acid sequence that is closely related to MmeI can be used to conduct a BLAST search. FIG. 16 shows the results of a Blast search using SpoDI which is closely related to MmeI which is used for a Blast search in FIG. 18. The Figures show that the results of the search are not identical. Performing multiple searches using different related proteins can result in the expansion of the set of aligned amino acid sequences.

The standard BLAST search blastp may be performed, although the parameters of the search may be varied by those skilled in the art. Because the method utilizes only closely related amino acid sequences, the standard blastp program search will identify sequences that can be usefully employed in the method. Alternative forms of the BLAST search may be performed, such as tblastn using the amino acid sequence of the starting query binding protein to search against translated nucleotide sequences in the database. This tblastn search is particularly useful for searching databases containing environmental DNA, and it is also useful to identify extended regions of similarity to the query binding protein when there are frameshifts or stop codons in the putative binding protein that cause the amino acid sequence reported in the database to be shortened relative to the full length query sequence. In another form of the BLAST search, the DNA sequence of the binding protein may be used to search either against protein sequences in the database (tblastp program), or against nucleotide sequences in the database (blastn program). The Expectation value from the BLAST search may be used to determine inclusion or exclusion of sequences from the set. Proteins that are only distantly related are unlikely to share enough sequence similarity to reliably align their sequences in order to observe residues and positions that correlate with module recognition. Requiring a relatively stringent BLAST E value threshold for inclusion in the chosen set of sequences ensures that distantly related sequences will be excluded.

The Expectation value chosen for inclusion in the set of related sequences is influenced by the length of the input sequence. For binding proteins having amino acid sequences longer than 200 amino acids, such as the majority of restriction endonucleases, an Expectation value of $E<e-20$ is employed. For shorter sequences, a larger E value is employed, such as $E<e-10$ for sequences between 100 and 200 amino acids in length.

The set of protein sequences employed may be further divided into subsets during the analysis in cases where this allows better alignment of the sequences within the subsets (fewer gaps and higher alignment scores), as this will reflect closer evolutionary and structural relationships between the members of the subsets, which will increase the likelihood that statistically significant correlations can be observed between amino acid residues and position-specific modules (e.g., DNA bases).

The sequences identified through the BLAST search may be sorted into those that have a known recognition sequence and those for which the sequence recognized is unknown. If there are sufficient protein sequences having known recognition sequences to produce statistically significant results, the analysis may be performed using these sequences. However, if there are not enough protein sequences for which the recognition sequence is known, then some of the identified putative binding proteins may have their recognition sequence determined biochemically (WO 2007/097778). This was the case for Example I, in which MmeI was used to identify homolog peptides in Genbank. The majority of the proteins identified in this search were uncharacterized as to their function, including their DNA recognition sequence specificity at the start of analysis. Therefore, a number of these peptides were characterized to determine their respective DNA recognition sequences, after which they were employed in the method described to create novel DNA binding proteins. For identified members of the binding protein set wherein the recognition sequence is not known, the recognition sequence may be determined biochemically. For example, a DNA recognition sequence for an uncharacterized member of the MmeI-like family of binding proteins may be determined by analyzing the location of DNA cutting and the size of the DNA fragments produced from various DNA substrates (Schildkraut *Genet. Eng.* 6:117-140 (1984)) or alternatively by analyzing the location of DNA modification in various DNA substrates.

An example of determining the DNA recognition sequence by characterizing the activity of the binding protein has been demonstrated for two related restriction endonucleases—CstMI and NmeAIII (see U.S. Pat. No. 7,186,538 and International Application No. PCT/US07/88522, respectively).

2) Align the recognition sequences of the binding proteins. The recognition sequences are preferably aligned to accurately reflect the nature of the interaction between the binding protein and the sequence recognized. To do this, the recognition sequence alignment is anchored about a common function.

For example, with respect to DNA binding proteins, the DNA recognition sequence will often consist of a different linear sequence of bases on each strand of the two strands in the DNA double helix. The exception to this is the case of DNA binding proteins that recognize symmetrical DNA sequences, in which the linear sequence of DNA bases recognized is the same from 5' to 3' in both DNA strands. It is important to choose the correct DNA strand to be aligned, since the two strands of the recognition sequence may have a different linear sequence of bases. The correct DNA strand is determined by the functional attribute(s) chosen to guide the alignment. For example, for restriction endonucleases, the functional attributes that enable accurate alignment of the DNA recognition sequences may consist of the methylation of a conserved adenine or cytosine base, and/or the direction of DNA cleavage downstream from the targeted specific DNA sequence recognized. In Example 1, the DNA recognition sequences were aligned using the strand containing the adenine base that is methylated, and which has the position of cleavage located 3' to the recognition sequence on this strand. The alignment was fixed about this methylation target adenine. The linear sequence of bases in the second DNA strand is defined by the sequence of the strand employed in the alignment.

The position of methylation may be determined by incorporating a labeled methyl group such as radioactive tritium methyl group into various DNAs and mapping where the labeled methyl groups are located in the DNAs. Methylation can also be analyzed by protection against restriction endonucleases whose recognition sequences overlap the methylated base produced by the enzyme being characterized.

3) Align the amino acid sequences of the set of highly similar binding proteins. This may be done using any of a number of sequence alignment programs, such as ClustalW (www.ebi.ac.uk/clustalw/),

PROMALS (prodata.swmed.edu/promals), MUSCLE (phylogenomics-.berkeley.edu/cgi-bin/muscle/input muscle.py), or T-Coffee (www.ebi.ac.uk/t-coffee/), or other similar programs. Generally the default alignment values of programs such as ClustalW or PROMALS algorithm may be used. The PROMALS algorithm is slower but provides improved alignment results. It should be understood that the skilled artisan may vary the parameters of the alignment programs to produce optimal alignment results, or the alignments may be refined manually by the skilled artisan. Since the method uses a set of closely related binding proteins, suitable alignments may be produced with the default settings of most widely used alignment programs. When one or more of the input binding protein sequences are less similar to the others, there may be a benefit to adjusting the alignment parameters or, if one or more sequences fails to align closely with the majority, or if it produces numerous gaps or otherwise degrades the alignment of the majority of sequences, such sequences may be excluded from the initial alignment in order to preserve the overall correctness of the amino acid sequence alignment produced.

4) Information contained in the recognition sequence alignment and the amino acid protein sequence alignment is combined to identify the amino acid positions, and the amino acids occurring at those positions, responsible for specific-sequence recognition.

The amino acid sequence alignment is interrogated to identify positions in which the amino acid residues present correlate with the module recognized by the binding proteins at a given position within the aligned DNA recognition sequences. A statistically significant, for example $P<0.01$, correlation indicates that specific module recognition is accomplished by the particular amino acid residue present at this position in the amino acid sequence of the binding protein. Recognition of a given base pair may require two or more amino acid residues located at different positions within the linear amino acid sequence of the protein. Such correlations may be identified using the computer program described in the examples, or other similar programs. The skilled artisan may also identify such correlations by eye.

Embodiments of the method presented have the advantage of identifying amino acid positions that interact to recognize a given module even when the positions are widely separated in the primary amino acid sequence. Such widely separated positions are predicted to be spatially close in the three dimensional structure of the binding protein in order to recognize the given module.

Once correlations are observed, the respective amino acid residues are altered so as to recognize a different base pair at the position interrogated, and the altered proteins are tested for binding at the expected new recognition sequence. Successful identification of the amino acid residues conferring module specificity is confirmed by the altered binding protein, specifically binding the new, predicted recognition sequence (see for example FIGS. 1-9).

5) Rationally alter binding proteins such that they recognize novel recognition sequences. Once the amino acid residue positions and the individual amino acid residues that confer specificity for a given module at a given position within the recognition sequence are identified, novel binding proteins may be created by site-directed mutagenesis of the polynucleotide sequence encoding the identified amino acid residues. The amino acid residues at the positions conferring recognition specificity are specifically changed to those residues identified that specify recognition of the different, desired module in the recognition sequence. Such changes result in the creation of a binding protein that now predictably recognizes a new recognition sequence containing the position-specific module recognized by the altered residues. By employing combinatorial methods to change various combinations of the amino acid residues responsible for position-specific module recognition at different positions within the recognition sequence, large numbers of binding proteins that recognize novel recognition sequences may be synthesized (see FIG. 23).

Uses of the Method

Embodiments of the method are powerful tools for using sequence data that is either new or already in sequence databases for: mining for enzymes with particular functions; analyzing functions of existing proteins; designing and creating novel enzymes with a desired specificity; and providing a rational means to increase the length of the specific recognition sequence for certain binding proteins, thereby conferring an increased specificity.

Rational design methodology can provide predictions of: the DNA recognition sequence of uncharacterized binding proteins in a set of proteins; a position-specific portion of the recognition sequence of uncharacterized binding protein sequences that match a set of characterized binding proteins with a defined relationship (E value); and/or rational design and creation of a binding protein with a desired recognition sequence.

New restriction endonucleases that recognize novel sequences provide greater opportunities and ability for genetic manipulation. Each new unique endonuclease enables scientists to precisely cleave DNA at new positions within the DNA molecule, with all the opportunities this offers. Such novel restriction endonucleases may enable detection of single nucleotide polymorphisms that previous restriction endonucleases could not differentiate. New recognition specificities enable new restriction fragment-linked polymorphism analysis as well as offer increased flexibility in cloning techniques that require specific DNA cutting and reassembly. The methyltransferase activity of the altered enzymes may also be used to introduce methyl or other chemical groups into DNA at the new specific recognition sequences. DNA may thus be specifically labeled at the various recognition sequences by the action of the novel enzymes. The introduction of methyl groups can also be used to block the action of restriction endonucleases where the site-modified overlaps the recognition sequence of the restriction endonuclease. Engineered methyl transferases may provide a useful resource for cloning naturally occurring restriction endonucleases for which no methylase is known to exist to protect the transformed host cells.

Methyl transferases with altered binding specificities may be used to introduce labels into DNA at specific sites. These labels may depend on the introduction of a methyl group or alternatively another chemical group.

Prediction of Binding Specificity for Uncharacterized Proteins

There are often numerous uncharacterized homologs to a given set of characterized proteins in public databases, such as Genbank. The recognition sequences of the homologs are generally unknown. Without knowledge of the specific sequence recognized, these proteins cannot participate in the method described herein. However, once the position(s) within the set of amino acid sequences that determine recognition become known along with the module specificity determined by particular amino acid residues at these position(s), then the recognition specificity of these uncharacterized homologs can be predicted when their position-specific amino acid sequence matches residues conferring known module recognition at these positions.

Identification in Naturally Occurring Protein Sequences of Likely Novel Position-Specific Module Recognition Sequences Where the amino acid residues of the uncharacterized homologs do not match amino acid residues known to recognize certain modules, these homologs are identified as likely candidates to recognize a different module at these positions in the recognition sequence. Thus, the position-specific amino acid residues of those uncharacterized homolog proteins may be exchanged for the position-specific amino acid residues of a characterized binding protein, and the altered protein can then be characterized for binding specificity, with the expectation that it will likely bind to the recognition sequence with an altered module specificity at that particular position within the recognition sequence.

Position-specific amino acid residues known to confer specific recognition of a given module can be changed to alternative residues observed at these aligned positions in homologous protein sequences in the databases having an unknown recognition sequence. Such substitutions reflect the variety of naturally occurring binding proteins without requiring the foreknowledge of the specific recognition specificity of each such protein sequence. In this manner, recognition of modules not observed in the currently known recognition sequence may be obtained. An example of this embodiment is presented in Example 2, wherein the MmeI restriction endonuclease/methyltransferase is altered to generate an enzyme recognizing a novel DNA sequence. The amino acids that confer recognition of the DNA base pair at position 6 of the recognition sequence ($E_{806}(S)R_{808}$) were altered to those residues observed in several naturally occurring but uncharacterized sequences that align with the known position-specific residues, (G(N)G), which results in the creation of a restriction enzyme that recognizes a novel DNA binding sequence, 5'-TCCRAR-3' (see FIGS. 6 and 23).

Generation of Novel Position-Specific Module Recognition Sequences by Random Mutagenesis of Identified Amino Acid Positions that Confer Position-Specific Module Specificity The identification of positions within the binding protein sequence that confer DNA binding specificity allows for the alteration of the amino acid residues at these positions to all possible amino acid residues (see for example FIG. 23). This represents a rational, targeted mutation of those residues identified as conferring specificity. The proteins thus altered may then be tested biochemically to determine their recognition specificity to identify novel binding proteins. A major benefit of this approach is that it is easily tractable to change a few amino acid positions, such as the two positions conferring DNA base pair specificity at position 6 of MmeI restriction endonuclease (Example 1), whereas random mutagenesis of an entire protein sequence, or even a relatively small subset of that sequence, quickly becomes intractable due to the exponential number of mutations required. For example, randomly changing the two amino acid residue positions identified for MmeI position 6 would require 20×20, or 400 different sequences. In the case of zinc finger protein mutagenesis, randomly altering all seven amino acid positions believed to interact with DNA to form the recognition of the three base pair triplet recognized would require $20^7$, or $1.28\times10^9$ different mutations (Durai, S. et al. *NAR* 33(18): 5978-5990 (2005)). For combinations of zinc fingers to recognize longer DNA base pair sequences, such as 6 or 9 base pairs, the number of mutations required quickly becomes intractable ($\sim10^{18}$ for 6 base pairs, or $\sim10^{27}$ for 9 base pairs). Identifying those few amino acid positions that interact with the DNA to confer base specificity using the method presented herein allows the alteration of these identified residues to be performed, allowing identification of new DNA binding proteins that recognize novel DNA sequences.

Generation of Binding Proteins Having Increased Module-Binding Specificity

When some members of the set of closely related binding-proteins specifically recognize more modules than other members of the set, the aligned recognition sequences and aligned amino acid sequences are examined to identify correlations between the position-specific amino acid sequence alignment and those recognition sequences that specify a particular module at a position where other recognition sequences do not recognize a specific module. In the example of the MmeI restriction endonuclease family, several of the members recognize a seven base pair sequence, while others recognize only six base pairs. For example, MmeI recognizes specific DNA bases in the four positions 5' to the adenine that is methylated, as well as one base 3' to that adenine, but does not recognize a specific base in the fifth position 5' to the methylation target adenine, whereas SpoDI recognizes a specific DNA base, “G”, in the fifth position 5' to the methylation target adenine in addition to recognizing specific bases in the four positions immediately 5' to the methylation target adenine and one base 3' to that adenine. The amino acid position(s) and position-specific amino acid residue(s) that confer specificity at this extended position are identified by the method of correlation described, wherein the correlation will consist of significant identities among those sequences that recognize a given DNA base at the extended position, while those sequences that do not specify any DNA base at the extended position will not exhibit such correlations. Using the method described herein, once the amino acid position(s) and residue(s) responsible for the specific recognition of the additional extra DNA base(s) are identified, the amino acid sequence responsible for this extra base recognition may be introduced by site-directed mutagenesis into the genes of the related DNA binding proteins recognizing a shorter recognition sequence to extend their specificity to include the additional base pair(s).

All references cited above and below, as well as U.S. provisional application No. 60/936,504 filed Jun. 20, 2007 and U.S. patent application Ser. No. 12/143,498 filed Jun. 20, 2008, are herein incorporated by reference.

EXAMPLES

Example 1

Rational Generation of Novel Functional Type IIG Restriction Endonucleases that Specifically Recognize Novel DNA Sequences from MmeI, NmeAIII, SdeAI And Related Type IIG Restriction Endonucleases MmeI is a DNA binding protein that specifically binds to the double-stranded DNA sequence 5'-TCCRAC-3'/5-GTYGGA-3'. MmeI functions to methylate the adenine base in the DNA strand 5'-TCCRAC-3'. MmeI also functions as an endonuclease, cleaving the double-stranded DNA 20 nucleotides 3' to the TCCRAC strand and 18 nucleotides 5' to the GTYGGA strand to leave a two base 3' extension (1,2).

A set of polypeptides having members with a high degree of similarity to the Type IIG restriction endonuclease MmeI was identified through performing a BLAST search of the Genbank non-redundant database employing the blastp program (Altschul et al.

*J. Mol. Biol.* 215:403-410 (1990); Altschul et al. *Nucleic Acids Res.* 25:3389-3402 (1997); and Madden et al. *Methods Enzymol.* 266:131-141 (1996)) (FIG. 18 and #1 in FIG. 25B-1). The MmeI amino acid sequence (U.S. Pat. No. 7,115,407) was used as query and a cut-off value for inclusion in the dataset of an Expectation score, E, of E<e-20 was employed. The default parameters of the NCBI web based blastp program were utilized (www.ncbi.nlm.nih.gov/BLAST/). A number of polypeptide sequences were identified as highly similar to MmeI; however, none of these sequences was characterized as to function, particularly regarding the specific DNA sequence recognized by the given polypeptide. Therefore, a number of these hypothetical sequences were cloned and expressed. The expressed proteins were tested for endonuclease activity, and the specific DNA sequence at which they bound DNA was characterized (U.S. Pat. No. 7,186, 538). Among the set of sequences identified through the BLAST search as highly similar to MmeI, the specific DNA recognition sequence of the following active Type II endonucleases were identified. These enzymes also possess DNA methyltransferase activity.

CstMI, from Genbank Accession number GI:32479387, recognizes the DNA sequence 5'-AAGGAG-3' and cuts 20 nucleotides 3' to this sequence on this strand, and 18 nucleotides 5' to the complement on the opposite DNA strand, to give a 2 base, 3' extension: AAGGAGN20/N18(7).

NmeAIII, from Genbank accession number NC__003116, peptide accession GI:15794682, was made active by correcting a stop codon within the reading frame identified as highly significantly similar to MmeI. NmeAIII was found to recognize 5'-GCCGAG-3' and cut downstream: GCCGAGN21/N19 (international application no. PCT/US07/88522).

SdeAI, (formerly known as TdeAI) from Genbank accession number: NC__007575.1, peptide accession YP__392994.1, was cloned, expressed and characterized. SdeAI recognizes the DNA sequence 5'-CAGRAG-3' and cuts downstream: CAGRAGN21/N19.

EsaSSI, from Genbank accession number AACY01071935.1, is an environmental DNA sequence from the Sargasso Sea, which meant that there was no available template DNA from which to amplify and clone the gene. Therefore, the gene encoding EsaSSI was made synthetically, and the amino acid codons for the peptide sequence were optimized to commonly used *E. coli* codons. The synthesized gene was assembled and cloned into *E. coli*, expressed and the enzyme activity characterized. EsaSSI was found to recognize the DNA sequence 5'-GACCAC-3'.

SpoDI, from Genbank accession number NC__003911.11, peptide accession YP__167160, was cloned, expressed and characterized to recognize the DNA sequence 5'-GCGGAAG-3 and cut downstream GCGGAAGN20/N18.

DraRI, from Genbank accession number NC__001264.1, peptide accession NP__285443, was cloned; a false stop error in the gene was corrected by changing a TAA stop codon at position 2521 (amino acid position 841) to a GAA codon. The gene was expressed and the protein product characterized. DraRI was found to recognize the DNA sequence 5'-CAAGNAC-3' and to cut downstream CAAGNACN20/N18.

ApyPI, from Genbank accession locus NC__005206.1, protein accession NP__940747, was cloned. A frameshift near the C-terminus of the protein was corrected using similarity to the CstMI protein to guide the correction position. The active, full-length protein and the corrected DNA sequence encoding this polypeptide were reported. The corrected ApyPI enzyme was expressed and characterized to recognize 5'-ATCGAC-3' and to cut downstream ATCGACN20/N18.

PspPRI, from Genbank accession locus YP__001274371, peptide accession NC__009516.1, was cloned, expressed and characterized to recognize 5'-CCYCAG-3' and to cut downstream CCYCAGN21/N19 or CCYCAGN20/N18.

NhaXI, from Genbank accession locus CP000319.1, peptide accession YP__579008, was cloned, expressed and characterized to recognize 5'-CAAGRAG-3' and to cut downstream CAAGRAGN20/N18.

CdpI, from Genbank accession locus NC__002935.2, peptide accession: NP__940094, was cloned, expressed and characterized to recognize 5'-GCGGAG-3' and to cut downstream GCGGAGN20/N18.

RpaB5I, from Genbank accession locus NC__007958.1, peptide accession YP__570364, was cloned, expressed and characterized to recognize the DNA sequence 5'-CGRGGAC-3' and cut downstream CGRGGACN20/N18.

NlaCI, from *Neisseria lactamica* ST640, was cloned, expressed and characterized to recognize 5'-CATCAC-3', and to cut downstream CATCACN19/N17 or CATCACN20/N18.

DrdIV, from *Deinococcus radiodurans* NEB479, was cloned, expressed and characterized to recognize 5'-GCGGAG-3' and to cut downstream GCGGAGN20/N18.

PspOMII, from *Pseudomonas* species OM2164, was cloned, expressed and characterized to recognize 5'-GCGGAG-3' and to cut downstream GCGGAGN20/N18.

MaqI, from Genbank accession locus NC__008738.2, peptide accession: YP__956924, was cloned, expressed and characterized to recognize 5'-CRTTGAC-3' and to cut downstream CRTTGACN20/N18.

PlaDI, from Genbank accession locus NC 009719.1, peptide accession: YP__001413872, was cloned, expressed and characterized to recognize 5'-CATCAG-3' and to cut downstream CATCAGN20/N18.

AquIII, from Genbank accession locus NC__010475, peptide accession: YP__001735369, was cloned, expressed and characterized to recognize 5'-GAGGAG-3' and to cut downstream GAGGAGN20/N18.

AquIV, from Genbank accession locus NC__010475, peptide accession: YP__001735547, was cloned, expressed and characterized to recognize 5'-GRGGAAG-3' and to cut downstream GRGGAAGN20/N18.

The DNA recognition sequences of MmeI and these newly characterized homolog enzymes were aligned. The alignment was made using the DNA strand that contains the adenine base, that is, modified by the DNA methyltransferase activity of these enzymes, and that is also the strand that is cleaved 3' to the DNA recognition sequence. The DNA sequences were aligned so that the adenine base that is methylated is aligned for each enzyme. The DNA recognition sequence alignment is given in FIGS. 10 and 15 and #7 in FIG. 25B.

A multiple sequence alignment was constructed from the primary amino acid sequences of the highly similar restriction endonuclease polypeptide sequences having the known DNA recognition sequences described in FIG. 10. The alignment program ClustalW was used: www.ebi.ac.uk/clustalw/. The default settings were employed in the algorithm, except that the alignment was returned with the sequences in the input order, rather than the alignment score order. A portion of the multiple sequence alignment obtained is presented in FIG. 13 and #8 in FIG. 25B). A multiple sequence alignment for the entire amino acid sequences of the enzymes formed using the more rigorous alignment program PROMALS, prodata.swmed.edu/promals/promals.php, is shown in FIG. 20.

The polypeptide sequences were grouped according to the function of the DNA base recognized in the position 3' to the methylation target adenine. The enzymes recognizing cytosine, "C", are MmeI, EsaSS217I, ApyPI, NlaCI, DrdIV, RpaB5I, DraRI and MaqI. The enzymes recognizing guanine, "G", at this position, are NhaXI, NmeAIII, CdpI, AquIII, CstMI, SdeAI, PspPRI, PlaDI, SpoDI and AquIV. PspOMII recognizes "R" at this position. The alignment was interrogated for amino acid residues at a given position in the alignment that were the same within the C and within the G group but which differed between the groups. For a small group of sequences such as this, the alignment can be examined manually, or interrogated by a computer program that can identify when there is a statistically significant correlation between the position-specific amino acid residues and the DNA base recognition. An example of such an algorithm is presented in FIG. 21. Upon examination of the alignment, one position was observed in which there was a 100% correlation between the amino acid residue present at this position and the DNA base recognized at this position within the DNA recognition sequence alignment. At this position, the cytosine is recognized by a group of amino acid sequences that has an Arginine residue, "R", while the guanine recognizing group has an Aspartate residue, "D." Both of these residues are charged and can readily form hydrogen bonds with DNA bases. The position of this residue in the MmeI sequence is R808, while in NmeAIII the residue is D818.

The candidate amino acid residue for recognizing cytosine, R808 in MmeI, and the equivalent position residue for recognizing guanine, D818 in NmeAIII, were changed to the amino acid residue expected to confer recognition of the other DNA base (R808 to D for MmeI and D818 to R for NmeAIII) by site-directed mutagenesis. For each enzyme, two oligonucleotide primers were synthesized for use according to the Phusion™ site-directed mutagenesis kit procedure (New England Biolabs, Ipswich, Mass.). For MmeI, the primers were: forward: 5'-pGATTATAGATATTCTGCCAGCCTGGTT-3' (SEQ ID NO:27), where p is a phosphate, and reverse: 5'-pACTTTCTAACCTTCCTCCTACATTTCTC-3' (SEQ ID NO:28). The first three nucleotides of the forward primer changed the amino acid codon for the arginine, "R808" of MmeI to a codon, "GAT" coding for aspartic acid, "D".

The oligonucleotide primers to change NmeAIII were: forward: 5'-pCGCTATCGCTACTCTAATACCGTCGT-3' (SEQ ID NO:29) and reverse: 5'-p GCTTTTCAGACGACCTGCAAC-3' (SEQ ID NO:30). The first three nucleotides of the forward primer changed the coding of this position, D818, in NmeAIII from "D" to "R". Mutagenesis was performed according to the manufacturer's directions and polynucleotides expressing the desired altered amino acid residue polypeptides were obtained. The altered MmeI polynucleotide, R808D, and the altered NmeAIII polynucleotide, D818R, were cloned into *E. coli* and expressed, but the polypeptides did not exhibit any restriction endonuclease activity. From this we concluded that they do not specifically bind the desired new recognition sequence, nor do they bind their original DNA recognition sequence, nor a different, unpredicted sequence. However, this position is likely to be involved in DNA recognition or some critical function or fold, since the altered proteins have lost the function of specific DNA binding.

Because it has been observed in other DNA binding proteins that specific base pairs are often recognized by two amino acid residues working cooperatively, the sequences were further examined for a second residue that would correlate with the recognition of the G or C base at the position immediately 3' to the methylation target adenine. It was observed that the amino acid residue two positions toward the amino terminus of the polypeptides from the R or D position correlated, albeit with some variability, with the G or C base recognition. For those sequences recognizing the C base, this residue was most commonly a glutamic acid, "E", while for those recognizing a G base, this residue was most often a lysine, "K". This position thus has a charge opposite that of the "R" or "D" position identified as correlating 100% with the DNA base recognized, i.e., for the positive "R" residue correlating with the C base there is a negative charge "E" at this position, while for the negative "D" residue correlating with the G base there is a positive charged "K". The two most diverged sequences, SpoDI and DraRI, both had different residues than the other members of their group at this position, with DraRI having a threonine residue, "T" rather than the "E", while SpoDI has an insertion of two additional residues, glycine-valine, "GV", immediately preceding the glycine "G" residue at this position. PspOMII had a "D" at this position, which forms a unique combination with the "D" residue at the 1:1 correlating position, which is consistent with the unique base recognition for PspOMII, "R". Thus while the residues at this position (MmeI E806) were not the same within each base recognition grouping, they exhibited significant correlation with the DNA base recognized, and there was no example of the same residue present in more than one base recognition group. The amino acid residues at this second position identified (MmeI E806) were then altered in conjunction with that of the first position identified (MmeI R808) in order to change the DNA recognition at the base position following the methylation target adenine from C to G for MmeI, and from G to C for NmeAIII.

The correlated amino acid residues E806 and R808 in MmeI, and the equivalent position K816 and D818 in NmeAIII, were changed to the amino acid residue of the group recognizing the differing base by site-directed mutagenesis to generate the MmeI double mutant E806K, R808D, and the NmeAIII double mutant K816E and D818R. For each enzyme, two oligonucleotide primers were synthesized and used in the Phusion™ site-directed mutagenesis kit procedure. The MmeI primers were:

forward: 5'-pGATTATAGATATTCTGCCAGCCTGGTT-3' (SEQ ID NO:27), where p is a phosphate, and reverse: 5'-p ACTTTTTAACCTTCCTGCTACAGTTCTCATCCAGCAGTTGTGCA-3' (SEQ ID NO:31). The primers to change NmeAIII were:

forward: 5'-pCGCTATCGCTACTCTAATACCGTCGT-3' (SEQ ID NO:29) and reverse: 5'-p GCTTTCCAGACGACCTCCAACGTTACGCATAAAGGCGTTGTG-3' (SEQ ID NO:32).

Figure 2:
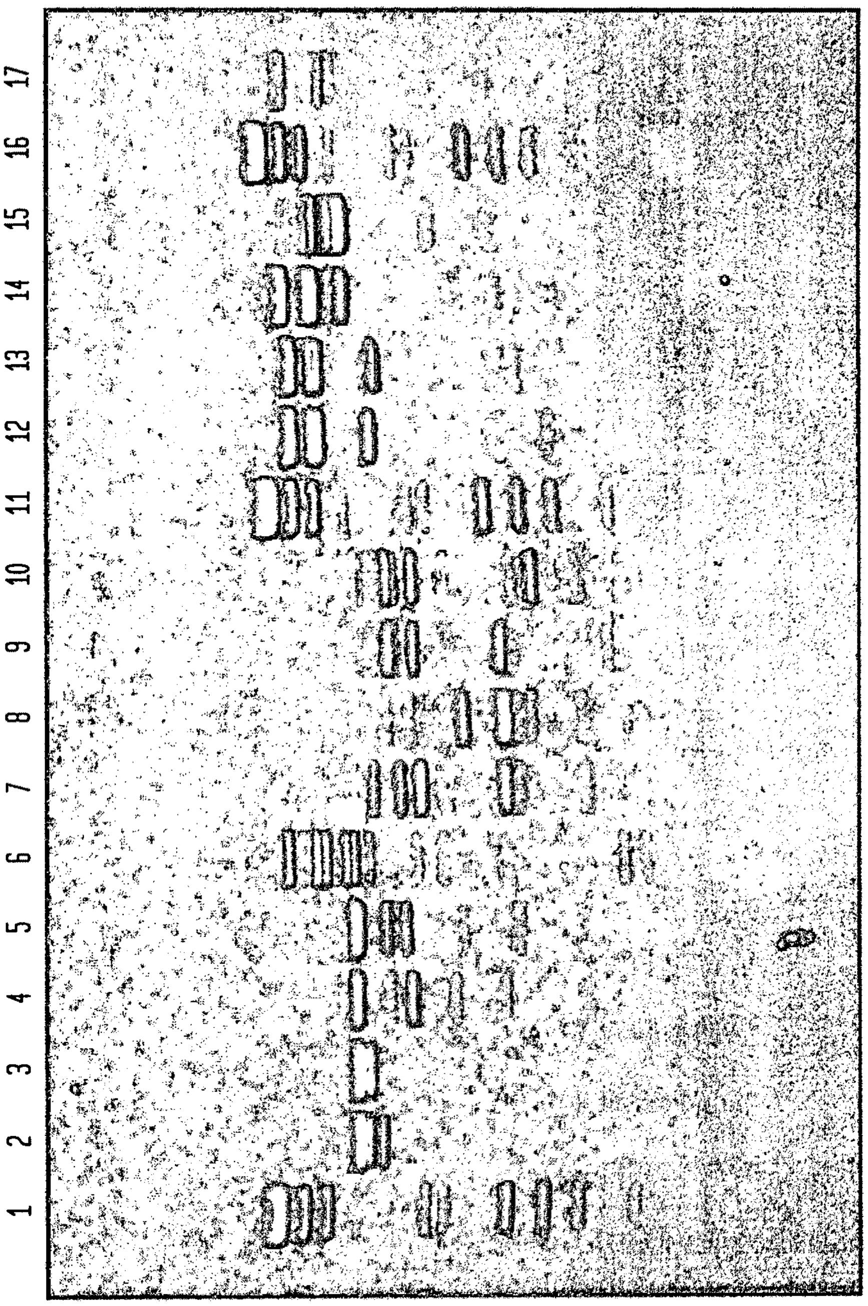
FIG. 2 shows mapping of rationally altered NmeAIII K816E+D818R on pBR322, PhiX and pBC4 DNAs. Lanes 2-5 are pBR322 DNA cut with the rationally altered NmeAIII K816E+D818R enzyme plus the following single site enzymes: lane 2-EcoRI, lane 3-NruI, lane 4-PvuII, and lane 5-PstI. Lanes 7-10 are PhiX174 DNA cut with the rationally altered NmeAIII K816E+D818R enzyme plus the following single site enzymes: lane 7-PstI, lane 8-SspI, lane 9-NciI, and lane 10-StuI. Lanes 12-15 and 17 are pBC4 DNA cut with the rationally altered NmeAIII K816E+D818R enzyme plus the following single site enzymes: lane 12-AvrII, lane 13-PmeI, lane 14-AscI, lane 15-EcoRV, and lane 17-NdeI. Lanes 1, 11 and 16 are Lambda-HindIII+PhiX-HaeIII size standard. Lane 6 is Lambda-BstEII+pBR322-MspI size standard.
Figure 3B:
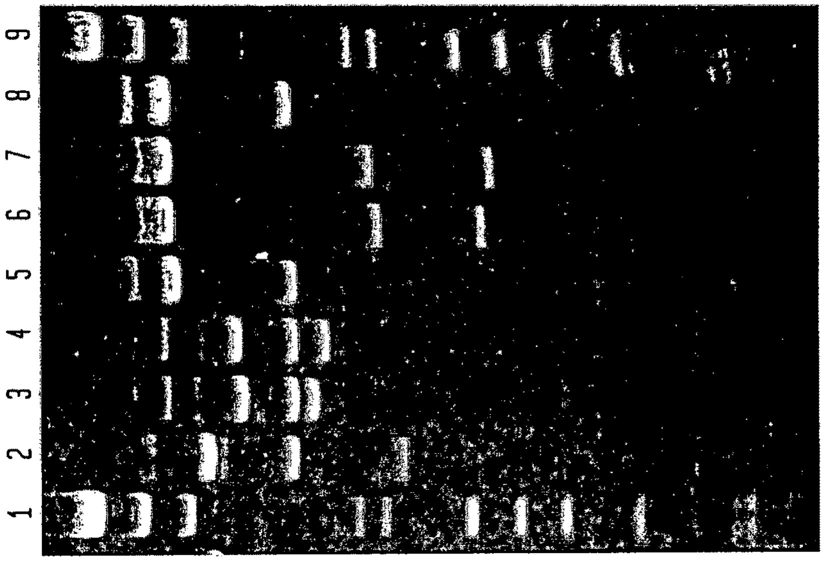
In FIG. 3B, lanes 2-8 show mapping of the cleavage activity of rationally altered MmeI A774L on pBC4 DNA. Lanes 2-8 are pBC4 DNA cut with the rationally altered MmeI A774L enzyme plus the following single site enzymes: lane 2-NdeI, lane 3-AvrII, lane 4-PmeI, lane 5-AscI, lane 6-SpeI, lane 7-EcoRV, and lane 8-rationally altered MmeI only. Lanes 1 and 8 are Lambda-HindIII+PhiX174-HaeIII size standards.
Figure 3A:
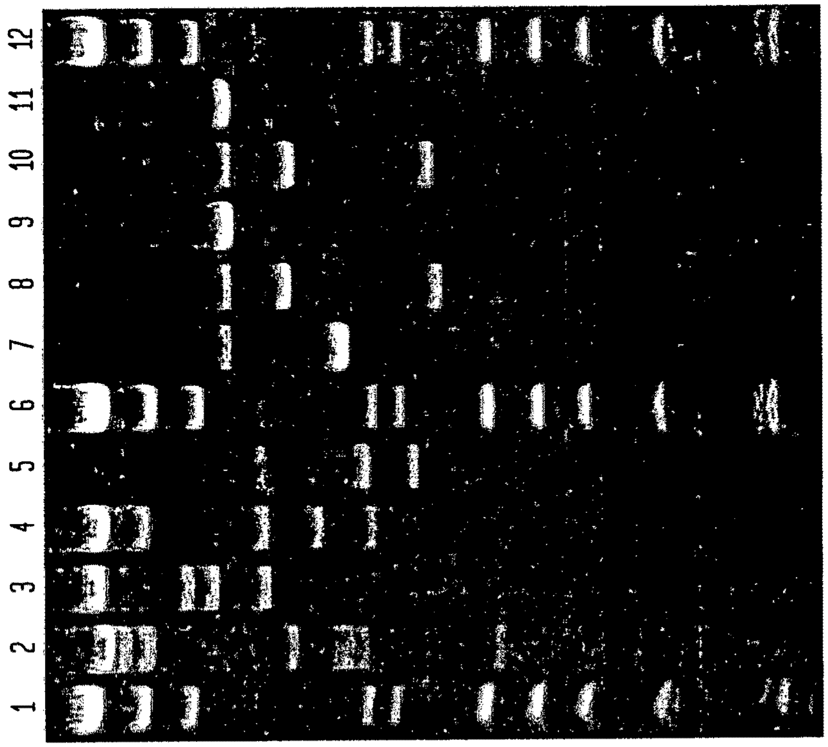
In FIG. 3A, lanes 2-5 show the cleavage pattern produced by the rationally altered MmeI A774L enzyme on various DNA substrates. Lane 2 is lambda DNA, lane 3-T7 DNA, lane 4-T3 DNA and lane 5-pBR322 DNA. Lanes 7-11 show mapping of the cleavage activity of rationally altered MmeI A774L on PhiX DNA. Lanes 7-11 are PhiX DNA cut with the rationally altered MmeI A774L enzyme plus the following single site enzymes: lane 7-PstI, lane 8-SspI, lane 9-NciI, lane 10-StuI, and lane 11-rationally altered MmeI only. Lanes 1, 6 and 12 are Lambda-HindIII+PhiX174-HaeIII size standards.
Figure 4A:
In FIG. 4A, lanes 2-4 show the cleavage pattern produced by the rationally altered MmeI A774K+R801S enzyme on various DNA substrates: lane 2 is lambda DNA, lane 3-T7 DNA and lane 4-T3 DNA. Lanes 1 and 5 are Lambda-HindIII+PhiX174-HaeIII size standards.
Figure 4B:
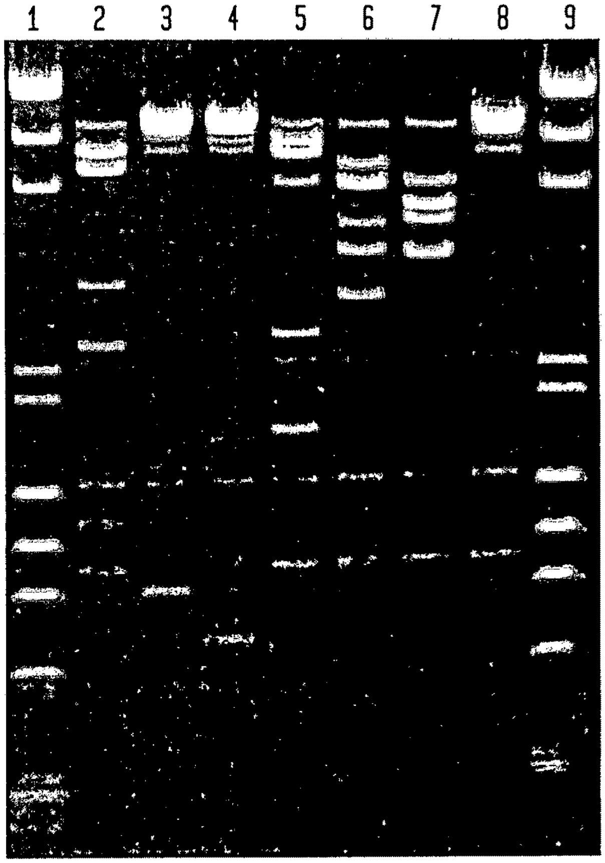
FIG. 4B shows mapping of the cleavage activity of rationally altered MmeI A774K+R801S on pBC4 DNA. Lanes 2-8 are pBC4 DNA cut with the rationally altered MmeI A774K+R801S enzyme plus the following single site enzymes: lane 2-NdeI, lane 3-AvrII, lane 4-PmeI, lane 5-AscI, lane 6-SpeI, lane 7-EcoRV, and lane 8-rationally altered MmeI only. Lanes 1 and 8 are Lambda-HindIII+PhiX174-HaeIII size standards.
Figure 5D:
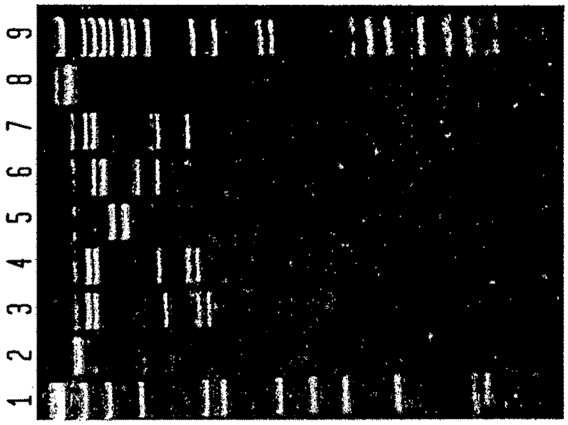
FIG. 5D shows mapping of the cleavage activity of rationally altered MmeI E751R+N773D on pBC4 DNA. Lanes 2-8 are pBC4 DNA cut with the rationally altered MmeI E751R+N773D enzyme plus the following single site enzymes: lane 2-NdeI, lane 3-AvrII, lane 4-PmeI, lane 5-AscI, lane 6-SpeI, lane 7-EcoRV, and lane 8-rationally altered MmeI only. Lane 1 is Lambda-HindIII+PhiX-HaeIII size standard. Lane 8 is Lambda-BstEII+pBR322-MspI size standard.
Figure 5C:
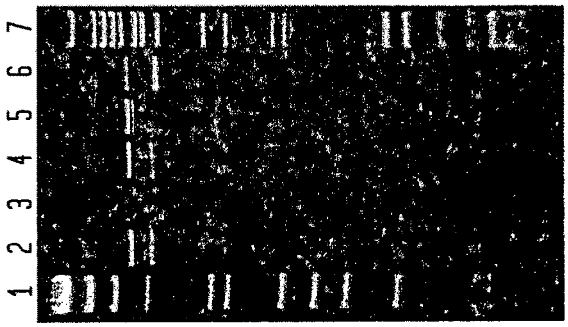
FIG. 5C shows mapping of the cleavage activity of rationally altered MmeI E751R+N773D on PhiX DNA. Lanes 2-6 are PhiX DNA cut with the rationally altered MmeI E751R+N773D plus the following single site enzymes: lane 2-PstI, lane 3-SspI, lane 4-NciI, lane 5-StuI, lane 6-MmeI E751R+N773D enzyme alone. Lane 1 is Lambda-HindIII+PhiX-HaeIII size standard. Lane 7 is Lambda-BstEII+pBR322-MspI size standard.
Figure 5B:
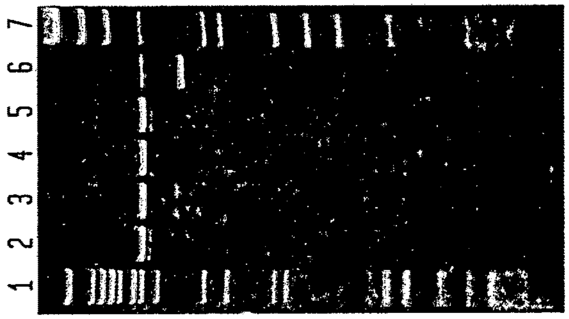
FIG. 5B shows mapping of the cleavage activity of rationally altered MmeI E751R+N773D on pBR322 DNA. Lanes 2-6 are pBR322 DNA cut with the rationally altered MmeI E751R+N773D plus the following single site enzymes: lane 2-EcoRI, lane 3-NruI, lane 4-PvuII, lane 5-PstI, and lane 6-MmeI E751R+N773D enzyme alone. Lane 6 is Lambda-HindIII+PhiX-HaeIII size standard. Lane 1 is Lambda-BstEII+pBR322-MspI size standard.
Figure 5A:
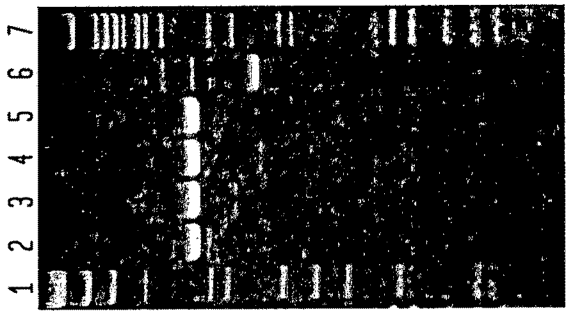
FIG. 5A shows mapping of the cleavage activity of rationally altered MmeI E751R+N773D on pUC19 DNA. Lanes 2-6 are pUC19 DNA cut with the rationally altered MmeI E751R+N773D plus the following single site enzymes: lane 2-EcoO109I, lane 3-PstI, lane 4-AlwNI, lane 5-XmnI, and lane 6-MmeI E751R+N773D enzyme alone. Lane 1 is Lambda-HindIII+PhiX-HaeIII size standard. Lane 7 is Lambda-BstEII+pBR322-MspI size standard.

Mutagenesis was performed according to the manufacturer's directions. The altered polynucleotides encoding the desired altered polypeptide sequences in their respective expression vectors were transformed into *E. coli* host cells. Two individual transformants of the altered MmeI and the altered NmeAIII were each inoculated into 30 ml of LB containing 100 micrograms/ml ampicillin and grown to mid-log phase, then IPTG was added to 0.4 mM and the cells were grown for two hours to induce expression of the altered protein. The cells were harvested by centrifugation, resuspended in 1.5 ml of sonication buffer SB (20 mM Tris, pH7.5, 1 mM DTT, 0.1 mM EDTA) and lysed by sonication. The extract was clarified by centrifugation. To test for endonuclease activity, serial dilutions of the extract were performed in NEBuffer 4, using pBC4 DNA (New England Biolabs, Inc., Ipswich, Mass.) linearized with NdeI as the DNA substrate. Discrete banding was observed for the altered MmeI, E806K and R808D, and the altered NmeAIII, K816E and D818R, indicating that the altered polynucleotide sequences encoded active endonucleases (FIGS. 1 and 2, and #14 and #17 in FIG. 25B).

Characterization of the Altered MmeI DNA Recognition Sequence

The crude extract for the altered MmeI was purified over a 1 ml Heparin HiTrap column (GE Healthcare, Piscataway, N.J.). The 1.5 ml crude extract was applied to the column, which had been previously equilibrated in buffer A (20 mM Tris pH7.5, 1 mM DTT, 0.1 mM EDTA) containing 50 mM NaCl. The column was washed with 5 column volumes of buffer A containing 50 mM NaCl, then a 30 ml linear gradient in buffer A from 0.05M NaCl to 1M NaCl was applied and 1 ml fractions were collected. The altered MmeI was eluted at approximately 0.48M NaCl. It was expected that the rationally changed MmeI enzyme would recognize 5'-TCCRAG-3'. To determine the DNA recognition sequence for the altered polypeptide, the positions of cleavage for the purified enzyme were mapped on pBR322 DNA (FIG. 1 and #17 in FIG. 25B). The DNA was cut with the purified MmeI mutant, purified, and then were cut with an enzyme that cleaves once at a known position. The size of the unique fragments produced by the double digestion of the DNA showed the distance from the location of the known enzyme cutting position to the position of cutting by the MmeI mutant enzyme. The altered MmeI enzyme cutting positions on pBR322 were mapped to approximate positions 260, 310, 1340 and 2790. The sequence TCCRAG occurs in pBR322 at positions 276, 330, 1314 and 2772, which matches the observed cutting positions. The wild type MmeI recognition sequence, TCCRAC, occurs in pBR322 at positions 197, 283, 2662 and 2846, which did not match the observed cutting positions. The pattern of DNA fragments produced from endonuclease cleavage of phage lambda DNA, phage T3 DNA, pBC4 (Schildkraut *Genet. Eng.* 6:117-140 (1984)).) DNA and phage PhiX DNA was determined to match cleavage at the new recognition sequence TCCRAG (FIG. 1). These results indicate that the DNA base recognized by the altered MmeI at position six has been changed from C to G, as predicted by the rational, site-directed change of the amino acid residues at the positions identified as correlating with recognition of the DNA base at the 3'-most position in the recognition sequence alignment. The altered MmeI restriction endonuclease binds at the novel DNA sequence 5'-TCCRAG-3' and cleaves the DNA 20 nucleotides 3' to this sequence on this strand, and 18 nucleotides 5' to the complementary sequence of the opposite strand 5'-CTYGGA-3' to leave a two base, 3' overhang. Application of the method resulted in the creation of a novel restriction endonuclease.

Characterization of the Altered NmeAIII DNA Recognition Sequence

The crude extract for the altered NmeAIII was used directly to map the cutting positions of this endonuclease in various DNAs. It was predicted that the rationally altered NmeAIII would recognize 5'-GCCGAC-3'. To determine the DNA recognition sequence for the altered polypeptide, the positions of cleavage for the altered enzyme were mapped on pBR322, PhiX174 and pBC4 DNAs (FIG. 2 and #17 in FIG. 19B). DNA was digested with the altered NmeAIII enzyme, purified on a spin column. The size of the unique fragments produced by the double digestion of the DNA indicated the distance from the location of the known enzyme cutting position to the position of cutting by the NmeAIII mutant enzyme.

Figure 9:
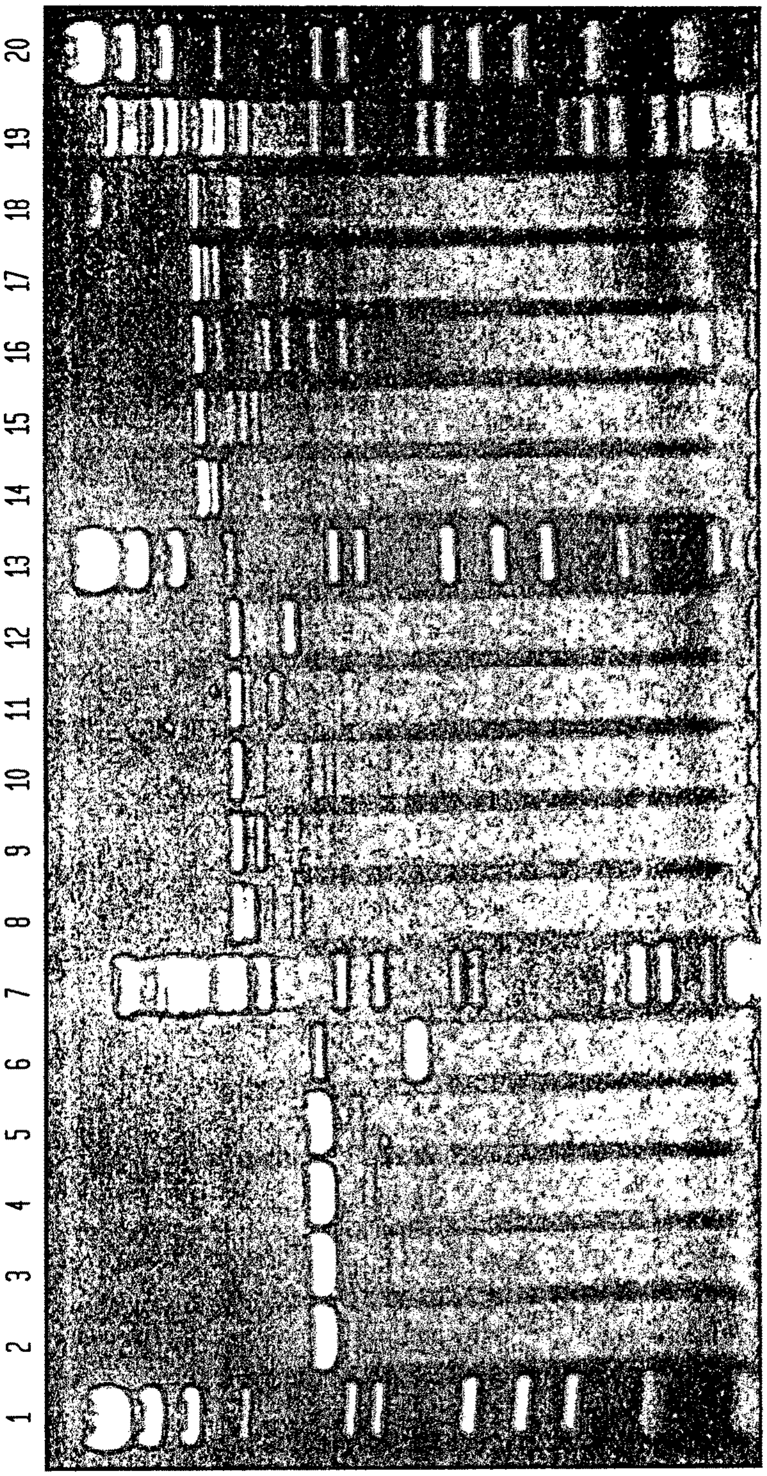
FIG. 9 shows the cleavage activity of rationally altered SdeA6CI enzyme: SdeAI K791E+D793R on pUC19, pBR322 and PhiX DNAs. Lanes 2-6 are pUC19 DNA cut with the rationally altered SdeAI K791E+D793R enzyme plus the following single site enzymes: lane 2-EcoO109I, lane 3-PstI, lane 4-AlwNI, lane 5-XmnI, and lane 6-SdeAI K791E+D793R enzyme alone. Lanes 8-12 are pBR322 DNA cut with the rationally altered SdeAI K791E+D793R enzyme plus the following single site enzymes: lane 8-EcoRI, lane 9-NruI, lane 10-PvuII, lane 11-PstI, and lane 12-SdeAI K791E+D793R enzyme alone. Lanes 14-18 are PhiX DNA cut with the rationally altered SdeAI K791E+D793R enzyme plus the following single site enzymes: lane 14-PstI, lane 15-SspI, lane 16-NciI, lane 17-StuI, and lane 18-SdeAI K791E+D793R enzyme alone. Lanes 1, 13 and 20 are Lambda-HindIII+PhiX-HaeIII size standard. Lanes 7 and 19 are Lambda-BstEII+pBR322-MspI size standard.

The altered NmeAIII enzyme cut pBR322 at positions approximately 450 and 950. The sequence GCCGAC occurs in pBR322 at positions 446 and 941, which matches the observed cutting positions. The wild type NmeAIII recognition sequence, GCCGAG, occurs in pBR322 at positions 120, 1172 and 3489, which differed from altered NmeAIII recognition sequence. Similarly for phiX174 DNA, altered NmeAIII-cut positions in PhiX174 were mapped to approximately 2300, 2675, 3435, 4740 and 5335. The expected NmeAIII-altered recognition sequence, GCCGAC, occurs at positions 2251, 2641, 3474, 4710 and 5298, which matched the observed position of cutting. The wild type NmeAIII recognition sequence occurred in PhiX174 at positions 1022, 3426 and 4680, which differed from the recognition sequence of the altered NmeAIII. Similar results were obtained for pBC4 DNA mapping. These results indicated that the recognition sequence of NmeAIII was altered from G to C at the final base position as predicted by our rational, site-directed change of the amino acid residues found to correlate to the DNA base recognized at this position. These results are examples of how a directed change of the recognition sequence of a restriction endonuclease can be achieved where the amino acid residues confer specificity for a DNA base altered in a rational way to generate a predictable new DNA recognition specificity. The recognition specificity of SdeAI has also been changed through application of the same method from 5'-CAGRAG-3' to 5'-CAGRAC-3' (FIG. 9).

Example 2

Position-Specific Mutagenesis to Create a Novel DNA Recognition Sequence

Figure 12:
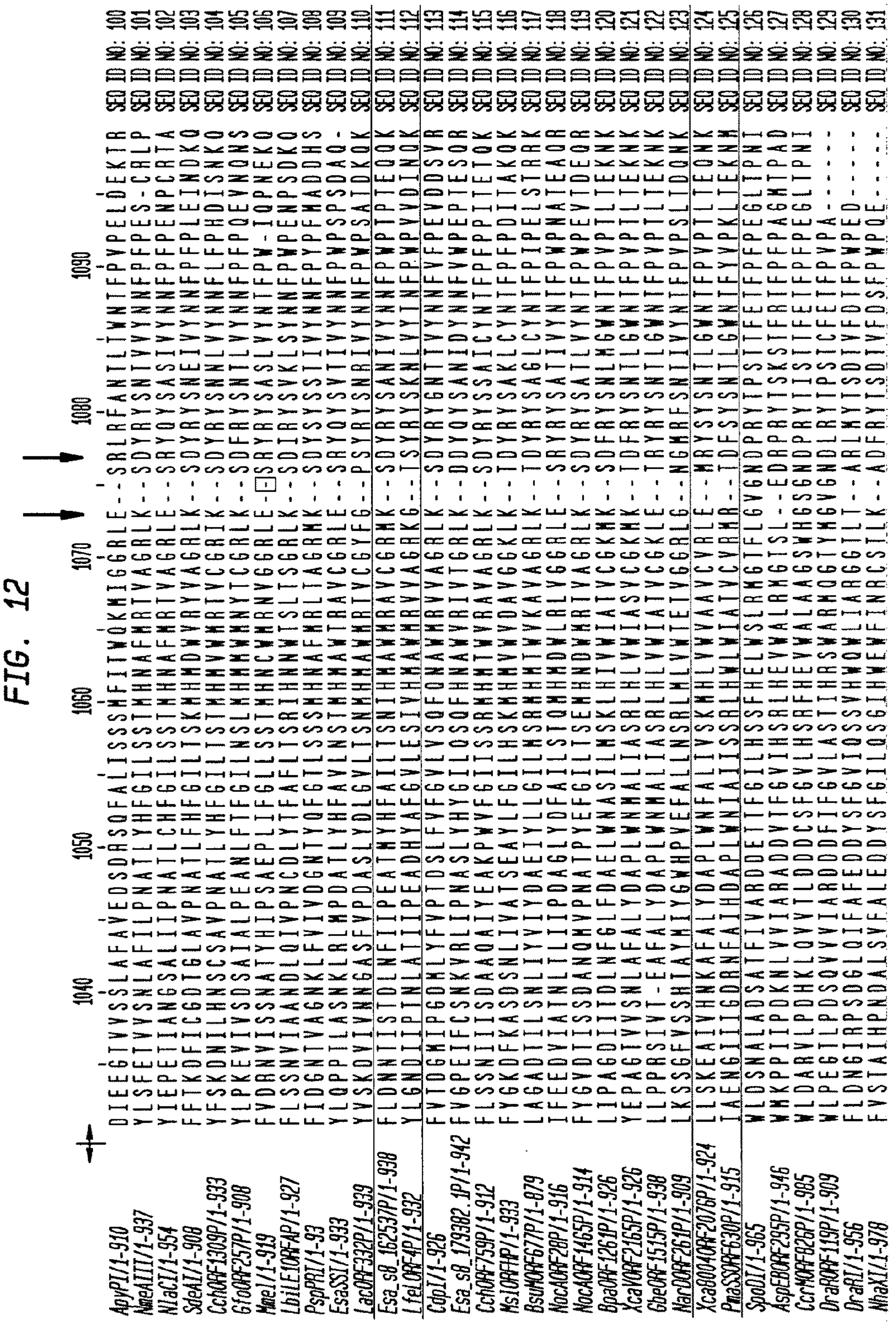
FIG. 12 shows an amino acid sequence alignment of SEQ ID NOS:100-131 (an MmeI-like set) in which amino acid residues are identified, at positions characterized as determining recognition at position 6 in the recognition sequence, that differ from known DNA base recognition determinants. Members of the set for which the DNA recognition sequence has not yet been characterized have been included in this alignment. The two arrows indicate the positions identified that determine recognition of the DNA base at position 6 (position 1073 and 1077 in this gapped CLUSTALW alignment). There are four sequences, which are underlined, in which the amino acid residue pairs observed do not match the pairs present in any previously characterized member of the set. These position-specific pairs are naturally occurring variations that are targets for introduction into a characterized enzyme as a means of altering the specificity of the characterized enzyme at the targeted DNA base recognition position. Two of the observed differing pairs, GXS (two occurrences) and G(N)G were introduced into the characterized enzyme MmeI and the DNA recognition specificity of the resulting rationally altered enzyme was investigated (see FIG. 6)

Identification of the two positions within the amino acid sequence alignment of the set of proteins that determine recognition of the first base at the 3' end in the aligned recognition sequences enabled the creation of novel restriction endonucleases using two approaches. In the first approach, the amino acid residues for all members of the set, including those for which the recognition sequence has not yet been determined, were aligned. The alignment was examined at the identified positions responsible for recognition to see if there were any naturally occurring variations that did not match the amino acids known to specify recognition of a given base (FIG. 12 and #32 in FIG. 25B). In the case of the characterized enzymes in Example 1, the amino acids at the alignment positions determining recognition at the position of the first base at the 3' end of the DNA recognition sequence for nucleotide “C” were ExR and TxR. Those amino acids determining recognition of a G were KxD and GxD. The aligned members of the set were examined and several amino acid combinations that were not one of these C or G determining combinations were observed. Two of these amino acid residue combinations, GxS observed in Genbank accession number gi|28373198, and GxG, observed in Genbank accession number gi|87198286, were introduced into the MmeI polypeptide by site-directed mutagenesis, using the same procedure as in Example 1.

To introduce coding for the GxS amino acid combination into the polynucleotide encoding the MmeI protein, two oligonucleotide primers were synthesized and used in the Phusion™ site-directed mutagenesis kit procedure. The primers utilized were forward: 5'-pCGATATTCTGCCAGCCTGGTTTACAACAC-3' (SEQ ID NO:165), where p is a phosphate, and reverse: 5'-pGTAACTAGTACCTAACCTTCCTCCTACATTTCTCATCCAGCA-3' (SEQ ID NO:166). The reverse primer introduced the directed mutations into the MmeI gene. Mutagenesis was performed according to the manufacturer's directions. The same procedure was followed to introduce the GxG combination of position-specific amino acid residues into MmeI, using as primers: forward: 5'-pCGATATTCTGCCAGCCTGGTTTACAACAC-3' (SEQ ID NO:167), where p is a phosphate, and reverse: 5'-pGTAACCGTTACCTAACCTTCCTCCTACATTTCTCATCCAGCA-3' (SEQ ID NO:168). The altered polynucleotides in the expression vector pRRS, encoding the desired altered polypeptide sequences, were transformed into *E. coli* host cells. One individual transformant of each altered MmeI were each inoculated into 30 ml of LB containing 100 micrograms/ml ampicillin and grown to mid-log phase, then IPTG was added to 0.4 mM and the cells were grown for two hours to induce expression of the altered protein. The cells were harvested by centrifugation, resuspended in 1.5 ml of sonication buffer SB (20 mM Tris, pH7.5, 1 mM DTT, 0.1 mM EDTA) and lysed by sonication. The extract was clarified by centrifugation. To test for endonuclease activity, the crude extract was used to cut PhiX174 DNA in NEBuffer 4 (New England Biolabs, Inc., Ipswich, Mass.) supplemented with SAM (80 micromolar). The cleaved DNA was purified over a Zymo Research "DNA Clean and Concentrate" spin column according to the manufacturer's instructions (Zymo Research, Orange, Calif.). The purified cut DNA was then used for mapping by cutting with four different known endonucleases. Discrete banding was observed for both the altered MmeI, E806G plus R808S, and the E806G plus R808G constructs, indicating that the altered polynucleotide sequences encoded active endonucleases.

Figure 6B:
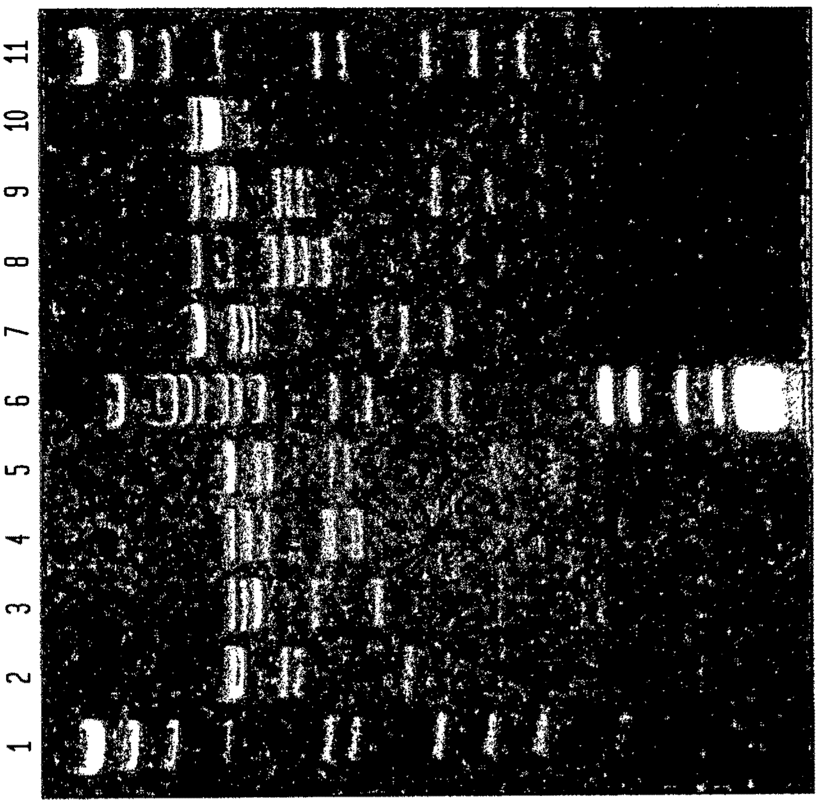
FIG. 6B shows the cleavage activity of rationally altered MmeI: E806G+R808G (+S807N) on pBR322 and PhiX174 DNAs. Lanes 2-5 are pBR322 cut with the rationally altered MmeI E806G+R808G (+S807N) plus the following single site enzymes: lane 2-EcoRI, lane 3-NruI, lane 4-PvuII, lane 5-PstI. Lanes 7-10 are PhiX174 cut with the rationally altered MmeI E806G+R808G (+S807N) plus the following single site enzymes: lane 7-PstI, lane 8-SspI, lane 9-NciI, and lane 10-StuI. Lanes 1 and 11 are Lambda-HindIII+PhiX-HaeIII size standard. Lane 7 is Lambda-BstEII+pBR322-MspI size standard.
Figure 6A:
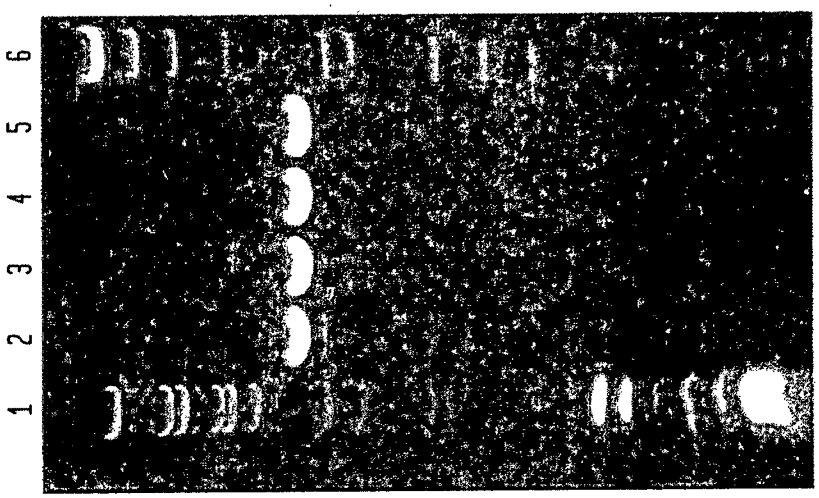
FIG. 6A shows the cleavage activity of rationally altered MmeI: E806G+R808G (+S807N) on pUC19 DNA. Lanes 2-5 are pUC19 cut with the rationally altered MmeI E806G+R808G (+S807N) plus the following single site enzymes: lane 2-EcoO109I, lane 3-PstI, lane 4-AlwNI, lane 5-XmnI. Lane 1 is Lambda-BstEII+pBR322-MspI size standard. Lane 6 is Lambda-HindIII+PhiX-HaeIII size standard.

The altered MmeI E806G plus R808G enzyme cut pUC19 at positions approximately 1135 and 1335 (FIG. 6A and #36 in FIG. 25B). The sequence TCCRAR occurs in pUC19 at positions 1105 (TCCRAG) and 1352 (TCCRAA), which matches the observed cutting positions. The wild type MmeI recognition sequence, TCCRAC, occurs in pUC19 at positions 996 and 1180, which did not match the positions observed for the altered enzyme. For pBR322 and phiX174 DNA, similar results were obtained (FIG. 6B). The altered enzyme cut positions in PhiX174 were mapped to approximately 25, 500, 3600, 3835 and 4135. The TCCRAR sequence occurs near these positions at 41, 471, 518, 3588, 3606, 3857 and 4143, which matches the observed position of cutting. The TCCRAR sequence also occurs at additional positions, 1510, 1671, 2998, 3959 and 3970. While cutting was not observed at these positions, the amount of enzyme available for cutting was limited and thus the digestion of the DNA was incomplete. The sites mapped were consistent with the altered enzyme cutting at TCCRAR, and were not consistent with cutting at the wild type unaltered specificity, TCCRAC, indicating the altered enzyme cleaves at a new specificity, namely TCCRAR.

Example 3

Creation of Enzymes that Recognize Novel DNA Recognition Sequences

Further enzymes that specifically recognize new DNA sequences were formed and characterized using the methods exemplified in Example 1 and 2 above. The oligonucleotide primers used for site-directed mutagenesis are shown in Table 1.

One such enzyme recognizing 5'-TCCGAC-3' was formed by site-directed mutagenesis of MmeI, changing alanine 774 to leucine, using primers SEQ ID NO:151 and SEQ ID NO:152. The recognition specificity of this altered enzyme is demonstrated in FIG. 3.

Another such enzyme recognizing 5'-TCCCAC-3' was formed by site-directed mutagenesis of MmeI, changing alanine 774 to lysine using primers SEQ ID NO:153 and SEQ ID NO:154, followed by altering arginine 810 to serine using primers SEQ ID NO:155 and SEQ ID NO:156. The recognition specificity of this altered enzyme is demonstrated in FIG. 4.

Another new enzyme recognizing 5'-TCGRAC-3' was formed by site-directed mutagenesis of MmeI, changing glutamate 751 to arginine and asparagine 773 to aspartate, using primers SEQ ID NO:157 and SEQ ID NO:158. The recognition specificity of this altered enzyme is demonstrated in FIG. 5.

Another new enzyme recognizing 5'-TCCRAB-3' was formed by site-directed mutagenesis of MmeI, changing glutamate 806 to glycine and arginine 808 to threonine, using primers SEQ ID NO:159 and SEQ ID NO:160. The recognition specificity of this altered enzyme is demonstrated in FIG. 7.

Another new enzyme recognizing 5'-TCCRAN-3' was formed by site-directed mutagenesis of MmeI, changing glutamate 806 to trytophan and arginine 808 to alanine, using primers SEQ ID NO:161 and SEQ ID NO:162. The recognition specificity of this altered enzyme is demonstrated in FIG. 8.

Another new enzyme recognizing 5'-CAGRAC-3' was formed by site-directed mutagenesis of SdeAI, changing lysine 791 to glutamate and aspartate 793 to arginine, using primers SEQ ID NO:163 and SEQ ID:164. The recognition specificity of this altered enzyme is demonstrated in FIG. 9.

TABLE 1

List of oligonucleotide primers

Figure 7:
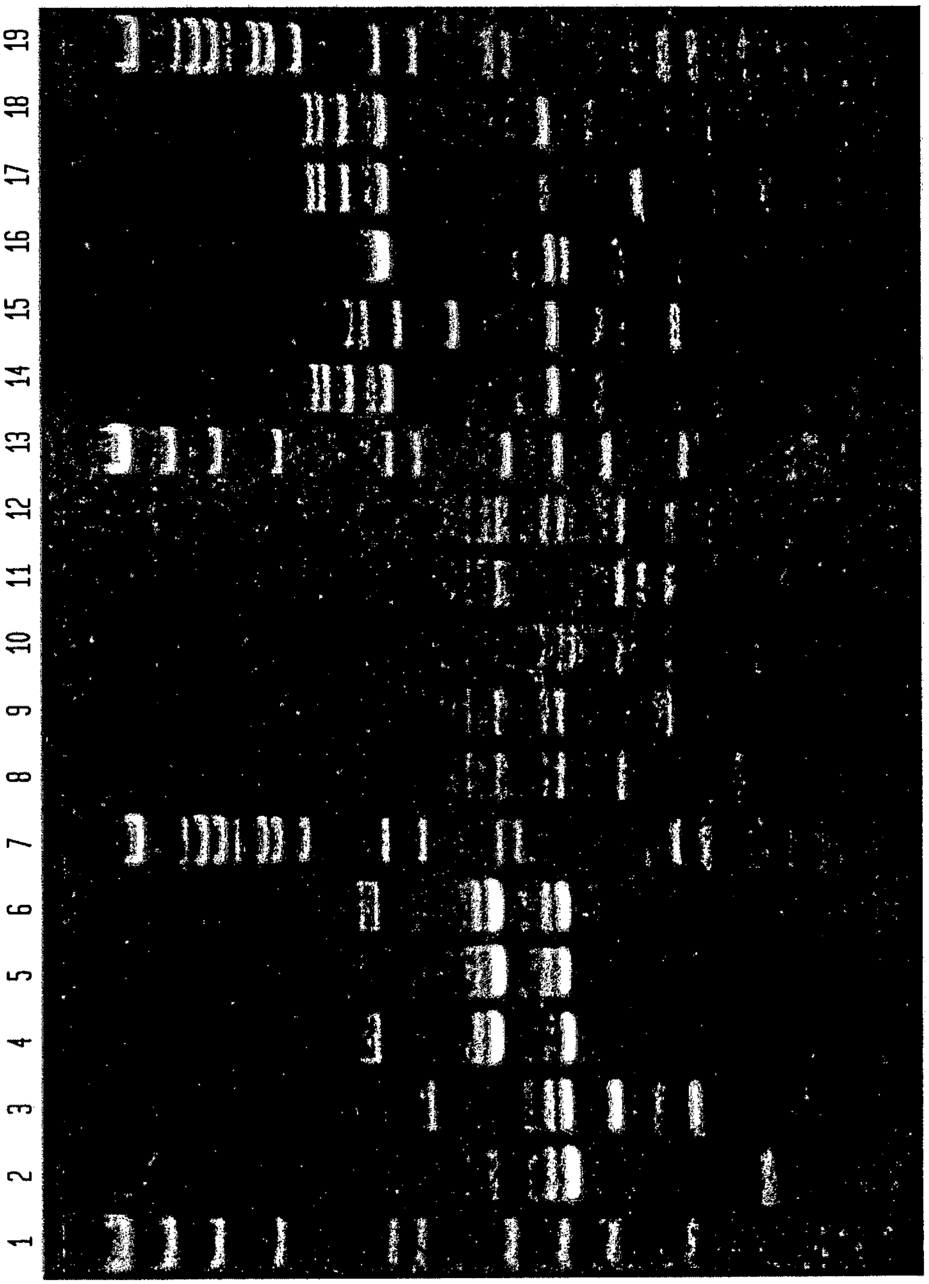
FIG. 7 shows the cleavage activity of rationally altered Mme6BI enzyme: MmeI E806G+R808T on pUC19, pBR322 and PhiX DNAs. Lanes 2-6 are pUC19 DNA cut with the rationally altered MmeI E806G+R808T enzyme plus the following single site enzymes: lane 2-EcoO109I, lane 3-PstI, lane 4-AlwNI, lane 5-XmnI, and lane 6-MmeI E806G+R808T enzyme alone. Lanes 8-12 are pBR322 DNA cut with the rationally altered MmeI E806G+R808T enzyme plus the following single site enzymes: lane 8-ClaI, lane 9-NruI, lane 10-NdeI, lane 11-PstI, and lane 12-MmeI E806G+R808T enzyme alone. Lanes 14-18 are PhiX DNA cut with the rationally altered MmeI E806G+R808T enzyme plus the following single site enzymes: lane 14-PstI, lane 15-SspI, lane 16-NciI, lane 17-StuI, and lane 18-MmeI E806G+R808T enzyme alone. Lanes 1 and 13 are Lambda-HindIII+PhiX-HaeIII size standard. Lanes 7 and 19 are Lambda-BstEII+pBR322-MspI size standard.
Figure 8:
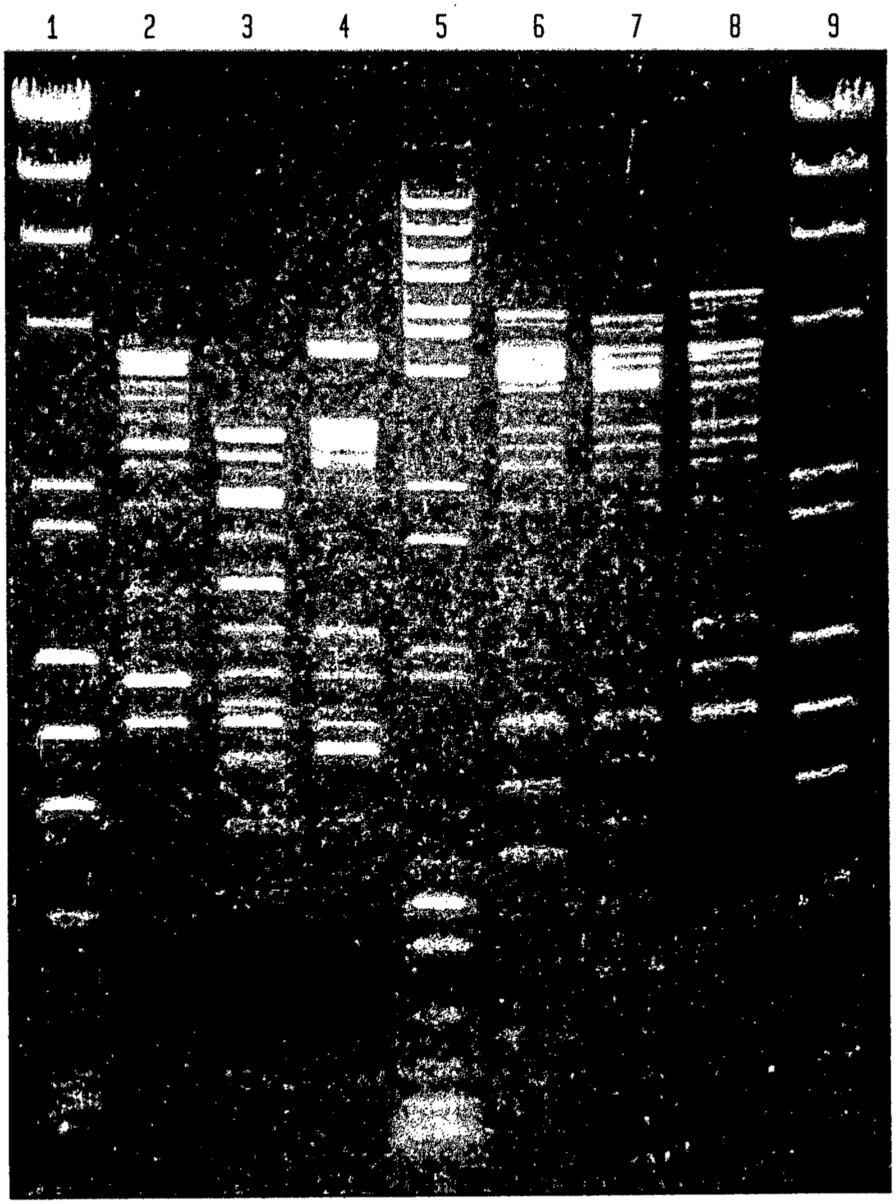
FIG. 8 shows the cleavage activity of rationally altered Mme6NI enzyme: MmeI E806W+R808A on phage ϕX DNA. Lanes 2-4 and 6-8 are phage ϕX DNA cut with the rationally altered MmeI E806W+R808A enzyme plus the following single site enzymes: lane 2-PstI, Lane 3-SspI, lane 4-NciI, lane 6-StuI, lane 7-BsiEI, and lane 8-MmeI E806W+R808A enzyme alone. Lanes 1 and 9 are Lambda-HindIII+PhiX-HaeIII size standard. Lane 5 is Lambda-BstEII+pBR322-MspI size standard.

| | | | |
|---|---|---|---|
| Mme4GI | A774L | CTGACGTATCATATTCCTAGTGCTGAACCT (SEQ ID NO: 151) and | FIG. 3 |
| | A774L | GTTACTTGAAATGACATTTCTATCAACAAAAC (SEQ ID NO: 152)) | |
| Mme4CI | A774K | AAGACGTATCATATTCCTAGTGCTGAACCT (SEQ ID NO: 153) and | FIG. 4 |
| | A774K | GTTACTTGAAATGACATTTCTATCAACAAAAC (SEQ ID NO: 154) | |
| | R810S | AGCTATTCTGCCAGCCTGGTTTACA (SEQ ID NO: 155) and | |
| | R810S | GTAACGACTTTCTAACCTTCCTCCTACA (SEQ ID NO: 156) | |
| Mme3GI | E751R | CAATTGGAATAAATTGTCTGTTTTCAGATGATGTGCGAGGTATCAACAGATAGTCCGTATCCG (SEQ ID NO: 157) and | FIG. 5 |
| | N773D | GTTTTGTTGATAGAAATGTCATTTCAAGTGACGCAACGTATCATATTCCTAGTGCTGAAC (SEQ ID NO: 158) | |
| Mme6BI | E806G | GCTGCCTAACCTTCCTCCTACATTTCTCATCCA (SEQ ID NO: 159) and | FIG. 7 |
| | R808T | ACCTATAGATATTCTGCCAGCCTGGTTTACA (SEQ ID NO: 160) | |
| Mme6NI | R808A | GTGCCTATAGATATTCTGCCAGCCTGGTTTACA (SEQ ID NO: 161) and | FIG. 8 |
| | E806W | TCCATAACCTTCCTCCTACATTTCTCATCCA (SEQ ID NO: 162) | |
| SdeA6CI | D793R | CGTTATTCAAATGAAATTGTTTATAACAACTTCCCT (SEQ ID NO: 163) and | FIG. 9 |

TABLE 1-continued

| List of oligonucleotide primers | |
|---|---|
| K791E | GTAACGACTTTCTAATCTTCCAGCAACATA CCGCA (SEQ ID NO: 164) |

In summary, Examples 1, 2 and 3 demonstrate alteration of a DNA binding protein to recognize a novel DNA sequence through identifying the positions in the DNA binding protein that determine position-specific DNA base recognition and alteration of those positions to differing amino acid residues observed in uncharacterized naturally occurring sequences.

Example 4

Prediction of DNA Recognition Specificity for Uncharacterized DNA Binding Proteins Once the position(s) within an amino acid alignment and the specific amino acid residues at those position(s) that confer position-specific DNA base recognition were identified, the DNA recognition specificity of uncharacterized polypeptides homologs could be accurately predicted. We have shown that the amino acids ExR corresponding to positions E806-(S)-R808 in MmeI specify recognition of a “C” in the DNA recognition sequence position immediately 3' to the methylation target adenine in the family of homolog sequences related to MmeI. Any homolog found in a database, such as Genbank, that has the same amino acid residues, ExR at this position in the amino acid sequence alignment within the MmeI family of polypeptides is predicted with a high degree of certainty to recognize a “C” at this position. Similarly, the presence of the residues “KxD” at this position predicted that the polypeptide would recognize a “G” at this position. Variations in correlation of amino acids with type and position of nucleotide in the recognition sequence could be factored into the prediction. For example, residues “TxR” (from DraRI) had a predicted recognition of “C”, while “GVGND” (from SpoDI) had a predicted recognition of “G.” This prediction scheme has provided accurate predictions of DNA bases that are recognized for all members of the set characterized to date, such as EsaSSI where the DNA recognition sequence was found experimentally to be 5'-GACCAC-3', and in which C was correctly predicted at the 3'-most position (FIG. 10A).

Example 5

Assembly of the Methyltransferase Family

The gamma-class N6A DNA methyltransferases shown in FIG. 22 were assembled by collecting sequences of enzymes for which the specific DNA recognition sequence was known and that recognized six DNA bases from the list of gamma class adenine methyltransferases in the REBASE database. The collected amino acid sequences were aligned using the PROMALS algorithm (prodata.swmed.edu/promals/promals.php). The DNA recognition sequences were aligned, placing the adenine that is presumed to be the modified adenine at position 5 of the alignment. The position in the aligned amino acid sequences identified by the box is significantly correlated with the DNA base recognized at position 3 of the recognition sequence alignment (Chi square P value <0.001). This is an example of using the method described to identify recognition sequence determinants in a family of proteins other than the MmeI-like family.

Example 6

Identification of the Position Specific Amino Acid Residues that Specify Recognition for Position 0 in MmeI Family Enzymes, and Creation of Enzymes that Recognize Novel DNA Recognition Sequences The DNA recognition sequences of characterized MmeI-family enzymes that recognize 7 or 8 base pair sequences were aligned. The alignment was made using the DNA strand that contains the adenine base that is modified by the DNA methyltransferase activity of these enzymes, and that is also the strand that is cleaved 3' to the DNA recognition sequence. The DNA recognition sequences alignment was put in register by aligning so that the adenine base that is methylated is aligned for each enzyme. The DNA recognition sequence alignment is given in FIG. 26.

A multiple sequence alignment was constructed from the primary amino acid sequences of the characterized MmeI-family enzymes that recognize 7 or 8 base pair sequences described in FIG. 1. The alignment program PROMALS was used: http://prodata.swmed.edu/promals3d/promals3d.php. The default settings were employed in the algorithm, except that the ‘identity threshold above which fast alignment is applied’ was set to 0.85. A portion of the multiple sequence alignment obtained is presented in FIG. 26.

The polypeptide sequences were grouped according to the DNA base recognized at the DNA recognition sequence alignment position 0 (the 5' most base recognized in these enzymes). The enzymes recognizing cytosine, “C”, are RceI, RpaBI, SstE37I, GauT27I, PspOMII, RpaB5I, PliMI and MaqI. The enzymes recognizing guanine, “G”, at this position, are AquII, AquIV, SpoDI and RpaTI. As described above in Examples 1, 2 and 3, the alignment was interrogated for amino acid residues at a given position in the alignment that were the same within the C and within the G group but which differed between the groups. Upon examination of the alignment, two positions were observed having significant correlation between the amino acid residue present at the amino acid alignment position and the DNA base recognized at this DNA recognition sequence alignment position. The identified positions are shown in FIG. 26. The amino acid residues present at both positions are charged and can readily form hydrogen bonds with DNA bases. The positions of these residues in the GauT27I sequence are R790 and E802, while in MaqI these residues are R817 and E829.

Further enzymes that specifically recognize new DNA sequences were formed and characterized using the methods exemplified in Examples 1 and 2 above. The correlated amino acid residues, R790 and E802 in GauT27I, and the equivalent position residues R817 and E829 in MaqI, were changed to the amino acid residue of the group recognizing the differing base by site-directed mutagenesis to generate the GauT27I double mutant R790D and E802R, and the MaqI double mutant R817D and E829R. For each enzyme, two oligonucleotide primers were synthesized and used in the Phusion™ site-directed mutagenesis kit procedure. The GauT27I primers were:

forward: 5'-pTGGCGATTCGGAAGAGCGCGCCGAGATTGGC-3' (SEQ ID NO:169), where p is a phosphate, and reverse: 5'-p CCAATAAGTCCGATACACCGCATCCGCGTTCGCATCGCGCT-3' (SEQ ID NO:170). The primers to change MaqI were:

forward: 5'-pTGGATTTACGGCCGAGCCAGAAA-CACTTTCCGGC-3' (SEQ ID NO:171) and reverse: 5'-p CCAACGCTCCTTTAGACTGGCATCAT-TGTTCTGTTCGCGCTCCG-3' (SEQ ID NO:172).

One such enzyme recognizing 5'-GGCGCAGG19/17-3' was formed by site-directed mutagenesis of GauT27I, changing arginine 790 to aspartate and glutamate 802 to arginine, using primers SEQ ID NO:169 and SEQ ID NO:170. The recognition specificity of this altered enzyme is demonstrated in FIG. 27 and FIG. 28.

Another such enzyme recognizing 5'-GRTTGAC20/18-3' was formed by site-directed mutagenesis of MaqI, changing arginine 817 to aspartate and glutamate 829 to arginine, using primers SEQ ID NO:171 and SEQ ID NO:172. The recognition specificity of this altered enzyme is demonstrated in FIGS. 29 and 30.

In summary, Example 6 demonstrates rational alteration of recognition specificity in MmeI-family enzymes at the 5'-most base of their recognition sequence, that is, position 0 in the recognition sequence alignment.

FIG. 26 shows correlation between the DNA base recognized in the aligned DNA recognition sequences at position 0 and two positions in the amino acid sequence alignment.

On the left, the aligned DNA recognition sites are grouped into the 8 enzymes which recognize a C at position 0, followed by the 4 enzymes which recognize a G at position 0.

On the right, a portion of the amino acid sequence for twelve enzymes from the MmeI-like set, those that specifically recognize a DNA base pair at position 0 of the recognition sequence alignment, is aligned to reveal a region where a correlation is observed between the DNA base recognized at position 0 and the amino acid residue(s) present in the aligned protein sequences. Arrows indicate the two correlating amino acid positions identified. They correspond to R790 and E802 of GauT27I. At position E802 of the gapped alignment shown there is a 1:1 correspondence between the amino acid and the DNA base recognized in position 0, with one exception in RceI, such that whenever an enzyme recognizes a C:G base pair there is an glutamic acid, E, at this position, while those enzymes recognizing a G:C base pair have an arginine residue, R, at this position. The R790 position does not have complete 1:1 correspondence, due to the biological flexibility allowing more than one amino acid residue to partner with either the glutamic acid at E802 to recognize a C:G base pair, or with arginine of position E802 to recognize a G:C base pair. There is a 1:1 correspondence between recognition of a C:G base pair and the presence of arginine (R) at position R790.

Figure 27:
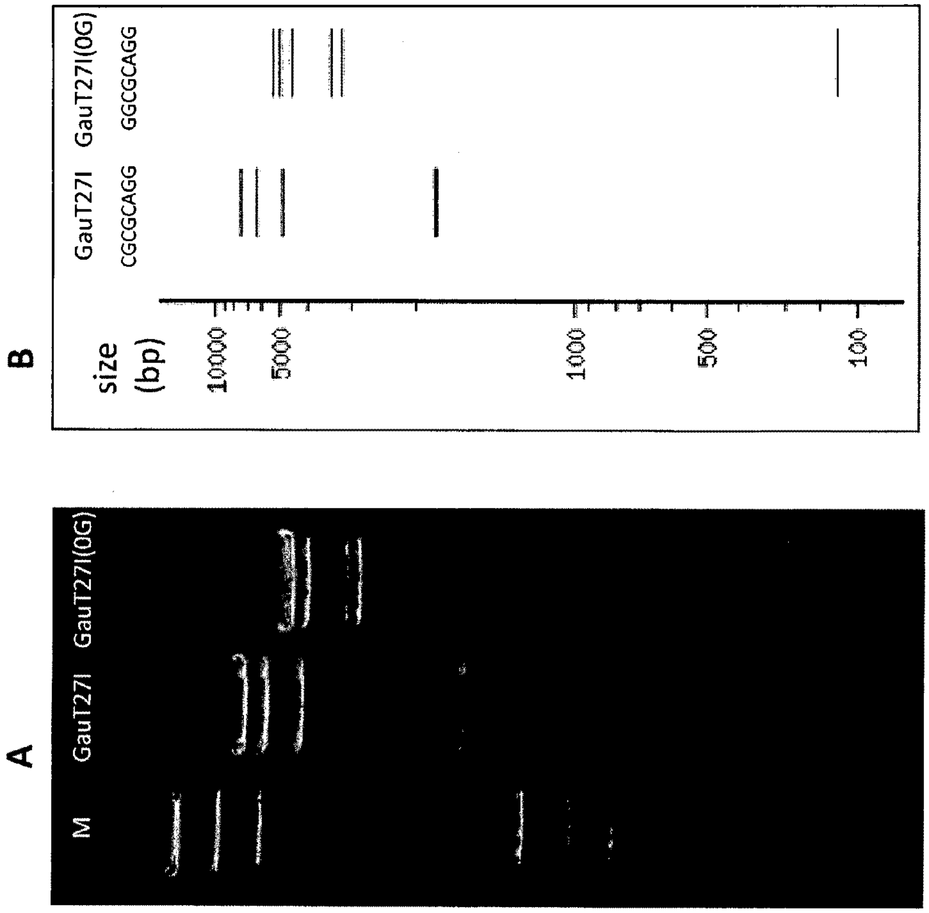

FIG. 27 demonstrates alteration of recognition specificity for GauT27I. The DNA cleavage patterns produced by the wild type and rationally altered GauT27I $R_{790}D/E_{802}R$ enzyme, GauT27I(0G), on plasmid pBsaBI DNA substrate are shown, as are the computer generated digestion patterns for cleavage at the wild type (CGCGCAGG19/17) and altered (GGCGCAGG19/17) recognition sequences. Lanes M is a size standard: Lambda-HindIII+PhiX174-HaeIII.

Figure 28:
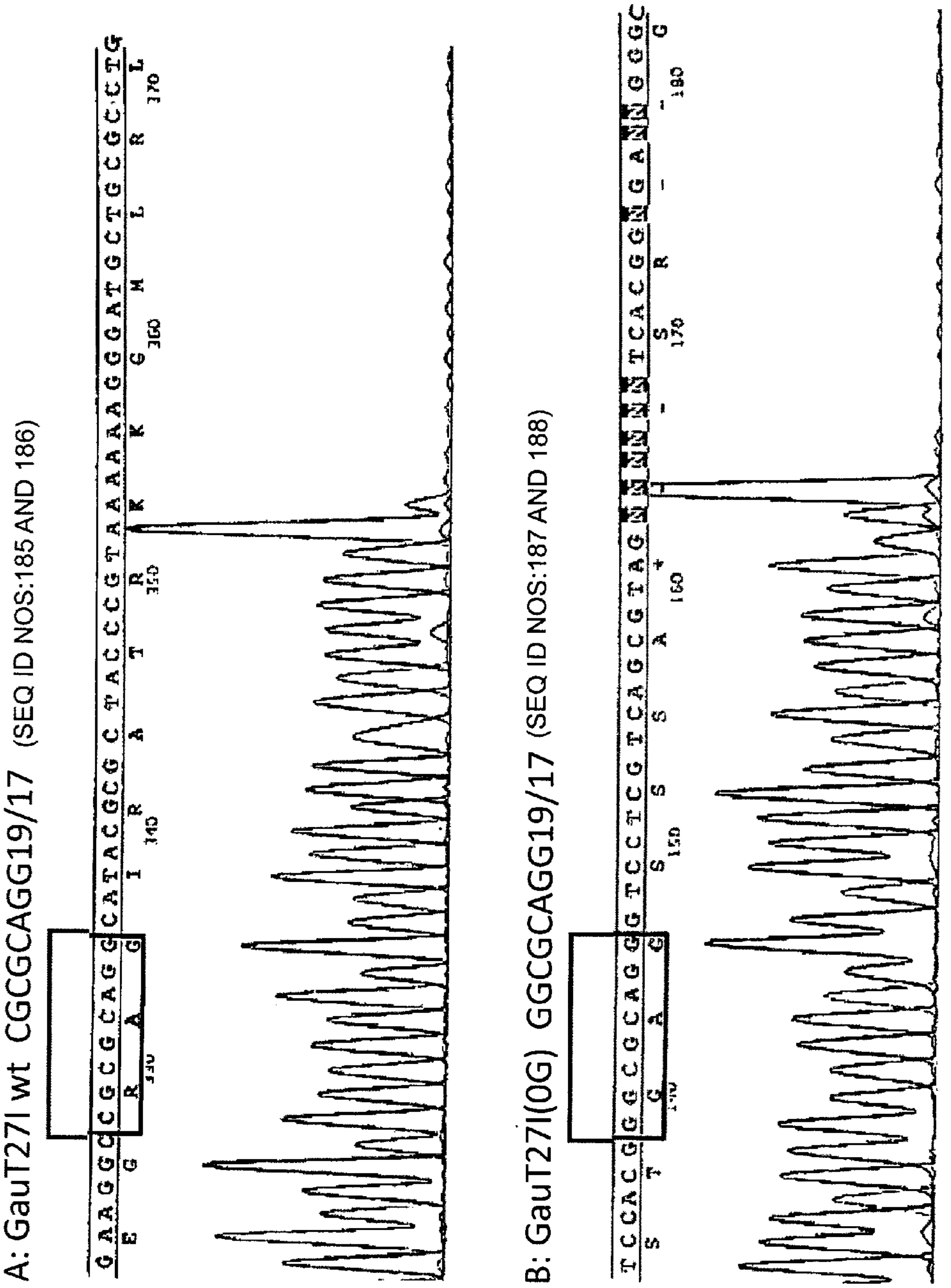

FIG. 28 shows the position of DNA cleavage relative to the recognition sequence for wild type GauT27I and the rationally altered GauT27I $R_{790}D/E_{802}R$ enzyme GauT27I(0G), demonstrating that the altered GauT27I(0G) enzyme cuts specifically at the new GGCGCAGG recognition sequence, and that it cuts this new sequence at the same position relative to the wild type recognition sequence.

Figure 29:
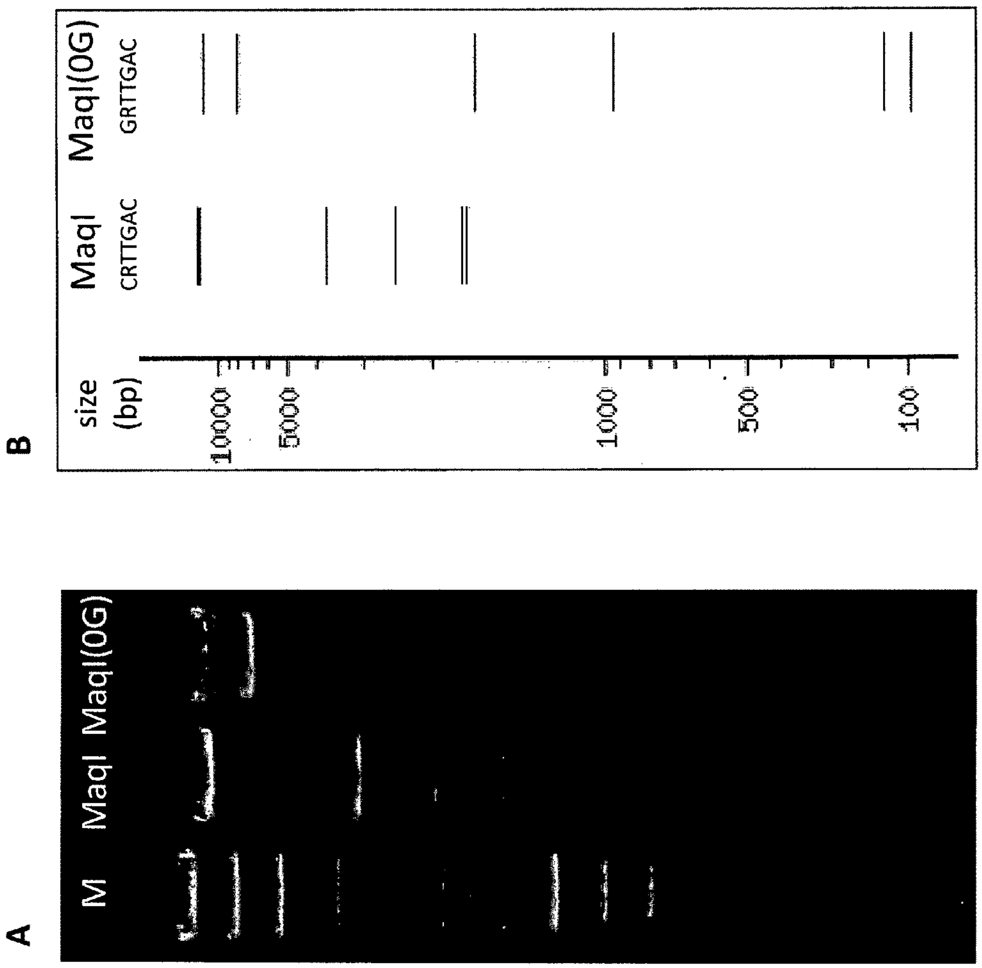

FIG. 29 demonstrates alteration of recognition specificity for MaqI. The DNA cleavage patterns produced by the wild type MaqI and rationally altered MaqI $R_{817}D/E_{829}R$ enzyme, MaqI(0G), on plasmid pBsaBI DNA substrate are shown, as are the computer generated digestion patterns for cleavage at the wild type (CRTTGAC20/18) and altered (GRTTGAC20/18) recognition sequences. Lanes M is a size standard: Lambda-HindIII+PhiX174-HaeIII.

Figure 30:
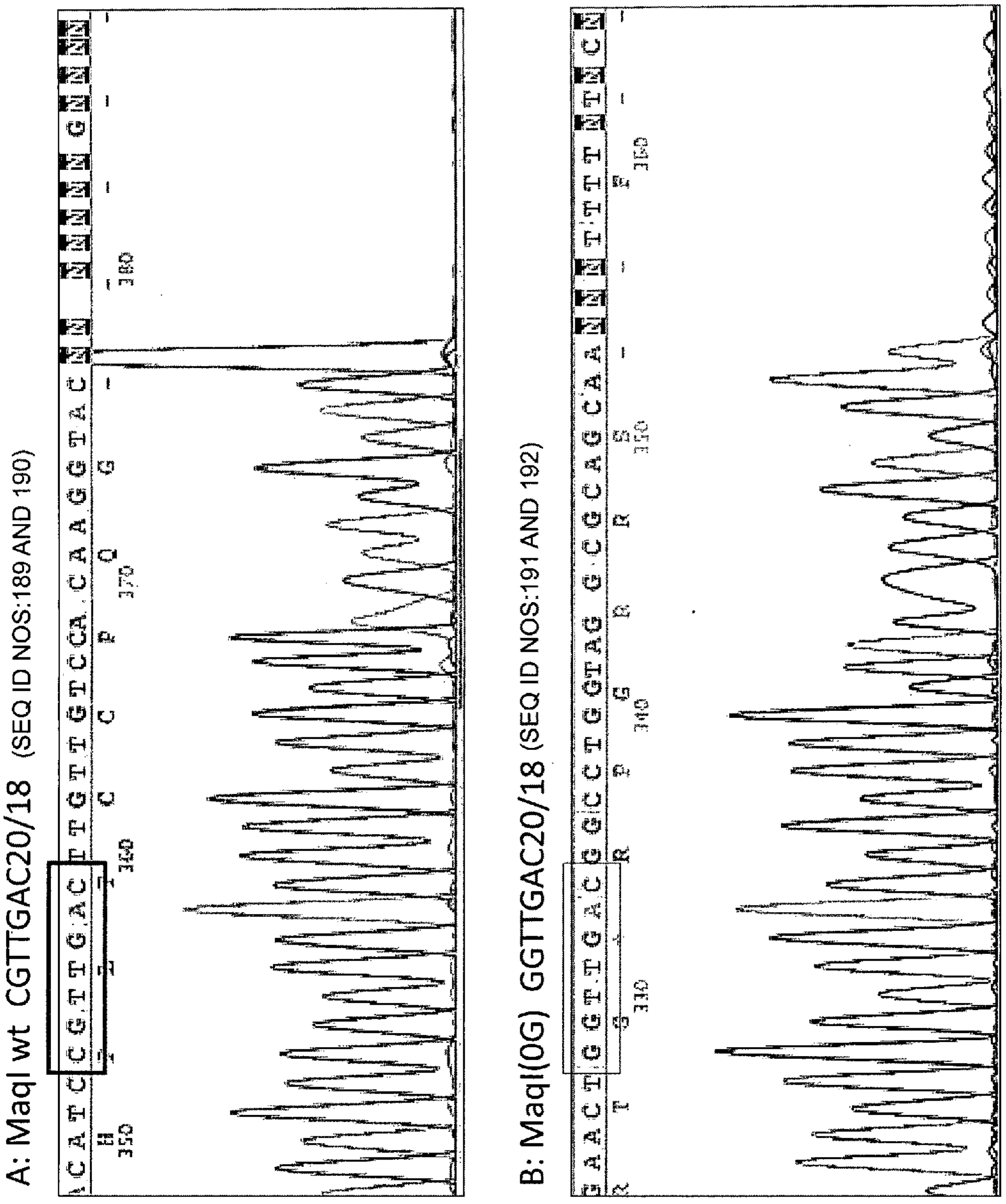

FIG. 30 shows the position of DNA cleavage relative to the recognition sequence for wild type MaqI and the rationally altered MaqI $R_{817}D/E_{829}R$ enzyme, MaqI(0G), demonstrating that the altered MaqI(0G) enzyme cuts specifically at the new GRTTGAC recognition sequence, and that it cuts this new sequence at the same position relative to the wild type recognition sequence.

What is claimed is:

1. A system comprising: a memory for storing instructions and a computer programmed to execute the instructions stored in memory, such that the computer is programmed to perform the steps of:

(a) using an initial restriction endonuclease or methyltransferase to query a database in a BLAST search, thereby creating a set of binding proteins wherein each binding protein has a defined amino acid sequence, the amino acid sequences sharing an expectation value (E) of less than e-20 for sequences of more than 200 amino acids or less than e-10 for sequences of less than 200 amino acids; the binding proteins binding to specific target recognition sequences in a substrate;

(b) aligning the target recognition sequences recognized by the binding proteins in the set;

(c) aligning the amino acid sequences of the binding proteins of the set; and (d) identifying correlations between single nucleotides the aligned recognition sequences and one or more position-specific amino acids in the aligned amino acid sequences of the binding proteins.

2. A system according to claim 1, further comprising: a means for receiving data from a device for protein synthesis and protein binding analysis wherein the computer is programmed to perform the additional steps of:

using the data to validate the correlations by confirming a prediction of binding to a predetermined recognition sequence by a mutated protein; and organizing the data into a catalog of validated amino acid or amino acids at identified positions that determine recognition for a position and type of nucleotide in the recognition sequence.

3. A system according to claim 1, wherein the binding proteins aligned in step (c) include MmeI and MmeI-like proteins identified in (a), and the computer is programmed to identify changes in the amino acid residues at a predetermined position or positions in the amino acid sequence of Mmel, or an Mmel-like protein that change the DNA recognition sequence of that protein.

* * * * *

SEQUENCE LISTING

```
<160> NUMBER OF SEQ ID NOS: 199

<210> SEQ ID NO 1
<211> LENGTH: 2760
<212> TYPE: DNA
<213> ORGANISM: Methylophilus methylotrophus

<400> SEQUENCE: 1

gtggctttaa gctggaacga gataagaaga aaagctattg agttttctaa aagatgggaa     60

gacgcctcag atgaaaacag tcaagccaaa ccctttttaa tagatttttt cgaagttttt    120

ggaataacta ataagagagt tgcaacattt gagcatgctg tgaaaaagtt cgccaaggcc    180

cataaggaac aatctcgagg attcgtagat ttgttttggc ctggcattct tcttattgaa    240

atgaaaagca gaggtaaaga cctcgacaaa gcgtatgacc aggcacttga ttacttttct    300

ggcattgcag aaagagactt acccagatac gttttagttt gcgacttcca gcgtttcaga    360

ttaacagacc taataacaaa agagtcagtt gaatttcttt taaaggactt ataccaaaat    420

gtgaggtctt ttggttttat agctggttat caaactcaag taatcaagcc acaagaccct    480

attaatatta aggcggctga acggatgggt aagcttcatg acaccctgaa gttggttgga    540

tatgagggac acgctttaga actttatcta gtgcgtttac ttttttgctt attcgcagaa    600
```

```
gacacaacta tttttgagaa aagtttattc caagaatata tcgagacaaa gacgctagag    660
gacggcagtg accttgcaca tcatatcaat acactttttt atgttctcaa taccccagaa    720
caaaaaagat taaagaatct agacgaacac cttgctgcat ttccatatat caatggaaaa    780
cttttcgagg agccacttcc gccagctcag tttgataaag caatgagaga ggcattgctt    840
gacttgtgct cattagattg gagcaggatt tcaccagcaa tatttggaag tttattccaa    900
agcattatgg atgctaaaaa gagaagaaat cttggggcac actacaccag cgaagcaaat    960
attctcaagt taatcaagcc attgtttctt gacgagctct gggtagagtt cgagaaagtt   1020
aaaaataata aaaataaatt actagcgttc cacaaaaaac taagaggact tacatttttc   1080
gaccctgcat gcggttgcgg aaattttctt gtaatcacat accgagaact aagactttta   1140
gaaattgaag tgttaagagg attgcataga ggtggtcaac aagttttgga tattgagcat   1200
cttattcaga ttaacgtaga ccagtttttt ggtatcgaaa tagaggagtt tcccgcacag   1260
attgctcagg ttgctctctg gcttacagac caccaaatga atatgaaaat ttcagatgag   1320
tttggaaact actttgcccg tatcccacta aaatctactc ctcacatttt gaatgctaat   1380
gctttacaga ttgattggaa cgatgtttta gaggctaaaa aatgttgctt catattagga   1440
aatcctccat ttgttggtaa aagtaaacaa acaccgggac aaaaagcgga tttactatct   1500
gtttttggaa atcttaaatc cgcttcagac ttagacctag ttgctgcttg gtatcccaaa   1560
gcagcacatt acattcaaac aaatgcaaac atacgctgtg catttgtctc aacgaatagt   1620
attactcaag gtgagcaagt atcgttgctt tggccgcttc tgctctcatt aggcataaaa   1680
ataaactttg ctcacagaac tttcagctgg acaaatgagg cgtcaggagt agcggcggtt   1740
cactgcgtaa ttatcggatt tgggttgaag gattcagatg aaaaaataat ctatgagtat   1800
gaaagtatta atggagaacc attagctatt aaggcaaaaa atattaatcc atatttgaga   1860
gacggggtgg atgtgattgc ctgcaagcgt cagcagccaa tctcaaaatt accaagcatg   1920
cgttatggca acaaaccaac agatgatgga aatttcctat ttactgacga agaaaaaaac   1980
caatttatta caaatgagcc atcttccgaa aaatacttca gacggtttgt gggcggggat   2040
gagttcataa acaatacaag tcgatggtgt ttatggcttg acggtgctga catttcagaa   2100
atacgagcga tgcctttggt cttggctagg ataaaaaaag tccaagaatt cagattaaaa   2160
agctcggcca aaccaactcg acaaagtgct tcgacaccaa tgaagttctt ttatatatct   2220
cagccggata cggactatct gttgatacct gaaacatcat ctgaaaacag acaatttatt   2280
ccaattggtt ttgttgatag aaatgtcatt tcaagtaacg caacgtatca tattcctagt   2340
gctgaacctt tgatatttgg cctgctttca tcgaccatgc acaactgctg gatgagaaat   2400
gtaggaggaa ggttagaaag tcgttataga tattctgcca gcctggttta caacacgttt   2460
ccatggattc aacccaacga aaaacaatcg aaagcgatag aagaagctgc atttgcgatt   2520
ttaaaagcta gaagcaatta tccaaacgaa agtttagctg gtttatacga cccaaaaaca   2580
atgcctagtg agcttcttaa agcacatcaa aaacttgata aggctgtgga ttctgtctat   2640
ggatttaaag gaccaaacac agaaattgct cgaatagctt ttttgtttga aacataccaa   2700
aagatgactt cactcttacc accagaaaaa gaaattaaga aatctaaggg caaaaattaa   2760
```

<210> SEQ ID NO 2
<211> LENGTH: 919
<212> TYPE: PRT
<213> ORGANISM: Methylophilus methylotrophus

<400> SEQUENCE: 2

-continued

```
Met Ala Leu Ser Trp Asn Glu Ile Arg Arg Lys Ala Ile Glu Phe Ser
1               5                   10                  15

Lys Arg Trp Glu Asp Ala Ser Asp Glu Asn Ser Gln Ala Lys Pro Phe
            20                  25                  30

Leu Ile Asp Phe Phe Glu Val Phe Gly Ile Thr Asn Lys Arg Val Ala
        35                  40                  45

Thr Phe Glu His Ala Val Lys Lys Phe Ala Lys Ala His Lys Glu Gln
    50                  55                  60

Ser Arg Gly Phe Val Asp Leu Phe Trp Pro Gly Ile Leu Leu Ile Glu
65                  70                  75                  80

Met Lys Ser Arg Gly Lys Asp Leu Asp Lys Ala Tyr Asp Gln Ala Leu
                85                  90                  95

Asp Tyr Phe Ser Gly Ile Ala Glu Arg Asp Leu Pro Arg Tyr Val Leu
            100                 105                 110

Val Cys Asp Phe Gln Arg Phe Arg Leu Thr Asp Leu Ile Thr Lys Glu
        115                 120                 125

Ser Val Glu Phe Leu Leu Lys Asp Leu Tyr Gln Asn Val Arg Ser Phe
    130                 135                 140

Gly Phe Ile Ala Gly Tyr Gln Thr Gln Val Ile Lys Pro Gln Asp Pro
145                 150                 155                 160

Ile Asn Ile Lys Ala Ala Glu Arg Met Gly Lys Leu His Asp Thr Leu
                165                 170                 175

Lys Leu Val Gly Tyr Glu Gly His Ala Leu Glu Leu Tyr Leu Val Arg
            180                 185                 190

Leu Leu Phe Cys Leu Phe Ala Glu Asp Thr Thr Ile Phe Glu Lys Ser
        195                 200                 205

Leu Phe Gln Glu Tyr Ile Glu Thr Lys Thr Leu Glu Asp Gly Ser Asp
    210                 215                 220

Leu Ala His His Ile Asn Thr Leu Phe Tyr Val Leu Asn Thr Pro Glu
225                 230                 235                 240

Gln Lys Arg Leu Lys Asn Leu Asp Glu His Leu Ala Ala Phe Pro Tyr
                245                 250                 255

Ile Asn Gly Lys Leu Phe Glu Glu Pro Leu Pro Pro Ala Gln Phe Asp
            260                 265                 270

Lys Ala Met Arg Glu Ala Leu Leu Asp Leu Cys Ser Leu Asp Trp Ser
        275                 280                 285

Arg Ile Ser Pro Ala Ile Phe Gly Ser Leu Phe Gln Ser Ile Met Asp
    290                 295                 300

Ala Lys Lys Arg Arg Asn Leu Gly Ala His Tyr Thr Ser Glu Ala Asn
305                 310                 315                 320

Ile Leu Lys Leu Ile Lys Pro Leu Phe Leu Asp Glu Leu Trp Val Glu
                325                 330                 335

Phe Glu Lys Val Lys Asn Asn Lys Asn Lys Leu Leu Ala Phe His Lys
            340                 345                 350

Lys Leu Arg Gly Leu Thr Phe Phe Asp Pro Ala Cys Gly Cys Gly Asn
        355                 360                 365

Phe Leu Val Ile Thr Tyr Arg Glu Leu Arg Leu Leu Glu Ile Glu Val
    370                 375                 380

Leu Arg Gly Leu His Arg Gly Gly Gln Gln Val Leu Asp Ile Glu His
385                 390                 395                 400

Leu Ile Gln Ile Asn Val Asp Gln Phe Phe Gly Ile Glu Ile Glu Glu
                405                 410                 415

Phe Pro Ala Gln Ile Ala Gln Val Ala Leu Trp Leu Thr Asp His Gln
```

-continued

```
            420                 425                 430

Met Asn Met Lys Ile Ser Asp Glu Phe Gly Asn Tyr Phe Ala Arg Ile
        435                 440                 445

Pro Leu Lys Ser Thr Pro His Ile Leu Asn Ala Asn Ala Leu Gln Ile
    450                 455                 460

Asp Trp Asn Asp Val Leu Glu Ala Lys Lys Cys Cys Phe Ile Leu Gly
465                 470                 475                 480

Asn Pro Pro Phe Val Gly Lys Ser Lys Gln Thr Pro Gly Gln Lys Ala
                485                 490                 495

Asp Leu Leu Ser Val Phe Gly Asn Leu Lys Ser Ala Ser Asp Leu Asp
            500                 505                 510

Leu Val Ala Ala Trp Tyr Pro Lys Ala Ala His Tyr Ile Gln Thr Asn
        515                 520                 525

Ala Asn Ile Arg Cys Ala Phe Val Ser Thr Asn Ser Ile Thr Gln Gly
    530                 535                 540

Glu Gln Val Ser Leu Leu Trp Pro Leu Leu Leu Ser Leu Gly Ile Lys
545                 550                 555                 560

Ile Asn Phe Ala His Arg Thr Phe Ser Trp Thr Asn Glu Ala Ser Gly
                565                 570                 575

Val Ala Ala Val His Cys Val Ile Ile Gly Phe Gly Leu Lys Asp Ser
            580                 585                 590

Asp Glu Lys Ile Ile Tyr Glu Tyr Glu Ser Ile Asn Gly Glu Pro Leu
        595                 600                 605

Ala Ile Lys Ala Lys Asn Ile Asn Pro Tyr Leu Arg Asp Gly Val Asp
    610                 615                 620

Val Ile Ala Cys Lys Arg Gln Gln Pro Ile Ser Lys Leu Pro Ser Met
625                 630                 635                 640

Arg Tyr Gly Asn Lys Pro Thr Asp Asp Gly Asn Phe Leu Phe Thr Asp
                645                 650                 655

Glu Glu Lys Asn Gln Phe Ile Thr Asn Glu Pro Ser Ser Glu Lys Tyr
            660                 665                 670

Phe Arg Arg Phe Val Gly Gly Asp Glu Phe Ile Asn Asn Thr Ser Arg
        675                 680                 685

Trp Cys Leu Trp Leu Asp Gly Ala Asp Ile Ser Glu Ile Arg Ala Met
    690                 695                 700

Pro Leu Val Leu Ala Arg Ile Lys Lys Val Gln Glu Phe Arg Leu Lys
705                 710                 715                 720

Ser Ser Ala Lys Pro Thr Arg Gln Ser Ala Ser Thr Pro Met Lys Phe
                725                 730                 735

Phe Tyr Ile Ser Gln Pro Asp Thr Asp Tyr Leu Leu Ile Pro Glu Thr
            740                 745                 750

Ser Ser Glu Asn Arg Gln Phe Ile Pro Ile Gly Phe Val Asp Arg Asn
        755                 760                 765

Val Ile Ser Ser Asn Ala Thr Tyr His Ile Pro Ser Ala Glu Pro Leu
    770                 775                 780

Ile Phe Gly Leu Leu Ser Ser Thr Met His Asn Cys Trp Met Arg Asn
785                 790                 795                 800

Val Gly Gly Arg Leu Glu Ser Arg Tyr Arg Tyr Ser Ala Ser Leu Val
                805                 810                 815

Tyr Asn Thr Phe Pro Trp Ile Gln Pro Asn Glu Lys Gln Ser Lys Ala
            820                 825                 830

Ile Glu Glu Ala Ala Phe Ala Ile Leu Lys Ala Arg Ser Asn Tyr Pro
        835                 840                 845
```

-continued

```
Asn Glu Ser Leu Ala Gly Leu Tyr Asp Pro Lys Thr Met Pro Ser Glu
    850                 855                 860

Leu Leu Lys Ala His Gln Lys Leu Asp Lys Ala Val Asp Ser Val Tyr
865                 870                 875                 880

Gly Phe Lys Gly Pro Asn Thr Glu Ile Ala Arg Ile Ala Phe Leu Phe
                885                 890                 895

Glu Thr Tyr Gln Lys Met Thr Ser Leu Leu Pro Pro Glu Lys Glu Ile
            900                 905                 910

Lys Lys Ser Lys Gly Lys Asn
        915


<210> SEQ ID NO 3
<211> LENGTH: 2802
<212> TYPE: DNA
<213> ORGANISM: unknown
<220> FEATURE:
<223> OTHER INFORMATION: Environmental sample Sargasso Sea

<400> SEQUENCE: 3

atggctgccc tctcgttccc ggaaatccgc acccgcttgc aagcgttcgc caaacaatgg      60

aagcaagcgg agcgcgaaaa cgccgacgca aagttgtttt gggcacggtt ttacgagtgc     120

ttcggcatcc gcccggagtc cgcgaccatc tacgagaagg cggtggacaa acttgatggc     180

tcgcggggct tcatcgactc gtttattccg gggctgttga tcgtcgagca caagagtaag     240

ggcaaggacc tgaactcggc cttcacccaa gcctccgact acttcacggc gctggctgaa     300

ggtgagcgtc cgcggtacat catcgtgtcg gatttcgccc gttttaggct gtacgacctg     360

aaaaccgaca cccaggtgga gtgcaaactc gcggacatct ccaagcacgc cggctggttc     420

cggttcctag tcgagggtga ggctacgcca gaaatcgtcg aggagtcacc gatcaaccgg     480

caggctgcgt acgccgtctc gaagttgcac gaggcgctgt tgcaggcaaa cttccgaggc     540

cgtgacttgg aggtgttcct gacgcggctg ctgttctgct tcttcgccga tgatactggc     600

atctttggcc aagacggtgt cttccgtcgg tacgtcgaag ccacgcgcga caatggccgg     660

gacaccgggc aaagcctcgc gatcctgttt gacgtgctgg acacgccgga taaccagcgt     720

tcgtccaacc tggacgagca cctgaccgcg ttcgcctaca tcaacgggtc gctgttttct     780

gagcgtacgc gtatcccgtc attcgacgcg gacatgcgaa ccttgttggt gaagtgcgca     840

gaactggact ggagcgggat cagccccgcg atcttcgggg cgatgtttca aggcgtgctg     900

gaagcccaca cgccagacga aaagcgccag gccagtcgtc gggaactggg tgctcactac     960

acctcggaac gtaacatctt gcgggtgatc aatccgctgt tcatggacga cttgcgcgta    1020

gagttcgaga gggcgcgcag gaacaagccc cgattgcagg cgctgtacga gaagttgcca    1080

acgctcacat tcttcgatcc cgcgtgcggc tgcgggaact tcttggtgat cgcgtaccgg    1140

gaactgcgcc gtctggaaaa cgatgtcatc gccgcactgt tcgcggactt ccagcacggc    1200

aagggtttgc tagacgtgtc gacgctctgc agggttcggg tcaatcagtt ttacggcctg    1260

gagatcgacg acgcggcggc gcacatcgcg cgcgtggcca tgtggatcac ggaccatcag    1320

atgaacctgg agtcggcaga ccgcttcggc aatactcgcc cgacagttcc gctggtcgac    1380

actccccaca ttcacaaaga gaacgcgcta cgcgccgatt ggacatcggt tctcgcgccc    1440

gcgcagtgtt cgtacgtgat gggcaatcct ccgttcgtag gtgcgaagtg gctgaacgag    1500

gaacagcgtg ccgacgcccg ggcggtgttc gctaacgtta agaacggcgg actgttggac    1560

tacgtggccg cttggtatgt taaggcgctg gcttacatcc aagctaaccc ggccatcgac    1620

gtggcgtttg tttcaaccaa ctcgatcacg caaggtgagc aagtgtcagc cctctggccg    1680
```

```
acgctgctgc aaggtggggt aaaaatccgc tttgcccacc ggacgtttca gtggagcaac   1740

gaagggaaag gcaatgctgc cgtccattgc gtcatcatcg gcttcggcct gcgtgtcccg   1800

gatcgctgca cgatcttcga ttacagccac gacatcaagg ccgacctggg ttcggttctt   1860

cacgcgtctc gcatcaatcc gtacttggtg gacgccccgg acgtcgtgct gacaaatcgg   1920

cgtgcgccga tttgtcaggt gccggaaatc ggcatagga acaaacccat cgacggcggg   1980

cattacctgt ttactgacga aggaaaggcc gcgttcctgg ccgtcgagcc gaaagccgcc   2040

ccgtttttcc atcgctgggt cggcgcggaa gagttcatca acaacacaag ccgttggtgt   2100

ctatggttgg gtaacgcgaa gccgcatgaa ctccgcgcgc tccccgaatg tatgaagcgc   2160

gttgaggcag tgcgtcaata tcgcctcgcc agccccagcg ctccgacgca gaaactggcc   2220

gagaccccga cccggtttca cgtcgagttc atgccagacg ccccgttcat ggtgatccct   2280

gaagtatcgt ccgaacgtcg cgagttcatc ccactggggt acctgcaacc gccaacgctg   2340

gcgagcaaca aactgcgctt gatgccagat gcgacgctgt atcacttcgc ggtgttgaac   2400

tccaccatgc atatggcttg gacacgggcg gtatgcggcc ggctggaaag ccgatatcag   2460

tactcggtca ccatcgtgta caacaacttt ccatggccca gtccatccga cgcccaactt   2520

gaagcgctgg aagcggcagg acaggcaatc ctcgatgccc aggctatgta tttggaccag   2580

ggttcatcgc tagccgatct gtacgatccg cgcacgatgc cgtcagaact tcgcaaggcc   2640

catgctgcga acgatcgcgc cgttgatgcg gcgtacaagt tcaagggcga caagtccgac   2700

gccgtgcggg tcgctttctt gtttagcctg tacggaaggt tgacgagcct tcttccgtcc   2760

gagaagccga agcgtgctcg gaaagagaaa gcagtcgcgt aa                      2802
```

<210> SEQ ID NO 4
<211> LENGTH: 933
<212> TYPE: PRT
<213> ORGANISM: unknown
<220> FEATURE:
<223> OTHER INFORMATION: Environmental sample Sargasso Sea

<400> SEQUENCE: 4

```
Met Ala Ala Leu Ser Phe Pro Glu Ile Arg Thr Arg Leu Gln Ala Phe
1               5                   10                  15

Ala Lys Gln Trp Lys Gln Ala Glu Arg Glu Asn Ala Asp Ala Lys Leu
            20                  25                  30

Phe Trp Ala Arg Phe Tyr Glu Cys Phe Gly Ile Arg Pro Glu Ser Ala
        35                  40                  45

Thr Ile Tyr Glu Lys Ala Val Asp Lys Leu Asp Gly Ser Arg Gly Phe
    50                  55                  60

Ile Asp Ser Phe Ile Pro Gly Leu Leu Ile Val Glu His Lys Ser Lys
65                  70                  75                  80

Gly Lys Asp Leu Asn Ser Ala Phe Thr Gln Ala Ser Asp Tyr Phe Thr
                85                  90                  95

Ala Leu Ala Glu Gly Glu Arg Pro Arg Tyr Ile Ile Val Ser Asp Phe
            100                 105                 110

Ala Arg Phe Arg Leu Tyr Asp Leu Lys Thr Asp Thr Gln Val Glu Cys
        115                 120                 125

Lys Leu Ala Asp Ile Ser Lys His Ala Gly Trp Phe Arg Phe Leu Val
    130                 135                 140

Glu Gly Glu Ala Thr Pro Glu Ile Val Glu Glu Ser Pro Ile Asn Arg
145                 150                 155                 160

Gln Ala Ala Tyr Ala Val Ser Lys Leu His Glu Ala Leu Leu Gln Ala
```

-continued

```
                165                 170                 175

Asn Phe Arg Gly Arg Asp Leu Glu Val Phe Leu Thr Arg Leu Leu Phe
            180                 185                 190

Cys Phe Phe Ala Asp Asp Thr Gly Ile Phe Gly Gln Asp Gly Val Phe
        195                 200                 205

Arg Arg Tyr Val Glu Ala Thr Arg Asp Asn Gly Arg Asp Thr Gly Gln
    210                 215                 220

Ser Leu Ala Ile Leu Phe Asp Val Leu Asp Thr Pro Asp Asn Gln Arg
225                 230                 235                 240

Ser Ser Asn Leu Asp Glu His Leu Thr Ala Phe Ala Tyr Ile Asn Gly
                245                 250                 255

Ser Leu Phe Ser Glu Arg Thr Arg Ile Pro Ser Phe Asp Ala Asp Met
            260                 265                 270

Arg Thr Leu Leu Val Lys Cys Ala Glu Leu Asp Trp Ser Gly Ile Ser
        275                 280                 285

Pro Ala Ile Phe Gly Ala Met Phe Gln Gly Val Leu Glu Ala His Thr
    290                 295                 300

Pro Asp Glu Lys Arg Gln Ala Ser Arg Arg Glu Leu Gly Ala His Tyr
305                 310                 315                 320

Thr Ser Glu Arg Asn Ile Leu Arg Val Ile Asn Pro Leu Phe Met Asp
                325                 330                 335

Asp Leu Arg Val Glu Phe Glu Arg Ala Arg Arg Asn Lys Pro Arg Leu
            340                 345                 350

Gln Ala Leu Tyr Glu Lys Leu Pro Thr Leu Thr Phe Phe Asp Pro Ala
        355                 360                 365

Cys Gly Cys Gly Asn Phe Leu Val Ile Ala Tyr Arg Glu Leu Arg Arg
    370                 375                 380

Leu Glu Asn Asp Val Ile Ala Ala Leu Phe Ala Asp Phe Gln His Gly
385                 390                 395                 400

Lys Gly Leu Leu Asp Val Ser Thr Leu Cys Arg Val Arg Val Asn Gln
                405                 410                 415

Phe Tyr Gly Leu Glu Ile Asp Asp Ala Ala Ala His Ile Ala Arg Val
            420                 425                 430

Ala Met Trp Ile Thr Asp His Gln Met Asn Leu Glu Ser Ala Asp Arg
        435                 440                 445

Phe Gly Asn Thr Arg Pro Thr Val Pro Leu Val Asp Thr Pro His Ile
    450                 455                 460

His Lys Glu Asn Ala Leu Arg Ala Asp Trp Thr Ser Val Leu Ala Pro
465                 470                 475                 480

Ala Gln Cys Ser Tyr Val Met Gly Asn Pro Pro Phe Val Gly Ala Lys
                485                 490                 495

Trp Leu Asn Glu Glu Gln Arg Ala Asp Ala Arg Ala Val Phe Ala Asn
            500                 505                 510

Val Lys Asn Gly Gly Leu Leu Asp Tyr Val Ala Ala Trp Tyr Val Lys
        515                 520                 525

Ala Leu Ala Tyr Ile Gln Ala Asn Pro Ala Ile Asp Val Ala Phe Val
    530                 535                 540

Ser Thr Asn Ser Ile Thr Gln Gly Glu Gln Val Ser Ala Leu Trp Pro
545                 550                 555                 560

Thr Leu Leu Gln Gly Gly Val Lys Ile Arg Phe Ala His Arg Thr Phe
                565                 570                 575

Gln Trp Ser Asn Glu Gly Lys Gly Asn Ala Ala Val His Cys Val Ile
            580                 585                 590
```

-continued

```
Ile Gly Phe Gly Leu Arg Val Pro Asp Arg Cys Thr Ile Phe Asp Tyr
        595                 600                 605

Ser His Asp Ile Lys Ala Asp Leu Gly Ser Val Leu His Ala Ser Arg
    610                 615                 620

Ile Asn Pro Tyr Leu Val Asp Ala Pro Asp Val Val Leu Thr Asn Arg
625                 630                 635                 640

Arg Ala Pro Ile Cys Gln Val Pro Glu Ile Gly Ile Gly Asn Lys Pro
                645                 650                 655

Ile Asp Gly Gly His Tyr Leu Phe Thr Asp Glu Gly Lys Ala Ala Phe
            660                 665                 670

Leu Ala Val Glu Pro Lys Ala Ala Pro Phe Phe His Arg Trp Val Gly
        675                 680                 685

Ala Glu Glu Phe Ile Asn Asn Thr Ser Arg Trp Cys Leu Trp Leu Gly
    690                 695                 700

Asn Ala Lys Pro His Glu Leu Arg Ala Leu Pro Glu Cys Met Lys Arg
705                 710                 715                 720

Val Glu Ala Val Arg Gln Tyr Arg Leu Ala Ser Pro Ser Ala Pro Thr
                725                 730                 735

Gln Lys Leu Ala Glu Thr Pro Thr Arg Phe His Val Glu Phe Met Pro
            740                 745                 750

Asp Ala Pro Phe Met Val Ile Pro Glu Val Ser Ser Glu Arg Arg Glu
        755                 760                 765

Phe Ile Pro Leu Gly Tyr Leu Gln Pro Pro Thr Leu Ala Ser Asn Lys
    770                 775                 780

Leu Arg Leu Met Pro Asp Ala Thr Leu Tyr His Phe Ala Val Leu Asn
785                 790                 795                 800

Ser Thr Met His Met Ala Trp Thr Arg Ala Val Cys Gly Arg Leu Glu
                805                 810                 815

Ser Arg Tyr Gln Tyr Ser Val Thr Ile Val Tyr Asn Asn Phe Pro Trp
            820                 825                 830

Pro Ser Pro Ser Asp Ala Gln Leu Glu Ala Leu Glu Ala Ala Gly Gln
        835                 840                 845

Ala Ile Leu Asp Ala Gln Ala Met Tyr Leu Asp Gln Gly Ser Ser Leu
    850                 855                 860

Ala Asp Leu Tyr Asp Pro Arg Thr Met Pro Ser Glu Leu Arg Lys Ala
865                 870                 875                 880

His Ala Ala Asn Asp Arg Ala Val Asp Ala Ala Tyr Lys Phe Lys Gly
                885                 890                 895

Asp Lys Ser Asp Ala Val Arg Val Ala Phe Leu Phe Ser Leu Tyr Gly
            900                 905                 910

Arg Leu Thr Ser Leu Leu Pro Ser Glu Lys Pro Lys Arg Ala Arg Lys
        915                 920                 925

Glu Lys Ala Val Ala
    930
```

<210> SEQ ID NO 5
<211> LENGTH: 2727
<212> TYPE: DNA
<213> ORGANISM: Sulfurimonas denitrificans

<400> SEQUENCE: 5

```
atgataagct taagagagat acgagaacga agcataaagt ttgccaaaga gtgggagggt      60

gcttctcatg aaaaacaaga agcgcagagt ttttggatag attttttaa aatatttgat      120

gtaagtccac gaagtatgca gtttgagtat cccatcaaaa aaatagacgg ctcttatggt     180
```

-continued

```
tacatagatg ttttttggag agggcagctt cttatagagc aaaaaagcag aggcaaggat    240
ttagtaaagg caaaagaaca agcgttagag taccttccaa atctaaaaca gagagattta    300
ccgaagttta ttttggtttg tgattttgta agcttctatc tttacgattt ggacacaaat    360
caagattata aatttctact ccatgagtta ccaaaaaata tagagctgtt ttcatttata    420
gcaggataca caaaaaaaac ctacaaagaa gaggaaccga ccaaccgcaa agccgccgaa    480
cttatgggta aacttcatga caagctactt gaaaacggtt acagcggaca tcaactcgaa    540
ctctttttaa caaggcttct tttttgtatg tttgcagaag atacgggcat atttgctaaa    600
aactcttttc gtgaatttat agaaaatcaa acagatgaga gcggcagaga tttaggctcg    660
cagataagct acctctttga gctttttgac actccaaatg aggagcgaca aaaaaatctt    720
gatgagagtt ttactcagtt tccttacatc aacggctcaa tttttacaga acagctcaaa    780
acagcccact ttgaccgctc catgcgtgaa atgcttttgg atgcgtgtgc ctttgactgg    840
agtttgataa gtccttccat tttcggttca atgtttcaag cttctatgga cgttagtaaa    900
agaggcgaac tcggtgcgca ctttacaagt gagacaaata tattaaaagc catcaaaccg    960
ctatttttgg atgaacttag cgaagagttt gcaaaaataa aaaacaaccc aaaacagctt   1020
caaatttttc atgcaaaaat ctcaaatctc aaatttttag acccagcatg tggaagtggg   1080
aactttttgg taatcgctta cagagagttg aagcttgtag agtttgaagt gctgaaatct   1140
cttaaaatac tcacacaact cgtccatata gaccaatttt atggtttcga gatagaagag   1200
ttgccaagtc gaataactca aactgcgatg cttctcatcg accatcaaat gaacctgctt   1260
tttgctcaaa tgtttggaga gccacatttt aatatcccca taaaagatag tgcaaatatt   1320
tttaatgtca atgctttgag ggtggattgg gaaaagattt tggatggtgt gaaaattgat   1380
tttattattg gaaatccgcc gtttttaggt tcaaaaatgc aatctaaaga gcaaaaagag   1440
gatatggcag aggtttttag cggtgttaaa aatggaaaag aacttgattt tgtaacggct   1500
tggtatataa aatctgcaaa atatttacaa ggtaaaaaca caaaagtagc cttagtttca   1560
acgaactcca ttacgcaagg cgaacaagta gggattttgt ggcaagagat gtttaacaaa   1620
tataaaatca aaatccactt tgcacacaaa acttttaaat ggaataatga tgcaaaaggc   1680
gttgcacaag tttattgtgt aattatcggt tttgcggggt ttgacatcaa agaaaaaaga   1740
ctttttgagt atgagagcgt aaaatctgaa ccgcatgaga taaaagttgc aaatataaat   1800
ccctatcttg taaacggaga tgattttttt atcagctcaa gaagaaagca tatacagagc   1860
tttatacctc aaatagtttt tggaagtatg ccaaatgacg gtggtaacct gctttttgac   1920
gataaagaaa aagaggagtt tttagccctt gaaccaaaag cagagctgta catgaagcct   1980
cttatctctg caaaagagta tcttaacggc aaaacaagat ggtgtttatg gctaaaagat   2040
tgtccgccaa atgaactaaa atctatgccc aaagtgattg agagagttga aaatatcaga   2100
aaacttagga acgaaagctc aagagaagca actcaaaaat tagcaaagtt cccagcactt   2160
tttggagaag atagacagcc tgagagtgat tatattttta ttcctcgtgt atcgtcagaa   2220
aacagagatt atattccaat ggaatttttt acaaaagatt ttatttgtgg agatactgga   2280
cttgccgttc caaatgccac actttttcat ttcggaattt tgacttcaaa aatgcacatg   2340
gactgggtgc ggtatgttgc tggaagatta aaaagtgatt atagatattc aaatgaaatt   2400
gtttataaca acttcccttt tcctttagaa ataaacgaca aacaaaaaga tcaaatcgaa   2460
caattagcac aaaatattct agacataaga gccgaatttg taggaagctc tttagccgat   2520
ttgtacaatc ctctaactat gccaccaaaa ctcctaaaag ctcacgaaac gctagacaga   2580
```

```
gcagtagata aactctactc aaaaacactc ttcaaaacag atacagaaag agtcgcccat   2640

ttgtttgaat taaataaaca acttactagc ttgattgtgg aaaatgagaa aaaagctaaa   2700

aaagttaaaa aaataataac aaaatga                                       2727


<210> SEQ ID NO 6
<211> LENGTH: 908
<212> TYPE: PRT
<213> ORGANISM: Sulfurimonas denitrificans

<400> SEQUENCE: 6

Met Ile Ser Leu Arg Glu Ile Arg Glu Arg Ser Ile Lys Phe Ala Lys
1               5                   10                  15

Glu Trp Glu Gly Ala Ser His Glu Lys Gln Glu Ala Gln Ser Phe Trp
            20                  25                  30

Ile Asp Phe Phe Lys Ile Phe Asp Val Ser Pro Arg Ser Met Gln Phe
        35                  40                  45

Glu Tyr Pro Ile Lys Lys Ile Asp Gly Ser Tyr Gly Tyr Ile Asp Val
    50                  55                  60

Phe Trp Arg Gly Gln Leu Leu Ile Glu Gln Lys Ser Arg Gly Lys Asp
65                  70                  75                  80

Leu Val Lys Ala Lys Glu Gln Ala Leu Glu Tyr Leu Pro Asn Leu Lys
                85                  90                  95

Gln Arg Asp Leu Pro Lys Phe Ile Leu Val Cys Asp Phe Val Ser Phe
            100                 105                 110

Tyr Leu Tyr Asp Leu Asp Thr Asn Gln Asp Tyr Lys Phe Leu Leu His
        115                 120                 125

Glu Leu Pro Lys Asn Ile Glu Leu Phe Ser Phe Ile Ala Gly Tyr Thr
    130                 135                 140

Lys Lys Thr Tyr Lys Glu Glu Glu Pro Thr Asn Arg Lys Ala Ala Glu
145                 150                 155                 160

Leu Met Gly Lys Leu His Asp Lys Leu Leu Glu Asn Gly Tyr Ser Gly
                165                 170                 175

His Gln Leu Glu Leu Phe Leu Thr Arg Leu Leu Phe Cys Met Phe Ala
            180                 185                 190

Glu Asp Thr Gly Ile Phe Ala Lys Asn Ser Phe Arg Glu Phe Ile Glu
        195                 200                 205

Asn Gln Thr Asp Glu Ser Gly Arg Asp Leu Gly Ser Gln Ile Ser Tyr
    210                 215                 220

Leu Phe Glu Leu Phe Asp Thr Pro Asn Glu Glu Arg Gln Lys Asn Leu
225                 230                 235                 240

Asp Glu Ser Phe Thr Gln Phe Pro Tyr Ile Asn Gly Ser Ile Phe Thr
                245                 250                 255

Glu Gln Leu Lys Thr Ala His Phe Asp Arg Ser Met Arg Glu Met Leu
            260                 265                 270

Leu Asp Ala Cys Ala Phe Asp Trp Ser Leu Ile Ser Pro Ser Ile Phe
        275                 280                 285

Gly Ser Met Phe Gln Ala Ser Met Asp Val Ser Lys Arg Gly Glu Leu
    290                 295                 300

Gly Ala His Phe Thr Ser Glu Thr Asn Ile Leu Lys Ala Ile Lys Pro
305                 310                 315                 320

Leu Phe Leu Asp Glu Leu Ser Glu Glu Phe Ala Lys Ile Lys Asn Asn
                325                 330                 335

Pro Lys Gln Leu Gln Ile Phe His Ala Lys Ile Ser Asn Leu Lys Phe
            340                 345                 350
```

-continued

```
Leu Asp Pro Ala Cys Gly Ser Gly Asn Phe Leu Val Ile Ala Tyr Arg
        355                 360                 365

Glu Leu Lys Leu Val Glu Phe Glu Val Leu Lys Ser Leu Lys Ile Leu
    370                 375                 380

Thr Gln Leu Val His Ile Asp Gln Phe Tyr Gly Phe Glu Ile Glu Glu
385                 390                 395                 400

Leu Pro Ser Arg Ile Thr Gln Thr Ala Met Leu Leu Ile Asp His Gln
                405                 410                 415

Met Asn Leu Leu Phe Ala Gln Met Phe Gly Glu Pro His Phe Asn Ile
            420                 425                 430

Pro Ile Lys Asp Ser Ala Asn Ile Phe Asn Val Asn Ala Leu Arg Val
        435                 440                 445

Asp Trp Glu Lys Ile Leu Asp Gly Val Lys Ile Asp Phe Ile Ile Gly
    450                 455                 460

Asn Pro Pro Phe Leu Gly Ser Lys Met Gln Ser Lys Glu Gln Lys Glu
465                 470                 475                 480

Asp Met Ala Glu Val Phe Ser Gly Val Lys Asn Gly Lys Glu Leu Asp
                485                 490                 495

Phe Val Thr Ala Trp Tyr Ile Lys Ser Ala Lys Tyr Leu Gln Gly Lys
            500                 505                 510

Asn Thr Lys Val Ala Leu Val Ser Thr Asn Ser Ile Thr Gln Gly Glu
        515                 520                 525

Gln Val Gly Ile Leu Trp Gln Glu Met Phe Asn Lys Tyr Lys Ile Lys
    530                 535                 540

Ile His Phe Ala His Lys Thr Phe Lys Trp Asn Asn Asp Ala Lys Gly
545                 550                 555                 560

Val Ala Gln Val Tyr Cys Val Ile Ile Gly Phe Ala Gly Phe Asp Ile
                565                 570                 575

Lys Glu Lys Arg Leu Phe Glu Tyr Glu Ser Val Lys Ser Glu Pro His
            580                 585                 590

Glu Ile Lys Val Ala Asn Ile Asn Pro Tyr Leu Val Asn Gly Asp Asp
        595                 600                 605

Phe Phe Ile Ser Ser Arg Arg Lys His Ile Gln Ser Phe Ile Pro Gln
    610                 615                 620

Ile Val Phe Gly Ser Met Pro Asn Asp Gly Gly Asn Leu Leu Phe Asp
625                 630                 635                 640

Asp Lys Glu Lys Glu Glu Phe Leu Ala Leu Glu Pro Lys Ala Glu Leu
                645                 650                 655

Tyr Met Lys Pro Leu Ile Ser Ala Lys Glu Tyr Leu Asn Gly Lys Thr
            660                 665                 670

Arg Trp Cys Leu Trp Leu Lys Asp Cys Pro Pro Asn Glu Leu Lys Ser
        675                 680                 685

Met Pro Lys Val Ile Glu Arg Val Glu Asn Ile Arg Lys Leu Arg Asn
    690                 695                 700

Glu Ser Ser Arg Glu Ala Thr Gln Lys Leu Ala Lys Phe Pro Ala Leu
705                 710                 715                 720

Phe Gly Glu Asp Arg Gln Pro Glu Ser Asp Tyr Ile Phe Ile Pro Arg
                725                 730                 735

Val Ser Ser Glu Asn Arg Asp Tyr Ile Pro Met Glu Phe Phe Thr Lys
            740                 745                 750

Asp Phe Ile Cys Gly Asp Thr Gly Leu Ala Val Pro Asn Ala Thr Leu
        755                 760                 765

Phe His Phe Gly Ile Leu Thr Ser Lys Met His Met Asp Trp Val Arg
    770                 775                 780
```

```
Tyr Val Ala Gly Arg Leu Lys Ser Asp Tyr Arg Tyr Ser Asn Glu Ile
785                 790                 795                 800

Val Tyr Asn Asn Phe Pro Phe Pro Leu Glu Ile Asn Asp Lys Gln Lys
                805                 810                 815

Asp Gln Ile Glu Gln Leu Ala Gln Asn Ile Leu Asp Ile Arg Ala Glu
            820                 825                 830

Phe Val Gly Ser Ser Leu Ala Asp Leu Tyr Asn Pro Leu Thr Met Pro
        835                 840                 845

Pro Lys Leu Leu Lys Ala His Glu Thr Leu Asp Arg Ala Val Asp Lys
    850                 855                 860

Leu Tyr Ser Lys Thr Leu Phe Lys Thr Asp Thr Glu Arg Val Ala His
865                 870                 875                 880

Leu Phe Glu Leu Asn Lys Gln Leu Thr Ser Leu Ile Val Glu Asn Glu
                885                 890                 895

Lys Lys Ala Lys Lys Val Lys Lys Ile Ile Thr Lys
            900                 905


<210> SEQ ID NO 7
<211> LENGTH: 2865
<212> TYPE: DNA
<213> ORGANISM: Neisseria lactamica ST640

<400> SEQUENCE: 7

atgccgtctg aaagcacact tcagacggca ttttcccaac aggcacgcat catgacccca     60

gacctccaaa ccctccaaca caacgccgaa caattcatcc gcgactgcga acccctgcat    120

tacgaaatgg gtcatgccca aaaattcatc gccgccctat gcaaagtgta cggcctcgat    180

gcccacttcg ccgtccaata cgaacaccgc gtccgcaaag ctgacctcaa aggcatcaac    240

cgcatcgacg gcttcttccc cggcctgctg atgatagaaa tgaaatccgc cggcgaagac    300

ctcgaagccg ccttcatcca agccctggaa tacgtccaac tcatagagcg catcgaagac    360

aagccccgcc acatcctcgt ctccgacttc aaaaacctcc acctttacga gctgaatcaa    420

ggatttaccg gcatcgtcct cgacaaaacc ctcaaaatca aactcaccgg cttccgcgcc    480

cacgtccaag acttcgcctt catcgcaggc tacgaagccg ccattgccga gcgcaacgaa    540

gccctgacca tagccgccgc cgccaaactc gccgcccctgc accaagaatt ccacaaacaa    600

ggctaccaag gcgcagaact ccaaaccatg ctcgtccgca tcctcttctg cctctttgcc    660

gacgacaccg gactcttcgc ccaaaacaaa gccttcgagc agcttgtcga agaaagcctc    720

gccgacggcg cagacctcgg cagccgcctc aacgccctct acaaatggct tgacaccccc    780

gaagacaaac gccgcaccac cccgcgggcc ctgcttgacc aatacagcgg cttccgcctc    840

aaattcccct acatcaacgg caaactcttt tcagacggca tagacgaatt cgtcttcaac    900

gcctccatgc gccgcaccct cctcgaatgc tgcgaaatcg actggagcct catctccccc    960

gacatcttcg gcacactctt ccaaaacatc atggaaaacg ccgacgcact cggcggcggc   1020

aaaaaatctg cccaccgccg cgaactcggc gcacactaca ccagcgaaaa aaacatcaaa   1080

cgcgccatcg cccccctctt tctcgaccgc ctcaaagccg agcttgagca ggctgccggc   1140

gaccccaaaa aactcgcccg ctacattacc cgcctgcaaa ccctccaaat cctcgatccc   1200

gcctgtggct gcggcaactt cctcatcgtc gcctaccgcg aaatccgcct gctcgaaatg   1260

caggcaatcc gccaactcgc ccgcatcccc ggcgcgcagc aaatgcagtc ccaatgcgac   1320

gtccaccaat tccacggcat cgaaatcgac cccgccgccg tcgaaatcgc caccgttgcc   1380

atgtggctca ccgaccacca gatgaaccgc ctctaccaag acggctacaa acgcatcccc   1440
```

-continued

```
ctcgcccaca aagccgacat ccgctgcgcc aacgccctcc aaaccgactg ggcagacacc   1500

atatcccccc aaaacctcga ctatatcgtc ggcaaccccc cgtttttagg caaaaaagaa   1560

caaaatgccg aacagaaaaa agatatggaa aaagtggtag gacatctcaa aggttcgggg   1620

attctcgatt acgttacggc ttggtatttc aaagcaaacg aattgatgaa acacaacccc   1680

aaaatccgca ccgccttcgt ttccaccaac tccatcaccc aaggcgaaca agtccccgcc   1740

ctctggaagc ccctgctttc agacggcatc cgcatccgct tcgcccaccg caccttcaaa   1800

tggaacaacg aaggcaaagg caccgccgcc gtccactgcg tcatcatcgg cttcgaccgc   1860

gacgaaatcc aaaaaggcga acgcctcagc ctttgggatt acagccaagg catcggcggc   1920

gacggcaaag aacaccaagt ccgcaaaatc aatccttatc tgcttgaagc agacaatatc   1980

ctgcccgcca aaagaagccg ccccgtatca gcagatgttc cggcaatgaa ttacggaagt   2040

atgccgattg acaacggctt gctgattctg tcccaagaag cgtttcagac ggcattaaac   2100

gaagaccccg aaaatagcga actgatccgc ccctatatgg gcggcagcga attcctgaac   2160

aatgaaaaac gttattgcct gtggttggaa aacgtcgatc aagaacgcct gtcccaaagc   2220

aaatttgctt cggaacgggt agggcaagtc agagcctacc gcctgtccag ttcgcgcgca   2280

gccactgtaa aactggctgg aacaccgcac ttgttcggcg aaatccgcca acctgacagc   2340

cgttatctgc tgttgcccaa agtgtcgtct gaaaaccgcc gttttcttcc catcggttac   2400

atcgaacctg aaaccattgc caacggaagc gcattgatta tccccaacgc caccctctgc   2460

cacttcggca tcctaagctc caccatgcac aacgccttca tgcgcaccgt cgcaggcaga   2520

ttggaaagcc gttaccaata ctcggcaagt atcgtgtaca acaatttccc cttccccgaa   2580

aacccctgcc gcaccgccat cgaaaccgca gcccaagccg tcctcgacgc acgcgccgcc   2640

gaaaccgaac gcatccgccg cctcaaccgg atcctgcccg aaaaagaaca ccgccccatg   2700

cccacacccg ccaccctcta caaccccgac accatgcccc ccgccctcgc cgccgcccac   2760

aacgccctcg acgatgccgt ggacgaagcc tacggctaca cgggcggcaa cagcgacagc   2820

gaacgcaccg ccttcctctt ccgcctctac aaaaatgccg tctga                   2865
```

<210> SEQ ID NO 8
<211> LENGTH: 954
<212> TYPE: PRT
<213> ORGANISM: Neisseria lactamica ST640

<400> SEQUENCE: 8

```
Met Pro Ser Glu Ser Thr Leu Gln Thr Ala Phe Ser Gln Gln Ala Arg
1               5                   10                  15

Ile Met Thr Pro Asp Leu Gln Thr Leu Gln His Asn Ala Glu Gln Phe
            20                  25                  30

Ile Arg Asp Cys Glu Pro Leu His Tyr Glu Met Gly His Ala Gln Lys
        35                  40                  45

Phe Ile Ala Ala Leu Cys Lys Val Tyr Gly Leu Asp Ala His Phe Ala
    50                  55                  60

Val Gln Tyr Glu His Arg Val Arg Lys Ala Asp Leu Lys Gly Ile Asn
65                  70                  75                  80

Arg Ile Asp Gly Phe Phe Pro Gly Leu Leu Met Ile Glu Met Lys Ser
                85                  90                  95

Ala Gly Glu Asp Leu Glu Ala Ala Phe Ile Gln Ala Leu Glu Tyr Val
            100                 105                 110

Gln Leu Ile Glu Arg Ile Glu Asp Lys Pro Arg His Ile Leu Val Ser
        115                 120                 125
```

```
Asp Phe Lys Asn Leu His Leu Tyr Glu Leu Asn Gln Gly Phe Thr Gly
    130                 135                 140

Ile Val Leu Asp Lys Thr Leu Lys Ile Lys Leu Thr Gly Phe Arg Ala
145                 150                 155                 160

His Val Gln Asp Phe Ala Phe Ile Ala Gly Tyr Glu Ala Ala Ile Ala
                165                 170                 175

Glu Arg Asn Glu Ala Leu Thr Ile Ala Ala Ala Ala Lys Leu Ala Ala
            180                 185                 190

Leu His Gln Glu Phe His Lys Gln Gly Tyr Gln Gly Ala Glu Leu Gln
        195                 200                 205

Thr Met Leu Val Arg Ile Leu Phe Cys Leu Phe Ala Asp Asp Thr Gly
    210                 215                 220

Leu Phe Ala Gln Asn Lys Ala Phe Glu Gln Leu Val Glu Glu Ser Leu
225                 230                 235                 240

Ala Asp Gly Ala Asp Leu Gly Ser Arg Leu Asn Ala Leu Tyr Lys Trp
                245                 250                 255

Leu Asp Thr Pro Glu Asp Lys Arg Arg Thr Thr Pro Arg Ala Leu Leu
            260                 265                 270

Asp Gln Tyr Ser Gly Phe Arg Leu Lys Phe Pro Tyr Ile Asn Gly Lys
        275                 280                 285

Leu Phe Ser Asp Gly Ile Asp Glu Phe Val Phe Asn Ala Ser Met Arg
    290                 295                 300

Arg Thr Leu Leu Glu Cys Cys Glu Ile Asp Trp Ser Leu Ile Ser Pro
305                 310                 315                 320

Asp Ile Phe Gly Thr Leu Phe Gln Asn Ile Met Glu Asn Ala Asp Ala
                325                 330                 335

Leu Gly Gly Gly Lys Lys Ser Ala His Arg Arg Glu Leu Gly Ala His
            340                 345                 350

Tyr Thr Ser Glu Lys Asn Ile Lys Arg Ala Ile Ala Pro Leu Phe Leu
        355                 360                 365

Asp Arg Leu Lys Ala Glu Leu Glu Gln Ala Ala Gly Asp Pro Lys Lys
    370                 375                 380

Leu Ala Arg Tyr Ile Thr Arg Leu Gln Thr Leu Gln Ile Leu Asp Pro
385                 390                 395                 400

Ala Cys Gly Cys Gly Asn Phe Leu Ile Val Ala Tyr Arg Glu Ile Arg
                405                 410                 415

Leu Leu Glu Met Gln Ala Ile Arg Gln Leu Ala Arg Ile Pro Gly Ala
            420                 425                 430

Gln Gln Met Gln Ser Gln Cys Asp Val His Gln Phe His Gly Ile Glu
        435                 440                 445

Ile Asp Pro Ala Ala Val Glu Ile Ala Thr Val Ala Met Trp Leu Thr
    450                 455                 460

Asp His Gln Met Asn Arg Leu Tyr Gln Asp Gly Tyr Lys Arg Ile Pro
465                 470                 475                 480

Leu Ala His Lys Ala Asp Ile Arg Cys Ala Asn Ala Leu Gln Thr Asp
                485                 490                 495

Trp Ala Asp Thr Ile Ser Pro Gln Asn Leu Asp Tyr Ile Val Gly Asn
            500                 505                 510

Pro Pro Phe Leu Gly Lys Lys Glu Gln Asn Ala Glu Gln Lys Lys Asp
        515                 520                 525

Met Glu Lys Val Val Gly His Leu Lys Gly Ser Gly Ile Leu Asp Tyr
    530                 535                 540

Val Thr Ala Trp Tyr Phe Lys Ala Asn Glu Leu Met Lys His Asn Pro
```

```
545                 550                 555                 560

Lys Ile Arg Thr Ala Phe Val Ser Thr Asn Ser Ile Thr Gln Gly Glu
                565                 570                 575

Gln Val Pro Ala Leu Trp Lys Pro Leu Leu Ser Asp Gly Ile Arg Ile
            580                 585                 590

Arg Phe Ala His Arg Thr Phe Lys Trp Asn Asn Glu Gly Lys Gly Thr
        595                 600                 605

Ala Ala Val His Cys Val Ile Ile Gly Phe Asp Arg Asp Glu Ile Gln
    610                 615                 620

Lys Gly Glu Arg Leu Ser Leu Trp Asp Tyr Ser Gln Gly Ile Gly Gly
625                 630                 635                 640

Asp Gly Lys Glu His Gln Val Arg Lys Ile Asn Pro Tyr Leu Leu Glu
                645                 650                 655

Ala Asp Asn Ile Leu Pro Ala Lys Arg Ser Arg Pro Val Ser Ala Asp
            660                 665                 670

Val Pro Ala Met Asn Tyr Gly Ser Met Pro Ile Asp Asn Gly Leu Leu
        675                 680                 685

Ile Leu Ser Gln Glu Ala Phe Gln Thr Ala Leu Asn Glu Asp Pro Glu
    690                 695                 700

Asn Ser Glu Leu Ile Arg Pro Tyr Met Gly Gly Ser Glu Phe Leu Asn
705                 710                 715                 720

Asn Glu Lys Arg Tyr Cys Leu Trp Leu Glu Asn Val Asp Gln Glu Arg
                725                 730                 735

Leu Ser Gln Ser Lys Phe Ala Ser Glu Arg Val Gly Gln Val Arg Ala
            740                 745                 750

Tyr Arg Leu Ser Ser Ser Arg Ala Ala Thr Val Lys Leu Ala Gly Thr
        755                 760                 765

Pro His Leu Phe Gly Glu Ile Arg Gln Pro Asp Ser Arg Tyr Leu Leu
    770                 775                 780

Leu Pro Lys Val Ser Ser Glu Asn Arg Arg Phe Leu Pro Ile Gly Tyr
785                 790                 795                 800

Ile Glu Pro Glu Thr Ile Ala Asn Gly Ser Ala Leu Ile Ile Pro Asn
                805                 810                 815

Ala Thr Leu Cys His Phe Gly Ile Leu Ser Ser Thr Met His Asn Ala
            820                 825                 830

Phe Met Arg Thr Val Ala Gly Arg Leu Glu Ser Arg Tyr Gln Tyr Ser
        835                 840                 845

Ala Ser Ile Val Tyr Asn Asn Phe Pro Phe Pro Glu Asn Pro Cys Arg
    850                 855                 860

Thr Ala Ile Glu Thr Ala Ala Gln Ala Val Leu Asp Ala Arg Ala Ala
865                 870                 875                 880

Glu Thr Glu Arg Ile Arg Arg Leu Asn Arg Ile Leu Pro Glu Lys Glu
                885                 890                 895

His Arg Pro Met Pro Thr Pro Ala Thr Leu Tyr Asn Pro Asp Thr Met
            900                 905                 910

Pro Pro Ala Leu Ala Ala Ala His Asn Ala Leu Asp Asp Ala Val Asp
        915                 920                 925

Glu Ala Tyr Gly Tyr Thr Gly Gly Asn Ser Asp Ser Glu Arg Thr Ala
    930                 935                 940

Phe Leu Phe Arg Leu Tyr Lys Asn Ala Val
945                 950
```

<210> SEQ ID NO 9
<211> LENGTH: 2805

<212> TYPE: DNA
<213> ORGANISM: Psychrobacter sp. PRwf-1

<400> SEQUENCE: 9

```
atgagtatag attacaagca cgtcagacaa caattacaac aaatcgttca cgactataaa     60
gactctgagg gctatgagcg tggccaaagc caaaactttt ggactcaagt gtttaatgct    120
tatggcgtgt ctggccaaac tcaaactaaa gcatttgaac atcgtcttaa agacaaatct    180
aatcaaaaat acgttgatgc tttcatcccc aaattggtca taattgagca aaaaagtcgt    240
ggtgtagatt taaataaagc ctatacacag gtgtctgagt attacgatcg tattaacgct    300
aaagacaagc ctagatacat catcttatgc aacttcgatg aaatttggct gtatgacatc    360
aacaacccat tagatattaa aaagcatcaa tgtccactct ctgatctgcc aaacaacgct    420
gaatggttcg agttcttatc gcctgaaagc caacaatcta atgagattat cgaagaaaac    480
cccatcaacc gacaagctac tgaaaagcta gctaaactgc accaggcttt cattgaggat    540
ggtgtagatc ctgatgaatt agccttattt ttaacacgcc taatcttctg tttctttgct    600
gacgacaccg ctatttttgg taaaaaacac gtactgcaca atttgttaaa aaaccatgca    660
gccaccgatg gtagtaactt acagcagata ctaaccactt tatttgacac attaaacact    720
gagcatcgtt caagcagatt gcctgagcat tatgctcaat tcgcctatat caatggcggt    780
ctttttgaag aaactatcaa catcccttat ttcgatgaaa agctatataa cctagttatg    840
gagtgtgatg cactcgattg gactgagatt agccctgcaa tcttcggttc gatgttccag    900
agtgtattgg atgctagtgg gggagatagc actgaggata aacggcgtga gtttggtgct    960
cactacacca gtgagaagaa tattctaaaa gtcatcaact cattgttttt acaagagtta   1020
cgtgatgagt tttctaagtg tactaacaac acaccaagag ccgtacagct atatgaaaaa   1080
ctgcctacac taaagttctt tgaccctgct tgtggttgcg gtaacttttt aatcattgcc   1140
tatcgtgaat tacgtctatt agaaaaccag ttgattgcca agatatttgg tgatcaaaag   1200
ggattacttg atattagcag tatgtgtaat gtgaccgtag atcagtttta cggcattgag   1260
attgaacctc atgccgttca tatcgctcgt gttgctatgt ggatcactga ccaccagtta   1320
aacatgacca ctgcggagcg ttttggcaca accagaccga ccacaccgat tgtttatagc   1380
cctcatatta ttgaaggtaa tgccttacaa atagattggg aaacagtctt acctgccaat   1440
gattgtagct atgtaatggg aaatcctcca tttatcggga aatccaatca aagttctgaa   1500
caaaagtcag atataaaatt agtagctagc catattaaaa atcacaagtc tttagactat   1560
gtagcaggtt ggtatataaa atccatgcat tatatgcaat cagttaataa tgcaaatcat   1620
tatatagata cagcttttgt atcaacaaac tcgatagttc aaggtgagca agttgacatc   1680
ctatggagat atctaattga tgattgcaaa ggccatataa acttcgcaca tcatacettt   1740
aaatggagca atgagggcaa agggatagct gcggttcatt gcattattgt tggcttttct   1800
ttagtagaaa agaaagagaa aaccatcttc gaatactctg acatttcgtc agaaccaagc   1860
cccaaaaaag ctagaaccat caatgcatat ttaactgacg ctccaatagt tttctttagt   1920
agaagaagta aacaagtttc caacgaaagt agtatggtta gtggcaacaa ggcaacagat   1980
ggaggtaact taattctgtc agactcagag tatatagatt taattaattc agagccatta   2040
gctaagaaat acattaaacg ttttatgatg ggctatgaat ttcttaacaa tattaagcga   2100
tggtgtctgt ggtttgataa tgttgaccca atacaattaa gtaaagatct tgaaaaaatg   2160
cctcttatta aaaagcgcat tcataatgtc aaagaactgc gtttgaacag cactaaaaag   2220
tctactgtca aaaaggcaga aacacctcat ttgttcgatg aaagacggca tactaataaa   2280
```

ccttacgttg caatacccgt cgtatcatca gagaacagaa gatttatacc gattggcttt 2340
attgatggta acaccgtagc aggtaacaag ttatttgtaa ttgtagatgg taatacctat 2400
cagttcggta ctctgtctag cagtatgcat aacgcattta tgagactaac agcgggtaga 2460
atgaaaagtg actatagcta ttcaagcacc attgtttata acaactttcc ttacccattt 2520
atggctgatg atcatagtga taaagcacaa aaagcgagag aaagcatagc taaggcttca 2580
caacaggttt tagatgctcg taaacactat caagacggta gtgagaacgc accaaccctg 2640
gctcagttat acaataccta tctaattgat ccatatccac tactaaccaa ggctcataaa 2700
gcgttagata aggccgttga tagtgcttat ggttatcgtg gcaaaggtga tgatgcgagt 2760
cgagtcgagt tttgattaa gaagattgct gagttaaaaa attaa 2805

<210> SEQ ID NO 10
<211> LENGTH: 934
<212> TYPE: PRT
<213> ORGANISM: Psychrobacter sp. PRwf-1

<400> SEQUENCE: 10

Met Ser Ile Asp Tyr Lys His Val Arg Gln Gln Leu Gln Gln Ile Val
1 5 10 15

His Asp Tyr Lys Asp Ser Glu Gly Tyr Glu Arg Gly Gln Ser Gln Asn
20 25 30

Phe Trp Thr Gln Val Phe Asn Ala Tyr Gly Val Ser Gly Gln Thr Gln
35 40 45

Thr Lys Ala Phe Glu His Arg Leu Lys Asp Lys Ser Asn Gln Lys Tyr
50 55 60

Val Asp Ala Phe Ile Pro Lys Leu Val Ile Ile Glu Gln Lys Ser Arg
65 70 75 80

Gly Val Asp Leu Asn Lys Ala Tyr Thr Gln Val Ser Glu Tyr Tyr Asp
85 90 95

Arg Ile Asn Ala Lys Asp Lys Pro Arg Tyr Ile Ile Leu Cys Asn Phe
100 105 110

Asp Glu Ile Trp Leu Tyr Asp Ile Asn Asn Pro Leu Asp Ile Lys Lys
115 120 125

His Gln Cys Pro Leu Ser Asp Leu Pro Asn Asn Ala Glu Trp Phe Glu
130 135 140

Phe Leu Ser Pro Glu Ser Gln Gln Ser Asn Glu Ile Ile Glu Glu Asn
145 150 155 160

Pro Ile Asn Arg Gln Ala Thr Glu Lys Leu Ala Lys Leu His Gln Ala
165 170 175

Phe Ile Glu Asp Gly Val Asp Pro Asp Glu Leu Ala Leu Phe Leu Thr
180 185 190

Arg Leu Ile Phe Cys Phe Phe Ala Asp Asp Thr Ala Ile Phe Gly Lys
195 200 205

Lys His Val Leu His Asn Leu Leu Lys Asn His Ala Ala Thr Asp Gly
210 215 220

Ser Asn Leu Gln Gln Ile Leu Thr Thr Leu Phe Asp Thr Leu Asn Thr
225 230 235 240

Glu His Arg Ser Ser Arg Leu Pro Glu His Tyr Ala Gln Phe Ala Tyr
245 250 255

Ile Asn Gly Gly Leu Phe Glu Glu Thr Ile Asn Ile Pro Tyr Phe Asp
260 265 270

Glu Lys Leu Tyr Asn Leu Val Met Glu Cys Asp Ala Leu Asp Trp Thr
275 280 285

-continued

```
Glu Ile Ser Pro Ala Ile Phe Gly Ser Met Phe Gln Ser Val Leu Asp
    290                 295                 300

Ala Ser Gly Gly Asp Ser Thr Glu Asp Lys Arg Arg Glu Phe Gly Ala
305                 310                 315                 320

His Tyr Thr Ser Glu Lys Asn Ile Leu Lys Val Ile Asn Ser Leu Phe
                325                 330                 335

Leu Gln Glu Leu Arg Asp Glu Phe Ser Lys Cys Thr Asn Asn Thr Pro
            340                 345                 350

Arg Ala Val Gln Leu Tyr Glu Lys Leu Pro Thr Leu Lys Phe Phe Asp
        355                 360                 365

Pro Ala Cys Gly Cys Gly Asn Phe Leu Ile Ile Ala Tyr Arg Glu Leu
    370                 375                 380

Arg Leu Leu Glu Asn Gln Leu Ile Ala Lys Ile Phe Gly Asp Gln Lys
385                 390                 395                 400

Gly Leu Leu Asp Ile Ser Ser Met Cys Asn Val Thr Val Asp Gln Phe
                405                 410                 415

Tyr Gly Ile Glu Ile Glu Pro His Ala Val His Ile Ala Arg Val Ala
            420                 425                 430

Met Trp Ile Thr Asp His Gln Leu Asn Met Thr Thr Ala Glu Arg Phe
        435                 440                 445

Gly Thr Thr Arg Pro Thr Thr Pro Ile Val Tyr Ser Pro His Ile Ile
    450                 455                 460

Glu Gly Asn Ala Leu Gln Ile Asp Trp Glu Thr Val Leu Pro Ala Asn
465                 470                 475                 480

Asp Cys Ser Tyr Val Met Gly Asn Pro Pro Phe Ile Gly Lys Ser Asn
                485                 490                 495

Gln Ser Ser Glu Gln Lys Ser Asp Ile Lys Leu Val Ala Ser His Ile
            500                 505                 510

Lys Asn His Lys Ser Leu Asp Tyr Val Ala Gly Trp Tyr Ile Lys Ser
        515                 520                 525

Met His Tyr Met Gln Ser Val Asn Asn Ala Asn His Tyr Ile Asp Thr
    530                 535                 540

Ala Phe Val Ser Thr Asn Ser Ile Val Gln Gly Glu Gln Val Asp Ile
545                 550                 555                 560

Leu Trp Arg Tyr Leu Ile Asp Asp Cys Lys Gly His Ile Asn Phe Ala
                565                 570                 575

His His Thr Phe Lys Trp Ser Asn Glu Gly Lys Gly Ile Ala Ala Val
            580                 585                 590

His Cys Ile Ile Val Gly Phe Ser Leu Val Glu Lys Lys Glu Lys Thr
        595                 600                 605

Ile Phe Glu Tyr Ser Asp Ile Ser Ser Glu Pro Ser Pro Lys Lys Ala
    610                 615                 620

Arg Thr Ile Asn Ala Tyr Leu Thr Asp Ala Pro Ile Val Phe Phe Ser
625                 630                 635                 640

Arg Arg Ser Lys Gln Val Ser Asn Glu Ser Ser Met Val Ser Gly Asn
                645                 650                 655

Lys Ala Thr Asp Gly Gly Asn Leu Ile Leu Ser Asp Ser Glu Tyr Ile
            660                 665                 670

Asp Leu Ile Asn Ser Glu Pro Leu Ala Lys Lys Tyr Ile Lys Arg Phe
        675                 680                 685

Met Met Gly Tyr Glu Phe Leu Asn Asn Ile Lys Arg Trp Cys Leu Trp
    690                 695                 700

Phe Asp Asn Val Asp Pro Ile Gln Leu Ser Lys Asp Leu Glu Lys Met
```

705 710 715 720

Pro Leu Ile Lys Lys Arg Ile His Asn Val Lys Glu Leu Arg Leu Asn
725 730 735

Ser Thr Lys Lys Ser Thr Val Lys Lys Ala Glu Thr Pro His Leu Phe
740 745 750

Asp Glu Arg Arg His Thr Asn Lys Pro Tyr Val Ala Ile Pro Val Val
755 760 765

Ser Ser Glu Asn Arg Arg Phe Ile Pro Ile Gly Phe Ile Asp Gly Asn
770 775 780

Thr Val Ala Gly Asn Lys Leu Phe Val Ile Val Asp Gly Asn Thr Tyr
785 790 795 800

Gln Phe Gly Thr Leu Ser Ser Ser Met His Asn Ala Phe Met Arg Leu
805 810 815

Thr Ala Gly Arg Met Lys Ser Asp Tyr Ser Tyr Ser Ser Thr Ile Val
820 825 830

Tyr Asn Asn Phe Pro Tyr Pro Phe Met Ala Asp Asp His Ser Asp Lys
835 840 845

Ala Gln Lys Ala Arg Glu Ser Ile Ala Lys Ala Ser Gln Gln Val Leu
850 855 860

Asp Ala Arg Lys His Tyr Gln Asp Gly Ser Glu Asn Ala Pro Thr Leu
865 870 875 880

Ala Gln Leu Tyr Asn Thr Tyr Leu Ile Asp Pro Tyr Pro Leu Leu Thr
885 890 895

Lys Ala His Lys Ala Leu Asp Lys Ala Val Asp Ser Ala Tyr Gly Tyr
900 905 910

Arg Gly Lys Gly Asp Asp Ala Ser Arg Val Glu Phe Leu Ile Lys Lys
915 920 925

Ile Ala Glu Leu Lys Asn
930

<210> SEQ ID NO 11
<211> LENGTH: 2859
<212> TYPE: DNA
<213> ORGANISM: Corynebacterium striatum M82B

<400> SEQUENCE: 11
atggttatgg cccctacgac tgtttttgac cgcgctacca ttcgccacaa tctcaccgaa 60
ttcaaactcc ggtggcttga ccgcattaag caatgggagg cggaaaaccg acccgcaacc 120
gagtcgagtc acgaccaaca gttctggggt gacctgctcg actgcttcgg tgtcaacgcc 180
cgcgacctgt acttgtacca acgcagcgct aaacgcgctt cgacggggcg caccggcaag 240
atcgacatgt ttatgccggg caaagtcata ggcgaggcta agtccctcgg cgtcccgctc 300
gatgatgctt atgcccaagc tttggattat ttgctgggcg gtactatcgc gaactcgcac 360
atgccggcct atgttgtctg ctccaacttc gagaccctgc gggttacccg tcttaaccgc 420
acctatgtcg gcgatagcgc cgactgggac attacattcc ctttagctga gattgacgag 480
cacatcgaac aactcgcttt tctcgccgac tatgaaacct ccgcctaccg ggaggaagaa 540
aaggcttccc tggaagcctc tcggttaatg gtggagctct tccgcgccat gaacggcgac 600
gacgtggacg aggcagtagg cgatgacgct cccaccacgc cggaggaaga agacgagcgc 660
gtcatgcgca cctctatcta cctcacccga atcctcttcc ttctcttcgg cgacgacgca 720
ggactctggg ataccccgca tttgtttgcg gactttgtgc gcaatgaaac caccccagaa 780
tcgctcggcc cgcagctcaa tgagctattt agcgtgctta ataccgcccc ggaaaagcgg 840

-continued

```
cctaagcgtt tgccatcaac gttggcgaag tttccttatg tcaatggtgc cctatttgct    900

gaaccgttgg cctcggagta cttcgactac cagatgcgcg aagcattgct tgctgcctgc    960

gacttcgact ggtcgaccat tgacgtctcc gtctttggtt cgttgttcca attggtgaaa   1020

tcgaaggaag cgcgccgcag cgacggcgaa cactacacgt ctaaggccaa catcatgaag   1080

accatcggcc cgctgttttt ggacgagctg agggctgagg ccgataagtt ggtgtcttct   1140

ccgtcgacgt cggtggccgc attagagcgc ttccgcgact ccctgtctga gctggtattc   1200

gctgatatgg cttgtggttc tggaaacttc ctgcttctgg cgtatcggga gttgcgccgg   1260

attgaaaccg acatcattgt cgctatacgc cagcgccgcg gtgaaacggg catgtcgttg   1320

aatattgagt gggagcagaa actgtccatt gggcagttct acggcattga gctgaattgg   1380

tggcctgcca agattgctga gactgccatg ttcctagttg accatcaggc caacaaggag   1440

cttgccaacg ctgtgggtag gcctccggag cggttgccga ttaagattac cgcgcacatt   1500

gtgcacggca atgccctgca gcttgattgg gcagacatac tctcggcttc tgccgccaag   1560

acgtatatct tcggtaaccc gccgtttttg gggcatgcga cgagaactgc tgaacaagct   1620

caagaactcc gagacttgtg gggcactaag gacatttcac gcttggacta cgtcaccggc   1680

tggcatgcaa agtgcttgga tttctttaag tcccgagagg gtcgttttgc gtttgtcacc   1740

accaattcaa ttactcaagg tgatcaagtt ccacggctat ttgggcctat cttcaaagca   1800

gggtggcgta ttcgtttcgc tcaccgcacg tttgcgtggg actctgaagc acccggtaaa   1860

gctgctgttc actgcgtcat tgttggcttc gataaggaga gtcaaccacg tccacgtctg   1920

tgggattatc ccgatgtaaa gggcgagcca gtctcagtgg aagtaggcca gtccattaat   1980

gcctatttag tagacggccc taatgttctt gtcgataaat cccggcatcc tatttcgtcg   2040

gaaatatcgc ccgcaacttt tggaaatatg gcgcgagatg gcggcaacct tctagttgag   2100

gtcgacgaat acgacgaggt tatgagtgac cccgtagcgg caaagtatgt tcgccctttc   2160

cggggtagtc gagagctaat gaacggctta gatcggtggt gtctatggct tgtagatgta   2220

gcaccgtcag acattgccca gagtccggtt ctgaaaaagc gtctagaagc ggttaagtct   2280

tttcgagccg acagtaaagc ggcaagtaca cggaaaatgg ctgaaactcc gcacttattc   2340

ggccagcggt cgcaaccgga tactgattac ctttgcctgc cgaaggtagt aagcgaacgc   2400

cgctcgtatt tcaccgtaca aaggtatcca tcaaacgtaa tcgcttctga cctagtattc   2460

catgctcaag atccagacgg cctgatgttt gcgctagcgt cgtcgtcgat gttcattacg   2520

tggcagaaaa gcatcggagg acgactcaag tctgatctcc gttttgctaa cactttgacg   2580

tggaatactt tcccagtgcc agaactcgac gagaagacgc ggcagcgaat tattaaagcg   2640

ggcaagaagg tgctcgacgc ccgcgcgctg cacccagaac gctcgctggc cgagcactac   2700

aacccactcg cgatggcacc ggaactcatc aaagcgcatg atgcgctcga ccgcgaggtg   2760

gataaagcgt ttggcgcgcc acgaaagctg acaactgttc ggcagcgcca ggagctattg   2820

tttgccaatt acgaaaaact catctcacac cagccctag                          2859


<210> SEQ ID NO 12
<211> LENGTH: 952
<212> TYPE: PRT
<213> ORGANISM: Corynebacterium striatum M82B

<400> SEQUENCE: 12

Met Val Met Ala Pro Thr Thr Val Phe Asp Arg Ala Thr Ile Arg His
1               5                   10                  15

Asn Leu Thr Glu Phe Lys Leu Arg Trp Leu Asp Arg Ile Lys Gln Trp
```

```
            20                  25                  30

Glu Ala Glu Asn Arg Pro Ala Thr Glu Ser Ser His Asp Gln Gln Phe
        35                  40                  45

Trp Gly Asp Leu Leu Asp Cys Phe Gly Val Asn Ala Arg Asp Leu Tyr
    50                  55                  60

Leu Tyr Gln Arg Ser Ala Lys Arg Ala Ser Thr Gly Arg Thr Gly Lys
65                  70                  75                  80

Ile Asp Met Phe Met Pro Gly Lys Val Ile Gly Glu Ala Lys Ser Leu
                85                  90                  95

Gly Val Pro Leu Asp Asp Ala Tyr Ala Gln Ala Leu Asp Tyr Leu Leu
            100                 105                 110

Gly Gly Thr Ile Ala Asn Ser His Met Pro Ala Tyr Val Val Cys Ser
        115                 120                 125

Asn Phe Glu Thr Leu Arg Val Thr Arg Leu Asn Arg Thr Tyr Val Gly
    130                 135                 140

Asp Ser Ala Asp Trp Asp Ile Thr Phe Pro Leu Ala Glu Ile Asp Glu
145                 150                 155                 160

His Ile Glu Gln Leu Ala Phe Leu Ala Asp Tyr Glu Thr Ser Ala Tyr
                165                 170                 175

Arg Glu Glu Glu Lys Ala Ser Leu Glu Ala Ser Arg Leu Met Val Glu
            180                 185                 190

Leu Phe Arg Ala Met Asn Gly Asp Asp Val Asp Glu Ala Val Gly Asp
        195                 200                 205

Asp Ala Pro Thr Thr Pro Glu Glu Glu Asp Glu Arg Val Met Arg Thr
    210                 215                 220

Ser Ile Tyr Leu Thr Arg Ile Leu Phe Leu Leu Phe Gly Asp Asp Ala
225                 230                 235                 240

Gly Leu Trp Asp Thr Pro His Leu Phe Ala Asp Phe Val Arg Asn Glu
                245                 250                 255

Thr Thr Pro Glu Ser Leu Gly Pro Gln Leu Asn Glu Leu Phe Ser Val
            260                 265                 270

Leu Asn Thr Ala Pro Glu Lys Arg Pro Lys Arg Leu Pro Ser Thr Leu
        275                 280                 285

Ala Lys Phe Pro Tyr Val Asn Gly Ala Leu Phe Ala Glu Pro Leu Ala
    290                 295                 300

Ser Glu Tyr Phe Asp Tyr Gln Met Arg Glu Ala Leu Leu Ala Ala Cys
305                 310                 315                 320

Asp Phe Asp Trp Ser Thr Ile Asp Val Ser Val Phe Gly Ser Leu Phe
                325                 330                 335

Gln Leu Val Lys Ser Lys Glu Ala Arg Arg Ser Asp Gly Glu His Tyr
            340                 345                 350

Thr Ser Lys Ala Asn Ile Met Lys Thr Ile Gly Pro Leu Phe Leu Asp
        355                 360                 365

Glu Leu Arg Ala Glu Ala Asp Lys Leu Val Ser Ser Pro Ser Thr Ser
    370                 375                 380

Val Ala Ala Leu Glu Arg Phe Arg Asp Ser Leu Ser Glu Leu Val Phe
385                 390                 395                 400

Ala Asp Met Ala Cys Gly Ser Gly Asn Phe Leu Leu Leu Ala Tyr Arg
                405                 410                 415

Glu Leu Arg Arg Ile Glu Thr Asp Ile Ile Val Ala Ile Arg Gln Arg
            420                 425                 430

Arg Gly Glu Thr Gly Met Ser Leu Asn Ile Glu Trp Glu Gln Lys Leu
        435                 440                 445
```

```
Ser Ile Gly Gln Phe Tyr Gly Ile Glu Leu Asn Trp Trp Pro Ala Lys
    450                 455                 460

Ile Ala Glu Thr Ala Met Phe Leu Val Asp His Gln Ala Asn Lys Glu
465                 470                 475                 480

Leu Ala Asn Ala Val Gly Arg Pro Pro Glu Arg Leu Pro Ile Lys Ile
                485                 490                 495

Thr Ala His Ile Val His Gly Asn Ala Leu Gln Leu Asp Trp Ala Asp
            500                 505                 510

Ile Leu Ser Ala Ser Ala Ala Lys Thr Tyr Ile Phe Gly Asn Pro Pro
        515                 520                 525

Phe Leu Gly His Ala Thr Arg Thr Ala Glu Gln Ala Gln Glu Leu Arg
    530                 535                 540

Asp Leu Trp Gly Thr Lys Asp Ile Ser Arg Leu Asp Tyr Val Thr Gly
545                 550                 555                 560

Trp His Ala Lys Cys Leu Asp Phe Phe Lys Ser Arg Glu Gly Arg Phe
                565                 570                 575

Ala Phe Val Thr Thr Asn Ser Ile Thr Gln Gly Asp Gln Val Pro Arg
            580                 585                 590

Leu Phe Gly Pro Ile Phe Lys Ala Gly Trp Arg Ile Arg Phe Ala His
        595                 600                 605

Arg Thr Phe Ala Trp Asp Ser Glu Ala Pro Gly Lys Ala Ala Val His
    610                 615                 620

Cys Val Ile Val Gly Phe Asp Lys Glu Ser Gln Pro Arg Pro Arg Leu
625                 630                 635                 640

Trp Asp Tyr Pro Asp Val Lys Gly Glu Pro Val Ser Val Glu Val Gly
                645                 650                 655

Gln Ser Ile Asn Ala Tyr Leu Val Asp Gly Pro Asn Val Leu Val Asp
            660                 665                 670

Lys Ser Arg His Pro Ile Ser Ser Glu Ile Ser Pro Ala Thr Phe Gly
        675                 680                 685

Asn Met Ala Arg Asp Gly Gly Asn Leu Leu Val Glu Val Asp Glu Tyr
    690                 695                 700

Asp Glu Val Met Ser Asp Pro Val Ala Ala Lys Tyr Val Arg Pro Phe
705                 710                 715                 720

Arg Gly Ser Arg Glu Leu Met Asn Gly Leu Asp Arg Trp Cys Leu Trp
                725                 730                 735

Leu Val Asp Val Ala Pro Ser Asp Ile Ala Gln Ser Pro Val Leu Lys
            740                 745                 750

Lys Arg Leu Glu Ala Val Lys Ser Phe Arg Ala Asp Ser Lys Ala Ala
        755                 760                 765

Ser Thr Arg Lys Met Ala Glu Thr Pro His Leu Phe Gly Gln Arg Ser
    770                 775                 780

Gln Pro Asp Thr Asp Tyr Leu Cys Leu Pro Lys Val Val Ser Glu Arg
785                 790                 795                 800

Arg Ser Tyr Phe Thr Val Gln Arg Tyr Pro Ser Asn Val Ile Ala Ser
                805                 810                 815

Asp Leu Val Phe His Ala Gln Asp Pro Asp Gly Leu Met Phe Ala Leu
            820                 825                 830

Ala Ser Ser Ser Met Phe Ile Thr Trp Gln Lys Ser Ile Gly Gly Arg
        835                 840                 845

Leu Lys Ser Asp Leu Arg Phe Ala Asn Thr Leu Thr Trp Asn Thr Phe
    850                 855                 860

Pro Val Pro Glu Leu Asp Glu Lys Thr Arg Gln Arg Ile Ile Lys Ala
865                 870                 875                 880
```

-continued

```
Gly Lys Lys Val Leu Asp Ala Arg Ala Leu His Pro Glu Arg Ser Leu
            885                 890                 895

Ala Glu His Tyr Asn Pro Leu Ala Met Ala Pro Glu Leu Ile Lys Ala
        900                 905                 910

His Asp Ala Leu Asp Arg Glu Val Asp Lys Ala Phe Gly Ala Pro Arg
    915                 920                 925

Lys Leu Thr Thr Val Arg Gln Arg Gln Glu Leu Leu Phe Ala Asn Tyr
    930                 935                 940

Glu Lys Leu Ile Ser His Gln Pro
945                 950


<210> SEQ ID NO 13
<211> LENGTH: 2814
<212> TYPE: DNA
<213> ORGANISM: Neisseria meningitidis Z2491

<400> SEQUENCE: 13

atgaaaaccc tgctccaact ccaaaccgcc gcacaaaact tcgccgccta ctacaaagac     60

caaaccgacg aacgccgcga gaaagacacc ttctggaacg aatttttcgc cattttcggc    120

atcgaccgca aaaacgtcgc ccacttcgaa taccccgtca aagaccctgc cgacaacacc    180

caattcgtcg atatattttg ggaaggcatc ttccttgccg aacacaaatc cgccaacaaa    240

aacctgacca aggccaaaga gcaggcggaa cgttatttac aggaaatcgg gcgcaccaag    300

ccctccgcgc tgcccgaata ttacgccgtc agcgattttg cccatttcca cctttaccgc    360

cgcgtacctg aagaaggcgc agaaaaccaa tggcagttcc ctttggaaga attgcctgaa    420

tacatcacgc gcggcgtttt cgacttcatg ttcggcatcg aagccaaagt ccgccaaatt    480

caagaagaag ccaacattca agcggcggcg accatcggca ggctgcacga cgcgctcaaa    540

gaagaaggca tttacgaaga acacgagctg cgcctcttca tcacgcgcct gcttttcctc    600

ttttttgccg acgacagcgc cgttttccgg cgcaactacc ttttccaaga ctttttagaa    660

aactgcaaag aagccgacac gctcggcgac aagctcaatc aactctttga atttctcaac    720

acacccgacc aaaagcgcag caagacccaa agcgaaaaat ttaaaggttt cgaatacgtc    780

aacggcggtc ttttcaaaga acgcctgcgc actttcgact tcactgccaa gcagcaccgc    840

gccttaatcg actgcggcaa tttcgactgg cgcaacatca gtccagaaat cttcggcacg    900

ctcttccaat ccgtcatgga cgcgcaagag cggcgcgaag cgggcgcgca ctacaccgaa    960

gccgccaata tcgacaaagt catcaacggc ctttttttag aaaacctgcg tgccgaattt   1020

gaagccgtca aagccctcaa acgcgacaaa gccaaaaaac tcgccgcctt ctaccaaaaa   1080

atccaaaacc tgcaattcct cgaccctgcc tgcggctgcg gcaacttcct tatcgtcgcc   1140

tacgaccgca tccgcgccct tgaagacgac atcatcgccg aagccctcaa agacaaagca   1200

gacggcctgt tcgacagccc gtccgtccaa tgccgtctga aacagtttca cggcatcgaa   1260

atagacgaat ttgccgtcct catcgcccgc accgccatgt ggctcaaaaa ccaccaatgc   1320

aacatccgca cacaaatccg cttcgacggc gaagtcgcct gccatacgct gccgctcgaa   1380

gacgccgccg aaatcatcca cgccaacagc ctccgcacac cttggcaggc ggcggactac   1440

atcttcggca atccccccctt tatcggctcg acctaccaaa ccaaagagca gaaaaacgac   1500

ctcgaaagca tctgcggcca tatcaaaggc tacggcctgt tggattacgt ctgcaactgg   1560

tacgtcaaag ccgcaggcat catggcgcag catccccaag ttcagacggc atttgtttcc   1620

accaattcca tctgccaagg ccagcaggtc gaaatcctct ggggcagcct tttaaaccaa   1680
```

ggcatcgaaa tccactttgc ccaccgcacc ttccaatgga cgagccaagc cgcaggcaaa 1740
gccgccgtcc actgcatcat cgtcggcttc cgccaaaagc cgccaatgcc gtctgaaaaa 1800
accctctacg actatcccga catcaaaggc gaacccgaaa aacacgccgt agccaacatc 1860
aatccttatc tgatcgatgc gcccgatttg attatcgcca agcgcagccg tcccatacat 1920
tgcgaacctg atatggtcaa cggaagcaaa ccgaccgaag gcggcaacct tatcctttca 1980
accgccgaaa aagatgccct gattgccgcc gaacccttgg cggagcaata catccgcccc 2040
tttatcggcg cggatgagtt tctcaacggc aaaacccgtt ggtgcctgtg gtttcacggc 2100
gtatccgatg tcaaacgcaa ccacgacctg aaacaaatgc cccaagttca agcccgtatt 2160
caggcggtca aaaccatgcg cgaagccagc agcgacaaac aaactcaaaa agatgcagca 2220
accccgtggc tttttcaaaa aatccgccag ccttcagacg gcaattatct gattattccg 2280
agcgtgtcgt ctgaaagccg ccgtttcatc cccatcggtt atctgtcgtt tgaaacagtt 2340
gtcagcaatc tggcatttat ccttccaaac gccaccctct accacttcgg catcctcagc 2400
tccaccatgc acaacgcctt tatgcgtacc gttgcaggtc gtctgaaaag cgattatcgc 2460
tactctaata ccgtcgtgta caacaacttc cccttccccg aaagctgccg gttgccgtct 2520
gaaaacgacc gccccgaccc gctccgcgcc gccgtcgaag ccgccgccca aaccgtcctc 2580
gacgcgcgcg gacaataccg ccgagaagcg caggaagccg gtttgcccga gccgaccctc 2640
gccgaactct atgcgcccga cgcaggctat accgccctcg acaaagccca cgccaccctc 2700
gacaaggcag tcgataaagc ctacggctac aaaacaggca aaaataccga cgacgaggca 2760
gaacgcgtcg ccttcctgtt cgagctgtac cgcaaggcgg cggcaattgc gtag 2814

<210> SEQ ID NO 14
<211> LENGTH: 937
<212> TYPE: PRT
<213> ORGANISM: Neisseria meningitidis Z2491

<400> SEQUENCE: 14

Met Lys Thr Leu Leu Gln Leu Gln Thr Ala Ala Gln Asn Phe Ala Ala
1 5 10 15

Tyr Tyr Lys Asp Gln Thr Asp Glu Arg Arg Glu Lys Asp Thr Phe Trp
20 25 30

Asn Glu Phe Phe Ala Ile Phe Gly Ile Asp Arg Lys Asn Val Ala His
35 40 45

Phe Glu Tyr Pro Val Lys Asp Pro Ala Asp Asn Thr Gln Phe Val Asp
50 55 60

Ile Phe Trp Glu Gly Ile Phe Leu Ala Glu His Lys Ser Ala Asn Lys
65 70 75 80

Asn Leu Thr Lys Ala Lys Glu Gln Ala Glu Arg Tyr Leu Gln Glu Ile
85 90 95

Gly Arg Thr Lys Pro Ser Ala Leu Pro Glu Tyr Tyr Ala Val Ser Asp
100 105 110

Phe Ala His Phe His Leu Tyr Arg Arg Val Pro Glu Glu Gly Ala Glu
115 120 125

Asn Gln Trp Gln Phe Pro Leu Glu Glu Leu Pro Glu Tyr Ile Thr Arg
130 135 140

Gly Val Phe Asp Phe Met Phe Gly Ile Glu Ala Lys Val Arg Gln Ile
145 150 155 160

Gln Glu Glu Ala Asn Ile Gln Ala Ala Ala Thr Ile Gly Arg Leu His
165 170 175

Asp Ala Leu Lys Glu Glu Gly Ile Tyr Glu Glu His Glu Leu Arg Leu

-continued

```
            180                 185                 190

Phe Ile Thr Arg Leu Leu Phe Leu Phe Phe Ala Asp Asp Ser Ala Val
        195                 200                 205

Phe Arg Arg Asn Tyr Leu Phe Gln Asp Phe Leu Glu Asn Cys Lys Glu
    210                 215                 220

Ala Asp Thr Leu Gly Asp Lys Leu Asn Gln Leu Phe Glu Phe Leu Asn
225                 230                 235                 240

Thr Pro Asp Gln Lys Arg Ser Lys Thr Gln Ser Glu Lys Phe Lys Gly
                245                 250                 255

Phe Glu Tyr Val Asn Gly Gly Leu Phe Lys Glu Arg Leu Arg Thr Phe
            260                 265                 270

Asp Phe Thr Ala Lys Gln His Arg Ala Leu Ile Asp Cys Gly Asn Phe
        275                 280                 285

Asp Trp Arg Asn Ile Ser Pro Glu Ile Phe Gly Thr Leu Phe Gln Ser
    290                 295                 300

Val Met Asp Ala Gln Glu Arg Arg Glu Ala Gly Ala His Tyr Thr Glu
305                 310                 315                 320

Ala Ala Asn Ile Asp Lys Val Ile Asn Gly Leu Phe Leu Glu Asn Leu
                325                 330                 335

Arg Ala Glu Phe Glu Ala Val Lys Ala Leu Lys Arg Asp Lys Ala Lys
            340                 345                 350

Lys Leu Ala Ala Phe Tyr Gln Lys Ile Gln Asn Leu Gln Phe Leu Asp
        355                 360                 365

Pro Ala Cys Gly Cys Gly Asn Phe Leu Ile Val Ala Tyr Asp Arg Ile
    370                 375                 380

Arg Ala Leu Glu Asp Asp Ile Ile Ala Glu Ala Leu Lys Asp Lys Ala
385                 390                 395                 400

Asp Gly Leu Phe Asp Ser Pro Ser Val Gln Cys Arg Leu Lys Gln Phe
                405                 410                 415

His Gly Ile Glu Ile Asp Glu Phe Ala Val Leu Ile Ala Arg Thr Ala
            420                 425                 430

Met Trp Leu Lys Asn His Gln Cys Asn Ile Arg Thr Gln Ile Arg Phe
        435                 440                 445

Asp Gly Glu Val Ala Cys His Thr Leu Pro Leu Glu Asp Ala Ala Glu
    450                 455                 460

Ile Ile His Ala Asn Ser Leu Arg Thr Pro Trp Gln Ala Ala Asp Tyr
465                 470                 475                 480

Ile Phe Gly Asn Pro Pro Phe Ile Gly Ser Thr Tyr Gln Thr Lys Glu
                485                 490                 495

Gln Lys Asn Asp Leu Glu Ser Ile Cys Gly His Ile Lys Gly Tyr Gly
            500                 505                 510

Leu Leu Asp Tyr Val Cys Asn Trp Tyr Val Lys Ala Ala Gly Ile Met
        515                 520                 525

Ala Gln His Pro Gln Val Gln Thr Ala Phe Val Ser Thr Asn Ser Ile
    530                 535                 540

Cys Gln Gly Gln Gln Val Glu Ile Leu Trp Gly Ser Leu Leu Asn Gln
545                 550                 555                 560

Gly Ile Glu Ile His Phe Ala His Arg Thr Phe Gln Trp Thr Ser Gln
                565                 570                 575

Ala Ala Gly Lys Ala Ala Val His Cys Ile Ile Val Gly Phe Arg Gln
            580                 585                 590

Lys Pro Pro Met Pro Ser Glu Lys Thr Leu Tyr Asp Tyr Pro Asp Ile
        595                 600                 605
```

-continued

```
Lys Gly Glu Pro Glu Lys His Ala Val Ala Asn Ile Asn Pro Tyr Leu
    610                 615                 620

Ile Asp Ala Pro Asp Leu Ile Ile Ala Lys Arg Ser Arg Pro Ile His
625                 630                 635                 640

Cys Glu Pro Asp Met Val Asn Gly Ser Lys Pro Thr Glu Gly Gly Asn
                645                 650                 655

Leu Ile Leu Ser Thr Ala Glu Lys Asp Ala Leu Ile Ala Ala Glu Pro
            660                 665                 670

Leu Ala Glu Gln Tyr Ile Arg Pro Phe Ile Gly Ala Asp Glu Phe Leu
        675                 680                 685

Asn Gly Lys Thr Arg Trp Cys Leu Trp Phe His Gly Val Ser Asp Val
    690                 695                 700

Lys Arg Asn His Asp Leu Lys Gln Met Pro Gln Val Gln Ala Arg Ile
705                 710                 715                 720

Gln Ala Val Lys Thr Met Arg Glu Ala Ser Ser Asp Lys Gln Thr Gln
                725                 730                 735

Lys Asp Ala Ala Thr Pro Trp Leu Phe Gln Lys Ile Arg Gln Pro Ser
            740                 745                 750

Asp Gly Asn Tyr Leu Ile Ile Pro Ser Val Ser Ser Glu Ser Arg Arg
        755                 760                 765

Phe Ile Pro Ile Gly Tyr Leu Ser Phe Glu Thr Val Val Ser Asn Leu
    770                 775                 780

Ala Phe Ile Leu Pro Asn Ala Thr Leu Tyr His Phe Gly Ile Leu Ser
785                 790                 795                 800

Ser Thr Met His Asn Ala Phe Met Arg Thr Val Ala Gly Arg Leu Lys
                805                 810                 815

Ser Asp Tyr Arg Tyr Ser Asn Thr Val Val Tyr Asn Asn Phe Pro Phe
            820                 825                 830

Pro Glu Ser Cys Arg Leu Pro Ser Glu Asn Asp Arg Pro Asp Pro Leu
        835                 840                 845

Arg Ala Ala Val Glu Ala Ala Ala Gln Thr Val Leu Asp Ala Arg Gly
    850                 855                 860

Gln Tyr Arg Arg Glu Ala Gln Glu Ala Gly Leu Pro Glu Pro Thr Leu
865                 870                 875                 880

Ala Glu Leu Tyr Ala Pro Asp Ala Gly Tyr Thr Ala Leu Asp Lys Ala
                885                 890                 895

His Ala Thr Leu Asp Lys Ala Val Asp Lys Ala Tyr Gly Tyr Lys Thr
            900                 905                 910

Gly Lys Asn Thr Asp Asp Glu Ala Glu Arg Val Ala Phe Leu Phe Glu
        915                 920                 925

Leu Tyr Arg Lys Ala Ala Ala Ile Ala
    930                 935
```

<210> SEQ ID NO 15
<211> LENGTH: 2781
<212> TYPE: DNA
<213> ORGANISM: Corynebacterium diphtheriae

<400> SEQUENCE: 15

```
atgtcatcga gttctccaag tgaaaagaaa ctagccgcca agctatttgc taataagtgg     60

gcagaccgtg gcaatgagaa aagcgacact cacagtttct ggttggagct tcttcgtgat    120

gttgtaggta tgcaagatgt gactaccaac gtgcgattcg aatcgcgcac gagtcaacgc    180

ggctacatcg atgtggtgat ccaagacgcc aaaactttca ttgaacaaaa atccatcgat    240

gttagtttgg acaaagctga tatccgtcag gggcgagttg tcactgcttt tagacaagca    300
```

-continued

```
ctgaattacg ccaacactat gccgaacaaa ctgcgacctg actacattat tacgtgtaat    360
ttcgcagagt ttcgtattca tgacttaaat aaggtgaatg cggaaactga ctatatttcc    420
tttaccttgg cagaattgcc tgaccaaatc catcttctag attttctcat cgacccacaa    480
aaatctcgtg ctgttcgtga agaaaaagtg tcgatggatg ctggcacact cgtcggcaag    540
ctttacgacg ccctgcgtga tcagtattta gaccccaaca gtgatgcgag ccagcactcc    600
ctcaacgttt tgtgcgtgcg ccttgtattt tgtttgtttg ctgaagacgc cggcctcttt    660
gaaaaggatg cgttttatcg ttatcttgac ggattacgcg ccgatcaagt tcgcgtcgcg    720
ctgagagatt tgttcgaagt actcaataca ccagttgatt cacgtgaccc ttatctttct    780
gaacagctta aaaacttccc ttatgtcaac ggtggtttat tcgccaaagt cgagcagatc    840
cctaatttca ctgatgaaat tcttgaccta ttagttcatg aggtatcgga gaaaactaac    900
tgggccgaaa tctcgcctac aatctttggc ggtgtttttg aatccaccct caacccagaa    960
actcgcgccc gtggaggcat gcattacacg agtcccgaaa acatccataa ggtgattgac   1020
ccgctgtttc ttgactctct caaggcagag ctagattcca tccttaacgc atcagggata   1080
actgcaaaca agcgcaagaa acaactcgag gcattccaca ccaagatctc agagctaaaa   1140
tttttcgacc ctgcctgcgg ttcgggaaac ttcctcacag aaacctatat ccacctgcgc   1200
aagatcgaaa acaagatcct ttcagagctt gccggcgacc aaacccagct cggctttagc   1260
aacgtcactc tcaaggtcag cttggaccag ttctacggca tcgagatcaa tgatttcgcc   1320
gtctccgtcg cctccaccgc cctatggatt gcgcagctcc aggccaacat cgaggccgaa   1380
tcgatcgtca ccgcaaacat cgaaagtctt ccgcttcgcg acgccgccca catccacctc   1440
ggtaatgcgc tgcgcaccga ctgggcttcg gtactcgcgc ctgaacagtg caattacatt   1500
attggaaatc cgccgttttt aggctactcg cggcttgacg acgctcaaaa ggaagaccgc   1560
aaggccatct tcggcaagaa tggcggtgtg ctcgattacg tagcgtgctg gcaccgcaaa   1620
gccgccgaat atatgcacgg aacggatgct gaagccgcgc tcgtttccac caattcgatc   1680
tgccaaggcc agcaagtcac tccgctgtgg aagccgcttt tcgacgccgg gatccacatc   1740
aacttcgccc accgcacttt cgtgtggagc aacgaggcag cagatcaggc gcatgtctta   1800
tgtatcatcg tcgggttttc ctacatcgat cgaccagtca agcaggcgtg gacctaccgg   1860
aagaacgagg tggaatactc ggagcctgta catttgaacg gttacttggc agatgccccg   1920
gatgcgttcc tgacacgcag gtcaaagccg atttcggatg tgctggaaat ggctcaggga   1980
ttcaagcccg ccgatggtgg acatctcttg ctcactcaag aagaacgaga cgaactcctt   2040
gcaaaagaac cactagctgc gccgtggatt cgaaagttct ccatgggcgc cgaattcatc   2100
aacggcaagg accgctattg cctatggttg ccggaaatta caggcgttga gctaaagaga   2160
ttgcctctcg ttcgcgcgcg aattgacgca tgccgtgagt ggaggcttga acaaatcaaa   2220
actggagatg catacaaatt gtcagaccgg ccacacctac tgcggccaac cagcaggttt   2280
aaggacggaa cctacatcgg catcccaaag gtttcttcag agcgacggaa gtatgtaccg   2340
tttgcttttg tgacagatgg aatgattcct ggcgacatgc tctacttcgt ccctacggat   2400
tctctatttg tgtttggggt tctcgtttca caattccaaa acgcctggat gcgtgtagtg   2460
gcaggccgtc tcaagagcga ctaccgctat ggcaacacca ctgtctacaa caacttcgtt   2520
ttccccgagg tagatgattc agtgcgagtg gacgtcgaaa agcgtgctca ggcggtgatc   2580
gacgcacgct ctctttaccc cgaagcgacg cttgctgaca tgtatgatcc cgacaatgac   2640
ttcctctacc ccgagctcat gaaggcccac cgcgagctag accgcgctgt cgagatggct   2700
```

```
tatggcgtgg acttcggtgg cgacgagcag cagatagtgg ctcacctctt caagctgtac   2760

aacgagaaag tagagaaatg a                                             2781


<210> SEQ ID NO 16
<211> LENGTH: 926
<212> TYPE: PRT
<213> ORGANISM: Corynebacterium diphtheriae

<400> SEQUENCE: 16

Met Ser Ser Ser Ser Pro Ser Glu Lys Lys Leu Ala Ala Lys Leu Phe
1               5                   10                  15

Ala Asn Lys Trp Ala Asp Arg Gly Asn Glu Lys Ser Asp Thr His Ser
            20                  25                  30

Phe Trp Leu Glu Leu Leu Arg Asp Val Val Gly Met Gln Asp Val Thr
        35                  40                  45

Thr Asn Val Arg Phe Glu Ser Arg Thr Ser Gln Arg Gly Tyr Ile Asp
    50                  55                  60

Val Val Ile Gln Asp Ala Lys Thr Phe Ile Glu Gln Lys Ser Ile Asp
65                  70                  75                  80

Val Ser Leu Asp Lys Ala Asp Ile Arg Gln Gly Arg Val Val Thr Ala
                85                  90                  95

Phe Arg Gln Ala Leu Asn Tyr Ala Asn Thr Met Pro Asn Lys Leu Arg
            100                 105                 110

Pro Asp Tyr Ile Ile Thr Cys Asn Phe Ala Glu Phe Arg Ile His Asp
        115                 120                 125

Leu Asn Lys Val Asn Ala Glu Thr Asp Tyr Ile Ser Phe Thr Leu Ala
    130                 135                 140

Glu Leu Pro Asp Gln Ile His Leu Leu Asp Phe Leu Ile Asp Pro Gln
145                 150                 155                 160

Lys Ser Arg Ala Val Arg Glu Glu Lys Val Ser Met Asp Ala Gly Thr
                165                 170                 175

Leu Val Gly Lys Leu Tyr Asp Ala Leu Arg Asp Gln Tyr Leu Asp Pro
            180                 185                 190

Asn Ser Asp Ala Ser Gln His Ser Leu Asn Val Leu Cys Val Arg Leu
        195                 200                 205

Val Phe Cys Leu Phe Ala Glu Asp Ala Gly Leu Phe Glu Lys Asp Ala
    210                 215                 220

Phe Tyr Arg Tyr Leu Asp Gly Leu Arg Ala Asp Gln Val Arg Val Ala
225                 230                 235                 240

Leu Arg Asp Leu Phe Glu Val Leu Asn Thr Pro Val Asp Ser Arg Asp
                245                 250                 255

Pro Tyr Leu Ser Glu Gln Leu Lys Asn Phe Pro Tyr Val Asn Gly Gly
            260                 265                 270

Leu Phe Ala Lys Val Glu Gln Ile Pro Asn Phe Thr Asp Glu Ile Leu
        275                 280                 285

Asp Leu Leu Val His Glu Val Ser Glu Lys Thr Asn Trp Ala Glu Ile
    290                 295                 300

Ser Pro Thr Ile Phe Gly Gly Val Phe Glu Ser Thr Leu Asn Pro Glu
305                 310                 315                 320

Thr Arg Ala Arg Gly Gly Met His Tyr Thr Ser Pro Glu Asn Ile His
                325                 330                 335

Lys Val Ile Asp Pro Leu Phe Leu Asp Ser Leu Lys Ala Glu Leu Asp
            340                 345                 350

Ser Ile Leu Asn Ala Ser Gly Ile Thr Ala Asn Lys Arg Lys Lys Gln
```

-continued

```
        355                 360                 365

Leu Glu Ala Phe His Thr Lys Ile Ser Glu Leu Lys Phe Phe Asp Pro
    370                 375                 380

Ala Cys Gly Ser Gly Asn Phe Leu Thr Glu Thr Tyr Ile His Leu Arg
385                 390                 395                 400

Lys Ile Glu Asn Lys Ile Leu Ser Glu Leu Ala Gly Asp Gln Thr Gln
                405                 410                 415

Leu Gly Phe Ser Asn Val Thr Leu Lys Val Ser Leu Asp Gln Phe Tyr
            420                 425                 430

Gly Ile Glu Ile Asn Asp Phe Ala Val Ser Val Ala Ser Thr Ala Leu
        435                 440                 445

Trp Ile Ala Gln Leu Gln Ala Asn Ile Glu Ala Glu Ser Ile Val Thr
    450                 455                 460

Ala Asn Ile Glu Ser Leu Pro Leu Arg Asp Ala Ala His Ile His Leu
465                 470                 475                 480

Gly Asn Ala Leu Arg Thr Asp Trp Ala Ser Val Leu Ala Pro Glu Gln
                485                 490                 495

Cys Asn Tyr Ile Ile Gly Asn Pro Pro Phe Leu Gly Tyr Ser Arg Leu
            500                 505                 510

Asp Asp Ala Gln Lys Glu Asp Arg Lys Ala Ile Phe Gly Lys Asn Gly
        515                 520                 525

Gly Val Leu Asp Tyr Val Ala Cys Trp His Arg Lys Ala Ala Glu Tyr
    530                 535                 540

Met His Gly Thr Asp Ala Glu Ala Ala Leu Val Ser Thr Asn Ser Ile
545                 550                 555                 560

Cys Gln Gly Gln Gln Val Thr Pro Leu Trp Lys Pro Leu Phe Asp Ala
                565                 570                 575

Gly Ile His Ile Asn Phe Ala His Arg Thr Phe Val Trp Ser Asn Glu
            580                 585                 590

Ala Ala Asp Gln Ala His Val Leu Cys Ile Ile Val Gly Phe Ser Tyr
        595                 600                 605

Ile Asp Arg Pro Val Lys Gln Ala Trp Thr Tyr Arg Lys Asn Glu Val
    610                 615                 620

Glu Tyr Ser Glu Pro Val His Leu Asn Gly Tyr Leu Ala Asp Ala Pro
625                 630                 635                 640

Asp Ala Phe Leu Thr Arg Arg Ser Lys Pro Ile Ser Asp Val Leu Glu
                645                 650                 655

Met Ala Gln Gly Phe Lys Pro Ala Asp Gly Gly His Leu Leu Leu Thr
            660                 665                 670

Gln Glu Glu Arg Asp Glu Leu Leu Ala Lys Glu Pro Leu Ala Ala Pro
        675                 680                 685

Trp Ile Arg Lys Phe Ser Met Gly Ala Glu Phe Ile Asn Gly Lys Asp
    690                 695                 700

Arg Tyr Cys Leu Trp Leu Pro Glu Ile Thr Gly Val Glu Leu Lys Arg
705                 710                 715                 720

Leu Pro Leu Val Arg Ala Arg Ile Asp Ala Cys Arg Glu Trp Arg Leu
                725                 730                 735

Glu Gln Ile Lys Thr Gly Asp Ala Tyr Lys Leu Ser Asp Arg Pro His
            740                 745                 750

Leu Leu Arg Pro Thr Ser Arg Phe Lys Asp Gly Thr Tyr Ile Gly Ile
        755                 760                 765

Pro Lys Val Ser Ser Glu Arg Arg Lys Tyr Val Pro Phe Ala Phe Val
    770                 775                 780
```

```
Thr Asp Gly Met Ile Pro Gly Asp Met Leu Tyr Phe Val Pro Thr Asp
785                 790                 795                 800

Ser Leu Phe Val Phe Gly Val Leu Val Ser Gln Phe Gln Asn Ala Trp
                805                 810                 815

Met Arg Val Val Ala Gly Arg Leu Lys Ser Asp Tyr Arg Tyr Gly Asn
            820                 825                 830

Thr Thr Val Tyr Asn Asn Phe Val Phe Pro Glu Val Asp Asp Ser Val
        835                 840                 845

Arg Val Asp Val Glu Lys Arg Ala Gln Ala Val Ile Asp Ala Arg Ser
    850                 855                 860

Leu Tyr Pro Glu Ala Thr Leu Ala Asp Met Tyr Asp Pro Asp Asn Asp
865                 870                 875                 880

Phe Leu Tyr Pro Glu Leu Met Lys Ala His Arg Glu Leu Asp Arg Ala
                885                 890                 895

Val Glu Met Ala Tyr Gly Val Asp Phe Gly Gly Asp Glu Gln Gln Ile
            900                 905                 910

Val Ala His Leu Phe Lys Leu Tyr Asn Glu Lys Val Glu Lys
        915                 920                 925


<210> SEQ ID NO 17
<211> LENGTH: 2847
<212> TYPE: DNA
<213> ORGANISM: Arcanobacterium pyogenes

<400> SEQUENCE: 17

atgctctctg atcctgtctt tgaccgtgcc accatccgcc ataaactcat tgagttcaaa     60

atccgctggc gcggccatat cgaccagtgg aaagcagaaa accgccccgc caccgagtcc    120

agccacgatc aacagttctg ggtgacctc ctagcctgct tcggcgtcaa cgcccgcgac    180

ctttacctgt atcagcgcag cgcgaaacga gcctccaccg gccacaccgg caagattgac    240

atgttcatcc ccggcaaagt catcggcgag gccaagtccc tcggtatcga cctggacaag    300

gctcacgagc aagcactcga ctacctgctc ggcggcacca ttccgaactc acaaatgccg    360

gcctatgtcc tctgctccaa cttcgagacc ctgcgcatca cccgccttaa ccgcgactac    420

gtcggcgact ctgcagaatg ggacgttacc ttcgacctgg acgaaatcga cgagcatctg    480

gaacagctcg cgttcctggc ggactatgag acctcggcct atcacgagga agaacaagcc    540

tcccttgagg cctcacgcct gatggtcgag ctgttccgcg ccatgaacgg cgacgaggca    600

gacgaagccg tgggcgatga agccccaacc accccggagg aagaagacga aagggtcatg    660

cgcacctcgg tctacctaac gcgcatcctc ttcctccttt tcggcgacga tgcaggcctg    720

tgggacaccc cgcacctgtt tacgacgttc gtgcgcaacg aaaccacccc ggaatctctc    780

ggacctcagc tcaacgaact tttccgagtc ctcaacaccc cggaggacaa gcggcctaag    840

cgcttgcccg gcaccttggc gaaattcccc tacgtcaacg gcgcaatctt cgccgaacag    900

ctcgaccctg aatacttcga ctacgccatg cgcgaagccc tgctcaacgc ctgcgacttc    960

gactggtcaa aaatcgacgt gtccgtcttc ggctcactgt tccagctggt taagtcgaaa   1020

gaagcccgcc gtggcgatgg tgagcactac acctcgaaga ccaacatcct caagaccatc   1080

ggaccgctct tcctcgacga gttgcgtgcc caggctgaca agctggtctc caaccccgcc   1140

accccggtgc gcaagttaga agaattccgc gactcactgg ctgcccatat tttctgcgac   1200

ccggcctgtg gtgcgggaaa cttcctgctc accgcctata aagaactgcg ccgtattgaa   1260

acggacctta tcgtggctat ccgtcagcgc cgtggcgaga cgggtatgtc gctaaatatt   1320

gagtgggagc agaaactgtc gattgggcag ttctacggat ttgagctgaa ctggtggccg   1380
```

```
gcaaagattg cagagacggc gatgttcctg gtggatcatc aggcgaataa ggagttggcg   1440
aatgcggtgg ggcgtccgcc gcagcgtttg cctattacga ttaccgccca catcgtccac   1500
ggaaacgctc tcgccctgga ctggacggaa gcgctgccca aagcagtggg ggagacgttt   1560
atctttggca acccaccatt tatcggtcaa gatacgcgca caaaacagca gctcgaggaa   1620
atgaaagctg tatggagacg taaaaacatc tcgagattgg actacgtcac gtgttggcac   1680
ataaaaagcc ttgacctttt cagtacccgt aacggacggt tcgctttcgt aacaactaac   1740
tcgattaccc aaggcgaaca agtgccgctt ttattcggcc ccatcttcgc agcaggttgg   1800
cgtatccgct tcgcccatcg cacattctca tgggattccg atgctcccgg taaagcctca   1860
gtccactgcg tcatcgtcgg tttcgaccgt gcacacgaac ctcgccccca gctctgggat   1920
tacccgaatg tcagcagtgc ccccgtggct gtgcctgtgg agcgcgtgat taatgcttac   1980
ctcgtcgacg gccctaatgt ccttgtccaa aagatgactt cgcccatctc ctgcgagatt   2040
aaacccgcag ttctaggcgc aatggcaaaa gacggaggtg gcttgatagt tgaagcccag   2100
gacgtgcaag aagctttgga cgatccgata gcggcaaagt acctacgtcc gtacgttggc   2160
tcgcgagaac ttgttcgcgg ccttagtcgg tggtgtctct ggatggtcga tctcgacccc   2220
gccgacgttc aggcaagtac ttttctgcgt tcacgaattg aacaagtacg cgcctacaga   2280
acaacgtcct cggctcctac tacacggagc atggcaaaga ttcctcatct tttcgcacaa   2340
cgttatcggc cacaaacaga tttcctttgc gttccatccg ttgttagcga gaaccggcca   2400
tacttcacag ctgcggatat tgaggaagga acagttgtct ccagccttgc gtttgcggtt   2460
gaagattctg ataggtcaca gttcgcgttg atttcttcgt caatgttcat tacttggcaa   2520
aagatgattg gaggaaggct agaatctcgc ctgcgttttg cgaacacact gacgtggaac   2580
acgttccccg taccagaact cgatgagaag acgcgcaagc ggattattaa ggctgggcag   2640
aaagtactcg ccgcgcgcgc actgcacccg gagcgttccc tcgcggagca ctacaacccg   2700
ctggctatga caccagaact ggtgaaggcg catgacgcgc tcgaccggga agtggataaa   2760
gcaatggggg cggcgcgcaa gctcacttcg gagcggcagc gccaggagct actgtttgcc   2820
aattacgcga aactcaccaa caactag                                        2847
```

<210> SEQ ID NO 18
<211> LENGTH: 948
<212> TYPE: PRT
<213> ORGANISM: Arcanobacterium pyogenes

<400> SEQUENCE: 18

```
Met Leu Ser Asp Pro Val Phe Asp Arg Ala Thr Ile Arg His Lys Leu
1               5                   10                  15

Ile Glu Phe Lys Ile Arg Trp Arg Gly His Ile Asp Gln Trp Lys Ala
            20                  25                  30

Glu Asn Arg Pro Ala Thr Glu Ser Ser His Asp Gln Gln Phe Trp Gly
        35                  40                  45

Asp Leu Leu Ala Cys Phe Gly Val Asn Ala Arg Asp Leu Tyr Leu Tyr
    50                  55                  60

Gln Arg Ser Ala Lys Arg Ala Ser Thr Gly His Thr Gly Lys Ile Asp
65                  70                  75                  80

Met Phe Ile Pro Gly Lys Val Ile Gly Glu Ala Lys Ser Leu Gly Ile
                85                  90                  95

Asp Leu Asp Lys Ala His Glu Gln Ala Leu Asp Tyr Leu Leu Gly Gly
            100                 105                 110
```

-continued

```
Thr Ile Pro Asn Ser Gln Met Pro Ala Tyr Val Leu Cys Ser Asn Phe
        115                 120                 125

Glu Thr Leu Arg Ile Thr Arg Leu Asn Arg Asp Tyr Val Gly Asp Ser
    130                 135                 140

Ala Glu Trp Asp Val Thr Phe Asp Leu Asp Glu Ile Asp Glu His Leu
145                 150                 155                 160

Glu Gln Leu Ala Phe Leu Ala Asp Tyr Glu Thr Ser Ala Tyr His Glu
                165                 170                 175

Glu Glu Gln Ala Ser Leu Glu Ala Ser Arg Leu Met Val Glu Leu Phe
            180                 185                 190

Arg Ala Met Asn Gly Asp Glu Ala Asp Glu Ala Val Gly Asp Glu Ala
        195                 200                 205

Pro Thr Thr Pro Glu Glu Glu Asp Glu Arg Val Met Arg Thr Ser Val
    210                 215                 220

Tyr Leu Thr Arg Ile Leu Phe Leu Leu Phe Gly Asp Asp Ala Gly Leu
225                 230                 235                 240

Trp Asp Thr Pro His Leu Phe Thr Thr Phe Val Arg Asn Glu Thr Thr
                245                 250                 255

Pro Glu Ser Leu Gly Pro Gln Leu Asn Glu Leu Phe Arg Val Leu Asn
            260                 265                 270

Thr Pro Glu Asp Lys Arg Pro Lys Arg Leu Pro Gly Thr Leu Ala Lys
        275                 280                 285

Phe Pro Tyr Val Asn Gly Ala Ile Phe Ala Glu Gln Leu Asp Pro Glu
    290                 295                 300

Tyr Phe Asp Tyr Ala Met Arg Glu Ala Leu Leu Asn Ala Cys Asp Phe
305                 310                 315                 320

Asp Trp Ser Lys Ile Asp Val Ser Val Phe Gly Ser Leu Phe Gln Leu
                325                 330                 335

Val Lys Ser Lys Glu Ala Arg Arg Gly Asp Gly Glu His Tyr Thr Ser
            340                 345                 350

Lys Thr Asn Ile Leu Lys Thr Ile Gly Pro Leu Phe Leu Asp Glu Leu
        355                 360                 365

Arg Ala Gln Ala Asp Lys Leu Val Ser Asn Pro Ala Thr Pro Val Arg
    370                 375                 380

Lys Leu Glu Glu Phe Arg Asp Ser Leu Ala Ala His Ile Phe Cys Asp
385                 390                 395                 400

Pro Ala Cys Gly Ala Gly Asn Phe Leu Leu Thr Ala Tyr Lys Glu Leu
                405                 410                 415

Arg Arg Ile Glu Thr Asp Leu Ile Val Ala Ile Arg Gln Arg Arg Gly
            420                 425                 430

Glu Thr Gly Met Ser Leu Asn Ile Glu Trp Glu Gln Lys Leu Ser Ile
        435                 440                 445

Gly Gln Phe Tyr Gly Phe Glu Leu Asn Trp Trp Pro Ala Lys Ile Ala
    450                 455                 460

Glu Thr Ala Met Phe Leu Val Asp His Gln Ala Asn Lys Glu Leu Ala
465                 470                 475                 480

Asn Ala Val Gly Arg Pro Pro Gln Arg Leu Pro Ile Thr Ile Thr Ala
                485                 490                 495

His Ile Val His Gly Asn Ala Leu Ala Leu Asp Trp Thr Glu Ala Leu
            500                 505                 510

Pro Lys Ala Val Gly Glu Thr Phe Ile Phe Gly Asn Pro Pro Phe Ile
        515                 520                 525

Gly Gln Asp Thr Arg Thr Lys Gln Gln Leu Glu Glu Met Lys Ala Val
    530                 535                 540
```

-continued

Trp Arg Arg Lys Asn Ile Ser Arg Leu Asp Tyr Val Thr Cys Trp His
545 550 555 560

Ile Lys Ser Leu Asp Leu Phe Ser Thr Arg Asn Gly Arg Phe Ala Phe
565 570 575

Val Thr Thr Asn Ser Ile Thr Gln Gly Glu Gln Val Pro Leu Leu Phe
580 585 590

Gly Pro Ile Phe Ala Ala Gly Trp Arg Ile Arg Phe Ala His Arg Thr
595 600 605

Phe Ser Trp Asp Ser Asp Ala Pro Gly Lys Ala Ser Val His Cys Val
610 615 620

Ile Val Gly Phe Asp Arg Ala His Glu Pro Arg Pro Gln Leu Trp Asp
625 630 635 640

Tyr Pro Asn Val Ser Ser Ala Pro Val Ala Val Pro Val Glu Arg Val
645 650 655

Ile Asn Ala Tyr Leu Val Asp Gly Pro Asn Val Leu Val Gln Lys Met
660 665 670

Thr Ser Pro Ile Ser Cys Glu Ile Lys Pro Ala Val Leu Gly Ala Met
675 680 685

Ala Lys Asp Gly Gly Gly Leu Ile Val Glu Ala Gln Asp Val Gln Glu
690 695 700

Ala Leu Asp Asp Pro Ile Ala Ala Lys Tyr Leu Arg Pro Tyr Val Gly
705 710 715 720

Ser Arg Glu Leu Val Arg Gly Leu Ser Arg Trp Cys Leu Trp Met Val
725 730 735

Asp Leu Asp Pro Ala Asp Val Gln Ala Ser Thr Phe Leu Arg Ser Arg
740 745 750

Ile Glu Gln Val Arg Ala Tyr Arg Thr Thr Ser Ser Ala Pro Thr Thr
755 760 765

Arg Ser Met Ala Lys Ile Pro His Leu Phe Ala Gln Arg Tyr Arg Pro
770 775 780

Gln Thr Asp Phe Leu Cys Val Pro Ser Val Val Ser Glu Asn Arg Pro
785 790 795 800

Tyr Phe Thr Ala Ala Asp Ile Glu Glu Gly Thr Val Val Ser Ser Leu
805 810 815

Ala Phe Ala Val Glu Asp Ser Asp Arg Ser Gln Phe Ala Leu Ile Ser
820 825 830

Ser Ser Met Phe Ile Thr Trp Gln Lys Met Ile Gly Gly Arg Leu Glu
835 840 845

Ser Arg Leu Arg Phe Ala Asn Thr Leu Thr Trp Asn Thr Phe Pro Val
850 855 860

Pro Glu Leu Asp Glu Lys Thr Arg Lys Arg Ile Ile Lys Ala Gly Gln
865 870 875 880

Lys Val Leu Ala Ala Arg Ala Leu His Pro Glu Arg Ser Leu Ala Glu
885 890 895

His Tyr Asn Pro Leu Ala Met Thr Pro Glu Leu Val Lys Ala His Asp
900 905 910

Ala Leu Asp Arg Glu Val Asp Lys Ala Met Gly Ala Ala Arg Lys Leu
915 920 925

Thr Ser Glu Arg Gln Arg Gln Glu Leu Leu Phe Ala Asn Tyr Ala Lys
930 935 940

Leu Thr Asn Asn
945

<210> SEQ ID NO 19
<211> LENGTH: 2898
<212> TYPE: DNA
<213> ORGANISM: Silicibacter pomeroyi DSS-3

<400> SEQUENCE: 19

```
atgacgcccc aagatttcat caccaaatgg cgcaacaccg aactcaagga acggtccgca     60
tcccagtcgc atttcattga cctgtgccgc cttctggaca tcgaagaccc gacaaccgca    120
gaccccaagg gcgagtggtt caccttcgaa aaaggagcgt ccaagacaag tggcggcgaa    180
ggctgggcgg acgtctggcg caaggattgc tttgcgtggg aatacaaggg caagcgcgcc    240
aatctggaca aggcgtttga ccagctcttg caatacgcca tcgcgctgga gaacccgccg    300
cttctgatcg tgtcggacat ggatgtgata cgcatccaca ccaactggac caacacggtg    360
cagcaggtgc acacccttac actggacgac ctcaaggacg ccgccaaccg tgacaagcta    420
cgcaacgctt ttctcaaccc cgacgtcttc aagccctcca agacccggca acttgttacc    480
gaacaggcgg cacagaactt tgccaacctt gcccagcgtc tccgggaacg tggccacgac    540
gcgcaacagg tggcgcattt cgtcaaccgt ctggtgttct gcatgtttgc cgaggatgtg    600
gagcttttgc cgaacaagat gttcgagcgg atgatcaagg ccgcgcgccc tgaccccgcc    660
agctttgcca tccacgccaa ggcgctcttt gcagctatga aagacggcgg gcttgtgggc    720
ttcgaaaagg tggactggtt caacggcggc ctgttcgaca atgacgacgt gctgccgctg    780
gaatgggaag acttagacga cctcattcgc gcggcacatc tggactggtc cgacattgac    840
ccgtccatcc ttggcacctt gttcgaacgc gggttggacc cggccaagcg cagccagttg    900
ggcgcgcatt acaccgaccg cgacaagatc atgcagatcg tgaacccggt cattgtcgaa    960
ccgctcttgg ccgaatgggc cgaggtgaaa gcccagatcg aagacctgat cgacaaagcc   1020
cccaaggcga cgaaggacaa gcttctcagc acgtcgcaga aggccgcccg cacccgcgcg   1080
ctggacaagg ccgaggcgct gcaccaagcg tttctggacc ggctcaaggc gttccgtgtg   1140
ctggacccgg cctgtgggtc tggcaacttc ctctacatcg cgcttctgga actcaagaac   1200
atcgaacatc gggtgaacct agaggccgag gcgctgggcc tgccccgagg gttcccgcaa   1260
atcggccccg aggttgtgct gggcatcgaa ctcagcgcct atgcggcgga actggcccgc   1320
gtgtcagtct ggattggcga aatccaatgg atgcgccgca acggattcga ggcggcgaag   1380
aacccgatct tgcggtccct taagacgatt gagaaccggg acgcggtgtt gaacccggac   1440
gggacgcggg cggactggcc gaaggcggat gtggttgtcg ggaacccccc gtttttgggc   1500
gtctacaaaa tgggagaaga actaggggaa gattacacaa ttgcattgcg cgatgcttgg   1560
ccggaaatgc cgggagccgc agaccttgtt acctattggt tcgccaaagc ttggtcacag   1620
atgcaatgcg gagacctaag tcgtgctgga cttgtggcaa cgaactctat tcgcggtggt   1680
gcaaatagga ctgtcctaaa accgattgcc gaacatggcg gaatttttga tgcatggtcg   1740
gacgaagcat ggacagtaga gggcgcagca gtgcgtgtat ctatgatttg ctttggaagc   1800
aaactgccgt ctcaccccaa gttaaatggc aaagttgtgg ataaaattct ttctgattta   1860
actgcaaacg ctgccgggtt tgatcttaca aaatcatctc gaatttcaga aaataaaggt   1920
gtttgcatcc ggggcattga aaccggcggt ccatttgaat tttcgcaggc ggatttcgaa   1980
gcacttgcta caaagcctct gaatcccaac gggctaccca acacacgagt tatccggaga   2040
attctaaatg ggaacaatat tctgaagcgg caaccagaac gttatgcgat agacttctct   2100
gacttccgca cgaaggaaga ggccgcattg ttcgaagcgg tctattcatg gcttgaacaa   2160
gcctacgaaa gctatgagcg gaaatcgaag cgccggattg taagacgtca ggactggtgg   2220
```

ctgcatcgaa gatcaggagc agcgctcaaa aatgcggtaa gtagactttc ccgatttatt 2280
gttacaccgc gtgttggaaa acacagaata ttcgtatggc ttgactcaaa tgcacttgca 2340
gatagcgcca cgttcatagt ggcccgcgac gatgaaacca ccttcggcat tctgcattcc 2400
agttttcatg aactctggtc actgcgtatg ggcactttcc ttggggtggg taacgacccc 2460
cgctacaccc cctctaccac cttcgaaacc tttcccttcc ccgaaggcct cacccccaac 2520
atccccgccg acgagtatgc cgatgccccc cgcgccatca aaatcgccgc cgccgccaag 2580
cgcctaaacg agtttcggga aaactggctc aaccccgccg atctggtgga ccgcgtgcca 2640
gaggtcgttt ccggctaccc cgaccgcatc cttcccaaga acgacgccgc cgccaaggaa 2700
ctcaagaaac gcaccctgac gaacctctac aacgcccgcc ccgcatggct cgaccacgcc 2760
cacaaggcgt tagacgaagc ggtggccgaa gcctacggct ggggcgacga ctggcgcgcg 2820
ggcgtgctga ccgaagacga aatcctggcc cgcctgttca agctcaacca agagcgcgca 2880
gcgaaggaga aagcatga 2898

<210> SEQ ID NO 20
<211> LENGTH: 965
<212> TYPE: PRT
<213> ORGANISM: Silicibacter pomeroyi DSS-3

<400> SEQUENCE: 20

Met Thr Pro Gln Asp Phe Ile Thr Lys Trp Arg Asn Thr Glu Leu Lys
1 5 10 15

Glu Arg Ser Ala Ser Gln Ser His Phe Ile Asp Leu Cys Arg Leu Leu
20 25 30

Asp Ile Glu Asp Pro Thr Thr Ala Asp Pro Lys Gly Glu Trp Phe Thr
35 40 45

Phe Glu Lys Gly Ala Ser Lys Thr Ser Gly Gly Glu Gly Trp Ala Asp
50 55 60

Val Trp Arg Lys Asp Cys Phe Ala Trp Glu Tyr Lys Gly Lys Arg Ala
65 70 75 80

Asn Leu Asp Lys Ala Phe Asp Gln Leu Leu Gln Tyr Ala Ile Ala Leu
85 90 95

Glu Asn Pro Pro Leu Leu Ile Val Ser Asp Met Asp Val Ile Arg Ile
100 105 110

His Thr Asn Trp Thr Asn Thr Val Gln Gln Val His Thr Leu Thr Leu
115 120 125

Asp Asp Leu Lys Asp Ala Ala Asn Arg Asp Lys Leu Arg Asn Ala Phe
130 135 140

Leu Asn Pro Asp Val Phe Lys Pro Ser Lys Thr Arg Gln Leu Val Thr
145 150 155 160

Glu Gln Ala Ala Gln Asn Phe Ala Asn Leu Ala Gln Arg Leu Arg Glu
165 170 175

Arg Gly His Asp Ala Gln Gln Val Ala His Phe Val Asn Arg Leu Val
180 185 190

Phe Cys Met Phe Ala Glu Asp Val Glu Leu Leu Pro Asn Lys Met Phe
195 200 205

Glu Arg Met Ile Lys Ala Ala Arg Pro Asp Pro Ala Ser Phe Ala Ile
210 215 220

His Ala Lys Ala Leu Phe Ala Ala Met Lys Asp Gly Gly Leu Val Gly
225 230 235 240

Phe Glu Lys Val Asp Trp Phe Asn Gly Gly Leu Phe Asp Asn Asp Asp
245 250 255

```
Val Leu Pro Leu Glu Trp Glu Asp Leu Asp Asp Leu Ile Arg Ala Ala
            260                 265                 270

His Leu Asp Trp Ser Asp Ile Asp Pro Ser Ile Leu Gly Thr Leu Phe
        275                 280                 285

Glu Arg Gly Leu Asp Pro Ala Lys Arg Ser Gln Leu Gly Ala His Tyr
    290                 295                 300

Thr Asp Arg Asp Lys Ile Met Gln Ile Val Asn Pro Val Ile Val Glu
305                 310                 315                 320

Pro Leu Leu Ala Glu Trp Ala Glu Val Lys Ala Gln Ile Glu Asp Leu
                325                 330                 335

Ile Asp Lys Ala Pro Lys Ala Thr Lys Asp Lys Leu Leu Ser Thr Ser
            340                 345                 350

Gln Lys Ala Ala Arg Thr Arg Ala Leu Asp Lys Ala Glu Ala Leu His
        355                 360                 365

Gln Ala Phe Leu Asp Arg Leu Lys Ala Phe Arg Val Leu Asp Pro Ala
    370                 375                 380

Cys Gly Ser Gly Asn Phe Leu Tyr Ile Ala Leu Leu Glu Leu Lys Asn
385                 390                 395                 400

Ile Glu His Arg Val Asn Leu Glu Ala Glu Ala Leu Gly Leu Pro Arg
                405                 410                 415

Gly Phe Pro Gln Ile Gly Pro Glu Val Val Leu Gly Ile Glu Leu Ser
            420                 425                 430

Ala Tyr Ala Ala Glu Leu Ala Arg Val Ser Val Trp Ile Gly Glu Ile
        435                 440                 445

Gln Trp Met Arg Arg Asn Gly Phe Glu Ala Ala Lys Asn Pro Ile Leu
    450                 455                 460

Arg Ser Leu Lys Thr Ile Glu Asn Arg Asp Ala Val Leu Asn Pro Asp
465                 470                 475                 480

Gly Thr Arg Ala Asp Trp Pro Lys Ala Asp Val Val Val Gly Asn Pro
                485                 490                 495

Pro Phe Leu Gly Val Tyr Lys Met Gly Glu Glu Leu Gly Glu Asp Tyr
            500                 505                 510

Thr Ile Ala Leu Arg Asp Ala Trp Pro Glu Met Pro Gly Ala Ala Asp
        515                 520                 525

Leu Val Thr Tyr Trp Phe Ala Lys Ala Trp Ser Gln Met Gln Cys Gly
    530                 535                 540

Asp Leu Ser Arg Ala Gly Leu Val Ala Thr Asn Ser Ile Arg Gly Gly
545                 550                 555                 560

Ala Asn Arg Thr Val Leu Lys Pro Ile Ala Glu His Gly Gly Ile Phe
                565                 570                 575

Asp Ala Trp Ser Asp Glu Ala Trp Thr Val Glu Gly Ala Ala Val Arg
            580                 585                 590

Val Ser Met Ile Cys Phe Gly Ser Lys Leu Pro Ser His Pro Lys Leu
        595                 600                 605

Asn Gly Lys Val Val Asp Lys Ile Leu Ser Asp Leu Thr Ala Asn Ala
    610                 615                 620

Ala Gly Phe Asp Leu Thr Lys Ser Ser Arg Ile Ser Glu Asn Lys Gly
625                 630                 635                 640

Val Cys Ile Arg Gly Ile Glu Thr Gly Gly Pro Phe Glu Phe Ser Gln
                645                 650                 655

Ala Asp Phe Glu Ala Leu Ala Thr Lys Pro Leu Asn Pro Asn Gly Leu
            660                 665                 670

Pro Asn Thr Arg Val Ile Arg Arg Ile Leu Asn Gly Asn Asn Ile Leu
```

-continued

```
        675                 680                 685

Lys Arg Gln Pro Glu Arg Tyr Ala Ile Asp Phe Ser Asp Phe Arg Thr
    690                 695                 700

Lys Glu Glu Ala Ala Leu Phe Glu Ala Val Tyr Ser Trp Leu Glu Gln
705                 710                 715                 720

Ala Tyr Glu Ser Tyr Glu Arg Lys Ser Lys Arg Arg Ile Val Arg Arg
                725                 730                 735

Gln Asp Trp Trp Leu His Arg Arg Ser Gly Ala Ala Leu Lys Asn Ala
            740                 745                 750

Val Ser Arg Leu Ser Arg Phe Ile Val Thr Pro Arg Val Gly Lys His
        755                 760                 765

Arg Ile Phe Val Trp Leu Asp Ser Asn Ala Leu Ala Asp Ser Ala Thr
    770                 775                 780

Phe Ile Val Ala Arg Asp Asp Glu Thr Thr Phe Gly Ile Leu His Ser
785                 790                 795                 800

Ser Phe His Glu Leu Trp Ser Leu Arg Met Gly Thr Phe Leu Gly Val
                805                 810                 815

Gly Asn Asp Pro Arg Tyr Thr Pro Ser Thr Thr Phe Glu Thr Phe Pro
            820                 825                 830

Phe Pro Glu Gly Leu Thr Pro Asn Ile Pro Ala Asp Glu Tyr Ala Asp
        835                 840                 845

Ala Pro Arg Ala Ile Lys Ile Ala Ala Ala Ala Lys Arg Leu Asn Glu
    850                 855                 860

Phe Arg Glu Asn Trp Leu Asn Pro Ala Asp Leu Val Asp Arg Val Pro
865                 870                 875                 880

Glu Val Val Ser Gly Tyr Pro Asp Arg Ile Leu Pro Lys Asn Asp Ala
                885                 890                 895

Ala Ala Lys Glu Leu Lys Lys Arg Thr Leu Thr Asn Leu Tyr Asn Ala
            900                 905                 910

Arg Pro Ala Trp Leu Asp His Ala His Lys Ala Leu Asp Glu Ala Val
        915                 920                 925

Ala Glu Ala Tyr Gly Trp Gly Asp Asp Trp Arg Ala Gly Val Leu Thr
    930                 935                 940

Glu Asp Glu Ile Leu Ala Arg Leu Phe Lys Leu Asn Gln Glu Arg Ala
945                 950                 955                 960

Ala Lys Glu Lys Ala
                965


<210> SEQ ID NO 21
<211> LENGTH: 2871
<212> TYPE: DNA
<213> ORGANISM: Deinococcus radiophilus R1

<400> SEQUENCE: 21

atgcctcaga ccgagaccgc gcagcgtatg gaagacttcg ttgcctactg gcgcaccctg      60

aaaggggacg agaagggcga aagtcaggta tttctggacc ggctctttca ggcctttggg     120

cacgccggat acaaggaagc gggcgcggaa ctggagtacc gggtcgccaa gcagggcggc     180

ggcaaaaaat tcgctgacct gctgtggcgg ccccgcgtgc tgatagagat gaaaaagcgc     240

ggcgagaaac tggcgaacca ctaccagcag gccttcgact actggctcaa gctggtgccg     300

gaccgcccac gttacgccgt gctgtgcaat ttcgacgagc tgtgggtcta cgacttcaat     360

cagcagctcg acgagccgat ggaccggctg cggatagaag aactgcctga gcggtacacg     420

gtgctgaact tcatgtttga gcaggaaagg gcgccgctgt tcggcaacaa ccgggtggac     480
```

-continued

```
gtaacccgcg aggccgccga cagcgtagcg aaggtgctca acagtgtgat tgcccgtggt    540
gaagaccgcg cccgcgctca gcgtttcctc ttgcagtgcg tcatggcgat gttcgccgag    600
gacttcgagt tgattccgcg tggctttttt accgaattgg ccgacgacgc cagggcaggc    660
cggggaagca gcttcgacct cttcggcggg ctgttccggc agatgaatac ctccgaacgg    720
gcacggggcg ggcgttttgc gcccattccg tatttcaacg gcgggctgtt ccgcgccgtg    780
gaccccattg aacttaaccg cgatgagctt tacctgctgc acaaagccgc gctggaaaac    840
aactgggcca ggattcagcc gcagattttc ggggtgctgt ttcagagcag catggacaag    900
aaagagcagc acgccaaggg ggcgcactac accagcgagg ccgacatcat gcgggtggtg    960
ttgcccacca tcgtcacccc gtttcagcgg caaatcgagg cggcgaccac gcaaaaggaa   1020
ctgcgggcca ttctggacga actcgccagc tttcaggtgc tcgaccccgc gtgtggcagc   1080
ggcaacttcc tgtatgtcgc ctaccgcgaa ctgcgccgcc tggaagcccg cgccctgctg   1140
cggctgcgtg acctctccgc accggggacc gccctgccgc ctgcccgcgt gagcatccgg   1200
cagatgcacg ggctggaata cgaccccttc ggcgtggaac tcgccaaagt gaccctcacg   1260
ctcgccaaag aactcgccat ccgtgagatg cacgacctgc tgggcaacac cggcctggac   1320
ttcgaccagc cgctgccgct ggacaacctc gacgaccgta tcgtgcaggg cgacgccctc   1380
tttaccccgt ggccccgtgt ggacgccatc gtcggcaacc ccccgtttca gagcaaaaac   1440
aagttgcagc gcgagatggg cgcggcctat gtcaaaaagc tccgtgccca ctaccccgac   1500
gtgccgggcc gcgccgacta ctgcgtctac tggattcgca aggcgcatga ccaactgggc   1560
agcggccagc gggcgggtct ggtgggcacc aacaccattc gtcagaacga cagccgtgtc   1620
ggggggctgg attatgtcgt gcagcacggc ggcaccatca ccgacgccgt gggcacgcaa   1680
gtctggtccg gcgacgccgc tgtgcatgtc agcatcgtca actgggtcaa ggggccagcc   1740
gaaggcccca agcatctggc gtggcaggtg ggcgaccacc gcaccagccc ctggcaaagc   1800
accgagttgc ccgtcatcaa ctctgccctg tctgccggaa ccgatgtcac gcaggcgcaa   1860
aagctgcgcg tcaacatgaa cagcggcgcg tgctaccagg gccagaccca cggccacaaa   1920
ggctttttgc tggacggtct ggaagccggg cagatgctca gcgccgagcg caaaaacgcc   1980
gaggttattt ttccgtacct cacgggtgat gaactgctcc gcaccagccc gccgcacccg   2040
acccgttatg tcattgattt tcagccgcgt gacgtgttcg gcgcgagggc ctacaaattg   2100
ccctttgccc gcatagaacg cgaagtgctg cctacgcgcc aggccgccgc cgccgaggaa   2160
gaagcccgca acgccgaagt gctggccgcc aacccaaagg ccaagaccaa caaacaccac   2220
cgcaatttcc tgaatcagtg gtgggcactg tcgtatgggc gcagtgaaat gattgagaaa   2280
atttcatcac tgagccgtta tattgtctgc tcgcgcgtta ccaaaaggca agtatttgag   2340
tttctagata atggtatccg tcctagtgac ggtcttcaaa ttttcgcctt tgaagatgat   2400
tattcatttg gagtcatcca aagttctgtc cattggcagt ggttaattgc acgtggggga   2460
acattaacgg cccgtcttat gtacacctcc gataccgttt tcgacacctt cccctggcct   2520
caagacccga cactggcgca ggtgcgggcg gtggcggcgg cagcggtgaa gctgcgggaa   2580
ctgcggaaca aggtgatgcg cgagcagggc tggagcctgc gcgacctgta ccggacgctg   2640
gacatgccgg gcaaaaaccc gctgcgtgac gctcaggaac ggctggacgc ggcggtgagt   2700
gcggcttatg gcctgccagc gggggcggac atgttggact tttgctggc cctgaacgca    2760
raagtggcgg cggcggaagc gcggggcgcg gcggtgacgg ggccgggcct gcctgcgggc   2820
ctgaacacgg cggacttcgt gacggcagat gcggtgcggc ctctgggctg a            2871
```

<210> SEQ ID NO 22
<211> LENGTH: 956
<212> TYPE: PRT
<213> ORGANISM: Deinococcus radiophilus R1

<400> SEQUENCE: 22

Met Pro Gln Thr Glu Thr Ala Gln Arg Met Glu Asp Phe Val Ala Tyr
1               5                   10                  15

Trp Arg Thr Leu Lys Gly Asp Glu Lys Gly Glu Ser Gln Val Phe Leu
            20                  25                  30

Asp Arg Leu Phe Gln Ala Phe Gly His Ala Gly Tyr Lys Glu Ala Gly
        35                  40                  45

Ala Glu Leu Glu Tyr Arg Val Ala Lys Gln Gly Gly Gly Lys Lys Phe
    50                  55                  60

Ala Asp Leu Leu Trp Arg Pro Arg Val Leu Ile Glu Met Lys Lys Arg
65                  70                  75                  80

Gly Glu Lys Leu Ala Asn His Tyr Gln Gln Ala Phe Asp Tyr Trp Leu
                85                  90                  95

Lys Leu Val Pro Asp Arg Pro Arg Tyr Ala Val Leu Cys Asn Phe Asp
            100                 105                 110

Glu Leu Trp Val Tyr Asp Phe Asn Gln Gln Leu Asp Glu Pro Met Asp
        115                 120                 125

Arg Leu Arg Ile Glu Glu Leu Pro Glu Arg Tyr Thr Val Leu Asn Phe
    130                 135                 140

Met Phe Glu Gln Glu Arg Ala Pro Leu Phe Gly Asn Asn Arg Val Asp
145                 150                 155                 160

Val Thr Arg Glu Ala Ala Asp Ser Val Ala Lys Val Leu Asn Ser Val
                165                 170                 175

Ile Ala Arg Gly Glu Asp Arg Ala Arg Ala Gln Arg Phe Leu Leu Gln
            180                 185                 190

Cys Val Met Ala Met Phe Ala Glu Asp Phe Glu Leu Ile Pro Arg Gly
        195                 200                 205

Phe Phe Thr Glu Leu Ala Asp Asp Ala Arg Ala Gly Arg Gly Ser Ser
    210                 215                 220

Phe Asp Leu Phe Gly Gly Leu Phe Arg Gln Met Asn Thr Ser Glu Arg
225                 230                 235                 240

Ala Arg Gly Gly Arg Phe Ala Pro Ile Pro Tyr Phe Asn Gly Gly Leu
                245                 250                 255

Phe Arg Ala Val Asp Pro Ile Glu Leu Asn Arg Asp Glu Leu Tyr Leu
            260                 265                 270

Leu His Lys Ala Ala Leu Glu Asn Asn Trp Ala Arg Ile Gln Pro Gln
        275                 280                 285

Ile Phe Gly Val Leu Phe Gln Ser Ser Met Asp Lys Lys Glu Gln His
    290                 295                 300

Ala Lys Gly Ala His Tyr Thr Ser Glu Ala Asp Ile Met Arg Val Val
305                 310                 315                 320

Leu Pro Thr Ile Val Thr Pro Phe Gln Arg Gln Ile Glu Ala Ala Thr
                325                 330                 335

Thr Gln Lys Glu Leu Arg Ala Ile Leu Asp Glu Leu Ala Ser Phe Gln
            340                 345                 350

Val Leu Asp Pro Ala Cys Gly Ser Gly Asn Phe Leu Tyr Val Ala Tyr
        355                 360                 365

Arg Glu Leu Arg Arg Leu Glu Ala Arg Ala Leu Leu Arg Leu Arg Asp
    370                 375                 380

```
Leu Ser Ala Pro Gly Thr Ala Leu Pro Pro Ala Arg Val Ser Ile Arg
385                 390                 395                 400

Gln Met His Gly Leu Glu Tyr Asp Pro Phe Gly Val Glu Leu Ala Lys
                405                 410                 415

Val Thr Leu Thr Leu Ala Lys Glu Leu Ala Ile Arg Glu Met His Asp
            420                 425                 430

Leu Leu Gly Asn Thr Gly Leu Asp Phe Asp Gln Pro Leu Pro Leu Asp
        435                 440                 445

Asn Leu Asp Asp Arg Ile Val Gln Gly Asp Ala Leu Phe Thr Pro Trp
    450                 455                 460

Pro Arg Val Asp Ala Ile Val Gly Asn Pro Pro Phe Gln Ser Lys Asn
465                 470                 475                 480

Lys Leu Gln Arg Glu Met Gly Ala Ala Tyr Val Lys Lys Leu Arg Ala
                485                 490                 495

His Tyr Pro Asp Val Pro Gly Arg Ala Asp Tyr Cys Val Tyr Trp Ile
            500                 505                 510

Arg Lys Ala His Asp Gln Leu Gly Ser Gly Gln Arg Ala Gly Leu Val
        515                 520                 525

Gly Thr Asn Thr Ile Arg Gln Asn Asp Ser Arg Val Gly Gly Leu Asp
    530                 535                 540

Tyr Val Val Gln His Gly Gly Thr Ile Thr Asp Ala Val Gly Thr Gln
545                 550                 555                 560

Val Trp Ser Gly Asp Ala Ala Val His Val Ser Ile Val Asn Trp Val
                565                 570                 575

Lys Gly Pro Ala Glu Gly Pro Lys His Leu Ala Trp Gln Val Gly Asp
            580                 585                 590

His Arg Thr Ser Pro Trp Gln Ser Thr Glu Leu Pro Val Ile Asn Ser
        595                 600                 605

Ala Leu Ser Ala Gly Thr Asp Val Thr Gln Ala Gln Lys Leu Arg Val
    610                 615                 620

Asn Met Asn Ser Gly Ala Cys Tyr Gln Gly Gln Thr His Gly His Lys
625                 630                 635                 640

Gly Phe Leu Leu Asp Gly Leu Glu Ala Gly Gln Met Leu Ser Ala Glu
                645                 650                 655

Arg Lys Asn Ala Glu Val Ile Phe Pro Tyr Leu Thr Gly Asp Glu Leu
            660                 665                 670

Leu Arg Thr Ser Pro Pro His Pro Thr Arg Tyr Val Ile Asp Phe Gln
        675                 680                 685

Pro Arg Asp Val Phe Gly Ala Arg Ala Tyr Lys Leu Pro Phe Ala Arg
    690                 695                 700

Ile Glu Arg Glu Val Leu Pro Thr Arg Gln Ala Ala Ala Ala Glu Glu
705                 710                 715                 720

Glu Ala Arg Asn Ala Glu Val Leu Ala Ala Asn Pro Lys Ala Lys Thr
                725                 730                 735

Asn Lys His His Arg Asn Phe Leu Asn Gln Trp Trp Ala Leu Ser Tyr
            740                 745                 750

Gly Arg Ser Glu Met Ile Glu Lys Ile Ser Ser Leu Ser Arg Tyr Ile
        755                 760                 765

Val Cys Ser Arg Val Thr Lys Arg Gln Val Phe Glu Phe Leu Asp Asn
    770                 775                 780

Gly Ile Arg Pro Ser Asp Gly Leu Gln Ile Phe Ala Phe Glu Asp Asp
785                 790                 795                 800

Tyr Ser Phe Gly Val Ile Gln Ser Ser Val His Trp Gln Trp Leu Ile
                805                 810                 815
```

```
Ala Arg Gly Gly Thr Leu Thr Ala Arg Leu Met Tyr Thr Ser Asp Thr
            820                 825                 830

Val Phe Asp Thr Phe Pro Trp Pro Glu Asp Pro Thr Leu Ala Gln Val
        835                 840                 845

Arg Ala Val Ala Ala Ala Ala Val Lys Leu Arg Glu Leu Arg Asn Lys
    850                 855                 860

Val Met Arg Glu Gln Gly Trp Ser Leu Arg Asp Leu Tyr Arg Thr Leu
865                 870                 875                 880

Asp Met Pro Gly Lys Asn Pro Leu Arg Asp Ala Gln Glu Arg Leu Asp
                885                 890                 895

Ala Ala Val Ser Ala Ala Tyr Gly Leu Pro Ala Gly Ala Asp Met Leu
            900                 905                 910

Asp Phe Leu Leu Ala Leu Asn Ala Glu Val Ala Ala Ala Glu Ala Arg
        915                 920                 925

Gly Ala Ala Val Thr Gly Pro Gly Leu Pro Ala Gly Leu Asn Thr Ala
    930                 935                 940

Asp Phe Val Thr Ala Asp Ala Val Arg Pro Leu Gly
945                 950                 955


<210> SEQ ID NO 23
<211> LENGTH: 2937
<212> TYPE: DNA
<213> ORGANISM: Nitrobacter hamburgensis X14

<400> SEQUENCE: 23

gtgagcgaac gggtcgagca gatcgaggca tttgttgcct atgcgaaaac gttaaagggt      60

gacgagaagg gcgaagcaca ggtgttctgt gatcgccttt tccaagcttt tggccacgaa     120

ggttataagg aagccggcgc ggaactggag agtcgggtga agaaggcgtc cggaaagggc     180

gtcaacttcg cagacttgat ctggaaaccc cgggttctga tcgaaatgaa gaaaagcagc     240

gaaaagctgc atcttcatta ccagcaagcc ttcgattact ggctgaacgc ggtccctaac     300

cgcccgcgat atgtggtgct ctgcaatttc aaagagttct ggatttacga ctttgataag     360

caattaaacg agccagtaga cgtcgtccgg cttcaagacc tgcccgcccg gtacacggcg     420

ctaaactttc tttttccaga caatccagac ccgctgtttg gcaacgatcg cgaagaggtc     480

tcgcgtgtag cggcctcaaa ggtcgcgcag ttatttcggt cgatggtcgc tcgcggcatt     540

ccgcgagagc aggcacaacg atttgtactg caggccgtgg tggcgatgtt tgctgaagat     600

atcgacatga tgccggccgg gacgaccctg cggctagtgc aggactgcct ggagcacggc     660

caaaattcgt acgacgtgtt cggtggcctg tttctccaaa tgaacaataa ggcggcggcg     720

cagggcggcc gctacaaggg agttccttat tttaacggcg ggctatttgc gacggtccag     780

ccgatcgaat tgactacgga cgagctagag ttgctcggca agaaggatga aggtgctgct     840

tggcaaaact gggccaagat caaccctgcc atcttcggca ccattttcca acagagcatg     900

gacaaggggg agcggcatgc gttcggcgcg cacttcaccc atgaggccga cattcagcgg     960

attgtcgggc ccacgattgt gcgtccctgg cgcgaacgca tcgatgcagc gaagaccatg    1020

gcggagctgc tggagattcg caaagcgctt ctcaatttcc gcgtcctcga tcccgcctgc    1080

ggaagcggca attttctgta cgtggcctac agagagatgg tgcgtctcga aatcaagctc    1140

atggccagac tggacaagga gtttagctgg aagaccgtac aaaagcaggc tcaggccaca    1200

tcgctcatca gccctcgcca gttttttggt gtcgagcggg attcgttcgg cgtcgagttg    1260

accaaggtca ccctaatgct ggcaaaaaag ctggccctag acgaggccgc cgatgttttg    1320
```

gagcgcgacc agattgagtt gccattggcg gaggatgagg cgctcccact ggacaacctc 1380
gatggcaaca ttctttgccg cgatgcgctc ctatcggact ggcccgaagt agacaccatt 1440
atcggaaatc ccccgtacca aagcaaaaac aaggcacagc aagagttcgg gcgtgcctat 1500
ctgaacaaga ttcgatcggt tttcccggag attgacggaa gggccgatta ttgcgtctac 1560
tggtttagaa aagcgcacga ccagctgaag caaggccaaa gagctggtct cgtcggcacc 1620
aatacgatcc ggcaaaacta ttcccgaatc agcgggctgg attacatagc caagcacaac 1680
ggtacgatta cggaagcggt ctctaccatg ccgtggtcgg gcgacgcggt cgtgcacgtt 1740
tccatcgtca actgggtgaa aggcgaggat gacggcaaga aacgcctgta cattcagtca 1800
ggcaatgatc cggccggcgg ctgggattac aaggacctcg acgaaatcaa cacctcgctt 1860
tcgttttcaa cggatgtgag ccaggcgcaa cgcatcaatg cgaacgctga aaagggcggt 1920
tgctatcagg gccagacaca cgggcataag ggttttctcc cggaaccggc cgaagcgaag 1980
gcgatgatca aggccagcaa ggcaaacgct aaggtcctct tcccattttt gatcgccgac 2040
gatttcttgg gtgcggtaga caaactcgaa tgcagatacg tcatcgattt ccaaacccgc 2100
gacctcctcc aggccaaggc gttcaaaaga ccgtttgagc atcttgaaaa gacggtcctt 2160
cctacccgaa aggaagctgc aaagaaggaa aaggatcgaa acaaggaagc tttggacgcc 2220
gacccggaag ccaaggtcaa caagcaccac gaaaactttc taaagcgctg gtggctgatg 2280
tcttacgcgc gcgaggacct gatgcagacg ttggctcctt tgagccgcta catcgtttgc 2340
gcacgcgtta cgcacaggcc aatctttgaa ttcgtctcga cagccattca tccgaatgac 2400
gcactgagcg ttttcgcctt ggaggatgat tactcctttg gaatccttca atcgggcatc 2460
cattgggagt ggtttatcaa tcgatgctcg accctcaagg ctgactttcg ctacacttcg 2520
gatactgtct ttgatagttt tccgtggccc caggaaccca gtgccgatgc ggtgcgcctg 2580
gtcgcgaagc gagctgtcga ggttaggcaa cttcggtcta agctgaaggt caaacatcac 2640
ctgtcgctaa gggagttgta tcgagcaatc gaaggtcctg gagaacacgc tctcaagaaa 2700
gcccacaagc ttctggacga ggccgtgcgc ggagcttacg gcatgtctaa gaaggcggat 2760
gtattagaaa cattactgga actgaacgag accgtagtag ctgcggaggc cgacggaaaa 2820
caagtcgtcg gccctggaat cccgccttcg gcctcgaagc taaagaacct cgtcactact 2880
gataagctga cgatctcgcc gacgagttgg gccaataatg ctcctgtaaa aacgtga 2937

<210> SEQ ID NO 24
<211> LENGTH: 978
<212> TYPE: PRT
<213> ORGANISM: Nitrobacter hamburgensis X14

<400> SEQUENCE: 24

Met Ser Glu Arg Val Glu Gln Ile Glu Ala Phe Val Ala Tyr Ala Lys
1 5 10 15

Thr Leu Lys Gly Asp Glu Lys Gly Glu Ala Gln Val Phe Cys Asp Arg
20 25 30

Leu Phe Gln Ala Phe Gly His Glu Gly Tyr Lys Glu Ala Gly Ala Glu
35 40 45

Leu Glu Ser Arg Val Lys Lys Ala Ser Gly Lys Gly Val Asn Phe Ala
50 55 60

Asp Leu Ile Trp Lys Pro Arg Val Leu Ile Glu Met Lys Lys Ser Ser
65 70 75 80

Glu Lys Leu His Leu His Tyr Gln Gln Ala Phe Asp Tyr Trp Leu Asn
85 90 95

```
Ala Val Pro Asn Arg Pro Arg Tyr Val Val Leu Cys Asn Phe Lys Glu
            100                 105                 110

Phe Trp Ile Tyr Asp Phe Asp Lys Gln Leu Asn Glu Pro Val Asp Val
        115                 120                 125

Val Arg Leu Gln Asp Leu Pro Ala Arg Tyr Thr Ala Leu Asn Phe Leu
    130                 135                 140

Phe Pro Asp Asn Pro Asp Pro Leu Phe Gly Asn Asp Arg Glu Glu Val
145                 150                 155                 160

Ser Arg Val Ala Ala Ser Lys Val Ala Gln Leu Phe Arg Ser Met Val
                165                 170                 175

Ala Arg Gly Ile Pro Arg Glu Gln Ala Gln Arg Phe Val Leu Gln Ala
            180                 185                 190

Val Val Ala Met Phe Ala Glu Asp Ile Asp Met Met Pro Ala Gly Thr
        195                 200                 205

Thr Leu Arg Leu Val Gln Asp Cys Leu Glu His Gly Gln Asn Ser Tyr
    210                 215                 220

Asp Val Phe Gly Gly Leu Phe Leu Gln Met Asn Asn Lys Ala Ala Ala
225                 230                 235                 240

Gln Gly Gly Arg Tyr Lys Gly Val Pro Tyr Phe Asn Gly Gly Leu Phe
                245                 250                 255

Ala Thr Val Gln Pro Ile Glu Leu Thr Thr Asp Glu Leu Glu Leu Leu
            260                 265                 270

Gly Lys Lys Asp Glu Gly Ala Ala Trp Gln Asn Trp Ala Lys Ile Asn
        275                 280                 285

Pro Ala Ile Phe Gly Thr Ile Phe Gln Gln Ser Met Asp Lys Gly Glu
    290                 295                 300

Arg His Ala Phe Gly Ala His Phe Thr His Glu Ala Asp Ile Gln Arg
305                 310                 315                 320

Ile Val Gly Pro Thr Ile Val Arg Pro Trp Arg Glu Arg Ile Asp Ala
                325                 330                 335

Ala Lys Thr Met Ala Glu Leu Leu Glu Ile Arg Lys Ala Leu Leu Asn
            340                 345                 350

Phe Arg Val Leu Asp Pro Ala Cys Gly Ser Gly Asn Phe Leu Tyr Val
        355                 360                 365

Ala Tyr Arg Glu Met Val Arg Leu Glu Ile Lys Leu Met Ala Arg Leu
    370                 375                 380

Asp Lys Glu Phe Ser Trp Lys Thr Val Gln Lys Gln Ala Gln Ala Thr
385                 390                 395                 400

Ser Leu Ile Ser Pro Arg Gln Phe Phe Gly Val Glu Arg Asp Ser Phe
                405                 410                 415

Gly Val Glu Leu Thr Lys Val Thr Leu Met Leu Ala Lys Lys Leu Ala
            420                 425                 430

Leu Asp Glu Ala Ala Asp Val Leu Glu Arg Asp Gln Ile Glu Leu Pro
        435                 440                 445

Leu Ala Glu Asp Glu Ala Leu Pro Leu Asp Asn Leu Asp Gly Asn Ile
    450                 455                 460

Leu Cys Arg Asp Ala Leu Leu Ser Asp Trp Pro Glu Val Asp Thr Ile
465                 470                 475                 480

Ile Gly Asn Pro Pro Tyr Gln Ser Lys Asn Lys Ala Gln Gln Glu Phe
                485                 490                 495

Gly Arg Ala Tyr Leu Asn Lys Ile Arg Ser Val Phe Pro Glu Ile Asp
            500                 505                 510

Gly Arg Ala Asp Tyr Cys Val Tyr Trp Phe Arg Lys Ala His Asp Gln
        515                 520                 525
```

```
Leu Lys Gln Gly Gln Arg Ala Gly Leu Val Gly Thr Asn Thr Ile Arg
    530                 535                 540

Gln Asn Tyr Ser Arg Ile Ser Gly Leu Asp Tyr Ile Ala Lys His Asn
545                 550                 555                 560

Gly Thr Ile Thr Glu Ala Val Ser Thr Met Pro Trp Ser Gly Asp Ala
                565                 570                 575

Val Val His Val Ser Ile Val Asn Trp Val Lys Gly Glu Asp Asp Gly
            580                 585                 590

Lys Lys Arg Leu Tyr Ile Gln Ser Gly Asn Asp Pro Ala Gly Gly Trp
        595                 600                 605

Asp Tyr Lys Asp Leu Asp Glu Ile Asn Thr Ser Leu Ser Phe Ser Thr
    610                 615                 620

Asp Val Ser Gln Ala Gln Arg Ile Asn Ala Asn Ala Glu Lys Gly Gly
625                 630                 635                 640

Cys Tyr Gln Gly Gln Thr His Gly His Lys Gly Phe Leu Pro Glu Pro
                645                 650                 655

Ala Glu Ala Lys Ala Met Ile Lys Ala Ser Lys Ala Asn Ala Lys Val
            660                 665                 670

Leu Phe Pro Phe Leu Ile Ala Asp Asp Phe Leu Gly Ala Val Asp Lys
        675                 680                 685

Leu Glu Cys Arg Tyr Val Ile Asp Phe Gln Thr Arg Asp Leu Leu Gln
    690                 695                 700

Ala Lys Ala Phe Lys Arg Pro Phe Glu His Leu Glu Lys Thr Val Leu
705                 710                 715                 720

Pro Thr Arg Lys Glu Ala Ala Lys Lys Glu Lys Asp Arg Asn Lys Glu
                725                 730                 735

Ala Leu Asp Ala Asp Pro Glu Ala Lys Val Asn Lys His His Glu Asn
            740                 745                 750

Phe Leu Lys Arg Trp Trp Leu Met Ser Tyr Ala Arg Glu Asp Leu Met
        755                 760                 765

Gln Thr Leu Ala Pro Leu Ser Arg Tyr Ile Val Cys Ala Arg Val Thr
    770                 775                 780

His Arg Pro Ile Phe Glu Phe Val Ser Thr Ala Ile His Pro Asn Asp
785                 790                 795                 800

Ala Leu Ser Val Phe Ala Leu Glu Asp Asp Tyr Ser Phe Gly Ile Leu
                805                 810                 815

Gln Ser Gly Ile His Trp Glu Trp Phe Ile Asn Arg Cys Ser Thr Leu
            820                 825                 830

Lys Ala Asp Phe Arg Tyr Thr Ser Asp Thr Val Phe Asp Ser Phe Pro
        835                 840                 845

Trp Pro Gln Glu Pro Ser Ala Asp Ala Val Arg Leu Val Ala Lys Arg
    850                 855                 860

Ala Val Glu Val Arg Gln Leu Arg Ser Lys Leu Lys Val Lys His His
865                 870                 875                 880

Leu Ser Leu Arg Glu Leu Tyr Arg Ala Ile Glu Gly Pro Gly Glu His
                885                 890                 895

Ala Leu Lys Lys Ala His Lys Leu Leu Asp Glu Ala Val Arg Gly Ala
            900                 905                 910

Tyr Gly Met Ser Lys Lys Ala Asp Val Leu Glu Thr Leu Leu Glu Leu
        915                 920                 925

Asn Glu Thr Val Val Ala Ala Glu Ala Asp Gly Lys Gln Val Val Gly
    930                 935                 940

Pro Gly Ile Pro Pro Ser Ala Ser Lys Leu Lys Asn Leu Val Thr Thr
```

-continued 945 950 955 960

Asp Lys Leu Thr Ile Ser Pro Thr Ser Trp Ala Asn Asn Ala Pro Val
965 970 975

Lys Thr

<210> SEQ ID NO 25
<211> LENGTH: 3555
<212> TYPE: DNA
<213> ORGANISM: Rhodopseudomonas palustris BisB5

<400> SEQUENCE: 25
atgggggact caataagcgt accggcagtc gagcagttca tcgcgcgttg gcaaggccgt 60
gaaggcggac aggaacgcgc gaactacgtc tcgtttctca ccgagttgat cgcgctgctc 120
gggctggaca agcccgaccc ggccgacgcg acgcatgagc acaacgacta cgtgttcgaa 180
cgcgcggtga agaagaccgc cgaagacagc gcttcctatg gccgcatcga tctctacaag 240
cgcaacagct tcgtcctcga agccaagcag agccggatca agggcggcaa gaaggaagtc 300
aggggacagt acgatctgtt gaagaccgag gccaccgcag caacgctcgg ccgccgcggc 360
gccgatcgcg cctgggacgt gctgatgctg aacgccaagc ggcaggccga ggaatatgcc 420
cgcgccctgc ccgcctcgca cggctggccg cccttcattc tggtctgcga cgtcggccat 480
tgtatcgagg tctatgccga cttctccggc cagggaaaga actacacgca gtttcccgat 540
cgccagaact tccgcatcta tctcgaggat ctgcgcgacc acgacgtccg cgagcggctg 600
cgcaagatct ggagcgagcc gaccgcgctc gacccgtcgc agcaatcggc gaaagtcacg 660
cgcgacatcg ccaagcggct cgcgcaagtg tcgctggcgc tggagaaaca gaactatccg 720
gccgacgacg tcgcgatgtt cctgatgcgc tgcctgttca cgatgttcgc cgaggacgtc 780
gaactgttgc cggaaaaatc cttcaagctg ctgctcgaag actgcgagaa aaaccccgag 840
gccttcgtcc acgacgtcgg tcagctctgg gaggcgatgg acaccgggca atgggcgcac 900
gcgctcaaga ccaaggtcaa gaaattcaac ggcgagttct tcaagagccg cgccgcgctg 960
ccgctcggcc gcgaggagat cggcgagctg cggcgggccg ccgagtatga ctggaacgag 1020
gtcgatccct cgatcttcgg cacgctgctg gaacaggcgc tcgatccgac cgaccgcaag 1080
aagctcggcg cgcactacac gccgcgcgct tatgtcgaac ggctggtgat cgccaccatc 1140
atcgagccgc tgcgcgagga ctggcgcaac gtccaggcca ccgccgaaac gctgcgcggc 1200
gcaggcgatc tcgctgccgc cgccgccgcg gtgcaggcgt atcacgaccg gctgtgcgag 1260
acgcgggtgc tcgacccggc ctgcggcacc ggcaacttcc tttacgtctc gctcgaactg 1320
atgaagcggc tggaaggcga agtgctggaa gctttgctcg acctcggcgg ccaggaagcg 1380
ctgcgcggcc tcggctcgca ctcggtcgat ccgcatcagt tcctcggcct cgaaatcaat 1440
ccgcgcgccg cggcgatcgc cgagctggtg ctgtggatcg gctatctgca atggcacttc 1500
cgcaccaagg gcgccccgcc cgacgagccg atcctgcgcg ccttcaagaa catcaaggtc 1560
aagaacgcgg tgctcgactg ggacggcgcg ccgctgccga agatcgtcga gggcaaagag 1620
acctatccga acccgcgccg gccggaatgg ccggcggcgg aattcatcgt ggggaatccg 1680
ccgttcattg ggcgagcttt tttgcgagcg cggcttggtg acacccacgc tgaagcgctt 1740
tggagtgccc atcctcaaat gaatgagtcg gccgacttcg tgatgtactg gtgggaccgc 1800
gcggccgaat tgctgacccg caaaggaacg gtgctgcggc ggttcggttt tgtcacgaca 1860
aactcgataa cccaagtatt tcagcgtcga gtgatcgaaa ggcacttcaa ggcaaagagg 1920
ccgatttcgc ttgctatggc aattccagat catccctgga ccaaagctac aacggatgcc 1980

```
gcagcggtac ggatcgcaat gagcgttgga gagactggcc gaggcgatgg actgctccag   2040

atcgtcgtca acgaggctca cttggattca gatactccaa tcgttgagct tcagggccgc   2100

gtaggaccga taaactcaga cctcacaatt ggcacagacc tgaccaccac cgtgcctcta   2160

cgtgcatctg aaggcttggc atctcgtgga gttacgcttg caggctctgg attcttgata   2220

acttcagaag aagccgaaca ttttggtctc ggtacgcacg agaagctaaa gcaacatatt   2280

cgaggactcc ataatggacg cgacctgaat cagacatcac gtcgaattct tgtgctcgac   2340

ttcttagggc tgagcgaaga ggaagtccga aggcattttc cagaagcata tcagcatcta   2400

ctccggacag tgaaacccga acgggaaacg aacaagagag catcctatag gcagaattgg   2460

tgggtgtttg ctgagccgcg gaaggagatg cgtcccgcgc tgaaggactt ggggcgctat   2520

atcggtacgg cacgcaccgc taagcatagg attttctcca tgttggcggg ccactcctta   2580

ccagagagtg aggttattgc ggtggggtca gacgacgcgt ttatattggg agtactttcg   2640

tcacgacttc atgttcgctg gagtctgtcc aaaggtggca cgctggaaga caggcctcgg   2700

tacaataaca gcatgtgctt cgatcccttc cccttccccg acgccaatcc gattcagaag   2760

cagaccattc gggtcatcgc cgaggagctc gacgcgcatc gcaagcgggt gctggcggag   2820

catccgcatc tgacgctgac cgggctgtat aatgtgctgg agcggttgcg ggcgggggct   2880

gtgccgcagg cacagccgtc acccgcgggc ttgacccgcg ggtccacgtc gtcacgcggt   2940

gcggcgaaga aagacctgga tggccggggc actggacggc aagacggcgc ttcgcgcctt   3000

tcgcccggcc atgacgatgc agagatggtg ctcacacccg acgagcagtg catcttcgac   3060

gatggcctgg tgctgatcct gaaagaactg cacgacaggc tcgatgtcgc ggtggccgag   3120

gcctatggct ggccggcgaa cctgtccgac gacgagattt tggcgcggct cgtcgctttg   3180

aacaagcagc gcgccgacga ggaaaagcgc gggctggtgc gctggctgcg gcccgactac   3240

cagattccgc gattcgccaa gggcgtcgac aagcaggcgg cgaaggaaga aggcgcgcag   3300

atcgcagcgt cgctcgatct cggcgagacc cggcagaagc cgtcgttccc gaccggtgcg   3360

gtggagcaga ccgccgcggt gttcgcagcg ctggccgcag cctccggccc gctcgacgcc   3420

aaatcgctcg ccgcgcagtt caggcgcacg aagacgaccg agaagaaact cgccgaggtg   3480

ctcgcctcac tggcgcggct cggctacgtg gcgaccaccg acggcgtcag cttcgcgctg   3540

cgccgggtcg cgtag                                                    3555
```

<210> SEQ ID NO 26
<211> LENGTH: 1184
<212> TYPE: PRT
<213> ORGANISM: Rhodopseudomonas palustris BisB5

<400> SEQUENCE: 26

```
Met Gly Asp Ser Ile Ser Val Pro Ala Val Glu Gln Phe Ile Ala Arg
1               5                   10                  15

Trp Gln Gly Arg Glu Gly Gly Gln Glu Arg Ala Asn Tyr Val Ser Phe
            20                  25                  30

Leu Thr Glu Leu Ile Ala Leu Leu Gly Leu Asp Lys Pro Asp Pro Ala
        35                  40                  45

Asp Ala Thr His Glu His Asn Asp Tyr Val Phe Glu Arg Ala Val Lys
    50                  55                  60

Lys Thr Ala Glu Asp Ser Ala Ser Tyr Gly Arg Ile Asp Leu Tyr Lys
65                  70                  75                  80

Arg Asn Ser Phe Val Leu Glu Ala Lys Gln Ser Arg Ile Lys Gly Gly
                85                  90                  95
```

-continued

```
Lys Lys Glu Val Arg Gly Gln Tyr Asp Leu Leu Lys Thr Glu Ala Thr
            100                 105                 110

Ala Ala Thr Leu Gly Arg Arg Gly Ala Asp Arg Ala Trp Asp Val Leu
        115                 120                 125

Met Leu Asn Ala Lys Arg Gln Ala Glu Glu Tyr Ala Arg Ala Leu Pro
    130                 135                 140

Ala Ser His Gly Trp Pro Pro Phe Ile Leu Val Cys Asp Val Gly His
145                 150                 155                 160

Cys Ile Glu Val Tyr Ala Asp Phe Ser Gly Gln Gly Lys Asn Tyr Thr
                165                 170                 175

Gln Phe Pro Asp Arg Gln Asn Phe Arg Ile Tyr Leu Glu Asp Leu Arg
            180                 185                 190

Asp His Asp Val Arg Glu Arg Leu Arg Lys Ile Trp Ser Glu Pro Thr
        195                 200                 205

Ala Leu Asp Pro Ser Gln Gln Ser Ala Lys Val Thr Arg Asp Ile Ala
    210                 215                 220

Lys Arg Leu Ala Gln Val Ser Leu Ala Leu Glu Lys Gln Asn Tyr Pro
225                 230                 235                 240

Ala Asp Asp Val Ala Met Phe Leu Met Arg Cys Leu Phe Thr Met Phe
                245                 250                 255

Ala Glu Asp Val Glu Leu Leu Pro Glu Lys Ser Phe Lys Leu Leu Leu
            260                 265                 270

Glu Asp Cys Glu Lys Asn Pro Glu Ala Phe Val His Asp Val Gly Gln
        275                 280                 285

Leu Trp Glu Ala Met Asp Thr Gly Gln Trp Ala His Ala Leu Lys Thr
    290                 295                 300

Lys Val Lys Lys Phe Asn Gly Glu Phe Phe Lys Ser Arg Ala Ala Leu
305                 310                 315                 320

Pro Leu Gly Arg Glu Glu Ile Gly Glu Leu Arg Arg Ala Ala Glu Tyr
                325                 330                 335

Asp Trp Asn Glu Val Asp Pro Ser Ile Phe Gly Thr Leu Leu Glu Gln
            340                 345                 350

Ala Leu Asp Pro Thr Asp Arg Lys Lys Leu Gly Ala His Tyr Thr Pro
        355                 360                 365

Arg Ala Tyr Val Glu Arg Leu Val Ile Ala Thr Ile Ile Glu Pro Leu
    370                 375                 380

Arg Glu Asp Trp Arg Asn Val Gln Ala Thr Ala Glu Thr Leu Arg Gly
385                 390                 395                 400

Ala Gly Asp Leu Ala Ala Ala Ala Ala Ala Val Gln Ala Tyr His Asp
                405                 410                 415

Arg Leu Cys Glu Thr Arg Val Leu Asp Pro Ala Cys Gly Thr Gly Asn
            420                 425                 430

Phe Leu Tyr Val Ser Leu Glu Leu Met Lys Arg Leu Glu Gly Glu Val
        435                 440                 445

Leu Glu Ala Leu Leu Asp Leu Gly Gly Gln Glu Ala Leu Arg Gly Leu
    450                 455                 460

Gly Ser His Ser Val Asp Pro His Gln Phe Leu Gly Leu Glu Ile Asn
465                 470                 475                 480

Pro Arg Ala Ala Ala Ile Ala Glu Leu Val Leu Trp Ile Gly Tyr Leu
                485                 490                 495

Gln Trp His Phe Arg Thr Lys Gly Ala Pro Pro Asp Glu Pro Ile Leu
            500                 505                 510

Arg Ala Phe Lys Asn Ile Lys Val Lys Asn Ala Val Leu Asp Trp Asp
```

```
        515                 520                 525

Gly Ala Pro Leu Pro Lys Ile Val Glu Gly Lys Glu Thr Tyr Pro Asn
    530                 535                 540

Pro Arg Arg Pro Glu Trp Pro Ala Ala Glu Phe Ile Val Gly Asn Pro
545                 550                 555                 560

Pro Phe Ile Gly Ala Ser Phe Leu Arg Ala Arg Leu Gly Asp Thr His
                565                 570                 575

Ala Glu Ala Leu Trp Ser Ala His Pro Gln Met Asn Glu Ser Ala Asp
            580                 585                 590

Phe Val Met Tyr Trp Trp Asp Arg Ala Ala Glu Leu Leu Thr Arg Lys
        595                 600                 605

Gly Thr Val Leu Arg Arg Phe Gly Phe Val Thr Thr Asn Ser Ile Thr
    610                 615                 620

Gln Val Phe Gln Arg Arg Val Ile Glu Arg His Phe Lys Ala Lys Arg
625                 630                 635                 640

Pro Ile Ser Leu Ala Met Ala Ile Pro Asp His Pro Trp Thr Lys Ala
                645                 650                 655

Thr Thr Asp Ala Ala Ala Val Arg Ile Ala Met Ser Val Gly Glu Thr
            660                 665                 670

Gly Arg Gly Asp Gly Leu Leu Gln Ile Val Val Asn Glu Ala His Leu
        675                 680                 685

Asp Ser Asp Thr Pro Ile Val Glu Leu Gln Gly Arg Val Gly Pro Ile
    690                 695                 700

Asn Ser Asp Leu Thr Ile Gly Thr Asp Leu Thr Thr Thr Val Pro Leu
705                 710                 715                 720

Arg Ala Ser Glu Gly Leu Ala Ser Arg Gly Val Thr Leu Ala Gly Ser
                725                 730                 735

Gly Phe Leu Ile Thr Ser Glu Glu Ala Glu His Phe Gly Leu Gly Thr
            740                 745                 750

His Glu Lys Leu Lys Gln His Ile Arg Gly Leu His Asn Gly Arg Asp
        755                 760                 765

Leu Asn Gln Thr Ser Arg Arg Ile Leu Val Leu Asp Phe Leu Gly Leu
    770                 775                 780

Ser Glu Glu Glu Val Arg Arg His Phe Pro Glu Ala Tyr Gln His Leu
785                 790                 795                 800

Leu Arg Thr Val Lys Pro Glu Arg Glu Thr Asn Lys Arg Ala Ser Tyr
                805                 810                 815

Arg Gln Asn Trp Trp Val Phe Ala Glu Pro Arg Lys Glu Met Arg Pro
            820                 825                 830

Ala Leu Lys Asp Leu Gly Arg Tyr Ile Gly Thr Ala Arg Thr Ala Lys
        835                 840                 845

His Arg Ile Phe Ser Met Leu Ala Gly His Ser Leu Pro Glu Ser Glu
    850                 855                 860

Val Ile Ala Val Gly Ser Asp Asp Ala Phe Ile Leu Gly Val Leu Ser
865                 870                 875                 880

Ser Arg Leu His Val Arg Trp Ser Leu Ser Lys Gly Gly Thr Leu Glu
                885                 890                 895

Asp Arg Pro Arg Tyr Asn Asn Ser Met Cys Phe Asp Pro Phe Pro Phe
            900                 905                 910

Pro Asp Ala Asn Pro Ile Gln Lys Gln Thr Ile Arg Val Ile Ala Glu
        915                 920                 925

Glu Leu Asp Ala His Arg Lys Arg Val Leu Ala Glu His Pro His Leu
    930                 935                 940
```

```
Thr Leu Thr Gly Leu Tyr Asn Val Leu Glu Arg Leu Arg Ala Gly Ala
945                 950                 955                 960

Val Pro Gln Ala Gln Pro Ser Pro Ala Gly Leu Thr Arg Gly Ser Thr
                965                 970                 975

Ser Ser Arg Gly Ala Ala Lys Lys Asp Leu Asp Gly Arg Gly Thr Gly
            980                 985                 990

Arg Gln Asp Gly Ala Ser Arg Leu  Ser Pro Gly His Asp  Asp Ala Glu
        995                 1000                 1005

Met Val  Leu Thr Pro Asp Glu  Gln Cys Ile Phe Asp  Asp Gly Leu
    1010                 1015                 1020

Val Leu  Ile Leu Lys Glu Leu  His Asp Arg Leu Asp  Val Ala Val
    1025                 1030                 1035

Ala Glu  Ala Tyr Gly Trp Pro  Ala Asn Leu Ser Asp  Asp Glu Ile
    1040                 1045                 1050

Leu Ala  Arg Leu Val Ala Leu  Asn Lys Gln Arg Ala  Asp Glu Glu
    1055                 1060                 1065

Lys Arg  Gly Leu Val Arg Trp  Leu Arg Pro Asp Tyr  Gln Ile Pro
    1070                 1075                 1080

Arg Phe  Ala Lys Gly Val Asp  Lys Gln Ala Ala Lys  Glu Glu Gly
    1085                 1090                 1095

Ala Gln  Ile Ala Ala Ser Leu  Asp Leu Gly Glu Thr  Arg Gln Lys
    1100                 1105                 1110

Pro Ser  Phe Pro Thr Gly Ala  Val Glu Gln Thr Ala  Ala Val Phe
    1115                 1120                 1125

Ala Ala  Leu Ala Ala Ala Ser  Gly Pro Leu Asp Ala  Lys Ser Leu
    1130                 1135                 1140

Ala Ala  Gln Phe Arg Arg Thr  Lys Thr Thr Glu Lys  Lys Leu Ala
    1145                 1150                 1155

Glu Val  Leu Ala Ser Leu Ala  Arg Leu Gly Tyr Val  Ala Thr Thr
    1160                 1165                 1170

Asp Gly  Val Ser Phe Ala Leu  Arg Arg Val Ala
    1175                 1180
```

<210> SEQ ID NO 27
<211> LENGTH: 27
<212> TYPE: DNA
<213> ORGANISM: artificial
<220> FEATURE:
<223> OTHER INFORMATION: primer

<400> SEQUENCE: 27
gattatagat attctgccag cctggtt 27

<210> SEQ ID NO 28
<211> LENGTH: 28
<212> TYPE: DNA
<213> ORGANISM: artificial
<220> FEATURE:
<223> OTHER INFORMATION: primer

<400> SEQUENCE: 28
actttctaac cttcctccta catttctc 28

<210> SEQ ID NO 29
<211> LENGTH: 26
<212> TYPE: DNA
<213> ORGANISM: artificial
<220> FEATURE:
<223> OTHER INFORMATION: primer

<400> SEQUENCE: 29
cgctatcgct actctaatac cgtcgt 26

<210> SEQ ID NO 30
<211> LENGTH: 21
<212> TYPE: DNA
<213> ORGANISM: artificial
<220> FEATURE:
<223> OTHER INFORMATION: primer

<400> SEQUENCE: 30
gcttttcaga cgacctgcaa c 21

<210> SEQ ID NO 31
<211> LENGTH: 44
<212> TYPE: DNA
<213> ORGANISM: artificial
<220> FEATURE:
<223> OTHER INFORMATION: primer

<400> SEQUENCE: 31
actttttaac cttcctgcta cagttctcat ccagcagttg tgca 44

<210> SEQ ID NO 32
<211> LENGTH: 42
<212> TYPE: DNA
<213> ORGANISM: artificial
<220> FEATURE:
<223> OTHER INFORMATION: primer

<400> SEQUENCE: 32
gctttccaga cgacctccaa cgttacgcat aaaggcgttg tg 42

<210> SEQ ID NO 33
<211> LENGTH: 3483
<212> TYPE: DNA
<213> ORGANISM: Pseudomonas species OM2164

<400> SEQUENCE: 33
ctggaaatcg gcttgagtgt cccgaaacag gcaggaccga tcttgagcgt cgatgatttc 60
atcgcccgct ggacgacctc gggtggcagc gagcgggcca atttccagca gttcgccatc 120
gagctgacgc agctcttgga cgttccggcc cccaagcccg cgacggcgga tgcgcagaac 180
gacgactacc gcttcgagcg gcccgtgacc ttcattcata ccggcacgca gtcgcgcggc 240
ttcatcgacc tctaccggcg cggctgcttc gtcatggaag ccaagcaggg cacaggcgcc 300
gcgcccgagg aaggccagct tgatcttcta gccgcggccc cgcccgtgca gcggcaaggg 360
catggcgttc gcggctcgaa gcgatgggac gacaccatgc tgcgcgcccg caaccaggcc 420
gacggctatg cccgcgccgt ggcgcgcgag gacggctggc ccccgttcct gctgatcgtg 480
gacgtgggcc atgtgatcga ggtctatgcc gacttctcgg gccaggggca gggctacacg 540
cagttcccgg acggcaaccg ctaccggatc acgctggacg acctgcgcga cgcggcgacc 600
cttgaccgcc tgcaagccat ctggaccgat ccgcacagcc tcgacccgac ccgcgtcagc 660
gcccaggtca cgcggcaggt ggccgagcat ctggccgaac tgggtcggtc cttcgaggcg 720
cagggccatg cccccgaggc ggtggcgcgc ttcctgatgc gcgccctgtt caccatgttc 780
gccgaggacg tgcaactgat ccccgagggg gccttttcga agctgctgca ggacaggcgc 840
ggccaccccg aacacgccgc cccgatgctg gaaagcctgt ggcagacgat gaacaccggc 900
ggcttttccc cggcgctgtc ctgcgacctc aaacggttca acggcggcct gtttcgggag 960

-continued

```
gcaaccgccc tgccgctgtc cgccatgcag cttggcctgc tgatccaggc cgcgtcccac   1020
gactggcgcg aggtcgagcc ggcgatcttc ggcaccctgc tggaacgcgc gctcgacacg   1080
cggcagcgcc acaagctggg cgcgcactac accccccgcg cctatgtcga acggctggtg   1140
aaccccacgg tgatcgagcc gctgcgggcc gaatggcgcg acatccaggc cgcggccgtc   1200
acgctggcag gccaggacaa gctggacgag gcgcgcgcga ccgtgcgcga cttccaccgg   1260
cgcctgtgcg aggtgcgggt ggtggacccg gcctgcgggt cgggaaactt cctgtatgtc   1320
gcgctggagc tgatgaagcg cctggaaggc gaggtgatcg cgctgctgcg cgagttgggc   1380
gaggaccagg gcgcccttgc cctggcaggc cacaccgttg acccgcacca gttcctgggc   1440
atcgaggtga acccctgggc cgccgccgtg gccgagctgg tgctgtggat cggctatctg   1500
caatggcatt tccgcaccca tggcaccgcc agcccggccg agccggtcct gcgcgacttc   1560
cgcaacatcg agaaccgcga cgccgtgctg gcctgggacg gcacccggcc gaggctggac   1620
gatgccgggc agcccgtgac ccgctgggac ggggtgtcca ccatccgcca cccggtcacg   1680
ggcgaacagg tgcccgatcc ggccgcgcgg gtgcaggttc tggattacct caagccgcgc   1740
ccggccagat ggcccgaggc cgagttcatc gtcggcaacc cgcccttcat cggcgcgtcg   1800
cggatgcgcg aggccctggg cgacggctat gccgaggcct tgcgcgcggc ctatcccagg   1860
atgcccgaaa gcgccgattt cgtgatgttc tggtgggata aggcggcgct ggcgacccgc   1920
gcgggcaaga cccggcgctt tggcttcatc accaccaatt cgctgcgcca gaccttcaac   1980
cggcaggtgc tggaaccgca tctggccgac ccgaagaagc ccttgtcgct ggccttcgcc   2040
atccccgatc accccctgggt cgatgcgggg gacggcgcgg cggtgcggat cgccatgacc  2100
gtggcagcgg ccggatcggc gccggggcgg ctgtttaccg tcacggacga acgccggggc   2160
gagcgcgagg ccgaggggcg ccccgtcacc ctgtccgggc agatcggcaa gatccacgcc   2220
aacctgcgga ttggcgcgga tgtggcggga gcgaaaccgc tgcgggcgaa cgcaggcatc   2280
tcatcgccgg gggtgaagct gcacggcgca ggcttcatcg tcaccccggc cgaggcacag   2340
gcgcttggct tgggcaccgt gccgggtctt gaggcgcata tccgcagcta tcgcaacggc   2400
cgcgacctga ccgccacccc gcgtggcgtc atggtgatcg acctgttcgg cctgtccgag   2460
gccgaggtgc ggacccggtt tcccgccgtt tatcagcacg tcctggacaa ggtgaaaccc   2520
gagcgcgacc agaacaaccg cgacagctac aagcgcaact ggtggattca cggcgagccg   2580
cgccgcgacc tgcgcccggc cttggaaggc ttgccccgct acatcgccac ggtggaaacg   2640
gccaaacata gaatattcag cttactcgac gcgacgattt tacccgacaa caagttgatc   2700
atcatcgctc tggcagacac atggcatttt tcgattgtgt catcgcgtat ccactgggtc   2760
tgggcgatag caaatgctgc gaaaatcggc atgtatgatg gcgatgccgt ttaccccaag   2820
ggtcaatgct tcgacccctt ccctttccca gatgccaccg aggcacagaa agcccgcctg   2880
cgcgccttgg gcgaggaact ggacgcgcat cgcaaggcgc agcaggccgc gcatccccgg   2940
ctgaccctga cggccctcta caacgtgctg gaaaagctgc gcgccggcga gcggatcgag   3000
gggcgcgacc gggaaaccta tgacgcgggc ctcgtcggca tcctgcggga catccacgac   3060
cgcatcgacg ccgccgtggc cgaggcctat ggctggcctg ccgacctgga cgacgaggcc   3120
atcctgaccc gcctggtcga tctgaaccgc gcccgcgccg ccgaggaagc ggcgggcctg   3180
gtccgctggc tgcgccccga ctatcagaac cccgcaggcc gcattgccgc cgccaagggc   3240
cagcaggtcg aactggacgt gggcgcggcg gccgaggccg ccgacaaggc gctgtggccc   3300
aaggccctgc ccgaacagat cgccgccgtc cgcgccgtcc tgtcggacat gggcgaggcc   3360
```

-continued acgcccgaac aggtcgcgcg ccagttcaaa cgcgcccgcg cggcgtcggt gaagcccctg 3420
ctggaaagcc tcagcgcctt gggtcaagcc cgcctcatcg aaggcgggcg gttcgcggcc 3480
tga 3483

<210> SEQ ID NO 34
<211> LENGTH: 1160
<212> TYPE: PRT
<213> ORGANISM: Pseudomonas species OM2164

<400> SEQUENCE: 34

Met Glu Ile Gly Leu Ser Val Pro Lys Gln Ala Gly Pro Ile Leu Ser
1 5 10 15

Val Asp Asp Phe Ile Ala Arg Trp Thr Thr Ser Gly Gly Ser Glu Arg
20 25 30

Ala Asn Phe Gln Gln Phe Ala Ile Glu Leu Thr Gln Leu Leu Asp Val
35 40 45

Pro Ala Pro Lys Pro Ala Thr Ala Asp Ala Gln Asn Asp Asp Tyr Arg
50 55 60

Phe Glu Arg Pro Val Thr Phe Ile His Thr Gly Thr Gln Ser Arg Gly
65 70 75 80

Phe Ile Asp Leu Tyr Arg Arg Gly Cys Phe Val Met Glu Ala Lys Gln
85 90 95

Gly Thr Gly Ala Ala Pro Glu Glu Gly Gln Leu Asp Leu Leu Ala Ala
100 105 110

Ala Pro Pro Val Gln Arg Gln Gly His Gly Val Arg Gly Ser Lys Arg
115 120 125

Trp Asp Asp Thr Met Leu Arg Ala Arg Asn Gln Ala Asp Gly Tyr Ala
130 135 140

Arg Ala Val Ala Arg Glu Asp Gly Trp Pro Pro Phe Leu Leu Ile Val
145 150 155 160

Asp Val Gly His Val Ile Glu Val Tyr Ala Asp Phe Ser Gly Gln Gly
165 170 175

Gln Gly Tyr Thr Gln Phe Pro Asp Gly Asn Arg Tyr Arg Ile Thr Leu
180 185 190

Asp Asp Leu Arg Asp Ala Ala Thr Leu Asp Arg Leu Gln Ala Ile Trp
195 200 205

Thr Asp Pro His Ser Leu Asp Pro Thr Arg Val Ser Ala Gln Val Thr
210 215 220

Arg Gln Val Ala Glu His Leu Ala Glu Leu Gly Arg Ser Phe Glu Ala
225 230 235 240

Gln Gly His Ala Pro Glu Ala Val Ala Arg Phe Leu Met Arg Ala Leu
245 250 255

Phe Thr Met Phe Ala Glu Asp Val Gln Leu Ile Pro Glu Gly Ala Phe
260 265 270

Ser Lys Leu Leu Gln Asp Arg Arg Gly His Pro Glu His Ala Ala Pro
275 280 285

Met Leu Glu Ser Leu Trp Gln Thr Met Asn Thr Gly Gly Phe Ser Pro
290 295 300

Ala Leu Ser Cys Asp Leu Lys Arg Phe Asn Gly Gly Leu Phe Arg Glu
305 310 315 320

Ala Thr Ala Leu Pro Leu Ser Ala Met Gln Leu Gly Leu Leu Ile Gln
325 330 335

Ala Ala Ser His Asp Trp Arg Glu Val Glu Pro Ala Ile Phe Gly Thr
340 345 350

-continued

```
Leu Leu Glu Arg Ala Leu Asp Thr Arg Gln Arg His Lys Leu Gly Ala
        355                 360                 365

His Tyr Thr Pro Arg Ala Tyr Val Glu Arg Leu Val Asn Pro Thr Val
    370                 375                 380

Ile Glu Pro Leu Arg Ala Glu Trp Arg Asp Ile Gln Ala Ala Ala Val
385                 390                 395                 400

Thr Leu Ala Gly Gln Asp Lys Leu Asp Glu Ala Arg Ala Thr Val Arg
                405                 410                 415

Asp Phe His Arg Arg Leu Cys Glu Val Arg Val Val Asp Pro Ala Cys
            420                 425                 430

Gly Ser Gly Asn Phe Leu Tyr Val Ala Leu Glu Leu Met Lys Arg Leu
        435                 440                 445

Glu Gly Glu Val Ile Ala Leu Leu Arg Glu Leu Gly Glu Asp Gln Gly
    450                 455                 460

Ala Leu Ala Leu Ala Gly His Thr Val Asp Pro His Gln Phe Leu Gly
465                 470                 475                 480

Ile Glu Val Asn Pro Trp Ala Ala Ala Val Ala Glu Leu Val Leu Trp
                485                 490                 495

Ile Gly Tyr Leu Gln Trp His Phe Arg Thr His Gly Thr Ala Ser Pro
            500                 505                 510

Ala Glu Pro Val Leu Arg Asp Phe Arg Asn Ile Glu Asn Arg Asp Ala
        515                 520                 525

Val Leu Ala Trp Asp Gly Thr Arg Pro Arg Leu Asp Asp Ala Gly Gln
    530                 535                 540

Pro Val Thr Arg Trp Asp Gly Val Ser Thr Ile Arg His Pro Val Thr
545                 550                 555                 560

Gly Glu Gln Val Pro Asp Pro Ala Ala Arg Val Gln Val Leu Asp Tyr
                565                 570                 575

Leu Lys Pro Arg Pro Ala Arg Trp Pro Glu Ala Glu Phe Ile Val Gly
            580                 585                 590

Asn Pro Pro Phe Ile Gly Ala Ser Arg Met Arg Glu Ala Leu Gly Asp
        595                 600                 605

Gly Tyr Ala Glu Ala Leu Arg Ala Ala Tyr Pro Arg Met Pro Glu Ser
    610                 615                 620

Ala Asp Phe Val Met Phe Trp Trp Asp Lys Ala Ala Leu Ala Thr Arg
625                 630                 635                 640

Ala Gly Lys Thr Arg Arg Phe Gly Phe Ile Thr Thr Asn Ser Leu Arg
                645                 650                 655

Gln Thr Phe Asn Arg Gln Val Leu Glu Pro His Leu Ala Asp Pro Lys
            660                 665                 670

Lys Pro Leu Ser Leu Ala Phe Ala Ile Pro Asp His Pro Trp Val Asp
        675                 680                 685

Ala Gly Asp Gly Ala Ala Val Arg Ile Ala Met Thr Val Ala Ala Ala
    690                 695                 700

Gly Ser Ala Pro Gly Arg Leu Phe Thr Val Thr Asp Glu Arg Arg Gly
705                 710                 715                 720

Glu Arg Glu Ala Glu Gly Arg Pro Val Thr Leu Ser Gly Gln Ile Gly
                725                 730                 735

Lys Ile His Ala Asn Leu Arg Ile Gly Ala Asp Val Ala Gly Ala Lys
            740                 745                 750

Pro Leu Arg Ala Asn Ala Gly Ile Ser Ser Pro Gly Val Lys Leu His
        755                 760                 765

Gly Ala Gly Phe Ile Val Thr Pro Ala Glu Ala Gln Ala Leu Gly Leu
    770                 775                 780
```

```
Gly Thr Val Pro Gly Leu Glu Ala His Ile Arg Ser Tyr Arg Asn Gly
785                 790                 795                 800

Arg Asp Leu Thr Ala Thr Pro Arg Gly Val Met Val Ile Asp Leu Phe
                805                 810                 815

Gly Leu Ser Glu Ala Glu Val Arg Thr Arg Phe Pro Ala Val Tyr Gln
            820                 825                 830

His Val Leu Asp Lys Val Lys Pro Glu Arg Asp Gln Asn Asn Arg Asp
        835                 840                 845

Ser Tyr Lys Arg Asn Trp Trp Ile His Gly Glu Pro Arg Arg Asp Leu
    850                 855                 860

Arg Pro Ala Leu Glu Gly Leu Pro Arg Tyr Ile Ala Thr Val Glu Thr
865                 870                 875                 880

Ala Lys His Arg Ile Phe Ser Leu Leu Asp Ala Thr Ile Leu Pro Asp
                885                 890                 895

Asn Lys Leu Ile Ile Ile Ala Leu Ala Asp Thr Trp His Phe Ser Ile
            900                 905                 910

Val Ser Ser Arg Ile His Trp Val Trp Ala Ile Ala Asn Ala Ala Lys
        915                 920                 925

Ile Gly Met Tyr Asp Gly Asp Ala Val Tyr Pro Lys Gly Gln Cys Phe
    930                 935                 940

Asp Pro Phe Pro Phe Pro Asp Ala Thr Glu Ala Gln Lys Ala Arg Leu
945                 950                 955                 960

Arg Ala Leu Gly Glu Glu Leu Asp Ala His Arg Lys Ala Gln Gln Ala
                965                 970                 975

Ala His Pro Arg Leu Thr Leu Thr Ala Leu Tyr Asn Val Leu Glu Lys
            980                 985                 990

Leu Arg Ala Gly Glu Arg Ile Glu  Gly Arg Asp Arg Glu  Thr Tyr Asp
        995                 1000                1005

Ala Gly  Leu Val Gly Ile Leu  Arg Asp Ile His Asp  Arg Ile Asp
    1010                1015                1020

Ala Ala  Val Ala Glu Ala Tyr  Gly Trp Pro Ala Asp  Leu Asp Asp
    1025                1030                1035

Glu Ala  Ile Leu Thr Arg Leu  Val Asp Leu Asn Arg  Ala Arg Ala
    1040                1045                1050

Ala Glu  Glu Ala Ala Gly Leu  Val Arg Trp Leu Arg  Pro Asp Tyr
    1055                1060                1065

Gln Asn  Pro Ala Gly Arg Ile  Ala Ala Ala Lys Gly  Gln Gln Val
    1070                1075                1080

Glu Leu  Asp Val Gly Ala Ala  Ala Glu Ala Ala Asp  Lys Ala Leu
    1085                1090                1095

Trp Pro  Lys Ala Leu Pro Glu  Gln Ile Ala Ala Val  Arg Ala Val
    1100                1105                1110

Leu Ser  Asp Met Gly Glu Ala  Thr Pro Glu Gln Val  Ala Arg Gln
    1115                1120                1125

Phe Lys  Arg Ala Arg Ala Ala  Ser Val Lys Pro Leu  Leu Glu Ser
    1130                1135                1140

Leu Ser  Ala Leu Gly Gln Ala  Arg Leu Ile Glu Gly  Gly Arg Phe
    1145                1150                1155

Ala Ala
    1160
```

<210> SEQ ID NO 35
<211> LENGTH: 3435
<212> TYPE: DNA

<213> ORGANISM: Deinococcus radiodurans

<400> SEQUENCE: 35
atgacgcctg aggaatttat aacccgctgg tcgccctccg gaggcgcgga acgcgccaat 60
tacgtcctct ttctcagtga gctgtgcgat ctgctcggcg tgcccaagcc cgaccccacc 120
caggccgatg aagctaagaa cgcttacgtc ttcgagaagg acgttcccga cctgcacgat 180
gacggcggcc tcagccagcg ccgcatcgac ctctaccggc ggggcgcgtt catcttggag 240
gccaagcagg gggtcgagaa ggaagctacc gctgaagaag ctctcctcag caccaagggc 300
aagaagaaaa agggacatgg cacgcggggc accaaaggct gggacacctt catgcgccgc 360
gccagggagc aagcggagcg ctacgcgcac ctgctgcccg catccgaggg ccggcccccc 420
ttcctgctcg tggtggatgt cgggcatgtc atcgaggtct acgctgagtt cacgcgtacc 480
ggtggggcgt atctcccctt ccccagtgcc agagcgcacc agatccaatt ggctgacctg 540
gcccgacctg aagtccgtga gctgctgcgc accatctggc tcgatcccct gagtctcgac 600
cccagcatcc acgcggctga ggtcaccaag gacgtggccc gcaagctcgc ggagatcagc 660
cgcagcatgg aagggcagcc cgatgcccag ggacaggcga tgacgccaga gcgcgtttcg 720
cagttcctga tgcgcatgat cttcaccatg ttcgccgagg acgtcggcct gctgcccaac 780
accaagttcc gcgacaagct caagtccttg ctcggacggc cccaggcctt cattcccacc 840
atcaccgatc tgtggcaggc aatggcgaag ggcggataca gcgtggccct cgatgcacag 900
atcaagcatt tcaacggcgg tctgttcgag ggcgtggaag tcctgcctgt gaccgatggg 960
cagctcaagc tctttatcga agctgccgag tccgactgga gccgcgtcga acccagcatc 1020
ttcggcacgc tcgtcgagcg tgccctgaac cccgcgagc gccaccgcct gggagcccac 1080
tacacccccc gtgcctatgt cgagcgcctg gtgcatcagg tggtgatgga gcctctgcgc 1140
gaggactggc gcaccgtgca ggttcaggtg caggacaccc tcgaccgggg caacggggac 1200
gacaaggccc gggccagggc acagcaactc gtcgcgcagt tccatgccca gctgcggcag 1260
acccaggtgc tcgatcctgc ctgtgggacg gggaacttca tctacgtcag catggaactg 1320
atcaagcggc tggaggcgga ggtcattgaa acgctggtgg ccctgggcgg cctgccgccc 1380
ctgatcgagg tgaaccccga gcagtttcac ggcatcgagg tcaacccacg tgccgcgagc 1440
gtggccgagc tggtgctgtg gatcggctac ctgcagctct acgcccgtga gcacggcaac 1500
gccgcgccgc ccgagccgat cctgcgggcc ttccacaaca tcgagaaccg cgacgccgtg 1560
ctgagttaca gccatacgac gccgaaagta gatagggacg gccagcccgt gacccgctgg 1620
gacggggtga cattcaggcg tcacccagtg accggagatc ctgtgcccga cgaaagggca 1680
cagataccgg aagaggtcta ccacaatcca atgactaccg agtggcccaa ggcggacttt 1740
attgtcggca atcctccgtt cattggtagt aaacgcatgc gggaactgct gggcaatggt 1800
tatgtggacg ctttacaaag ggtatttgct gacgtgccac aggccaccga ttttgttctt 1860
cgttggtggt ataaagctgc gttactgacc aggcaggagg aagttaggcg attcggtttc 1920
atcacgacta acagcattag ccaagcgttt aatcgccgtg ctatcgaacc tcacttaaac 1980
gctgacgtta gacctctttc actcgtgtac gtcacaccag accatccgtg ggtagatgaa 2040
tccgacggtg cagccgtacg tattgcgagt acggttgggg agctcggaca acgccctggc 2100
ttacttgcgc gtgtggtcaa agaatatgat gaagctgcag agggcgatct ggtagctgaa 2160
tttgcctttg aaacaggtgt aattcatgct gacttgagca taggggcgga cttaacggag 2220
actcagccac tcatggcaaa tctcggtctt tgtgccgtag gcatgaagac tatagggggcc 2280

```
ggttttctcg tggagcgtac gaaagccgag gctctgggcc ttggtcagga taatcggatt   2340

cgtccctata tcaacgggcg cgatctaatg ggtcgtactc gcggtgtgta tgtaatcgat   2400

ctcttcggtg tctcggaaga agatgtgcgc gatcaatatc caaaactcta tcaacatttg   2460

agaaatgctg tgtacgacat acgtcgccag aacaacaata gggtttttcg tgatttatgg   2520

tgggttattg gccatccacg tccaatcttc cgtgaattta cgcggggctt gaaaagatat   2580

gtggttactt tagaaactgc caagcaccaa gtattccaat tccttgacag ctctatcgtt   2640

ccagacagta ccatcgtcac ctttggaact gaggatgcat ttcaccttgg cgtcctgagc   2700

agccgtgtcc atgtcacctg ggcgctcgcg caaggggca ccctggagga caggccccgc   2760

tacaacaaga cccggtgctt cgaaaccttc cccttcccgg cggccacgcc tgagcagcag   2820

caacgcatcc gtgacctcgc cgagcgcctg gacgcccacc gcaaggcgag actggccgag   2880

catcccaagc tgaccatgac ggatatgtac aacgccctgg ccgcccttcg tgccgggcaa   2940

cccctggagg gcaagctcaa gacggcccac gaccagggcc tggtgaccac cctcaggcag   3000

ctgcatgacg acctcgacgt ggcagtcctg gctgcctacg gctggcctac aggactcgat   3060

gagcaaggcc tgctggaaag gctcgctgcc ctgaacgccg agcgggtaca ggaggaaaag   3120

gcaggccgca ttcgctatct ccggccggcc taccaggatc cgcacggcac cgcgcaggag   3180

aacctaggga tggccgtggc cagccgcccg gcgaaggctg ctcaggtcat gccctttccc   3240

acggccctgc cccttcaggt gcaggccgtc agaagtgccc ttatgcaggc ggggcaggcc   3300

ctcagccccc aggaggtcgc ccaggccttc caaggggcca aagaaaagca ggtcgaggac   3360

atcatgcaga ccctggtgct gctggggcag gcccacctcc gcgagcacaa tggggaggtg   3420

aggtatgccg cctga                                                    3435
```

<210> SEQ ID NO 36
<211> LENGTH: 1144
<212> TYPE: PRT
<213> ORGANISM: Deinococcus radiodurans

<400> SEQUENCE: 36

```
Met Thr Pro Glu Glu Phe Ile Thr Arg Trp Ser Pro Ser Gly Gly Ala
1               5                   10                  15

Glu Arg Ala Asn Tyr Val Leu Phe Leu Ser Glu Leu Cys Asp Leu Leu
            20                  25                  30

Gly Val Pro Lys Pro Asp Pro Thr Gln Ala Asp Glu Ala Lys Asn Ala
        35                  40                  45

Tyr Val Phe Glu Lys Asp Val Pro Asp Leu His Asp Asp Gly Gly Leu
    50                  55                  60

Ser Gln Arg Arg Ile Asp Leu Tyr Arg Arg Gly Ala Phe Ile Leu Glu
65                  70                  75                  80

Ala Lys Gln Gly Val Glu Lys Glu Ala Thr Ala Glu Glu Ala Leu Leu
                85                  90                  95

Ser Thr Lys Gly Lys Lys Lys Lys Gly His Gly Thr Arg Gly Thr Lys
            100                 105                 110

Gly Trp Asp Thr Phe Met Arg Arg Ala Arg Glu Gln Ala Glu Arg Tyr
        115                 120                 125

Ala His Leu Leu Pro Ala Ser Glu Gly Arg Pro Pro Phe Leu Leu Val
    130                 135                 140

Val Asp Val Gly His Val Ile Glu Val Tyr Ala Glu Phe Thr Arg Thr
145                 150                 155                 160

Gly Gly Ala Tyr Leu Pro Phe Pro Ser Ala Arg Ala His Gln Ile Gln
                165                 170                 175
```

```
Leu Ala Asp Leu Ala Arg Pro Glu Val Arg Glu Leu Leu Arg Thr Ile
            180                 185                 190

Trp Leu Asp Pro Leu Ser Leu Asp Pro Ser Ile His Ala Ala Glu Val
        195                 200                 205

Thr Lys Asp Val Ala Arg Lys Leu Ala Glu Ile Ser Arg Ser Met Glu
    210                 215                 220

Gly Gln Pro Asp Ala Gln Gly Gln Ala Met Thr Pro Glu Arg Val Ser
225                 230                 235                 240

Gln Phe Leu Met Arg Met Ile Phe Thr Met Phe Ala Glu Asp Val Gly
                245                 250                 255

Leu Leu Pro Asn Thr Lys Phe Arg Asp Lys Leu Lys Ser Leu Leu Gly
            260                 265                 270

Arg Pro Gln Ala Phe Ile Pro Thr Ile Thr Asp Leu Trp Gln Ala Met
        275                 280                 285

Ala Lys Gly Gly Tyr Ser Val Ala Leu Asp Ala Gln Ile Lys His Phe
    290                 295                 300

Asn Gly Gly Leu Phe Glu Gly Val Glu Val Leu Pro Val Thr Asp Gly
305                 310                 315                 320

Gln Leu Lys Leu Phe Ile Glu Ala Ala Glu Ser Asp Trp Ser Arg Val
                325                 330                 335

Glu Pro Ser Ile Phe Gly Thr Leu Val Glu Arg Ala Leu Asn Pro Arg
            340                 345                 350

Glu Arg His Arg Leu Gly Ala His Tyr Thr Pro Arg Ala Tyr Val Glu
        355                 360                 365

Arg Leu Val His Gln Val Val Met Glu Pro Leu Arg Glu Asp Trp Arg
    370                 375                 380

Thr Val Gln Val Gln Val Gln Asp Thr Leu Asp Arg Gly Asn Gly Asp
385                 390                 395                 400

Asp Lys Ala Arg Ala Arg Ala Gln Gln Leu Val Ala Gln Phe His Ala
                405                 410                 415

Gln Leu Arg Gln Thr Gln Val Leu Asp Pro Ala Cys Gly Thr Gly Asn
            420                 425                 430

Phe Ile Tyr Val Ser Met Glu Leu Ile Lys Arg Leu Glu Ala Glu Val
        435                 440                 445

Ile Glu Thr Leu Val Ala Leu Gly Gly Leu Pro Pro Leu Ile Glu Val
    450                 455                 460

Asn Pro Glu Gln Phe His Gly Ile Glu Val Asn Pro Arg Ala Ala Ser
465                 470                 475                 480

Val Ala Glu Leu Val Leu Trp Ile Gly Tyr Leu Gln Leu Tyr Ala Arg
                485                 490                 495

Glu His Gly Asn Ala Ala Pro Pro Glu Pro Ile Leu Arg Ala Phe His
            500                 505                 510

Asn Ile Glu Asn Arg Asp Ala Val Leu Ser Tyr Ser His Thr Thr Pro
        515                 520                 525

Lys Val Asp Arg Asp Gly Gln Pro Val Thr Arg Trp Asp Gly Val Thr
    530                 535                 540

Phe Arg Arg His Pro Val Thr Gly Asp Pro Val Pro Asp Glu Arg Ala
545                 550                 555                 560

Gln Ile Pro Glu Glu Val Tyr His Asn Pro Met Thr Thr Glu Trp Pro
                565                 570                 575

Lys Ala Asp Phe Ile Val Gly Asn Pro Pro Phe Ile Gly Ser Lys Arg
            580                 585                 590

Met Arg Glu Leu Leu Gly Asn Gly Tyr Val Asp Ala Leu Gln Arg Val
```

```
        595                 600                 605

Phe Ala Asp Val Pro Gln Ala Thr Asp Phe Val Leu Arg Trp Trp Tyr
    610                 615                 620

Lys Ala Ala Leu Leu Thr Arg Gln Glu Glu Val Arg Arg Phe Gly Phe
625                 630                 635                 640

Ile Thr Thr Asn Ser Ile Ser Gln Ala Phe Asn Arg Arg Ala Ile Glu
                645                 650                 655

Pro His Leu Asn Ala Asp Val Arg Pro Leu Ser Leu Val Tyr Val Thr
            660                 665                 670

Pro Asp His Pro Trp Val Asp Glu Ser Asp Gly Ala Ala Val Arg Ile
        675                 680                 685

Ala Ser Thr Val Gly Glu Leu Gly Gln Arg Pro Gly Leu Leu Ala Arg
    690                 695                 700

Val Val Lys Glu Tyr Asp Glu Ala Ala Glu Gly Asp Leu Val Ala Glu
705                 710                 715                 720

Phe Ala Phe Glu Thr Gly Val Ile His Ala Asp Leu Ser Ile Gly Ala
                725                 730                 735

Asp Leu Thr Glu Thr Gln Pro Leu Met Ala Asn Leu Gly Leu Cys Ala
            740                 745                 750

Val Gly Met Lys Thr Ile Gly Ala Gly Phe Leu Val Glu Arg Thr Lys
        755                 760                 765

Ala Glu Ala Leu Gly Leu Gly Gln Asp Asn Arg Ile Arg Pro Tyr Ile
    770                 775                 780

Asn Gly Arg Asp Leu Met Gly Arg Thr Arg Gly Val Tyr Val Ile Asp
785                 790                 795                 800

Leu Phe Gly Val Ser Glu Glu Asp Val Arg Asp Gln Tyr Pro Lys Leu
                805                 810                 815

Tyr Gln His Leu Arg Asn Ala Val Tyr Asp Ile Arg Arg Gln Asn Asn
            820                 825                 830

Asn Arg Val Phe Arg Asp Leu Trp Trp Val Ile Gly His Pro Arg Pro
        835                 840                 845

Ile Phe Arg Glu Phe Thr Arg Gly Leu Lys Arg Tyr Val Val Thr Leu
    850                 855                 860

Glu Thr Ala Lys His Gln Val Phe Gln Phe Leu Asp Ser Ser Ile Val
865                 870                 875                 880

Pro Asp Ser Thr Ile Val Thr Phe Gly Thr Glu Asp Ala Phe His Leu
                885                 890                 895

Gly Val Leu Ser Ser Arg Val His Val Thr Trp Ala Leu Ala Gln Gly
            900                 905                 910

Gly Thr Leu Glu Asp Arg Pro Arg Tyr Asn Lys Thr Arg Cys Phe Glu
        915                 920                 925

Thr Phe Pro Phe Pro Ala Ala Thr Pro Glu Gln Gln Gln Arg Ile Arg
    930                 935                 940

Asp Leu Ala Glu Arg Leu Asp Ala His Arg Lys Ala Arg Leu Ala Glu
945                 950                 955                 960

His Pro Lys Leu Thr Met Thr Asp Met Tyr Asn Ala Leu Ala Ala Leu
                965                 970                 975

Arg Ala Gly Gln Pro Leu Glu Gly Lys Leu Lys Thr Ala His Asp Gln
            980                 985                 990

Gly Leu Val Thr Thr Leu Arg Gln  Leu His Asp Asp Leu  Asp Val Ala
        995                 1000                1005

Val Leu  Ala Ala Tyr Gly Trp  Pro Thr Gly Leu Asp  Glu Gln Gly
    1010                1015                1020
```

-continued

```
Leu Leu  Glu Arg Leu Ala Ala  Leu Asn Ala Glu Arg  Val Gln Glu
    1025                 1030                 1035

Glu Lys  Ala Gly Arg Ile Arg  Tyr Leu Arg Pro Ala  Tyr Gln Asp
    1040                 1045                 1050

Pro His  Gly Thr Ala Gln Glu  Asn Leu Gly Met Ala  Val Ala Ser
    1055                 1060                 1065

Arg Pro  Ala Lys Ala Ala Gln  Val Met Pro Phe Pro  Thr Ala Leu
    1070                 1075                 1080

Pro Leu  Gln Val Gln Ala Val  Arg Ser Ala Leu Met  Gln Ala Gly
    1085                 1090                 1095

Gln Ala  Leu Ser Pro Gln Glu  Val Ala Gln Ala Phe  Gln Gly Ala
    1100                 1105                 1110

Lys Glu  Lys Gln Val Glu Asp  Ile Met Gln Thr Leu  Val Leu Leu
    1115                 1120                 1125

Gly Gln  Ala His Leu Arg Glu  His Asn Gly Glu Val  Arg Tyr Ala
    1130                 1135                 1140

Ala
```

<210> SEQ ID NO 37
<211> LENGTH: 3456
<212> TYPE: DNA
<213> ORGANISM: Marinobacter aquaeolei VT8

<400> SEQUENCE: 37

```
ttggaagcct tcattgcagc ctccgctgct gtcgacgaat tcctcaaacg ctggaaaggc     60

aacacaggta gtgaacgcgc aaactttcaa tcgttcatgc gagacctgtg tacgctgctg    120

gaccttcctc atccagaccc aggtgaaggt gacaccactc agaacgccta tgtatttgag    180

cggtttatcg cgtcggctcg agtcgatggc aataccgaca accggtacat cgacctgtat    240

cgtcgggact gcttcgtact ggaagggaag cagactggca aggagctggc atcccgaagc    300

caacagaacg ctgttaatgc agctgtagca caggctgagc gatacattcg aggactgccc    360

caggaagaag tagagcatgg ccgcccgcca ttcatcgtga tcgtcgatgt gggcaacgcc    420

atctacacgt actccgagtt ctcgcgaact ggcggtaact atgttccatt ccctgatccc    480

agacactatg agatccgact ggaagacctg cacaaaccag atgttcagca ccgtcttcgt    540

cagttatggc tagaaccgga tcagctcgat ccgagtaagc atgctgccag ggtgacccga    600

gaggtcagca ccaagctggc tgaattggca aagtccctgg agcataatgg atacgatgtc    660

gagcgagtag ccagctttct caagcgctgc ctgttcacga tgtttgccga agacgtagag    720

ttgctgccca aggcatcctt ccagaacctt ttgatcgaca ttaaggaccg gaaccctgaa    780

gccttccccc acgccgtgaa ggcgctttgg gaaaccatga atgctggtgg ctacagtgag    840

cgtctgatgc agaccatcaa gcgatttaac ggtgggttgt tcaaaggcat cgatccaatc    900

ccgctgaatg ttcagcagat ccaacttctc atagatgcgg ccaaagccga ctggcgtttc    960

gttgaacctg ccatcttcgg gacgctgcta gagcgtgccc ttgatcctcg ggagcgccac   1020

aagctgggcg cccattacac tcccagggcc tacgttgaac gcttggtcat gccgaccctg   1080

attgaaccgc ttcgtgagca atggggcgac atccgaggtg cggcggaaac cctgctgcgg   1140

caaggcaaaa cagacaaagc tcttcaggaa gtccaagcct tccattatca gctttgccag   1200

acccgagtac ttgatcccgc ttgtggtagc gctaacttcc tttacgtggc ccttgaacac   1260

atgaagcgcc tggagggga ggtcctgggt tttatctccg agctgaccca ggggcaaggc   1320

gtgctggaaa gtgaaggcct gaccgtcgat ccgcaccagt tcctgggctt ggagataaac   1380
```

```
ccacgagcag cccagattgc cgaactcgtt ttgtggattg gctaccttca gtggcactac   1440
cggctgaacg accggctgga cctccccgag cccatcttgc gggacttcaa aaacattgag   1500
tgcagggatg ctctgatcga gtatgacagt cgagaaccgg agctaaataa aaatggggaa   1560
ccggtgacca tctgggatgg catcagcatg aaggtgagcc cgacaacggg tgaattaatc   1620
cccgatgaaa cagggcgagc taaggtctac cgttaccaca atccacgcag ggctgagtgg   1680
ccagcagcag agtacataat aggaaatcct ccttatattg gcgctcgccg aattagatcc   1740
gccttgggtg acggttattt acaagcgttg cgaggcgtat acaccgatat tccagaacac   1800
gtcgatttcg tcatgtattg gtgggcaaag gcttcagaga acatggcaag tggtaaaaca   1860
aaagcgtttg gattaattac cacgaatagt cttcggcaaa gcttttctcg aaaggttgta   1920
gaaaaaacct tagatatcaa ttcggactgt tccataaaat tcgtgattcc tgatcatccg   1980
tgggttgata gcgccgacgg tgcggcggtt cgggtcacat tgatttctgt tgacagcaat   2040
aaagcgcccg gaatagttgc tctcatcaga aacgaggaag cagaaggtag tggagcctac   2100
aagattacct tggataacaa gtcggggcat ataacgccga acctcacgat aggggcggac   2160
cccggagaag ctacgtgctt atcatcaaat tcctcagtgt catgcgtagg ttatcaacta   2220
accggcaaag ggtttgttct tactcaaagc caaaaagaag agcacgaaaa tgaatggccc   2280
gaaagtgtca ttaaaccttt gtggagcggg cgtgacatca cgcagtcacc cagaaaaaac   2340
tgggcaattg atgtttgtga ttggggaatt gacgctttaa aagtttcatc accaagtctc   2400
tatcaatggc ttctcactcg ggtaaagccg gagcgcgaac agaacaatag agccagtcta   2460
aaggagcgtt ggtggattta cggcgaagcc agaaacactt tccggcccgc tcttattggc   2520
atagaaacag ctatcgcaac ttctttaact gcgaaacatc gggtgtttgt gcacctagat   2580
tcaaacagca tttgcgatag caccactgtc atgttcgcac taccaggagc ccagtacctt   2640
ggtgttttaa gttccagggt gcatgtactt tggtcacttt ttgctggggg gacactcgag   2700
aatcgtccga ggtataacaa gacactgtgc tttgaaacat ttccttttcc aaaaatgagt   2760
tctgatcagt ctgaaaaaat aagtgacctc gcagaaaaaa tagatcaagt acgcaaaggc   2820
caacaggcaa aacaccccga tctaacacta acggggatgt acaacgtgct cgaaaaacta   2880
cgttccggtg aagagctaac caacaaagaa aagaccatcc acgaacaagg cttggtgtcc   2940
gtactccgtg agctccacga cgacctcgat cgtgccgttt tccaggccta tggttggtca   3000
gacttggcag ataagcttgt aggtcgccca ggcgccacaa ccccacttcc agacaaaccg   3060
gctgaacaag cggaggctga ggacgagctg ttgatgcgat tgctcgaact caacaagcag   3120
cgtgcagagg aagaatcacg gggcatagtt cgctggttac gtccggatta ccaggcgcgc   3180
gatgctgtac agacagaagt ggatatcgcg ccgaaggccg ccgccacaaa aacggaagcc   3240
tctaccagca aaggaaaagc ctcattcccg aaagcgattc ccgatcagct tcgagtgctc   3300
cgagaggcac tcgcagagcg atctcacacg acggaaagtt tggctgagat gttcaagcgg   3360
aaacctatga aatcggtcga ggagggtttg cagtcacttg tagctgtggg tgttgccgaa   3420
tacgacccgg aaactcaaac atggcatacg gtatga                             3456
```

<210> SEQ ID NO 38
<211> LENGTH: 1151
<212> TYPE: PRT
<213> ORGANISM: Marinobacter aquaeolei VT8

<400> SEQUENCE: 38

```
Met Glu Ala Phe Ile Ala Ala Ser Ala Ala Val Asp Glu Phe Leu Lys
1               5                   10                  15
```

```
Arg Trp Lys Gly Asn Thr Gly Ser Glu Arg Ala Asn Phe Gln Ser Phe
            20                  25                  30

Met Arg Asp Leu Cys Thr Leu Leu Asp Leu Pro His Pro Asp Pro Gly
        35                  40                  45

Glu Gly Asp Thr Thr Gln Asn Ala Tyr Val Phe Glu Arg Phe Ile Ala
    50                  55                  60

Ser Ala Arg Val Asp Gly Asn Thr Asp Asn Arg Tyr Ile Asp Leu Tyr
65                  70                  75                  80

Arg Arg Asp Cys Phe Val Leu Glu Gly Lys Gln Thr Gly Lys Glu Leu
                85                  90                  95

Ala Ser Arg Ser Gln Gln Asn Ala Val Asn Ala Ala Val Ala Gln Ala
            100                 105                 110

Glu Arg Tyr Ile Arg Gly Leu Pro Gln Glu Glu Val Glu His Gly Arg
        115                 120                 125

Pro Pro Phe Ile Val Ile Val Asp Val Gly Asn Ala Ile Tyr Thr Tyr
    130                 135                 140

Ser Glu Phe Ser Arg Thr Gly Gly Asn Tyr Val Pro Phe Pro Asp Pro
145                 150                 155                 160

Arg His Tyr Glu Ile Arg Leu Glu Asp Leu His Lys Pro Asp Val Gln
                165                 170                 175

His Arg Leu Arg Gln Leu Trp Leu Glu Pro Asp Gln Leu Asp Pro Ser
            180                 185                 190

Lys His Ala Ala Arg Val Thr Arg Glu Val Ser Thr Lys Leu Ala Glu
        195                 200                 205

Leu Ala Lys Ser Leu Glu His Asn Gly Tyr Asp Val Glu Arg Val Ala
    210                 215                 220

Ser Phe Leu Lys Arg Cys Leu Phe Thr Met Phe Ala Glu Asp Val Glu
225                 230                 235                 240

Leu Leu Pro Lys Ala Ser Phe Gln Asn Leu Leu Ile Asp Ile Lys Asp
                245                 250                 255

Arg Asn Pro Glu Ala Phe Pro His Ala Val Lys Ala Leu Trp Glu Thr
            260                 265                 270

Met Asn Ala Gly Gly Tyr Ser Glu Arg Leu Met Gln Thr Ile Lys Arg
        275                 280                 285

Phe Asn Gly Gly Leu Phe Lys Gly Ile Asp Pro Ile Pro Leu Asn Val
    290                 295                 300

Gln Gln Ile Gln Leu Leu Ile Asp Ala Ala Lys Ala Asp Trp Arg Phe
305                 310                 315                 320

Val Glu Pro Ala Ile Phe Gly Thr Leu Leu Glu Arg Ala Leu Asp Pro
                325                 330                 335

Arg Glu Arg His Lys Leu Gly Ala His Tyr Thr Pro Arg Ala Tyr Val
            340                 345                 350

Glu Arg Leu Val Met Pro Thr Leu Ile Glu Pro Leu Arg Glu Gln Trp
        355                 360                 365

Gly Asp Ile Arg Gly Ala Ala Glu Thr Leu Leu Arg Gln Gly Lys Thr
    370                 375                 380

Asp Lys Ala Leu Gln Glu Val Gln Ala Phe His Tyr Gln Leu Cys Gln
385                 390                 395                 400

Thr Arg Val Leu Asp Pro Ala Cys Gly Ser Ala Asn Phe Leu Tyr Val
                405                 410                 415

Ala Leu Glu His Met Lys Arg Leu Glu Gly Glu Val Leu Gly Phe Ile
            420                 425                 430

Ser Glu Leu Thr Gln Gly Gln Gly Val Leu Glu Ser Glu Gly Leu Thr
```

```
        435                 440                 445

Val Asp Pro His Gln Phe Leu Gly Leu Glu Ile Asn Pro Arg Ala Ala
    450                 455                 460

Gln Ile Ala Glu Leu Val Leu Trp Ile Gly Tyr Leu Gln Trp His Tyr
465                 470                 475                 480

Arg Leu Asn Asp Arg Leu Asp Leu Pro Glu Pro Ile Leu Arg Asp Phe
                485                 490                 495

Lys Asn Ile Glu Cys Arg Asp Ala Leu Ile Glu Tyr Asp Ser Arg Glu
            500                 505                 510

Pro Glu Leu Asn Lys Asn Gly Glu Pro Val Thr Ile Trp Asp Gly Ile
        515                 520                 525

Ser Met Lys Val Ser Pro Thr Thr Gly Glu Leu Ile Pro Asp Glu Thr
    530                 535                 540

Gly Arg Ala Lys Val Tyr Arg Tyr His Asn Pro Arg Arg Ala Glu Trp
545                 550                 555                 560

Pro Ala Ala Glu Tyr Ile Ile Gly Asn Pro Pro Tyr Ile Gly Ala Arg
                565                 570                 575

Arg Ile Arg Ser Ala Leu Gly Asp Gly Tyr Leu Gln Ala Leu Arg Gly
            580                 585                 590

Val Tyr Thr Asp Ile Pro Glu His Val Asp Phe Val Met Tyr Trp Trp
        595                 600                 605

Ala Lys Ala Ser Glu Asn Met Ala Ser Gly Lys Thr Lys Ala Phe Gly
    610                 615                 620

Leu Ile Thr Thr Asn Ser Leu Arg Gln Ser Phe Ser Arg Lys Val Val
625                 630                 635                 640

Glu Lys Thr Leu Asp Ile Asn Ser Asp Cys Ser Ile Lys Phe Val Ile
                645                 650                 655

Pro Asp His Pro Trp Val Asp Ser Ala Asp Gly Ala Ala Val Arg Val
            660                 665                 670

Thr Leu Ile Ser Val Asp Ser Asn Lys Ala Pro Gly Ile Val Ala Leu
        675                 680                 685

Ile Arg Asn Glu Glu Ala Glu Gly Ser Gly Ala Tyr Lys Ile Thr Leu
    690                 695                 700

Asp Asn Lys Ser Gly His Ile Thr Pro Asn Leu Thr Ile Gly Ala Asp
705                 710                 715                 720

Pro Gly Glu Ala Thr Cys Leu Ser Ser Asn Ser Ser Val Ser Cys Val
                725                 730                 735

Gly Tyr Gln Leu Thr Gly Lys Gly Phe Val Leu Thr Gln Ser Gln Lys
            740                 745                 750

Glu Glu His Glu Asn Glu Trp Pro Glu Ser Val Ile Lys Pro Leu Trp
        755                 760                 765

Ser Gly Arg Asp Ile Thr Gln Ser Pro Arg Lys Asn Trp Ala Ile Asp
    770                 775                 780

Val Cys Asp Trp Gly Ile Asp Ala Leu Lys Val Ser Ser Pro Ser Leu
785                 790                 795                 800

Tyr Gln Trp Leu Leu Thr Arg Val Lys Pro Glu Arg Glu Gln Asn Asn
                805                 810                 815

Arg Ala Ser Leu Lys Glu Arg Trp Trp Ile Tyr Gly Glu Ala Arg Asn
            820                 825                 830

Thr Phe Arg Pro Ala Leu Ile Gly Ile Glu Thr Ala Ile Ala Thr Ser
        835                 840                 845

Leu Thr Ala Lys His Arg Val Phe Val His Leu Asp Ser Asn Ser Ile
    850                 855                 860
```

```
Cys Asp Ser Thr Thr Val Met Phe Ala Leu Pro Gly Ala Gln Tyr Leu
865                 870                 875                 880

Gly Val Leu Ser Ser Arg Val His Val Leu Trp Ser Leu Phe Ala Gly
                885                 890                 895

Gly Thr Leu Glu Asn Arg Pro Arg Tyr Asn Lys Thr Leu Cys Phe Glu
            900                 905                 910

Thr Phe Pro Phe Pro Lys Met Ser Ser Asp Gln Ser Glu Lys Ile Ser
        915                 920                 925

Asp Leu Ala Glu Lys Ile Asp Gln Val Arg Lys Gly Gln Gln Ala Lys
    930                 935                 940

His Pro Asp Leu Thr Leu Thr Gly Met Tyr Asn Val Leu Glu Lys Leu
945                 950                 955                 960

Arg Ser Gly Glu Glu Leu Thr Asn Lys Glu Lys Thr Ile His Glu Gln
                965                 970                 975

Gly Leu Val Ser Val Leu Arg Glu Leu His Asp Asp Leu Asp Arg Ala
            980                 985                 990

Val Phe Gln Ala Tyr Gly Trp Ser  Asp Leu Ala Asp Lys  Leu Val Gly
        995                 1000                 1005

Arg Pro  Gly Ala Thr Thr Pro  Leu Pro Asp Lys Pro  Ala Glu Gln
    1010                 1015                 1020

Ala Glu  Ala Glu Asp Glu Leu  Leu Met Arg Leu Leu  Glu Leu Asn
    1025                 1030                 1035

Lys Gln  Arg Ala Glu Glu Glu  Ser Arg Gly Ile Val  Arg Trp Leu
    1040                 1045                 1050

Arg Pro  Asp Tyr Gln Ala Arg  Asp Ala Val Gln Thr  Glu Val Asp
    1055                 1060                 1065

Ile Ala  Pro Lys Ala Ala Ala  Thr Lys Thr Glu Ala  Ser Thr Ser
    1070                 1075                 1080

Lys Gly  Lys Ala Ser Phe Pro  Lys Ala Ile Pro Asp  Gln Leu Arg
    1085                 1090                 1095

Val Leu  Arg Glu Ala Leu Ala  Glu Arg Ser His Thr  Thr Glu Ser
    1100                 1105                 1110

Leu Ala  Glu Met Phe Lys Arg  Lys Pro Met Lys Ser  Val Glu Glu
    1115                 1120                 1125

Gly Leu  Gln Ser Leu Val Ala  Val Gly Val Ala Glu  Tyr Asp Pro
    1130                 1135                 1140

Glu Thr  Gln Thr Trp His Thr  Val
    1145                 1150
```

<210> SEQ ID NO 39
<211> LENGTH: 2787
<212> TYPE: DNA
<213> ORGANISM: Parvibaculum lavamentivorans DS-1

<400> SEQUENCE: 39

```
atgcggctga gctggaacga gattcgcgcc cgcgcagcgc gtttttccga ggaatggaaa      60

ggtgtcacgc gcgaacgcgc cgagacgcag accttctata atgagttctt ccagattttc     120

gacatcccgc gccgtcgcgt cgcctcttac gaagagccgg taaagggcct tggcgacaag     180

cgcggctata tcgacctttt ctggaaaggc acgcttcttg tcgagcacaa gaccacgggc     240

cgcgacctca aaaaggcaaa gattcaggcg ctcgattatt tcccgggcct gaaggacaag     300

gaactcccac gctacctcct cctctgcgat ttccagagct tcgagcttta cgatctggac     360

gaagacaccg aggtccgttt ccgcctcgcc gatctgaaag atcatgtgga agccttcggc     420

ttcatgatcg gcgtccagaa gcgcaccttc aaggatcagg accccgtcaa catcgaagcc     480
```

-continued

```
tcggagctga tgggcaagct ccacgatgca ctgaaggaat cgggttacga cggccacgac    540
cttgagcaat atctggtccg gcttctcttc tgcctctttg ccgacgacac cggcattttc    600
gagcccaagg acatccttct cgatttcatc cagaaccgca caagcgcgga tggcagcgat    660
ctcggctccc gcctcaatga attgttcgag gtgttgaaca cgccggaaga caagcgccag    720
aaaacccttg atgaagacct cggaaatttc ccttatgtga atggcgcgct tttcgccgag    780
cgtctgcgca cgcctgcctt caacgccgcc atgcggctga tccttatcga agcctgcgag    840
ttcaaatggg aggcaatctc gcctgccatt ttcggtgctc tgttccagtc cgtcatgaac    900
aagacagagc gccgcgccct cggcgcgcat tacacgaccg agaaaaacat cctgaaactc    960
attcagccgc ttttcctcga cggcctgcat gaagagttcg cgcgcgcaaa ggcgctgaag   1020
cgcggccgcc agcaggcgct ggaagccttg cacgagaaac tcggccagct caccttcttc   1080
gatcccgcct gcggctgcgg taacttcctc gtcatcgcct atcgcgagct acgcgcgctg   1140
gaacaggaaa ttctgcgcgt cctgcacgac ggcaaagacc agcgcatttt cgacgtggcg   1200
caattgtcga aagtcaatgt cgatcagttt tacggcatcg aaataggcga gtttcccgcc   1260
cgcatagccg aagtcgcgat gtggatgatg gaccacatca tgaataacag gctcggcctc   1320
tccttcggct ccaactatgc gcgcatcccc cttcggacct caccgcacat cctccatgcc   1380
gacgcgctgg aagccgattg ggccgctctc ctcccgccgg aaaaatgctc ctatgtcttc   1440
ggcaatccgc ctttcatcgg ctcaaaattc cagacggcgg aacagcgtcg gcaagtgcgt   1500
gacatcgcaa agctcggcgg ctccggcggc acgcttgatt tcgtcaccgc atggttcctg   1560
aaggccggcg aatatgtgca gcatggaaaa gcggacatcg ccttcgtcgc caccaactca   1620
atcacgcagg gcgaacaggt cgcccagctc tggccgctcc tctttcagcg ctgcaagctc   1680
gaaatcgcct tcgcccaccg taccttcgcc tggggctcgg acgcgcgcgg cgtcgcccat   1740
gttcatgtcg tcatcatcgg cctcacaagg cgcgaccgcg aatggcccga gaagcgcctc   1800
ttctcttacg ccgacatcaa gggcgatccg gtcgagacac gccacaaggc tctgacggct   1860
tatctttttg atgccgtcaa tgtagctgac agacatctag tagtcgaaga acgaaacact   1920
cctttgtgcg aagcgccgaa actcaaaact ggcgttcaga tgatcgacaa cggcatcctc   1980
actttcacga caatggaaaa ggaggaattt cttcgtcagg agccggaagc ggaaccgctg   2040
ttccgcaaat acatcggtgg cgatgagtat ataaatggat tttccgatg gatactctat   2100
ctcgcagatg ccgagccgag ttttcttcga cagcttccgc ttgttcaaga aagaatacgg   2160
caggtacgtc aataccggtt atcgagttct cggcccagca cggtgagaat ggcggactat   2220
ccaacgcagg ttggtgtgga cgagcgattg agcggaccct atttggtgat acccaataca   2280
agctcggagc gacgcgacta cgtaccgatc ggctggctga ctcccgaggt agtagccaat   2340
cagaaattgc gcattcttcc tgacgcagat ccgtggatat tcggtttgct gacaagcggc   2400
atgcacatgg cttggatgcg cgcaatcacc ggtcgcatga aaagcgacta catgtattct   2460
gtcggcgtcg tctacaacac tttcccttgg ccggatatta ccgaagctca gaaacagaaa   2520
atccgtgcgc tagcgcaagc tgtgctcgac gcccgcgcgc tttatcccgg tgcaacgctg   2580
gccgatctct acgatcccga cctgatgaaa cgcgaactcc gtcaggctca ccgagccctc   2640
gatgccgccg tcgacaaact ctatcgcggc caagccttcg caaatgaccg cgagcgtgtc   2700
gaacacctct tcggcctata cgaaaaactc tcctccccgc tgacagcagc accgaagccc   2760
attaagcgga aacgaaagaa agagtag                                       2787
```

<210> SEQ ID NO 40
<211> LENGTH: 928
<212> TYPE: PRT
<213> ORGANISM: Parvibaculum lavamentivorans DS-1

<400> SEQUENCE: 40

Met Arg Leu Ser Trp Asn Glu Ile Arg Ala Arg Ala Ala Arg Phe Ser
1 5 10 15

Glu Glu Trp Lys Gly Val Thr Arg Glu Arg Ala Glu Thr Gln Thr Phe
20 25 30

Tyr Asn Glu Phe Phe Gln Ile Phe Asp Ile Pro Arg Arg Arg Val Ala
35 40 45

Ser Tyr Glu Glu Pro Val Lys Gly Leu Gly Asp Lys Arg Gly Tyr Ile
50 55 60

Asp Leu Phe Trp Lys Gly Thr Leu Leu Val Glu His Lys Thr Thr Gly
65 70 75 80

Arg Asp Leu Lys Lys Ala Lys Ile Gln Ala Leu Asp Tyr Phe Pro Gly
85 90 95

Leu Lys Asp Lys Glu Leu Pro Arg Tyr Leu Leu Leu Cys Asp Phe Gln
100 105 110

Ser Phe Glu Leu Tyr Asp Leu Asp Glu Asp Thr Glu Val Arg Phe Arg
115 120 125

Leu Ala Asp Leu Lys Asp His Val Glu Ala Phe Gly Phe Met Ile Gly
130 135 140

Val Gln Lys Arg Thr Phe Lys Asp Gln Asp Pro Val Asn Ile Glu Ala
145 150 155 160

Ser Glu Leu Met Gly Lys Leu His Asp Ala Leu Lys Glu Ser Gly Tyr
165 170 175

Asp Gly His Asp Leu Glu Gln Tyr Leu Val Arg Leu Leu Phe Cys Leu
180 185 190

Phe Ala Asp Asp Thr Gly Ile Phe Glu Pro Lys Asp Ile Leu Leu Asp
195 200 205

Phe Ile Gln Asn Arg Thr Ser Ala Asp Gly Ser Asp Leu Gly Ser Arg
210 215 220

Leu Asn Glu Leu Phe Glu Val Leu Asn Thr Pro Glu Asp Lys Arg Gln
225 230 235 240

Lys Thr Leu Asp Glu Asp Leu Gly Asn Phe Pro Tyr Val Asn Gly Ala
245 250 255

Leu Phe Ala Glu Arg Leu Arg Thr Pro Ala Phe Asn Ala Ala Met Arg
260 265 270

Leu Ile Leu Ile Glu Ala Cys Glu Phe Lys Trp Glu Ala Ile Ser Pro
275 280 285

Ala Ile Phe Gly Ala Leu Phe Gln Ser Val Met Asn Lys Thr Glu Arg
290 295 300

Arg Ala Leu Gly Ala His Tyr Thr Thr Glu Lys Asn Ile Leu Lys Leu
305 310 315 320

Ile Gln Pro Leu Phe Leu Asp Gly Leu His Glu Glu Phe Ala Arg Ala
325 330 335

Lys Ala Leu Lys Arg Gly Arg Gln Gln Ala Leu Glu Ala Leu His Glu
340 345 350

Lys Leu Gly Gln Leu Thr Phe Phe Asp Pro Ala Cys Gly Cys Gly Asn
355 360 365

Phe Leu Val Ile Ala Tyr Arg Glu Leu Arg Ala Leu Glu Gln Glu Ile
370 375 380

Leu Arg Val Leu His Asp Gly Lys Asp Gln Arg Ile Phe Asp Val Ala

```
385                 390                 395                 400

Gln Leu Ser Lys Val Asn Val Asp Gln Phe Tyr Gly Ile Glu Ile Gly
                405                 410                 415

Glu Phe Pro Ala Arg Ile Ala Glu Val Ala Met Trp Met Met Asp His
            420                 425                 430

Ile Met Asn Asn Arg Leu Gly Leu Ser Phe Gly Ser Asn Tyr Ala Arg
        435                 440                 445

Ile Pro Leu Arg Thr Ser Pro His Ile Leu His Ala Asp Ala Leu Glu
    450                 455                 460

Ala Asp Trp Ala Ala Leu Leu Pro Pro Glu Lys Cys Ser Tyr Val Phe
465                 470                 475                 480

Gly Asn Pro Pro Phe Ile Gly Ser Lys Phe Gln Thr Ala Glu Gln Arg
                485                 490                 495

Arg Gln Val Arg Asp Ile Ala Lys Leu Gly Gly Ser Gly Gly Thr Leu
            500                 505                 510

Asp Phe Val Thr Ala Trp Phe Leu Lys Ala Gly Glu Tyr Val Gln His
        515                 520                 525

Gly Lys Ala Asp Ile Ala Phe Val Ala Thr Asn Ser Ile Thr Gln Gly
    530                 535                 540

Glu Gln Val Ala Gln Leu Trp Pro Leu Leu Phe Gln Arg Cys Lys Leu
545                 550                 555                 560

Glu Ile Ala Phe Ala His Arg Thr Phe Ala Trp Gly Ser Asp Ala Arg
                565                 570                 575

Gly Val Ala His Val His Val Val Ile Ile Gly Leu Thr Arg Arg Asp
            580                 585                 590

Arg Glu Trp Pro Glu Lys Arg Leu Phe Ser Tyr Ala Asp Ile Lys Gly
        595                 600                 605

Asp Pro Val Glu Thr Arg His Lys Ala Leu Thr Ala Tyr Leu Phe Asp
    610                 615                 620

Ala Val Asn Val Ala Asp Arg His Leu Val Val Glu Glu Arg Asn Thr
625                 630                 635                 640

Pro Leu Cys Glu Ala Pro Lys Leu Lys Thr Gly Val Gln Met Ile Asp
                645                 650                 655

Asn Gly Ile Leu Thr Phe Thr Thr Met Glu Lys Glu Glu Phe Leu Arg
            660                 665                 670

Gln Glu Pro Glu Ala Glu Pro Leu Phe Arg Lys Tyr Ile Gly Gly Asp
        675                 680                 685

Glu Tyr Ile Asn Gly Phe Phe Arg Trp Ile Leu Tyr Leu Ala Asp Ala
    690                 695                 700

Glu Pro Ser Phe Leu Arg Gln Leu Pro Leu Val Gln Glu Arg Ile Arg
705                 710                 715                 720

Gln Val Arg Gln Tyr Arg Leu Ser Ser Ser Arg Pro Ser Thr Val Arg
                725                 730                 735

Met Ala Asp Tyr Pro Thr Gln Val Gly Val Asp Glu Arg Leu Ser Gly
            740                 745                 750

Pro Tyr Leu Val Ile Pro Asn Thr Ser Ser Glu Arg Arg Asp Tyr Val
        755                 760                 765

Pro Ile Gly Trp Leu Thr Pro Glu Val Val Ala Asn Gln Lys Leu Arg
    770                 775                 780

Ile Leu Pro Asp Ala Asp Pro Trp Ile Phe Gly Leu Leu Thr Ser Gly
785                 790                 795                 800

Met His Met Ala Trp Met Arg Ala Ile Thr Gly Arg Met Lys Ser Asp
                805                 810                 815
```

```
Tyr Met Tyr Ser Val Gly Val Val Tyr Asn Thr Phe Pro Trp Pro Asp
            820                 825                 830

Ile Thr Glu Ala Gln Lys Gln Lys Ile Arg Ala Leu Ala Gln Ala Val
        835                 840                 845

Leu Asp Ala Arg Ala Leu Tyr Pro Gly Ala Thr Leu Ala Asp Leu Tyr
    850                 855                 860

Asp Pro Asp Leu Met Lys Arg Glu Leu Arg Gln Ala His Arg Ala Leu
865                 870                 875                 880

Asp Ala Ala Val Asp Lys Leu Tyr Arg Gly Gln Ala Phe Ala Asn Asp
                885                 890                 895

Arg Glu Arg Val Glu His Leu Phe Gly Leu Tyr Glu Lys Leu Ser Ser
            900                 905                 910

Pro Leu Thr Ala Ala Pro Lys Pro Ile Lys Arg Lys Arg Lys Lys Glu
        915                 920                 925


<210> SEQ ID NO 41
<211> LENGTH: 2754
<212> TYPE: DNA
<213> ORGANISM: Agmenellum quadruplicatum PR-6

<400> SEQUENCE: 41

atgcctttaa gttggaatga aatcaaaagt cgggcgatcg ccttctcgaa ggagtgggaa     60

tttgaggagt cagaaaaatc agaagcacaa tcgttttgga atgatttttt tcaggtattt    120

ggcatttctc gtaagcgaat cgcaacattt gagaagtcag ttaacaaatt agggaataag    180

aaaggttcta ttgacctgtt atggaaggga aatatccttg ttgagcataa atcacgaggc    240

aaaagtttag ataaggcgtt tgaacaggca aaagattatt ttccggggtt aaaggagcat    300

gagctacctc gatatatttt ggtgtcggat ttcgctcaat tccggcttta tgacctcgaa    360

acggatcaga cccatgaatt tctactaaaa gatttcgtca attatgttca tctgtttgat    420

tttattgcgg gatatgagca gcgaacctat aaggatgaag atccggttaa tattcacgcg    480

gcggagttga tgggtaagct gcatgaccgt ctcagggaga ttggttatac gggtcatgat    540

ctagaagttt acttagtgag gttgttattt tgcttatttg cagatgacac aggcattttt    600

gaaaagggaa tttttgagga atatctcgat attcatacca aagaagatgg tagtgatttg    660

gcgatgcact tggggcatat tttccatgtg ttgaatacgc caccggagaa gcggttaaaa    720

aatctggatg agagtttagg acagtttccc tatgtgaatg gcaagttatt tgaagagcag    780

ttagcgcctg cggcttttga tcgcaaaatg cgagaaatgt tattagaagc ttgtggattt    840

aattggggga aaatttctcc ggccattttt gggtcaatgt tccaagcggc gatggatcaa    900

cagactcgac gaaatttggg ggcgcattat acgtctgaga aaaatattca gaaggtgatt    960

aagcctttgt ttttggatga gttgcacgag aaatttaaga aggcaaaagg cagtccaacg   1020

gcgttaaagc ggctccatga tgagcttggg gaattacatt ttcttgatcc ggcttgtggc   1080

tgtggaaatt ttttgattat ttcttatcgg gaattgcgag atctagagtt attgattctc   1140

aaagagcttt acaagaagaa ggaggggttt attgatattc gtttgttcct aaaggtggat   1200

gtggatcagt ttgggggcat tgaatatgat gagtttccgg cacgggtggc agaggtggcg   1260

atgtggctca tcgatcatca gatgaatatc aaggtgagta atgagtttgg gcagtatttt   1320

gtccggttgc cgctaaagaa ggctgccaga attgtgaatg ggaatgcgtt acggattgat   1380

tgggaagaag tgattccaaa ggaaaagtta aattacattc tcggtaatcc accttttgtg   1440

ggttcaaaga tgatgacgaa agatcagcga gcagatcttt tatctgtttt tgaaagtgcc   1500

aagggtgcag ggtaatgga ttatgtttct gcttggtatg ttaaagcggc agattttatt   1560
```

```
caagagaaaa agataaaaac agcttttgta agtacaaatt ctatctctca aggtgagcaa   1620

gttggaattt tatggggact actttttgaa aaatatcaaa ttaagattca ttttgcacac   1680

cgtactttta aatggtcaaa tgaggcaaaa gggaaagcgg ctgtttattg tgtgattatt   1740

ggatttgcaa cttttaacat taaaggaaag cgtttattcg agtatgaaga tatcaaggga   1800

gaagcgttag aaatcaaagt aagtaacatc aatccatatt tggtaaatgg tgatgattta   1860

attattctaa gacggcggca acctttatgt aatgtcccta atattggcat tggcaataag   1920

cccattgatg gcggccatta cttgttcacc acagaagaaa aggaggattt tttaaaacta   1980

gagccaaaag cagaaaaatg gtttaggaaa tggttgggtt ctagggagtt tatcaataaa   2040

gaagaaagat ggtgtttgtg gttgggagac tgtccaccta acgaactcaa aaaaatgccc   2100

catgctttag agcgagtcaa ggcagttaaa gaaactcgat taaatagcaa cagtaaaccg   2160

acccaaaagc tagcgcaaac accgacaaga tttcatgttg aaaatatgcc agaatcagaa   2220

tatttactta ttccaaaagt ttctagtgaa aggcgcaact atattcctat tgggttttta   2280

aatcaaagta cgttatctag tgacttggtg tttattgttg gtaatgccac cttgtttcat   2340

tttggtatct ttacttcagt aatgcacatg gcatgggtta aatatgtttg tggaagatta   2400

aaaagtgatt atcgttattc aaaagatatt gtctataata attttccttt tccgcagaac   2460

gtaactgaca aacaaaaaca aacagttgaa aaagcagcgc agttagtttt agacactaga   2520

gacaaatatc ccgatagtag ccttgccgat ctttacgatc ccctcaccat gccccccgac   2580

ttaatgaaag cccaccaaaa actcgataaa gcagtggatc tctgttaccg tcctcaagct   2640

tttaccagcg aactcaaccg catcgaattt ttatttaacg aatatgagaa actgataaca   2700

ccactcctac aaagtacaaa acagaaaaaa gcccgcaaaa acaaaacatc ttaa         2754
```

<210> SEQ ID NO 42
<211> LENGTH: 917
<212> TYPE: PRT
<213> ORGANISM: Agmenellum quadruplicatum PR-6

<400> SEQUENCE: 42

```
Met Pro Leu Ser Trp Asn Glu Ile Lys Ser Arg Ala Ile Ala Phe Ser
1               5                   10                  15

Lys Glu Trp Glu Phe Glu Glu Ser Glu Lys Ser Glu Ala Gln Ser Phe
            20                  25                  30

Trp Asn Asp Phe Phe Gln Val Phe Gly Ile Ser Arg Lys Arg Ile Ala
        35                  40                  45

Thr Phe Glu Lys Ser Val Asn Lys Leu Gly Asn Lys Lys Gly Ser Ile
    50                  55                  60

Asp Leu Leu Trp Lys Gly Asn Ile Leu Val Glu His Lys Ser Arg Gly
65                  70                  75                  80

Lys Ser Leu Asp Lys Ala Phe Glu Gln Ala Lys Asp Tyr Phe Pro Gly
                85                  90                  95

Leu Lys Glu His Glu Leu Pro Arg Tyr Ile Leu Val Ser Asp Phe Ala
            100                 105                 110

Gln Phe Arg Leu Tyr Asp Leu Glu Thr Asp Gln Thr His Glu Phe Leu
        115                 120                 125

Leu Lys Asp Phe Val Asn Tyr Val His Leu Phe Asp Phe Ile Ala Gly
    130                 135                 140

Tyr Glu Gln Arg Thr Tyr Lys Asp Glu Asp Pro Val Asn Ile His Ala
145                 150                 155                 160

Ala Glu Leu Met Gly Lys Leu His Asp Arg Leu Arg Glu Ile Gly Tyr
```

-continued

```
                165                 170                 175

Thr Gly His Asp Leu Glu Val Tyr Leu Val Arg Leu Leu Phe Cys Leu
            180                 185                 190

Phe Ala Asp Asp Thr Gly Ile Phe Glu Lys Gly Ile Phe Glu Glu Tyr
        195                 200                 205

Leu Asp Ile His Thr Lys Glu Asp Gly Ser Asp Leu Ala Met His Leu
    210                 215                 220

Gly His Ile Phe His Val Leu Asn Thr Pro Pro Glu Lys Arg Leu Lys
225                 230                 235                 240

Asn Leu Asp Glu Ser Leu Gly Gln Phe Pro Tyr Val Asn Gly Lys Leu
                245                 250                 255

Phe Glu Glu Gln Leu Ala Pro Ala Ala Phe Asp Arg Lys Met Arg Glu
            260                 265                 270

Met Leu Leu Glu Ala Cys Gly Phe Asn Trp Gly Lys Ile Ser Pro Ala
        275                 280                 285

Ile Phe Gly Ser Met Phe Gln Ala Ala Met Asp Gln Gln Thr Arg Arg
    290                 295                 300

Asn Leu Gly Ala His Tyr Thr Ser Glu Lys Asn Ile Gln Lys Val Ile
305                 310                 315                 320

Lys Pro Leu Phe Leu Asp Glu Leu His Glu Lys Phe Lys Lys Ala Lys
                325                 330                 335

Gly Ser Pro Thr Ala Leu Lys Arg Leu His Asp Glu Leu Gly Glu Leu
            340                 345                 350

His Phe Leu Asp Pro Ala Cys Gly Cys Gly Asn Phe Leu Ile Ile Ser
        355                 360                 365

Tyr Arg Glu Leu Arg Asp Leu Glu Leu Leu Ile Leu Lys Glu Leu Tyr
    370                 375                 380

Lys Lys Lys Glu Gly Phe Ile Asp Ile Arg Leu Phe Leu Lys Val Asp
385                 390                 395                 400

Val Asp Gln Phe Gly Gly Ile Glu Tyr Asp Glu Phe Pro Ala Arg Val
                405                 410                 415

Ala Glu Val Ala Met Trp Leu Ile Asp His Gln Met Asn Ile Lys Val
            420                 425                 430

Ser Asn Glu Phe Gly Gln Tyr Phe Val Arg Leu Pro Leu Lys Lys Ala
        435                 440                 445

Ala Arg Ile Val Asn Gly Asn Ala Leu Arg Ile Asp Trp Glu Glu Val
    450                 455                 460

Ile Pro Lys Glu Lys Leu Asn Tyr Ile Leu Gly Asn Pro Pro Phe Val
465                 470                 475                 480

Gly Ser Lys Met Met Thr Lys Asp Gln Arg Ala Asp Leu Leu Ser Val
                485                 490                 495

Phe Glu Ser Ala Lys Gly Ala Gly Val Met Asp Tyr Val Ser Ala Trp
            500                 505                 510

Tyr Val Lys Ala Ala Asp Phe Ile Gln Glu Lys Lys Ile Lys Thr Ala
        515                 520                 525

Phe Val Ser Thr Asn Ser Ile Ser Gln Gly Glu Gln Val Gly Ile Leu
    530                 535                 540

Trp Gly Leu Leu Phe Glu Lys Tyr Gln Ile Lys Ile His Phe Ala His
545                 550                 555                 560

Arg Thr Phe Lys Trp Ser Asn Glu Ala Lys Gly Lys Ala Ala Val Tyr
                565                 570                 575

Cys Val Ile Ile Gly Phe Ala Thr Phe Asn Ile Lys Gly Lys Arg Leu
            580                 585                 590
```

```
Phe Glu Tyr Glu Asp Ile Lys Gly Glu Ala Leu Glu Ile Lys Val Ser
        595                 600                 605

Asn Ile Asn Pro Tyr Leu Val Asn Gly Asp Asp Leu Ile Ile Leu Arg
    610                 615                 620

Arg Arg Gln Pro Leu Cys Asn Val Pro Asn Ile Gly Ile Gly Asn Lys
625                 630                 635                 640

Pro Ile Asp Gly Gly His Tyr Leu Phe Thr Thr Glu Glu Lys Glu Asp
                645                 650                 655

Phe Leu Lys Leu Glu Pro Lys Ala Glu Lys Trp Phe Arg Lys Trp Leu
            660                 665                 670

Gly Ser Arg Glu Phe Ile Asn Lys Glu Glu Arg Trp Cys Leu Trp Leu
        675                 680                 685

Gly Asp Cys Pro Pro Asn Glu Leu Lys Lys Met Pro His Ala Leu Glu
    690                 695                 700

Arg Val Lys Ala Val Lys Glu Thr Arg Leu Asn Ser Asn Ser Lys Pro
705                 710                 715                 720

Thr Gln Lys Leu Ala Gln Thr Pro Thr Arg Phe His Val Glu Asn Met
                725                 730                 735

Pro Glu Ser Glu Tyr Leu Leu Ile Pro Lys Val Ser Ser Glu Arg Arg
            740                 745                 750

Asn Tyr Ile Pro Ile Gly Phe Leu Asn Gln Ser Thr Leu Ser Ser Asp
        755                 760                 765

Leu Val Phe Ile Val Gly Asn Ala Thr Leu Phe His Phe Gly Ile Phe
    770                 775                 780

Thr Ser Val Met His Met Ala Trp Val Lys Tyr Val Cys Gly Arg Leu
785                 790                 795                 800

Lys Ser Asp Tyr Arg Tyr Ser Lys Asp Ile Val Tyr Asn Asn Phe Pro
                805                 810                 815

Phe Pro Gln Asn Val Thr Asp Lys Gln Lys Gln Thr Val Glu Lys Ala
            820                 825                 830

Ala Gln Leu Val Leu Asp Thr Arg Asp Lys Tyr Pro Asp Ser Ser Leu
        835                 840                 845

Ala Asp Leu Tyr Asp Pro Leu Thr Met Pro Pro Asp Leu Met Lys Ala
    850                 855                 860

His Gln Lys Leu Asp Lys Ala Val Asp Leu Cys Tyr Arg Pro Gln Ala
865                 870                 875                 880

Phe Thr Ser Glu Leu Asn Arg Ile Glu Phe Leu Phe Asn Glu Tyr Glu
                885                 890                 895

Lys Leu Ile Thr Pro Leu Leu Gln Ser Thr Lys Gln Lys Lys Ala Arg
            900                 905                 910

Lys Asn Lys Thr Ser
        915
```

<210> SEQ ID NO 43
<211> LENGTH: 2745
<212> TYPE: DNA
<213> ORGANISM: Agmenellum quadruplicatum PR-6

<400> SEQUENCE: 43

```
atggcagtaa cccgtgattc tctccaggcg tttgtggatt actgtaatgc ctacatccaa      60

ggggatgaga agtcagaggc acagacattt ttaacgcgat tttccaagc ctttggccat     120

gctgggatca aggaagttgg ggccgagttt gaggagcggg tcaaaaaagc gagcaagaaa     180

gataaaacag gttttgcgga tttggtctgg tcgcccgccc ctggggtaaa gggggtcgtg     240

gtggagatga aaaagcgcgg gacagatctg gcgctgcatt attctcagct cgaaaaatat     300
```

-continued

```
tggctgcggc tcaccccgaa accacgctat tcgattctct gtaattttga tgagttttgg    360
gtctatgact ttaacaacca ggtcgatgag cctgtagacc gggtcaagct agaagatctc    420
ccgaaccggg tagggacatt ttcgtttatg gagatcggtg gtcgggagcc gatctttcgg    480
aacaatcagg tcgaggtgac ggaacgcacg gccaagcgca tgggggaatt ttatcggctg    540
gtgcgatcgc ggggcgaaag ggaaaagttt gtttatttca cagaagcgca actgcaacgg    600
tttaccctgc aatgtgtgct agcgatgttt gccgaagacc ggaatctcct gccacgggat    660
ctgtttgtgg ggttggtgca ggactgttta gcggggcggg ataatgccta tgatgccttt    720
agtggtttgt ttcgggcgat gaacttgccg gggatcgtgc cccagggtcg ttacaagggg    780
gtggattatt ttaatggggg tttgtttggg gaaattcagc cgattccctt agaaaagaac    840
gagctagaaa ttctcgatgt gtgtgcgcgg gataattggg cgaatatccg accgtcgatt    900
tttggaaata tttttgagag tgccattgat gcggatgagc gccatgccag gggaattcat    960
tacacttctg agaaggatat ccggcagatt gtgcgcccga cgatcgccga ctattgggaa   1020
gggaaaatcg acgaggcgac gacctacgaa gatctcgaaa agctgaagca ggaattacgg   1080
gaatatcggg tattggatcc ggcgtgcggt tcgggaaatt tcctttatgt ggcttatcag   1140
gagttgaagc ggctggaacg ggttttgctc aacaaaatct atgagcggcg caaacggttc   1200
caggggggaag ttttacagca ggaagaaatc gggattgtga cgccgttgca gttttttggg   1260
atggatacga atccgtttgc ggtgcagttg gcgcgggtga cgatgatgat cgcccggaag   1320
attgcgattg ataagtttgg gttaactgag cctgctttgc cgttggattc tttggatcaa   1380
aatattgtct gccaagatgc gctatttaat gactggccaa aggctgacgc gattatcggc   1440
aatccgcctt ttcttggtgg ctcaagagta cgtttagagc ttggggataa atatgttgaa   1500
cgaatttttg aaaagtttc tgatgttaag gacaaagtag acttttgcgt ttattggttt   1560
cgtctagcac acgaaaatct taataaaact ggtcgagctg gtttagttgg gacaaattca   1620
attagtcaag gctttagcag aagggcaagc ttagaatata ttgtcaataa cggcggaatt   1680
attcacgatg caatctctac acaggtttgg tctggacaag cgaatgtcca cgttagcttg   1740
gttaattggc aatatttaaa gcctccagaa tatgtcttag atcatgaaat tgtcaaaaat   1800
ataaattcat ctttaaagtc tgaaacggat gtttccaatg ccgttaagct aaaagttaat   1860
ctgaatcaat ctttcaaagg tgtgcaaccc acgggaaaag actttctgat ttctgagaaa   1920
aaagtagaaa attggatcca gaaaaataca aaaaacaatc aagtcttgaa actatttgta   1980
tcagcttcag atttagccag caataaaaat ggtgaaccca gtcgatggat tattgatttt   2040
aatgattttt ctttagaaga cgcatctaca tacaaagagc cttttgatca tgttaatttt   2100
tttgttaagc ctcagcgtga aaataacaga gatcaaaaaa ctagggaata ctggtggtta   2160
tttccaagag ctaggcctgc aatgcgtcaa gcaatcgagt tactagctct ttactttgca   2220
gttcctagac attctaaatg gtttattttt attccttgta aattagattg gcttcctgct   2280
gactcaacaa ctgttgtggc ttcggatgat ttttatgtgt tgggaatttt gacatcagat   2340
gttcatcgcc aatgggtcaa agcccaaagc tcaaccctaa aggtgatac ccgctacacc    2400
cacaatacct gttttgaaac ttttcccttt ccccagacgg cgatcgcaaa actcacccaa   2460
cagatccgcc aagggatgat cgacctccac gaatatcgca ccgcccaaat ggaagccaaa   2520
caatggggga tcaccaaact ttacaacgcc tttttcgacg aacccgccag ccaactccat   2580
aaactccaca aaaagctcga tgcccttgtg ctcaaagcct acggcttcaa aaaagacgac   2640
gacattctcg aaaaactttt agacttgaac cttgccctgg ccgaaaaaga aaaaaatggc   2700
```

gaaaatatag ttggcccctg ggcgatcgat aacccaccaa aataa 2745

<210> SEQ ID NO 44
<211> LENGTH: 914
<212> TYPE: PRT
<213> ORGANISM: Agmenellum quadruplicatum PR-6

<400> SEQUENCE: 44

```
Met Ala Val Thr Arg Asp Ser Leu Gln Ala Phe Val Asp Tyr Cys Asn
1               5                   10                  15

Ala Tyr Ile Gln Gly Asp Glu Lys Ser Glu Ala Gln Thr Phe Leu Thr
            20                  25                  30

Arg Phe Phe Gln Ala Phe Gly His Ala Gly Ile Lys Glu Val Gly Ala
        35                  40                  45

Glu Phe Glu Glu Arg Val Lys Lys Ala Ser Lys Lys Asp Lys Thr Gly
    50                  55                  60

Phe Ala Asp Leu Val Trp Ser Pro Ala Pro Gly Val Lys Gly Val Val
65                  70                  75                  80

Val Glu Met Lys Lys Arg Gly Thr Asp Leu Ala Leu His Tyr Ser Gln
                85                  90                  95

Leu Glu Lys Tyr Trp Leu Arg Leu Thr Pro Lys Pro Arg Tyr Ser Ile
            100                 105                 110

Leu Cys Asn Phe Asp Glu Phe Trp Val Tyr Asp Phe Asn Asn Gln Val
        115                 120                 125

Asp Glu Pro Val Asp Arg Val Lys Leu Glu Asp Leu Pro Asn Arg Val
    130                 135                 140

Gly Thr Phe Ser Phe Met Glu Ile Gly Gly Arg Glu Pro Ile Phe Arg
145                 150                 155                 160

Asn Asn Gln Val Glu Val Thr Glu Arg Thr Ala Lys Arg Met Gly Glu
                165                 170                 175

Phe Tyr Arg Leu Val Arg Ser Arg Gly Glu Arg Glu Lys Phe Val Tyr
            180                 185                 190

Phe Thr Glu Ala Gln Leu Gln Arg Phe Thr Leu Gln Cys Val Leu Ala
        195                 200                 205

Met Phe Ala Glu Asp Arg Asn Leu Leu Pro Arg Asp Leu Phe Val Gly
    210                 215                 220

Leu Val Gln Asp Cys Leu Ala Gly Arg Asp Asn Ala Tyr Asp Ala Phe
225                 230                 235                 240

Ser Gly Leu Phe Arg Ala Met Asn Leu Pro Gly Ile Val Pro Gln Gly
                245                 250                 255

Arg Tyr Lys Gly Val Asp Tyr Phe Asn Gly Gly Leu Phe Gly Glu Ile
            260                 265                 270

Gln Pro Ile Pro Leu Glu Lys Asn Glu Leu Glu Ile Leu Asp Val Cys
        275                 280                 285

Ala Arg Asp Asn Trp Ala Asn Ile Arg Pro Ser Ile Phe Gly Asn Ile
    290                 295                 300

Phe Glu Ser Ala Ile Asp Ala Asp Glu Arg His Ala Arg Gly Ile His
305                 310                 315                 320

Tyr Thr Ser Glu Lys Asp Ile Arg Gln Ile Val Arg Pro Thr Ile Ala
                325                 330                 335

Asp Tyr Trp Glu Gly Lys Ile Asp Glu Ala Thr Thr Tyr Glu Asp Leu
            340                 345                 350

Glu Lys Leu Lys Gln Glu Leu Arg Glu Tyr Arg Val Leu Asp Pro Ala
        355                 360                 365
```

-continued

```
Cys Gly Ser Gly Asn Phe Leu Tyr Val Ala Tyr Gln Glu Leu Lys Arg
    370                 375                 380

Leu Glu Arg Val Leu Leu Asn Lys Ile Tyr Glu Arg Arg Lys Arg Phe
385                 390                 395                 400

Gln Gly Glu Val Leu Gln Gln Glu Glu Ile Gly Ile Val Thr Pro Leu
                405                 410                 415

Gln Phe Phe Gly Met Asp Thr Asn Pro Phe Ala Val Gln Leu Ala Arg
            420                 425                 430

Val Thr Met Met Ile Ala Arg Lys Ile Ala Ile Asp Lys Phe Gly Leu
        435                 440                 445

Thr Glu Pro Ala Leu Pro Leu Asp Ser Leu Asp Gln Asn Ile Val Cys
    450                 455                 460

Gln Asp Ala Leu Phe Asn Asp Trp Pro Lys Ala Asp Ala Ile Ile Gly
465                 470                 475                 480

Asn Pro Pro Phe Leu Gly Gly Ser Arg Val Arg Leu Glu Leu Gly Asp
                485                 490                 495

Lys Tyr Val Glu Arg Ile Phe Glu Lys Phe Ser Asp Val Lys Asp Lys
            500                 505                 510

Val Asp Phe Cys Val Tyr Trp Phe Arg Leu Ala His Glu Asn Leu Asn
        515                 520                 525

Lys Thr Gly Arg Ala Gly Leu Val Gly Thr Asn Ser Ile Ser Gln Gly
    530                 535                 540

Phe Ser Arg Arg Ala Ser Leu Glu Tyr Ile Val Asn Asn Gly Gly Ile
545                 550                 555                 560

Ile His Asp Ala Ile Ser Thr Gln Val Trp Ser Gly Gln Ala Asn Val
                565                 570                 575

His Val Ser Leu Val Asn Trp Gln Tyr Leu Lys Pro Pro Glu Tyr Val
            580                 585                 590

Leu Asp His Glu Ile Val Lys Asn Ile Asn Ser Ser Leu Lys Ser Glu
        595                 600                 605

Thr Asp Val Ser Asn Ala Val Lys Leu Lys Val Asn Leu Asn Gln Ser
    610                 615                 620

Phe Lys Gly Val Gln Pro Thr Gly Lys Asp Phe Leu Ile Ser Glu Lys
625                 630                 635                 640

Lys Val Glu Asn Trp Ile Gln Lys Asn Thr Lys Asn Asn Gln Val Leu
                645                 650                 655

Lys Leu Phe Val Ser Ala Ser Asp Leu Ala Ser Asn Lys Asn Gly Glu
            660                 665                 670

Pro Ser Arg Trp Ile Ile Asp Phe Asn Asp Phe Ser Leu Glu Asp Ala
        675                 680                 685

Ser Thr Tyr Lys Glu Pro Phe Asp His Val Asn Phe Phe Val Lys Pro
    690                 695                 700

Gln Arg Glu Asn Asn Arg Asp Gln Lys Thr Arg Glu Tyr Trp Trp Leu
705                 710                 715                 720

Phe Pro Arg Ala Arg Pro Ala Met Arg Gln Ala Ile Glu Leu Leu Ala
                725                 730                 735

Leu Tyr Phe Ala Val Pro Arg His Ser Lys Trp Phe Ile Phe Ile Pro
            740                 745                 750

Cys Lys Leu Asp Trp Leu Pro Ala Asp Ser Thr Thr Val Val Ala Ser
        755                 760                 765

Asp Asp Phe Tyr Val Leu Gly Ile Leu Thr Ser Asp Val His Arg Gln
    770                 775                 780

Trp Val Lys Ala Gln Ser Ser Thr Leu Lys Gly Asp Thr Arg Tyr Thr
785                 790                 795                 800
```

His Asn Thr Cys Phe Glu Thr Phe Pro Phe Pro Gln Thr Ala Ile Ala
805 810 815

Lys Leu Thr Gln Gln Ile Arg Gln Gly Met Ile Asp Leu His Glu Tyr
820 825 830

Arg Thr Ala Gln Met Glu Ala Lys Gln Trp Gly Ile Thr Lys Leu Tyr
835 840 845

Asn Ala Phe Phe Asp Glu Pro Ala Ser Gln Leu His Lys Leu His Lys
850 855 860

Lys Leu Asp Ala Leu Val Leu Lys Ala Tyr Gly Phe Lys Lys Asp Asp
865 870 875 880

Asp Ile Leu Glu Lys Leu Leu Asp Leu Asn Leu Ala Leu Ala Glu Lys
885 890 895

Glu Lys Asn Gly Glu Asn Ile Val Gly Pro Trp Ala Ile Asp Asn Pro
900 905 910

Pro Lys

<210> SEQ ID NO 45
<211> LENGTH: 36
<212> TYPE: PRT
<213> ORGANISM: Methylophilus methylotrophus
<220> FEATURE:
<221> NAME/KEY: MISC_FEATURE
<222> LOCATION: (1)..(36)
<223> OTHER INFORMATION: 1-36 correspond to 788-823 of seq id no. 2

<400> SEQUENCE: 45

Leu Leu Ser Ser Thr Met His Asn Cys Trp Met Arg Asn Val Gly Gly
1 5 10 15

Arg Leu Glu Ser Arg Tyr Arg Tyr Ser Ala Ser Leu Val Tyr Asn Thr
20 25 30

Phe Pro Trp Ile
35

<210> SEQ ID NO 46
<211> LENGTH: 36
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(36)
<223> OTHER INFORMATION: 1-36 corresponds to 798-833 of seq id no. 4

<400> SEQUENCE: 46

Val Leu Asn Ser Thr Met His Met Ala Trp Thr Arg Ala Val Cys Gly
1 5 10 15

Arg Leu Glu Ser Arg Tyr Gln Tyr Ser Val Thr Ile Val Tyr Asn Asn
20 25 30

Phe Pro Trp Pro
35

<210> SEQ ID NO 47
<211> LENGTH: 36
<212> TYPE: PRT
<213> ORGANISM: Arcanobacterium pyogenes
<220> FEATURE:
<221> NAME/KEY: MISC_FEATURE
<222> LOCATION: (1)..(36)
<223> OTHER INFORMATION: 1-36 correspond to 830-865 of seq id no. 18

<400> SEQUENCE: 47

```
Leu Ile Ser Ser Ser Met Phe Ile Thr Trp Gln Lys Met Ile Gly Gly
1               5                   10                  15

Arg Leu Glu Ser Arg Leu Arg Phe Ala Asn Thr Leu Thr Trp Asn Thr
            20                  25                  30

Phe Pro Val Pro
        35


<210> SEQ ID NO 48
<211> LENGTH: 36
<212> TYPE: PRT
<213> ORGANISM: Neisseria lactamica ST640
<220> FEATURE:
<221> NAME/KEY: MISC_FEATURE
<222> LOCATION: (1)..(36)
<223> OTHER INFORMATION: 1-36 correspond to 824-859 of seq id no. 8

<400> SEQUENCE: 48

Ile Leu Ser Ser Thr Met His Asn Ala Phe Met Arg Thr Val Ala Gly
1               5                   10                  15

Arg Leu Glu Ser Arg Tyr Gln Tyr Ser Ala Ser Ile Val Tyr Asn Asn
            20                  25                  30

Phe Pro Phe Pro
        35


<210> SEQ ID NO 49
<211> LENGTH: 36
<212> TYPE: PRT
<213> ORGANISM: Deinococcus radiodurans
<220> FEATURE:
<221> NAME/KEY: MISC_FEATURE
<222> LOCATION: (1)..(36)
<223> OTHER INFORMATION: 1-36 correspond to 898-933 of seq id no. 36

<400> SEQUENCE: 49

Val Leu Ser Ser Arg Val His Val Thr Trp Ala Leu Ala Gln Gly Gly
1               5                   10                  15

Thr Leu Glu Asp Arg Pro Arg Tyr Asn Lys Thr Arg Cys Phe Glu Thr
            20                  25                  30

Phe Pro Phe Pro
        35


<210> SEQ ID NO 50
<211> LENGTH: 36
<212> TYPE: PRT
<213> ORGANISM: Rhodopseudomonas palustris BisB5
<220> FEATURE:
<221> NAME/KEY: MISC_FEATURE
<222> LOCATION: (1)..(36)
<223> OTHER INFORMATION: 1-36 correspond to 878-913 of seq id no. 26

<400> SEQUENCE: 50

Val Leu Ser Ser Arg Leu His Val Arg Trp Ser Leu Ser Lys Gly Gly
1               5                   10                  15

Thr Leu Glu Asp Arg Pro Arg Tyr Asn Asn Ser Met Cys Phe Asp Pro
            20                  25                  30

Phe Pro Phe Pro
        35


<210> SEQ ID NO 51
<211> LENGTH: 36
<212> TYPE: PRT
<213> ORGANISM: Deinococcus radiophilus R1
<220> FEATURE:
<221> NAME/KEY: MISC_FEATURE
<222> LOCATION: (1)..(36)
```

<223> OTHER INFORMATION: 1-36 correspond to 805-840 of seq id no. 22

<400> SEQUENCE: 51

Val Ile Gln Ser Ser Val His Trp Gln Trp Leu Ile Ala Arg Gly Gly
1 5 10 15

Thr Leu Thr Ala Arg Leu Met Tyr Thr Ser Asp Thr Val Phe Asp Thr
20 25 30

Phe Pro Trp Pro
35

<210> SEQ ID NO 52
<211> LENGTH: 36
<212> TYPE: PRT
<213> ORGANISM: Marinobacter aquaeolei VT8
<220> FEATURE:
<221> NAME/KEY: MISC_FEATURE
<222> LOCATION: (1)..(36)
<223> OTHER INFORMATION: 1-36 correspond to 882-917 of seq id no. 38

<400> SEQUENCE: 52

Val Leu Ser Ser Arg Val His Val Leu Trp Ser Leu Phe Ala Gly Gly
1 5 10 15

Thr Leu Glu Asn Arg Pro Arg Tyr Asn Lys Thr Leu Cys Phe Glu Thr
20 25 30

Phe Pro Phe Pro
35

<210> SEQ ID NO 53
<211> LENGTH: 36
<212> TYPE: PRT
<213> ORGANISM: Nitrobacter hamburgensis X14
<220> FEATURE:
<221> NAME/KEY: MISC_FEATURE
<222> LOCATION: (1)..(36)
<223> OTHER INFORMATION: 1-36 correspond to 815-850 of seq id no. 24

<400> SEQUENCE: 53

Ile Leu Gln Ser Gly Ile His Trp Glu Trp Phe Ile Asn Arg Cys Ser
1 5 10 15

Thr Leu Lys Ala Asp Phe Arg Tyr Thr Ser Asp Thr Val Phe Asp Ser
20 25 30

Phe Pro Trp Pro
35

<210> SEQ ID NO 54
<211> LENGTH: 36
<212> TYPE: PRT
<213> ORGANISM: Neisseria meningitidis Z2491
<220> FEATURE:
<221> NAME/KEY: MISC_FEATURE
<222> LOCATION: (1)..(36)
<223> OTHER INFORMATION: 1-36 correspond to 798-833 of seq id no. 14

<400> SEQUENCE: 54

Ile Leu Ser Ser Thr Met His Asn Ala Phe Met Arg Thr Val Ala Gly
1 5 10 15

Arg Leu Lys Ser Asp Tyr Arg Tyr Ser Asn Thr Val Val Tyr Asn Asn
20 25 30

Phe Pro Phe Pro
35

<210> SEQ ID NO 55
<211> LENGTH: 36
<212> TYPE: PRT

<213> ORGANISM: Corynebacterium diphtheriae
<220> FEATURE:
<221> NAME/KEY: MISC_FEATURE
<222> LOCATION: (1)..(36)
<223> OTHER INFORMATION: 1-36 correspond to 807-842 of seq id no. 16

<400> SEQUENCE: 55

Val Leu Val Ser Gln Phe Gln Asn Ala Trp Met Arg Val Val Ala Gly
1               5                   10                  15

Arg Leu Lys Ser Asp Tyr Arg Tyr Gly Asn Thr Thr Val Tyr Asn Asn
            20                  25                  30

Phe Val Phe Pro
        35

<210> SEQ ID NO 56
<211> LENGTH: 36
<212> TYPE: PRT
<213> ORGANISM: Agmenellum quadruplicatum PR-6
<220> FEATURE:
<221> NAME/KEY: MISC_FEATURE
<222> LOCATION: (1)..(36)
<223> OTHER INFORMATION: 1-36 correspond to 807-842 of seq id no. 42

<400> SEQUENCE: 56

Ile Phe Thr Ser Val Met His Met Ala Trp Val Lys Tyr Val Cys Gly
1               5                   10                  15

Arg Leu Lys Ser Asp Tyr Arg Tyr Ser Lys Asp Ile Val Tyr Asn Asn
            20                  25                  30

Phe Pro Phe Pro
        35

<210> SEQ ID NO 57
<211> LENGTH: 36
<212> TYPE: PRT
<213> ORGANISM: Corynebacterium striatum M82B
<220> FEATURE:
<221> NAME/KEY: MISC_FEATURE
<222> LOCATION: (1)..(36)
<223> OTHER INFORMATION: 1-36 correspond to 832-867 of seq id no. 12

<400> SEQUENCE: 57

Leu Ala Ser Ser Ser Met Phe Ile Thr Trp Gln Lys Ser Ile Gly Gly
1               5                   10                  15

Arg Leu Lys Ser Asp Leu Arg Phe Ala Asn Thr Leu Thr Trp Asn Thr
            20                  25                  30

Phe Pro Val Pro
        35

<210> SEQ ID NO 58
<211> LENGTH: 36
<212> TYPE: PRT
<213> ORGANISM: Sulfurimonas denitrificans
<220> FEATURE:
<221> NAME/KEY: MISC_FEATURE
<222> LOCATION: (1)..(36)
<223> OTHER INFORMATION: 1-36 correspond to 773-808 of seq id no. 6

<400> SEQUENCE: 58

Ile Leu Thr Ser Lys Met His Met Asp Trp Val Arg Tyr Val Ala Gly
1               5                   10                  15

Arg Leu Lys Ser Asp Tyr Arg Tyr Ser Asn Glu Ile Val Tyr Asn Asn
            20                  25                  30

Phe Pro Phe Pro
        35

<210> SEQ ID NO 59
<211> LENGTH: 36
<212> TYPE: PRT
<213> ORGANISM: Psychrobacter sp. PRwf-1
<220> FEATURE:
<221> NAME/KEY: MISC_FEATURE
<222> LOCATION: (1)..(36)
<223> OTHER INFORMATION: 1-36 correspond to 804-839 of seq id no. 10

<400> SEQUENCE: 59

```
Thr Leu Ser Ser Ser Met His Asn Ala Phe Met Arg Leu Thr Ala Gly
1               5                   10                  15

Arg Met Lys Ser Asp Tyr Ser Tyr Ser Ser Thr Ile Val Tyr Asn Asn
            20                  25                  30

Phe Pro Tyr Pro
        35
```

<210> SEQ ID NO 60
<211> LENGTH: 36
<212> TYPE: PRT
<213> ORGANISM: Parvibaculum lavamentivorans DS-1
<220> FEATURE:
<221> NAME/KEY: MISC_FEATURE
<222> LOCATION: (1)..(36)
<223> OTHER INFORMATION: 1-36 correspond to 786-831 of seq id no. 40

<400> SEQUENCE: 60

```
Leu Leu Thr Ser Gly Met His Met Ala Trp Met Arg Ala Ile Thr Gly
1               5                   10                  15

Arg Met Lys Ser Asp Tyr Met Tyr Ser Val Gly Val Val Tyr Asn Thr
            20                  25                  30

Phe Pro Trp Pro
        35
```

<210> SEQ ID NO 61
<211> LENGTH: 38
<212> TYPE: PRT
<213> ORGANISM: Silicibacter pomeroyi DSS-3
<220> FEATURE:
<221> NAME/KEY: MISC_FEATURE
<222> LOCATION: (1)..(36)
<223> OTHER INFORMATION: 1-36 correspond to 797-835 of seq id no. 20

<400> SEQUENCE: 61

```
Ile Leu His Ser Ser Phe His Glu Leu Trp Ser Leu Arg Met Gly Thr
1               5                   10                  15

Phe Leu Gly Val Gly Asn Asp Pro Arg Tyr Thr Pro Ser Thr Thr Phe
            20                  25                  30

Glu Thr Phe Pro Phe Pro
        35
```

<210> SEQ ID NO 62
<211> LENGTH: 36
<212> TYPE: PRT
<213> ORGANISM: Agmenellum quadruplicatum PR-6
<220> FEATURE:
<221> NAME/KEY: MISC_FEATURE
<222> LOCATION: (1)..(36)
<223> OTHER INFORMATION: 1-36 correspond to 776-811 of seq id no. 44

<400> SEQUENCE: 62

```
Ile Leu Thr Ser Asp Val His Arg Gln Trp Val Lys Ala Gln Ser Ser
1               5                   10                  15

Thr Leu Lys Gly Asp Thr Arg Tyr Thr His Asn Thr Cys Phe Glu Thr
            20                  25                  30
```

```
Phe Pro Phe Pro
        35


<210> SEQ ID NO 63
<211> LENGTH: 39
<212> TYPE: PRT
<213> ORGANISM: Pseudomonas species OM2164
<220> FEATURE:
<221> NAME/KEY: MISC_FEATURE
<222> LOCATION: (1)..(39)
<223> OTHER INFORMATION: 1-39 correspond to 912-950 of seq id no. 34

<400> SEQUENCE: 63

Ile Val Ser Ser Arg Ile His Trp Val Trp Ala Ile Ala Asn Ala Ala
1               5                   10                  15

Lys Ile Gly Met Tyr Asp Gly Asp Ala Val Tyr Pro Lys Gly Gln Cys
            20                  25                  30

Phe Asp Pro Phe Pro Phe Pro
        35


<210> SEQ ID NO 64
<211> LENGTH: 79
<212> TYPE: PRT
<213> ORGANISM: Agmenellum quadruplicatum PR-6
<220> FEATURE:
<221> NAME/KEY: MISC_FEATURE
<222> LOCATION: (1)..(79)
<223> OTHER INFORMATION: 1-79 correspond to 740-818 of seq id no. 42

<400> SEQUENCE: 64

Glu Tyr Leu Leu Ile Pro Lys Val Ser Ser Glu Arg Arg Asn Tyr Ile
1               5                   10                  15

Pro Ile Gly Phe Leu Asn Gln Ser Thr Leu Ser Ser Asp Leu Val Phe
            20                  25                  30

Ile Val Gly Asn Ala Thr Leu Phe His Phe Gly Ile Phe Thr Ser Val
        35                  40                  45

Met His Met Ala Trp Val Lys Tyr Val Cys Gly Arg Leu Lys Ser Asp
    50                  55                  60

Tyr Arg Tyr Ser Lys Asp Ile Val Tyr Asn Asn Phe Pro Phe Pro
65                  70                  75


<210> SEQ ID NO 65
<211> LENGTH: 79
<212> TYPE: PRT
<213> ORGANISM: Sulfurimonas denitrificans
<220> FEATURE:
<221> NAME/KEY: MISC_FEATURE
<222> LOCATION: (1)..(79)
<223> OTHER INFORMATION: 1-79 correspond to 730-808 of seq id no. 6

<400> SEQUENCE: 65

Asp Tyr Ile Phe Ile Pro Arg Val Ser Ser Glu Asn Arg Asp Tyr Ile
1               5                   10                  15

Pro Met Glu Phe Phe Thr Lys Asp Phe Ile Cys Gly Asp Thr Gly Leu
            20                  25                  30

Ala Val Pro Asn Ala Thr Leu Phe His Phe Gly Ile Leu Thr Ser Lys
        35                  40                  45

Met His Met Asp Trp Val Arg Tyr Val Ala Gly Arg Leu Lys Ser Asp
    50                  55                  60

Tyr Arg Tyr Ser Asn Glu Ile Val Tyr Asn Asn Phe Pro Phe Pro
65                  70                  75
```

<210> SEQ ID NO 66
<211> LENGTH: 79
<212> TYPE: PRT
<213> ORGANISM: Psychrobacter sp. PRwf-1
<220> FEATURE:
<221> NAME/KEY: MISC_FEATURE
<222> LOCATION: (1)..(79)
<223> OTHER INFORMATION: 1-79 correspond to 761-839 of seq id no. 10

<400> SEQUENCE: 66

```
Pro Tyr Val Ala Ile Pro Val Val Ser Ser Glu Asn Arg Arg Phe Ile
1               5                   10                  15

Pro Ile Gly Phe Ile Asp Gly Asn Thr Val Ala Gly Asn Lys Leu Phe
            20                  25                  30

Val Ile Val Asp Gly Asn Thr Tyr Gln Phe Gly Thr Leu Ser Ser Ser
        35                  40                  45

Met His Asn Ala Phe Met Arg Leu Thr Ala Gly Arg Met Lys Ser Asp
    50                  55                  60

Tyr Ser Tyr Ser Ser Thr Ile Val Tyr Asn Asn Phe Pro Tyr Pro
65                  70                  75
```

<210> SEQ ID NO 67
<211> LENGTH: 79
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(79)
<223> OTHER INFORMATION: 1-79 correspond to 761-839 of seq id no. 4

<400> SEQUENCE: 67

```
Pro Phe Met Val Ile Pro Glu Val Ser Ser Glu Arg Arg Glu Phe Ile
1               5                   10                  15

Pro Leu Gly Tyr Leu Gln Pro Pro Thr Leu Ala Ser Asn Lys Leu Arg
            20                  25                  30

Leu Met Pro Asp Ala Thr Leu Tyr His Phe Ala Val Leu Asn Ser Thr
        35                  40                  45

Met His Met Ala Trp Thr Arg Ala Val Cys Gly Arg Leu Glu Ser Arg
    50                  55                  60

Tyr Gln Tyr Ser Val Thr Ile Val Tyr Asn Asn Phe Pro Trp Pro
65                  70                  75
```

<210> SEQ ID NO 68
<211> LENGTH: 79
<212> TYPE: PRT
<213> ORGANISM: Methylophilus methylotrophus
<220> FEATURE:
<221> NAME/KEY: MISC_FEATURE
<222> LOCATION: (1)..(79)
<223> OTHER INFORMATION: 1-79 correspond to 745-823 of seq idi no. 2

<400> SEQUENCE: 68

```
Asp Tyr Leu Leu Ile Pro Glu Thr Ser Ser Glu Asn Arg Gln Phe Ile
1               5                   10                  15

Pro Ile Gly Phe Val Asp Arg Asn Val Ile Ser Ser Asn Ala Thr Tyr
            20                  25                  30

His Ile Pro Ser Ala Glu Pro Leu Ile Phe Gly Leu Leu Ser Ser Thr
        35                  40                  45

Met His Asn Cys Trp Met Arg Asn Val Gly Gly Arg Leu Glu Ser Arg
    50                  55                  60

Tyr Arg Tyr Ser Ala Ser Leu Val Tyr Asn Thr Phe Pro Trp Ile
```

65 70 75

<210> SEQ ID NO 69
<211> LENGTH: 79
<212> TYPE: PRT
<213> ORGANISM: Parvibaculum lavamentivorans DS-1
<220> FEATURE:
<221> NAME/KEY: MISC_FEATURE
<222> LOCATION: (1)..(79)
<223> OTHER INFORMATION: 1-79 correspond to 753-831 of seq id no. 40

<400> SEQUENCE: 69

Pro Tyr Leu Val Ile Pro Asn Thr Ser Ser Glu Arg Arg Asp Tyr Val
1 5 10 15

Pro Ile Gly Trp Leu Thr Pro Glu Val Val Ala Asn Gln Lys Leu Arg
20 25 30

Ile Leu Pro Asp Ala Asp Pro Trp Ile Phe Gly Leu Leu Thr Ser Gly
35 40 45

Met His Met Ala Trp Met Arg Ala Ile Thr Gly Arg Met Lys Ser Asp
50 55 60

Tyr Met Tyr Ser Val Gly Val Val Tyr Asn Thr Phe Pro Trp Pro
65 70 75

<210> SEQ ID NO 70
<211> LENGTH: 79
<212> TYPE: PRT
<213> ORGANISM: Neisseria lactamica ST640
<220> FEATURE:
<221> NAME/KEY: MISC_FEATURE
<222> LOCATION: (1)..(79)
<223> OTHER INFORMATION: 1-79 correspond to 781-859 of seq id no. 8

<400> SEQUENCE: 70

Arg Tyr Leu Leu Leu Pro Lys Val Ser Ser Glu Asn Arg Arg Phe Leu
1 5 10 15

Pro Ile Gly Tyr Ile Glu Pro Glu Thr Ile Ala Asn Gly Ser Ala Leu
20 25 30

Ile Ile Pro Asn Ala Thr Leu Cys His Phe Gly Ile Leu Ser Ser Thr
35 40 45

Met His Asn Ala Phe Met Arg Thr Val Ala Gly Arg Leu Glu Ser Arg
50 55 60

Tyr Gln Tyr Ser Ala Ser Ile Val Tyr Asn Asn Phe Pro Phe Pro
65 70 75

<210> SEQ ID NO 71
<211> LENGTH: 79
<212> TYPE: PRT
<213> ORGANISM: Neisseria meningitidis Z2491
<220> FEATURE:
<221> NAME/KEY: MISC_FEATURE
<222> LOCATION: (1)..(79)
<223> OTHER INFORMATION: 1-79 correspond to 755-833 of seq id no. 14

<400> SEQUENCE: 71

Asn Tyr Leu Ile Ile Pro Ser Val Ser Ser Glu Ser Arg Arg Phe Ile
1 5 10 15

Pro Ile Gly Tyr Leu Ser Phe Glu Thr Val Val Ser Asn Leu Ala Phe
20 25 30

Ile Leu Pro Asn Ala Thr Leu Tyr His Phe Gly Ile Leu Ser Ser Thr
35 40 45

Met His Asn Ala Phe Met Arg Thr Val Ala Gly Arg Leu Lys Ser Asp
50 55 60

Tyr Arg Tyr Ser Asn Thr Val Val Tyr Asn Asn Phe Pro Phe Pro
65 70 75

<210> SEQ ID NO 72
<211> LENGTH: 79
<212> TYPE: PRT
<213> ORGANISM: Arcanobacterium pyogenes
<220> FEATURE:
<221> NAME/KEY: MISC_FEATURE
<223> OTHER INFORMATION: 1-79 correspond to 787-865 of seq id no. 18

<400> SEQUENCE: 72

Asp Phe Leu Cys Val Pro Ser Val Val Ser Glu Asn Arg Pro Tyr Phe
1 5 10 15

Thr Ala Ala Asp Ile Glu Glu Gly Thr Val Val Ser Ser Leu Ala Phe
20 25 30

Ala Val Glu Asp Ser Asp Arg Ser Gln Phe Ala Leu Ile Ser Ser Ser
35 40 45

Met Phe Ile Thr Trp Gln Lys Met Ile Gly Gly Arg Leu Glu Ser Arg
50 55 60

Leu Arg Phe Ala Asn Thr Leu Thr Trp Asn Thr Phe Pro Val Pro
65 70 75

<210> SEQ ID NO 73
<211> LENGTH: 79
<212> TYPE: PRT
<213> ORGANISM: Corynebacterium striatum M82B
<220> FEATURE:
<221> NAME/KEY: MISC_FEATURE
<222> LOCATION: (1)..(79)
<223> OTHER INFORMATION: 1-79 correspond to 789-867 of seq id no. 12

<400> SEQUENCE: 73

Asp Tyr Leu Cys Leu Pro Lys Val Val Ser Glu Arg Arg Ser Tyr Phe
1 5 10 15

Thr Val Gln Arg Tyr Pro Ser Asn Val Ile Ala Ser Asp Leu Val Phe
20 25 30

His Ala Gln Asp Pro Asp Gly Leu Met Phe Ala Leu Ala Ser Ser Ser
35 40 45

Met Phe Ile Thr Trp Gln Lys Ser Ile Gly Gly Arg Leu Lys Ser Asp
50 55 60

Leu Arg Phe Ala Asn Thr Leu Thr Trp Asn Thr Phe Pro Val Pro
65 70 75

<210> SEQ ID NO 74
<211> LENGTH: 79
<212> TYPE: PRT
<213> ORGANISM: Corynebacterium diphtheriae
<220> FEATURE:
<221> NAME/KEY: MISC_FEATURE
<222> LOCATION: (1)..(79)
<223> OTHER INFORMATION: 1-79 correspond to 764-842 of seq id no. 16

<400> SEQUENCE: 74

Thr Tyr Ile Gly Ile Pro Lys Val Ser Ser Glu Arg Arg Lys Tyr Val
1 5 10 15

Pro Phe Ala Phe Val Thr Asp Gly Met Ile Pro Gly Asp Met Leu Tyr
20 25 30

Phe Val Pro Thr Asp Ser Leu Phe Val Phe Gly Val Leu Val Ser Gln
35 40 45

Phe Gln Asn Ala Trp Met Arg Val Val Ala Gly Arg Leu Lys Ser Asp
50 55 60

-continued

```
Tyr Arg Tyr Gly Asn Thr Thr Val Tyr Asn Asn Phe Val Phe Pro
65                  70                  75


<210> SEQ ID NO 75
<211> LENGTH: 75
<212> TYPE: PRT
<213> ORGANISM: Rhodopseudomonas palustris BisB5
<220> FEATURE:
<221> NAME/KEY: MISC_FEATURE
<222> LOCATION: (1)..(75)
<223> OTHER INFORMATION: 1-75 correspond to 839-913

<400> SEQUENCE: 75

Arg Tyr Ile Gly Thr Ala Arg Thr Ala Lys His Arg Ile Phe Ser Met
1               5                   10                  15

Leu Ala Gly His Ser Leu Pro Glu Ser Glu Val Ile Ala Val Gly Ser
            20                  25                  30

Asp Asp Ala Phe Ile Leu Gly Val Leu Ser Ser Arg Leu His Val Arg
        35                  40                  45

Trp Ser Leu Ser Lys Gly Gly Thr Leu Glu Asp Arg Pro Arg Tyr Asn
    50                  55                  60

Asn Ser Met Cys Phe Asp Pro Phe Pro Phe Pro
65                  70                  75


<210> SEQ ID NO 76
<211> LENGTH: 78
<212> TYPE: PRT
<213> ORGANISM: Pseudomonas species OM2164
<220> FEATURE:
<221> NAME/KEY: MISC_FEATURE
<222> LOCATION: (1)..(78)
<223> OTHER INFORMATION: 1-78 correspond to 873-950 of seq id no. 34

<400> SEQUENCE: 76

Arg Tyr Ile Ala Thr Val Glu Thr Ala Lys His Arg Ile Phe Ser Leu
1               5                   10                  15

Leu Asp Ala Thr Ile Leu Pro Asp Asn Lys Leu Ile Ile Ile Ala Leu
            20                  25                  30

Ala Asp Thr Trp His Phe Ser Ile Val Ser Ser Arg Ile His Trp Val
        35                  40                  45

Trp Ala Ile Ala Asn Ala Ala Lys Ile Gly Met Tyr Asp Gly Asp Ala
    50                  55                  60

Val Tyr Pro Lys Gly Gln Cys Phe Asp Pro Phe Pro Phe Pro
65                  70                  75


<210> SEQ ID NO 77
<211> LENGTH: 75
<212> TYPE: PRT
<213> ORGANISM: Marinobacter aquaeolei VT8
<220> FEATURE:
<221> NAME/KEY: MISC_FEATURE
<222> LOCATION: (1)..(75)
<223> OTHER INFORMATION: 1-75 correspond to 843-917 of seq id no. 38

<400> SEQUENCE: 77

Thr Ala Ile Ala Thr Ser Leu Thr Ala Lys His Arg Val Phe Val His
1               5                   10                  15

Leu Asp Ser Asn Ser Ile Cys Asp Ser Thr Thr Val Met Phe Ala Leu
            20                  25                  30

Pro Gly Ala Gln Tyr Leu Gly Val Leu Ser Ser Arg Val His Val Leu
        35                  40                  45

Trp Ser Leu Phe Ala Gly Gly Thr Leu Glu Asn Arg Pro Arg Tyr Asn
    50                  55                  60
```

Lys Thr Leu Cys Phe Glu Thr Phe Pro Phe Pro
65 70 75

<210> SEQ ID NO 78
<211> LENGTH: 75
<212> TYPE: PRT
<213> ORGANISM: Deinococcus radiodurans
<220> FEATURE:
<221> NAME/KEY: MISC_FEATURE
<222> LOCATION: (1)..(75)
<223> OTHER INFORMATION: 1-75 correspond to 859-933 of seq id no. 36

<400> SEQUENCE: 78

Arg Tyr Val Val Thr Leu Glu Thr Ala Lys His Gln Val Phe Gln Phe
1 5 10 15

Leu Asp Ser Ser Ile Val Pro Asp Ser Thr Ile Val Thr Phe Gly Thr
20 25 30

Glu Asp Ala Phe His Leu Gly Val Leu Ser Ser Arg Val His Val Thr
35 40 45

Trp Ala Leu Ala Gln Gly Gly Thr Leu Glu Asp Arg Pro Arg Tyr Asn
50 55 60

Lys Thr Arg Cys Phe Glu Thr Phe Pro Phe Pro
65 70 75

<210> SEQ ID NO 79
<211> LENGTH: 77
<212> TYPE: PRT
<213> ORGANISM: Silicibacter pomeroyi DSS-3
<220> FEATURE:
<221> NAME/KEY: MISC_FEATURE
<222> LOCATION: (1)..(77)
<223> OTHER INFORMATION: 1-77 corresponds to 758-834 of seq id no. 20

<400> SEQUENCE: 79

Arg Phe Ile Val Thr Pro Arg Val Gly Lys His Arg Ile Phe Val Trp
1 5 10 15

Leu Asp Ser Asn Ala Leu Ala Asp Ser Ala Thr Phe Ile Val Ala Arg
20 25 30

Asp Asp Glu Thr Thr Phe Gly Ile Leu His Ser Ser Phe His Glu Leu
35 40 45

Trp Ser Leu Arg Met Gly Thr Phe Leu Gly Val Gly Asn Asp Pro Arg
50 55 60

Tyr Thr Pro Ser Thr Thr Phe Glu Thr Phe Pro Phe Pro
65 70 75

<210> SEQ ID NO 80
<211> LENGTH: 75
<212> TYPE: PRT
<213> ORGANISM: Agmenellum quadruplicatum PR-6
<220> FEATURE:
<221> NAME/KEY: MISC_FEATURE
<222> LOCATION: (1)..(75)
<223> OTHER INFORMATION: 1-75 correspond to 737-811 of seq id no. 44

<400> SEQUENCE: 80

Leu Tyr Phe Ala Val Pro Arg His Ser Lys Trp Phe Ile Phe Ile Pro
1 5 10 15

Cys Lys Leu Asp Trp Leu Pro Ala Asp Ser Thr Thr Val Val Ala Ser
20 25 30

Asp Asp Phe Tyr Val Leu Gly Ile Leu Thr Ser Asp Val His Arg Gln
35 40 45

Trp Val Lys Ala Gln Ser Ser Thr Leu Lys Gly Asp Thr Arg Tyr Thr 50 55 60

His Asn Thr Cys Phe Glu Thr Phe Pro Phe Pro
65 70 75

<210> SEQ ID NO 81
<211> LENGTH: 75
<212> TYPE: PRT
<213> ORGANISM: Nitrobacter hamburgensis X14
<220> FEATURE:
<221> NAME/KEY: MISC_FEATURE
<222> LOCATION: (1)..(75)
<223> OTHER INFORMATION: 1-75 correspond to 776-850 of seq id no. 24

<400> SEQUENCE: 81

Arg Tyr Ile Val Cys Ala Arg Val Thr His Arg Pro Ile Phe Glu Phe
1 5 10 15

Val Ser Thr Ala Ile His Pro Asn Asp Ala Leu Ser Val Phe Ala Leu
20 25 30

Glu Asp Asp Tyr Ser Phe Gly Ile Leu Gln Ser Gly Ile His Trp Glu
35 40 45

Trp Phe Ile Asn Arg Cys Ser Thr Leu Lys Ala Asp Phe Arg Tyr Thr
50 55 60

Ser Asp Thr Val Phe Asp Ser Phe Pro Trp Pro
65 70 75

<210> SEQ ID NO 82
<211> LENGTH: 75
<212> TYPE: PRT
<213> ORGANISM: Deinococcus radiophilus R1
<220> FEATURE:
<221> NAME/KEY: MISC_FEATURE
<222> LOCATION: (1)..(75)
<223> OTHER INFORMATION: 1-75 correspond to 766-840 of seq id no. 22

<400> SEQUENCE: 82

Arg Tyr Ile Val Cys Ser Arg Val Thr Lys Arg Gln Val Phe Glu Phe
1 5 10 15

Leu Asp Asn Gly Ile Arg Pro Ser Asp Gly Leu Gln Ile Phe Ala Phe
20 25 30

Glu Asp Asp Tyr Ser Phe Gly Val Ile Gln Ser Ser Val His Trp Gln
35 40 45

Trp Leu Ile Ala Arg Gly Gly Thr Leu Thr Ala Arg Leu Met Tyr Thr
50 55 60

Ser Asp Thr Val Phe Asp Thr Phe Pro Trp Pro
65 70 75

<210> SEQ ID NO 83
<211> LENGTH: 48
<212> TYPE: PRT
<213> ORGANISM: Bacillus stearothermophilus LV
<220> FEATURE:
<221> NAME/KEY: MISC_FEATURE
<222> LOCATION: (1)..(48)
<223> OTHER INFORMATION: 1-48 corresponds to 434-481 of the protein
M.BstLVI

<400> SEQUENCE: 83

Tyr Glu Ile Trp Val Pro His Asp Pro Ser Leu Trp Asp Lys Pro Lys
1 5 10 15

Ile Ile Phe Pro Asp Ile Ser Pro Glu Pro Lys Phe Phe Tyr Glu Asp
20 25 30

Lys Gly Ser Val Val Asp Gly Asn Cys Tyr Trp Ile Ile Pro Lys Lys
35 40 45

<210> SEQ ID NO 84
<211> LENGTH: 48
<212> TYPE: PRT
<213> ORGANISM: Bacillus aneurinolyticus
<220> FEATURE:
<221> NAME/KEY: MISC_FEATURE
<222> LOCATION: (1)..(48)
<223> OTHER INFORMATION: 1-48 correspond to 437-484 of the protein
M.BanIII

<400> SEQUENCE: 84

```
Tyr Gln Ile Trp Leu Pro Gln Asn Pro Asp His Trp Ala Leu Pro Lys
1               5                   10                  15

Ile Leu Phe Pro Asp Ile Ser Pro Glu Pro Lys Phe Phe Tyr Glu Asp
            20                  25                  30

Glu Gly Cys Cys Ile Asp Gly Asn Cys Tyr Trp Ile Ile Pro Lys Glu
        35                  40                  45
```

<210> SEQ ID NO 85
<211> LENGTH: 48
<212> TYPE: PRT
<213> ORGANISM: Bacillus stearothermophilus V
<220> FEATURE:
<221> NAME/KEY: MISC_FEATURE
<222> LOCATION: (1)..(48)
<223> OTHER INFORMATION: 1-48 correspond to 422-469 of the protein
M.BstVI

<400> SEQUENCE: 85

```
Phe Arg Thr Ile Asp Arg Ile Tyr Pro Glu Ile Val His Gln Pro Lys
1               5                   10                  15

Leu Leu Ile Pro Asp Met Lys Asn Thr Asn His Ile Val Lys Asp Asp
            20                  25                  30

Gly Ala Phe Tyr Pro His His Asn Leu Tyr Tyr Ile Leu Pro Gly Asn
        35                  40                  45
```

<210> SEQ ID NO 86
<211> LENGTH: 48
<212> TYPE: PRT
<213> ORGANISM: Xanthomonas holcicola
<220> FEATURE:
<221> NAME/KEY: MISC_FEATURE
<222> LOCATION: (1)..(48)
<223> OTHER INFORMATION: 1-48 correspond to 434-481 of the protein
M.XhoI

<400> SEQUENCE: 86

```
Phe Arg Thr Ile Asp Arg Ile Tyr Pro Ala Leu Ala Lys Thr Pro Lys
1               5                   10                  15

Leu Leu Val Pro Asp Ile Lys Gly Asp Ala His Ile Val Tyr Glu Glu
            20                  25                  30

Gly Lys Leu Tyr Pro His His Asn Leu Tyr Phe Ile Thr Ala Asn Glu
        35                  40                  45
```

<210> SEQ ID NO 87
<211> LENGTH: 48
<212> TYPE: PRT
<213> ORGANISM: Pseudomonas aeruginosa
<220> FEATURE:
<221> NAME/KEY: MISC_FEATURE
<222> LOCATION: (1)..(48)
<223> OTHER INFORMATION: 1-48 correspond to 392-439 of the protein
M.PaeR7I

<400> SEQUENCE: 87

Tyr Arg Thr Ile Asp Arg Ile Thr Pro Ala Leu Ala Ala Arg Pro Lys
1 5 10 15

Leu Leu Ile Pro Asp Ile Lys Gly Glu Ser His Ile Val Phe Glu Gly
20 25 30

Gly Glu Leu Tyr Pro Ser His Asn Leu Tyr Tyr Val Thr Ser Asp Asp
35 40 45

<210> SEQ ID NO 88
<211> LENGTH: 43
<212> TYPE: PRT
<213> ORGANISM: Xanthomonas amaranthicola
<220> FEATURE:
<221> NAME/KEY: MISC_FEATURE
<222> LOCATION: (1)..(43)
<223> OTHER INFORMATION: 1-43 correspond to 434-476 of the protein M.XamI

<400> SEQUENCE: 88

Trp Ser Val Gly Leu Lys Ala Pro Ala Pro Ile Leu Cys Thr Tyr Met
1 5 10 15

Ala Arg Arg Pro Pro Gln Phe Thr Leu Asn Ala Cys Asp Ala Arg His
20 25 30

Ile Asn Ile Ala His Gly Leu Tyr Pro Arg Glu
35 40

<210> SEQ ID NO 89
<211> LENGTH: 43
<212> TYPE: PRT
<213> ORGANISM: Acinetobacter calcoaceticus SRW4
<220> FEATURE:
<221> NAME/KEY: MISC_FEATURE
<222> LOCATION: (1)..(43)
<223> OTHER INFORMATION: 1-43 correspond to 384-426 of the protein M.AcuI

<400> SEQUENCE: 89

Phe Val Ile Pro Ser Ile Lys Leu Ser Asp Ala Leu Phe Ile Arg Arg
1 5 10 15

Asn Asn Leu Phe Pro Arg Leu Ile Leu Asn Glu Ala Gln Ala Tyr Thr
20 25 30

Thr Asp Thr Met His Arg Val Phe Ile Lys Gln
35 40

<210> SEQ ID NO 90
<211> LENGTH: 47
<212> TYPE: PRT
<213> ORGANISM: Xanthomonas campestris pv. vesicatoria
<220> FEATURE:
<221> NAME/KEY: MISC_FEATURE
<222> LOCATION: (1)..(47)
<223> OTHER INFORMATION: 1-47 correspond to 476-522 of the protein M.XveI

<400> SEQUENCE: 90

Lys Pro Cys Val Leu Leu Gln Arg Thr Thr Ala Lys Glu Gln Ala Arg
1 5 10 15

Arg Leu Ile Ala Ala Glu Met Pro Ala Ser Phe Ile Lys Arg His Ala
20 25 30

Gly Val Thr Ile Glu Asn His Leu Asn Met Met Ile Pro Thr Val
35 40 45

<210> SEQ ID NO 91
<211> LENGTH: 48
<212> TYPE: PRT
<213> ORGANISM: Bacillus subtilis
<220> FEATURE:
<221> NAME/KEY: MISC_FEATURE
<222> LOCATION: (1)..(48)
<223> OTHER INFORMATION: 1-48 correspond to 371-418 of the protein M.BsuBI

<400> SEQUENCE: 91

Pro Asn Gly His Tyr Val Val Val Lys Arg Phe Ser Ser Lys Glu Glu
1 5 10 15

Lys Arg Arg Ile Val Ala Gly Val Leu Thr Pro Glu Ser Val Asn Asp
20 25 30

Pro Val Val Gly Phe Glu Asn Gly Leu Asn Val Leu His Tyr Asn Lys
35 40 45

<210> SEQ ID NO 92
<211> LENGTH: 48
<212> TYPE: PRT
<213> ORGANISM: Providencia stuartii 164
<220> FEATURE:
<221> NAME/KEY: MISC_FEATURE
<222> LOCATION: (1)..(48)
<223> OTHER INFORMATION: 1-48 correspond to 383-430 of the protein M.PstI

<400> SEQUENCE: 92

Pro Asn Gly Ile Tyr Val Leu Thr Arg Arg Leu Thr Ala Lys Glu Glu
1 5 10 15

Lys Arg Arg Ile Val Ala Ser Ile Tyr Tyr Pro Asp Ile Ala Asn Val
20 25 30

Asp Thr Val Gly Phe Asp Asn Lys Ile Asn Tyr Phe His Ala Asn Gly
35 40 45

<210> SEQ ID NO 93
<211> LENGTH: 47
<212> TYPE: PRT
<213> ORGANISM: Rhizobium leguminosarum VF39SM
<220> FEATURE:
<221> NAME/KEY: MISC_FEATURE
<222> LOCATION: (1)..(47)
<223> OTHER INFORMATION: 1-47 correspond to 478-524 of the protein M.Rle39B

<400> SEQUENCE: 93

Val Pro Cys Val Leu Leu Gln Arg Thr Thr Ser Lys Glu Gln Ala Arg
1 5 10 15

Arg Leu Ile Ala Ala Glu Leu Pro Glu Ala Phe Ile Lys Ala His Gly
20 25 30

Arg Val Ile Val Glu Asn His Leu Asn Met Val Lys Pro Thr Ala
35 40 45

<210> SEQ ID NO 94
<211> LENGTH: 47
<212> TYPE: PRT
<213> ORGANISM: Xanthomonas phaseoli
<220> FEATURE:
<221> NAME/KEY: MISC_FEATURE
<222> LOCATION: (1)..(47)
<223> OTHER INFORMATION: 1-47 correspond to 475-521 of the protein M.XphI

<400> SEQUENCE: 94

Lys Pro Cys Val Leu Leu Gln Arg Thr Thr Ala Lys Glu Gln Ala Arg
1 5 10 15

Arg Leu Ile Ala Ala Glu Met Pro Ala Ser Phe Ile Lys Arg His Ala
20 25 30

```
Gly Val Thr Ile Glu Asn His Leu Asn Met Met Ile Pro Thr Val
        35                  40                  45


<210> SEQ ID NO 95
<211> LENGTH: 43
<212> TYPE: PRT
<213> ORGANISM: Bacillus pumilus
<220> FEATURE:
<221> NAME/KEY: MISC_FEATURE
<222> LOCATION: (1)..(43)
<223> OTHER INFORMATION: 1-43 correspond to 398-440 of the protein
      M.BpmI

<400> SEQUENCE: 95

Tyr Ile Thr Pro Ser Arg Trp Val Pro Asp Ala Phe Ala Leu Arg Gln
1               5                   10                  15

Val Asp Gly Tyr Pro Lys Leu Ile Leu Asn Glu Thr Asp Ala Ser Ser
            20                  25                  30

Thr Asp Thr Ile His Arg Val Arg Phe Lys Glu
        35                  40


<210> SEQ ID NO 96
<211> LENGTH: 48
<212> TYPE: PRT
<213> ORGANISM: Bacillus species R
<220> FEATURE:
<221> NAME/KEY: MISC_FEATURE
<222> LOCATION: (1)..(48)
<223> OTHER INFORMATION: 1-48 correspond to 533-580 of the protein
      M.BseRI

<400> SEQUENCE: 96

Tyr Met Leu Pro Arg Leu Thr Gly Arg His Lys Ser Glu Leu Phe Ile
1               5                   10                  15

Pro Arg Ile Asn Asn Leu His Pro Lys Thr Leu Leu Asn Ser Asn Asn
            20                  25                  30

Thr Val Ile Asp Ala Asn Phe Ser Thr Leu Trp Val Asn Lys Glu Thr
        35                  40                  45


<210> SEQ ID NO 97
<211> LENGTH: 36
<212> TYPE: PRT
<213> ORGANISM: Vibrio species 343
<220> FEATURE:
<221> NAME/KEY: MISC_FEATURE
<222> LOCATION: (1)..(36)
<223> OTHER INFORMATION: 1-36 correspond to 434-469 of the protein
      M.VspI

<400> SEQUENCE: 97

Ala Glu Glu Lys Leu Ile Tyr Lys Phe Ile Ser Ser Glu Leu Val Phe
1               5                   10                  15

Phe His Asp Thr Lys Lys Arg Phe Ile Leu Asn Ser Ala Asn Met Leu
            20                  25                  30

Val Leu Gln Asp
        35


<210> SEQ ID NO 98
<211> LENGTH: 47
<212> TYPE: PRT
<213> ORGANISM: Streptococcus faecalis
<220> FEATURE:
<221> NAME/KEY: MISC_FEATURE
<222> LOCATION: (1)..(47)
<223> OTHER INFORMATION: 1-47 correspond to 505-551 of the protein
      M.SfeI
```

<400> SEQUENCE: 98

Tyr Glu Tyr Gly Arg Ser Gln Ala Leu Asn Ser His Val Pro Lys Ile
1 5 10 15

Ile Phe Pro Thr Asn Ser Leu Asn Pro Asn Phe Val Tyr Phe Thr Asp
20 25 30

Tyr Ala Leu Phe Asn Asn Gly Tyr Ala Ile Tyr Gly Val Asn Asn
35 40 45

<210> SEQ ID NO 99
<211> LENGTH: 43
<212> TYPE: PRT
<213> ORGANISM: Acinetobacter calcoaceticus
<220> FEATURE:
<221> NAME/KEY: MISC_FEATURE
<222> LOCATION: (1)..(43)
<223> OTHER INFORMATION: 1-43 correspond to 397-439 of the protein M.AccI

<400> SEQUENCE: 99

Tyr Ser Leu Glu Asn Arg Lys Pro Ala Pro Ile Trp Val Ser Val Phe
1 5 10 15

Asn Arg Ser Gly Leu Arg Phe Ile Arg Asn Glu Ala Asn Ile Ser Asn
20 25 30

Leu Thr Ser Tyr His Cys Ile Ile Gln Asn Lys
35 40

<210> SEQ ID NO 100
<211> LENGTH: 67
<212> TYPE: PRT
<213> ORGANISM: Arcanobacterium pyogenes
<220> FEATURE:
<221> NAME/KEY: MISC_FEATURE
<222> LOCATION: (1)..(67)
<223> OTHER INFORMATION: 1-67 are a portion of the amino acid sequence of the protein ApyPI

<400> SEQUENCE: 100

Asp Ile Glu Glu Gly Thr Val Val Ser Ser Leu Ala Phe Ala Val Glu
1 5 10 15

Asp Ser Asp Arg Ser Gln Phe Ala Leu Ile Ser Ser Ser Met Phe Ile
20 25 30

Thr Trp Gln Lys Met Ile Gly Gly Arg Leu Glu Ser Arg Leu Arg Phe
35 40 45

Ala Asn Thr Leu Thr Trp Asn Thr Phe Pro Val Pro Glu Leu Asp Glu
50 55 60

Lys Thr Arg
65

<210> SEQ ID NO 101
<211> LENGTH: 66
<212> TYPE: PRT
<213> ORGANISM: Neisseria meningitidis Z2491
<220> FEATURE:
<221> NAME/KEY: MISC_FEATURE
<222> LOCATION: (1)..(66)
<223> OTHER INFORMATION: 1-66 are a portion of the amino acid sequence of the protein NmeAIII

<400> SEQUENCE: 101

Tyr Leu Ser Phe Glu Thr Val Val Ser Asn Leu Ala Phe Ile Leu Pro
1 5 10 15

Asn Ala Thr Leu Tyr His Phe Gly Ile Leu Ser Ser Thr Met His Asn
20 25 30

Ala Phe Met Arg Thr Val Ala Gly Arg Leu Lys Ser Asp Tyr Arg Tyr
35 40 45

Ser Asn Thr Val Val Tyr Asn Asn Phe Pro Phe Pro Glu Ser Cys Arg
50 55 60

Leu Pro
65

<210> SEQ ID NO 102
<211> LENGTH: 67
<212> TYPE: PRT
<213> ORGANISM: Neisseria lactamica ST640
<220> FEATURE:
<221> NAME/KEY: MISC_FEATURE
<222> LOCATION: (1)..(67)
<223> OTHER INFORMATION: 1-67 are a portion of the amino acid sequence of the protein NlaCI

<400> SEQUENCE: 102

Tyr Ile Glu Pro Glu Thr Ile Ala Asn Gly Ser Ala Leu Ile Ile Pro
1 5 10 15

Asn Ala Thr Leu Cys His Phe Gly Ile Leu Ser Ser Thr Met His Asn
20 25 30

Ala Phe Met Arg Thr Val Ala Gly Arg Leu Glu Ser Arg Tyr Gln Tyr
35 40 45

Ser Ala Ser Ile Val Tyr Asn Asn Phe Pro Phe Pro Glu Asn Pro Cys
50 55 60

Arg Thr Ala
65

<210> SEQ ID NO 103
<211> LENGTH: 67
<212> TYPE: PRT
<213> ORGANISM: Sulfurimonas denitrificans
<220> FEATURE:
<221> NAME/KEY: MISC_FEATURE
<222> LOCATION: (1)..(67)
<223> OTHER INFORMATION: 1-67 aer a portion of the amino acid sequence of the protein SdeAI

<400> SEQUENCE: 103

Phe Phe Thr Lys Asp Phe Ile Cys Gly Asp Thr Gly Leu Ala Val Pro
1 5 10 15

Asn Ala Thr Leu Phe His Phe Gly Ile Leu Thr Ser Lys Met His Met
20 25 30

Asp Trp Val Arg Tyr Val Ala Gly Arg Leu Lys Ser Asp Tyr Arg Tyr
35 40 45

Ser Asn Glu Ile Val Tyr Asn Asn Phe Pro Phe Pro Leu Glu Ile Asn
50 55 60

Asp Lys Gln
65

<210> SEQ ID NO 104
<211> LENGTH: 67
<212> TYPE: PRT
<213> ORGANISM: Chlorobium chlorochromatii CaD3
<220> FEATURE:
<221> NAME/KEY: MISC_FEATURE
<222> LOCATION: (1)..(67)
<223> OTHER INFORMATION: 1-67 are a portion of the amino acid sequence of the protein CchORF1309P

<400> SEQUENCE: 104

Tyr Phe Ser Lys Asp Asn Ile Leu His Asn Ser Cys Ser Ala Val Pro
1 5 10 15

Asn Ala Thr Leu Tyr His Phe Gly Ile Leu Thr Ser Thr Met His Met
20 25 30

Val Trp Met Arg Thr Val Cys Gly Arg Ile Lys Ser Asp Tyr Arg Tyr
35 40 45

Ser Asn Asn Leu Val Tyr Asn Asn Phe Leu Phe Pro His Asp Ile Ser
50 55 60

Asn Lys Gln
65

<210> SEQ ID NO 105
<211> LENGTH: 67
<212> TYPE: PRT
<213> ORGANISM: Gramella forsetii KT0803
<220> FEATURE:
<221> NAME/KEY: MISC_FEATURE
<222> LOCATION: (1)..(67)
<223> OTHER INFORMATION: 1-67 are a portion of the amino acid sequence of the protein GfoORF257P

<400> SEQUENCE: 105

Tyr Leu Pro Lys Glu Val Ile Val Ser Asp Ser Ala Ile Ala Leu Pro
1 5 10 15

Glu Ala Asn Leu Phe Thr Phe Gly Ile Leu Asn Ser Leu Met His Met
20 25 30

Met Trp Met Asn Tyr Thr Cys Gly Arg Leu Lys Ser Asp Phe Arg Tyr
35 40 45

Ser Asn Thr Leu Val Tyr Asn Asn Phe Pro Phe Pro Gln Glu Val Asn
50 55 60

Gln Asn Ser
65

<210> SEQ ID NO 106
<211> LENGTH: 66
<212> TYPE: PRT
<213> ORGANISM: Methylophilus methylotrophus
<220> FEATURE:
<221> NAME/KEY: MISC_FEATURE
<222> LOCATION: (1)..(66)
<223> OTHER INFORMATION: 1-66 are a portion of the amino acid sequence of the protein MmeI

<400> SEQUENCE: 106

Phe Val Asp Arg Asn Val Ile Ser Ser Asn Ala Thr Tyr His Ile Pro
1 5 10 15

Ser Ala Glu Pro Leu Ile Phe Gly Leu Leu Ser Ser Thr Met His Asn
20 25 30

Cys Trp Met Arg Asn Val Gly Gly Arg Leu Glu Ser Arg Tyr Arg Tyr
35 40 45

Ser Ala Ser Leu Val Tyr Asn Thr Phe Pro Trp Ile Gln Pro Asn Glu
50 55 60

Lys Gln
65

<210> SEQ ID NO 107
<211> LENGTH: 67
<212> TYPE: PRT
<213> ORGANISM: Leptospira biflexa phage LE1
<220> FEATURE:
<221> NAME/KEY: MISC_FEATURE
<222> LOCATION: (1)..(67)
<223> OTHER INFORMATION: 1-67 are a portion of the amino acid sequence of the protein LbiLE1ORFAP

<400> SEQUENCE: 107

Phe Leu Ser Ser Asn Val Ile Ala Ala Asn Asp Leu Gln Ile Val Pro
1               5                   10                  15

Asn Cys Asp Leu Tyr Thr Phe Ala Phe Leu Thr Ser Arg Ile His Asn
            20                  25                  30

Asn Trp Thr Ser Leu Thr Ser Gly Arg Leu Lys Ser Asp Ile Arg Tyr
        35                  40                  45

Ser Val Lys Leu Ser Tyr Asn Asn Phe Pro Trp Pro Glu Asn Pro Ser
    50                  55                  60

Asp Lys Gln
65

<210> SEQ ID NO 108
<211> LENGTH: 67
<212> TYPE: PRT
<213> ORGANISM: Psychrobacter sp. PRwf-1
<220> FEATURE:
<221> NAME/KEY: MISC_FEATURE
<222> LOCATION: (1)..(67)
<223> OTHER INFORMATION: 1-67 are a portion of the amino acid sequence of the protein PsPPRI

<400> SEQUENCE: 108

Phe Ile Asp Gly Asn Thr Val Ala Gly Asn Lys Leu Glu Val Ile Val
1               5                   10                  15

Asp Gly Asn Thr Tyr Gln Phe Gly Thr Leu Ser Ser Ser Met His Asn
            20                  25                  30

Ala Phe Met Arg Leu Thr Ala Gly Arg Met Lys Ser Asp Tyr Ser Tyr
        35                  40                  45

Ser Ser Thr Ile Val Tyr Asn Asn Phe Pro Tyr Pro Phe Met Ala Asp
    50                  55                  60

Asp His Ser
65

<210> SEQ ID NO 109
<211> LENGTH: 66
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(66)
<223> OTHER INFORMATION: 1-66 are a portion of the amino acid sequence of the protein EsaSSI

<400> SEQUENCE: 109

Tyr Leu Gln Pro Pro Thr Leu Ala Ser Asn Lys Leu Arg Leu Met Pro
1               5                   10                  15

Asp Ala Thr Leu Tyr His Phe Ala Val Leu Asn Ser Thr Met His Met
            20                  25                  30

Ala Trp Thr Arg Ala Val Cys Gly Arg Leu Glu Ser Arg Tyr Gln Tyr
        35                  40                  45

Ser Val Thr Ile Val Tyr Asn Asn Phe Pro Trp Pro Ser Pro Ser Asp
    50                  55                  60

Ala Gln
65

<210> SEQ ID NO 110
<211> LENGTH: 67
<212> TYPE: PRT
<213> ORGANISM: Lactobacillus acidophilus NCFM
<220> FEATURE:
<221> NAME/KEY: MISC_FEATURE
<222> LOCATION: (1)..(67)
<223> OTHER INFORMATION: 1-67 are a portion of the amino acid sequence
of the protein LacORF332P

<400> SEQUENCE: 110

```
Tyr Val Ser Lys Asp Val Ile Val Asn Asn Gly Ala Ser Phe Val Pro
1               5                   10                  15

Asp Ala Ser Leu Tyr Asp Leu Gly Val Leu Thr Ser Asn Met His Met
            20                  25                  30

Ala Trp Met Arg Thr Val Cys Gly Tyr Phe Gly Pro Ser Tyr Arg Tyr
        35                  40                  45

Ser Asn Arg Ile Val Tyr Asn Asn Phe Pro Trp Pro Ser Ala Thr Asp
    50                  55                  60

Lys Gln Lys
65
```

<210> SEQ ID NO 111
<211> LENGTH: 67
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(67)
<223> OTHER INFORMATION: 1-67 are a portion of the amino acid sequence
of the protein Esa_s8_162537P

<400> SEQUENCE: 111

```
Phe Leu Asp Asn Asn Thr Ile Ser Thr Asp Leu Asn Phe Ile Ile Pro
1               5                   10                  15

Glu Ala Thr Met Tyr His Phe Ala Ile Leu Thr Ser Asn Ile His Met
            20                  25                  30

Ala Trp Met Arg Ala Val Cys Gly Arg Met Lys Ser Asp Tyr Arg Tyr
        35                  40                  45

Ser Ala Asn Ile Val Tyr Asn Asn Phe Pro Trp Pro Thr Pro Thr Glu
    50                  55                  60

Gln Gln Lys
65
```

<210> SEQ ID NO 112
<211> LENGTH: 67
<212> TYPE: PRT
<213> ORGANISM: Lactobacillus fermentum
<220> FEATURE:
<221> NAME/KEY: MISC_FEATURE
<222> LOCATION: (1)..(67)
<223> OTHER INFORMATION: 1-67 are a portion of the amino acid sequence
of the protein LfeLORF4P

<400> SEQUENCE: 112

```
Tyr Leu Gly Asn Asp Ile Ile Pro Thr Asn Leu Ala Thr Ile Ile Pro
1               5                   10                  15

Glu Ala Asp His Tyr Ala Phe Gly Val Leu Glu Ser Ile Val His Met
            20                  25                  30

Ala Trp Met Arg Val Val Ala Gly Arg Lys Gly Thr Ser Tyr Arg Tyr
        35                  40                  45

Ser Lys Asn Leu Val Tyr Thr Asn Phe Pro Trp Pro Val Val Asp Ile
    50                  55                  60

Asn Gln Lys
65
```

<210> SEQ ID NO 113
<211> LENGTH: 67
<212> TYPE: PRT
<213> ORGANISM: Corynebacterium diphtheriae
<220> FEATURE:
<221> NAME/KEY: MISC_FEATURE
<222> LOCATION: (1)..(67)
<223> OTHER INFORMATION: 1-67 are a portion of the amino acid sequence
of the protein CdpI

<400> SEQUENCE: 113

```
Phe Val Thr Asp Gly Met Ile Pro Gly Asp Met Leu Tyr Phe Val Pro
1               5                   10                  15

Thr Asp Ser Leu Phe Val Phe Gly Val Leu Val Ser Gln Phe Gln Asn
            20                  25                  30

Ala Trp Met Arg Val Val Ala Gly Arg Leu Lys Ser Asp Tyr Arg Tyr
        35                  40                  45

Gly Asn Thr Thr Val Tyr Asn Asn Phe Val Phe Pro Glu Val Asp Asp
    50                  55                  60

Ser Val Arg
65
```

<210> SEQ ID NO 114
<211> LENGTH: 66
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(66)
<223> OTHER INFORMATION: 1-66 are a portion of the amino acid sequence
of the protein Esa_s8_179382.1P

<400> SEQUENCE: 114

```
Phe Val Pro Glu Ile Phe Cys Ser Asn Lys Val Arg Leu Ile Pro Asn
1               5                   10                  15

Ala Ser Leu Tyr His Tyr Gly Ile Leu Gln Ser Gln Phe His Asn Ala
            20                  25                  30

Trp Val Arg Ile Val Thr Gly Arg Leu Lys Asp Asp Tyr Gln Tyr Ser
        35                  40                  45

Ala Asn Ile Asp Tyr Asn Asn Phe Val Trp Pro Glu Pro Thr Glu Ser
    50                  55                  60

Gln Arg
65
```

<210> SEQ ID NO 115
<211> LENGTH: 67
<212> TYPE: PRT
<213> ORGANISM: Chlorobium chlorochromatii CaD3
<220> FEATURE:
<221> NAME/KEY: MISC_FEATURE
<222> LOCATION: (1)..(67)
<223> OTHER INFORMATION: 1-67 are a portion of the amino acid sequence
of the protein CchORF759P

<400> SEQUENCE: 115

```
Phe Leu Ser Ser Asn Ile Ile Ile Ser Asp Ala Ala Gln Ala Ile Tyr
1               5                   10                  15

Glu Ala Lys Pro Trp Val Phe Gly Ile Ile Ser Ser Arg Met His Met
            20                  25                  30

Thr Trp Val Arg Ala Val Ala Gly Arg Leu Lys Ser Asp Tyr Arg Tyr
        35                  40                  45
```

Ser Ser Ala Ile Cys Tyr Asn Thr Phe Pro Phe Pro Pro Ile Thr Glu
50 55 60

Thr Gln Lys
65

<210> SEQ ID NO 116
<211> LENGTH: 67
<212> TYPE: PRT
<213> ORGANISM: Moraxella osloensis
<220> FEATURE:
<221> NAME/KEY: MISC_FEATURE
<222> LOCATION: (1)..(67)
<223> OTHER INFORMATION: 1-67 are a portion of the amino acid sequence of the protein MslORFHP

<400> SEQUENCE: 116

Phe Tyr Gly Lys Asp Phe Lys Ala Ser Asp Ser Asn Leu Ile Val Ala
1 5 10 15

Thr Ser Glu Ala Tyr Leu Phe Gly Ile Leu His Ser Lys Met His Met
20 25 30

Val Trp Val Asp Ala Val Gly Gly Lys Leu Lys Thr Asp Tyr Arg Tyr
35 40 45

Ser Ala Lys Leu Cys Tyr Asn Thr Phe Pro Phe Pro Asp Ile Thr Ala
50 55 60

Lys Gln Lys
65

<210> SEQ ID NO 117
<211> LENGTH: 67
<212> TYPE: PRT
<213> ORGANISM: Bacillus subtilis 168
<220> FEATURE:
<221> NAME/KEY: MISC_FEATURE
<222> LOCATION: (1)..(67)
<223> OTHER INFORMATION: 1-67 aa are a portion of the amino acid sequence of the protein BsuMORF677P

<400> SEQUENCE: 117

Leu Ala Gly Ala Asp Thr Ile Leu Ser Asn Leu Ile Tyr Val Ile Tyr
1 5 10 15

Asp Ala Glu Ile Tyr Leu Leu Gly Ile Leu Met Ser Arg Met His Met
20 25 30

Thr Trp Val Lys Ala Val Ala Gly Arg Leu Lys Thr Asp Tyr Arg Tyr
35 40 45

Ser Ala Gly Leu Cys Tyr Asn Thr Phe Pro Ile Pro Glu Leu Ser Thr
50 55 60

Arg Arg Lys
65

<210> SEQ ID NO 118
<211> LENGTH: 67
<212> TYPE: PRT
<213> ORGANISM: nitrosococcus oceani
<220> FEATURE:
<221> NAME/KEY: MISC_FEATURE
<222> LOCATION: (1)..(67)
<223> OTHER INFORMATION: 1-67 aa are a portion fo the amino acid sequence of the protein NocAORF28P

<400> SEQUENCE: 118

Ile Phe Glu Glu Asp Val Ile Ala Thr Asn Leu Thr Leu Ile Ile Pro
1 5 10 15

Asp Ala Gly Leu Tyr Asp Phe Ala Ile Leu Ser Thr Gln Met His Met

```
        20                  25                  30

Asp Trp Leu Arg Leu Val Gly Gly Arg Leu Glu Ser Arg Tyr Arg Tyr
        35                  40                  45

Ser Ala Thr Ile Val Tyr Asn Thr Phe Pro Trp Pro Asn Ala Thr Glu
    50                  55                  60

Ala Gln Arg
65


<210> SEQ ID NO 119
<211> LENGTH: 67
<212> TYPE: PRT
<213> ORGANISM: nitrosococcus oceani
<220> FEATURE:
<221> NAME/KEY: MISC_FEATURE
<222> LOCATION: (1)..(67)
<223> OTHER INFORMATION: 1-67 aa are a portion of the amino acid
      sequence of the protein NocAORF1465P

<400> SEQUENCE: 119

Phe Tyr Gly Val Asp Thr Ile Ser Ser Asp Ala Asn Gln Met Val Pro
1               5                   10                  15

Asn Ala Thr Pro Tyr Glu Phe Gly Ile Leu Thr Ser Glu Met His Asn
            20                  25                  30

Asp Trp Met Arg Thr Val Ala Gly Arg Leu Lys Ser Asp Tyr Arg Tyr
        35                  40                  45

Ser Ala Thr Leu Val Tyr Asn Thr Phe Pro Trp Pro Glu Val Thr Asp
    50                  55                  60

Glu Gln Arg
65


<210> SEQ ID NO 120
<211> LENGTH: 67
<212> TYPE: PRT
<213> ORGANISM: Bordetella parapertussis 12822
<220> FEATURE:
<221> NAME/KEY: MISC_FEATURE
<222> LOCATION: (1)..(67)
<223> OTHER INFORMATION: 1-67 aa are a portion of the amino acid
      sequence of the protein BpaORF1261P

<400> SEQUENCE: 120

Leu Ile Pro Ala Gly Asp Ile Ile Thr Asp Leu Asn Phe Gly Leu Phe
1               5                   10                  15

Asp Ala Glu Leu Trp Asn Ala Ser Ile Leu Met Ser Lys Leu His Ile
            20                  25                  30

Val Trp Ile Ala Thr Val Cys Gly Lys Met Lys Ser Asp Phe Arg Tyr
        35                  40                  45

Ser Asn Leu Met Gly Trp Asn Thr Phe Pro Val Pro Thr Leu Thr Glu
    50                  55                  60

Lys Asn Lys
65


<210> SEQ ID NO 121
<211> LENGTH: 67
<212> TYPE: PRT
<213> ORGANISM: Xanthomonas campestris pv. vesicatoria str. 85-10
<220> FEATURE:
<221> NAME/KEY: MISC_FEATURE
<222> LOCATION: (1)..(67)
<223> OTHER INFORMATION: 1-67 aa are a portion of the amino acid
      sequence of the protein XcaVORF2165P

<400> SEQUENCE: 121
```

```
Tyr Glu Pro Ala Gly Thr Val Val Ser Asn Leu Ala Phe Ala Leu Tyr
1               5                   10                  15

Asp Ala Pro Leu Trp Asn Met Ala Leu Ile Ala Ser Arg Leu His Leu
            20                  25                  30

Val Trp Ile Ala Ser Val Cys Gly Lys Met Lys Thr Asp Phe Arg Tyr
        35                  40                  45

Ser Asn Thr Leu Gly Trp Asn Thr Phe Pro Val Pro Thr Leu Thr Glu
    50                  55                  60

Lys Asn Lys
65


<210> SEQ ID NO 122
<211> LENGTH: 66
<212> TYPE: PRT
<213> ORGANISM: Granulibacter bethesdensis CGDNIH1
<220> FEATURE:
<221> NAME/KEY: MISC_FEATURE
<222> LOCATION: (1)..(66)
<223> OTHER INFORMATION: 1-66 aa are a portion of the amino acid
      sequence of the protein GbeORF1515P

<400> SEQUENCE: 122

Leu Leu Pro Pro Arg Ser Ile Val Thr Glu Ala Phe Ala Leu Tyr Asp
1               5                   10                  15

Ala Pro Leu Trp Asn Met Ala Leu Ile Ala Ser Arg Leu His Leu Val
            20                  25                  30

Trp Ile Ala Thr Val Cys Gly Lys Leu Glu Thr Arg Tyr Arg Tyr Ser
        35                  40                  45

Asn Thr Leu Gly Trp Asn Thr Phe Pro Val Pro Thr Leu Thr Glu Lys
    50                  55                  60

Asn Lys
65


<210> SEQ ID NO 123
<211> LENGTH: 67
<212> TYPE: PRT
<213> ORGANISM: Novosphingobium aromaticivorans DSM 12444
<220> FEATURE:
<221> NAME/KEY: MISC_FEATURE
<222> LOCATION: (1)..(67)
<223> OTHER INFORMATION: 1-67 aa are a portion of the amino acid
      sequence of the protein NarDORF261P

<400> SEQUENCE: 123

Leu Lys Ser Ser Gly Phe Val Ser Ser His Thr Ala Tyr Met Ile Tyr
1               5                   10                  15

Gly Trp His Pro Val Glu Phe Ala Leu Leu Asn Ser Arg Leu Met Leu
            20                  25                  30

Val Trp Thr Glu Thr Val Gly Gly Arg Leu Gly Asn Gly Met Arg Phe
        35                  40                  45

Ser Asn Thr Ile Val Tyr Asn Thr Phe Pro Val Pro Ser Leu Thr Asp
    50                  55                  60

Gln Asn Lys
65


<210> SEQ ID NO 124
<211> LENGTH: 67
<212> TYPE: PRT
<213> ORGANISM: Xanthomonas campestris pv. campestris str. 8004
<220> FEATURE:
<221> NAME/KEY: MISC_FEATURE
<222> LOCATION: (1)..(67)
<223> OTHER INFORMATION: 1-67 aa are a portion of the amino acid
```

sequence of the protein Xca8004ORF2076P

<400> SEQUENCE: 124

Leu Leu Ser Lys Glu Ala Ile Val His Asn Lys Ala Phe Ala Leu Tyr
1 5 10 15

Asp Ala Pro Leu Trp Asn Phe Ala Leu Ile Val Ser Lys Met His Leu
20 25 30

Val Trp Val Ala Ala Val Cys Val Arg Leu Glu Met Arg Tyr Ser Tyr
35 40 45

Ser Asn Thr Leu Gly Trp Asn Thr Phe Pro Val Pro Thr Leu Thr Glu
50 55 60

Gln Asn Lys
65

<210> SEQ ID NO 125
<211> LENGTH: 67
<212> TYPE: PRT
<213> ORGANISM: prochlorococcus marinus SS120
<220> FEATURE:
<221> NAME/KEY: MISC_FEATURE
<222> LOCATION: (1)..(67)
<223> OTHER INFORMATION: 1-67 aa are a portion of the amino acid
sequence of the protein PmaSSORF630P

<400> SEQUENCE: 125

Ile Ala Glu Asn Gly Ile Ile Ile Gly Asp Arg Asn Phe Ala Ile His
1 5 10 15

Asp Ala Pro Leu Trp Asn Ile Ala Ile Ile Ser Ser Arg Leu His Trp
20 25 30

Leu Trp Ile Ala Thr Val Cys Val Arg Met Arg Thr Asp Phe Ser Tyr
35 40 45

Ser Asn Thr Leu Gly Trp Asn Thr Phe Tyr Val Pro Lys Leu Thr Glu
50 55 60

Lys Asn Met
65

<210> SEQ ID NO 126
<211> LENGTH: 69
<212> TYPE: PRT
<213> ORGANISM: Silicibacter pomeroyi DSS-3
<220> FEATURE:
<221> NAME/KEY: MISC_FEATURE
<222> LOCATION: (1)..(69)
<223> OTHER INFORMATION: 1-69 aa are a portion of the amino acid
sequence of the protein SpoDI

<400> SEQUENCE: 126

Trp Leu Asp Ser Asn Ala Leu Ala Asp Ser Ala Thr Phe Ile Val Ala
1 5 10 15

Arg Asp Asp Glu Thr Thr Phe Gly Ile Leu His Ser Ser Phe His Glu
20 25 30

Leu Trp Ser Leu Arg Met Gly Thr Phe Leu Gly Val Gly Asn Asp Pro
35 40 45

Arg Tyr Thr Pro Ser Thr Thr Phe Glu Thr Phe Pro Phe Pro Glu Gly
50 55 60

Leu Thr Pro Asn Ile
65

<210> SEQ ID NO 127
<211> LENGTH: 67
<212> TYPE: PRT
<213> ORGANISM: Azoarus sp. EbN1

```
<220> FEATURE:
<221> NAME/KEY: MISC_FEATURE
<222> LOCATION: (1)..(67)
<223> OTHER INFORMATION: 1-67 aa are a portion of the amino acid
      sequence of the protein AspEBORF295P

<400> SEQUENCE: 127

Trp Met Lys Pro Pro Ile Ile Pro Asp Lys Asn Leu Val Val Ile Ala
1               5                   10                  15

Arg Ala Asp Asp Val Thr Phe Gly Val Ile His Ser Arg Leu His Glu
            20                  25                  30

Val Trp Ala Leu Arg Met Gly Thr Ser Leu Glu Asp Arg Pro Arg Tyr
        35                  40                  45

Thr Ser Lys Ser Thr Phe Arg Thr Phe Pro Phe Pro Ala Gly Met Thr
    50                  55                  60

Pro Ala Asp
65


<210> SEQ ID NO 128
<211> LENGTH: 69
<212> TYPE: PRT
<213> ORGANISM: Caulobacter crescentus
<220> FEATURE:
<221> NAME/KEY: MISC_FEATURE
<222> LOCATION: (1)..(69)
<223> OTHER INFORMATION: 1-69 aa are a portion of the amino acid
      sequence of the protein CcrMORF826P

<400> SEQUENCE: 128

Trp Leu Asp Ala Arg Val Leu Pro Asp His Lys Leu Gln Val Val Thr
1               5                   10                  15

Leu Asp Asp Asp Cys Ser Phe Gly Val Leu His Ser Arg Phe His Glu
            20                  25                  30

Val Trp Ala Leu Ala Ala Gly Ser Trp His Gly Ser Gly Asn Asp Pro
        35                  40                  45

Arg Tyr Thr Ile Ser Thr Thr Phe Glu Thr Phe Pro Phe Pro Glu Gly
    50                  55                  60

Leu Thr Pro Asn Ile
65


<210> SEQ ID NO 129
<211> LENGTH: 63
<212> TYPE: PRT
<213> ORGANISM: Deinococcus radiophilus R1
<220> FEATURE:
<221> NAME/KEY: MISC_FEATURE
<222> LOCATION: (1)..(63)
<223> OTHER INFORMATION: 1-63 aa are a portion of the amino acid
      sequence of the protein DraRORF119P

<400> SEQUENCE: 129

Trp Leu Pro Glu Gly Thr Leu Pro Asp Ser Gln Val Val Val Ile Ala
1               5                   10                  15

Arg Asp Asp Asp Phe Ile Phe Gly Val Leu Ala Ser Thr Ile His Arg
            20                  25                  30

Ser Trp Ala Arg Met Gln Gly Thr Tyr Met Gly Val Gly Asn Asp Leu
        35                  40                  45

Arg Tyr Thr Pro Ser Thr Cys Phe Glu Thr Phe Pro Val Pro Ala
    50                  55                  60


<210> SEQ ID NO 130
<211> LENGTH: 62
<212> TYPE: PRT
```

<213> ORGANISM: Deinococcus radiophilus R1
<220> FEATURE:
<221> NAME/KEY: MISC_FEATURE
<222> LOCATION: (1)..(62)
<223> OTHER INFORMATION: 1-62 aa are a portion of the amino acid sequence of the protein DraRI

<400> SEQUENCE: 130

```
Phe Leu Asp Asn Gly Ile Arg Pro Ser Asp Gly Leu Gln Ile Phe Ala
1               5                   10                  15

Phe Glu Asp Asp Tyr Ser Phe Gly Val Ile Gln Ser Ser Val His Trp
            20                  25                  30

Gln Trp Leu Ile Ala Arg Gly Gly Thr Leu Thr Ala Arg Leu Met Tyr
        35                  40                  45

Thr Ser Asp Thr Val Phe Asp Thr Phe Pro Trp Pro Glu Asp
    50                  55                  60
```

<210> SEQ ID NO 131
<211> LENGTH: 62
<212> TYPE: PRT
<213> ORGANISM: Nitrobacter hamburgensis X14
<220> FEATURE:
<221> NAME/KEY: MISC_FEATURE
<222> LOCATION: (1)..(62)
<223> OTHER INFORMATION: 1-62 aa are a portion of the amino acid sequence of the protein NhaXI

<400> SEQUENCE: 131

```
Phe Val Ser Thr Ala Ile His Pro Asn Asp Ala Leu Ser Val Phe Ala
1               5                   10                  15

Leu Glu Asp Asp Tyr Ser Phe Gly Ile Leu Gln Ser Gly Ile His Trp
            20                  25                  30

Glu Trp Phe Ile Asn Arg Cys Ser Thr Leu Lys Ala Asp Phe Arg Tyr
        35                  40                  45

Thr Ser Asp Thr Val Phe Asp Ser Phe Pro Trp Pro Gln Glu
    50                  55                  60
```

<210> SEQ ID NO 132
<211> LENGTH: 38
<212> TYPE: PRT
<213> ORGANISM: Methylophilus methylotrophus
<220> FEATURE:
<221> NAME/KEY: MISC_FEATURE
<222> LOCATION: (1)..(38)
<223> OTHER INFORMATION: 1-38 aa are a portion of the amino acid sequence for MmeI

<400> SEQUENCE: 132

```
Phe Gly Leu Leu Ser Ser Thr Met His Asn Cys Trp Met Arg Asn Val
1               5                   10                  15

Gly Gly Arg Leu Glu Ser Arg Tyr Arg Tyr Ser Ala Ser Leu Val Tyr
            20                  25                  30

Asn Thr Phe Pro Trp Ile
        35
```

<210> SEQ ID NO 133
<211> LENGTH: 38
<212> TYPE: PRT
<213> ORGANISM: unknown
<220> FEATURE:
<223> OTHER INFORMATION: Environmental sample Sargasso Sea
<220> FEATURE:
<221> NAME/KEY: MISC_FEATURE
<222> LOCATION: (1)..(38)
<223> OTHER INFORMATION: 1-38 aa are a portion of the amino acid sequence of EsaSSI

<400> SEQUENCE: 133

Phe Ala Val Leu Asn Ser Thr Met His Met Ala Trp Thr Arg Ala Val
1 5 10 15

Cys Gly Arg Leu Glu Ser Arg Tyr Gln Tyr Ser Val Thr Ile Val Tyr
20 25 30

Asn Asn Phe Pro Trp Pro
35

<210> SEQ ID NO 134
<211> LENGTH: 38
<212> TYPE: PRT
<213> ORGANISM: Arcanobacterium pyogenes
<220> FEATURE:
<221> NAME/KEY: MISC_FEATURE
<222> LOCATION: (1)..(38)
<223> OTHER INFORMATION: 2-38 aa are a portion of the amino acid sequence of ApyPI

<400> SEQUENCE: 134

Phe Ala Leu Ile Ser Ser Ser Met Phe Ile Thr Trp Gln Lys Met Ile
1 5 10 15

Gly Gly Arg Leu Glu Ser Arg Leu Arg Phe Ala Asn Thr Leu Thr Trp
20 25 30

Asn Thr Phe Pro Val Pro
35

<210> SEQ ID NO 135
<211> LENGTH: 38
<212> TYPE: PRT
<213> ORGANISM: Neisseria lactamica ST640
<220> FEATURE:
<221> NAME/KEY: MISC_FEATURE
<222> LOCATION: (1)..(38)
<223> OTHER INFORMATION: 1-38 aa are a portion of the amino acid sequence of NlaCI

<400> SEQUENCE: 135

Phe Gly Ile Leu Ser Ser Thr Met His Asn Ala Phe Met Arg Thr Val
1 5 10 15

Ala Gly Arg Leu Glu Ser Arg Tyr Gln Tyr Ser Ala Ser Ile Val Tyr
20 25 30

Asn Asn Phe Pro Phe Pro
35

<210> SEQ ID NO 136
<211> LENGTH: 38
<212> TYPE: PRT
<213> ORGANISM: Deinococcus radiodurans
<220> FEATURE:
<221> NAME/KEY: MISC_FEATURE
<222> LOCATION: (1)..(38)
<223> OTHER INFORMATION: 1-38 aa are a portion of the amino acid sequence of DrdIV

<400> SEQUENCE: 136

Leu Gly Val Leu Ser Ser Arg Val His Val Thr Trp Ala Leu Ala Gln
1 5 10 15

Gly Gly Thr Leu Glu Asp Arg Pro Arg Tyr Asn Lys Thr Arg Cys Phe
20 25 30

Glu Thr Phe Pro Phe Pro
35

<210> SEQ ID NO 137

<211> LENGTH: 38
<212> TYPE: PRT
<213> ORGANISM: Rhodopseudomonas palustris BisB5
<220> FEATURE:
<221> NAME/KEY: MISC_FEATURE
<222> LOCATION: (1)..(38)
<223> OTHER INFORMATION: 1-38 aa are a portion of the amino acid sequence of RpaB5I

<400> SEQUENCE: 137

```
Leu Gly Val Leu Ser Ser Arg Leu His Val Arg Trp Ser Leu Ser Lys
1               5                   10                  15

Gly Gly Thr Leu Glu Asp Arg Pro Arg Tyr Asn Asn Ser Met Cys Phe
            20                  25                  30

Asp Pro Phe Pro Phe Pro
        35
```

<210> SEQ ID NO 138
<211> LENGTH: 38
<212> TYPE: PRT
<213> ORGANISM: Deinococcus radiophilus R1
<220> FEATURE:
<221> NAME/KEY: MISC_FEATURE
<222> LOCATION: (1)..(38)
<223> OTHER INFORMATION: 1-38 aa are a portion of the amino acid sequence for DraRI

<400> SEQUENCE: 138

```
Phe Gly Val Ile Gln Ser Ser Val His Trp Gln Trp Leu Ile Ala Arg
1               5                   10                  15

Gly Gly Thr Leu Thr Ala Arg Leu Met Tyr Thr Ser Asp Thr Val Phe
            20                  25                  30

Asp Thr Phe Pro Trp Pro
        35
```

<210> SEQ ID NO 139
<211> LENGTH: 38
<212> TYPE: PRT
<213> ORGANISM: Marinobacter aquaeolei VT8
<220> FEATURE:
<221> NAME/KEY: MISC_FEATURE
<222> LOCATION: (1)..(38)
<223> OTHER INFORMATION: 1-38 aa are a portion of the amino acid sequence of MaqI

<400> SEQUENCE: 139

```
Leu Gly Val Leu Ser Ser Arg Val His Val Leu Trp Ser Leu Phe Ala
1               5                   10                  15

Gly Gly Thr Leu Glu Asn Arg Pro Arg Tyr Asn Lys Thr Leu Cys Phe
            20                  25                  30

Glu Thr Phe Pro Phe Pro
        35
```

<210> SEQ ID NO 140
<211> LENGTH: 38
<212> TYPE: PRT
<213> ORGANISM: Nitrobacter hamburgensis X14
<220> FEATURE:
<221> NAME/KEY: MISC_FEATURE
<222> LOCATION: (1)..(38)
<223> OTHER INFORMATION: 1-38 aa are a portion of the amino acid sequence of NhaXI

<400> SEQUENCE: 140

```
Phe Gly Ile Leu Gln Ser Gly Ile His Trp Glu Trp Phe Ile Asn Arg
1               5                   10                  15
```

```
Cys Ser Thr Leu Lys Ala Asp Phe Arg Tyr Thr Ser Asp Thr Val Phe
            20                  25                  30

Asp Ser Phe Pro Trp Pro
        35


<210> SEQ ID NO 141
<211> LENGTH: 38
<212> TYPE: PRT
<213> ORGANISM: Neisseria meningitidis Z2491
<220> FEATURE:
<221> NAME/KEY: MISC_FEATURE
<222> LOCATION: (1)..(38)
<223> OTHER INFORMATION: 1-38 aa are a portion of the amino acid
      sequence of NmeAIII

<400> SEQUENCE: 141

Phe Gly Ile Leu Ser Ser Thr Met His Asn Ala Phe Met Arg Thr Val
1               5                   10                  15

Ala Gly Arg Leu Lys Ser Asp Tyr Arg Tyr Ser Asn Thr Val Val Tyr
            20                  25                  30

Asn Asn Phe Pro Phe Pro
        35


<210> SEQ ID NO 142
<211> LENGTH: 38
<212> TYPE: PRT
<213> ORGANISM: Corynebacterium diphtheriae
<220> FEATURE:
<221> NAME/KEY: MISC_FEATURE
<222> LOCATION: (1)..(38)
<223> OTHER INFORMATION: 1-38 aa are a portion of the amino acid
      sequence of CdpI

<400> SEQUENCE: 142

Phe Gly Val Leu Val Ser Gln Phe Gln Asn Ala Trp Met Arg Val Val
1               5                   10                  15

Ala Gly Arg Leu Lys Ser Asp Tyr Arg Tyr Gly Asn Thr Thr Val Tyr
            20                  25                  30

Asn Asn Phe Val Phe Pro
        35


<210> SEQ ID NO 143
<211> LENGTH: 38
<212> TYPE: PRT
<213> ORGANISM: Agmenellum quadruplicatum PR-6
<220> FEATURE:
<221> NAME/KEY: MISC_FEATURE
<222> LOCATION: (1)..(38)
<223> OTHER INFORMATION: 1-38 aa are a portion of the amino acid
      sequence of AquIII

<400> SEQUENCE: 143

Phe Gly Ile Phe Thr Ser Val Met His Met Ala Trp Val Lys Tyr Val
1               5                   10                  15

Cys Gly Arg Leu Lys Ser Asp Tyr Arg Tyr Ser Lys Asp Ile Val Tyr
            20                  25                  30

Asn Asn Phe Pro Phe Pro
        35


<210> SEQ ID NO 144
<211> LENGTH: 38
<212> TYPE: PRT
<213> ORGANISM: Corynebacterium striatum M82B
<220> FEATURE:
<221> NAME/KEY: MISC_FEATURE
<222> LOCATION: (1)..(38)
```

<223> OTHER INFORMATION: 1-38 aa are a portion of the amino acid sequence of CstMI

<400> SEQUENCE: 144

Phe Ala Leu Ala Ser Ser Ser Met Phe Ile Thr Trp Gln Lys Ser Ile
1               5                   10                  15

Gly Gly Arg Leu Lys Ser Asp Leu Arg Phe Ala Asn Thr Leu Thr Trp
            20                  25                  30

Asn Thr Phe Pro Val Pro
        35

<210> SEQ ID NO 145
<211> LENGTH: 38
<212> TYPE: PRT
<213> ORGANISM: Sulfurimonas denitrificans
<220> FEATURE:
<221> NAME/KEY: MISC_FEATURE
<222> LOCATION: (1)..(38)
<223> OTHER INFORMATION: 1-38 aa are a portion of the amino acid sequence of SdeAI

<400> SEQUENCE: 145

Phe Gly Ile Leu Thr Ser Lys Met His Met Asp Trp Val Arg Tyr Val
1               5                   10                  15

Ala Gly Arg Leu Lys Ser Asp Tyr Arg Tyr Ser Asn Glu Ile Val Tyr
            20                  25                  30

Asn Asn Phe Pro Phe Pro
        35

<210> SEQ ID NO 146
<211> LENGTH: 38
<212> TYPE: PRT
<213> ORGANISM: Psychrobacter sp. PRwf-1
<220> FEATURE:
<221> NAME/KEY: MISC_FEATURE
<222> LOCATION: (1)..(38)
<223> OTHER INFORMATION: 1-38 aa are a portion of the amino acid sequence for PspPRI

<400> SEQUENCE: 146

Phe Gly Thr Leu Ser Ser Ser Met His Asn Ala Phe Met Arg Leu Thr
1               5                   10                  15

Ala Gly Arg Met Lys Ser Asp Tyr Ser Tyr Ser Ser Thr Ile Val Tyr
            20                  25                  30

Asn Asn Phe Pro Tyr Pro
        35

<210> SEQ ID NO 147
<211> LENGTH: 38
<212> TYPE: PRT
<213> ORGANISM: Parvibaculum lavamentivorans DS-1
<220> FEATURE:
<221> NAME/KEY: MISC_FEATURE
<222> LOCATION: (1)..(38)
<223> OTHER INFORMATION: 1-38 aa are a portion of the amino acid sequence for PlaDI

<400> SEQUENCE: 147

Phe Gly Leu Leu Thr Ser Gly Met His Met Ala Trp Met Arg Ala Ile
1               5                   10                  15

Thr Gly Arg Met Lys Ser Asp Tyr Met Tyr Ser Val Gly Val Val Tyr
            20                  25                  30

Asn Thr Phe Pro Trp Pro
        35

<210> SEQ ID NO 148
<211> LENGTH: 40
<212> TYPE: PRT
<213> ORGANISM: Silicibacter pomeroyi DSS-3
<220> FEATURE:
<221> NAME/KEY: MISC_FEATURE
<222> LOCATION: (1)..(40)
<223> OTHER INFORMATION: 1-40 aa are a portion of the amino acid sequence of SpoDI

<400> SEQUENCE: 148

```
Phe Gly Ile Leu His Ser Ser Phe His Glu Leu Trp Ser Leu Arg Met
1               5                   10                  15

Gly Thr Phe Leu Gly Val Gly Asn Asp Pro Arg Tyr Thr Pro Ser Thr
            20                  25                  30

Thr Phe Glu Thr Phe Pro Phe Pro
        35                  40
```

<210> SEQ ID NO 149
<211> LENGTH: 38
<212> TYPE: PRT
<213> ORGANISM: Agmenellum quadruplicatum PR-6
<220> FEATURE:
<221> NAME/KEY: MISC_FEATURE
<222> LOCATION: (1)..(38)
<223> OTHER INFORMATION: 1-38 aa are a portion of the amino acid sequence of AquIV

<400> SEQUENCE: 149

```
Leu Gly Ile Leu Thr Ser Asp Val His Arg Gln Trp Val Lys Ala Gln
1               5                   10                  15

Ser Ser Thr Leu Lys Gly Asp Thr Arg Tyr Thr His Asn Thr Cys Phe
            20                  25                  30

Glu Thr Phe Pro Phe Pro
        35
```

<210> SEQ ID NO 150
<211> LENGTH: 41
<212> TYPE: PRT
<213> ORGANISM: Pseudomonas species OM2164
<220> FEATURE:
<221> NAME/KEY: MISC_FEATURE
<222> LOCATION: (1)..(41)
<223> OTHER INFORMATION: 1-41 aa are a portion of the amino acid sequence of PspOMII

<400> SEQUENCE: 150

```
Phe Ser Ile Val Ser Ser Arg Ile His Trp Val Trp Ala Ile Ala Asn
1               5                   10                  15

Ala Ala Lys Ile Gly Met Tyr Asp Gly Asp Ala Val Tyr Pro Lys Gly
            20                  25                  30

Gln Cys Phe Asp Pro Phe Pro Phe Pro
        35                  40
```

<210> SEQ ID NO 151
<211> LENGTH: 30
<212> TYPE: DNA
<213> ORGANISM: artificial
<220> FEATURE:
<223> OTHER INFORMATION: primer

<400> SEQUENCE: 151

```
ctgacgtatc atattcctag tgctgaacct                                      30
```

<210> SEQ ID NO 152

<211> LENGTH: 32
<212> TYPE: DNA
<213> ORGANISM: artificial
<220> FEATURE:
<223> OTHER INFORMATION: primer

<400> SEQUENCE: 152
gttacttgaa atgacatttc tatcaacaaa ac 32

<210> SEQ ID NO 153
<211> LENGTH: 30
<212> TYPE: DNA
<213> ORGANISM: artificial
<220> FEATURE:
<223> OTHER INFORMATION: primer

<400> SEQUENCE: 153
aagacgtatc atattcctag tgctgaacct 30

<210> SEQ ID NO 154
<211> LENGTH: 32
<212> TYPE: DNA
<213> ORGANISM: artificial
<220> FEATURE:
<223> OTHER INFORMATION: primer

<400> SEQUENCE: 154
gttacttgaa atgacatttc tatcaacaaa ac 32

<210> SEQ ID NO 155
<211> LENGTH: 25
<212> TYPE: DNA
<213> ORGANISM: artificial
<220> FEATURE:
<223> OTHER INFORMATION: primer

<400> SEQUENCE: 155
agctattctg ccagcctggt ttaca 25

<210> SEQ ID NO 156
<211> LENGTH: 28
<212> TYPE: DNA
<213> ORGANISM: artificial
<220> FEATURE:
<223> OTHER INFORMATION: primer

<400> SEQUENCE: 156
gtaacgactt tctaaccttc ctcctaca 28

<210> SEQ ID NO 157
<211> LENGTH: 63
<212> TYPE: DNA
<213> ORGANISM: artificial
<220> FEATURE:
<223> OTHER INFORMATION: primer

<400> SEQUENCE: 157
caattggaat aaattgtctg ttttcagatg atgtgcgagg tatcaacaga tagtccgtat 60
ccg 63

<210> SEQ ID NO 158
<211> LENGTH: 60
<212> TYPE: DNA
<213> ORGANISM: artificial
<220> FEATURE:
<223> OTHER INFORMATION: primer

<400> SEQUENCE: 158
gttttgttga tagaaatgtc atttcaagtg acgcaacgta tcatattcct agtgctgaac 60

<210> SEQ ID NO 159
<211> LENGTH: 33
<212> TYPE: DNA
<213> ORGANISM: artificial
<220> FEATURE:
<223> OTHER INFORMATION: primer

<400> SEQUENCE: 159
gctgcctaac cttcctccta catttctcat cca 33

<210> SEQ ID NO 160
<211> LENGTH: 31
<212> TYPE: DNA
<213> ORGANISM: artificial
<220> FEATURE:
<223> OTHER INFORMATION: primer

<400> SEQUENCE: 160
acctatagat attctgccag cctggtttac a 31

<210> SEQ ID NO 161
<211> LENGTH: 33
<212> TYPE: DNA
<213> ORGANISM: artificial
<220> FEATURE:
<223> OTHER INFORMATION: primer

<400> SEQUENCE: 161
gtgcctatag atattctgcc agcctggttt aca 33

<210> SEQ ID NO 162
<211> LENGTH: 31
<212> TYPE: DNA
<213> ORGANISM: artificial
<220> FEATURE:
<223> OTHER INFORMATION: primer

<400> SEQUENCE: 162
tccataacct tcctcctaca tttctcatcc a 31

<210> SEQ ID NO 163
<211> LENGTH: 36
<212> TYPE: DNA
<213> ORGANISM: artificial
<220> FEATURE:
<223> OTHER INFORMATION: primer

<400> SEQUENCE: 163
cgttattcaa atgaaattgt ttataacaac ttccct 36

<210> SEQ ID NO 164
<211> LENGTH: 35
<212> TYPE: DNA
<213> ORGANISM: artificial
<220> FEATURE:
<223> OTHER INFORMATION: primer

<400> SEQUENCE: 164
gtaacgactt tctaatcttc cagcaacata ccgca 35

<210> SEQ ID NO 165
<211> LENGTH: 29
<212> TYPE: DNA

<213> ORGANISM: artificial
<220> FEATURE:
<223> OTHER INFORMATION: primer

<400> SEQUENCE: 165
cgatattctg ccagcctggt ttacaacac 29

<210> SEQ ID NO 166
<211> LENGTH: 42
<212> TYPE: DNA
<213> ORGANISM: artificial
<220> FEATURE:
<223> OTHER INFORMATION: primer

<400> SEQUENCE: 166
gtaactagta cctaaccttc ctcctacatt tctcatccag ca 42

<210> SEQ ID NO 167
<211> LENGTH: 29
<212> TYPE: DNA
<213> ORGANISM: artificial
<220> FEATURE:
<223> OTHER INFORMATION: primer

<400> SEQUENCE: 167
cgatattctg ccagcctggt ttacaacac 29

<210> SEQ ID NO 168
<211> LENGTH: 42
<212> TYPE: DNA
<213> ORGANISM: artificial
<220> FEATURE:
<223> OTHER INFORMATION: primer

<400> SEQUENCE: 168
gtaaccgtta cctaaccttc ctcctacatt tctcatccag ca 42

<210> SEQ ID NO 169
<211> LENGTH: 31
<212> TYPE: DNA
<213> ORGANISM: artificial
<220> FEATURE:
<223> OTHER INFORMATION: primer

<400> SEQUENCE: 169
tggcgattcg gaagagcgcg ccgagattgg c 31

<210> SEQ ID NO 170
<211> LENGTH: 41
<212> TYPE: DNA
<213> ORGANISM: artificial
<220> FEATURE:
<223> OTHER INFORMATION: primer

<400> SEQUENCE: 170
ccaataagtc cgatacaccg catccgcgtt cgcatcgcgc t 41

<210> SEQ ID NO 171
<211> LENGTH: 34
<212> TYPE: DNA
<213> ORGANISM: artificial
<220> FEATURE:
<223> OTHER INFORMATION: primer

<400> SEQUENCE: 171
tggatttacg gccgagccag aaacactttc cggc 34

<210> SEQ ID NO 172
<211> LENGTH: 44
<212> TYPE: DNA
<213> ORGANISM: artificial
<220> FEATURE:
<223> OTHER INFORMATION: primer

<400> SEQUENCE: 172
ccaacgctcc tttagactgg catcattgtt ctgttcgcgc tccg 44

<210> SEQ ID NO 173
<211> LENGTH: 54
<212> TYPE: PRT
<213> ORGANISM: Rhodospirillum centenum

<400> SEQUENCE: 173

```
Pro Ala Ala Phe Gln His Val Met Leu Tyr Val Lys Pro Glu Arg Asp
1               5                   10                  15

His Asn Arg Arg Asp Ser Ile Lys Lys Leu Trp Trp Arg Phe Ala Trp
            20                  25                  30

Glu Arg Pro Thr Leu Arg Glu Ala Leu Lys Gly Leu Asp Arg Tyr Ile
        35                  40                  45

Ala Thr Thr Glu Thr Ser
    50
```

<210> SEQ ID NO 174
<211> LENGTH: 54
<212> TYPE: PRT
<213> ORGANISM: Rhodopseudomonas palustris

<400> SEQUENCE: 174

```
Pro Glu Ile Tyr Gln Lys Leu Leu Leu Lys Val Lys Pro Asp Arg Asp
1               5                   10                  15

Ala Asn Pro Arg Pro Ser Arg Arg Asp Asn Trp Trp Leu Phe Gly Glu
            20                  25                  30

Asn Gln Pro Lys Met Arg Asn Ala Ile Ala Ser Leu Gly Arg Tyr Ile
        35                  40                  45

Gly Thr Val Asp Thr Ser
    50
```

<210> SEQ ID NO 175
<211> LENGTH: 54
<212> TYPE: PRT
<213> ORGANISM: Sagittula stellata

<400> SEQUENCE: 175

```
Pro Thr Leu Phe Ala Tyr Leu Leu Asp Arg Val Lys Pro Val Arg Glu
1               5                   10                  15

Glu Asn Ser Arg Pro Gln Tyr Lys Lys Leu Trp Trp Ile Phe Ala Glu
            20                  25                  30

Pro Arg Pro Ala Leu Arg Ser Ala Ile Gly Gly Ile Arg Gln Phe Ile
        35                  40                  45

Gly Thr Thr Tyr Thr Ala
    50
```

<210> SEQ ID NO 176
<211> LENGTH: 54
<212> TYPE: PRT
<213> ORGANISM: Gemmatimonas aurantiaca

<400> SEQUENCE: 176

-continued

```
Pro Leu Leu Phe Asp Ile Val Arg Asp Arg Val Lys Pro Glu Arg Asp
1               5                   10                  15

Ala Asn Ala Arg Ala Val Tyr Arg Thr Tyr Trp Trp Arg Phe Gly Glu
            20                  25                  30

Ala Arg Arg Asp Trp Arg Ser Phe Val Ala Gly Leu Pro Arg Tyr Ile
        35                  40                  45

Ala Thr Val Lys Thr Ala
    50


<210> SEQ ID NO 177
<211> LENGTH: 54
<212> TYPE: PRT
<213> ORGANISM: Pseudomonas sp.

<400> SEQUENCE: 177

Pro Ala Val Tyr Gln His Val Leu Asp Lys Val Lys Pro Glu Arg Asp
1               5                   10                  15

Gln Asn Asn Arg Asp Ser Tyr Lys Arg Asn Trp Trp Ile His Gly Glu
            20                  25                  30

Pro Arg Arg Asp Leu Arg Pro Ala Leu Glu Gly Leu Pro Arg Tyr Ile
        35                  40                  45

Ala Thr Val Glu Thr Ala
    50


<210> SEQ ID NO 178
<211> LENGTH: 54
<212> TYPE: PRT
<213> ORGANISM: Rhodopseudomonas palustris

<400> SEQUENCE: 178

Pro Glu Ala Tyr Gln His Leu Leu Arg Thr Val Lys Pro Glu Arg Glu
1               5                   10                  15

Thr Asn Lys Arg Ala Ser Tyr Arg Gln Asn Trp Trp Val Phe Ala Glu
            20                  25                  30

Pro Arg Lys Glu Met Arg Pro Ala Leu Lys Asp Leu Gly Arg Tyr Ile
        35                  40                  45

Gly Thr Ala Arg Thr Ala
    50


<210> SEQ ID NO 179
<211> LENGTH: 54
<212> TYPE: PRT
<213> ORGANISM: Planctomyces limnophilus

<400> SEQUENCE: 179

Pro Ala Val Tyr Gln His Val His Asp His Val Lys Pro Glu Arg Asp
1               5                   10                  15

Gln Asn Asn Arg Ala Val Tyr Arg Asp Ser Trp Trp Met Phe Gly Glu
            20                  25                  30

Pro Arg Ala Ala Phe Arg Pro Ser Leu Lys Gly Leu Ala Arg Tyr Ile
        35                  40                  45

Ala Thr Val Glu Thr Ala
    50


<210> SEQ ID NO 180
<211> LENGTH: 54
<212> TYPE: PRT
<213> ORGANISM: Marinobacter aquaeolei

<400> SEQUENCE: 180
```

```
Pro Ser Leu Tyr Gln Trp Leu Leu Thr Arg Val Lys Pro Glu Arg Glu
1               5                   10                  15

Gln Asn Asn Arg Ala Ser Leu Lys Glu Arg Trp Trp Ile Tyr Gly Glu
            20                  25                  30

Ala Arg Asn Thr Phe Arg Pro Ala Leu Ile Gly Ile Glu Thr Ala Ile
        35                  40                  45

Ala Thr Ser Leu Thr Ala
    50


<210> SEQ ID NO 181
<211> LENGTH: 54
<212> TYPE: PRT
<213> ORGANISM: Agmenellum quadruplicatum

<400> SEQUENCE: 181

Pro Lys Thr Tyr Gln Trp Leu Ser Glu Thr Val Lys Leu Glu Arg Ser
1               5                   10                  15

Thr Asn Asn Asp Pro Lys Leu Lys Arg Glu Trp Trp Arg Tyr Arg Arg
            20                  25                  30

Ala Asn Thr Ser Ile Arg Asp Gly Ile Lys Asp Leu Asn Arg Tyr Ile
        35                  40                  45

Ala Thr Val Arg Thr Ala
    50


<210> SEQ ID NO 182
<211> LENGTH: 54
<212> TYPE: PRT
<213> ORGANISM: Agmenellum quadruplicatum

<400> SEQUENCE: 182

Lys Glu Pro Phe Asp His Val Asn Phe Phe Val Lys Pro Gln Arg Glu
1               5                   10                  15

Asn Asn Arg Asp Gln Lys Thr Arg Glu Tyr Trp Trp Leu Phe Pro Arg
            20                  25                  30

Ala Arg Pro Ala Met Arg Gln Ala Ile Glu Leu Leu Ala Leu Tyr Phe
        35                  40                  45

Ala Val Pro Arg His Ser
    50


<210> SEQ ID NO 183
<211> LENGTH: 55
<212> TYPE: PRT
<213> ORGANISM: Silicibacter pomeroyi

<400> SEQUENCE: 183

Glu Ala Val Tyr Ser Trp Leu Glu Gln Ala Tyr Glu Ser Tyr Glu Arg
1               5                   10                  15

Lys Ser Lys Arg Arg Ile Val Arg Arg Gln Asp Trp Trp Leu His Arg
            20                  25                  30

Arg Ser Gly Ala Ala Leu Lys Asn Ala Val Ser Arg Leu Ser Arg Phe
        35                  40                  45

Ile Val Thr Pro Arg Val Gly
    50                  55


<210> SEQ ID NO 184
<211> LENGTH: 54
<212> TYPE: PRT
<213> ORGANISM: Rhodopseudomonas palustris

<400> SEQUENCE: 184
```

```
Glu Gly Pro Phe Gln Tyr Ile Leu Glu His Val Lys Glu Tyr Arg Asn
1               5                   10                  15

Glu Glu Ala His Glu Ser Ser Lys Met Asn Trp Trp Ile His Gln Arg
            20                  25                  30

Pro Arg His Ala Leu Arg Leu Ala Ile Asp Gly Gln Ser Arg Tyr Leu
        35                  40                  45

Ala Thr Ala Arg Val Ala
    50


<210> SEQ ID NO 185
<211> LENGTH: 51
<212> TYPE: DNA
<213> ORGANISM: artificial
<220> FEATURE:
<223> OTHER INFORMATION: synthetic DNA substrate
<220> FEATURE:
<221> NAME/KEY: CDS
<222> LOCATION: (1)..(51)

<400> SEQUENCE: 185

gaa ggc cgc gca ggc ata cgc gct acc cgt aaa aaa ggg atg ctg cgc       48
Glu Gly Arg Ala Gly Ile Arg Ala Thr Arg Lys Lys Gly Met Leu Arg
1               5                   10                  15

ctg                                                                   51
Leu


<210> SEQ ID NO 186
<211> LENGTH: 17
<212> TYPE: PRT
<213> ORGANISM: artificial
<220> FEATURE:
<223> OTHER INFORMATION: Synthetic Construct

<400> SEQUENCE: 186

Glu Gly Arg Ala Gly Ile Arg Ala Thr Arg Lys Lys Gly Met Leu Arg
1               5                   10                  15

Leu


<210> SEQ ID NO 187
<211> LENGTH: 51
<212> TYPE: DNA
<213> ORGANISM: artificial
<220> FEATURE:
<223> OTHER INFORMATION: synthetic DNA substrate
<220> FEATURE:
<221> NAME/KEY: misc_feature
<222> LOCATION: (31)..(36)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 187

tccacgggcg cagggtcctc gtcagcgtag nnnnnntcac ggngannggg c              51


<210> SEQ ID NO 188
<211> LENGTH: 12
<212> TYPE: PRT
<213> ORGANISM: artificial
<220> FEATURE:
<223> OTHER INFORMATION: synthetic construct

<400> SEQUENCE: 188
```

Ser Thr Gly Ala Gly Ser Ser Ser Ala Ser Arg Gly
1 5 10

<210> SEQ ID NO 189
<211> LENGTH: 42
<212> TYPE: DNA
<213> ORGANISM: artificial
<220> FEATURE:
<223> OTHER INFORMATION: synthetic DNA substrate
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (39)..(42)
<223> OTHER INFORMATION: n is a, c, g, or t

<400> SEQUENCE: 189
acatccgttg acttgttgtc cacaaggtac nnnnnnngnn nn 42

<210> SEQ ID NO 190
<211> LENGTH: 9
<212> TYPE: PRT
<213> ORGANISM: artificial
<220> FEATURE:
<223> OTHER INFORMATION: synthetic construct

<400> SEQUENCE: 190

His Pro Leu Thr Cys Cys Pro Gln Gly
1 5

<210> SEQ ID NO 191
<211> LENGTH: 43
<212> TYPE: DNA
<213> ORGANISM: artificial
<220> FEATURE:
<223> OTHER INFORMATION: synthetic DNA construct
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 191
gaactggttg acggcctggt aggcgcagca annnttttnt ncn 43

<210> SEQ ID NO 192
<211> LENGTH: 10
<212> TYPE: PRT
<213> ORGANISM: artificial
<220> FEATURE:
<223> OTHER INFORMATION: synthetic construct

<400> SEQUENCE: 192

Arg Thr Gly Arg Pro Gly Arg Arg Ser Phe
1 5 10

<210> SEQ ID NO 193

<211> LENGTH: 1165
<212> TYPE: PRT
<213> ORGANISM: Rhodospirillum centenum

<400> SEQUENCE: 193

Met Pro Gln Thr Met Ser Met Pro Pro Val Leu Thr Ala Val Thr Asp
1 5 10 15

Pro Val Glu Arg Phe Pro Val Glu Arg Phe Ile Glu Arg Trp Ser Pro
20 25 30

Ser Gly Gly Ala Glu Leu Ala Asn Tyr Gly Leu Phe Ile Ser Glu Leu
35 40 45

Cys Asp Leu Ile Gly Val Pro Arg Pro Asp Pro Arg Thr Gly Asp Asp
50 55 60

Ala Arg Asp Ser Tyr Val Leu Glu Lys Pro Val Thr Ile Arg His Thr
65 70 75 80

Asp Asp Ser Thr Ser Ser Gly Arg Ile Asp Cys Tyr Arg Lys Asp Cys
85 90 95

Phe Val Leu Glu Ala Lys Gln Gly Val Asp Ala Glu Ser Gln Thr Ala
100 105 110

Leu Pro Leu Leu Gly Val Ala Gly Ala Pro Ala Ala Pro Ser Gly Thr
115 120 125

Arg Arg Arg Gly His Gly Val Arg Gly Ser Lys Gly Trp Asp Asp Ala
130 135 140

Met Ile Arg Ala Arg Gly Gln Ala Glu Lys Tyr Ala Lys Ala Leu Pro
145 150 155 160

Glu Trp Pro Pro Phe Leu Ile Val Leu Asp Val Gly His Glu Ile Gln
165 170 175

Leu Phe Ala Gly Phe Ser Arg Thr Gly Lys Asp Tyr Thr His Phe Pro
180 185 190

Asp Ala Ser Ser Phe Arg Ile Arg Met Thr Asp Leu Arg Arg Gln Glu
195 200 205

Thr Arg Asp Leu Leu Lys Ala Val Trp Leu Asp Pro Leu Ser Leu Asp
210 215 220

Pro Ser Lys Arg Thr Ala Lys Val Thr Arg Glu Ile Ala Glu Arg Leu
225 230 235 240

Ala Val Leu Ala Lys Ser Leu Glu Gln Ala Gly His Ser Ala Ala Asn
245 250 255

Val Ala Thr Phe Leu Met Arg Cys Leu Phe Thr Met Phe Ala Glu Asp
260 265 270

Val Glu Leu Leu Pro Lys Asp Ser Phe Arg Asp Leu Leu Arg Asn Leu
275 280 285

Arg Gly His Pro Gln Asp Phe Val Pro Thr Met Arg Val Leu Trp Lys
290 295 300

Ser Met Asn Asp Gly Asp Phe Cys Gly Val Leu Thr Gln Lys Val Leu
305 310 315 320

Arg Phe Asn Gly Gly Leu Phe Lys His Ala Asp Ala Leu Pro Leu Thr
325 330 335

Pro Glu Gln Leu Glu Leu Leu Ile Gln Ala Ala Glu Ala Asn Trp Arg
340 345 350

Asp Val Glu Pro Ala Ile Phe Gly Thr Leu Leu Glu Arg Ala Leu Asp
355 360 365

Lys Thr Glu Arg His Lys Leu Gly Ala His Tyr Thr Pro Arg Ala Tyr
370 375 380

Val Glu Arg Leu Val Leu Pro Thr Val Ile Glu Pro Leu Arg Glu Glu
385 390 395 400

```
Trp Glu Ala Val Lys Val Ala Ala Ala Glu Gln Glu Arg Asp Ala Ala
                405                 410                 415

Val Ala Leu Val Met Glu Phe His Arg Lys Leu Cys Asp Thr Arg Val
            420                 425                 430

Leu Asp Pro Ala Cys Gly Thr Gly Asn Phe Leu Tyr Val Thr Met Glu
        435                 440                 445

Leu Met Lys Lys Leu Glu Gly Glu Val Leu Asp Phe Leu Ser Ile Thr
    450                 455                 460

Leu Asp Val Arg Gln Asp Ala Leu Asp Leu Ala Gly His Thr Val Asp
465                 470                 475                 480

Pro His Gln Phe Leu Gly Ile Glu Val Asn Pro Arg Ala Ala Ala Ile
                485                 490                 495

Ala Glu Leu Val Leu Trp Ile Gly Tyr Leu Gln Trp His Phe Lys Thr
            500                 505                 510

Arg Gly Lys Val Met Pro Ala Glu Pro Val Leu Lys Asp Phe Lys Asn
        515                 520                 525

Ile Glu Asn Arg Asp Ala Ile Leu Ala Trp Asp Arg Thr Glu Ile Val
    530                 535                 540

Arg Asp Glu Ser Gly Arg Pro Val Thr Arg Trp Asp Gly Val Thr Met
545                 550                 555                 560

Lys Lys His Pro Val Thr Gly Glu Asp Val Pro Asp Glu Thr Ala Arg
                565                 570                 575

Val Glu Leu Val Arg Tyr Val Lys Pro Arg Pro Ala Lys Trp Pro Lys
            580                 585                 590

Ala Asp Tyr Ile Val Gly Asn Pro Pro Phe Ile Gly Thr Lys Leu Met
        595                 600                 605

Arg Ala Ala Leu Gly Asp Gly Tyr Val Asn Gln Leu Arg Glu Thr Ile
    610                 615                 620

Asp His Ile Pro Asp Ser Ala Asp Tyr Val Met Tyr Trp Trp Asp His
625                 630                 635                 640

Ala Ala Lys Leu Leu Trp Asn Gly Lys Ile Phe Arg Phe Gly Phe Val
                645                 650                 655

Thr Thr Asn Ser Ile Thr Gln Thr Phe Asn Arg Arg Val Leu Thr Asn
            660                 665                 670

Arg Leu Lys Thr Gly Ala Gln Ile Tyr Ile Ile Phe Ala Ile Pro Asp
        675                 680                 685

His Pro Trp Ser Asp Ala Asp Gly Ser Ala Ala Val Arg Ile Ser Met
    690                 695                 700

Thr Val Val Ala Lys Gly Asn Ser Ala Gly Arg Leu Leu Leu Pro Ile
705                 710                 715                 720

Arg Glu Glu His Leu Gly Ser Glu Thr Pro Asn Ile Glu Phe Asn Glu
                725                 730                 735

Lys His Gly Ala Ile Ser Ala Asp Leu Arg Ile Gly Ala Asn Ile Gly
            740                 745                 750

Asn Ala Thr Glu Leu Ile Ser Asn Glu Arg Ile Cys Gly Phe Gly Met
        755                 760                 765

Ala Leu His Gly Gln Gly Phe Leu Leu Ser Arg Ala Lys Ser Asp Glu
    770                 775                 780

Leu Lys Lys Phe Gly Ser Gln Val Ile Arg Pro Phe Leu Gly Gly Lys
785                 790                 795                 800

Asp Leu Leu Ser Ala Ala Arg Glu Arg Tyr Val Ile Asp Phe Ser Gly
                805                 810                 815

Leu Thr Glu Glu Glu Ala Gln Ile Ala Asn Pro Ala Ala Phe Gln His
```

```
            820                 825                 830

Val Met Leu Tyr Val Lys Pro Glu Arg Asp His Asn Arg Arg Asp Ser
        835                 840                 845

Ile Lys Lys Leu Trp Trp Arg Phe Ala Trp Glu Arg Pro Thr Leu Arg
    850                 855                 860

Glu Ala Leu Lys Gly Leu Asp Arg Tyr Ile Ala Thr Thr Glu Thr Ser
865                 870                 875                 880

Lys His Arg Val Phe Gln Phe Ile Glu Ala Ile Tyr Leu Thr Asp His
                885                 890                 895

Met Gly Ile Val Ile Ser Ser Gln Asp Ala Leu Ile Leu Gly Ala Leu
            900                 905                 910

Ser Ser Trp Pro His Arg Leu Trp Ala Ile Lys Ala Gly Gly Thr Leu
        915                 920                 925

Glu Asp Arg Pro Arg Tyr Asn Lys Thr Arg Cys Phe Asp Pro Phe Pro
    930                 935                 940

Phe Pro Asp Pro Ala Glu Glu Leu Lys Ala Arg Ile Arg Val Leu Gly
945                 950                 955                 960

Glu Arg Leu Asp Ser Phe Arg Lys Glu Arg Gln Ala Ala His Pro Asp
                965                 970                 975

Leu Thr Leu Thr Gln Met Tyr Asn Val Leu Glu Arg Leu Arg Glu Leu
            980                 985                 990

Asp Arg Asp Pro Ala Ala Lys Pro  Leu Asp Ala Lys Glu  Lys Ala Ile
        995                 1000                1005

His Glu  Lys Gly Leu Ile Ser  Val Leu Arg Gln Ile  His Asp Asp
    1010                1015                1020

Leu Asp  Arg Ala Val Phe Asp  Ala Tyr Gly Trp Pro  His Asp Leu
    1025                1030                1035

Thr Asp  Glu Gln Ile Leu Glu  Arg Leu Val Ala Leu  Asn Lys Glu
    1040                1045                1050

Arg Ala  Ala Glu Glu Lys Arg  Gly Ile Ile Arg Trp  Leu Arg Pro
    1055                1060                1065

Glu Phe  Gln Ala Pro Lys Thr  Ala Arg Pro Val Gln  Thr Ala Met
    1070                1075                1080

Glu Val  Gly Pro Glu Glu Thr  Ser Ala Pro Ala Ala  Pro Ala Ala
    1085                1090                1095

Lys Ala  Pro Trp Pro Lys Ser  Leu Pro Glu Gln Ala  Gln Gln Val
    1100                1105                1110

Leu Ala  Ala Leu Thr Ala Leu  Gly Arg Pro Ala Thr  Pro Thr Glu
    1115                1120                1125

Val Ala  Arg Thr Phe Arg Ser  Ala Pro Ala Pro Arg  Val Ala Glu
    1130                1135                1140

Val Met  Ala Thr Leu Glu Thr  Met Gly Arg Ala Trp  Lys Val Glu
    1145                1150                1155

Asn Thr  Asp Arg Tyr Ala Ala
    1160                1165


<210> SEQ ID NO 194
<211> LENGTH: 1186
<212> TYPE: PRT
<213> ORGANISM: Rhodopseudomonas palustris

<400> SEQUENCE: 194

Met Gly Thr Ala Ser Ile Pro Asp Val Glu Gln Phe Ile Ser Arg Trp
1               5                   10                  15

Gln Gly Arg Glu Gly Gly Gln Glu Arg Ala Asn Tyr Val Ser Phe Leu
```

-continued

```
            20                  25                  30

Asn Glu Leu Ile Ala Leu Leu Gly Leu Pro Lys Pro Asp Pro Ala Asp
        35                  40                  45

Ala Thr His Glu His Asn Asp Tyr Val Phe Glu Arg Ala Val Lys Lys
    50                  55                  60

His Lys Asp Asp Gly Ala Ser His Gly Arg Ile Asp Leu Tyr Lys Lys
65                  70                  75                  80

Asn Ser Phe Val Leu Glu Ala Lys Gln Ser Arg Leu Lys Gly Val Lys
                85                  90                  95

Lys Val Ala Gly Gln Asn Asp Leu Phe Asn Ala Asp Val Pro Glu Ala
            100                 105                 110

Ser Arg Gly Arg Arg Gly Ala Asp Arg Ala Trp Asp Val Leu Met Leu
        115                 120                 125

Asn Ala Lys Arg Gln Ala Glu Glu Tyr Ala Arg Ala Leu Pro Ala Ser
    130                 135                 140

His Gly Trp Pro Pro Phe Ile Leu Val Cys Asp Val Gly His Cys Ile
145                 150                 155                 160

Glu Val Tyr Ala Asp Phe Ser Gly Gln Gly Lys Asn Tyr Thr Gln Phe
                165                 170                 175

Pro Asp Arg Gln Ser Phe Arg Ile Tyr Leu Glu Asp Leu Arg Asp Glu
            180                 185                 190

Thr Val Arg Glu Arg Leu Gln Lys Ile Trp Thr Glu Pro Gln Ala Leu
        195                 200                 205

Asp Pro Ala Gln Ala Ser Ala Lys Val Thr Arg Asp Ile Ala Lys Arg
    210                 215                 220

Leu Ala Gln Val Ser Leu Ala Leu Glu Lys Lys Gly Phe Val Ala Asp
225                 230                 235                 240

Asp Val Ala Met Phe Leu Met Arg Cys Leu Phe Thr Met Phe Ala Glu
                245                 250                 255

Asp Val Gly Leu Leu Pro Asp Lys Ser Phe Lys Thr Val Leu Glu Glu
            260                 265                 270

Cys Glu Lys Asn Pro Glu Ala Phe Val His Asp Val Gly Gln Leu Trp
        275                 280                 285

Glu Ala Met Asp Leu Gly Ala Trp Ala His Ala Leu Lys Thr Lys Val
    290                 295                 300

Lys Lys Phe Asn Gly Glu Phe Phe Lys Asn Arg Ala Ala Leu Pro Leu
305                 310                 315                 320

Gly Arg Glu Glu Ile Gly Glu Leu Arg Gln Ala Ala Ser Tyr Asp Trp
                325                 330                 335

Asn Glu Val Asp Pro Ser Ile Phe Gly Thr Leu Leu Glu Gln Ala Leu
            340                 345                 350

Asp Pro Gln Asp Arg Lys Lys Leu Gly Ala His Tyr Thr Pro Arg Ala
        355                 360                 365

Tyr Val Glu Arg Leu Val Val Ala Thr Ile Ile Glu Pro Leu Arg Glu
    370                 375                 380

Asp Trp Arg Asn Val Gln Ala Thr Ala Glu Thr Arg Arg Gly Ala Gly
385                 390                 395                 400

Asp Leu Lys Gly Ala Ala Ala Ala Val Gln Ala Phe His Asp Lys Leu
                405                 410                 415

Cys Ala Thr Arg Val Leu Asp Pro Ala Cys Gly Thr Gly Asn Phe Leu
            420                 425                 430

Tyr Val Ser Leu Glu Leu Met Lys Arg Leu Glu Gly Glu Val Leu Glu
        435                 440                 445
```

-continued

```
Ala Leu Leu Asp Leu Gly Gly Gln Glu Ala Leu Arg Gly Leu Gly Ser
    450                 455                 460

His Ser Val Asp Pro Arg Gln Phe Leu Gly Leu Glu Ile Asn Pro Arg
465                 470                 475                 480

Ala Ala Ala Ile Ala Glu Leu Val Leu Trp Ile Gly Tyr Leu Gln Trp
                485                 490                 495

His Phe Arg Thr Lys Gly Gly Pro Pro Asp Glu Pro Ile Leu Lys Ala
            500                 505                 510

Phe Lys Asn Ile Gln Val Lys Asn Ala Val Leu Thr Trp Asp Gly Ala
        515                 520                 525

Pro Leu Pro Lys Ile Val Asp Gly Lys Glu Thr Tyr Pro Asn Ala Lys
    530                 535                 540

Arg Pro Glu Trp Pro Ala Ala Glu Phe Ile Val Gly Asn Pro Pro Phe
545                 550                 555                 560

Thr Ala Gly Gln Asp Phe Arg Arg Glu Phe Gly Glu Ser Tyr Ala Gln
                565                 570                 575

Ala Leu Trp Leu Asn Tyr Lys His Ile Ser Gly Ala Ala Asp Leu Val
            580                 585                 590

Met Tyr Trp Trp Asp Arg Ala Ala Glu Leu Leu Asn Arg Lys Gly Thr
        595                 600                 605

Ala Leu Arg Arg Phe Gly Phe Val Thr Thr Arg Thr Ile Thr His Glu
    610                 615                 620

Phe Ser Gly Arg Val Val Ala Arg His Leu Asn Ala Asn Asp Pro Ile
625                 630                 635                 640

Ser Ile Val Leu Ala Val Pro Asn His Pro Trp Thr Arg Gly Arg Asp
                645                 650                 655

Ala Ala Ala Val Arg Ile Ala Met Thr Val Val Glu Ala Gly His Arg
            660                 665                 670

Asn Gly Leu Leu Gln Asn Val Ile Ser Glu Ser Asp Leu Asp Ala Asp
        675                 680                 685

Glu Pro Thr Ile Leu Leu Glu Asp Arg Cys Gly Lys Ile Asn Pro Asn
    690                 695                 700

Leu Thr Ile Gly Ile Asp Leu Ala Ser Ala Gly Arg Leu Arg Ala Thr
705                 710                 715                 720

Asp Gly Ile Cys His Asp Gly Val Lys Leu His Gly Lys Gly Phe Ile
                725                 730                 735

Val Gln Ser Ala Glu Leu Glu His Leu Gly Leu Asp Arg Arg Lys Gly
            740                 745                 750

Ile Glu Lys Val Ile Arg Pro Tyr Leu Asn Gly Arg Asp Ile Asn Gln
        755                 760                 765

Arg Thr Arg Gly Leu Phe Val Ile Asp Leu Phe Gly Leu Ala Glu Asp
    770                 775                 780

Glu Val Arg Leu Asn Phe Pro Glu Ile Tyr Gln Lys Leu Leu Leu Lys
785                 790                 795                 800

Val Lys Pro Asp Arg Asp Ala Asn Pro Arg Pro Ser Arg Arg Asp Asn
                805                 810                 815

Trp Trp Leu Phe Gly Glu Asn Gln Pro Lys Met Arg Asn Ala Ile Ala
            820                 825                 830

Ser Leu Gly Arg Tyr Ile Gly Thr Val Asp Thr Ser Arg His Arg Ile
        835                 840                 845

Phe Ser Phe Leu Asp Glu Lys Met Leu Cys Asp Asp Lys Val Val Ile
    850                 855                 860

Val Ala Ser Thr Asp Ala Phe Asp Leu Gly Val Leu Ser Ser Arg Ile
865                 870                 875                 880
```

His Cys Thr Trp Ser Asn Lys Ser Gly Val Arg Leu Gly Val Gly Asn
885 890 895

Asp Pro Val Tyr Ala Ser Asn Arg Cys Phe Asp Pro Phe Pro Phe Pro
900 905 910

Ala Ala Asn Asn Ile Gln Lys Gln Thr Ile Arg Val Ile Ala Glu Glu
915 920 925

Leu Asp Ala His Arg Lys Arg Val Leu Lys Glu His Pro His Leu Thr
930 935 940

Leu Thr Gly Leu Tyr Asn Val Leu Glu Arg Leu Arg Ala Gly Ala Ala
945 950 955 960

Ile Ala Pro Ser Ser Ala Ser Ala Ala Arg Gly Ala Gly Gly Ala Gly
965 970 975

Gly Asp Ala Gly Ala Val Ala Arg Gly Lys Thr Pro His Pro Asn Pro
980 985 990

Pro His Arg Ser Ala Gly Gly Gly Asp Gln Ala Ala Ala Ala Ala Ser
995 1000 1005

Ala Val Pro Ala Leu Thr Pro Asp Glu Gln Arg Ile Phe Asp Asp
1010 1015 1020

Gly Leu Val Leu Ile Leu Lys Glu Leu His Asp Lys Leu Asp Val
1025 1030 1035

Ala Val Ala Glu Ala Tyr Gly Trp Pro Ala Asp Leu Ser Asp Asp
1040 1045 1050

Glu Ile Leu Ala Lys Leu Val Ala Leu Asn Lys Glu Arg Ala Glu
1055 1060 1065

Glu Glu Lys Arg Gly Leu Val Arg Trp Leu Arg Pro Asp Tyr Gln
1070 1075 1080

Ile Pro Arg Phe Gly Lys Gly Leu Asp Lys Gln Ala Ala Arg Glu
1085 1090 1095

Glu Gly Ala Gln Val Thr Ala Asp Leu Ile Gly Val Glu Thr Val
1100 1105 1110

Gln Lys Arg Ala Phe Pro Thr Val Ala Val Glu Gln Thr Ala Ala
1115 1120 1125

Val Phe Ala Ala Leu Ala Ala Ala Ser Ala Pro Leu Asp Ala Lys
1130 1135 1140

Thr Leu Ala Ala Gln Phe Lys Arg Thr Lys Thr Thr Glu Lys Lys
1145 1150 1155

Val Gly Glu Val Leu Ala Ser Leu Ala Arg Leu Gly Tyr Val Thr
1160 1165 1170

Ser Asp Asp Gly Met Thr Phe Ala Leu Arg Arg Val Ala
1175 1180 1185

<210> SEQ ID NO 195
<211> LENGTH: 1131
<212> TYPE: PRT
<213> ORGANISM: Sagittula stellata

<400> SEQUENCE: 195

Met Gln Asp Gln Glu Val Glu Glu Phe Ile Asp Arg Trp Lys Asn Thr
1 5 10 15

Gly Gly Ser Glu His Ala Asn Tyr Gln Leu Phe Val Ile Glu Leu Thr
20 25 30

Gly Leu Leu Gly Leu Asp Arg Pro Asn Pro Ala Thr Asp Asp Asp Ser
35 40 45

Asn Asp His Tyr Arg Phe Glu Arg Pro Val Ile Phe Ala His Thr Gln
50 55 60

```
Lys Arg Ser Thr Gly Phe Ile Asp Val Tyr Arg Ala Gly His Phe Val
65                  70                  75                  80

Leu Glu Thr Lys Gln Gly Val Asn Gln Lys Lys Ser Arg Ala Ala Asp
                85                  90                  95

Leu Thr Thr Gly Thr Ala Ala Arg Thr Gln Lys Arg Thr Gly His Gly
            100                 105                 110

Val Arg Gly Thr Ala Ala Trp Asp Asp Thr Met Leu Lys Ala Arg Asn
        115                 120                 125

Gln Ala Asp Asn Tyr Ala Arg Ala Val Ala Arg Asp Asp Gly Trp Pro
    130                 135                 140

Pro Phe Leu Met Ile Val Asp Val Gly His Val Ile Glu Leu Tyr Ala
145                 150                 155                 160

Asp Phe Ser Lys Gln Gly Gln Gly Tyr Asn Gln Tyr Pro Asp Gly Asn
                165                 170                 175

Arg Tyr Arg Ile Phe Leu Asp Asp Leu Arg Lys Asp Glu Thr Arg Asp
            180                 185                 190

Leu Leu Arg Thr Ile Trp Thr Glu Pro Phe Thr Leu Asp Pro Ser Leu
        195                 200                 205

Lys Ala Ala Glu Val Thr Arg Asp Ile Ala Ala His Leu Ala Glu Leu
    210                 215                 220

Gly Lys Ser Phe Glu Gly Gln Gly His Ser Ser Glu Thr Val Ala Arg
225                 230                 235                 240

Phe Leu Met Arg Cys Leu Phe Ser Met Phe Ala Glu Asp Val Asp Leu
                245                 250                 255

Ile Pro Arg Gly Ser Phe Thr Glu Leu Leu Arg Lys Leu Arg Gly His
            260                 265                 270

Pro Glu His Ala Glu Pro Ala Leu Lys Gly Leu Trp Glu Thr Met Asn
        275                 280                 285

Thr Gly Gly Phe Ser Gln Val Leu Met Gln Asp Leu Lys Arg Phe Asn
    290                 295                 300

Gly Gly Leu Phe Arg Asp Ala Asp Ala Leu Pro Leu Asn Asn Leu Gln
305                 310                 315                 320

Leu Gly Leu Leu Ile Glu Ala Ala Glu Ala Asp Trp Lys Gln Val Glu
                325                 330                 335

Pro Ala Ile Phe Gly Thr Leu Leu Glu Arg Ala Leu Asp Lys Arg Gln
            340                 345                 350

Arg His Lys Leu Gly Ala His Tyr Thr Pro Arg Ala Tyr Val Gln Arg
        355                 360                 365

Leu Val Thr Pro Thr Ile Ile Glu Pro Leu Arg Asp Asp Trp Arg Asp
    370                 375                 380

Val Gln Thr Ala Val Gln Arg Leu Thr Glu Asp Gly Lys Lys Asp Glu
385                 390                 395                 400

Ala Arg Lys Leu Val Ala Asp Phe His Ala Gln Leu Cys Glu Thr Thr
                405                 410                 415

Val Leu Asp Pro Ala Cys Gly Ser Gly Asn Phe Leu Tyr Val Ala Leu
            420                 425                 430

Glu Met Met Lys Arg Leu Glu Gly Glu Val Thr Ser Leu Met Val Asp
        435                 440                 445

Leu Gly Asp Thr Lys Pro Leu Ile Thr Val Asp Pro His Gln Phe Leu
    450                 455                 460

Gly Ile Glu Leu Asn Pro Trp Ala Ala Asn Val Ala Glu Leu Val Leu
465                 470                 475                 480

Trp Ile Gly Tyr Leu Gln Trp His Tyr Arg Thr His Gly Gln Ala Ala
```

-continued

```
                485                 490                 495

Pro Ser Glu Pro Val Leu Arg Asp Phe Arg Asn Ile Ala Asn Ala Asp
            500                 505                 510

Ala Val Leu Lys Trp Asp Asp Arg Thr Pro Arg Met Asp Ala Glu Gly
        515                 520                 525

Asn Pro Val Thr Arg Trp Asp Gly Val Thr Thr Met Arg His Pro Val
    530                 535                 540

Thr Gly Glu Glu Val Pro Asp Pro Ala Ala Arg Val Gln Val Tyr Asp
545                 550                 555                 560

Tyr Ala Lys Pro Arg Ala Thr Val Trp Pro Arg Ala Asn Phe Ile Val
                565                 570                 575

Gly Asn Pro Pro Phe Ile Gly Ala Arg Lys Ile Lys Ser Ala Leu Ser
            580                 585                 590

Glu Glu Tyr Val Glu Thr Leu Arg Ala Val Tyr Gln Asn Val Pro Asn
        595                 600                 605

Thr Val Asp Phe Val Met Tyr Trp Trp Ala Lys Ala Ala Glu Ala Val
    610                 615                 620

Lys His Lys Ser Ala Arg Arg Phe Gly Leu Ile Thr Thr Asn Ser Ile
625                 630                 635                 640

Thr Gln Asp Tyr Ser Arg Lys Leu Val Asp Lys Asn Ile Ser Gly Gly
                645                 650                 655

Lys Pro Lys Leu Asn Leu Val Phe Ala Thr Thr Asn His Pro Trp Val
            660                 665                 670

Asp Ser Ser Asp Gly Ala Ser Val Arg Ile Ala Met Thr Val Ala Ser
        675                 680                 685

Gly Arg Lys Ile Lys Lys Pro Arg Ile Leu Glu Asn Ala Gly Thr Glu
    690                 695                 700

Asp Gln Lys Glu Lys Ser Val Asp Arg Ile Asn Ser Arg Leu Ala Asp
705                 710                 715                 720

Val Pro Asp Phe Ser Glu Leu Gln Pro Leu Arg Ser Asn Tyr Arg Met
                725                 730                 735

Cys Phe Gln Gly Val Val Pro Ala Gly Asp Gly Phe Lys Leu Gly Ser
            740                 745                 750

Ser Glu Lys Asp Ala Leu Glu Met Arg Leu Ser Glu Lys Glu Lys Ala
        755                 760                 765

Lys Ile Lys Arg Tyr Tyr Ile Gly Lys Asp Ile Ile Asp Arg Pro Arg
    770                 775                 780

His Gln Ser Ile Ile Asp Leu Phe Gly Val Asp Leu Glu Glu Leu Lys
785                 790                 795                 800

Arg Asp Tyr Pro Thr Leu Phe Ala Tyr Leu Leu Asp Arg Val Lys Pro
                805                 810                 815

Val Arg Glu Glu Asn Ser Arg Pro Gln Tyr Lys Lys Leu Trp Trp Ile
            820                 825                 830

Phe Ala Glu Pro Arg Pro Ala Leu Arg Ser Ala Ile Gly Gly Ile Arg
        835                 840                 845

Gln Phe Ile Gly Thr Thr Tyr Thr Ala Lys His Arg Val Phe Gln Phe
    850                 855                 860

Cys Gly Ser Glu Ile Val Pro Asp Ala Met Val Tyr Ala Ile Ala Thr
865                 870                 875                 880

Asp Gln Pro Glu Leu Leu Ala Cys Leu Ser Ser Arg Val His Leu Val
                885                 890                 895

Trp Cys Lys Gly Ser Thr Gly Thr Leu Glu Asp Arg Pro Arg Tyr Asn
            900                 905                 910
```

Ser Ala Asn Thr Phe Ser Pro Phe Pro Phe Pro Asp Leu Gly Asn Asn
915 920 925

Glu Arg Glu Ser Leu Arg Thr Leu Gly Glu His Leu Asp Ala His Arg
930 935 940

Lys Arg Gln Gln Ala Ala His Pro Lys Leu Thr Leu Thr Gln Met Tyr
945 950 955 960

Asn Val Leu Glu Lys Leu Arg Ala Gly Glu Pro Ile Glu Gly Lys Asp
965 970 975

Arg Glu Ile Tyr Asp Gln Gly Leu Ile Gly Ile Leu Arg Asp Leu His
980 985 990

Asp Gln Ile Asp Ala Glu Val Ala Arg Ala Tyr Gly Trp Pro Ala Asp
995 1000 1005

Leu Ser Asp Glu Asp Ile Leu Phe Arg Leu Val Ala Leu Asn Lys
1010 1015 1020

Glu Arg Ala Glu Glu Glu Ala Gln Gly His Ile Arg Trp Leu Arg
1025 1030 1035

Pro Asp Tyr Gln Asn Pro Thr Gly Gln Gln Ala Thr Lys Gly Lys
1040 1045 1050

Gln Ala Glu Leu Asp Val Gly Met Ala Ala Lys Ile Glu Lys Ala
1055 1060 1065

Pro Trp Pro Lys Thr Leu Pro Asp Gln Ile Ala Ala Val Arg Glu
1070 1075 1080

Ala Leu Ala Glu Met Gly Glu Ala Thr Pro Glu Gln Ile Ala Arg
1085 1090 1095

Arg Phe Met Arg Ala Arg Thr Thr Ser Val Ala Pro Leu Leu Asp
1100 1105 1110

Ser Leu Ala Ala Leu Gly Gln Ala Glu Lys Gly Gly Asp Gly Arg
1115 1120 1125

Tyr Ala Ala
1130

<210> SEQ ID NO 196
<211> LENGTH: 1112
<212> TYPE: PRT
<213> ORGANISM: Gemmatimonas aurantiaca

<400> SEQUENCE: 196

Met Ser Ser Ser Asn Ala Ala Val Thr Pro Ala Val Ala Leu Arg Ala
1 5 10 15

Leu Arg Glu Arg Trp Ala Gly Val Pro Ala Ala Glu Arg Ala Asn Ala
20 25 30

Gln Ser Tyr Leu Arg Asp Leu Cys Glu Ala Leu Gly Val Pro Ala Pro
35 40 45

Leu Pro Ala Gly Ser Gly Tyr Glu Phe Glu Leu Pro Val Lys Leu Ile
50 55 60

Thr Arg Asp Gly Thr Glu Thr Thr Gly Phe Val Asp Cys Tyr Lys Val
65 70 75 80

Gly His Phe Ile Leu Glu Ala Lys Asp Val Gln Gly Gly Ala Ser Asp
85 90 95

Val Ala Leu Arg Arg Ala Tyr Gly Gln Ala Arg Gln Tyr Ala Ala His
100 105 110

Asp Pro Ser Gly Thr Ala Pro Pro Tyr Leu Leu Val Leu Asp Val Ala
115 120 125

Lys Thr Leu Leu Val Tyr His Arg Trp Gly Gly Val Tyr Gln Gly Phe
130 135 140

```
Ala Ala Gly His Arg Ile Asp Leu Pro Thr Leu Asp Gln Arg Pro Ser
145                 150                 155                 160

Asp Ile Glu Leu Leu Arg Asp Ile Trp Thr Gln Pro Thr Lys Arg Asp
                165                 170                 175

Pro Arg Gln His Ala Gln Ala Val Thr Gln Glu Ile Ala Ala Lys Leu
            180                 185                 190

Ala Thr Leu Ala Ala Thr Leu Glu Asp Arg Gly Phe Gly Pro Glu Arg
        195                 200                 205

Val Ala Arg Phe Leu Met Arg Val Val Phe Ser Cys Phe Ala Glu Asp
    210                 215                 220

Val Asp Leu Leu Pro Arg Glu Ala Phe Arg Gln Thr Val Gln Asn Ala
225                 230                 235                 240

Gly Val Gln Gly Asp Ala Ala Leu Phe Gln Arg Ala Leu Gly Ser Leu
                245                 250                 255

Trp Gln Thr Met Asp Ser Gly Gly Leu Phe Gly Phe Glu Asn Ile Leu
            260                 265                 270

Gln Phe Asn Gly His Phe Phe Lys Asp Ala Glu Val Leu Pro Leu Glu
        275                 280                 285

Arg Glu Glu Ile Ala Leu Val Leu Glu Ala Ala Arg Ala Asp Trp Arg
    290                 295                 300

Asp Val Glu Pro Thr Ile Phe Gly Thr Leu Leu Thr Arg Ala Leu Asp
305                 310                 315                 320

Pro Val Glu Arg His Arg Leu Gly Ala Glu Tyr Thr Pro Arg Ala Phe
                325                 330                 335

Ile Glu Arg Leu Val Arg Pro Thr Val Glu Glu Pro Val Arg Glu Arg
            340                 345                 350

Trp Thr Ala Val Gln Ala Glu Val Leu Gln Leu Arg Glu Ser Gly Lys
        355                 360                 365

Ala Lys Asp Arg Ala Ala Ala Glu Gln Arg Leu Arg Glu Phe Leu Gly
    370                 375                 380

Trp Leu Gln Gly Leu Arg Val Leu Asp Pro Ala Cys Gly Ser Gly Asn
385                 390                 395                 400

Phe Leu Tyr Val Thr Met His Val Leu Lys Asp Leu Glu Tyr Glu Val
                405                 410                 415

Val Arg Glu Leu Glu Ala Leu Thr Gly His Ala Glu Leu Arg Met Gln
            420                 425                 430

Glu Ile Gly Pro Lys Asn Phe Leu Gly Ile Glu Val Lys Pro Trp Ala
        435                 440                 445

Arg Glu Ile Ala Glu Leu Thr Leu Trp Ile Gly Phe His Gln Tyr Trp
    450                 455                 460

Lys Arg His His His Val Gln Pro Pro Glu Pro Val Leu Met Asp Thr
465                 470                 475                 480

Gly Thr Leu Glu Leu Arg Asp Ala Val Leu Ala Trp Asp Ala Val Arg
                485                 490                 495

His Val Pro Glu Lys Asp Arg Phe Asp Pro Thr Pro Arg Ile Thr His
            500                 505                 510

Thr Val Thr Gly Glu Leu Val Pro Asp Pro Ala Ala Thr Leu Pro Tyr
        515                 520                 525

Met Glu His Val Gly Ala Arg Gln Ala Pro Trp Pro Glu Ala Asp Phe
    530                 535                 540

Ile Val Gly Asn Pro Pro Phe Leu Gly Gln Phe Arg Gln Arg Glu Ser
545                 550                 555                 560

Leu Gly Asp Gly Tyr Val Glu Ala Leu Arg Ser Ala Tyr Pro Gly Val
                565                 570                 575
```

Pro Asp Ala Ala Asp Leu Val Met Tyr Trp Ile Ser Lys Ala Thr Arg
580 585 590

Ala Val Glu Ser Gly Arg Thr Leu Arg Ala Gly Leu Ile Thr Thr Gln
595 600 605

Ser Ile Thr Gln Lys Gln Asn Arg Lys Val Leu Glu Asp Ala Ala Val
610 615 620

Arg Gly Leu Arg Pro Val Trp Ala Ile Ala Asp His Tyr Trp Asn Asp
625 630 635 640

Gly Ser Asp Asp Ala Arg Val Arg Val Ala Met Thr Val Phe Ala Arg
645 650 655

Glu Pro Ala Ala Ala Thr Leu Val Thr Val Asp Gly Glu Ala Lys Val
660 665 670

Val Asn Thr Val Arg Val Pro Arg Leu Asn Thr Asp Leu Thr Val His
675 680 685

Ala Asp Val Pro Ser Ala Ala Ala Val Ala Leu Gln Ala Asn Ala Trp
690 695 700

Leu Cys Ser Asn Gly Tyr Lys Pro His Gly Thr Gly Phe Leu Leu Ser
705 710 715 720

Asp Glu Glu Ala Arg Arg Leu Leu Ser Leu Asp Pro Arg Asn Ala Glu
725 730 735

Val Leu Arg Pro Tyr Arg Asn Gly Met Asp Leu Ala Thr Gln Pro Arg
740 745 750

Arg Val Trp Ile Ile Asp Phe Gly Phe Ala Asp Glu Ser Glu Ala Arg
755 760 765

Thr Tyr Pro Leu Leu Phe Asp Ile Val Arg Asp Arg Val Lys Pro Glu
770 775 780

Arg Asp Ala Asn Ala Arg Ala Val Tyr Arg Thr Tyr Trp Trp Arg Phe
785 790 795 800

Gly Glu Ala Arg Arg Asp Trp Arg Ser Phe Val Ala Gly Leu Pro Arg
805 810 815

Tyr Ile Ala Thr Val Lys Thr Ala Lys His Arg Phe Phe Thr Phe Leu
820 825 830

Glu Ser Thr Val Ala Pro Asp Asp Lys Leu Thr Cys Ile Ala Ser Ser
835 840 845

Glu Gly Phe Val Leu Gly Val Leu Ser Ser Leu Ile His Ser Thr Trp
850 855 860

Ala Leu Ala Ala Gly Ser Arg Leu Gly Ile Asp Gly Thr Pro Ser Tyr
865 870 875 880

Asp Lys Gly Thr Cys Phe Asp Ala Phe Pro Phe Pro Asp Cys Ser Ala
885 890 895

Asp Val Arg Asn Arg Ile Ala Thr Ile Ala Glu Arg Ile Asp Ala His
900 905 910

Arg Lys Ser Ala Ile Glu Arg Ser Ala Lys Val Gly Met Thr Val Met
915 920 925

Tyr Asn Val Ile Asp Lys Leu Arg Val Gly Ala Thr Leu Thr Ser Lys
930 935 940

Glu Arg Glu Val His Glu Val Ala Ala Cys Gly Val Leu Arg Asp Leu
945 950 955 960

His Asp Glu Leu Asp Ala Thr Val Ala Glu Ala Tyr Gly Trp Ser Trp
965 970 975

Pro Glu Pro Pro Ala Leu Ile Leu Glu Arg Leu Val Ala Leu His Asp
980 985 990

Arg Arg Val Glu Glu Glu Ala Gly Gly Thr Ile Arg Trp Leu Arg Pro 995 1000 1005

Glu Tyr Gln Arg Pro Arg Phe Gly Gly Ala Thr Asp Gly Ala Asn
1010 1015 1020

Val Ala Pro Thr Leu Asp Leu Pro Ala Thr Pro Thr Thr Leu Thr
1025 1030 1035

Gly Ala Gly Thr Val Ile Ala Ser Ala Pro Trp Pro Ser Asp Ala
1040 1045 1050

Ile Gly Gln Ile Thr Val Leu Arg Ser Met Ala Ala Met Thr Pro
1055 1060 1065

Val Ser Ile Glu Glu Ala Val Gln Arg Leu Val Gly Ala Lys Arg
1070 1075 1080

Asp Ile Val His Arg His Leu Glu Thr Leu Ala Met Leu Gly Glu
1085 1090 1095

Val Arg Asp Val Gly Asp Gly Arg Tyr Ala Val Thr Gly Ser
1100 1105 1110

<210> SEQ ID NO 197
<211> LENGTH: 1173
<212> TYPE: PRT
<213> ORGANISM: Planctomyces limnophilus

<400> SEQUENCE: 197

Met Thr Ala Ala Ser Val Ala Ser Ile Asp Pro Ala Ala Phe Ile Ala
1 5 10 15

Arg Trp Ala Pro Ser Gly Gly Ser Glu Arg Ser Asn Tyr Thr Leu Phe
20 25 30

Leu Ser Glu Leu Cys Asp Leu Leu Gly Val Pro Arg Pro Glu Pro Ala
35 40 45

Gln Ala Asp Thr Ser Arg Ser Phe Tyr Val Phe Glu Arg Asp Val Thr
50 55 60

Phe His Asn Ser Asp Gly Thr Thr Ser Thr Gly Arg Ile Asp Leu Tyr
65 70 75 80

Lys Arg Gly Cys Phe Ile Leu Glu Ala Lys Gln Gly Val Glu Gln Ala
85 90 95

Asp Ala Val Glu Ile Leu Ser Ser Thr Pro Ala Lys Arg Arg Lys Gly
100 105 110

His Gly Thr Arg Gly Thr Lys Ala Tyr Asp Asp Thr Met Leu Arg Ala
115 120 125

Arg Ser Gln Ala Glu Gln Tyr Ala Lys Ala Leu Pro Ala Asp Glu Gly
130 135 140

Trp Pro Pro Phe Leu Ile Val Val Asp Val Gly His Ser Ile Glu Leu
145 150 155 160

Phe Ala Asp Phe Thr Arg Ser Gly Lys Thr Tyr Leu Pro Phe Pro Asp
165 170 175

Pro Lys Ser Tyr Arg Ile Leu Leu Asn Gln Leu Ala His Asp Asp Ile
180 185 190

Arg His Thr Leu Lys Thr Val Trp Thr Asp Pro Val Ser Leu Asp Pro
195 200 205

Ser Arg Arg Ala Ala Lys Val Thr Arg Glu Leu Ala Asp Arg Leu Ala
210 215 220

Arg Leu Ala Lys Ser Leu Glu Ala Ser Lys Phe Asp Pro Gly Arg Val
225 230 235 240

Ala Gln Phe Leu Met Arg Cys Leu Phe Thr Met Phe Ala Glu Asp Val
245 250 255

Asp Leu Ile Pro Arg Glu Ser Phe Thr Asn Leu Leu Lys Ser Leu Arg

```
            260                 265                 270

Asp Asp Val Ala Asn Phe Pro Glu Met Ile Arg Ser Leu Trp Val Ser
        275                 280                 285

Met Asp Lys Gly Gln Phe Asp Pro Val Leu Arg Lys Lys Leu Arg Arg
    290                 295                 300

Phe Asn Gly Gly Leu Phe Glu Asp Cys Glu Ala Leu Pro Leu Thr Arg
305                 310                 315                 320

Asp Gln Leu Glu Leu Leu Ile Glu Ala Ser Gln Ala Gln Trp Arg Asp
                325                 330                 335

Val Glu Pro Ala Ile Phe Gly Thr Leu Leu Glu Arg Ala Leu Asp Pro
            340                 345                 350

Arg Glu Arg His Lys Leu Gly Ala His Tyr Thr Pro Arg Ala Tyr Val
        355                 360                 365

Glu Arg Leu Val Met Pro Thr Ile Met Glu Pro Leu Arg Glu Glu Trp
    370                 375                 380

Asp Thr Val Arg Ala Ala Ala Phe Thr Glu Ala Gly Arg Gly His Arg
385                 390                 395                 400

Glu Ala Ala Ile Gln Ile Leu Arg Asp Phe His Arg Gln Leu Cys Glu
                405                 410                 415

Thr Arg Val Leu Asp Pro Ala Cys Gly Ser Gly Asn Phe Leu Tyr Val
            420                 425                 430

Ala Leu Glu His Met Lys Arg Leu Glu Gly Glu Val Leu Asn Thr Leu
        435                 440                 445

His Asp Leu Gly Tyr Lys Gln Arg Glu Ile Ile Thr Val Asp Pro His
    450                 455                 460

Gln Phe Lys Gly Ile Glu Val Asn Pro Arg Ala Ala Ala Ile Ala Asp
465                 470                 475                 480

Leu Val Leu Trp Ile Gly Tyr Leu Gln Trp His Thr Arg Thr Arg Asn
                485                 490                 495

Leu Asp Asp Ile Ser Glu Pro Ile Ile Gln Asn Phe His Asn Ile Glu
            500                 505                 510

Cys Arg Asp Ala Val Leu Ala Trp Asp Ala Ile Glu Glu Val Arg Asp
        515                 520                 525

Glu His Gly Gln Pro Val Thr Arg Trp Asp Gly Arg Thr Met Lys Lys
    530                 535                 540

His Pro Val Thr Gly Glu Asp Val Pro Asp Asp Thr Ala Arg Val Pro
545                 550                 555                 560

Val Val Lys Tyr Ile Asn Pro Arg Lys Ala Glu Trp Pro Lys Ala Glu
                565                 570                 575

Tyr Ile Val Gly Asn Pro Pro Phe Ile Gly Asn Ser Arg Met Arg His
            580                 585                 590

Ala Leu Gly Asp Gly Tyr Ala Glu Cys Ile Arg Gln Thr Tyr Asn Arg
        595                 600                 605

Leu Pro Glu Thr Cys Asp Phe Val Met Tyr Trp Trp Asp Arg Ala Ala
    610                 615                 620

Glu Phe Thr Ser Asp Asn Gln Val Asn Arg Phe Gly Phe Ile Thr Thr
625                 630                 635                 640

Asn Ser Ile Arg Gln Lys Phe Ser Arg Arg Ile Leu Glu Gln Tyr Ile
                645                 650                 655

Asn Gly Pro Val Ala Ala Leu Ser Leu Ile Phe Ala Ile Pro Asp His
            660                 665                 670

Pro Trp Val Asp Ser Ser Asp Gly Ala Ala Val Arg Ile Ala Met Thr
        675                 680                 685
```

```
Val Ala Ala Pro Gly Thr Lys Val Gly Arg Leu Asn Asn Val Ala Ser
    690                 695                 700

Glu Ser Ile Gly Val Asp Asp Val Ala Glu Val Asn Leu Arg Glu Arg
705                 710                 715                 720

Ile Gly Arg Ile Gln Thr Asp Leu Thr Ile Gly Ala Asn Val Ala Gly
                725                 730                 735

Thr Leu Thr Leu Lys Ala Thr Gln Gly Leu Ser Cys Pro Gly Val Lys
            740                 745                 750

Leu His Gly Ala Gly Phe Ile Val Ser Pro Glu Glu Ala Arg His Leu
        755                 760                 765

Gly Leu Gly Ser Val Pro Gly Leu Glu Leu His Ile Arg Gln Tyr Arg
    770                 775                 780

Asn Gly Arg Asp Leu Thr Ala Ser Pro Arg Glu Val Met Val Ile Asp
785                 790                 795                 800

Leu Phe Gly Leu Gly Val Asp Glu Leu Arg Gln Arg Phe Pro Ala Val
                805                 810                 815

Tyr Gln His Val His Asp His Val Lys Pro Glu Arg Asp Gln Asn Asn
            820                 825                 830

Arg Ala Val Tyr Arg Asp Ser Trp Trp Met Phe Gly Glu Pro Arg Ala
        835                 840                 845

Ala Phe Arg Pro Ser Leu Lys Gly Leu Ala Arg Tyr Ile Ala Thr Val
    850                 855                 860

Glu Thr Ala Lys His Arg Val Phe Gln Phe Leu Asp Ala Ser Ile Leu
865                 870                 875                 880

Pro Asp Asn Met Leu Val Val Ile Ala Leu Asn Glu Ser Leu His Leu
                885                 890                 895

Gly Val Leu Ser Ser Arg Ile His Ile Val Trp Ser Leu Ala Ala Gly
            900                 905                 910

Gly Thr Leu Glu Asp Arg Pro Arg Tyr Asn Lys Ser Arg Cys Phe Glu
        915                 920                 925

Pro Phe Pro Phe Pro Glu Met Pro Asn Pro Arg Thr Pro Arg Ile Arg
    930                 935                 940

Glu Leu Gly Glu Gln Leu Asp Ala His Arg Lys Arg Gln Gln Ala Ala
945                 950                 955                 960

His Pro Asp Leu Thr Leu Thr Gly Met Tyr Asn Val Leu Glu Lys Leu
                965                 970                 975

Arg Ser Gly Glu Leu Leu Thr Ala Lys Glu Lys Val Ile His Glu Gln
            980                 985                 990

Gly Leu Val Ser Val Leu Lys Gln  Ile His Asp Asp Leu  Asp Ala Ala
        995                 1000                1005

Val Phe  Glu Ala Tyr Gly Trp  Pro Val Thr Leu Thr  Asp Glu Glu
    1010                1015                1020

Ile Leu  Glu Arg Leu Val Ala  Leu Asn Ala Glu Arg  Ala Glu Glu
    1025                1030                1035

Glu Lys  Arg Gly Leu Ile Arg  Trp Leu Arg Pro Glu  Phe Gln Asn
    1040                1045                1050

Pro Ser  Gly Gly Gln Ala Ile  Gln Pro Glu Leu Glu  Leu Glu Leu
    1055                1060                1065

Glu Thr  Glu Ala Glu Asp Glu  Glu Glu Thr Ala Ala  Ala Thr Thr
    1070                1075                1080

Lys Lys  Gly Gly Lys Ala Lys  Lys Gly Ala Gly Lys  Thr Ala Pro
    1085                1090                1095

Gly Gly  Lys Thr Lys Ala Pro  Ala Lys Gln Pro Trp  Pro Thr Lys
    1100                1105                1110
```

Leu Ser Glu Gln Val Gln Ala Leu Ile Gln Lys Leu Gln Thr Ala
1115 1120 1125

Asp Ser Pro Leu Thr Ala Gln Glu Leu Ala Lys Ala Phe Thr Arg
1130 1135 1140

Ala Asn Ala Asp Thr Ile Asp Glu Leu Leu Glu Thr Leu Val Ala
1145 1150 1155

Ile Gly Lys Ala Arg Gln Val Gly Asp Asp Lys Phe Thr Ala Val
1160 1165 1170

<210> SEQ ID NO 198
<211> LENGTH: 1168
<212> TYPE: PRT
<213> ORGANISM: Agmenellum quadruplicatum

<400> SEQUENCE: 198

Met Thr Asp Phe Ile Gln Lys Trp Gln Asn Ser Glu Gly Asn Glu Arg
1 5 10 15

Ala Asn Tyr Gln Ser Phe Leu Asn Asp Phe Cys Glu Phe Leu Gly Val
20 25 30

Glu Lys Ser Pro Pro Lys Gly Ser Gly Asn Asn Ser Tyr Cys Phe Asp
35 40 45

Arg Asp Val Lys Ile Ile Ala Pro Ser Gly Ala Glu Thr Thr Asn Phe
50 55 60

Ile Asp Phe Tyr Lys Glu Asp Cys Phe Val Leu Glu Thr Lys Gln Gly
65 70 75 80

Ser Asn Thr Ser Asn Lys Gly His Gly Lys Arg Gly Thr Ala Ala Tyr
85 90 95

Arg Lys Glu Met Lys Lys Ala Phe Gly Gln Ala Leu Lys Tyr Ala Arg
100 105 110

Phe Val Glu Pro Lys Pro Pro Phe Leu Ile Thr Cys Asp Ile Gly Asp
115 120 125

His Phe Arg Val Trp Gln Asp Phe Ser Glu Ser Trp Leu Ser Ala Asn
130 135 140

Gly Asn Tyr Gly Thr Tyr Asp Ser Val Pro Lys Ile Pro Phe Thr Asp
145 150 155 160

Leu Glu Lys Pro Glu Ile Gln Asp Phe Phe Tyr Lys Val Phe Thr Asp
165 170 175

Pro Gln Ser Leu Asn Pro Glu Lys Ile Ala Ala Gln Val Thr Arg Glu
180 185 190

Val Ala Ala Asp Leu Ala Glu Leu Ala Lys Thr Leu Glu Gln Thr Thr
195 200 205

Lys Pro Gln Glu Val Ala Gln Phe Leu Met Arg Cys Ile Phe Thr Met
210 215 220

Phe Ala Glu Asp Val Gly Leu Leu Lys Glu His Leu Phe Thr Glu Ala
225 230 235 240

Leu Lys Glu Arg Trp Ile Pro Gln Pro Gln Asp Phe Lys Pro Gln Val
245 250 255

Glu Ala Leu Trp Gln Ala Met Asn Asp Gly Thr Ser Phe Gly Phe His
260 265 270

Gly Gln Leu Leu Arg Phe Asn Gly Gly Leu Phe Ala Lys Pro Gln Ala
275 280 285

Ile Ala Leu Thr Ala Asp Gln Leu Lys Ile Leu Leu Thr Ala Ala Glu
290 295 300

Arg Asp Trp Lys Asn Val Glu Pro Ala Ile Phe Gly Thr Leu Leu Glu
305 310 315 320

```
Arg Ala Leu Glu Lys Lys Glu Arg Ser Lys Leu Gly Ala His Tyr Thr
                325                 330                 335

Pro Arg Ala Tyr Val Glu Arg Leu Val Arg Pro Val Ile Ile Glu Pro
            340                 345                 350

Leu Gln Glu Lys Trp Gln Leu Ile Gln Gly Glu Val Glu Thr Leu Leu
        355                 360                 365

Glu Glu Glu Glu Ala Ala Lys Ser Ala Ser Ala Lys Thr Lys Lys Arg
    370                 375                 380

Asn Ala Ala Ala Glu Lys Leu Thr Glu Phe Leu Gly Glu Leu Arg Lys
385                 390                 395                 400

Ile Arg Val Leu Asp Pro Ala Cys Gly Ser Gly Asn Phe Leu Tyr Val
                405                 410                 415

Thr Met Asp Leu Met Lys Thr Leu Glu Leu Glu Val Leu Asn Arg Leu
            420                 425                 430

Gly Thr Val Met Gly Ala Ser Gln Leu Arg Leu Asp Phe Asp Gln Ile
        435                 440                 445

Asn Pro Ser Gln Phe Leu Gly Ile Glu Ile Asn Pro Arg Ala Ala Glu
    450                 455                 460

Ile Ala Asp Leu Val Ile Trp Ile Gly Tyr Leu Gln Trp His Phe Arg
465                 470                 475                 480

Leu Phe Gly Ser Leu Pro Pro Val Glu Pro Val Leu Arg Glu Tyr Lys
                485                 490                 495

Asn Ile Glu Asn Arg Asp Ala Val Leu Asp Tyr Asp Gly Thr Lys Pro
            500                 505                 510

Ala Ile Asp Pro Lys Thr Gly Lys Val Arg Thr Arg Trp Gly Gly Arg
        515                 520                 525

Thr Met Lys His Pro Val Thr Gly Glu Asp Val Pro Asp Pro Ser Asp
    530                 535                 540

Gln Val Glu Ile Leu Glu Tyr Ile Asn Pro Arg Glu Ala Gln Trp Gln
545                 550                 555                 560

Gln Ala Asp Tyr Ile Val Ser Asn Pro Pro Phe Leu Gly Asn Ala Arg
                565                 570                 575

Met Arg Glu Tyr Leu Gly Asp Gly Tyr Thr Glu Thr Leu Arg Lys Val
            580                 585                 590

Tyr Lys Asp Val Pro Asp Thr Val Asp Phe Val Met Tyr Trp Trp His
        595                 600                 605

Lys Ala Ala Glu Leu Ile Arg Lys Glu Lys Thr Leu Arg Phe Gly Phe
    610                 615                 620

Ile Thr Thr Asn Ser Ile Arg Gln Ala Arg Leu Arg Ser Val Ile Asp
625                 630                 635                 640

Phe His Phe Asn Gln Lys Lys Arg Ile Arg Leu Phe Phe Ala Ile Pro
                645                 650                 655

Asp His Pro Trp Ser Asp Gly Glu Val Ala Val Arg Ile Ser Met Thr
            660                 665                 670

Gly Val Glu Leu Lys Lys Lys Arg Arg Gln Tyr Ser Gln Leu Thr His
        675                 680                 685

Ile Leu Glu Glu Ser Lys Leu Asn Thr Pro Glu Glu Thr Ala Phe Ser
    690                 695                 700

Leu Lys Phe Ser Tyr Val Lys Ala Asn Glu Ile Phe Ser Asn Leu Gln
705                 710                 715                 720

Phe Gly Tyr Asp Val Asn Gln Ala Asn Ser Leu Ser Ser Asn Gln Asn
                725                 730                 735

Leu Ala Ser Gln Gly Phe Val Val Gly Gly Ser Gly Phe Val Leu Lys
```

```
            740                 745                 750

Asn Gln Ala Leu Val Glu Asn Leu Glu Gln Glu Ile Ile His Pro Phe
        755                 760                 765

Lys Thr Gly Arg Asp Leu Thr Gln Ser Pro Glu Phe Arg Gln Thr Ile
    770                 775                 780

Asp Val Asn His Leu Ser Lys Lys Gln Leu Leu Ser Ser Tyr Pro Lys
785                 790                 795                 800

Thr Tyr Gln Trp Leu Ser Glu Thr Val Lys Leu Glu Arg Ser Thr Asn
                805                 810                 815

Asn Asp Pro Lys Leu Lys Arg Glu Trp Trp Arg Tyr Arg Arg Ala Asn
            820                 825                 830

Thr Ser Ile Arg Asp Gly Ile Lys Asp Leu Asn Arg Tyr Ile Ala Thr
        835                 840                 845

Val Arg Thr Ala Lys His Arg Val Phe Gln Phe Leu Asn Ser Glu Ile
    850                 855                 860

Met Ala Glu Ser Gly Val Val Met Ile Phe Leu Asp Asp Ser Tyr Phe
865                 870                 875                 880

Leu Gly Ile Cys Ser Ser Ser Leu His Ile Ile Trp Ala Leu Ala Gln
                885                 890                 895

Gly Gly Arg Leu Glu Asp Arg Pro Val Tyr Asn His Asp Ala Cys Phe
            900                 905                 910

Tyr Arg Phe Pro Phe Pro Asp Pro Ser Glu Glu Leu Lys Gln Glu Ile
        915                 920                 925

Arg Glu Leu Gly Glu Arg Leu Asp Ser His Arg Lys Gln Val Gln Ala
    930                 935                 940

Ala His Pro Glu Val Thr Ile Thr Ala Met Tyr Asn Cys Leu Glu Lys
945                 950                 955                 960

Met Arg Ser Gly Glu Pro Phe Thr Asp Gly Asp Arg Glu Phe Asn Asn
                965                 970                 975

Lys Ala Leu Ile Thr Thr Leu Lys Gln Ile His Asp Asp Leu Asp Gln
            980                 985                 990

Ala Val Phe Cys Ala Tyr Gly Trp  Glu Asp Leu Ile Pro  Leu Trp Gln
        995                 1000                 1005

Lys Val  Ser Leu Pro Lys Gly  Asp Leu Glu Gly Cys  Gln Thr Glu
    1010                 1015                 1020

Pro Asn  Asn Thr Glu Thr Lys  Glu Gln Leu Glu Gln  Ser Ile Leu
    1025                 1030                 1035

Gln Arg  Leu Val Asp Leu Asn  Ala Glu Arg Ala Glu  Glu Glu Arg
    1040                 1045                 1050

Asn Gly  Phe Val Arg Trp Leu  Arg Pro Glu Tyr Gln  Ala Pro Asp
    1055                 1060                 1065

Gln Val  Val Thr Gln Lys Val  Ile Glu Gly Ile Gly  Val Glu Glu
    1070                 1075                 1080

Glu Thr  Lys Glu Ala Val Ile  Ala Pro Pro Glu Gln  Gln Lys Phe
    1085                 1090                 1095

Pro Thr  Lys Leu Lys Gly Gln  Leu Ala Ala Ile Arg  Asp Leu Leu
    1100                 1105                 1110

Arg Thr  Gln Gly Gly Glu Trp  Thr Ile Thr Gln Ile  Ala Ala Gln
    1115                 1120                 1125

Phe Lys  Gly Thr Ser Ala Lys  Lys Leu Glu Thr Ile  Gln Asn Cys
    1130                 1135                 1140

Leu Glu  Ile Leu Glu Asp Leu  Gly Val Ile Leu Ser  His Thr Glu
    1145                 1150                 1155
```

Thr Glu Thr Lys Cys Tyr Tyr Ala Thr Leu
1160 1165

<210> SEQ ID NO 199
<211> LENGTH: 973
<212> TYPE: PRT
<213> ORGANISM: Rhodopseudomonas palustris

<400> SEQUENCE: 199

Met Thr Pro Ala Glu Phe Ile Lys Lys Trp Lys Pro Val Ala Leu Thr
1 5 10 15

Glu Arg Ala Ala Ala Gln Thr His Phe Leu Asp Leu Cys Lys Leu Phe
20 25 30

Glu His Glu Asp Pro Val Ser Ala Asp Pro Thr Gly Glu Trp Phe Thr
35 40 45

Phe Glu Lys Gly Ala Thr Lys Thr Gly Gly Gly Asp Gly Phe Ala Asp
50 55 60

Val Trp Lys Lys Asn Tyr Phe Ala Trp Glu Tyr Lys Lys Lys Lys Arg
65 70 75 80

Asp Leu Gly Val Ala Met Asn Gln Leu Val Arg Tyr Ala Ala Ala Leu
85 90 95

Glu Asn Pro Pro Leu Gln Val Val Cys Asp Thr Asp Arg Phe Val Ile
100 105 110

Arg Thr Ala Trp Thr Asn Thr Val Pro Lys Glu Tyr Glu Ile Glu Leu
115 120 125

Asp Asp Leu Ala Asp Pro Glu Lys Arg Lys Ile Leu Trp Ala Val Phe
130 135 140

His Asp Pro Glu Gln Leu Arg Pro Gln Gln Thr Arg Thr Ala Ile Thr
145 150 155 160

Lys Glu Ala Ala Asp Lys Phe Ser Thr Ile Ala Leu Arg Leu Gln Gly
165 170 175

Arg Gly Thr Pro Glu Glu Ile Ala His Phe Val Asn Gln Leu Val Phe
180 185 190

Cys Phe Phe Ala Ser Ser Val Lys Leu Leu Pro Glu Gly Phe Phe Pro
195 200 205

Lys Leu Leu Lys Arg Ala Ala Gln Lys Pro Gln His Ala Ile Asp Tyr
210 215 220

Phe Asn Lys Leu Phe Glu Ala Met Glu Asn Gly Gly Glu Tyr Asp Leu
225 230 235 240

Thr Asp Ile Ala His Phe Asn Gly Gly Leu Phe Asp Gly Arg Arg Ala
245 250 255

Leu Lys Leu Asp Glu Gly Asp Ile Gly Leu Leu Ile Glu Ala Gly Ser
260 265 270

Leu Asp Trp Gly Gln Ile Asp Pro Thr Ile Phe Gly Thr Leu Phe Glu
275 280 285

Arg Phe Leu Asp Pro Asp Lys Arg Ala Gln Ile Gly Ala His Tyr Thr
290 295 300

Asp Pro Asp Lys Ile Leu Met Ile Val Glu Pro Val Ile Leu Arg Pro
305 310 315 320

Leu Arg Ala Glu Trp Asp Ala Ala Arg Ala Lys Ile Ala Glu Ile Ala
325 330 335

Gly Glu Ala Asn Ala Leu Gln Gln Thr Gly Phe Ser Lys Gln Gly Ala
340 345 350

Lys Ser Phe Asp Lys Lys Ile Thr Asn Ile Arg Ala Lys Ala Glu Val
355 360 365

```
Ile Arg Asp Gln Phe Ile Glu Arg Leu Arg Gly Ile Thr Ile Leu Asp
    370                 375                 380

Pro Ala Cys Gly Ser Gly Asn Phe Leu Tyr Leu Ala Leu Gln Gly Val
385                 390                 395                 400

Lys Asp Ile Glu Leu Arg Ala Asn Leu Glu Cys Glu Ala Leu Gly Leu
                405                 410                 415

Ser Pro Arg Leu Pro Val Ile Gly Pro Glu Ile Val His Gly Leu Glu
            420                 425                 430

Ile Asn Glu Leu Ala Ala Glu Leu Ala Arg Thr Thr Ile Trp Ile Gly
        435                 440                 445

Asp Ile Gln Trp Arg Ile Arg Asn Gly Ile Tyr Ser Asn Pro Arg Pro
    450                 455                 460

Ile Leu Arg Lys Leu Asp Ser Ile Glu Cys Arg Asp Ala Leu Ile Thr
465                 470                 475                 480

Lys Leu Thr Asp Gly Thr Tyr Ala Glu Ala Glu Trp Pro Thr Ala Glu
                485                 490                 495

Phe Ile Val Gly Asn Pro Pro Phe Leu Gly Asp Lys Phe Met Leu Asp
            500                 505                 510

Arg Leu Gly Val Arg Tyr Thr Gln Ala Leu Arg Glu Ala Phe Leu Gly
        515                 520                 525

Arg Val Pro Gly Gly Ser Asp Leu Val Cys Tyr Trp Leu Glu Lys Ala
    530                 535                 540

Arg Ala Gln Ile Leu Ser Asn Glu Thr Phe Gly Ala Gly Phe Val Ala
545                 550                 555                 560

Thr Asn Ser Ile Arg Gly Gly Ala Asn Arg Thr Val Val Asp Arg Val
                565                 570                 575

Thr Ala Asp Leu Asp Ile Phe Cys Ala Trp Ala Asp Glu Asp Trp Thr
            580                 585                 590

Ile Glu Gly Ala Asp Val Arg Val Ser Leu Ile Cys Phe Ser Ser Lys
        595                 600                 605

Gly Arg Ala Gln Leu Leu Val Glu Leu Asn Gly Gln Ser Val Ala Arg
    610                 615                 620

Ile Phe Ser Asp Leu Thr Ser Ser Ala Thr Asp Phe Thr Arg Ala Arg
625                 630                 635                 640

Ser Leu Arg Ser Cys Arg Glu Val Ala Phe Ile Gly Asn Gln Lys Gly
                645                 650                 655

Gly Ala Phe Asp Leu Pro Gly Ser Ile Ala Arg Ser Phe Leu Thr Leu
            660                 665                 670

Pro Gln Asn Pro Asn Gly Asn Ser Asn Ala Asp Val Val Lys Pro Trp
        675                 680                 685

Ile Asn Gly Leu Asp Ile Val Arg Arg Pro Arg Asp Tyr Trp Ile Ile
    690                 695                 700

Asp Phe Thr Gly Leu Gln Glu Ser Glu Ala Ala Leu Tyr Glu Gly Pro
705                 710                 715                 720

Phe Gln Tyr Ile Leu Glu His Val Lys Glu Tyr Arg Asn Glu Glu Ala
                725                 730                 735

His Glu Ser Ser Lys Met Asn Trp Trp Ile His Gln Arg Pro Arg His
            740                 745                 750

Ala Leu Arg Leu Ala Ile Asp Gly Gln Ser Arg Tyr Leu Ala Thr Ala
        755                 760                 765

Arg Val Ala Lys His Arg Leu Phe Ile Trp Val Asp His Gln Val Val
    770                 775                 780

Pro Asp Ser Gln Val Val Ala Ile Ala Arg Ser Asp Asp Ala Thr Phe
785                 790                 795                 800
```

-continued

```
Gly Ile Leu His Ser Ser Phe His Glu Ser Trp Thr Leu Arg Leu Cys
                805                 810                 815

Thr Trp Leu Gly Val Gly Asn Asp Pro Arg Tyr Thr Pro Thr Thr Thr
            820                 825                 830

Phe Glu Thr Phe Pro Phe Pro Glu Gly Leu Thr Pro Asp Ile Pro Ala
        835                 840                 845

Gly Asp Tyr Ala Asp Asp Pro Arg Ala Gln Ala Ile Ala Lys Ala Ala
    850                 855                 860

Lys Arg Leu Asp Glu Leu Arg Lys Ala Trp Leu Asn Pro Pro Asp Leu
865                 870                 875                 880

Val Arg Ile Glu Pro Glu Val Val Pro Gly Tyr Pro Asp Arg Ile Leu
                885                 890                 895

Pro Lys Asp Thr Lys Ala Ala Ser Glu Leu Lys Lys Arg Thr Leu Thr
            900                 905                 910

Asn Leu Tyr Asn Ala Arg Pro Gln Trp Leu Ala Asp Ala His Arg Asp
        915                 920                 925

Leu Asp Ala Ala Val Ala Ala Ala Tyr Gly Trp Pro Ala Asp Ile Thr
    930                 935                 940

Glu Asp Asp Ala Leu Ala Lys Leu Leu Glu Leu Asn Leu Ser Arg Ala
945                 950                 955                 960

Gly Ala Ser Ser Pro Pro Pro Ala Asn Lys Asp Glu Gly
                965                 970
```